(12) United States Patent
Batt et al.

(10) Patent No.: US 8,202,858 B2
(45) Date of Patent: Jun. 19, 2012

(54) VASOPRESSIN $V_{1a}$ ANTAGONISTS

(75) Inventors: Andrzej Roman Batt, Southampton (GB); Martin Lee Stockley, Lordshill (GB); Michael Bryan Roe, Hampshire (GB); Celine Marguerite Simone Heeney, Portswood (GB); Andrew John Baxter, Woodley (GB); Peter Hudson, Copenhagen S (DK); Rachel Handy, Hampshire (GB)

(73) Assignee: Vantia Limited, Chilworth (GB)

( * ) Notice: Subject to any disclaimer, the term of this patent is extended or adjusted under 35 U.S.C. 154(b) by 680 days.

(21) Appl. No.: 11/659,798

(22) PCT Filed: Aug. 24, 2005

(86) PCT No.: PCT/DK2005/000540
§ 371 (c)(1),
(2), (4) Date: Jan. 14, 2008

(87) PCT Pub. No.: WO2006/021213
PCT Pub. Date: Mar. 2, 2006

(65) Prior Publication Data
US 2009/0029965 A1    Jan. 29, 2009

Related U.S. Application Data

(60) Provisional application No. 60/603,557, filed on Aug. 24, 2004.

(30) Foreign Application Priority Data

Aug. 24, 2004 (EP) .................................. 04104062

(51) Int. Cl.
*A61K 31/55* (2006.01)
(52) U.S. Cl. ......... 514/217; 514/220; 540/562; 540/586
(58) Field of Classification Search .................. 540/562, 540/586
See application file for complete search history.

(56) References Cited

U.S. PATENT DOCUMENTS

| | | |
|---|---|---|
| 3,960,886 A | 6/1976 | Schulenberg |
| 3,987,102 A | 10/1976 | Karrer |
| 3,987,108 A | 10/1976 | Karrer |
| 5,516,774 A | 5/1996 | Albright et al. |
| 5,760,031 A | 6/1998 | Albright et al. |
| 5,843,952 A | 12/1998 | Albright et al. |
| 5,968,930 A | 10/1999 | Albright et al. |
| 6,583,141 B1 | 6/2003 | Freyne et al. |

FOREIGN PATENT DOCUMENTS

| | | |
|---|---|---|
| DE | 2 418 295 | 11/1974 |
| EP | 0 186 817 | 8/1989 |
| EP | 0 620 216 B1 | 1/2003 |
| EP | 1 449 844 A1 | 8/2004 |
| JP | 7157486 | 6/1995 |
| JP | 10512572 | 12/1998 |
| JP | 11508244 | 7/1999 |
| WO | WO 95/34540 | 12/1995 |
| WO | WO 96/022294 | 7/1996 |
| WO | WO 96/041795 | 12/1996 |
| WO | WO 01/29005 A1 | 4/2001 |
| WO | WO 02/00626 A1 | 1/2002 |
| WO | WO 02/04403 A1 | 1/2002 |
| WO | WO 03/000692 | 1/2003 |
| WO | WO 03/016316 A1 | 2/2003 |
| WO | WO 2004/037788 A1 | 5/2004 |
| WO | WO 2005/082859 | 9/2005 |
| WO | WO 2006/018443 | 2/2006 |

OTHER PUBLICATIONS

Akerlund et al., "Receptor binding of oxytocin and vasopressin antagonists and inhibitory effects on isolated myometrium from preterm and term pregnant women", Br J Obstet Gynaecol, Oct. 1999, 106(10), 1047-1053.
Adrogué, "Consequences of inadequate management of hyponatremia", Am J Nephrol, Epub May 25, 2005, Jun. 2005, 25(3), 240-249.
Bemana et al., "Treatment of Brain Edema with a Nonpeptide Arginine Vasopressin V1 Receptor Antagonist OPC-21268 in Rats", Neurosurgery, Jan. 1999 , 44(1), 148-154.
Bemana et al., "OPC-21268, an orally effective, nonpeptide arginine vasopressin V1 receptor antagonist reduces vasogenic brain edema", Acta Neurochair Suppl, Jan. 1997, 70, 194-197.
Bielsky et al., "Profound impairment in social recognition and reduction in anxiety-like behavior in vasopressin V1a receptor knockout mice", Neuropsychopharmacology, Mar. 2004, 29(3), 483-493.
Bossmar et al., "Effects of SR 49059, an orally active V1a vasopressin receptor antagonist, on vasopressin-induced uterine contractions", Br J Obstet Gynaecol, Apr. 1997, 104(4), 471-477.
Brouard et al., "Effect of SR49059, an orally active V1a vasopressin receptor antagonist, in the prevention of dysmenorrhoea", BJOG, May 2000, 107(5), 614-619.
Burrell et al., "Blood pressure-lowering effect of an orally active vasopressin V1 receptor antagonist in mineralocorticoid hypertension in the rat", Hypertension, Jun. 1994, 23(6 Pt 1), 737-743.
Cheung et al., "Etiologic significance of arginine vasopressin in motion sickness Etiologic significance of arginine vasopressin in motion sickness", J Clin Pharmacol, Jun. 1994, 34(6), 664-670.
Database Beilstein (English Summary Included), Beilstein Institute for Organic Chemistry, Frankfurt-Main, DE, XP002383170, Database Accession No. BRN 2132233, Abstract & Arzneimittel Forschung, vol. 14, 1964, 324-328.

(Continued)

*Primary Examiner* — James O Wilson
*Assistant Examiner* — Brian McDowell
(74) *Attorney, Agent, or Firm* — Woodcock Washburn LLP

(57) ABSTRACT

The present invention concerns compounds inter alia according to general formula 1a. Compounds according to the invention are vasopressin $V_{1a}$ receptor antagonists. Pharmaceutical compositions of the compounds are useful as treatment of dysmenorrhoea.

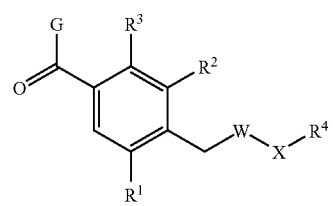

1a

29 Claims, No Drawings

OTHER PUBLICATIONS

Database Beilstein, Beilstein Institute for Organic Chemistry, Frankfurt-Main, DE, XP002357863, Database Accession No. BRN 2173418, Abstract & DE 2418295 A.

Database Beilstein, Beilstein Institute for Organic Chemistry, Frankfurt-Main, DE, XP002383169, Database Accession No. BRN 2886892, Abstract & US 3960886 A.

Decaux et al., "Non-peptide arginine-vasopressin antagonists: the vaptans", Lancet, May 10, 2008, 371(9624), 1624-1632.

Trybulski (Doherty (Ed.)), "Vasopressin receptor modulators: From non-peptide antagonists to agonists", Annual Reports in Medicinal Chemistry, Academic Press, Aug. 2001, 36(Chapter 16), 159-168.

Gard et al., "Reclovaptan Sanofi-Synthelabo", Current Opinion in Oncologic, Endocrine, & Metabolic Investigational Drugs, 2000, 2(2), 265-272.

Hayoz et al., "Effect of SR 49059, a V1a vasopressin receptor antagonist, in Raynaud's phenomenon", Rheumatology, Oct. 2000, 39(10), 1132-1138.

Kim et al., "Role of plasma vasopressin as a mediator of nausea and gastric slow wave dysrhythmias in motion sickness", Am J Physiol, Apr. 1997, 272(4 Pt 1), G853-G862.

Kortas et al., "Vasopressin in congestive heart failure", J Cardiovasc Pharmacol, 1986, 8(Suppl 7), 5107-5110.

Mayinger et al., "Nonpeptide vasopressin antagonists: a new group of hormone blockers entering the scene", Exp Clin Endocrinol Diabetes, 1999,107(3), 157-165.

Morita et al., "Molecular analysis of antilipemic effects of FR218944, a novel vasopressin V1a receptor antagonist; in genetically diabetic db/db mice in comparison with ploglitazone and fenofibrate", Drug Development Research, Dec. 2003, 60(4), 241-251.

Muller et al., "Vasopressin, major depression, and hypothalamic-pituitary-adrenocortical desensitization", Biol Psychiatry, Aug. 15, 2000, 48(4), 330-333.

Naitoh et al., "Effects of oral AVP receptor antagonists OPC-21268 and OPC-31260 on congestive heart failure in conscious dogs", Am J Physiol, Dec. 1994, 267(6 Pt 2), H2245-H2254.

Naitoh et al., "Neurohormonal antagonism in heart failure; beneficial effects of vasopressin V(1a) and V(2) receptor blockade and ACE inhibition", Cardiovasc Res, Apr. 2002, 54(1), 5157.

Péqueux et al., "Oxytocin- and vasopressin-induced growth of human small-cell lung cancer is mediated by the mitogen-activated protein kinase pathway", Endocr Relat Cancer, Dec. 2004, 11(4), 871-885.

Pitt et al., "Non-peptide oxytocin agonists", Bioorg Med Chem Lett, Sep. 6, 2004, 14(17), 4585-4589.

Pociecha et al., "New Mesogenic Compounds Having Fork-Like or Cyclic Amide Terminal Groups", Liquid Crystals, Taylor and Francis, Abingdon, GB, 2002, 29(5), 663-667.

Rouleau et al., "Prognostic value of neurohumoral activation in patients with an acute myocardial infarction: effect of captopril", J Am Coll Cardiol, Sep. 1994, 24(3), 583-591.

Scott et al., "Vasopressin and the regulation of hypothalamic-pituitary-adrenal axis function: implications for the pathophysiology of depression", Life Sci, Apr. 24, 1998, 62(22),1985-1998.

Scott et al., "Vasopressin as a target for antidepressant development: an assessment of the available evidence", J affect Disord, Nov. 2002, 72(2), 113-124.

Shuaib et al., "Effects of nonpeptide V(1) vasopressin receptor antagonist SR-49059 on infarction volume and recovery of function in a focal embolic stroke model", Stroke, Dec. 2002, 33(12), 3033-3037.

Steinwall et al., "Inhibitory effects of SR 49059 on oxytocin-and vasopressin-induced uterine contractions in non-pregnant women", Acta Obstet Gynaecol Scand, Jan. 2004, 83(1), 12-18.

Steinwall et al., "The effect of relcovaptan (SR 49059), an orally active vasopressin V1a receptor antagonist, on uterine contractions in preterm labor", Gynaecol Endocrinol, Feb. 2005, 20(2), 104-109.

Vågnes et al., "Age-dependent regulation of vasopressin V1a receptors in preglomerular vessels from the spontaneously hypertensive rat", Am J Physiol Renal Physiol, Epub Dec. 30, 2003, May 2004, 286(5), F997-F1003.

Yamada et al., "OPC-21268, a vasopressin V1 antagonist, produces hypotension in spontaneously hypertensive rats", Hypertension, Feb. 1994, 23(2), 200-204.

VASOPRESSIN $V_{1a}$ ANTAGONISTS

CROSS REFERENCE TO RELATED APPLICATIONS

This application is the National Phase of PCT/DK2005/000540, filed Aug. 24, 2005, and published as WO 2006/021213, which in turn claims priority to European Patent Application No. 04104062.7 filed Aug. 24, 2004, and U.S. Provisional Application No. 60/603,557, filed Aug. 24, 2004, the entirety of these applications are incorporated herein by reference.

FIELD OF THE INVENTION

The present invention relates to compounds with vasopressin $V_{1a}$ antagonist activity and to pharmaceutical compositions comprising such compounds. The present invention also relates to the use of vasopressin $V_{1a}$ antagonists for the treatment of certain physiological disorders, such as Raynaud's disease and dysmenorrhoea (primary dysmenorrhoea and/or secondary dysmenorrhoea).

Priority is claimed from EP patent application number 04104062 and U.S. patent application No. 60/603,557, both filed 24 Aug. 2004.

BACKGROUND

The neurophyseal hormones vasopressin (VP) and oxytocin (OT) are cyclic nonapeptides secreted by the posterior pituitary gland.

Only one OT receptor has so far been well characterised, while three VP receptors are known. These are designated the $V_{1a}$, $V_{1b}$ and $V_2$ receptors.

Vasopressin acts on the blood vessels, where it is a potent vasoconstrictor, and on the kidneys, where it promotes water reuptake leading to an antidiuretic effect.

The $V_{1a}$, $V_{1b}$, and $V_2$, as well as the OT receptors, are members of the super-family of seven transmembrane receptors known as G-protein coupled receptors. The $V_{1a}$ receptor mediates phospholipase C activation and intra-cellular calcium mobilisation. Localisation of the receptors includes blood platelets, blood vessels, hepatocytes, brain and uterus-cervix. Thus a $V_{1a}$ antagonist may have effects on any or all of these tissues. For example, selective $V_{1a}$ antagonists have been cited as having clinical utility in dysmenorrhoea, preterm labour, hypertension, Raynaud's disease, brain oedema, motion sickness, hyperlipemia, small cell lung cancer, depression, anxiety, hyponatremia, liver cirrhosis and congestive heart failure.

With respect to dysmenorrhoea it has been proposed that myometrial activity is markedly increased in women with dysmenorrhoea during menstruation. It is proposed that the myometrial ischemia caused by increased uterine contractility might explain the menstrual pain. Furthermore, on the first day of menstruation, higher plasma concentrations of vasopressin have been measured in dysmenorroeic women than in controls.

In healthy women without dysmenorrhoea, intravenous infusion of lysine-vasopressin resulted in decreased uterine blood flow, increased uterine contractility and slight to moderate dysmenorrhoea-like pain, these effects being inhibited by a selective human $V_{1a}$ receptor antagonist. (Bossmar, T. et al., BRITISH JOURNAL OF OBSTETRICS AND GYNAECOLOGY (1997 April), 104(4), 471-7). Also, it is known that vasopressin contracts human uterine arteries in a dose-dependent and $V_{1a}$-mediated fashion.

The above evidence suggests that a $V_{1a}$ antagonist would be an appropriate and effective treatment for dysmenorrhoea (primary dysmenorrhoea and/or secondary dysmenorrhoea). Further evidence is taken from the clinical study carried out on the selective $V_{1a}$ antagonist SR49059 ("Effect of SR49059, an orally active $V_{1a}$ vasopressin receptor antagonist, in the prevention of dysmenorrhea". Brouard, R. et al., BRITISH JOURNAL OF OBSTETRICS AND GYNAECOLOGY (2000), 107(5), 614-619). It was found that there was a dose-related decrease in pain and a dose-related decrease in the amount of additional pain-killer taken compared to patients taking placebo.

The International Patent Application WO 03/016316 A1, published 27 Feb. 2003, discloses a number of compounds which are claimed to be oxytocin agonists and to find use in the treatment of male erectile dysfunction. No $V_{1a}$ antagonist activity is reported. The European Patent Application EP 1 449 844 A1, published 25 Aug. 2004, discloses a number of compounds which are claimed to be $V_{1a}$ antagonists and to find use in the treatment of primary dysmenorrhoea.

There exists a need for treatments for conditions which are associated with the $V_{1a}$ receptors. There further continues to exist a need for alternative Via antagonists. Simple synthesis and oral availability are additional desirable characteristics.

DISCLOSURE OF THE INVENTION

According to an aspect, the present invention relates to compounds, preferably VP antagonists, and in particular specific antagonists of the $V_{1a}$ receptor, and pharmaceutically acceptable salts thereof.

According to another aspect, the present invention relates to pharmaceutical compositions comprising these compounds, which compositions are useful for the treatment of, inter alia, dysmenorrhoea (primary dysmenorrhoea and/or secondary dysmenorrhoea).

According to another aspect, the present invention relates to the use of the compounds for the manufacture of a pharmaceutical composition for treatment of dysmenorrhoea.

According to further aspects, the present invention relates to the medical use and to the use of the above mentioned compounds and compositions in therapy and to therapeutic methods wherein the above mentioned compounds and compositions are used.

DETAILED DESCRIPTION OF THE INVENTION

According to an aspect the invention concerns a compound according to general formula 1a, or a compound which is a tautomer or a pharmaceutically acceptable salt thereof,

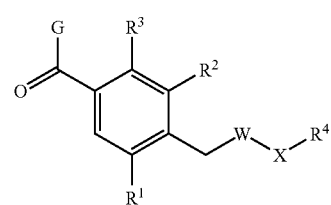

1a wherein G is a group selected among general formula 2a, 3a, 4a, 5a, and 6a,

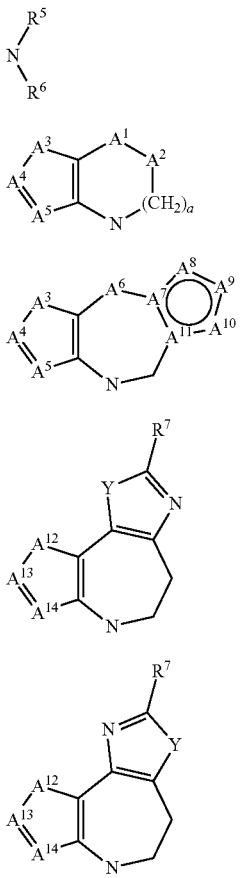

wherein:
A$^1$ is selected among CH$_2$, CH(OH), NH, N-alkyl, O and S;
A$^2$ is selected among CH$_2$, CH(OH), C(=O) and NH;
A$^3$ and A$^{12}$ are independently selected among S, NH, N-alkyl, —C(R$^8$)=CH—, —C(R$^8$)=N—, —N=C(R$^8$)— and —CH=C(R$^8$)—;
A$^4$ and A$^{13}$ are independently selected among C(R$^9$) and N;
A$^5$ and A$^{14}$ are independently selected among C(R$^{10}$) and N;
A$^6$ is selected among CH$_2$, NH, N-alkyl and O;
A$^7$ and A$^{11}$ are independently selected among C and N;
A$^8$ and A$^9$ are independently selected among CH, N, NH, N(CH$_2$)$_b$R$^{11}$ and S;
A$^{10}$ is selected among —CH=CH—, CH, N, NH, N—(CH$_2$)$_b$—R$^{11}$ and S;
wherein the ring constituted by A$^7$, A$^8$, A$^9$, A$^{10}$ and A$^{11}$ is aromatic;
R$^1$, R$^2$ and R$^3$ are independently selected among H, alkyl, O-alkyl, NO$_2$, F, Cl and Br;
R$^4$ is selected among H, alkyl, aryl, heteroaryl, —(CH$_2$)$_c$—R$^{12}$, and

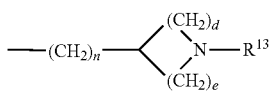

R$^5$ and R$^6$ are independently selected among alkyl, aryl, —(CH$_2$)$_f$-aryl, and —(CH$_2$)$_f$-heteroaryl;
R$^7$ is selected among H, alkyl, aryl, heteroaryl, and —(CH$_2$)$_g$—R$^{14}$;

R$^8$, R$^9$ and R$^{10}$ are independently selected among H, alkyl, alkoxy, F, Cl, Br, CN, NH$_2$, NO$_2$, NH(alkyl), N(alkyl)$_2$; with the provisos that when G is 3a, and R$^4$ is H, alkyl, aryl, heteroaryl or —(CH$_2$)$_c$—R$^{12}$, then the ring containing A$^3$, A$^4$ and A$^5$ is substituted in at least one position by alkyl, alkoxy, F, Cl, Br, CN, NH$_2$, NO$_2$, NH(alkyl) or N(alkyl)$_2$; and
when G is 4a, R$^4$ is H, alkyl, aryl, heteroaryl or —(CH$_2$)$_c$—R$^{12}$, and A$^8$ is NH, NCH$_3$ or S, then the ring containing A$^3$, A$^4$ and A$^5$ is substituted in at least one position by alkyl, alkoxy, F, Cl, Br, CN, NH$_2$, NO$_2$, NH(alkyl) or N(alkyl)$_2$;
R$^{11}$ and R$^{12}$ are independently selected among H, alkyl, aryl, heteroaryl, F, OH, O-alkyl, S-alkyl, O-acyl, NH$_2$, NH-alkyl, N(alkyl)$_2$, NH-acyl, N(alkyl)-acyl, CO$_2$H, CO$_2$-alkyl, CONH$_2$, CONH-alkyl, CON(alkyl)$_2$, CN and CF$_3$;
R$^{13}$ is selected among H, alkyl, aryl, heteroaryl, —(CH$_2$)$_h$—R$^{15}$ and Z—R$^{16}$;
R$^{14}$ and R$^{15}$ are independently selected among H, alkyl, alkenyl, aryl, heteroaryl, F, OH, O-alkyl, S-alkyl, O-acyl, NH$_2$, NH-alkyl, N(alkyl)$_2$, NH-acyl, N(alkyl)-acyl, CO$_2$H, CO$_2$-alkyl, CO-alkyl, CO-aryl, CONH$_2$, CONH-alkyl, CON(alkyl)$_2$, alkenyl-CO$_2$-alkyl, alkenyl-aryl, CN and CF$_3$;
R$^{16}$ is selected among H, alkyl, alkenyl, aryl, heteroaryl, O-aryl, —(CH$_2$)$_i$—R$^{17}$, cyclopropyl-aryl and O—(CH$_2$)$_i$—R$^{17}$;
R$^{17}$ is selected among H, alkyl, aryl, heteroaryl, F, OH, O-alkyl, S-alkyl, O-acyl, NH$_2$, NH-alkyl, N(alkyl)$_2$, NH-acyl, N(alkyl)-acyl, CO$_2$H, CO$_2$-alkyl, CONH$_2$, CONH-alkyl, CON(alkyl)$_2$, CN and CF$_3$;
W is selected among O and NH;
X is selected among (CH$_2$)$_m$, C(=O) and S(=O)$_j$
Y is selected among O, S, NH and N-alkyl;
Z is selected among —C(=O), —C(=O)—O and —S(=O)$_k$;
a is selected among 1 and 2;
b and c are independently selected among 0, 1, 2 and 3;
d, e and f are independently selected among 1 and 2;
g, h and i are independently selected among 1, 2 and 3;
j and k are independently selected among 1 and 2; and
m and n are independently selected among 0, 1 and 2.

According to an aspect, R$^{16}$ may further be selected among O-alkyl and O-alkenyl, and Z is different from —C(=O)—O.

It appears that the compounds of formula 1a are subject to the following constraints. When G is 3a, and R$^4$ is H, alkyl, aryl, heteroaryl or —(CH$_2$)$_c$—R$^{12}$, then the ring containing A$^3$, A$^4$ and A$^5$ is substituted in at least one position by alkyl, alkoxy, F, Cl, Br, CN, NH$_2$, NO$_2$, NH(alkyl) or N(alkyl)$_2$. When G is 4a, R$^4$ is H, alkyl, aryl, heteroaryl or —(CH$_2$)$_c$—R$^{12}$, and A$^8$ is NH, NCH$_3$ or S, then the ring containing A$^3$, A$^4$ and A$^5$ is substituted in at least one position by alkyl, alkoxy, F, Cl, Br, CN, NH$_2$, NO$_2$, NH(alkyl) or N(alkyl)$_2$. The ring constituted by A$^7$, A$^8$, A$^9$, A$^{10}$ and A$^{11}$ is aromatic, and accordingly the groups must satisfy certain requirements. When A$^{10}$ is —CH=CH— the ring is a six membered ring. As such, it can only comprise atoms of the type —C(R)= and —N=. Hence A$^7$ and A$^{11}$ must both be C and A$^8$ and A$^9$ must be either CH or N. When A$^{10}$ is not —CH=CH— then the ring is a five-membered ring. In this case one, and only one, of the atoms in the ring must be S or a trigonal nitrogen. In this context, a "trigonal nitrogen" is a nitrogen atom linked covalently to three different atoms. Two of these atoms are the immediate neighbours to the nitrogen atom in the five-membered ring. The third is a hydrogen, carbon or other atom linked to the five-membered ring. Thus it follows that, when A$^{10}$ is not —CH=CH— then one (and only one) of A$^7$, A$^8$, A$^9$, A$^{10}$ and A$^{11}$ must be S or a trigonal nitrogen. Hence the selection of A$^7$, A$^8$, A$^9$, A$^{10}$ and A$^{11}$ is subject to the following restrictions. If $A^{10}$ is not —CH=CH— then one of $A^8$, $A^9$ and $A^{10}$ is NH, N—$(CH_2)_b$-$R^{11}$ or S or one of $A^7$ and $A^{11}$ is N. Not more than one of $A^8$, $A^9$ and $A^{10}$ may be NH, N—$(CH_2)_b$-$R^{11}$ or S. $A^7$ and $A^{11}$ may not both simultaneously be N. Neither $A^7$ nor $A^{11}$ may be N if one of $A^8$, $A^9$ and $A^{10}$ is NH, N—$(CH_2)_b$-$R^{11}$ or S.

According to aspects of the invention, additional and preferred embodiments of the invention are as set out below, in the description and the claims.

The term "alkyl" includes saturated hydrocarbon residues including:
  linear groups up to 10 atoms ($C_1$-$C_{10}$). Examples of such alkyl groups include, but are not limited to, $C_1$-methyl, $C_2$-ethyl, $C_3$-propyl and $C_4$-n-butyl;
  branched groups of between 3 and 10 atoms ($C_3$-$C_{10}$). Examples of such alkyl groups include, but are not limited to, $C_3$-iso-propyl, $C_4$-sec-butyl, $C_4$-iso-butyl, $C_4$-tert-butyl and $C_5$-neo-pentyl;
  cyclic groups of between 3 and 8 atoms ($C_3$-$C_8$). Examples of such groups include but are not limited to, $C_3$-cyclopropyl, $C_4$-cyclobutyl, $C_5$-cyclopentyl and $C_6$-cyclohexyl;
  combinations of linear, branched and cyclic groups. Examples of such groups include, but are not limited to,

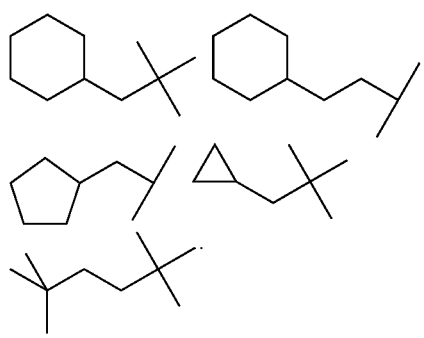

The term "alkoxy" is used to denote O-alkyl groups.

The term "alkenyl" includes monounsaturated hydrocarbon residues including
  linear groups of between two and six atoms ($C_2$-$C_6$). Examples of such alkenyl groups include, but are not limited to, $C_2$-vinyl, $C_3$-1-propenyl, $C_3$-allyl and $C_4$-2-butenyl;
  branched groups of between 3 and 8 atoms ($C_3$-$C_8$). Examples of such alkenyl groups include, but are not limited to, $C_4$-2-methyl-2-propenyl and $C_6$-2,3-dimethyl-2-butenyl;
  cyclic groups of between 3 and 8 atoms ($C_3$-$C_8$). Examples of such groups include, but are not limited to, $C_5$-3-cyclopentenyl and $C_6$-1-cyclohexenyl.

The term "aryl" includes optionally substituted phenyl and optionally substituted naphthyl. Examples of such aryl groups include, but are not limited to, phenyl, 2-tolyl, 3-chlorophenyl, 4-chlorophenyl, 3-fluorophenyl, 2-methoxyphenyl, 3-methoxyphenyl, 4-methoxyphenyl, 2,5-difluorophenyl, 1-naphthyl and 2-naphthyl.

The term "heteroaryl" includes optionally substituted heterocycles. Such heteroaryl groups include, but are not limited to, pyridyl, 2-chloropyridyl, 4-methylpyridyl, thienyl, 3-chlorothienyl, 2,3-dimethylthiophenyl, furyl, 2-methylfuryl, pyrrole, N-methylpyrrole, oxazole, imidazole, pyrazole and triazole.

The term "acyl" denotes a group R—C(=O), where R is H, a saturated or unsaturated hydrocarbon moiety of up to seven carbon atoms or an optionally substituted phenyl, optionally substituted pyridyl or optionally substituted thienyl group. Examples of acyl groups include, but are not limited to: formyl, acetyl, pivaloyl, benzoyl and nicotinoyl.

Certain compounds of the present invention are capable of forming salts with acids or bases. For example, compounds containing one or more basic nitrogen atoms can form addition salts with mineral and organic acids such as hydrochloric acid, sulphuric acid, phosphoric acid, acetic acid, trifluoroacetic acid, methanesulphonic acid, citric acid and benzoic acid. Compounds containing acidic groups can form salts with bases. Examples of such salts include the sodium, potassium, calcium, triethylammonium and tetraethylammonium salts. Furthermore, compounds that have both acidic and basic groups can form internal salts (zwitterions). Insofar as these salts are pharmaceutically acceptable, they are included within the scope of the invention.

Certain compounds within the scope of the present invention may exist as tautomers. For example, where $G^1$ is general formula 4a (4b, 4c, 4d) and $X^2$ is NH the resulting imidazole can exist as its tautomer which is defined by $G^1$ as general formula 5a (5b, 5c, 5d) and $X^2$ as NH. All such tautomers are considered to be within the scope of the present invention.

The compounds according to the present invention may have one or more stereogenic centres ("asymmetric carbon atoms") and so may exhibit optical isomerism. The scope of the present invention includes all epimers, enantiomers and diastereomers of compounds according to the present invention, including single isomers, mixtures and racemates.

According to an aspect, it is preferred that G is selected among:

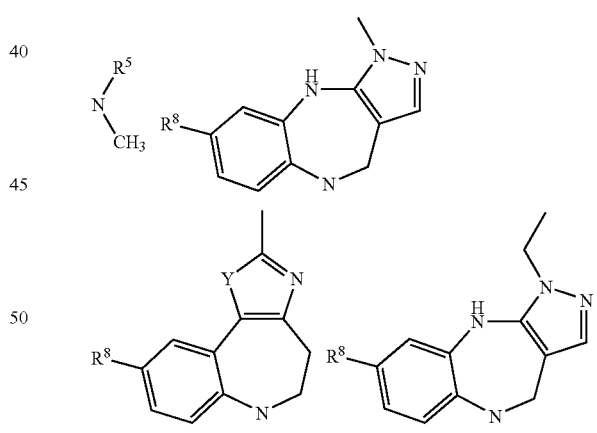

According to an aspect, it is further preferred that G is selected among:

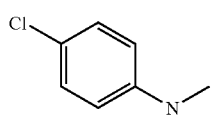

7a

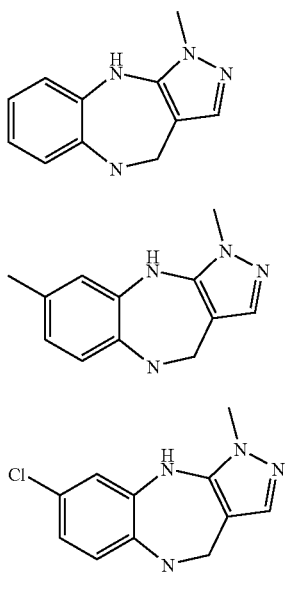

According to an aspect, it is preferred that at least one of $R^1$, $R^2$ and $R^3$ is other than hydrogen; preferably one of $R^1$, $R^2$ and $R^3$ is selected among methyl, chlorine and fluorine, and the others are hydrogen.

According to different aspects, it is preferred that W is NH; $R^4$ is alkyl; d is 2 and e is 2; $R^{13}$ is alkyl; and/or n is 0.

According to an aspect, it is preferred that $R^2$ is H, $R^4$ is a piperidine where d is 2 and e is 2, W is NH, X is C(=O) and n is 0, as shown in formula 18a:

wherein $R^1$ is selected among methyl, chlorine and fluorine, and $R^3$ is H; or $R^1$ is H, and $R^3$ is selected among methyl, chlorine and fluorine, and $R^{13}$ is alkyl.

According to an aspect, it is preferred that X is C(=O), n is 0 and $R^4$ is a piperidine where d is 2 and e is 2, as shown in formula 19a:

wherein G is selected among general formulae 7a to 17a, and $R^{13}$ is alkyl.

According to an aspect, it is preferred that $R^2$ is H and W is NH as shown in formula 20a:

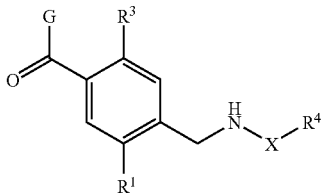

20a wherein either $R^1$ is selected among methyl, chlorine and fluorine, and $R^3$ is H; or $R^1$ is H, and $R^3$ is selected among methyl, chlorine and fluorine; and G is selected from general formulae 7a to 17a.

According to an aspect, it is preferred that $R^2$ is H, W is NH and X is C(=O) as shown in formula 21a:

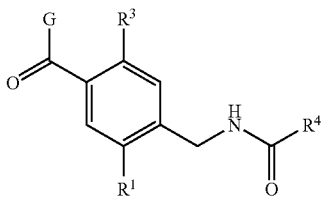

21a wherein $R^1$ is selected among methyl, chlorine and fluorine, and $R^3$ is H; or $R^1$ is H, and $R^3$ is selected among methyl, chlorine and fluorine; and $R^4$ is alkyl.

According to an aspect, it is preferred that X is C(=O) as shown in formula 22a:

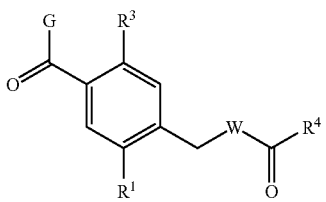

22a wherein G is selected among general formulae 7a to 17a, and $R^4$ is alkyl.

According to an aspect, it is preferred that $R^2$ and $R^3$ are both H, W is NH and X is C(=O) as shown in formula 23a:

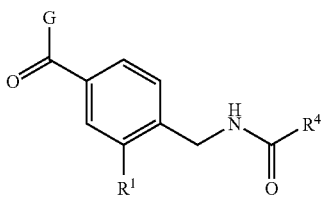

23a wherein G is selected among general formulae 9a, 10a, 15a, 16a and 17a, $R^1$ is selected among methyl, chlorine and fluorine, and $R^4$ is alkyl.

According to an aspect, it is preferred that $R^2$ and $R^3$ are both H, $R^4$ is a piperidine where d is 2 and e is 2, W is NH, X is C(=O) and n is 0 as shown in formula 24a:

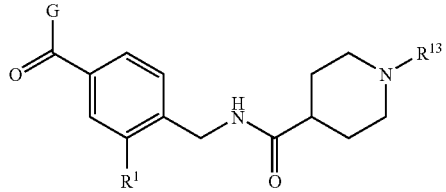

24a wherein G is selected among general formulae 9a, 10a, 15a, 16a and 17a, $R^1$ is selected among methyl, chlorine and fluorine, and $R^{13}$ is alkyl.

According to an aspect, particularly preferred compounds include
- 1-(3,3-Dimethyl-butyl)-piperidine-4-carboxylic acid 2-chloro-4-(6-chloro-3-methyl-4,10-dihydro-3H-2,3,4,9-tetraaza-benzo-[f]azulene-9-carbonyl)-benzylamide;
- 1-(3,3-Dimethyl-butyl)-piperidine-4-carboxylic acid 3-chloro-4-(6-chloro-3-methyl-4,10-dihydro-3H-2,3,4,9-tetraaza-benzo-[f]azulene-9-carbonyl)-benzylamide;
- 1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-2-methyl-benzylamide;
- 1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-2-fluoro-benzylamide;
- 1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-3-methyl-benzylamide;
- 1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-3-fluoro-benzylamide;
- 1-Cyclopropylmethyl-piperidine-4-carboxylic acid 2-chloro-4-(6-chloro-3-methyl-4,10-dihydro-3H-2,3,4,9-tetraaza-benzo[f]azulene-9-carbonyl)-benzylamide;
- 1-Cyclopropylmethyl-piperidine-4-carboxylic acid 3-chloro-4-(6-chloro-3-methyl-4,10-dihydro-3H-2,3,4,9-tetraaza-benzo[f]azulene-9-carbonyl)-benzylamide;
- 1-Cyclopropylmethyl-piperidine-4-carboxylic acid 4-(6-chloro-3-methyl-4,10-dihydro-3H-2,3,4,9-tetraaza-benzo[f]azulene-9-carbonyl)-2-fluoro-benzylamide;
- 1-Cyclopropylmethyl-piperidine-4-carboxylic acid 4-(6-chloro-3-methyl-4,10-dihydro-3H-2,3,4,9-tetraaza-benzo[f]azulene-9-carbonyl)-2-methyl-benzylamide;
- 1-Cyclopropylmethyl-piperidine-4-carboxylic acid 4-(6-chloro-3-methyl-4,10-dihydro-3H-2,3,4,9-tetraaza-benzo[f]azulene-9-carbonyl)-3-methyl-benzylamide;
- 1-Cyclopropylmethyl-piperidine-4-carboxylic acid 4-(6-chloro-3-methyl-4,10-dihydro-3H-2,3,4,9-tetraaza-benzo[f]azulene-9-carbonyl)-3-fluoro-benzylamide;
- Cyclobutanecarboxylic acid 2-chloro-4-(6-chloro-3-methyl-4,10-dihydro-3H-2,3,4,9-tetraaza-benzo[f]azulene-9-carbonyl)-benzylamide;
- Cyclobutanecarboxylic acid 4-(6-chloro-3-methyl-4,10-dihydro-3H-2,3,4,9-tetraaza-benzo[f]azulene-9-carbonyl)-2-fluoro-benzylamide;
- Cyclopentanecarboxylic acid 2-chloro-4-(6-chloro-3-methyl-4,10-dihydro-3H-2,3,4,9-tetraaza-benzo[f]azulene-9-carbonyl)-benzylamide;

Cyclopentanecarboxylic acid 4-(6-chloro-3-methyl-4,10-dihydro-3H-2,3,4,9-tetraaza-benzo[f]azulene-9-carbonyl)-2-fluoro-benzylamide;
Cyclopropanecarboxylic acid 2-chloro-4-(6-chloro-3-methyl-4,10-dihydro-3H-2,3,4,9-tetraaza-benzo[f]azulene-9-carbonyl)-benzylamide;
Cyclopropanecarboxylic acid 3-chloro-4-(6-chloro-3-methyl-4,10-dihydro-3H-2,3,4,9-tetraaza-benzo[f]azulene-9-carbonyl)-benzylamide;
Cyclopropanecarboxylic acid 4-(6-chloro-3-methyl-4,10-dihydro-3H-2,3,4,9-tetraaza-benzo[f]azulene-9-carbonyl)-2-methyl-benzylamide;
Cyclopropanecarboxylic acid 4-(6-chloro-3-methyl-4,10-dihydro-3H-2,3,4,9-tetraaza-benzo[f]azulene-9-carbonyl)-3-fluoro-benzylamide;
Cyclopropanecarboxylic acid 4-(6-chloro-3-methyl-4,10-dihydro-3H-2,3,4,9-tetraazabenzo[f]azulene-9-carbonyl)-2-fluoro-benzylamide;
Cyclopropanecarboxylic acid 4-(6-chloro-3-methyl-4,10-dihydro-3H-2,3,4,9-tetraaza-benzo[f]azulene-9-carbonyl)-3-methyl-benzylamide;
N-[2-Chloro-4-(6-chloro-3-methyl-4,10-dihydro-3H-2,3,4,9-tetraaza-benzo[f]azulene-9-carbonyl)-benzyl]-propionamide;
N-[2-Chloro-4-(6-chloro-3-methyl-4,10-dihydro-3H-2,3,4,9-tetraaza-benzo[f]azulene-9-carbonyl)-benzyl]-2,2-dimethyl-propionamide;
N-[2-Chloro-4-(6-chloro-3-methyl-4,10-dihydro-3H-2,3,4,9-tetraaza-benzo[f]azulene-9-carbonyl)-benzyl]-isobutyramide;
N-[2-Chloro-4-(6-chloro-3-methyl-4,10-dihydro-3H-2,3,4,9-tetraaza-benzo[f]azulene-9-carbonyl)-benzyl]-butyramide;
N-[4-(6-Chloro-3-methyl-4,10-dihydro-3H-2,3,4,9-tetraaza-benzo[f]azulene-9-carbonyl)-2-fluoro-benzyl]-propionamide;
N-[4-(6-Chloro-3-methyl-4,10-dihydro-3H-2,3,4,9-tetraaza-benzo[f]azulene-9-carbonyl)-2-fluoro-benzyl]-2,2-dimethyl-propionamide;
N-[4-(6-Chloro-3-methyl-4,10-dihydro-3H-2,3,4,9-tetraaza-benzo[f]azulene-9-carbonyl)-2-fluoro-benzyl]-isobutyramide;
N-[4-(6-Chloro-3-methyl-4,10-dihydro-3H-2,3,4,9-tetraaza-benzo[f]azulene-9-carbonyl)-2-fluoro-benzyl]-acetamide;
N-[4-(6-Chloro-3-methyl-4,10-dihydro-3H-2,3,4,9-tetraaza-benzo[f]azulene-9-carbonyl)-2-fluoro-benzyl]-butyramide;
N-[4-(6-Chloro-3-methyl-4,10-dihydro-3H-2,3,4,9-tetraaza-benzo[f]azulene-9-carbonyl)-2-fluoro-benzyl]-formamide;
N-[4-(6-Chloro-3-ethyl-4,10-dihydro-3H-2,3,4,9-tetraaza-benzo[f]azulene-9-carbonyl)-2-fluoro-benzyl]-propionamide;
Cyclopropanecarboxylic acid 4-(6-chloro-3-ethyl-4,10-dihydro-3H-2,3,4,9-tetraaza-benzo[f]azulene-9-carbonyl)-2-fluoro-benzylamide;
N-[2-Fluoro-4-(6-fluoro-3-methyl-4,10-dihydro-3H-2,3,4,9-tetraaza-benzo[f]azulene-9-carbonyl)-benzyl]-propionamide;
N-[2-Fluoro-4-(6-fluoro-3-methyl-4,10-dihydro-3H-2,3,4,9-tetraaza-benzo[f]azulene-9-carbonyl)-benzyl]-isobutyramide;
Cyclopropanecarboxylic acid 2-fluoro-4-(6-fluoro-3-methyl-4,10-dihydro-3H-2,3,4,9-tetraaza-benzo[f]azulene-9-carbonyl)-benzylamide; and
N-[4-(9-Chloro-2-methyl-4,5-dihydro-1H-1,3,6-triaza-benzo[e]azulene-6-carbonyl)-2-methyl-benzyl]-isobutyramide.

The particularly preferred compounds of the invention are $V_{1a}$ antagonists of high activity.

According to an aspect, at least one of the compounds, identified as follows, is not part of the present invention: claim 1 and ex. 286 (3-Pyridin-3-yl-4,5-dihydro-isoxazole-5-carboxylic acid [4-(4-dimethylamino-benzylcarbamoyl)-phenyl]-amide) of U.S. Pat. No. 6,583,141; ex. 5 and 6 of WO 02/04403 (N-[4-(N-Methyl-N-phenylaminocarbonyl)-phenhylmethyl]-3-(4'-trifluormethylbiphenyl-2-carbonylamino) benzoic acid amide and N-[4-(N-Methyl-N-phenylaminocarbonyl)-phenhylmethyl]-3-(biphenyl-2-carbonylamino) benzoic acid amide); abstract, J. Org. Chem. USSR, vol. 18, no. 6, 1982, p. 1115-1119 (p-(N,N-diethylcarbamoyloxy)-N,N-diethylbenzamide); p. 3, 1. 16-p. 4, 1. 11, ex. 1-4, 11, and 14-19 of WO 01/29005; p. 3, 1. 9-p. 5, 1. 23, ex. 11, 28-31, 38, and 71-77 of WO 02/00626; and p. 3, 1. 1-p. 4, 1. 17, ex. 12-18 of WO 03/016316.

According to an aspect, the invention concerns a pharmaceutical composition comprising a compound according to the invention as an active agent.

The invention is further related to pharmaceutical compositions incorporating a compound according to the invention used as a $V_{1a}$ antagonist, which compositions are particularly useful for medical indications such as the treatment of dysmenorrhoea (primary dysmenorrhoea and/or secondary dysmenorrhoea), pre-term labour, hypertension, Raynaud's disease, brain oedema, motion sickness, hyperlipemia, small cell lung cancer, depression, anxiety, hyponatremia, liver cirrhosis and congestive heart failure.

Any excipients used will depend on the intended nature of the formulation, which will, in turn, depend on the intended route of administration. Administration may be oral, transmucosal (such as sublingual, buccal, intranasal, vaginal and rectal), transdermal or by injection (such as subcutaneous, intramuscular and intravenous). Oral administration is generally preferred. For oral administration, the formulation may be a tablet, a capsule or a sachet. Other formulations include dry powders, solutions, suspensions, suppositories and the like.

According to an aspect, the invention concerns the use of a compound of the invention for the manufacture of a medicament for the treatment of a disease selected among dysmenorrhoea (primary dysmenorrhoea and/or secondary dysmenorrhoea), pre-term labour, hypertension, Raynaud's disease, brain oedema, motion sickness, hyperlipemia, small cell lung cancer, depression, anxiety, hyponatremia, liver cirrhosis and congestive heart failure.

The compounds according to the present invention may be useful for treatment of several diseases, disorders or conditions. The term "treatment" used herein relates to both treatment in order to cure or alleviate a disease, disorder or a condition, and to treatment in order to prevent the development of a disease, disorder or a condition. The treatment may either be performed in an acute or in a chronic way. The human or animal to be treated, i.e. the patient, may be any human or non-human mammal in need of treatment according to the invention.

The administration of the compositions of the present invention will generally be under the control of a physician. The physician will determine the amount of composition to be administered and the dosing schedule, taking into account the patient's physical condition and the therapeutic goals.

Further aspects of the invention relates to methods of treatment of the above mentioned diseases, disorders or conditions. According to a method according to the invention a therapeutically effective amount of the compound, or of the pharmaceutical composition described above, is administered to a patient in need of this treatment. According to different aspects of the invention, it concerns a method of treatment of a disorder selected among dysmenorrhoea (primary dysmenorrhoea and/or secondary dysmenorrhoea), preterm labour, hypertension, Raynaud's disease, brain oedema, motion sickness, hyperlipemia, small cell lung cancer, depression, anxiety, hyponatremia, liver cirrhosis and congestive heart failure.

The term "therapeutically effective amount" relates to an amount that will lead to the desired therapeutical effect. The therapeutically effective amount will be determined by the attending physician taking into consideration all appropriate factors. Generally a single dose will comprise between 0.1 mg and 1000 mg, preferably between 1 mg and 250 mg, of the active compound according to the invention. The dose may be given on a single occasion or repeatedly. When given repeatedly, it may be given at regular intervals, such as once, twice or three times daily, or on demand, according to the condition being treated.

The pharmaceutical composition according to the present invention may be presented in any form that is known in the art. For example, the formulation may be presented as a tablet, capsule, powder, suppository, cream, solution or suspension, or in a more complex form such as an adhesive patch. The formulation will generally include one or more excipients, such as diluents, bulking agents, binding agents, dispersants, solvents, preservatives, flavouring agents and the like. The formulation may also include one or more additional pharmacologically active species. Preferably the formulation includes no such additional active agents.

When used as therapeutic agents, the compositions of the present invention may be administered by any appropriate route that is known in the art. For example, they may be administered by the oral, buccal, sublingual, rectal, intravaginal, nasal, pulmonary or transdermal routes. Alternatively, they may be given by injection, including intravenous, subcutaneous and intramuscular injection.

The compounds of the present invention can be prepared using standard chemical manipulations. These are described in detail in WO 03/016316 A1, pages 12-17. (Hudson, P. J. et al., "Diazacycloalkanes as Oxytocin Agonists").

The following examples are to be considered as enabling and not limiting for the invention.

EXAMPLES

The following abbreviations are used:
AIBN 2,2'-azobisisobutyronitrile
Boc carboxylic acid tert-butyl ester or tert-butoxycarbonylamino
Bu butyl-alkyl residues may be further denoted as n (normal, i.e. unbranched), i (iso) and t (tertiary)
DIEA N,N-diisopropylethylamine
DMAP 4-(dimethylamino)pyridine
DMF dimethylformamide
Et ethyl
EtOAc ethyl acetate
HOBt 1-hydroxybenzotriazole
HPLC High performance liquid chromatography
H hour(s)
Me methyl
Min minute(s)
MS mass spectrum
NMR nuclear magnetic resonance spectrum—NMR spectra were recorded in $CDCl_3$ at a frequency of 270 MHz unless otherwise indicated
OVA ornithine vasotocin analogue
pet. petroleum ether boiling in the range 60-80° C.
Ether
Ph phenyl
Pn pentyl
Pr propyl
THF tetrahydrofuran
Tos toluene-4-sulphonyl
WSCD water-soluble carbodiimide (N-ethyl-N'-(3-dimethylaminopropyl)carbodiimide hydrochloride Examples E1-E125 describe the synthesis of intermediates and compounds of the present invention. Example A describes how compounds can be assayed based on their ability to inhibit the cellular consequences of AVP stimulation on intact cells. Example B describes tab-lets for oral administration comprising a compound according to the invention.

Example E1

6-Chloro-3-methyl-3,4,9,10-tetrahydro-2,3,4,9-tetraaza-benzo[f]azulene

Example E1.1

5-(4-Chloro-2-nitro-phenylamino)-1-methyl-1H-pyrazole-4-carboxylic Acid Ethyl Ester Sodium hydride (60% dispersion in oil, 7.28 g, 180 mmol) was added portionwise to a solution of ethyl 5-amino-1-methylpyrazole-4-carboxylate (21.8 g, 148 mmol) in anhydrous THF at 0° C. The mixture was allowed to warm to room temperature and stirred for 1 h. A solution of 4-chloro-2-fluoronitrobenzene (22.6 g, 129 mmol) in anhydrous THF (50 ml) was added dropwise. The resultant deep purple solution was stirred at room temperature for 18 h then poured into ice-cold 1N hydrochloric acid. The resulting mixture was extracted with dichloromethane (200 ml×2), and the combined organic extracts were washed with brine and concentrated in vacuo. The residue was purified by flash chromatography on silica gel (eluant; 60% pet ether:40% EtOAc) to yield the title compound (27.5 g, 62%).

Example E1.2

5-(2-Amino-4-chloro-phenylamino)-1-methyl-1H-pyrazole-4-carboxylic Acid Ethyl Ester Zinc powder (26.17 g, 400 mmol) was added to a suspension of 5-(4-chloro-2-nitro-phenylamino)-1-methyl-1H-pyrazole-4-carboxylic acid ethyl ester from Example E1.1 (26.0 g, 80 mmol) in methanol/acetic acid (10:1, 330 ml) at room temperature. After the exothermic reaction which followed, the resulting suspension was stirred at room temperature for 18 h before being filtered through Celite® filter agent. The filtrate was concentrated in vacuo. The residue was dissolved in EtOAc, and the solution was washed with saturated $NaHCO_3$ and brine, and concentrated in vacuo. The residue was purified by flash chromatography on silica gel (eluant;

65% EtOAc:35% pet ether to 80% EtOAc:20% pet ether) to yield the title compound (18.41 g, 78.0%).

Example E1.3

6-Chloro-3-methyl-4,9-dihydro-3H-2,3,4,9-tetraaza-benzo[f]azulen-10-one

Sodium (methylsulphinyl)methanide (53.4 mmol) was pre-pared from sodium hydride (60% dispersion in oil, 2.14 g, 53.4 mmol) and anhydrous dimethyl sulphoxide (35 ml) by heating at 65° C. until a solution was observed. To this was added a solution of 5-(2-amino-4-chloro-phenylamino)-1-methyl-1H-pyrazole-4-carboxylic acid ethyl ester from Example E1.2 (9.02 g, 30.5 mmol) in anhydrous dimethyl sulphoxide (20 ml), and stirring continued at 65° C. for 30 min. The mixture was poured into ice (200 ml), and the resulting solid collected and purified by recrystallisation from methanol/EtOAc to yield the title compound (5.56 g, 73.3%).

Example E1.4

6-Chloro-3-methyl-3,4,9,10-tetrahydro-2,3,4,9-tetraaza-benzo[f]azulene

To a suspension of 6-chloro-3-methyl-4,9-dihydro-3H-2,3,4,9-tetraaza-benzo[f]azulen-10-one from Example E1.3 (5.56 g, 22.4 mmol) in anhydrous THF (200 ml) at 0° C. was added lithium aluminium hydride (4.24 g, 112 mmol), and the resulting suspension was heated at reflux for 18 h, then allowed to cool to room temperature. A further portion of lithium aluminium hydride (4.24 g, 112 mmol) was added, and the mixture was heated at re-flux for 18 h. The mixture was cooled to 0° C., 35% ammonia solution (10 ml) was added dropwise over 15 min and the mixture was stirred at room temperature for 30 min. The resulting suspension was filtered through Celite® filter agent and the filtrate concentrated in vacuo. The residue was purified by flash chromatography on silica gel (eluant; 0.5% 35% ammonia:5% methanol:dichloromethane) to yield the title compound (3.88 g, 74%).

Example E2

3,6-Dimethyl-3,4,9,10-tetrahydro-2,3,4,9-tetraaza-benzo[f]azulene

Example E2.1

1-Methyl-5-(4-methyl-2-nitro-phenylamino)-1H-pyrazole-4-carboxylic Acid Ethyl Ester Sodium hydride (60% dispersion in oil, 7.28 g, 180 mmol) was added portionwise to a solution of ethyl 5-amino-1-methylpyrazole-4-carboxylate (21.8 g, 148 mmol) in anhydrous THF at 0° C. The mixture was allowed to warm to room temperature and stirred for 1 h then a solution of 3-fluoro-4-nitrotoluene (20 g, 129 mmol) in anhydrous THF (50 ml) was added dropwise. The resultant deep purple solution was stirred at room temperature for 18 h then poured into ice-cold 1N hydrochloric acid. The resulting mixture was extracted with dichloromethane (200 ml×2), and the combined organic extracts were washed with brine and concentrated in vacuo. The residue was purified by flash chromatography on silica gel (eluant; 60% pet ether:40% EtOAc) to yield the title compound (28.00 g, 61%).

Example E2.2

5-(2-Amino-4-methyl-phenylamino)-1-methyl-1H-pyrazole-4-carboxylic Acid Ethyl Ester Tin (II) chloride (86.65 g, 457.0 mmol) was added to a solution of 1-methyl-5-(4-methyl-2-nitro-phenylamino)-1H-pyrazole-4-carboxylic acid ethyl ester from Example E2.1 (28.00 g, 91.4 mmol) in methanol and the mixture heated at reflux for 3 days. The solvent was removed in vacuo and the residue taken up in EtOAc (400 ml) and cooled to 0° C. 35% Ammonia solution was added to pH 14, and the mixture was stirred for 15 min before being filtered through Celite® filter agent. The filtrate was washed with 2M $NH_3$ and brine and concentrated in vacuo. The residue was purified by flash chromatography on silica gel (eluant; 6% methanol:94% dichloromethane rising to 10% methanol:90% dichloromethane) to yield the title compound (12.8 g, 52%).

Example E2.3

3,6-Dimethyl-4,9-dihydro-3H-2,3,4,9-tetraaza-benzo[f]azulen-10-one

Sodium (methylsulphinyl)methanide (22.7 mmol) was prepared from sodium hydride (60% dispersion in oil, 912 mg, 22.7 mmol) and anhydrous dimethyl sulphoxide (5.5 ml) by heating at 65° C. until a solution was observed. To this was added a solution of 5-(2-amino-4-methyl-phenylamino)-1-methyl-1H-pyrazole-4-carboxylic acid ethyl ester from Example E2.2 (3.56 g, 13.0 mmol) in anhydrous dimethyl sulphoxide (10 ml), and stirring continued at 65° C. for 30 min. The mixture was then poured into ice (200 ml), the resulting solid collected and purified by flash chromatography on silica gel (eluant; 10% methanol:90% dichloromethane) to yield the title compound (1.12 g, 38%).

Example E2.4

3,6-Dimethyl-3,4,9,10-tetrahydro-2,3,4,9-tetraaza-benzo[f]azulene

To a suspension of 3,6-dimethyl-4,9-dihydro-3H-2,3,4,9-tetraaza-benzo[f]azulen-10-one from Example E2.3 (2.35 g, 10.3 mmol) in anhydrous THF (100 ml) at 0° C. was added lithium aluminium hydride (1.56 g, 41.2 mmol), and the resulting suspension was heated at reflux for 18 h then allowed to cool to room temperature. A further portion of lithium aluminium hydride (781 mg, 20.6 mmol) was added, and the mixture was heated at reflux for 3 h. The mixture was cooled to 0° C., 35% ammonia solution (10 ml) was added dropwise over 15 min and the mixture was stirred at room temperature for 30 min. The resulting suspension was filtered through Celite® filter agent and the filtrate concentrated in vacuo. The residue was purified by flash chromatography on silica gel (eluant; 10% methanol:90% dichloromethane) to yield the title compound (1.60 g, 72%).

Examples E2a-g are described in WO 03/016316 A1, (Hudson, P. et al. "Diazacycloalkanes as Oxytocin Agonists"), pages 26-31.

Example E2h

4-(tert-Butoxycarbonylamino-methyl)-3-methyl-benzoic Acid

Example E2h.1

4-Cyano-3-methyl-benzoic Acid Methyl Ester

A mixture of 4-cyano-3-methyl-benzoic acid from Example E2d (1.5 g, 9.3 mmol) and thionyl chloride (5 ml, 68.5 mmol) in dichloromethane (20 ml) was heated at re-flux for 2 h then solvents were removed in vacuo and azeotroped with toluene. The residue was redissolved in dichloromethane (25 ml). Methanol (10 ml) was added and the solution was stirred at room temperature for 2 h then concentrated in vacuo. The residue was redissolved in EtOAc, washed with saturated NaHCO$_3$ then brine, dried and concentrated in vacuo to yield the title compound (1.6 g, 100%).

Example E2h.2

4-Aminomethyl-3-methyl-benzoic Acid Methyl Ester

A solution of 4-cyano-3-methyl-benzoic acid methyl ester from Example E2h.1 (1.6 g, 9.3 mmol) in methanol (50 ml) to 0° C. was treated with cobalt(II) chloride hexahydrate (5.1 g, 18.6 mmol). The mixture was stirred for 15 min at room temperature then sodium borohydride (3.5 g, 93 mmol) was added portionwise. The reaction mixture was stirred for 90 min then concentrated NH$_3$ (5 ml) was added drop-wise. The mixture was warmed up to room temperature over 30 min, filtered through Celite® filter agent, washed with methanol and the filtrate was concentrated in vacuo. The residue was purified by flash chromatography on silica gel (eluant; 1% 35% ammonia:10% methanol:89% dichloromethane) to yield the title compound (670 mg, 37%).

Example E2h.3

4-(tert-Butoxycarbonylamino-methyl)-3-methyl-benzoic Acid Methyl Ester

Di-tert-butyl dicarbonate (900 mg, 4.1 mmol) was added to a solution of 4-aminomethyl-3-methyl-benzoic acid methyl ester from Example E2h.2 (670 mg, 3.7 mmol) in di-chloromethane (50 ml) and triethylamine (to pH9) at room temperature. The mixture was stirred for 1 h then concentrated in vacuo. The residue was redissolved in EtOAc, washed with 0.3N KHSO$_4$ then brine, dried and concentrated in vacuo to yield the title compound (1.04 g, 100%).

Example E2h.4

4-(tert-Butoxycarbonylamino-methyl)-3-methyl-benzoic Acid 4-(tert-Butoxycarbonylamino-methyl)-3-methyl-benzoic acid methyl ester from Example E2h.3 (1.04 g, 3.7 mmol) was dissolved in dioxan (20 ml). 1N NaOH solution (5.6 ml, 5.6 mmol) was added and the mixture was stirred for 18 h at room temperature then concentrated in vacuo. The residue was redissolved in EtOAc, washed with 1N KHSO$_4$ then brine, dried and concentrated in vacuo to yield the title compound (800 mg, 81%).

Example E3

4-(tert-Butoxycarbonylamino-methyl)-3-fluoro-benzoic Acid

Example E3.1

3-Fluoro-4-methylbenzoic Acid Methyl Ester

Thionyl chloride (9.62 g, 81 mmol) was added to a solution of 3-fluoro-4-methylbenzoic acid (5.0 g, 32.4 mmol) in toluene (50 ml). The mixture was stirred at room temperature for 1.5 h and heated at reflux for 3 h. The sol-vent was removed in vacuo and the residue was taken up in methanol (30 ml) and CH$_2$Cl$_2$ (30 ml) and stirred for 18 h. The mixture was evaporated in vacuo and the residue was taken up in EtOAc (50 ml), washed with saturated NaHCO$_3$ solution (3×75 ml), dried and evaporated in vacuo to yield the title compound (4.5 g, 83%).

Example E3.2

4-Bromomethyl-3-fluorobenzoic Acid Methyl Ester

3-Fluoro-4-methylbenzoic acid methyl ester from Example E3.1 (4.5 g, 26.6 mmol) was dissolved in carbon tetra-chloride (150 ml). AIBN (457 mg, 2.7 mmol) and N-bromosuccinimide (5.2 g, 29.3 mmol) were added and the mixture was heated at reflux for 18 h. The mixture was allowed to cool and further portions of AIBN (457 mg, 2.7 mmol) and N-bromosuccinimide (5.2 g, 29.3 mmol) were added. The mixture was heated at reflux for 56 h. The mixture was allowed to cool and evaporated in vacuo. The residue was purified by flash chromatography on silica gel (eluant; 10% EtOAc:90% pet ether) to yield the title compound (2.7 g, 41%).

Example E3.3

4-Azidomethyl-3-fluorobenzoic Acid Methyl Ester

Sodium azide (609 mg) was added to a solution of 4-bromomethyl-3-fluorobenzoic acid methyl ester from Example E3.2 (2.1 g, 8.5 mmol) in DMF (30 ml). The mixture was stirred for 18 h, diluted with EtOAc, washed with water and brine and concentrated in vacuo to give a colourless oil identified as the title compound (1.8 g, 100%).

Example E3.4

4-Aminomethyl-3-fluorobenzoic Acid Methyl Ester

Hydrogen was passed through a degassed solution of 4-azidomethyl-3-fluorobenzoic acid methyl ester from Example E3.3 (2.11 g, 10 mmol) in methanol containing 10% palladium on carbon for 2 h. The reaction mixture was filtered through Celite® filter agent and the filtrate was concentrated in vacuo to give a colourless oil identified as the title compound (1.51 g, 83%).

Example E3.5

4-(tert-Butoxycarbonylamino-methyl)-3-fluorobenzoic Acid Methyl Ester

To a solution of 4-aminomethyl-3-fluorobenzoic acid methyl ester from Example E3.4 (1.5 g, 8.2 mmol) in dichloromethane (20 ml) were added di-tert-butyl dicarbonate (2.3 g, 11 mmol) and triethylamine (1.4 ml, 10 mmol). The mixture was stirred for 18 h, washed with 0.3M KHSO$_4$ and brine and concentrated in vacuo. The residue was purified by flash chromatography on silica gel (eluant; 10% EtOAc:90% pet. ether) to give a white solid identified as the title compound (1.4 g, 60%).

Example E3.6

4-(tert-Butoxycarbonylamino-methyl)-3-fluorobenzoic Acid

To a solution of 4-(tert-butoxycarbonylamino-methyl)-3-fluorobenzoic acid methyl ester from Example E3.5 (640 mg, 2.25 mmol) in dioxan (40 ml) was added 1N NaOH (4.5 ml, 4.5 mmol). The mixture was stirred for 18 h, diluted with EtOAc, washed with 1N KHSO$_4$, water and brine and concentrated in vacuo to give a white solid identified as the title compound (608 mg, 100%).

Example E4

1-(3,3-Dimethyl-butyl)-piperazine dihydrochloride

Example E4.1

4-(3,3-Dimethyl-butyl)-piperazine-1-carboxylic Acid tert-butyl Ester

To a solution of 1-boc-piperazine (8.19 g, 43.9 mmol) in methanol/acetic acid (99:1, v/v, 100 ml) was added 3,3-dimethylbutyraldehyde (4.0 g, 40.0 mmol) and the resulting mixture was stirred at room temperature for 1 h. Sodium cyanoborohydride (3.27 g, 51.9 mmol) was added, and the resulting mixture was stirred at room temperature for 18 h then concentrated in vacuo. The residue was dissolved in EtOAc and the resulting solution was washed with saturated NaHCO$_3$, water and brine, dried and concentrated in vacuo. The residue was purified by flash chromatography on silica gel (eluant; 5% methanol:95% EtOAc) to yield the title compound (9.1 g, 84%).

Example E4.2

1-(3,3-Dimethyl-butyl)-piperazine dihydrochloride

A solution of 4-(3,3-dimethyl-butyl)-piperazine-1-carboxylic acid tert-butyl ester from Example E4.1 (9.1 g, 31.8 mmol) in methanol (100 ml) was treated with 4N HCl/dioxan (100 ml) and the mixture was stirred at room temperature for 30 min then concentrated in vacuo. The residue was triturated with diethyl ether and the resulting solid recrystallised from methanol/diethyl ether to yield 1-(3,3-dimethyl-butyl)-piperazine dihydrochloride (7.4 g, 90%).

Example E5

2-Methyl-1,4,5,6-tetrahydro-1,3,6-triaza-benzo[e]azulene

Example E5.1

2-(Toluene-4-sulfonylamino)-benzoic Acid Methyl Ester

Methyl anthranilate (110 g, 0.73 mol) was dissolved in dichloromethane (1 liter) at 0° C. and triethylamine (115 ml, 0.8 mol) was added. Tosyl chloride (133 g, 0.745 mol) was added portionwise at 0° C. The reaction mixture was stirred for 30 min at 0° C. and 64 h at room temperature. The mixture was reduced in vacuo. The residue was dissolved in EtOAc and the organic layer was washed with 5% KHCO$_3$ (aq) solution, 1N HCl solution and brine, dried, filtered and concentrated in vacuo. The residue was crystallised from EtOAc/hexane to yield the title compound (181 g, 81%).

Example E5.2

2-[(3-Ethoxycarbonyl-propyl)-(toluene-4-sulfonyl)-amino]-benzoic Acid Methyl Ester 2-(Toluene-4-sulfonylamino)-benzoic acid methyl ester from Example E5.1 (100 g) was dissolved in DMF (250 ml). Potassium carbonate (125 g) and ethyl 4-bromobutanoate (60 g) were added and the mixture was heated at 80° C. for 18 h. The mixture was cooled to room temperature, filtered and reduced in vacuo. The residue was partitioned between chloroform and 1M HCl solution. The aqueous layer was extracted with chloroform. The organic layers were combined, washed with brine, dried, filtered and concentrated in vacuo. The material was crystallised from EtOAc/hexane and dried in a vacuum oven at 60° C. for 3 hours to yield the title compound (98.6 g, 72%).

Example E5.3

5-Hydroxy-1-(toluene-4-sulfonyl)-2,3-dihydro-1H-benzo[b]azepine-4-carboxylic Acid Methyl Ester and 5-hydroxy-1-(toluene-4-sulfonyl)-2,3-dihydro-1H-benzo[b]azepine-4-carboxylic Acid Ethyl Ester 2-[3-Ethoxycarbonyl-propyl)-(toluene-4-sulfonyl)-amino]-benzoic acid methyl ester from Example E5.2 (98.6 g, 0.235 mol) was taken up in warm toluene (600 ml) and was added dropwise to a mixture of potassium tert-butoxide (40 g) in toluene (1 liter) refluxing under Dean-Stark conditions. The mixture was heated at reflux under Dean-Stark conditions for 1 h further and cooled to room temperature. It was diluted with EtOAc (500 ml) and washed with 1M HCl solution, saturated NaHCO$_3$ (aq) and brine. The organic layer was dried, filtered and reduced in vacuo. The residue was precipitated from EtOAc/hexane and dried in a vacuum oven to yield a mixture of 5-hydroxy-1-(toluene-4-sulfonyl)-2,3-dihydro-1H-benzo[b]azepine-4-carboxylic acid methyl ester and 5-hydroxy-1-(toluene-4-sulfonyl)-2,3-dihydro-1H-benzo[b]azepine-4-carboxylic acid ethyl ester (53.5 g).

Example E5.4

1-(Toluene-4-sulfonyl)-1,2,3,4-tetrahydro-benzo[b]azepin-5-one

A mixture of 5-hydroxy-1-(toluene-4-sulfonyl)-2,3-dihydro-1H-benzo[b]azepine-4-carboxylic acid methyl ester and 5-hydroxy-1-(toluene-4-sulfonyl)-2,3-dihydro-1H-benzo[b]azepine-4-carboxylic acid ethyl ester from Example E5.3 were heated at reflux in a mixture of ethanol (100 ml), acetic acid (300 ml), concentrated HCl (100 ml) and water (50 ml) for 18 h. The mixture was cooled to room temperature, diluted with water (800 ml) and extracted with chloroform. The combined organic ex-tracts were dried, filtered and reduced in vacuo. The residue was crystallised twice from methanol to yield the title compound (44 g, 60% over two steps).

Example E5.5

1,2,3,4-Tetrahydro-benzo[b]azepin-5-one

Polyphosphoric acid (25 g) was heated at 100° C. under nitrogen until it could be stirred. 1-(Toluene-4-sulfonyl)-1,2,3,4-tetrahydro-benzo[b]azepin-5-one from Example E5.4 (2.6 g, 8.26 mmol) was added portionwise and the reaction mixture was heated at 100° C. for 1.5 h. It was poured into ice and basified with 2M NaOH(aq). The aqueous layer was extracted twice with dichloromethane. The organic extracts were combined, washed with brine, dried and reduced in vacuo. The residue was purified by flash chromatography on silica gel (eluant; 40% EtOAc:60% hexane) to yield the title compound (1.05 g, 79%).

Example E5.6

1-Benzoyl-1,2,3,4-tetrahydro-benzo[b]azepin-5-one 1,2,3,4-Tetrahydro-benzo[b]azepin-5-one from Example E5.5 (480 mg, 2.98 mmol) was dissolved in a mixture of dichloromethane (30 ml) and triethylamine (1.3 ml). Benzoyl chloride (0.46 g, 3.28 mmol) was added and the reaction mixture was heated for at reflux for 2 h. The mixture was cooled and reduced in vacuo. The residue was dissolved in EtOAc and washed with 1M $KHSO_4$ (aq), water and brine. The organic layer was dried, filtered and reduced in vacuo. The residue was purified by flash chromatography on silica gel (eluant; 50% EtOAc: 50% hexane) to yield the title compound (440 mg, 56%).

Example E5.7

1-Benzoyl-4-bromo-1,2,3,4-tetrahydro-benzo[b]azepin-5-one

1-Benzoyl-1,2,3,4-tetrahydro-benzo[b]azepin-5-one from Example E5.6 (54.2 g, 205 mmol), N-bromosuccinimide (3.6 g, 20.4 mmol) and bromine (11.1 ml, 214.7 mmol) were dissolved in dichloromethane (1.0 liter). Triethylamine (30 ml, 215 mmol) was added dropwise over 30 minutes then the reaction mixture was heated at reflux for 4 h. Additional bromine (1.1 ml, 21.5 mmol) and triethylamine (3.0 ml, 21.5 mmol) were added and the reaction mixture was heated at reflux for a further 4 h. Additional bromine (1.1 ml, 21.5 mmol) and triethylamine (3.0 ml, 21.5 mmol) were added again and the reaction mixture was heated at reflux for a further 4 h. On cooling to room temperature, the reaction solution was washed with 5% aqueous sodium metabisulfate solution (150 ml) and the aqueous phase was diluted with water (600 ml). The organic phase was separated, washed with saturated Na—$HCO_3$ (aq), dried over sodium sulphate and filtered. The filtrate was diluted with EtOAc (100 ml), filtered through a silica pad (eluant; $CH_2Cl_2$) and reduced in vacuo to yield the title compound (73.6 g) which was used without further purification.

Example E5.8

6-Benzoyl-2-methyl-1,4,5,6-tetrahydro-1,3,6-triaza-benzo[e]azulene

1-Benzoyl-4-bromo-1,2,3,4-tetrahydro-benzo[b]azepin-5-one (67.5 g, 200 mmol) from Example E5.7, acetamidine hydrochloride (92.7 g, 980 mmol) and potassium carbonate (136.0 g, 980 mmol) were suspended in acetonitrile (2.0 liters) and heated at reflux for 17 h under nitrogen. Additional acetamidine hydrochloride (18.5 g, 200 mmol) and potassium carbonate (27.7 g, 200 mmol) were added and the reaction mixture was heated at reflux for a further 6 h. Additional acetamidine hydrochloride (18.5 g, 200 mmol) and potassium carbonate (27.7 g, 200 mmol) were added again and the reaction mixture was heated at reflux for a further 6 h. On cooling to room temperature, the reaction mixture was filtered and the filtrate was concentrated in vacuo. The residue was taken up in dichloromethane (1.4 liters), washed with water (500 ml), dried over sodium sulfate, filtered and reduced in vacuo. The crude products were purified by flash chromatography on silica gel (eluant; 45% EtOAc:45% acetonitrile: 10% methanol) to yield the title compound (26.7 g, 34%) and 6-benzoyl-2-methyl-5,6-dihydro-4H-1-oxa-3,6-diaza-benzo[e]azulene (3.3 g, 4%).

Example E5.9

2-Methyl-1,4,5,6-tetrahydro-1,3,6-triaza-benzo[e]azulene

6-Benzoyl-2-methyl-1,4,5,6-tetrahydro-1,3,6-triaza-benzo[e]azulene from Example E5.8 (160 mg, 0.53 mmol) was dissolved in a 6M HCl/dioxan solution (50 ml) and heated at reflux for 18 h. The reaction mixture was cooled to room temperature and reduced in vacuo. The residue was partitioned between EtOAc and saturated $NaHCO_3$ (aq) and the layers were separated. The organic layer was washed with brine, dried, filtered and reduced in vacuo to yield the title compound (69 mg, 66%).

Example E5a

1-Benzyl-2-methyl-1,4,5,6-tetrahydro-1,3,6-triaza-benzo[e]azulene

Example E5a.1

(1-Benzyl-2-methyl-4,5-dihydro-1H-1,3,6-triaza-benzo[e]azulen-6-yl)-phenyl-methanone Sodium hydride (60% dispersion in oil, 905 mg, 22.5 mmol) was placed in anhydrous THF (200 ml) and cooled down to 0° C. 6-Benzoyl-2-methyl-1,4,5,6-tetrahydro-1,3,6-triaza-benzo[e]azulene from Example E5.8 (4.9 g, 16.1 mmol) was added dropwise and the mixture was stirred for 1 h at room temperature. Benzyl bromide (2.31 ml, 19.3 mmol) and potassium iodide (1.34 g, 8.0 mmol) were added and the mixture was stirred for 16 h. The solution was diluted with EtOAC, washed with saturated $NaHCO_3$ then brine, dried and concentrated in vacuo. The residue was purified by flash chromatography on silica gel (eluant; EtOAc) to yield the title compound (5.73 g, 90%).

Example E5a.2

1-Benzyl-2-methyl-1,4,5,6-tetrahydro-1,3,6-triaza-benzo[e]azulene (1-Benzyl-2-methyl-4,5-dihydro-1H-1,3,6-triaza-benzo[e]azulen-6-yl)-phenyl-methanone from Example E5a.1 (5.73 g, 14.6 mmol) was placed in methanol (50 ml) and a 6M HCl aqueous solution (200 ml) was added. The reaction mixture was heated at reflux for 18 h then concentrated in vacuo. The residue was dissolved in dichloromethane, basified with saturated $NaHCO_3$ then washed with brine, dried and concentrated in vacuo to yield the title compound (3.30 g, 78%).

Example E6

2-Methyl-5,6-dihydro-4H-1-oxa-3,6-diaza-benzo[e]azulene

6-Benzoyl-2-methyl-5,6-dihydro-4H-1-oxa-3,6-diaza-benzo[e]azulene from Example E5.8 (11.0 g, 3.25 mmol) was reacted with a 6M HCl/dioxan solution (100 ml) using an analogous procedure to that described for Example E5.9 to yield the title compound (540 mg, 82%).

Example E7

2-Methyl-5,6-dihydro-4H-3-thia-1,6-diaza-benzo[e]
azulene

Example E7.1

(2-Methyl-4,5-dihydro-3-thia-1,6-diaza-benzo[e]
azulen-6-yl)-phenyl-methanone

To a solution of 1-benzoyl-4-bromo-1,2,3,4-tetrahydrobenzo[b]azepin-5-one (11.0 g, 2.9 mmol) from Example E5.7 in ethanol (50 ml) was added thioacetamide (0.75 g, 10 mmol). The solution was stirred for 16 h. The resultant suspension was reduced in volume by evaporation and cooled. The precipitate was collected by filtration and the solid was washed with cold ethanol and dried to yield the title compound as a white solid (0.65 g, 70%).

Example E7.2

2-Methyl-5,6-dihydro-4H-3-thia-1,6-diaza-benzo[e]
azulene

A suspension of (2-methyl-4,5-dihydro-3-thia-1,6-diazabenzo[e]azulen-6-yl)-phenyl-methanone from Example E7.1 (0.42 g, 1.3 mmol) in 6M hydrochloric acid (45 ml) was heated at reflux for 16 h. The solution was cooled and treated with saturated NaHCO$_3$ (aq) (10 ml). Additional solid NaHCO$_3$ was added until the solution was basic. The mixture was extracted with dichloromethane and the organic extracts were dried and reduced in vacuo to yield the title compound as a yellow oil (0.21 g, 76%).

Example E8

4-(3,3-Dimethyl-butyl)-piperazine-1-carboxylic Acid
4-(3,6-dimethyl-4,10-dihydro-3H-2,3,4,9-tetraaza-
benzo[f]azulene-9-carbonyl)-2-fluoro-benzylamide

Example E8.1

[4-(3,6-Dimethyl-4,10-dihydro-3H-2,3,4,9-tetraaza-
benzo[f]azulene-9-carbonyl)-2-fluoro-benzyl]-car-
bamic Acid Tert-butyl Ester A solution of 4-(tert-butoxycarbonylamino-methyl)-3-fluorobenzoic acid from Example E3.1 (538 mg, 2.0 mmol) and DMAP (220 mg, 1.8 mmol) in dichloromethane (20 ml) at room temperature was treated with DIEA (0.93 ml, 5.4 mmol) and WSCD (460 mg, 2.4 mmol), and the resulting solution was stirred at room temperature for 1 h. 3,6-Dimethyl-3,4,9,10-tetrahydro-2,3,4,9-tetraaza-benzo[f]azulene from Example E2 (385 mg, 1.8 mmol) was added and the resulting solution was heated at reflux for 20 h and allowed to cool to room temperature. The solution was diluted with dichloromethane, washed with saturated NaHCO$_3$ and brine and concentrated in vacuo. The residue was purified by preparative HPLC (eluant 10% methanol:90% dichloromethane) to yield the title compound (265 mg, 32%).

Example E8.2

(4-Aminomethyl-3-fluoro-phenyl)-(3,6-dimethyl-4,
10-dihydro-3H-2,3,4,9-tetraaza-benzo[f]azulen-9-
yl)-methanone Hydrochloride

[4-(3,6-dimethyl-4,10-dihydro-3H-2,3,4,9-tetraaza-benzo
[f]azulene-9-carbonyl)-2-fluoro-benzyl]-carbamic acid tert-butyl ester from Example E8.1 (237 mg, 0.51 mmol) was reacted with 4N HCl/dioxan using an analogous procedure to that described for Example E4.2 to yield the title compound (205 mg, 100%).

Example E8.3

4-(3,3-Dimethyl-butyl)-piperazine-1-carboxylic Acid
4-(3,6-dimethyl-4,10-dihydro-3H-2,3,4,9-tetraaza-
benzo[f]azulene-9-carbonyl)-2-fluoro-benzylamide DIEA (0.10 ml, 0.60 mmol) and 1,1'-carbonyldiimidazole (28 mg, 0.17 mmol) were added to a solution of (4-aminomethyl-3-fluoro-phenyl)-(3,6-dimethyl-4,10-dihydro-3H-2,3, 4,9-tetraaza-benzo[f]azulen-9-yl)-methanone hydrochloride from Example E8.2 (57 mg, 0.14 mmol) in DMF (5.0 ml) and the mixture was stirred at room temperature for 4 h. 1-(3,3-Dimethyl-butyl)-piperazine dihydrochloride from Example E4 (38 mg, 0.16 mmol) was added and the mixture was stirred at room temperature for 24 h and concentrated in vacuo. The residue was dissolved in EtOAc and the resulting solution was washed with brine and concentrated in vacuo. The residue was purified by preparative HPLC (eluant; 10% methanol: 90% dichloromethane) to give a white solid identified as the title compound (45 mg, 56%).

Example E9

4-(tert-Butoxycarbonylamino-methyl)-cyclohexan-
ecarboxylic Acid

To a solution of 4-aminomethyl-cyclohexanecarboxylic acid (20.0 g, 127.39 mmol) in dioxan (400 ml) was added 1N KHCO$_3$ (300 ml, 300 mol) and di-tert-butyl dicarbonate (33.3 g, 129.57 mmol). The mixture was stirred for 18 h and concentrated in vacuo. The aqueous residue was washed with ether, then acidified with 1N KHSO$_4$ and extracted with EtOAc (×3). The combined organic extracts were washed with water and brine and concentrated in vacuo to give a white solid identified as the title compound (31.9 g, 98%).

Example E10

Cyclopropanecarboxylic acid [4-(6-chloro-3-methyl-
4,10-dihydro-3H-2,3,4,9-tetraaza-benzo[f]azulene-9-
carbonyl)-cyclohexylmethyl]-amide

Example E10.1

[4-(6-Chloro-3-methyl-4,10-dihydro-3H-2,3,4,9-
tetraaza-benzo[f]azulene-9-carbonyl)-cyclohexylm-
ethyl]-carbamic Acid Tert-butyl Ester A solution of 4-(tert-butoxycarbonylamino-methyl)-cyclohexanecarboxylic acid from Example E9 (510 mg, 2.0 mmol) in dichloromethane (25 ml) at room temperature was treated with DIEA (0.70 ml, 4.0 mmol), PyBrop (2.40 g, 5.1 mmol), and 6-chloro-3-methyl-3,4,9,10-tetrahydro-2,3,4,9-tetraaza-benzo[f]azulene from Example E1 (422 mg, 1.8 mmol) and the resulting solution was heated at reflux for 20 h and allowed to cool to room temperature. The solution was diluted with dichloromethane, washed with brine and concentrated in vacuo. The residue was purified by flash chromatography on silica gel (eluant EtOAc) to yield the title compound (775 mg, 91%).

Example E10.2

(4-Aminomethyl-cyclohexyl)-(6-chloro-3-methyl-4,
10-dihydro-3H-2,3,4,9-tetraaza-benzo[f]azulen-9-
yl)-methanone Hydrochloride A solution of [4-(6-chloro-3-methyl-4,10-dihydro-3H-2,3,
4,9-tetraaza-benzo[f]azulene-9-carbonyl)-cyclohexylmethyl]-carbamic acid tert-butyl ester from Example E10.1 (775 mg, 1.63 mmol) was reacted with 4N HCl/dioxan using an analogous procedure to that described for Example E4.2 to yield the title compound (655 mg, 100%).

Example E10.3

Cyclopropanecarboxylic acid [4-(6-chloro-3-methyl-
4,10-dihydro-3H-2,3,4,9-tetraaza-benzo[f]azulene-9-
carbonyl)-cyclohexylmethyl]-amide DIEA (0.50 ml, 2.90 mmol) and cyclopropanedarbonyl chloride (0.045 ml, 0.50 mmol) were added to a solution of (4-aminomethyl-cyclohexyl)-(6-chloro-3-methyl-4,10-dihydro-3H-2,3,4,9-tetraaza-benzo[f]azulen-9-yl)-methanone hydrochloride from Example E10.2 (220 mg, 0.53 mmol) in dichloromethane (5 ml). The mixture was stirred for 2 h then diluted with dichloromethane, washed with water and concentrated in vacuo. The residue was purified by preparative HPLC (eluant; 0.5% 35% ammonia/10% methanol/90% dichloromethane) to give a white solid identified as the title compound (132 mg, 60%).

Example E11

3-Methyl-3,4,9,10-tetrahydro-2,3,4,9-tetraaza-benzo
[f]azulene

Example E11.1

1-Methyl-5-(2-nitro-phenylamino)-1H-pyrazole-4-
carboxylic Acid Ethyl Ester

Sodium hydride (60% dispersion in oil, 7.0 g, 170 mmol) was added portionwise to a suspension of 5-amino-1-methyl-1H-pyrazole-4-carboxylic acid ethyl ester (21.1 g, 125 mmol) in anhydrous THF (300 ml) at 0° C. The mixture was allowed to warm to room temperature and stirred for 0.75 h then cooled to 0° C. 1-fluoro-2-nitrobenzene (17.6 g, 125 mmol) was added and the resultant suspension was stirred at room temperature for 18 h. EtOAc and 0.3M $KHSO_4$ were added and separated. The aqueous layer was extracted with EtOAc and the combined organic layers were washed with brine, dried and concentrated in vacuo. The residue was purified by flash chromatography on silica gel (eluant 50% hexanes/50% ethyl acetate) to yield the title compound (20.8 g, 58%).

Example E11.2

5-(2-Amino-phenylamino)-1-methyl-1H-pyrazole-4-
carboxylic Acid Ethyl Ester

1-Methyl-5-(2-nitro-phenylamino)-1H-pyrazole-4-carboxylic acid ethyl ester (20.8 g, 72 mmol) from Example E11.1 was dissolved in methanol (330 ml) and hydrogenated over 10% Pd/C catalyst for 4 h. The mixture was filtered through Celite® filter agent and the filtrate was concentrated in vacuo to give a white solid identified as the title compound (16.2 g, 87%).

Example E11.3

3-Methyl-4,9-dihydro-3H-2,3,4,9-tetraaza-benzo[f]
azulen-10-one

Sodium (methylsulphinyl)methanide (29.7 mmol) was pre-pared from sodium hydride (60% dispersion in oil, 1.19 g, 29.7 mmol) and anhydrous dimethyl sulphoxide (7 ml) by heating at 65° C. until a solution was observed. To this was added a solution of 5-(2-amino-phenylamino)-1-methyl-1H-pyrazole-4-carboxylic acid ethyl ester from Example E11.2 (3.63 g, 16.9 mmol) in anhydrous dimethyl sulphoxide (10 ml), and stirring continued at 65° C. for 2.5 h. The mixture was poured into ice (100 ml), and the resulting solid collected and purified by recrystallisation from methanol/EtOAc/60-80 pet ether to yield the title compound (1.46 g, 40%).

Example E11.4

3-Methyl-3,4,9,10-tetrahydro-2,3,4,9-tetraaza-benzo
[f]azulene

To a suspension of 3-methyl-4,9-dihydro-3H-2,3,4,9-tetraaza-benzo[f]azulen-10-one from Example E11.3 (3.01 g, 14.1 mmol) in anhydrous THF (100 ml) at 0° C. was added lithium aluminium hydride (2.13 g, 56.2 mmol), and the resulting suspension was heated at reflux for 18 h, then allowed to cool to room temperature. The mixture was cooled to 0° C., 35% ammonia solution (10 ml) was added dropwise over 15 min and the mixture was stirred at room temperature for 30 min. The resulting suspension was filtered through Celite® filter agent and the filtrate concentrated in vacuo. The residue was purified by flash chromatography on silica gel (eluant; 2% methanol:chloroform rising to 5% methanol: chloroform) to yield the title compound (1.60 g, 57%).

Example E12

[4-(Isobutylamino-methyl)-cyclohexyl]-(3-methyl-4,
10-dihydro-3H-2,3,4,9-tetraaza-benzo[f]azulen-9-
yl)-methanone A solution of isobutyraldehyde (0.36 mg, 0.005 mmol) in 1,2-dichloroethane (0.05 ml) was added to a solution of (4-Aminomethyl-cyclohexyl)-(3-methyl-4,10-dihydro-3H-2,3,4,9-tetraaza-benzo[f]azulen-9-yl)-methanone hydrochloride from Example E10.2 (1.88 mg, 0.005 mmol) in 1,2-dichloroethane (0.05 ml) and DIEA (0.0026 ml). The mixture was stirred at room temperature for 1 h then a solution of sodium triacetoxyborohydride (1.59 mg, 0.0075 mmol) in DMF (0.05 ml) was added. The mixture was stirred for 20 h at room temperature then solvents were removed in vacuo to yield the title compound. (ESI)+: [M+H]+=396.4

Example E13

[4-(3,6-Dimethyl-4,10-dihydro-3H-2,3,4,9-tetraaza-
benzo[f]azulene-9-carbonyl)-cyclohexylmethyl]-
carbamic Acid 4-nitro-benzyl Ester A solution of 4-nitrobenzyl chloroformate (1.08 mg, 0.005 mmol) in dichloromethane (0.05 ml) was added to a solution of (4-Aminomethyl-cyclohexyl)-(3,6-dimethyl-4,10-dihydro-3H-2,3,4,9-tetraaza-benzo[f]azulen-9-yl)-methanone hydrochloride (Compound number 149) (1.95 mg, 0.005 mmol) in dichloromethane (0.05 ml) and triethyl-amine (0.0035 ml). The mixture was stirred at room temperature for

Example E14

(6-Chloro-3-methyl-4,10-dihydro-3H-2,3,4,9-tetraaza-benzo[f]azulen-9-yl)-(4-hexylaminomethyl-cyclohexyl)-methanone A solution of 1-bromohexane (0.83 mg, 0.005 mmol) in DMF (0.05 ml) was added to a solution of (4-Aminomethyl-cyclohexyl)-(6-chloro-3-methyl-4,10-dihydro-3H-2,3,4,9-tetraaza-benzo[f]azulen-9-yl)-methanone hydrochloride from Example E10.2 (2.05 mg, 0.005 mmol) in DMF (0.05 ml) and triethylamine (0.0021 ml). The mixture was stirred for 20 h at room temperature then solvents were removed in vacuo to yield the title compound. (ESI)+: [M+H]+=458.4

Example E15

1-(3,3-Dimethyl-butyl)-piperidine-4-carboxylic Acid

Example E15.1

1-(3,3-Dimethyl-butyl)-piperidine-4-carboxylic Acid Ethyl Ester 3,3-Dimethylbutyraldehyde (5.26 ml, 42.0 mmol) was added to a solution of ethyl isonipecotate (6.6 g, 42.0 mmol) in methanol/acetic acid (99:1, v/v, 50 ml) and the mixture was stirred at room temperature for 1 h. Sodium cyanoborohydride (3.43 g, 54.6 mmol) was added, and the mixture was stirred at room temperature for 4 days then concentrated in vacuo. The residue was purified by flash chromatography on silica gel (eluant; 25% EtOAc:75% cyclohexane) to yield the title compound (7.16 g, 71%).

Example E15.2

1-(3,3-Dimethyl-butyl)-piperidine-4-carboxylic Acid

Lithium hydroxide monohydrate (1.37 g, 32.6 mmol) was added to a solution of 1-(3,3-dimethyl-butyl)-piperidine-4-carboxylic acid ethyl ester from Example E15.1 (7.16 g, 29.7 mmol) in THF (50 ml) and water (5 ml). The mixture was stirred at room temperature for 18 h then concentrated in vacuo. The residue was purified by flash chromatography on silica gel through an isolute (eluant; 90% dichloromethane: 9% methanol:1% acetic acid) to yield the title compound (5.51 g, 87%).

Example E15a

1-Cyclopropylmethyl-piperidine-4-carboxylic Acid

The title compound was prepared from cyclopropanecarboxaldehyde and ethyl isonipecotate using similar procedures to those described for Example E15.

Example E16

1-(3,3-Dimethyl-butyl)-piperidine-4-carboxylic Acid [4-(3-methyl-4,10-dihydro-3H-2,3,4,9-tetraaza-benzo[f]azulene-9-carbonyl)-cyclohexylmethyl]-amide

Example E16.1

4-(3,3-Dimethyl-butyl)-piperazine-4-carboxylic Acid [4-(3-methyl-4,10-dihydro-3H-2,3,4,9-tetraaza-benzo[f]azulene-9-carbonyl)-cyclohexylmethyl]-amide HBTU (84 mg, 0.22 mmol) was added to a solution of 1-(3,3-dimethyl-butyl)-piperidine-4-carboxylic acid from Example E15 (42 mg, 0.17 mmol) in DMF (5 ml) and DIEA (to pH9). The mixture was stirred at room temperature for 1 h. (4-Aminomethyl-cyclohexyl)-(3-methyl-4,10-dihydro-3H-2,3,4,9-tetraaza-benzo[f]azulen-9-yl)-methanone hydrochloride (Compound Number 150) (42 mg, 0.11 mmol) was added and the mixture was stirred at room temperature for 18 h. Solvents were removed in vacuo and azeotroped with toluene. The residue was redissolved in EtOAc, washed with saturated NaHCO$_3$ then brine, dried and concentrated in vacuo. The residue was purified by preparative HPLC (eluant; 10% methanol:90% dichloromethane) to give a white solid identified as the title compound (34 mg, 57%).

Example E17

N-[4-(3,6-Dimethyl-4,10-dihydro-3H-2,3,4,9-tetraaza-benzo[f]azulene-9-carbonyl)-cyclohexylmethyl]-2-piperidin-4-yl-acetamide Hydrochloride A solution of 4-({[4-(3,6-dimethyl-4,10-dihydro-3H-2,3,4,9-tetraaza-benzo[f]azulene-9-carbonyl)-cyclohexylmethyl]-carbamoyl}-methyl)-piperidine-1-carboxylic acid tert-butyl ester (Compound Number 228)(259 mg, 0.45 mmol) was reacted with 4N HCl/dioxan using an analogous procedure to that described for Example E4.2 to yield the title compound (230 mg, 93%).

Example E18

N-[4-(3,6-Dimethyl-4,10-dihydro-3H-2,3,4,9-tetraaza-benzo[f]azulene-9-carbonyl)-cyclohexylmethyl]-methanesulfonamide A solution of methanesulfonyl chloride (0.57 mg, 0.005 mmol) in dichloromethane (0.05 ml) was added to a solution of (4-aminomethyl-cyclohexyl)-(3,6-dimethyl-4,10-dihydro-3H-2,3,4,9-tetraaza-benzo[f]azulen-9-yl)-methanone (Compound number 149) (1.95 mg, 0.005 mmol) in dichloromethane (0.05 ml) and triethylamine (0.0035 ml). The mixture was stirred at room temperature for 1 h then solvents were removed in vacuo to yield the title compound. (ESI)+: [M+H]+=432.1

Example E19

N-[4-(3,6-Dimethyl-4,10-dihydro-3H-2,3,4,9-tetraaza-benzo[f]azulene-9-carbonyl)-cyclohexylmethyl]-2-(1-methanesulfonyl-piperidin-4-yl)-acetamide A solution of methanesulfonyl chloride (0.57 mg, 0.005 mmol) in dichloromethane (0.05 ml) was added to a solution of N-[4-(3,6-dimethyl-4,10-dihydro-3H-2,3,4,9-tetraaza-benzo[f]azulene-9-carbonyl)-cyclohexylmethyl]-2-piperidin-4-yl-acetamide hydrochloride from Example E17 (2.57 mg, 0.005 mmol) in dichloro-methane (0.05 ml) and triethylamine (0.0035 ml). The mixture was stirred at room temperature for 1 h then sol-vents were removed in vacuo to yield the title compound. (ESI)+: [M+H]+=557.4

Example E20

2-(1-Acetyl-piperidin-4-yl)-N-[4-(3,6-dimethyl-4,10-dihydro-3H-2,3,4,9-tetraaza-benzo[f]azulene-9-carbonyl)-cyclohexylmethyl]-acetamide A solution of acetyl chloride (0.39 mg, 0.005 mmol) in dichloromethane (0.05 ml) was added to a solution of N-[4-(3,6-dimethyl-4,10-dihydro-3H-2,3,4,9-tetraaza-benzo[f]azulene-9-carbonyl)-cyclohexylmethyl]-2-piperidin-4-yl-acetamide hydrochloride from Example E17 (2.57 mg, 0.005 mmol) in dichloromethane (0.05 ml) and triethylamine (0.0035 ml). The mixture was stirred at room temperature for 1 h then solvents were removed in vacuo to yield the title compound. (ESI)+: [M+H]+=521.5

Example E21

1-Isobutyl-piperidine-4-carboxylic acid [4-(3-methyl-4,10-dihydro-3H-2,3,4,9-tetraaza-benzo[f]azulene-9-carbonyl)-cyclohexylmethyl]-amide A solution of isobutyraldehyde (0.36 mg, 0.005 mmol) in 1,2-dichloroethane (0.05 ml) was added to a solution of piperidine-4-carboxylic acid [4-(3-methyl-4,10-dihydro-3H-2,3,4,9-tetraaza-benzo[f]azulene-9-carbonyl)-cyclohexylmethyl]-amide hydrochloride (Compound number 238) (2.43 mg, 0.005 mmol) in 1,2-dichloroethane (0.05 ml) and DIEA (0.0026 ml). The mixture was stirred at room temperature for 1 h then a solution of sodium triacetoxyborohydride (1.59 mg, 0.0075 mmol) in DMF (0.05 ml) was added. The mixture was stirred for 20 h at room temperature then solvents were removed in vacuo to yield the title compound. (ESI)+: [M+H]+=507.4

Example E22

N-[4-(6-Chloro-3-methyl-4,10-dihydro-3H-2,3,4,9-tetraaza-benzo[f]azulene-9-carbonyl)-cyclohexylmethyl]-3-(1-hexyl-piperidin-4-yl)-propionamide A solution of 1-bromohexane (0.83 mg, 0.005 mmol) in DMF (0.05 ml) was added to a solution of N-[4-(6-chloro-3-methyl-4,10-dihydro-3H-2,3,4,9-tetraaza-benzo[f]azulene-9-carbonyl)-cyclohexylmethyl]-3-piperidin-4-yl-propionamide hydrochloride (Compound number 237) (2.57 mg, 0.005 mmol) in DMF (0.05 ml) and triethylamine (0.0021 ml). The mixture was stirred for 20 h at room temperature then solvents were removed in vacuo to yield the title compound. (ESI)+: [M+H]+=597.6/599.6

Example E23

4-({[4-(3,6-Dimethyl-4,10-dihydro-3H-2,3,4,9-tetraaza-benzo[f]azulene-9-carbonyl)-cyclohexylmethyl]-carbamoyl}-methyl)-piperidine-1-carboxylic Acid 4-nitro-benzyl Ester A solution of 4-nitrobenzyl chloroformate (1.08 mg, 0.005 mmol) in dichloromethane (0.05 ml) was added to a solution of N-[4-(3,6-Dimethyl-4,10-dihydro-3H-2,3,4,9-tetraaza-benzo[f]azulene-9-carbonyl)-cyclohexylmethyl]-2-piperidin-4-yl-acetamide hydrochloride from Example E17 (2.58 mg, 0.005 mmol) in dichloromethane (0.05 ml) and triethylamine (0.0035 ml). The mixture was stirred at room temperature for 1 h then solvents were removed in vacuo to yield the title compound. (ESI)+: [M+H]+=658.5

Example E24

4-(3,3-Dimethyl-butyl)-piperazine-1-carboxylic Acid [4-(3,6-dimethyl-4,10-dihydro-3H-2,3,4,9-tetraaza-benzo[f]azulene-9-carbonyl)-cyclohexylmethyl]-amide DIEA (0.30 ml, 1.7 mmol) and 1,1'-carbonyldiimidazole (39 mg, 0.24 mmol) were added to a solution of (4-aminomethyl-cyclohexyl)-(3,6-dimethyl-4,10-dihydro-3H-2,3,4,9-tetraaza-benzo[f]azulen-9-yl)-methanone hydro-chloride (Compound number 149) (78 mg, 0.20 mmol) in DMF (4.0 ml) and the mixture was stirred at room temperature for 2 h. 1-(3,3-Dimethyl-butyl)-piperazine dihydrochloride from Example E4 (56 mg, 0.23 mmol) was added and the mixture was stirred at room temperature for 18 h. The mixture was diluted with EtOAc, washed with brine, dried and concentrated in vacuo. The residue was purified by preparative HPLC (eluant; 10% methanol:90% di-chloromethane) to give a white solid identified as the title compound (32 mg, 29%).

Example E25

3-Chloro-6,7,8,9-tetrahydro-5-oxa-9-aza-benzocycloheptene

Example E25.1

N-(4-Chloro-2-hydroxy-phenyl)-benzamide

2-Amino-5-chlorophenol (1.45 g, 10 mmol) was dissolved in EtOAc (30 ml) and water (20 ml). Sodium bicarbonate (1.25 g, 15 mmol) then benzoyl chloride (1.42 g, 10 mmol) were added and the mixture was stirred at room temperature for 1 h. The layers were partitioned and the organic layer was washed with brine, dried and concentrated in vacuo. The residue was triturated with di-ethyl ether to yield the title compound (2.05 g, 82%).

Example E25.2

(3-Chloro-7,8-dihydro-6H-5-oxa-9-aza-benzocyclohepten-9-yl)-phenyl-methanone

N-(4-Chloro-2-hydroxy-phenyl)-benzamide from Example E25.1 (1.0 g, 4 mmol) was dissolved in acetonitrile (10 ml) and dichloromethane (15 ml). 1,3-Dibromopropane (3.26 g, 16 mmol), aliquat 336 (170 mg, 0.4 mmol) and sodium hydroxide (750 mg, 16 mmol) were added and the mixture was heated at 60° C. for 3 h. The solid was filtered off and the filtrate concentrated in vacuo. The residue was purified by flash chromatography on silica gel (eluant; 30% EtOAc:70% hexane) to yield the title compound (783 mg, 83%).

Example E25.3

3-Chloro-6,7,8,9-tetrahydro-5-oxa-9-aza-benzocycloheptene (3-Chloro-7,8-dihydro-6H-5-oxa-9-aza-benzocyclohepten-9-yl)-phenyl-methanone from Example E25.2 (783 mg, 2.7 mmol) was dissolved in dioxan (10 ml) and 6M HCl aqueous solution (50 ml) was added. The mixture was heated at reflux for 20 h then concentrated in vacuo and azeotroped with toluene. The residue was dissolved in diethyl ether and water, basified with $NaHCO_3$ and the layers were partitioned. The organic layer was washed with brine, dried and concentrated in vacuo to yield the title compound (280 mg, 47%).

Example E26

N-Cyclohexyl-N'-methyl-benzene-1,2-diamine

Example E26.1

Cyclohexyl-(2-nitro-phenyl)-amine

A mixture of 2-fluoronitrobenzene (5.0 g, 35.4 mmol), cyclohexylamine (4.5 ml, 39.0 mmol) and potassium carbonate (17.1 g, 124 mmol) in acetonitrile (100 ml) was heated at reflux for 2 days. The mixture was diluted with EtOAC, washed with water then brine, dried and partially concentrated in vacuo. The solid which precipitated was collected and washed with hexane to yield the title compound (6.7 g, 86%).

Example E26.2

N-Cyclohexyl-benzene-1,2-diamine

Cyclohexyl-(2-nitro-phenyl)-amine from Example E26.1 (3.0 g, 13.6 mmol) was dissolved in methanol (100 ml) and tin (II) chloride (12.9 g, 68.1 mmol) was added. The mixture was stirred for 20 h at room temperature then heated at reflux for 18 h and concentrated in vacuo. The residue was placed in EtOAC (100 ml), cooled down to 0° C. and pH was adjusted to 14 with conc. $NH_3$. The precipitate was filtered off and washed with EtOAc. The filtrate was washed with 2M $NH_3$, water then brine, dried and concentrated in vacuo to yield the title compound (2.25 g, 86%).

Example E26.3

N-Cyclohexyl-N'-methyl-benzene-1,2-diamine

Potassium carbonate (2.45 g, 17.7 mmol) and iodomethane (0.81 ml, 13.0 mmol) were added to a solution of N-cyclohexyl-benzene-1,2-diamine from Example E26.2 (2.25 g, 11.8 mmol) in DMF (10 ml). The mixture was stirred for 6 h at room temperature then poured into water and extracted with EtOAc. The organic layer was washed with water then brine, dried and concentrated in vacuo. The residue was purified by flash chromatography on silica gel (eluant; 5% EtOAc:95% hexane) to yield the title compound (950 mg, 39%).

Example E27

3-Fluoro-4-hydroxy-benzoic Acid Ethyl Ester

A solution of 3-fluoro-4-hydroxy-benzoic acid (5.16 g, 33.1 mmol) in ethanol (100 ml) was treated with conc. sulphuric acid (5 ml), and the mixture heated at reflux for 4 days. The volatiles were removed in vacuo, and the aqueous residue was basified with saturated $NaHCO_3$ and extracted twice with diethyl ether. The combined organic extracts were dried and concentrated in vacuo to yield the title compound (5.16 g, 85%).

Example E28

2-Chloro-4-hydroxy-benzoic Acid Ethyl Ester

A solution of 2-chloro-4-hydroxy-benzonitrile (5.0 g, 32.6 mmol) in ethanol (125 ml) was treated with conc. sulphuric acid (25 ml) and the mixture heated at reflux for 3 days. Conc. sulphuric acid (25 ml) was added and the mixture was heated at reflux for another 2 days. The volatiles were removed in vacuo, and the aqueous residue was basified with saturated $NaHCO_3$ and extracted 4 times with diethyl ether. The combined organic extracts were dried and concentrated in vacuo to yield the title compound (2.5 g, 38%).

Example E29

4-Hydroxy-3-methyl-benzoic Acid Methyl Ester

4-Amino-3-methyl-benzoic acid methyl ester (5.25 g, 32.0 mmol) was treated with a 35% solution of sulphuric acid (50 ml) and the mixture was stirred and heated until dissolution then cooled to 0° C. Sodium nitrite (2.82 g, 41.6 mmol) in water (50 ml) was added dropwise and the mixture was stirred for 5 min at 0° C. Urea was added to destroy the excess nitrite. Copper nitrate (121 g, 320 mmol) in water (1 l) was added then copper oxide (4.25 g, 32.0 mmol). The mixture was warmed up to room temperature over 30 min and extracted with EtOAc (×3). The organics were combined, washed with brine, dried and concentrated in vacuo. The residue was purified by flash chromatography on silica gel (eluant; 30% EtOAc:70% hexane) to yield the title compound (2.2 g, 42%).

Example E30

4-(3-Carboxy-propyl)-3-methyl-benzoic Acid Methyl Ester

Example E30.1

4-((E)-2-tert-Butoxycarbonyl-vinyl)-3-methyl-benzoic Acid Methyl Ester

Tetrakis(triphenylphosphine)palladium (0) (5.0 g, 4.33 mmol) was added to a stirred solution of methyl 4-bromo-3-methylbenzoate (9.93 g, 43.3 mmol), tert-butyl acrylate (50 ml, 341.3 mmol) and sodium acetate (35.8 g, 436.4 mmol) in DMA (350 ml). The mixture was heated at 140° C. for 5 h, filtered through Celite® filter agent and the filtrate was concentrated in vacuo. The residue was redissolved in EtOAc, washed with 0.3M $KHSO_4$ then brine, dried and concentrated in vacuo. The residue was purified by flash chromatography on silica gel (eluant; 15% EtOAc:85% hexane to 20% EtOAc:80% hexane) to yield the title compound (4.81 g, 40%).

Example E30.2

4-(2-tert-Butoxycarbonyl-ethyl)-3-methyl-benzoic Acid Methyl Ester 4-((E)-2-tert-Butoxycarbonyl-vinyl)-3-methyl-benzoic acid methyl ester from Example E30.1 (4.00 g, 14.5 mmol)

was dissolved in methanol (100 ml) and hydrogenated over 10% Pd/C catalyst (480 mg) for 5 h. The mixture was filtered through Celite® filter agent and the filtrate was concentrated in vacuo to yield the title compound (3.41 g, 84%).

Example E30.3

4-(2-Carboxy-ethyl)-3-methyl-benzoic Acid Methyl Ester

Trifluoroacetic acid (40 ml) was added slowly to a stirred solution of 4-(2-tert-butoxycarbonyl-ethyl)-3-methyl-benzoic acid methyl ester from Example E30.2 (4.9 g, 17.6 mmol) in dichloromethane (80 ml) at room temperature. The mixture was stirred for 2 h then concentrated in vacuo and azeotroped with dichloromethane. The residue was recrystallised in EtOAc to yield the title compound (2.77 g, 71%).

Example E30.4

4-(3-Carboxy-propyl)-3-methyl-benzoic Acid Methyl Ester 4-(2-Carboxy-ethyl)-3-methyl-benzoic acid methyl ester from Example E30.3 (500 mg, 2.25 mmol) was dissolved in dry dichloromethane (10 ml) and a few drops of DMF. Oxalyl chloride (0.393 ml, 4.5 mmol) was added dropwise and the mixture was stirred for 1 h at room temperature. Solvents were removed in vacuo and azeotroped with toluene. The residue was redissolved in acetonitrile (20 ml) and cooled to 0° C. A solution of 2M (trimethyl-silyl)diazomethane in hexanes (2.25 ml, 4.5 mmol) was added dropwise and the reaction mixture was stirred for 5 h at 0° C. then 20 h at room temperature. Ethyl acetate then 10% citric acid solution were added and the layers were partitioned. The organic layer was washed with saturated NaHCO$_3$ then brine, dried and concentrated in vacuo. The residue was purified by flash chromatography on silica gel (eluant; 50% ethyl acetate:50% cyclohexane). The product obtained was dissolved in a mixture of acetonitrile and water. A solution of silver benzo-ate (103 mg, 0.45 mmol) in triethylamine (1.25 ml, 9 mmol) was added gradually while the mixture was sonicated in an ultrasound bath. After 30 min at room temperature, solvents were removed in vacuo. Ethyl acetate and 10% aqueous citric acid solution were added and the layers were partitioned. The organic layer was washed with brine, dried and concentrated in vacuo. The residue was purified by flash chromatography on silica gel (eluant; 50% EtOAc:50% cyclohexane) to yield the title compound (378 mg, 71%).

Example E31

4-(4-Methoxycarbonyl-butyl)-3-methyl-Benzoic Acid

Example E31.1

4-Bromo-3-methyl-benzoic Acid Tert-butyl Ester

4-Bromo-3-methyl-benzoic acid (2.06 g, 9.6 mmol) and thionyl chloride (2.2 ml, 30.2 mmol) in toluene (50 ml) were heated at reflux for 2 h then concentrated in vacuo and azeotroped with toluene. The residue was dissolved in THF (100 ml) and triethylamine (2.8 ml, 20.1 mmol), cooled down to 0° C. and lithium tert-butoxide (1.24 g, 15.5 mmol) was added portionwise. The mixture was stirred for 18 h at room temperature then concentrated in vacuo. The residue was dissolved in EtOAc, washed with 1M HCl, saturated NaHCO$_3$ then brine, dried and concentrated in vacuo. The residue was purified by flash chromatography on silica gel (eluant; 5% EtOAc:95% pet. ether) to yield the title compound (1.86 g, 71%).

Example E31.2

4-((1E,3E)-4-Methoxycarbonyl-buta-1,3-dienyl)-3-methyl-benzoic Acid Tert-butyl Ester Tetrakis(triphenylphosphine)palladium (0) (852 mg, 0.7 mol) was added to a stirred solution of 4-bromo-3-methyl-benzoic acid tert-butyl ester from Example E31.1 (1.86 g, 6.8 mmol), 1-acetoxy-1,3-butadiene (7.5 ml, 64.5 mmol) and sodium acetate (5.69 g, 69.4 mmol) in DMA (75 ml). The mixture was heated at 140° C. for 3 h, filtered through Celite® filter agent and the filtrate was concentrated in vacuo. The residue was purified by flash chromatography on silica gel (eluant; 20% EtOAc:80% pet. ether) to yield the title compound (1.54 g, 74%).

Example E31.3

4-(4-Methoxycarbonyl-butyl)-3-methyl-benzoic Acid Tert-butyl Ester 4-((1E,3E)-4-Methoxycarbonyl-buta-1,3-dienyl) 3-methyl-benzoic acid tert-butyl ester from Example E31.2 (1.54 g, 5.1 mmol) was dissolved in methanol (40 ml) and hydrogenated over 10% Pd/C catalyst (200 mg) for 5 h. The mixture was filtered through Celite® filter agent and the filtrate was concentrated in vacuo to yield the title compound (1.43 g, 92%).

Example E31.4

4-(4-Methoxycarbonyl-butyl)-3-methyl-benzoic Acid

Trifluoroacetic acid (20 ml) was added to a solution of 4-(4-methoxycarbonyl-butyl)-3-methyl-benzoic acid tert-butyl ester from Example E31.3 (1.43 g, 4.7 mmol) in dichloromethane (40 ml) and the mixture was stirred for 2 h at room temperature. Solvents were concentrated in vacuo and azeotroped with dichloromethane to yield the title compound (1.07 g, 92%).

Example E32

4-Carboxymethyl-3-methyl-benzoic Acid Methyl Ester

Example E32.1

4-tert-Butoxycarbonylmethyl-3-methyl-benzoic Acid Methyl Ester

Copper (II) fluoride (4.08 g, 40.1 mmol) and bis-[tri-(o-tolyl)phosphine]palladium dichloride (473 mg, 0.6 mmol) were added to a solution of methyl 4-bromo-3-methyl benzoate (4.60 g, 20.1 mmol) in THF (30 ml). The mixture was heated at reflux before silyl ketene acetal (18.5 g, 80.3 mmol) was added. The mixture was heated at reflux for 2 days then diluted with Et$_2$O. Aqueous NH$_4$Cl solution (250 ml) was added and the mixture was stirred for 30 min at room temperature. The layers were partitioned and the aqueous layer extracted twice with Et$_2$O. The organics were combined, dried and concentrated in vacuo. The residue was purified by flash chromatography on silica gel (eluant; 5% EtOAc:95% hexane) to yield the title compound (2.84 g, 53%).

Example E32.2

4-Carboxymethyl-3-methyl-benzoic Acid Methyl Ester

Trifluoroacetic acid (15 ml) was added to a solution of 4-tert-butoxycarbonylmethyl-3-methyl-benzoic acid methyl ester from Example E32.1 (2.84 g, 10.7 mmol) in dichloromethane (15 ml). The mixture was stirred for 90 min at room temperature, concentrated in vacuo and azeotroped with toluene. The residue was recrystallised from EtOAc and hexane to yield the title compound (1.81 g, 81%).

Example E33

4-[1,3]Dioxolan-2-yl-piperidine

Example E33.1

4-Hydroxymethyl-piperidine-1-carboxylic Acid Benzyl Ester

4-Piperidinemethanol (5.0 g, 43 mmol) was dissolved in dichloromethane (100 ml) and triethylamine (12 ml, 86 mmol) at 0° C. Benzylchloroformate (6.8 ml, 47.3 mmol) was added and the mixture was stirred for 20 h at room temperature then solvents were removed in vacuo. The residue was redissolved in EtOAc, washed with 1M KHSO$_4$, water then brine, dried and concentrated in vacuo to yield the title compound (8.33 g, 77%).

Example E33.2

4-Formyl-piperidine-1-carboxylic Acid Benzyl Ester

Dess-Martin reagent (17 g, 39.6 mmol) was added portionwise to a solution of 4-hydroxymethyl-piperidine-1-carboxylic acid benzyl ester from Example E33.1 (8.33 g, 33 mmol) in dichloromethane (100 ml) at room temperature. The mixture was stirred for 3 h under an inert atmosphere then diluted with chloroform and water and the layers were partitioned. The organic layer was washed with brine, dried and concentrated in vacuo. The residue was purified by flash chromatography on silica gel (eluant; 40% EtOAc:60% hexane) to yield the title compound (5.5 g, 66%).

Example E33.3

4-[1,3]Dioxolan-2-yl-piperidine-1-carboxylic Acid Benzyl Ester

Ethylene glycol (5 ml) and a catalytic amount of p-toluenesulfonic acid were added to 4-formyl-piperidine-1-carboxylic acid benzyl ester from Example E33.2 (5.6 g, 22.6 mmol) in toluene (100 ml) and the mixture was heated at reflux under Dean and Stark conditions for 2.5 h. Solvents were removed in vacuo and the residue was redissolved in EtOAc, washed with saturated NaHCO$_3$ then brine, dried and concentrated in vacuo. The residue was purified by flash chromatography on silica gel (eluant; 50% EtOAc:50% pet. ether) to yield the title compound (5.14 g, 78%).

Example E33.4

4-[1,3]Dioxolan-2-yl-piperidine

4-[1,3]Dioxolan-2-yl-piperidine-1-carboxylic acid benzyl ester from Example E33.3 (5.14 g, 17.7 mmol) was dissolved in methanol (100 ml) and hydrogenated over 10% Pd/C catalyst (551 mg) for 4 h. The mixture was filtered through Celite® filter agent and the filtrate was concentrated in vacuo to yield the title compound (2.84 g, 100%).

Example E34

4-(3-Hydroxy-propyl)-piperazine-1-carboxylic Acid Tert-butyl Ester

A solution of piperazine-1-carboxylic acid tert-butyl ester (26.5 g, 142 mmol) in acetone (300 ml) at room temperature was treated with 3-bromo-propan-1-ol (14.5 ml, 156.2 mmol), potassium carbonate (50 g, 361.8 mmol) and potassium iodide (2.4 g, 14.2 mmol), and the mixture was heated at reflux for 18 h then allowed to cool to room temperature. The suspension was filtered and the filtrate concentrated in vacuo. The residue was purified by flash chromatography on silica gel (eluant; 5% methanol:95% dichloromethane) to yield the title compound (27.7 g, 80%).

Example E35

1-Cyclopropylmethyl-imidazolidine ditrifluoroacetate

Example E35.1

[2-(Cyclopropylmethyl-amino)-ethyl]-carbamic Acid Tert-butyl Ester

Potassium hydrogen carbonate (220 mg, 2.2 mmol) and (bromoethyl)cyclopropane (270 mg, 2.0 mmol) were added to a solution of tert-butyl-N-(2-aminoethyl)carbamate (320 mg, 2.0 mmol) in THF (10 ml). The mixture was heated at 66° C. for 20 h and solvents were concentrated in vacuo. The residue was dissolved in chloroform, washed with water, dried and concentrated in vacuo. The residue was purified by flash chromatography on silica gel (eluant; 1% triethylamine: 4% methanol:95% chloroform) to yield the title compound (130 mg, 30%).

Example E35.2

1-Cyclopropylmethyl-imidazolidine ditrifluoroacetate

Trifluoroacetic acid (5 ml) was added to a solution of [2-(cyclopropylmethyl-amino)-ethyl]-carbamic acid tert-butyl ester from Example E35.1 (180 mg, 0.84 mmol) in dichloromethane (3 ml) and the mixture was stirred for 75 min at room temperature. Solvents were removed in vacuo and azeotroped with toluene. The residue was placed in water (10 ml) and formaldehyde (37% w/w solution, 0.10 ml, 1.36 mmol) was added. The mixture was stirred for 6 days at room temperature, concentrated in vacuo, azeotroped with toluene then pet. ether to yield the title compound (255 mg, 86%).

Example E36

2-piperazin-1-yl-1-p-tolyl-ethanone Dihydrochloride

Example E36.1

4-(2-Oxo-2-p-tolyl-ethyl)-piperazine-1-carboxylic Acid Tert-butyl Ester

2-Bromo-4-methylacetophenone (572 mg, 2.68 mmol) was added to a solution of piperazine-1-carboxylic acid tert-butyl ester (500 mg, 2.68 mmol) in dichloromethane (5 ml) and triethylamine (0.45 ml, 3.22 mmol). The mixture was stirred for 3 days at room temperature and solvents were removed in vacuo. The residue was purified by flash chromatography on silica gel (eluant; 40% hexane:60% EtOAc) to yield the title compound (661 mg, 77%).

Example E36.2

2-piperazin-1-yl-1-p-tolyl-ethanone Dihydrochloride 4-(2-Oxo-2-p-tolyl-ethyl)-piperazine-1-carboxylic acid tert-butyl ester from Example E36.1 (661 mg, 2.08 mmol) was dissolved in 4M HCl solution in dioxan (25 ml) at 0° C. and the mixture was stirred for 45 min at room temperature. Solvents were concentrated in vacuo and azeotroped with diethyl ether to yield the title compound (536 mg, 88%).

Example E37

2-Bromo-1-[4-(3,3-dimethyl-butyl)-piperazin-1-yl]-ethanone

Bromoacetyl bromide (0.52 ml, 6.0 mmol) was added to a solution of 1-(3,3-dimethyl-butyl)-piperazine hydro-chloride from Example E4 (1.5 g, 5.7 mmol) in dichloromethane (20 ml) and triethylamine (3.57 ml, 25.6 mmol) at 0° C. The mixture was stirred for 20 h at room temperature, washed with saturated NaHCO$_3$, dried and concentrated in vacuo. The residue was purified by flash chromatography on silica gel (eluant; 5% methanol:95% dichloromethane) to yield the title compound (220 mg, 13%).

Example E38

Cyclopropyl-piperidin-4-ylmethyl-carbamic Acid Tert-butyl Ester

Example E38.1

4-Cyclopropylaminomethyl-piperidine-1-carboxylic Acid Benzyl Ester

Cyclopropylamine (1.4 g, 24.4 mmol) and acetic acid (0.5 ml) were added to a solution of 4-formyl-piperidine-1-carboxylic acid benzyl ester from Example E33.2 (5.5 g, 22.2 mmol) in methanol (49.5 ml) and the mixture was stirred for 1 h at room temperature. Sodium cyanoborohydride (1.84 g, 28.9 mmol) was added and the mixture was stirred for 20 h at room temperature under an inert atmosphere. Solvents were removed in vacuo and azeotroped with toluene. The residue was dissolved in EtOAC, washed with saturated NaHCO$_3$ then brine, dried and concentrated in vacuo. The residue was purified by flash chromatography on silica gel (eluant; 10% methanol:90% dichloromethane) to yield the title compound (3.0 g, 47%).

Example E38.2

4-[(tert-Butoxycarbonyl-cyclopropyl-amino)-methyl]-piperidine-1-carboxylic Acid Benzyl Ester DMAP (127 mg, 1.04 mmol) and di-tert-butyl dicarbonate (3.4 g, 12.5 mmol) were added to a solution of 4-cyclopropylaminomethyl-piperidine-1-carboxylic acid benzyl ester from Example E38.1 (3.0 g, 10.4 mmol) in dichloromethane (50 ml) and triethylamine (to pH9). The mixture was stirred for 20 h at room temperature then concentrated in vacuo. The residue was dissolved in EtOAC, washed with saturated NaHCO$_3$ then brine, dried and concentrated in vacuo. The residue was purified by flash chromatography on silica gel (eluant; 40% EtOAc:60% hexane) to yield the title compound (3.67 g, 92%).

Example E38.3

Cyclopropyl-piperidin-4-ylmethyl-carbamic Acid Tert-butyl Ester

4-[(tert-Butoxycarbonyl-cyclopropyl-amino)-methyl]-piperidine-1-carboxylic acid benzyl ester from Example E38.2 (3.67 g, 9.4 mmol) was dissolved in methanol (100 ml) and hydrogenated over 10% Pd/C catalyst (3 g) for 1 h. The mixture was filtered through Celite® filter agent and the filtrate was concentrated in vacuo to yield the title compound (2.07 g, 87%).

Example E39

4-[3-(4-Carboxy-2-fluoro-phenoxy)-propyl]-piperazine-1-carboxylic Acid Tert-butyl Ester

Example E39.1

4-[3-(4-Ethoxycarbonyl-2-fluoro-phenoxy)-propyl]-piperazine-1-carboxylic Acid Tert-butyl Ester Triphenylphosphine polystyrene (loading 1.0 mmol/g, 11 g, 11.0 mmol) and DEAD (2.45 g, 11.0 mmol) were added to a solution of 3-fluoro-4-hydroxy-benzoic acid ethyl ester from Example E27 (1.3 g, 7.4 mmol) and 4-(3-hydroxy-propyl)-piperazine-1-carboxylic acid tert-butyl ester from Example E34 (1.8 g, 7.4 mmol) in tetrahydrofuran (100 ml) at 0° C. The suspension was allowed to warm to room temperature and stirred for 18 h. The mixture was filtered and the filtrate concentrated in vacuo. The residue was purified by flash chromatography on silica gel (eluant; EtOAC) to yield the title compound (1.7 g, 57%).

Example E39.2

4-[3-(4-Carboxy-2-fluoro-phenoxy)-propyl]-piperazine-1-carboxylic Acid Tert-butyl Ester A solution of 4-[3-(4-ethoxycarbonyl-2-fluoro-phenoxy)-propyl]-piperazine-1-carboxylic acid tert-butyl ester from Example E39.1 (1.7 g, 4.1 mmol) in dioxan (25 ml) was treated with 2N NaOH (3 ml) and the mixture stirred at 50° C. for 18 h. A further aliquot of 2N NaOH was added (2 ml), and stirring continued at 50° C. for 3 h. Solvents were removed in vacuo and azeotroped with toluene. The residue was purified by flash chromatography on silica gel (eluant; 1% acetic acid:9% methanol:90% chloroform) to yield the title compound (1.45 g, 92%).

Example E40

4-{2-[4-(3,3-Dimethyl-butyl)-piperazin-1-yl]-ethoxy}-3-methyl-benzoic Acid

Example E40.1

4-[2-(4-Methoxycarbonyl-2-methyl-phenoxy)-ethyl]-piperazine-1-carboxylic Acid Tert-butyl Ester 4-(2-Hydroxy-ethyl)-piperazine-1-carboxylic acid tert-butyl ester (500 mg, 2.2 mmol) was dissolved in THF (30 ml) and cooled down to 0° C. Polymer-supported triphenylphosphine (2.2 g, 2.2 mmol), DEAD (378 mg, 2.2 mmol) and 4-hydroxy-3-methyl-benzoic acid methyl ester from Example E29 (361 mg, 2.2 mmol) were added and the mixture was stirred for 20 h at room temperature. The resin was filtered off and the filtrate concentrated in vacuo. The residue was purified by flash chromatography on silica gel (eluant; EtOAc) to yield the title compound (495 mg, 60%).

Example E40.2

3-Methyl-4-(2-piperazin-1-yl-ethoxy)-benzoic Acid Methyl Ester Dihydrochloride

4-[2-(4-Methoxycarbonyl-2-methyl-phenoxy)-ethyl]-piperazine-1-carboxylic acid tert-butyl ester from Example E40.1 (200 mg, 0.53 mmol) was dissolved in 4M HCl solution in dioxan (5 ml). The mixture was stirred for 30 min at room temperature, concentrated in vacuo and azeotroped with toluene to yield the title compound (185 mg, 100%).

Example E40.3

4-{2-[4-(3,3-Dimethyl-butyl)-piperazin-1-yl]-ethoxy}-3-methyl-benzoic Acid Methyl Ester 3,3-Dimethylbutyraldehyde (54 mg, 0.53 mmol) was added to a solution of 3-methyl-4-(2-piperazin-1-yl-ethoxy)-benzoic acid methyl ester dihydrochloride from Example E40.2 (146 mg, 0.42 mmol) in methanol/acetic acid (99:1, v/v, 10 ml) and the mixture was stirred at room temperature for 1 h. Sodium cyanoborohydride (42 mg, 0.69 mmol) was added, and the mixture was stirred at room temperature for 18 h then concentrated in vacuo. The residue was dissolved in EtOAc, washed with saturated NaHCO$_3$, water then brine, dried and concentrated in vacuo. The residue was purified by flash chromatography on silica gel through an isolute (eluant; EtOAc) to yield the title compound (64 mg, 34%).

Example E40.4

4-{2-[4-(3,3-Dimethyl-butyl)-piperazin-1-yl]-ethoxy}-3-methyl-benzoic Acid

4-{2-[4-(3,3-Dimethyl-butyl)-piperazin-1-yl]-ethoxy}-3-methyl-benzoic acid methyl ester from Example E40.3 (42 mg, 0.12 mmol) was dissolved in dioxan (5 ml) and 1M NaOH (1 ml) was added. The mixture was heated at reflux for 2 h then solvents were concentrated in vacuo. The residue was dissolved in EtOAc, washed with saturated NaHCO$_3$, water then brine, dried and concentrated in vacuo to yield the title compound (40 mg, 100%).

Example E41

4-{2-[4-(3,3-Dimethyl-butyl)-piperazin-1-yl]-2-oxo-ethoxy}-3-methyl-benzoic Acid

Example E41.1

4-tert-Butoxycarbonylmethoxy-3-methyl-benzoic Acid Methyl Ester

Potassium carbonate (4.6 g, 33 mmol), potassium iodide (0.25 g, 1.5 mmol) and tert-butylbromoacetate (2.5 ml, 16.5 mmol) were added to a solution of 4-hydroxy-3-methyl-benzoic acid methyl ester from Example E29 (2.5 g, 15 mmol) in acetone (150 ml) and the mixture was heated at reflux for 20 h. The solid was filtered off and the filtrate concentrated in vacuo. The residue was dissolved in EtOAc, washed with 1N KHSO$_4$, water then brine, dried and concentrated in vacuo. The residue was purified by flash chromatography on silica gel (eluant; 15% EtOAc:85% hexane) to yield the title compound (3.8 g, 90%).

Example E41.2

4-Carboxymethoxy-3-methyl-benzoic Acid Methyl Ester

Trifluoroacetic acid (20 ml) was added to a solution of 4-tert-butoxycarbonylmethoxy-3-methyl-benzoic acid methyl ester from Example E41.1 (3.8 g, 13.6 mmol) in di-chloromethane (40 ml) and the mixture was stirred for 1 h at room temperature. Volatiles were removed in vacuo and azeotroped with dichloromethane to yield the title compound (3.04 g, 100%).

Example E41.3

4-{2-[4-(3,3-Dimethyl-butyl)-piperazin-1-yl]-2-oxo-ethoxy}-3-methyl-benzoic Acid Methyl Ester WSCD (5.14 g, 27.2 mmol) and DMAP (1.64 g, 13.6 mmol) were added to a solution of 4-carboxymethoxy-3-methyl-benzoic acid methyl ester from Example E41.2 (3.04 g, 13.6 mmol) in dichloromethane (100 ml) and triethylamine (5 ml). The mixture was stirred for 1 h at room temperature then 1-(3,3-dimethyl-butyl)-piperazine dihydro-chloride from Example E4 (3.67 g, 14.9 mmol) was added. The mixture was stirred for 20 h at room temperature then solvents were removed in vacuo. The residue was dissolved in EtOAc, washed with saturated NaHCO$_3$ then brine, dried and concentrated in vacuo. The residue was purified by flash chromatography on silica gel (eluant; EtOAc) to yield the title compound (2.8 g, 55%).

Example E41.4

4-{2-[4-(3,3-Dimethyl-butyl)-piperazin-1-yl]-2-oxo-ethoxy}-3-methyl-benzoic Acid 1M Boron tribromide solution (2.66 ml, 2.66 mmol) was added dropwise to a solution of 4-{2-[4-(3,3-dimethyl-butyl)-piperazin-1-yl]-2-oxo-ethoxy}-3-methyl-benzoic acid methyl ester from Example E41.3 (500 mg, 1.33 mmol) in dichloromethane (20 ml) at 0° C. under an inert atmosphere. The mixture was stirred for 20 h at room temperature then cooled down to 0° C. 1M Boron tribromide solution (1.33 ml, 1.33 mmol) was added and the mixture was stirred for 2 h at room temperature. Solvents were re-moved in vacuo and azeotroped with toluene. The residue was purified by flash chromatography on silica gel (eluant; 1% acetic acid:5% methanol:94% chloroform) to yield the title compound (350 mg, 72%).

Example E41a

4-(2-Bromo-acetyl)-piperazine-1-carboxylic Acid Tert-butyl Ester

A solution of bromoacetyl bromide (8.5 ml, 97 mmol) in DCM (250 ml) at 0° C. was treated dropwise with a solution of 1-Boc-piperazine (15.9, 85.3 mmol) and triethylamine (18.0 ml, 130 mmol) in DCM (150 ml). After addition was complete, the mixture was stirred at room temperature for 4 h. The solution was washed with ice-cold 1M HCl, sat. aq. NaHCO$_3$, dried and concentrated in vacuo. The residue was purified by flash chromatography on silica gel (eluant; 20% EtOAc:80% cyclohexane to 50% EtOAc:50% cyclohexane) to yield the title compound (15.7 g, 60.0%).

Example E41b

2-Chloro-4-hydroxy-benzoic Acid Methyl Ester

Example E41b.1

4-Amino-2-chloro-benzoic Acid Methyl Ester

A solution of 4-Amino-2-chloro-benzoic acid (5.3 g, 31 mmol) in methanol (100 ml) was treated with acetyl chloride (5 ml) and then heated at reflux for 16 hours. The solvents were evaporated in vacuo. The residue was dissolved in EtOAc, washed with saturated sodium hydrogen carbonate, dried and concentrated in vacuo to yield the title compound as a purple solid, 5.45 g, 95%.

Example E41b.2

2-Chloro-4-hydroxy-benzoic Acid

4-Amino-2-chloro-benzoic acid methyl ester from Example E41b.1 (5.45 g, 29.4 mmol) was treated with a 35% solution of sulphuric acid (120 ml) and the mixture was stirred and heated until dissolution then cooled to 0° C. Sodium nitrite (4.30 g, 62.5 mmol) in water (25 ml) was added dropwise and the mixture was stirred for 15 min at 0° C. Urea was added to destroy the excess nitrite. Cop-per nitrate (200 mg, 0.83 mmol) was added and heated to 90° C. The reaction mixture was cooled to room temperature, extracted into ethyl acetate×3, dried and concentrated in vacuo. The residue was purified by flash chromatography on silica gel (eluant; 30% EtOAc:70% hexane to 50% EtOAc: 49% hexane:1% AcOH) to yield the title compound (3.7 g, 73%).

Example E41b.3

2-Chloro-4-hydroxy-benzoic Acid Methyl Ester

A solution of 2-chloro-4-hydroxy-benzoic acid (3.70 g, 21.4 mmol)) in methanol (50 ml) was treated with thionyl chloride (2.4 ml, 32 mmol) dropwise and stirred for 24 hours and the solvents were removed in vacuo. The residue was dissolved in ethyl acetate and washed with sat. sodium hydrogen carbonate, dried and solvents were removed in vacuo. The residue was purified by column chromatography on silica gel (eluant with 30% EtOAc:70% cyclohexane) to yield the desired product as a yellow solid, 3.68 g, 92%.

Example E41c

4-[2-(4-Carboxy-3-chloro-phenoxy)-acetyl]-piperazine-1-carboxylic Acid Tert-butyl Ester

Example E41c.1

4-[2-(3-Chloro-4-methoxycarbonyl-phenoxy)-acetyl]-piperazine-1-carboxylic Acid Tert-butyl Ester 2-Chloro-4-hydroxy-benzoic acid methyl ester from example E41b (2.0 g, 10.9 mmol) and 4-(2-Bromo-acetyl)-piperazine-1-carboxylic acid tert-butyl ester from Example E41a (3.68 g, 12.0 mmol) in acetonitrile (30 ml) were treated with potassium carbonate (1.6 g, 11.5 mmol), and the mixture heated at reflux 18 h. before the solvents were removed in vacuo. The residue was adsorbed onto silica gel and purified by flash chromatography on silica gel (eluant; 20% EtOAc: 80% cyclohexane to 50% EtOAc:50% cyclohexane to 70% EtOAc:30% cyclohexane) to yield the title compound (4.5 g, 100%).

Example E41c.2

4-[2-(4-Carboxy-3-chloro-phenoxy)-acetyl]-piperazine-1-carboxylic Acid Tert-butyl Ester A solution of 4-[2-(3-Chloro-4-methoxycarbonyl-phenoxy)-acetyl]-piperazine-1-carboxylic acid tert-butyl ester from Example E41c.1 (4.5 g, 10.8 mmol) in THF at 0° C. was treated with potassium trimethylsilanolate (1.6 g, 10.9 mmol), and the mixture stirred at room temperature for 18 h. A further 1.6 g (10.9 mmol) potassium silanolate was added, and stirring continued at room temperature for 2 h. A further 1.6 g (10.9 mmol) potassium silanolate was added, and the mixture was stirred at 45° C. for 2 h. The mixture was then diluted with water and THF was removed in vacuo. The residue was washed with ether, cooled in an ice-bath and adjusted to pH5 with solid KHSO$_4$ whereupon it was extracted with CHCl$_3$ and CHCl$_3$/isopropanol (90:10 v/v). The combined organics were dried and solvents were removed in vacuo to yield the title compound (3.7 g, 85%).

Example E42

4-(3-tert-Butoxycarbonyl-propoxy)-3-methyl-benzoic Acid

Example E42.1

4-Bromo-butyric Acid Tert-butyl Ester

1M Boron tribromide (39 ml, 39=mol) was added to a solution of butyrolactone (3 ml, 39 mmol) in dichloromethane (30 ml). The mixture was stirred for 20 h at room temperature then quenched with an excess of tert-butylalcohol. The mixture was stirred for 2 h at room temperature, diluted with dichloromethane, washed with saturated NaHCO$_3$, saturated Na$_2$S$_2$O$_3$ then brine, dried and concentrated in vacuo. The residue was purified by flash chromatography on silica gel through an isolute (eluant; 5% EtOAc:95% hexane) to yield the title compound (3 g, 34%).

Example E42.2

4-(3-tert-Butoxycarbonyl-propoxy)-3-methyl-benzoic Acid Methyl Ester

Potassium carbonate (580 mg, 4.20 mmol) and potassium iodide (72 mg, 0.43 mmol) were added to a solution of 4-hydroxy-3-methyl-benzoic acid methyl ester from Example E29 (293 mg, 1.76 mmol) and 4-bromo-butyric acid tert-butyl ester from Example E42.1 (397 mg, 1.78 mmol) in acetone (50 ml). The mixture was heated at reflux for 18 h then the solid was filtered off and the filtrate concentrated in vacuo. The residue was dissolved in EtOAc, washed with water then brine, dried and concentrated in vacuo. The residue was purified by flash chromatography on silica gel (eluant; 20% EtOAc:80% pet. ether) to yield the title compound (414 mg, 76%).

Example E42.3

4-(3-tert-Butoxycarbonyl-propoxy)-3-methyl-benzoic Acid

Lithium hydroxide monohydrate (137 mg, 3.26 mmol) was added to a solution of 4-(3-tert-butoxycarbonyl-propoxy)-3-methyl-benzoic acid methyl ester from Example E42.2 (414 mg, 1.34 mmol) in THF (10 ml) and water (5 ml). The mixture was stirred for 48 h at room temperature and concentrated in vacuo. The residue was dissolved in chloroform, acidified with 1M HCl then washed with brine, dried and concentrated in vacuo to yield the title compound (275 mg, 70%).

Example E43

4-{4-[4-(3,3-Dimethyl-butyl)-piperazin-1-yl]-4-oxo-butyl}-3-methyl-benzoic Acid

Example E43.1

4-{4-[4-(3,3-Dimethyl-butyl)-piperazin-1-yl]-4-oxo-butyl}-3-methyl-benzoic Acid Methyl Ester HBTU (910 mg, 2.4 mmol) was added to a solution of 4-(3-carboxy-propyl)-3-methyl-benzoic acid methyl ester from Example E30 (378 mg, 1.6 mmol) and 1-(3,3-dimethyl-butyl)-piperazine hydrochloride from Example E4 (467 mg, 1.9 mmol) in dichloromethane (15 ml) and DIEA (0.836 ml, 4.8 mmol). The mixture was stirred for 20 h at room temperature, washed with saturated NaHCO$_3$ then brine, dried and concentrated in vacuo. The residue was purified by flash chromatography on silica gel through an isolute (eluant; 5% methanol:95% dichloromethane) to yield the title compound (582 mg, 94%).

Example E43.2

4-{4-[4-(3,3-Dimethyl-butyl)-piperazin-1-yl]-4-oxo-butyl}-3-methyl-benzoic Acid

Lithium hydroxide monohydrate (108 mg, 2.6 mmol) was added to a solution of 4-{4-[4-(3,3-dimethyl-butyl)-piperazin-1-yl]-4-oxo-butyl}-3-methyl-benzoic acid methyl ester from Example E43.1 (500 mg, 1.3 mmol) in THF (12 ml) and water (6 ml). The mixture was stirred for 20 h at room temperature then solvents were removed in vacuo. The residue was purified by flash chromatography on silica gel (eluant; 2% acetic acid:4% methanol:94% dichloromethane) then recrystallised from chloroform and pet. ether to yield the title compound (439 mg, 91%).

Example E44

4-(3-[4-(3,3-Dimethyl-butyl)-piperazin-1-yl]-3-oxo-propyl)-3-methyl-benzoic Acid Example E44.1

4-{3-[4-(3,3-Dimethyl-butyl)-piperazin-1-yl]-3-oxo-propyl}-3-methyl-benzoic Acid Methyl Ester Oxalyl chloride (2.6 ml, 30 mmol) was added slowly to a solution of 4-(2-carboxy-ethyl)-3-methyl-benzoic acid methyl ester from Example E30.3 (5.33 g, 24 mmol) in dichloromethane (60 ml) and few drops of DMF at 0° C. The mixture was stirred for 2 h at room temperature then concentrated in vacuo and azeotroped with toluene. The residue was dissolved in dichloromethane (30 ml) and added to a solution of 1-(3,3-dimethyl-butyl)-piperazine hydrochloride from Example E4 (6.3 g, 26 mmol) in dichloromethane (45 ml) and DIEA (17 ml, 96 mmol) at 0° C. The mixture was stirred for 1 h at room temperature then concentrated in vacuo. The residue was purified by flash chromatography on silica gel (eluant; 5% methanol:95% dichloromethane) to yield the title compound (8.5 g, 96%).

Example E44.2

4-{3-[4-(3,3-Dimethyl-butyl)-piperazin-1-yl]-3-oxo-propyl}-3-methyl-benzoic Acid Lithium hydroxide monohydrate (2.4 g, 56.7 mmol) was added to a solution of 4-{3-[4-(3,3-dimethyl-butyl)-piperazin-1-yl]-3-oxo-propyl}-3-methyl-benzoic acid methyl ester from Example E44.1 (8.5 g, 22.7 mmol) in THF (200 ml) and water (100 ml). The mixture was stirred for 24 h at room temperature then solvents were removed in vacuo. The residue was purified by flash chromatography on silica gel (eluant; 2% acetic acid:4% methanol:94% dichloromethane) to yield the title compound (8.1 g, 99%).

Example E45

3-[2-Methyl-4-(3-methyl-4,10-dihydro-3H-2,3,4,9-tetraaza-benzo[f]azulene-9-carbonyl)-phenyl]-propionic Acid Example E45.1

4-((E)-2-tert-Butoxycarbonyl-vinyl)-3-methyl-benzoic Acid

Lithium hydroxide monohydrate (384 mg, 9.2 mmol) was added to a solution of 4-((E)-2-tert-butoxycarbonyl-vinyl)-3-methyl-benzoic acid methyl ester from Example E30.1 (1.27 g, 4.6 mmol) in THF (50 ml) and water (20 ml). The mixture was stirred for 20 h at room temperature then solvents were removed in vacuo. The residue was dissolved in EtOAc, washed with 1M KHSO$_4$, water then brine, dried and concentrated in vacuo to yield the title compound (1.1 g, 92%).

Example E45.2

(E)-3-[2-Methyl-4-(3-methyl-4,10-dihydro-3H-2,3,4, 9-tetraaza-benzo[f]azulene-9-carbonyl)-phenyl]-acrylic Acid Tert-butyl Ester 4-((E)-2-tert-Butoxycarbonyl-vinyl)-3-methyl-benzoic acid from Example E45.1 (1.1 g, 4.2 mmol) and 3-methyl-3, 4,9,10-tetrahydro-2,3,4,9-tetraaza-benzo[f]azulene from Example E11 (720 mg, 3.6 mmol) were dissolved in dichloromethane (50 ml) and triethylamine (0.75 ml). DMAP (4.45 g, 3.6 mmol) and WSCD (1.36 g, 7.1 mmol) were added and the mixture was heated at re-flux for 2 days. The solution was diluted with di-chloromethane, washed with 0.3M $KHSO_4$, saturated $NaHCO_3$ then brine, dried and concentrated in vacuo. The residue was purified by flash chromatography on silica gel (eluant; EtOAc) to yield the title compound (1.35 g, 82%).

Example E45.3

3-[2-Methyl-4-(3-methyl-4,10-dihydro-3H-2,3,4,9-tetraaza-benzo[f]azulene-9-carbonyl)-phenyl]-propionic Acid Tert-butyl Ester (E)-3-[2-Methyl-4-(3-methyl-4,10-dihydro-3H-2,3,4,9-tetraaza-benzo[f]azulene-9-carbonyl)-phenyl]-acrylic acid tert-butyl ester from Example E45.2 (436 mg, 0.99 mmol) was dissolved in methanol (40 ml) and hydrogenated over 10% Pd/C catalyst (91 mg) for 5 h. The mixture was filtered through Celite® filter agent and the filtrate was concentrated in vacuo and azeotroped with dichloromethane to yield the title compound (426 mg, 96%).

Example E45.4

3-[2-Methyl-4-(3-methyl-4,10-dihydro-3H-2,3,4,9-tetraaza-benzo[f]azulene-9-carbonyl)-phenyl]-propionic Acid Trifluoroacetic acid (5 ml) was added to a solution of 3-[2-methyl-4-(3-methyl-4,10-dihydro-3H-2,3,4,9-tetraaza-benzo[f]azulene-9-carbonyl)-phenyl]-propionic acid tert-butyl ester from Example E45.3 (413 mg, 0.92 mmol) in dichloromethane (10 ml) and the mixture was stirred for 45 min at room temperature. Solvents were removed in vacuo and azeotroped with dichloromethane. The residue was crystallised with MeOH/$Et_2O$ to yield the title compound (322 mg, 90%).

Example E46

(E)-3-[2-Methyl-4-(3-methyl-4,10-dihydro-3H-2,3,4, 9-tetraaza-benzo[f]azulene-9-carbonyl)-phenyl]-acrylic Acid Trifluoroacetic acid (5 ml) was added to a solution of (E)-3-[2-methyl-4-(3-methyl-4,10-dihydro-3H-2,3,4,9-tetraaza-benzo[f]azulene-9-carbonyl)-phenyl]-acrylic acid tert-butyl ester from Example E45.2 (338 mg, 0.76 mmol) in dichloromethane (10 ml) and the mixture was stirred for 45 min at room temperature. Solvents were removed in vacuo and azeotroped with dichloromethane to yield the title compound (337 mg, 80%).

Example E47

3-[2-Methyl-4-(3-methyl-4,10-dihydro-3H-2,3,4,9-tetraaza-benzo[f]azulene-9-carbonyl)-phenyl]-1-piperazin-1-yl-propan-1-one

Example E47.1

4-{3-[2-Methyl-4-(3-methyl-4,10-dihydro-3H-2,3,4, 9-tetraaza-benzo[f]azulene-9-carbonyl)-phenyl]-propionyl}-piperazine-1-carboxylic Acid Tert-butyl Ester PyBroP (1.54 g, 3.3 mmol) was added to a solution of 3-[2-methyl-4-(3-methyl-4,10-dihydro-3H-2,3,4,9-tetraaza-benzo[f]azulene-9-carbonyl)-phenyl]-propionic acid from Example E45 (850 mg, 2.25 mmol) and DMAP (275 mg, 2.25 mmol) in dichloromethane (20 ml) and DIEA (0.90 ml, 5.2 mmol). The mixture was stirred for 15 mins at room temperature then 3-methyl-3,4,9,10-tetrahydro-2,3,4,9-tetraaza-benzo[f]azulene from Example E11 (450 mg, 2.25 mmol) was added. The mixture was heated at reflux for 18 h, diluted with dichloromethane, washed with 0.3M $KHSO_4$ solution then saturated $NaHCO_3$, dried and concentrated in vacuo. The residue was purified by flash chromatography on silica gel (eluant; 5% methanol:95% EtOAc) to yield the title compound (1.09 g, 87%).

Example E47.2

3-[2-Methyl-4-(3-methyl-4,10-dihydro-3H-2,3,4,9-tetraaza-benzo[f]azulene-9-carbonyl)-phenyl]-1-piperazin-1-yl-propan-1-one 4-{3-[2-Methyl-4-(3-methyl-4,10-dihydro-3H-2,3,4,9-tetraaza-benzo[f]azulene-9-carbonyl)-phenyl]-propionyl}-piperazine-1-carboxylic acid tert-butyl ester from Example E47.1 (1.09 g, 1.95 mmol) was dissolved in methanol (20 ml) and 4M HCl/dioxan solution (20 ml) was added. The mixture was stirred for 3 h at room temperature, concentrated in vacuo and azeotroped with toluene. The residue was dissolved in methanol (30 ml) and ammonia (5 ml) then concentrated in vacuo. The residue was purified by flash chromatography on silica gel (eluant; 0.5% 35% ammonia:4.5% methanol:95% dichloro-methane to 1% 35% ammonia:9% methanol:90% dichloro-methane) to yield the title compound (759 mg, 73%).

Example E48

{4-[3-(4-Cyclopropyl-piperazin-1-yl)-propoxy]-3-fluoro-phenyl}-(3-methyl-4,10-dihydro-3H-2,3,4,9-tetraaza-benzo[f]azulen-9-yl)-methanone

Example E48.1

4-(3-Bromo-propoxy)-3-fluoro-benzoic Acid Ethyl Ester 1,3-Dibromopropane (2.2 g, 11.0 mmol), potassium carbon-ate (1.86 g, 13.6 mmol) and potassium iodide (90 mg, 0.5 mmol) were added to 3-fluoro-4-hydroxy-benzoic acid ethyl ester from Example E27 (11.0 g, 5.4 mmol) in acetone (25 ml) and the mixture was heated at reflux for 20 h. The solid was filtered off and washed with EtOAc. The filtrate was concentrated in vacuo and azeotroped with toluene. The residue was purified by flash chromatography on silica gel (eluant; 20% EtOAc:80% hexane) to yield the title compound (1.18 g, 71%).

Example E48.2

4-[3-(4-Cyclopropyl-piperazin-1-yl)-propoxy]-3-fluoro-benzoic Acid Ethyl Ester

1-Cyclopropyl-piperazine dihydrochloride (642 mg, 3.2 mmol, according to the procedure described by G. S. Poindexter, M. A. Bruce, K. L. Le Boulluec, I. Monkovic, Tet. Lett., 35(44), 7331-7334, 1994), potassium carbonate (2.1 g, 15.2 mmol) and potassium iodide (50 mg, 0.3 mmol) were added to 4-(3-bromo-propoxy)-3-fluoro-benzoic acid ethyl ester from Example E48.1 (1.2 g, 3.9 mmol) in acetone (25 ml). The mixture was heated at reflux for 20 h. The solid was filtered off, washed with EtOAc and the filtrate was concentrated in vacuo. The residue was purified by flash chromatography on silica gel (eluant; EtOAc then 1% 35% ammonia:9% methanol:90% dichloromethane) to yield the title compound (1.0 g, 89%).

Example E48.3

4-[3-(4-Cyclopropyl-piperazin-1-yl)-propoxy]-3-fluoro-benzoic Acid

4-[3-(4-Cyclopropyl-piperazin-1-yl)-propoxy]-3-fluoro-benzoic acid ethyl ester from Example E48.2 (1.0 g, 2.9 mmol) was dissolved in dioxan (10 ml) and 2N NaOH solution (3 ml, 6.0 mmol) was added. The mixture was heated at 60° C. for 18 h then concentrated in vacuo. The residue was purified by flash chromatography on silica gel (eluant; 1% 35% ammonia:19% methanol:80% dichloro-methane) to yield the title compound (920 mg, 100%).

Example E48.4

{4-[3-(4-Cyclopropyl-piperazin-1-yl)-propoxy]-3-fluoro-phenyl}-(3-methyl-4,10-dihydro-3H-2,3,4,9-tetraaza-benzo[f]azulen-9-yl)-methanone HBTU (325 mg, 0.9 mmol) and 4M HCl in dioxan (0.45 ml, 1.8 mmol) were added to a solution of 4-[3-(4-cyclopropyl-piperazin-1-yl)-propoxy]-3-fluoro-benzoic acid from Example E48.3 (230 mg, 0.7 mmol) in DMF (5 ml). The mixture was stirred at room temperature for 30 min. 3-Methyl-3,4,9,10-tetrahydro-2,3,4,9-tetraaza-benzo[f]azulene from Example E65 (186 mg, 0.9 mmol) and DIEA (pH=9) were added and the mixture was stirred at room temperature for 18 h. The mixture was heated at 60° C. for 3 h then HBTU (300 mg, 0.8 mmol) was added. The mixture was heated at 60° C. for 2 days then solvents were removed in vacuo and azeotroped with toluene. The residue was redissolved in EtOAc, washed with saturated Na—HCO$_3$ then brine, dried and concentrated in vacuo. The residue was purified by preparative HPLC (eluant; 0.5% 35% ammonia:9.5% methanol:90% dichloromethane) to give a brown solid identified as the title compound (55 mg, 15%).

Example E49

[3-Fluoro-4-(3-piperazin-1-yl-propoxy)-phenyl]-(3-methyl-4,10-dihydro-3H-2,3,4,9-tetraaza-benzo[f]azulen-9-yl)-methanone Dihydrochloride

Example E49.1

4-{3-[2-Fluoro-4-(3-methyl-4,10-dihydro-3H-2,3,4,9-tetraaza-benzo[f]azulene-9-carbonyl)-phenoxy]-propyl}-piperazine-1-carboxylic Acid Tert-butyl Ester A solution of 4-[3-(4-carboxy-2-fluoro-phenoxy)-propyl]-piperazine-1-carboxylic acid tert-butyl ester from Example E39 (865 mg, 2.3 mmol) in dichloromethane (50 ml) was treated with triethylamine (to pH9), WSCD (865 mg, 4.5 mmol) and DMAP (276 mg, 2.3 mmol), and the mixture was stirred at room temperature for 10 min. 3-Methyl-3,4,9,10-tetrahydro-2,3,4,9-tetraaza-benzo[f]azulene from Example E11 (541 mg, 2.7 mmol) was added. The mixture was heated at reflux for 18 h then concentrated in vacuo. The residue was dissolved in EtOAc, washed with saturated NaHCO$_3$ then brine and concentrated in vacuo. The residue was purified by flash chromatography on silica gel (eluant; 10% methanol:90% dichloromethane) to yield the title compound (615 mg, 48%).

Example E49.2

[3-Fluoro-4-(3-piperazin-1-yl-propoxy)-phenyl]-(3-methyl-4,10-dihydro-3H-2,3,4,9-tetraaza-benzo[f]azulen-9-yl)-methanone Dihydrochloride A solution of 4-{3-[2-fluoro-4-(3-methyl-4,10-dihydro-3H-2,3,4,9-tetraaza-benzo[f]azulene-9-carbonyl)-phenoxy]-propyl}-piperazine-1-carboxylic acid tert-butyl ester from Example E49.1 (615 mg, 1.09 mmol) in methanol (2 ml) at 0° C. was treated with 4N HCl in dioxan (5 ml). The solution was allowed to warm to room temperature and stirred for 1 h. Solvents were removed in vacuo to give a white foam identified as the title compound (585 mg, 100%).

Example E50

(4-{3-[4-(3,3-Dimethyl-butyl)-piperazin-1-yl]-propoxy}-3-fluoro-phenyl)-(3-methyl-4,10-dihydro-3H-2,3,4,9-tetraaza-benzo[f]azulen-9-yl)-methanone bis(trifluoroacetate)

3,3-Dimethylbutyraldehyde (120 mg, 1.20 mmol) and triethylamine (to pH9) were added to a solution of [3-fluoro-4-(3-piperazin-1-yl-propoxy)-phenyl]-(3-methyl-4,10-dihydro-3H-2,3,4,9-tetraaza-benzo[f]azulen-9-yl)-methanone dihydrochloride from Example E49 (585 mg, 1.09 mmol) in methanol/acetic acid (99:1, v/v, 20 ml) and the mixture was stirred at room temperature for 1 h. Sodium cyanoborohydride (103 mg, 1.30 mmol) was added and the mixture was stirred at room temperature for 18 h then concentrated in vacuo. The residue was purified by flash chromatography on silica gel (eluant; 10% methanol:90% dichloromethane) to yield (4-{3-[4-(3,3-dimethyl-butyl)-piperazin-1-yl]-propoxy}-3-fluoro-phenyl)-(3-methyl-4,10-dihydro-3H-2,3,4,9-tetraaza-benzo[f]azulen-9-yl)-methanone, which was lyophilised from aqueous trifluoroacetic acid to give a white solid identified as the title compound (700 mg, 83%).

Example E51

(3,6-Dimethyl-4,10-dihydro-3H-2,3,4,9-tetraaza-benzo[f]azulen-9-yl)-{4-[3-(1-isobutyl-piperidin-4-yl)-propoxy]-3-methyl-phenyl}-methanone A solution of isobutyraldehyde (0.36 mg, 0.005 mmol) in 1,2-dichloroethane (0.05 ml) was added to a solution of (3,6-dimethyl-4,10-dihydro-3H-2,3,4,9-tetraaza-benzo[f]azulen-9-yl)-[3-methyl-4-(3-piperidin-4-yl-propoxy)-phenyl]-methanone hydrochloride (2.6 mg, 0.005 mmol) in 1,2-dichloroethane (0.05 ml) and DIEA (0.0026 ml). The mixture was stirred at room temperature for 1 h then a solution of sodium triacetoxyborohydride (1.59 mg, 0.0075 mmol) in DMF (0.05 ml) was added. The mixture was stirred for 20 h at room temperature then solvents were removed in vacuo to yield the title compound. (ESI)+: [M+H]+=530.5

Example E52

(6-Chloro-3-methyl-4,10-dihydro-3H-2,3,4,9-tetraaza-benzo[f]azulen-9-yl)-{2-fluoro-4-[3-(4-hexyl-piperazin-1-yl)-propoxy]-phenyl}-methanone A solution of 1-bromohexane (0.83 mg, 0.005 mmol) in DMF (0.05 ml) was added to a solution of (6-chloro-3-methyl-4,10-dihydro-3H-2,3,4,9-tetraaza-benzo[f]azulen-9-yl)-[2-fluoro-4-(3-piperazin-1-yl-propoxy)-phenyl]-methanone dihydrochloride from Example E5a (2.85 mg, 0.005 mmol) in DMF (0.05 ml) and triethylamine (0.0021 ml). The mixture was stirred for 20 h at room temperature then solvents were removed in vacuo to yield the title compound. (ESI)+: [M+H]+=583.6

Example E53

1-(4-{3-[2-Methyl-4-(3-methyl-4,10-dihydro-3H-2,3,4,9-tetraaza-benzo[f]azulene-9-carbonyl)-phenoxy]-propyl}-piperazin-1-yl)-ethanone A solution of acetyl chloride (0.39 mg, 0.005 mmol) in dichloromethane (0.05 ml) was added to a solution of (3-methyl-4,10-dihydro-3H-2,3,4,9-tetraaza-benzo[f]azulen-9-yl)-[3-methyl-4-(3-piperazin-1-yl-propoxy)-phenyl]-methanone dihydrochloride (Compound number 408) (2.67 mg, 0.005 mmol) in dichloromethane (0.05 ml) and triethylamine (0.0035 ml). The mixture was stirred at room temperature for 1 h then solvents were removed in vacuo to yield the title compound. (ESI)+: [M+H]+=503.2

Example E54

{4-[3-(4-Methanesulfonyl-piperazin-1-yl)-propoxy]-3-methyl-phenyl}-(3-methyl-4,10-dihydro-3H-2,3,4,9-tetraaza-benzo[f]azulen-9-yl)-methanone A solution of methanesulfonyl chloride (0.57 mg, 0.005 mmol) in dichloromethane (0.05 ml) was added to a solution of (3-methyl-4,10-dihydro-3H-2,3,4,9-tetraaza-benzo[f]azulen-9-yl)-[3-methyl-4-(3-piperazin-1-yl-propoxy)-phenyl]-methanone dihydrochloride (Compound number 408) (2.67 mg, 0.005 mmol) in dichloromethane (0.05 ml) and triethylamine (0.0035 ml). The mixture was stirred at room temperature for 1 h then solvents were removed in vacuo to yield the title compound. (ESI)+: [M+H]+=539.2

Example E55

1-(4-[1,3]Dioxolan-2-yl-piperidin-1-yl)-3-[2-methyl-4-(3-methyl-4,10-dihydro-3H-2,3,4,9-tetraaza-benzo[f]azulene-9-carbonyl)-phenyl]-propan-1-one HBTU (327 mg, 0.86 mmol) was added to a solution of 4-[1,3]dioxolan-2-yl-piperidine from Example E33 (143 mg, 0.91 mmol) and 3-[2-methyl-4-(3-methyl-4,10-dihydro-3H-2,3,4,9-tetraaza-benzo[f]azulene-9-carbonyl)-phenyl]-propionic acid from Example E45 (320 mg, 0.82 mmol) in dichloromethane (20 ml) and DIEA (0.7 ml, 4.02 mmol) and the mixture was stirred for 20 h at room temperature. Dichloromethane was added and the solution was washed with saturated NaHCO$_3$ then brine, dried and concentrated in vacuo. The residue was purified by flash chromatography on silica gel (eluant; 4% methanol:96% dichloro-methane to 8% methanol:92% dichloromethane) to give a white solid identified as the title compound (359 mg, 83%).

Example E56

1-[4-(Furan-2-carbonyl)-piperazin-1-yl]-3-[2-methyl-4-(3-methyl-4,10-dihydro-3H-2,3,4,9-tetraaza-benzo[f]azulene-9-carbonyl)-phenyl]-propan-1-one A solution of HBTU (1.90 mg, 0.005 mmol) in DMF (0.05 ml) was added to a solution of 3-[2-methyl-4-(3-methyl-4,10-dihydro-3H-2,3,4,9-tetraaza-benzo[f]azulene-9-carbonyl)-phenyl]-propionic acid from Example E45 (1.95 mg, 0.005 mmol) in DMF (0.05 ml) and DIEA (0.0022 ml). The mixture was stirred at room temperature for 30 min then a solution of 1-(2-furoyl)piperazine (0.90 mg, 0.005 mmol) in DMF (0.05 ml) was added. The mixture was stirred for 18 h at room temperature then sol-vents were removed in vacuo to yield the title compound. (ESI)+: [M+H]+=553.4

Example E57

(E)-3-[2-Methyl-4-(3-methyl-4,10-dihydro-3H-2,3,4,9-tetraaza-benzo[f]azulene-9-carbonyl)-phenyl]-1-[4-(2-piperidin-1-yl-ethyl)-piperazin-1-yl]-propenone A solution of HBTU (1.90 mg, 0.005 mmol) in DMF (0.05 ml) was added to a solution of (E)-3-[2-Methyl-4-(3-methyl-4,10-dihydro-3H-2,3,4,9-tetraaza-benzo[f]azulene-9-carbonyl)-phenyl]-acrylic acid from Example E46 (1.95 mg, 0.005 mmol) in DMF (0.05 ml) and DIEA (0.0022 ml). The mixture was stirred at room temperature for 30 min then a solution of 1-(2-Piperidin-1-yl-ethyl)-piperazine (0.99 mg, 0.005 mmol) in DMF (0.05 ml) was added. The mixture was stirred for 18 h at room temperature then solvents were removed in vacuo to yield the title compound.

Example E58

1-{4-[(Butyl-methyl-amino)-methyl]-piperidin-1-yl}-3-[2-methyl-4-(3-methyl-4,10-dihydro-3H-2,3,4,9-tetraaza-benzo[f]azulene-9-carbonyl)-phenyl]-propan-1-one

Example E58.1

1-{3-[2-Methyl-4-(3-methyl-4,10-dihydro-3H-2,3,4,9-tetraaza-benzo[f]azulene-9-carbonyl)-phenyl]-propionyl}-piperidine-4-carbaldehyde Pyridinium p-toluenesulfonate (85 mg, 0.34 mmol) was added to a solution of 1-(4-[1,3]dioxolan-2-yl-1-piperidin-1- yl)-3-[2-methyl-4-(3-methyl-4,10-dihydro-3H-2,3,4,9-tetraaza-benzo[f]azulene-9-carbonyl)-phenyl]-propan-1-one from Example E55 (614 mg, 1.16 mmol) in acetone (20 ml) and water (20 ml). The mixture was heated at reflux for 7 days then solvents were removed in vacuo. The residue was redissolved in EtOAc, washed with 0.3M $KHSO_4$ then brine, dried, concentrated in vacuo then crystallised with chloroform and pet. ether to yield the title compound (451 mg, 80%).

Example E58.2

1-{4-[(Butyl-methyl-amino)-methyl]-piperidin-1-yl}-3-[2-methyl-4-(3-methyl-4,10-dihydro-3H-2,3,4,9-tetraaza-benzo[f]azulene-9-carbonyl)-phenyl]-propan-1-one A solution of 1-{3-[2-methyl-4-(3-methyl-4,10-dihydro-3H-2,3,4,9-tetraaza-benzo[f]azulene-9-carbonyl)-phenyl]-propionyl}-piperidine-4-carbaldehyde from Example E58.1 (2.43 mg, 0.005 mmol) in 1,2-dichloroethane (0.05 ml) was added to a solution of butyl-methyl-amine (0.43 mg, 0.005 mmol) in 1,2-dichloroethane (0.05 ml) and the mixture was heated at 50° C. for 3 h then stirred at room temperature for 2 days. A solution of sodium tri-acetoxyborohydride (1.59 mg, 0.0075 mmol) in DMF (0.05 ml) was added and the mixture was stirred for 20 h at room temperature. Solvents were removed in vacuo to yield the title compound. MS: $(ESI)^+$: $[M+H]^+=557.6$ Example E59

3-[2-Methyl-4-(3-methyl-4,10-dihydro-3H-2,3,4,9-tetraaza-benzo[f]azulene-9-carbonyl)-phenyl]-1-[4-(2-morpholin-4-yl-ethylamino)-piperidin-1-yl]-propan-1-one A solution of 1-{3-[2-methyl-4-(3-methyl-4,10-dihydro-3H-2,3,4,9-tetraaza-benzo[f]azulene-9-carbonyl)-phenyl]-propionyl}-piperidin-4-one (Compound number 701) (2.36 mg, 0.005 mmol) in 1,2-dichloroethane (0.05 ml) was added to a solution of 2-morpholin-4-yl-ethylamine (0.65 mg, 0.005 mmol) in 1,2-dichloroethane (0.05 ml) and the mixture was heated at 50° C. for 3 h then stirred at room temperature for 2 days. A solution of sodium tri-acetoxyborohydride (1.59 mg, 0.0075 mmol) in DMF (0.05 ml) was added and the mixture was stirred for 20 h at room temperature. Solvents were removed in vacuo to yield the title compound. MS: $(ESI)^+$: $[M+H]^+=586.6$ Example E60

1-(4-Hexyl-piperazin-1-yl)-3-[2-methyl-4-(3-methyl-4,10-dihydro-3H-2,3,4,9-tetraaza-benzo[f]azulene-9-carbonyl)-phenyl]-propan-1-one A solution of 1-bromohexane (0.83 mg, 0.005 mmol) in DMF (0.05 ml) was added to a solution of 3-[2-methyl-4-(3-methyl-4,10-dihydro-3H-2,3,4,9-tetraaza-benzo[f]azulene-9-carbonyl)-phenyl]-1-piperazin-1-yl-propan-1-one from Example E47 (2.29 mg, 0.005 mmol) in DMF (0.05 ml) and triethylamine (0.0021 ml). The mixture was stirred for 20 h at room temperature then solvents were removed in vacuo to yield the title compound. (ESI)+: [M+H]+=543.4

Example E61

3-[4-(3,6-Dimethyl-4,10-dihydro-3H-2,3,4,9-tetraaza-benzo[f]azulene-9-carbonyl)-2-methyl-phenyl]-1-(4-propyl-piperazin-1-yl)-propan-1-one A solution of propionaldehyde (0.29 mg, 0.005 mmol) in 1,2-dichloroethane (0.05 ml) was added to a solution of 3-[4-(3,6-dimethyl-4,10-dihydro-3H-2,3,4,9-tetraaza-benzo[f]azulene-9-carbonyl)-2-methyl-phenyl]-1-piperazin-1-yl-propan-1-one (2.36 mg, 0.005 mmol) in 1,2-dichloroethane (0.05 ml) and DIEA (0.0026 ml). The mixture was stirred at room temperature for 1 h then a solution of sodium triacetoxyborohydride (1.59 mg, 0.0075 mmol) in DMF (0.05 ml) was added. The mixture was stirred for 20 h at room temperature then solvents were removed in vacuo to yield the title compound. (ESI)+: [M+H]+=515.5

Example E62

1-(4-Acetyl-piperazin-1-yl)-3-[4-(6-chloro-3-methyl-4,10-dihydro-3H-2,3,4,9-tetraaza-benzo[f]azulene-9-carbonyl)-2-methyl-phenyl]-propan-1-one A solution of acetyl chloride (0.39 mg, 0.005 mmol) in dichloromethane (0.05 ml) was added to a solution of 3-[4-(6-chloro-3-methyl-4,10-dihydro-3H-2,3,4,9-tetraaza-benzo[f]azulene-9-carbonyl)-2-methyl-phenyl]-1-piperazin-1-yl-propan-1-one (2.47 mg, 0.005 mmol) in di-chloromethane (0.05 ml) and triethylamine (0.0035 ml). The mixture was stirred at room temperature for 20 h then solvents were removed in vacuo to yield the title compound. (ESI)+: [M+H]+=535.5

Example E63

3-[4-(3,6-Dimethyl-4,10-dihydro-3H-2,3,4,9-tetraaza-benzo[f]azulene-9-carbonyl)-2-methyl-phenyl]-1-(4-methanesulfonyl-piperazin-1-yl)-propan-1-one A solution of methanesulfonyl chloride (0.57 mg, 0.005 mmol) in dichloromethane (0.05 ml) was added to a solution of 3-[4-(3,6-dimethyl-4,10-dihydro-3H-2,3,4,9-tetraaza-benzo[f]azulene-9-carbonyl)-2-methyl-phenyl]-1-piperazin-1-yl-propan-1-one (2.36 mg, 0.005 mmol) in dichloromethane (0.05 ml) and triethylamine (0.0035 ml). The mixture was stirred at room temperature for 20 h then solvents were removed in vacuo to yield the title compound. (ESI)+: [M+H]+=551.3

Example E64

1-[4-(3,3-Dimethyl-butyl)-piperazin-1-yl]-4-[2-methyl-4-(3-methyl-4,10-dihydro-3H-2,3,4,9-tetraaza-benzo[f]azulene-9-carbonyl)-phenyl]-butan-1-one 4-{4-[4-(3,3-Dimethyl-butyl)-piperazin-1-yl]-4-oxo-butyl}-3-methyl-benzoic acid from Example E43 (139 mg, 0.37 mmol) and 3-methyl-3,4,9,10-tetrahydro-2,3,4,9-tetraaza-benzo[f]azulene from Example E11 (75 mg, 0.37 mmol) were dissolved in dichloromethane (5 ml) and DIEA (0.195 ml, 1.11 mmol). WSCD (93 mg, 0.48 mmol) and DMAP (9 mg, 0.07 mmol) were added and the mixture was heated at reflux for 3 days, then washed with saturated $NaHCO_3$ then brine, dried and concentrated in vacuo. The residue was purified by preparative HPLC (eluant; 0.5% 35% ammonia:9.5% methanol:90% dichloromethane) to give a white powder identified as the title compound (11 mg, 5%).

Example E65

N-Benzyl-3-[4-(2,3,4,5-tetrahydro-benzo[b]azepine-1-carbonyl)-phenyl]-propionamide Example E65.1

4-((E)-2-Methoxycarbonyl-vinyl)-benzoic Acid

Sodium hydride (60% dispersion in oil, 1.46 g, 36.6 mmol) was added to a solution of 4-formylbenzoic acid (5.0 g, 33.3 mmol) in toluene (200 ml) and the mixture was stirred for 2 h at room temperature. Methyl (triphenyl-phosphoranylidene) acetate (11.69 g, 35.0 mmol) was added and the mixture was heated at reflux for 20 h. Solvents were removed in vacuo and the residue was redissolved in dichloromethane and 1M NaHCO$_3$. The layers were partitioned and the aqueous layer was acidified with 1M HCl solution then extracted with chloroform. The organic layer was dried and concentrated in vacuo to yield the title compound (3.65 g, 53%).

Example E65.2

(E)-3-[4-(2,3,4,5-Tetrahydro-benzo[b]azepine-1-carbonyl)-phenyl]-acrylic Acid Methyl Ester WSCD (1.17 g, 6.16 mmol) was added to a solution of 4-((E)-2-methoxycarbonyl-vinyl)-benzoic acid from Example E65.1 (740 mg, 3.59 mmol), 2,3,4,5-tetrahydro-1H-benzo[b]azepine (445 mg, 3.02 mmol) and DMAP (370 mg, 3.02 mmol) in dichloromethane (40 ml) and triethylamine (0.7 ml, 5.02 mmol). The mixture was heated at reflux for 42 h then solvents were concentrated in vacuo. The residue was dissolved in EtOAc, washed with 1M KHSO$_4$ then brine, dried and concentrated in vacuo. The residue was purified by flash chromatography on silica gel (eluant; 30% EtOAc:70% pet. ether) to yield the title compound (484 mg, 48%).

Example E65.3

3-[4-(2,3,4,5-Tetrahydro-benzo[b]azepine-1-carbonyl)-phenyl]-propionic Acid Methyl Ester (E)-3-[4-(2,3,4,5-Tetrahydro-benzo[b]azepine-1-carbonyl)-phenyl]-acrylic acid methyl ester from Example E65.2 (485 mg, 1.44 mmol) was dissolved in methanol (60 ml) and hydrogenated over 10% Pd/C catalyst (214 mg) for 2 h. The mixture was filtered through Celite® filter agent and the filtrate was concentrated in vacuo to yield the title compound (415 mg, 85%).

Example E65.4

3-[4-(2,3,4,5-Tetrahydro-benzo[b]azepine-1-carbonyl)-phenyl]-propionic Acid

Lithium hydroxide monohydrate (114 mg, 2.72 mmol) was added to a solution of 3-[4-(2,3,4,5-tetrahydro-benzo[b] azepine-1-carbonyl)-phenyl]-propionic acid methyl ester from Example E65.3 (415 mg, 1.23 mmol) in water (5 ml) and dioxan (20 ml). The mixture was stirred for 18 h at room temperature then concentrated in vacuo. The residue was dissolved in chloroform, washed with 1M HCl solution then brine, dried and concentrated in vacuo to yield the title compound (241 mg, 61%).

Example E65.5

N-Benzyl-3-[4-(2,3,4,5-tetrahydro-benzo[b]azepine-1-carbonyl)-phenyl]-propionamide A mixture of 3-[4-(2,3,4,5-tetrahydro-benzo[b]azepine-1-carbonyl)-phenyl]-propionic acid from Example E65.4 (57 mg, 0.18 mmol) and thionyl chloride (0.2 ml, 2.74 mmol) in dichloromethane (6 ml) was heated at reflux for 2 h then volatiles were removed in vacuo. The residue was dissolved in dichloromethane (8 ml) then benzylamine (0.022 ml, 0.20 mmol) and triethylamine (0.05 ml, 0.36 mmol) were added. The mixture was stirred for 3 h at room temperature then concentrated in vacuo. The residue was purified by flash chromatography on silica gel (eluant; 30% pet. ether:70% EtOAc) to give a white fluffy solid identified as the title compound (36.5 mg, 50%).

Example E66

1-[4-(3,3-Dimethyl-butyl)-piperazin-1-yl]-3-[2-methyl-4-(2-methyl-4,5-dihydro-1H-1,3,6-triaza-benzo[e]azulene-6-carbonyl)-phenyl]-propan-1-one Oxalyl chloride (0.049 ml, 0.55 mmol) was added slowly to a solution of 4-{3-[4-(3,3-dimethyl-butyl)-piperazin-1-yl]-3-oxo-propyl}-3-methyl-benzoic acid from Example E44 (100 mg, 0.28 mmol) in dichloromethane (10 ml) and few drops of DMF. The mixture was stirred for 1 h at room temperature then concentrated in vacuo and azeotroped with toluene. The residue was redissolved in dichloro-methane (10 ml) and DIEA (0.144 ml, 0.84 mmol) then 2-methyl-1,4,5,6-tetrahydro-1,3,6-triaza-benzo[e]azulene from Example E5 (55 mg, 0.28 mmol) was added. The mixture was stirred for 20 h at room temperature then washed with saturated NaHCO$_3$ then brine, dried and concentrated in vacuo. The residue was purified by preparative HPLC (eluant; 0.5% 35% ammonia:9.5% methanol:90% dichloro-methane) to give a white fluffy solid identified as the title compound (42 mg, 28%).

Example E67

1-[4-(3,3-Dimethyl-butyl)-piperazin-1-yl]-3-[2-methyl-4-(6-methyl-3,4-dihydro-2H-quinoline-1-carbonyl)-phenyl]-propan-1-one DMAP (51 mg, 0.42 mmol) and WSCD (161 mg, 0.84 mmol) were added to a solution of 4-{3-[4-(3,3-dimethyl-butyl)-piperazin-1-yl]-3-oxo-propyl}-3-methyl-benzoic acid from Example E44 (150 mg, 0.42 mmol) in dichloromethane (10 ml) and triethylamine (0.176 ml, 1.26 mmol) and the mixture was stirred for 30 min at room temperature. 6-Methyl-1,2,3,4-tetrahydro-quinoline (67 mg, 0.46 mmol) was added and the mixture was stirred for 20 h at room temperature then solvents were removed in vacuo. The residue was redissolved in EtOAC, washed with saturated NaHCO$_3$ then brine, dried and concentrated in vacuo. The residue was purified by preparative HPLC (eluant; 0.5% 35% ammonia:9.5% methanol:90% dichloromethane) to give a white solid identified as the title compound (12 mg, 6%).

Example E68

(4-{3-[1-(3,3-Dimethyl-butyl)-piperidin-4-yl]-propoxy}-3-methyl-phenyl)-(3-methyl-4,10-dihydro-3H-2,3,4,9-tetraaza-benzo[f]azulen-9-yl)-methanone

Example E68.1

4-(3-Hydroxy-propyl)-piperidine-1-carboxylic Acid Tert-butyl Ester 4-(2-Carboxy-ethyl)-piperidine-1-carboxylic acid tert-butyl ester (1.0 g, 3.9 mmol, according to the procedure described in J. Med. Chem., 41(14), 2492, 1998) was dissolved in THF (50 ml) and cooled down to 0° C. 2M Borane solution in THF (3.9 ml, 7.8 mmol) was added slowly and the mixture was stirred for 20 h at room temperature. Water was added and solvents were concentrated in vacuo. The residue was dissolved in EtOAC, basified with $NaHCO_3$, washed with brine, dried and concentrated in vacuo to yield the title compound (938 mg, 99%).

Example E68.2

4-[3-(4-Methoxycarbonyl-2-methyl-phenoxy)-propyl]-piperidine-1-carboxylic Acid Tert-butyl Ester 4-(3-Hydroxy-propyl)-piperidine-1-carboxylic acid tert-butyl ester from Example E68.1 (400 mg, 1.64 mmol) and 4-hydroxy-3-methyl-benzoic acid methyl ester from Example E29 (274 mg, 1.64 mmol) were dissolved in THF (30 ml) and cooled down to 0° C. Polymer-supported triphenyl-phosphine (1.7 g, 2.46 mmol) then DEAD (0.387 ml, 2.46 mmol) were added and the mixture was heated at re-flux for 20 h. The resin was filtered off, washed with EtOAc and the filtrate was concentrated in vacuo. The residue was purified by flash chromatography on silica gel through an isolute (eluant; 20% EtOAC:80% cyclohexane) to yield the title compound (340 mg, 53%).

Example E68.3

4-[3-(4-Carboxy-2-methyl-phenoxy)-propyl]-piperidine-1-carboxylic Acid Tert-butyl Ester 2M NaOH solution (1.25 ml, 2.5 mmol) was added to 4-[3-(4-methoxycarbonyl-2-methyl-phenoxy)-propyl]-piperidine-1-carboxylic acid tert-butyl ester from Example E68.2 (340 mg, 0.87 mmol) in dioxan (10 ml) and the mixture was heated at 60° C. for 20 h. 2M NaOH solution (5 ml, 10 mmol) was added and the mixture was heated at 60° C. for 20 h then concentrated in vacuo. The residue was purified by flash chromatography on silica gel through an isolute (eluant; 1% acetic acid:9% methanol:90% dichloromethane) to yield the title compound (303 mg, 92%).

Example E68.4

4-{3-[2-Methyl-4-(3-methyl-4,10-dihydro-3H-2,3,4,9-tetraaza-benzo[f]azulene-9-carbonyl)-phenoxy]-propyl}-piperidine-1-carboxylic Acid Tert-butyl Ester PyBroP (224 mg, 0.48 mmol) and DMAP (39 mg, 0.32 mmol) were added to a solution of 4-[3-(4-carboxy-2-methyl-phenoxy)-propyl]-piperidine-1-carboxylic acid tert-butyl ester from Example E68.3 (120 mg, 0.32 mmol) and 3-methyl-3,4,9,10-tetrahydro-2,3,4,9-tetraaza-benzo[f]azulene from Example E11 (70 mg, 0.35 mmol) in dichloromethane (5 ml) and DIEA (0.111 ml, 0.64 mmol). The mixture was heated at reflux for 2 days, washed with saturated $NaHCO_3$ then brine, dried and concentrated in vacuo. The residue was purified by preparative HPLC (eluant; 0.5% 35% ammonia: 9.5% methanol:90% dichloro-methane) to yield the title compound (71 mg, 40%).

Example E68.5

(3-Methyl-4,10-dihydro-3H-2,3,4,9-tetraaza-benzo[f]azulen-9-yl)-[3-methyl-4-(3-piperidin-4-yl-propoxy)-phenyl]-methanone Hydrochloride 4M HCl solution in dioxan (1 ml) was added to a solution of 4-{3-[2-methyl-4-(3-methyl-4,10-dihydro-3H-2,3,4,9-tetraaza-benzo[f]azulene-9-carbonyl)-phenoxy]-propyl}-piperidine-1-carboxylic acid tert-butyl ester from Example E68.4 (71 mg, 0.13 mmol) in methanol (3 ml). The mixture was stirred for 20 h at room temperature then solvents were concentrated in vacuo. The residue was triturated with diethyl ether to yield the title compound (61 mg, 97%).

Example E68.6

(4-{3-[1-(3,3-Dimethyl-butyl)-piperidin-4-yl]-propoxy}-3-methyl-phenyl)-(3-methyl-4,10-dihydro-3H-2,3,4,9-tetraaza-benzo[f]azulen-9-yl)-methanone Acetic acid (0.05 ml) and 3,3-dimethylbutyraldehyde (0.024 ml, 0.19 mmol) were added to a solution of (3-methyl-4,10-dihydro-3H-2,3,4,9-tetraaza-benzo[f]azulen-9-yl)-[3-methyl-4-(3-piperidin-4-yl-propoxy)-phenyl]-methanone hydrochloride from Example E68.5 (60 mg, 0.12 mmol) in methanol (2.45 ml) and triethylamine (0.026 ml, 0.19 mmol). The mixture was stirred at room temperature for 1 h then sodium triacetoxyborohydride (40 mg, 0.19 mmol) was added. The mixture was stirred at room temperature for 18 h, diluted with dichloromethane, washed with saturated $NaHCO_3$ then brine, dried and concentrated in vacuo. The residue was purified by preparative HPLC (eluant; 0.5% 35% ammonia:9.5% methanol:90% dichloromethane) to give a white fluffy solid identified as the title compound (33 mg, 48%).

Example E69

(4-{3-[4-(3,3-Dimethyl-butyl)-piperazin-1-yl]-propoxy}-3-fluoro-phenyl)-(2-methyl-4,5-dihydro-1H-1,3,6-triaza-benzo[e]azulen-6-yl)-methanone

Example E69.1

4-{3-[4-(1-Benzyl-2-methyl-4,5-dihydro-1H-1,3,6-triaza-benzo[e]azulene-6-carbonyl)-2-fluoro-phenoxy]-propyl}-piperazine-1-carboxylic Acid Tert-butyl Ester 4-[3-(4-Carboxy-2-fluoro-phenoxy)-propyl]-piperazine-1-carboxylic acid tert-butyl ester from Example E39 (130 mg, 0.34 mmol) was dissolved in dichloromethane (5 ml) and a few drops of DMF. Oxalyl chloride (0.059 ml, 0.68 mmol) was added slowly and the mixture was stirred for 30 min at room temperature. Solvents were concentrated in vacuo and azeotroped with toluene. The residue was dissolved in dichloromethane (5 ml) and 1-benzyl-2-methyl-1,4,5,6-tetrahydro- 1,3,6-triaza-benzo[e]azulene from Example E5a (100 mg, 0.34 mmol) then DIEA (0.176 ml, 1.02 mmol) were added. The mixture was stirred for 2 h at room temperature, washed with saturated NaHCO₃ then brine, dried and concentrated in vacuo. The residue was purified by preparative HPLC (eluant; 0.5% 35% ammonia:9.5% methanol:90% dichloro-methane) to yield the title compound (110 mg, 50%).

Example E69.2

(1-Benzyl-2-methyl-4,5-dihydro-1H-1,3,6-triaza-benzo[e]azulen-6-yl)-[3-fluoro-4-(3-piperazin-1-yl-propoxy)-phenyl]-methanone Dihydrochloride 4-{3-[4-(1-Benzyl-2-methyl-4,5-dihydro-1H-1,3,6-triaza-benzo[e]azulene-6-carbonyl)-2-fluoro-phenoxy]-propyl}-piperazine-1-carboxylic acid tert-butyl ester from Example E69.1 (110 mg, 0.17 mmol) was dissolved in methanol (5 ml) and 4M HCl in dioxan (2 ml) was added. The mixture was stirred for 20 h at room temperature then concentrated in vacuo to yield the title compound (105 mg, 100%).

Example E69.3

(1-Benzyl-2-methyl-4,5-dihydro-1H-1,3,6-triaza-benzo[e]azulen-6-yl)-(4-{3-[4-(3,3-dimethyl-butyl)-piperazin-1-yl]-propoxy}-3-fluoro-phenyl)-methanone (1-Benzyl-2-methyl-4,5-dihydro-1H-1,3,6-triaza-benzo[e]azulen-6-yl)-[3-fluoro-4-(3-piperazin-1-yl-propoxy)-phenyl]-methanone dihydrochloride from Example E69.2 (105 mg, 0.17 mmol) was dissolved in methanol (2.45 ml) and triethylamine (0.07 ml, 0.50 mmol). Acetic acid (0.05 ml) then 3,3-dimethylbutyraldehyde (0.032 ml, 0.25 mmol) were added and the mixture was stirred for 1 h at room temperature. Sodium cyanoborohydride (16 mg, 0.25 mmol) was added and the mixture was stirred for 3 h at room temperature then concentrated in vacuo. The residue was dissolved in dichloromethane, washed with saturated NaHCO₃ then brine, dried and concentrated in vacuo. The residue was purified by flash chromatography on silica gel (eluant; 5% methanol:95% dichloromethane) to yield the title compound (102 mg, 95%).

Example E69.4

(4-{3-[4-(3,3-Dimethyl-butyl)-piperazin-1-yl]-propoxy}-3-fluoro-phenyl)-(2-methyl-4,5-dihydro-1H-1,3,6-triaza-benzo[e]azulen-6-yl)-methanone (1-Benzyl-2-methyl-4,5-dihydro-1H-1,3,6-triaza-benzo[e]azulen-6-yl)-(4-{3-[4-(3,3-dimethyl-butyl)-piperazin-1-yl]-propoxy}-3-fluoro-phenyl)-methanone from Example E69.3 (90 mg, 0.14 mmol) was dissolved in methanol (5 ml) and acetic acid (1 ml) and hydrogenated over 20 wt. % palladium hydroxide catalyst (90 mg) for 8 h. The mixture was filtered through Celite® filter agent and the filtrate concentrated in vacuo. The residue was dissolved in dichloromethane, washed with saturated NaHCO₃ then brine, dried and concentrated in vacuo. The residue was purified by preparative HPLC (eluant; 0.5% 35% ammonia:9.5% methanol: 90% dichloro-methane) to give a white powder identified as the title compound (39 mg, 51%).

Example E70

(4-{3-[4-(3,3-Dimethyl-butyl)-piperazin-1-yl]-propoxy}-3-methyl-phenyl)-(2-methyl-4,5-dihydro-1H-1,3,6-triaza-benzo[e]azulen-6-yl)-methanone Example E70.1

4-{3-[4-(1-Benzyl-2-methyl-4,5-dihydro-1H-1,3,6-triaza-benzo[e]azulene-6-carbonyl)-2-methyl-phenoxy]-propyl}-piperazine-1-carboxylic Acid Tert-butyl Ester 4-[3-(4-Carboxy-2-methyl-phenoxy)-propyl]-piperazine-1-carboxylic acid tert-butyl ester (350 mg, 0.92 mmol) was dissolved in dichloromethane (5 ml) and a few drops of DMF. Oxalyl chloride (0.162 ml, 1.84 mmol) was added slowly and the mixture was stirred for 30 min at room temperature. Solvents were concentrated in vacuo and azeotroped with toluene. The residue was dissolved in dichloromethane (10 ml) and 1-benzyl-2-methyl-1,4,5,6-tetrahydro-1,3,6-triaza-benzo[e]azulene from Example E5a (268 mg, 0.92 mmol) then DIEA (0.48 ml, 2.77 mmol) were added. The mixture was stirred for 2 days at room temperature, washed with saturated NaHCO₃ then brine, dried and concentrated in vacuo. The residue was purified by preparative HPLC (eluant; 0.5% 35% ammonia:9.5% methanol:90% dichloromethane) to yield the title compound (230 mg, 38%).

Example E70.2

(1-Benzyl-2-methyl-4,5-dihydro-1H-1,3,6-triaza-benzo[e]azulen-6-yl)-[3-methyl-4-(3-piperazin-1-yl-propoxy)-phenyl]-methanone Dihydrochloride 4-{3-[4-(1-Benzyl-2-methyl-4,5-dihydro-1H-1,3,6-triaza-benzo[e]azulene-6-carbonyl)-2-methyl-phenoxy]-propyl}-piperazine-1-carboxylic acid tert-butyl ester from Example E70.1 (230 mg, 0.35 mmol) was dissolved in methanol (5 ml) and 4M HCl in dioxan (2 ml) was added. The mixture was stirred for 2 h at room temperature then concentrated in vacuo and triturated with diethyl ether to yield the title compound (215 mg, 98%).

Example E70.3

(1-Benzyl-2-methyl-4,5-dihydro-1H-1,3,6-triaza-benzo[e]azulen-6-yl)-(4-{3-[4-(3,3-dimethyl-butyl)-piperazin-1-yl]-propoxy}-3-methyl-phenyl)-methanone (1-Benzyl-2-methyl-4,5-dihydro-1H-1,3,6-triaza-benzo[e]azulen-6-yl)-[3-methyl-4-(3-piperazin-1-yl-propoxy)-phenyl]-methanone dihydrochloride from Example E70.2 (100 mg, 0.16 mmol) was dissolved in methanol (2.45 ml) and triethylamine (0.068 ml, 0.48 mmol). Acetic acid (0.05 ml) then 3,3-dimethylbutyraldehyde (0.031 ml, 0.24 mmol) were added and the mixture was stirred for 1 h at room temperature. Sodium cyanoborohydride (16 mg, 0.24 mmol) was added and the mixture was stirred for 20 h at room temperature then concentrated in vacuo. The residue was dissolved in dichloromethane, washed with saturated NaHCO₃ then brine, dried and concentrated in vacuo to yield the title compound (98 mg, 96%).

Example E70.4

(4-{3-[4-(3,3-Dimethyl-butyl)-piperazin-1-yl]-propoxy}-3-methyl-phenyl)-(2-methyl-4,5-dihydro-1H-1,3,6-triaza-benzo[e]azulen-6-yl)-methanone (1-Benzyl-2-methyl-4,5-dihydro-1H-1,3,6-triaza-benzo[e]azulen-6-yl)-(4-{3-[4-(3,3-dimethyl-butyl)-piperazin-1-yl]-propoxy}-3-methyl-phenyl)-methanone from Example E70.3 (98 mg, 0.15 mmol) was dissolved in methanol (5 ml) and acetic acid (1 ml) and hydrogenated over 20 wt. % palladium hydroxide catalyst (98 mg) for 8 h. The mixture was filtered through glass-fibre paper and the filtrate was concentrated in vacuo. The residue was dissolved in dichloromethane, washed with saturated NaHCO$_3$ then brine, dried and concentrated in vacuo. The residue was purified by preparative HPLC (eluant; 0.5% 35% ammonia:9.5% methanol:90% dichloromethane) to give a white powder identified as the title compound (17 mg, 20%).

Example E71

N-(4-Chloro-phenyl)-4-{3-[4-(3,3-dimethyl-butyl)-piperazin-1-yl]-propoxy}-3-fluoro-N-methyl-benzamide

Example E71.1

4-(3-{4-[(4-Chloro-phenyl)-methyl-carbamoyl]-2-fluoro-phenoxy}-propyl)-piperazine-1-carboxylic Acid Tert-butyl Ester PyBroP (606 mg, 1.3 mmol) was added to a solution of 4-[3-(4-carboxy-2-fluoro-phenoxy)-propyl]-piperazine-1-carboxylic acid tert-butyl ester from Example E39 (382 mg, 11.0 mmol) in dichloromethane (20 ml) and DIEA (to pH9). The mixture was stirred for 1 h at room temperature then (4-chloro-phenyl)-methyl amine (156 mg, 1.1 mmol) was added. The mixture was stirred for 2 days at room temperature then solvents were concentrated in vacuo. The residue was dissolved in EtOAC, washed with saturated NaHCO$_3$ then brine, dried and concentrated in vacuo. The residue was purified by flash chromatography on silica gel (eluant; EtOAc) to yield the title compound (210 mg, 41%).

Example E71.2

N-(4-Chloro-phenyl)-3-fluoro-N-methyl-4-(3-piperazin-1-yl-propoxy)-benzamide Dihydrochloride 4-(3-{4-[(4-Chloro-phenyl)-methyl-carbamoyl]-2-fluoro-phenoxy}-propyl)-piperazine-1-carboxylic acid tert-butyl ester from Example E71.1 (210 mg, 0.4 mmol) was dissolved in 4M HCl in dioxan (5 ml) and stirred for 1 h at room temperature. Solvents were concentrated in vacuo and azeotroped with toluene to yield the title compound (184 mg, 100%).

Example E71.3

N-(4-Chloro-phenyl)-4-{3-[4-(3,3-dimethyl-butyl)-piperazin-1-yl]-propoxy}-3-fluoro-N-methyl-benzamide N-(4-Chloro-phenyl)-3-fluoro-N-methyl-4-(3-piperazin-1-yl-propoxy)-benzamide dihydrochloride from Example E71.2 (184 mg, 0.4 mmol) was dissolved in methanol (4.95 ml) and triethylamine (0.167 ml, 1.2 mmol). Acetic acid (0.05 ml) then 3,3-dimethylbutyraldehyde (46 mg, 0.44 mmol) were added and the mixture was stirred for 1 h at room temperature. Sodium cyanoborohydride (31 mg, 0.5 mmol) was added and the mixture was stirred for 20 h at room temperature then concentrated in vacuo. The residue was purified by flash chromatography on silica gel (eluant; 10% methanol:90% dichloromethane) to give a white foam identified as the title compound (77 mg, 37%).

Example E72

(4-(4-[4-(3,3-Dimethyl-butyl)-piperazin-1-yl]-butoxy)-3-fluoro-phenyl)-(3-methyl-4,10-dihydro-3H-2,3,4,9-tetraaza-benzo[f]azulen-9-yl)-methanone

Example E72.1

4-(4-Bromo-butoxy)-3-fluoro-benzoic Acid Ethyl Ester 1,4-Dibromobutane (2.34 g, 10.8 mmol), potassium carbonate (1.86 g, 13.5 mmol) and potassium iodide (90 mg, 0.5 mmol) were added to a solution of 3-fluoro-4-hydroxy-benzoic acid ethyl ester from Example E27 (11.0 g, 5.4 mmol) in acetone (25 ml) and the mixture was heated at reflux for 20 h. The solid was filtered off, washed with EtOAc and the filtrate was concentrated in vacuo. The residue was purified by flash chromatography on silica gel (eluant; 15% EtOAc:85% hexane) to yield the title compound (1.38 g, 80%).

Example E72.2

4-{4-[4-(3,3-Dimethyl-butyl)-piperazin-1-yl]-butoxy}-3-fluoro-benzoic Acid Ethyl Ester 1-(3,3-Dimethyl-butyl)-piperazine hydrochloride from Example E4 (874 mg, 3.7 mmol), potassium carbonate (2.5 g, 18.0 mmol) and potassium iodide (60 mg, 0.4 mmol) were added to a solution of 4-(4-bromo-butoxy)-3-fluoro-benzoic acid ethyl ester from Example E72.1 (1.4 g, 4.4 mmol) in acetone (35 ml) and the mixture was heated at reflux for 20 h. The solid was filtered off, washed with EtOAc and the filtrate was concentrated in vacuo. The residue was purified by flash chromatography on silica gel (eluant; EtOAc to 1% 35% ammonia:10% methanol:89% EtOAc) to yield the title compound (1.35 g, 90%).

Example E72.3

4-{4-[4-(3,3-Dimethyl-butyl)-piperazin-1-yl]-butoxy}-3-fluoro-benzoic Acid

Sodium hydroxide (0.5 g, 13.2 mmol) and water (5 ml) were added to a solution of 4-{4-[4-(3,3-dimethyl-butyl)-piperazin-1-yl]-butoxy}-3-fluoro-benzoic acid ethyl ester from Example E72.2 (1.35 g, 3.3 mmol) in dioxan (20 ml). The mixture was stirred for 1 h at room temperature then heated at 60° C. for 20 h. Solvents were concentrated in vacuo and azeotroped with toluene. The residue was purified by flash chromatography on silica gel (eluant; 1% 35% ammonia:19% methanol:80% chloroform) to yield the title compound (0.85 g, 67%).

Example E72.4

(4-{4-[4-(3,3-Dimethyl-butyl)-piperazin-1-yl]-butoxy}-3-fluoro-phenyl)-(3-methyl-4,10-dihydro-3H-2,3,4,9-tetraaza-benzo[f]azulen-9-yl)-methanone A mixture of 4-{4-[4-(3,3-dimethyl-butyl)-piperazin-1-yl]-butoxy}-3-fluoro-benzoic acid from Example E72.3 (190 mg, 0.5 mmol) and thionyl chloride (2 ml) in di-chloromethane (5 ml) was heated at reflux for 1 h. Sol-vents were concentrated in vacuo and the residue was dissolved in dichloromethane (10 ml). 3-Methyl-3,4,9,10-tetrahydro-2,3,4,9-tetraaza-benzo[f]azulene from Example E11 (110 mg, 0.55 mmol) and DIEA (to pH9) were added. The mixture was stirred at room temperature for 2 days and concentrated in vacuo. The residue was dissolved in EtOAC, washed with saturated NaHCO₃ then brine, dried and concentrated in vacuo. The residue was purified by preparative HPLC (eluant; 0.5% 35% ammonia:9.5% methanol:90% dichloromethane) to give a colourless oil identified as the title compound (48 mg, 17%).

Example E73

(4-(2-[4-(3,3-Dimethyl-butyl)-piperazin-1-yl]-ethoxy)-3-methyl-phenyl)-(3-methyl-4,10-dihydro-3H-2,3,4,9-tetraaza-benzo[f]azulen-9-yl)-methanone WSCD (58 mg, 0.30 mmol) and DMAP (20 mg, 0.15 mmol) were added to a solution of 3-methyl-3,4,9,10-tetrahydro-2,3,4,9-tetraaza-benzo[f]azulene from Example E11 (37 mg, 0.20 mmol) and 4-{2-[4-(3,3-dimethyl-butyl)-piperazin-1-yl]-ethoxy}-3-methyl-benzoic acid from Example E40 (53 mg, 0.15 mmol) in dichloromethane (5 ml) and triethylamine (to pH9). The mixture was heated at re-flux for 2 days then concentrated in vacuo. The residue was dissolved in EtOAC, washed with saturated NaHCO₃ then brine, dried and concentrated in vacuo. The residue was purified by flash chromatography on silica gel (eluant; 10% methanol:90% chloroform) to give an off-white solid identified as the title compound (3.5 mg, 4%).

Example E74

1-[4-(3,3-Dimethyl-butyl)-piperazin-1-yl]-2-[2-methyl-4-(3-methyl-4,10-dihydro-3H-2,3,4,9-tetraaza-benzo[f]azulene-9-carbonyl)-phenoxy]-ethanone Oxalyl chloride (42 mg, 0.34 mmol) and 2 drops of DMF were added to a solution of 4-{2-[4-(3,3-dimethyl-butyl)-piperazin-1-yl]-2-oxo-ethoxy}-3-methyl-benzoic acid from Example E41 (100 mg, 0.28 mmol) in dichloro-methane (5 ml) at 0° C. The mixture was stirred for 1 h at room temperature, concentrated in vacuo and azeotroped with toluene. The residue was dissolved in dichloro-methane (5 ml) and a solution of 3-methyl-3,4,9,10-tetrahydro-2,3,4,9-tetraaza-benzo[f]azulene from Example E11 (61 mg, 0.31 mmol) in dichloromethane (1 ml) and triethylamine (to pH9) was added. The mixture was stirred for 2 days at room temperature then concentrated in vacuo. The residue was dissolved in EtOAC, washed with saturated NaHCO₃ then brine, dried and concentrated in vacuo. The residue was purified twice by flash chromatography on silica gel (eluant; 5% methanol:95% chloroform to 10% methanol:90% chloroform then 5% methanol:95% EtOAc to 10% methanol:90% EtOAc) to give a white solid identified as the title compound (25 mg, 17%).

Example E75

1-[4-(3,3-Dimethyl-butyl)-piperazin-1-yl]-2-[4-(3-methyl-4,10-dihydro-3H-2,3,4,9-tetraaza-benzo[f]azulene-9-carbonyl)-phenoxy]-ethanone

Example E75.1

(4-Benzyloxy-phenyl)-(3-methyl-4,10-dihydro-3H-2,3,4,9-tetraaza-benzo[f]azulen-9-yl)-methanone Oxalyl chloride (0.41 ml, 4.7 mmol) and a few drops of DMF were added to a solution of 4-(benzyloxy)benzoic acid (855 mg, 3.7 mmol) in dichloromethane (15 ml). The mixture was stirred for 2 h at room temperature, concentrated in vacuo and azeotroped with toluene. The residue was dissolved in dichloromethane (10 ml) and a solution of 3-methyl-3,4,9,10-tetrahydro-2,3,4,9-tetraaza-benzo[f]azulene from Example E11 (500 mg, 2.5 mmol) in dichloromethane (10 ml) and triethylamine (0.87 ml, 6.2 mmol) was added. The mixture was stirred for 20 h at room temperature and concentrated in vacuo. The residue was purified by flash chromatography on silica gel (eluant; EtOAc to 3% methanol:97% EtOAc) to yield the title compound (820 mg, 80%).

Example E75.2

(4-Hydroxy-phenyl)-(3-methyl-4,10-dihydro-3H-2,3,4,9-tetraaza-benzo[f]azulen-9-yl)-methanone (4-Benzyloxy-phenyl)-(3-methyl-4,10-dihydro-3H-2,3,4,9-tetraaza-benzo[f]azulen-9-yl)-methanone from Example E75.1 (800 mg, 1.95 mmol) was dissolved in methanol (100 ml) and hydrogenated over 10% Pd/C catalyst (400 mg) for 7 h. The mixture was filtered through Celite® filter agent, washed with chloroform and methanol and the filtrate was concentrated in vacuo to yield the title compound (140 mg, 22%).

Example E75.3

1-[4-(3,3-Dimethyl-butyl)-piperazin-1-yl]-2-[4-(3-methyl-4,10-dihydro-3H-2,3,4,9-tetraaza-benzo[f]azulene-9-carbonyl)-phenoxy]-ethanone Potassium carbonate (104 mg, 0.76 mmol) was added to a mixture of 2-bromo-1-[4-(3,3-dimethyl-butyl)-piperazin-1-yl]-ethanone from Example E37 (110 mg, 0.38 mmol) and (4-hydroxy-phenyl)-(3-methyl-4,10-dihydro-3H-2,3,4,9-tetraaza-benzo[f]azulen-9-yl)-methanone from Example E75.2 (90 mg, 0.28 mmol) in acetonitrile (5 ml). The mixture was heated at reflux for 20 h then concentrated in vacuo. The residue was dissolved in dichloromethane, washed with 5% KHCO₃ solution, dried and concentrated in vacuo. The residue was purified by preparative HPLC (eluant; 0.5% 35% ammonia:9.5% methanol:90% dichloro-methane) to give a white powder identified as the title compound (21 mg, 11%).

Example E76

1-[4-(3,3-Dimethyl-butyl)-piperazin-1-yl]-4-[2-methyl-4-(3-methyl-4,10-dihydro-3H-2,3,4,9-tetraaza-benzo[f]azulene-9-carbonyl)-phenoxy]-butan-1-one

Example E76.1

4-[2-Methyl-4-(3-methyl-4,10-dihydro-3H-2,3,4,9-tetraaza-benzo[f]azulene-9-carbonyl)-phenoxy]-butyric Acid Tert-butyl Ester WSCD (391 mg, 2.06 mmol) and DMAP (133 mg, 1.09 mmol) were added to a solution of 4-(3-tert-butoxycarbonylpropoxy)-3-methyl-benzoic acid from Example E42 (275 mg, 0.94 mmol) and 3-methyl-3,4,9,10-tetrahydro-2,3,4,9-tetraaza-benzo[f]azulene from Example E11 (191 mg, 0.95 mmol) in dichloromethane (30 ml) and triethylamine (0.28 ml, 2.01 mmol). The mixture was heated at reflux for 72 h, washed with 0.3M KHSO$_4$, saturated NaHCO$_3$ then brine, dried and concentrated in vacuo. The residue was purified by flash chromatography on silica gel (eluant; EtOAc) to yield the title compound (80 mg, 18%).

Example E76.2

4-[2-Methyl-4-(3-methyl-4,10-dihydro-3H-2,3,4,9-tetraaza-benzo[f]azulene-9-carbonyl)-phenoxy]-butyric Acid Trifluoroacetic acid (5 ml) was added to a solution of 4-[2-methyl-4-(3-methyl-4,10-dihydro-3H-2,3,4,9-tetraaza-benzo[f]azulene-9-carbonyl)-phenoxy]-butyric acid tert-butyl ester from Example E76.1 (80 mg, 0.17 mmol) in dichloromethane (10 ml). The mixture was stirred for 2 h at room temperature, concentrated in vacuo and azeotroped with dichloromethane to yield the title compound (71 mg, 100%).

Example E76.3

1-[4-(3,3-Dimethyl-butyl)-piperazin-1-yl]-4-[2-methyl-4-(3-methyl-4,10-dihydro-3H-2,3,4,9-tetraaza-benzo[f]azulene-9-carbonyl)-phenoxy]-butan-1-one HBTU (101 mg, 0.27 mmol) was added to a solution of 4-[2-methyl-4-(3-methyl-4,10-dihydro-3H-2,3,4,9-tetraaza-benzo[f]azulene-9-carbonyl)-phenoxy]-butyric acid from E76.2 (71 mg, 0.17 mmol) and 1-(3,3-dimethyl-butyl)-piperazine dihydrochloride from Example E4 (54 mg, 0.22 mmol) in dichloromethane (10 ml) and DIEA (0.15 ml, 0.86 mmol). The mixture was stirred for 20 h at room temperature, washed with saturated NaHCO$_3$ then brine, dried and concentrated in vacuo. The residue was purified by flash chromatography on silica gel (eluant; 6% methanol:94% dichloromethane) to give a white powder identified as the title compound (52 mg, 53%).

Example E77

3-[2-Methyl-4-(3-methyl-4,10-dihydro-3H-2,3,4,9-tetraaza-benzo[f]azulene-9-carbonyl)-phenyl]-propionic Acid piperidin-4-ylmethyl Ester Example E77.1

4-{3-[2-Methyl-4-(3-methyl-4,10-dihydro-3H-2,3,4,9-tetraaza-benzo[f]azulene-9-carbonyl)-phenyl]-propionyloxymethyl}-piperidine-1-carboxylic Acid Benzyl Ester WSCD (107 mg, 0.54 mmol) and DMAP (33 mg, 0.27 mmol) were added to a solution of 3-[2-methyl-4-(3-methyl-4,10-dihydro-3H-2,3,4,9-tetraaza-benzo[f]azulene-9-carbonyl)-phenyl]-propionic acid from Example E45 (106 mg, 0.27 mmol) and 4-hydroxymethyl-piperidine-1-carboxylic acid benzyl ester (81 mg, 0.32 mmol) in di-chloromethane (5 ml) and DIEA (0.095 ml, 0.54 mmol). The mixture was stirred for 3 h at room temperature, washed with saturated NaHCO$_3$ then brine, dried and concentrated in vacuo. The residue was purified by flash chromatography on silica gel through an isolute (eluant; EtOAc) to yield the title compound (44 mg, 26%).

Example E77.2

3-[2-Methyl-4-(3-methyl-4,10-dihydro-3H-2,3,4,9-tetraaza-benzo[f]azulene-9-carbonyl)-phenyl]-propionic Acid piperidin-4-ylmethyl Ester 4-{3-[2-Methyl-4-(3-methyl-4,10-dihydro-3H-2,3,4,9-tetraaza-benzo[f]azulene-9-carbonyl)-phenyl]-propionyloxymethyl}-piperidine-1-carboxylic acid benzyl ester from Example E77.1 (44 mg, 0.07 mmol) was dissolved in methanol (5 ml) and hydrogenated over 10% Pd/C catalyst (5 mg) for 2 h. The mixture was filtered through Celite® filter agent and the filtrate concentrated in vacuo to give a white powder identified as the title compound (34 mg, 98%).

Example E78

Methyl (3-chloro-4-(3,6-dimethyl-4,10-dihydro-3H-2,3,4,9-tetraaza-benzo[f]azulene-9-carbonyl)-phenoxy)acetate Diisopropylethylamine (2.1 ml, 12.0 mmol), dimethylamino-pyridine (0.74 g, 6.0 mmol), PyBroP® (4.20 g, 9.0 mmol) and 3,6-dimethyl-4,10-dihydro-3H-2,3,4,9-tetraaza-benzo[f]azulene from Example E2 (1.28 g, 6.0 mmol) were added to a solution of tert-butyl 4-(2-(4-carboxy-3-chlorophenoxy)-acetyl)-piperazine-1-carboxylate from Example E41c (2.39 g, 6.0 mmol) in dichloromethane (50 ml) and the mixture was heated at reflux for 20 h. The reaction mixture was cooled, diluted with dichloromethane (50 ml), washed with saturated aqueous sodium hydrogen carbonate, dried and concentrated in vacuo. The residue was dissolved in methanol (150 ml) and treated with a 4M solution of hydrogen chloride in dioxan (50 ml), with cooling in an ice bath. The solution was stirred at room temperature for 16 h. The reaction mixture was evaporated and the residue taken up in water and washed with chloroform. The aqueous was treated with solid sodium hydrogen carbonate until basic pH, extracted into chloroform, dried and evaporated. The residue was purified by flash chromatography on silica gel (eluant; EtOAc followed by a 2% to 10% methanol:98% to 90% EtOAc gradient) to yield a white solid identified as the title compound (0.53 g, 20%).

Example E79

1-(4-Hydroxymethyl-piperidin-1-yl)-3-[2-methyl-4-(3-methyl-4,10-dihydro-3H-2,3,4,9-tetraaza-benzo[f]azulene-9-carbonyl)-phenyl]-propan-1-one Sodium borohydride (12 mg, 0.32 mmol) was added to a solution of 1-{3-[2-methyl-4-(3-methyl-4,10-dihydro-3H-2,3,4,9-tetraaza-benzo[f]azulene-9-carbonyl)-phenyl]-propionyl}-piperidine-4-carbaldehyde from Example E58.1 (74 mg, 0.15 mmol) in methanol (6 ml). The mixture was stirred for 1 h at room temperature, acidified with 1M HCl and concentrated in vacuo. The residue was dissolved in EtOAc, washed with saturated NaHCO$_3$ then brine, dried and concentrated in vacuo. The residue was crystallised from chloroform and pet. ether to give a white powder identified as the title compound (28 mg, 38%).

Example E80

1-[4-(3,3-Dimethyl-butyl)-piperazin-1-yl]-3-[4-(3,4-dimethyl-4,10-dihydro-3H-2,3,4,9-tetraaza-benzo[f]azulene-9-carbonyl)-2-methyl-phenyl]-propan-1-one

Example E80.1

3-[4-(3,4-Dimethyl-4,10-dihydro-3H-2,3,4,9-tetraaza-benzo[f]azulene-9-carbonyl)-2-methyl-phenyl]-propionic Acid Tert-butyl Ester Sodium hydride (14 mg, 0.34 mmol) was added to a solution of 3-[2-methyl-4-(3-methyl-4,10-dihydro-3H-2,3,4,9-tetraaza-benzo[f]azulene-9-carbonyl)-phenyl]-propionic acid tert-butyl ester from Example E45 (125 mg, 0.28 mmol) in DMF (2 ml) at 0° C. The mixture was stirred for 20 min at room temperature then cooled down to 0° C. Methyl iodide (0.09 ml, 1.4 mmol) was added and the mixture was stirred for 20 h at room temperature. EtOAc was added and the mixture was washed with 0.3M $KHSO_4$ then brine, dried, concentrated in vacuo and azeotroped with toluene. The residue was purified by flash chromatography on silica gel through an isolute (eluant; EtOAc) to yield the title compound (46 mg, 36%).

Example E80.2

3-[4-(3,4-Dimethyl-4,10-dihydro-3H-2,3,4,9-tetraaza-benzo[f]azulene-9-carbonyl)-2-methyl-phenyl]-propionic Acid Trifluoroacetic acid (2 ml) was added to 3-[4-(3,4-dimethyl-4,10-dihydro-3H-2,3,4,9-tetraaza-benzo[f]azulene-9-carbonyl)-2-methyl-phenyl]-propionic acid tert-butyl ester from Example E80.1 (46 mg, 0.10 mmol) in dichloromethane (5 ml). The mixture was stirred for 2 h at room temperature then concentrated in vacuo to yield the title compound (40 mg, 100%).

Example E80.3

1-[4-(3,3-Dimethyl-butyl)-piperazin-1-yl]-3-[4-(3,4-dimethyl-4,10-dihydro-3H-2,3,4,9-tetraaza-benzo[f]azulene-9-carbonyl)-2-methyl-phenyl]-propan-1-one Oxalyl chloride (0.018 ml, 0.20 mmol) was added to a solution of 3-[4-(3,4-dimethyl-4,10-dihydro-3H-2,3,4,9-tetraaza-benzo[f]azulene-9-carbonyl)-2-methyl-phenyl]-propionic acid from Example E80.2 (40 mg, 0.10 mmol) in dichloromethane (5 ml) and a few drops of DMF. The mixture was stirred for 1 h at room temperature, concentrated in vacuo and azeotroped with toluene. The residue was dissolved in dichloromethane (5 ml) and 1-(3,3-dimethyl-butyl)-piperazine dihydrochloride from Example E4 (30 mg, 0.12 mmol) and DIEA (0.052 ml, 0.30 mmol) were added. The mixture was stirred for 20 h at room temperature, washed with saturated $NaHCO_3$ then brine, dried and concentrated in vacuo. The residue was purified by preparative HPLC (eluant; 0.5% 35% ammonia:9.5% methanol:90% dichloromethane) to give a white powder identified as the title compound (36 mg, 65%).

Example E81

1-[4-(3,3-Dimethyl-butyl)-piperazin-1-yl]-4-[2-methyl-4-(2,3,4,5-tetrahydro-benzo[e][1,4]diazepine-1-carbonyl)-phenyl]-butan-1-one

Example E81.1

1-(4-{4-[4-(3,3-Dimethyl-butyl)-piperazin-1-yl]-4-oxo-butyl}-3-methyl-benzoyl)-1,2,3,5-tetrahydro-benzo[e][1,4]diazepine-4-carboxylic Acid Tert-butyl Ester WSCD (58 mg, 0.30 mmol) and DMAP (18 mg, 0.15 mmol) were added to a solution of 4-{4-[4-(3,3-dimethyl-butyl)-piperazin-1-yl]-4-oxo-butyl}-3-methyl-benzoic acid from Example E43 (55 mg, 0.15 mmol) and 1,2,3,5-tetrahydro-benzo[e][1,4]diazepine-4-carboxylic acid tert-butyl ester (73 mg, 0.30 mmol) in dichloromethane (3 ml) and DIEA (0.052 ml, 0.30 mmol). The mixture was heated at reflux for 5 days, washed with saturated $NaHCO_3$ then brine, dried and concentrated in vacuo. The residue was purified by preparative HPLC (eluant; 0.5% 35% ammonia:9.5% methanol:90% dichloromethane) to yield the title compound (25 mg, 28%).

Example E81.2

1-[4-(3,3-Dimethyl-butyl)-piperazin-1-yl]-4-[2-methyl-4-(2,3,4,5-tetrahydro-benzo[e][1,4]diazepine-1-carbonyl)-phenyl]-butan-1-one 1-(4-{4-[4-(3,3-Dimethyl-butyl)-piperazin-1-yl]-4-oxo-butyl}-3-methyl-benzoyl)-1,2,3,5-tetrahydro-benzo[e][1,4]diazepine-4-carboxylic acid tert-butyl ester from Example E81.1 (25 mg, 0.04 mmol) was dissolved in methanol (2 ml) and 4M HCl in dioxan (2 ml) was added. The mixture was stirred for 1 h at room temperature then concentrated in vacuo to give a white powder identified as the title compound (6 mg, 28%). (ESI)+: [M+H]+=505.5

Example E82

4-[4-(7,8-Dihydro-6H-5-oxa-9-aza-benzocycloheptene-9-carbonyl)-2-methyl-phenyl]-1-[4-(3,3-dimethyl-butyl)-piperazin-1-yl]-butan-1-one WSCD (58 mg, 0.30 mmol) and DMAP (18 mg, 0.15 mmol) were added to a solution of 4-{4-[4-(3,3-dimethyl-butyl)-piperazin-1-yl]-4-oxo-butyl}-3-methyl-benzoic acid from Example E43 (55 mg, 0.15 mmol) and 6,7,8,9-tetrahydro-5-oxa-9-aza-benzocycloheptene (44 mg, 0.30 mmol) in di-chloromethane (3 ml) and DIEA (0.052 ml, 0.30 mmol). The mixture was heated at reflux for 5 days, washed with saturated $NaHCO_3$ then brine, dried and concentrated in vacuo. The residue was purified by preparative HPLC (eluant; 0.5% 35% ammonia:9.5% methanol:90% dichloro-methane) to give a white solid identified as the title compound (6 mg, 10%).

Example E83

1-[4-(3,3-Dimethyl-butyl)-piperazin-1-yl]-5-[2-methyl-4-(3-methyl-4,10-dihydro-3H-2,3,4,9-tetraaza-benzo[f]azulene-9-carbonyl)-phenyl]-pentan-1-one

Example E83.1

5-[2-Methyl-4-(3-methyl-4,10-dihydro-3H-2,3,4,9-tetraaza-benzo[f]azulene-9-carbonyl)-phenyl]-pentanoic Acid Methyl Ester WSCD (822 mg, 4.3 mmol) and DMAP (273 mg, 2.2 mmol) were added to a solution of 4-(4-methoxycarbonyl-butyl)-3-methyl-benzoic acid from Example E31 (571 mg, 2.3 mmol) and 3-methyl-3,4,9,10-tetrahydro-2,3,4,9-tetraaza-benzo[f]azulene from Example E11 (424 mg, 2.1 mmol) in dichloromethane (50 ml) and triethylamine (0.6 ml, 4.3 mmol). The mixture was heated at reflux for 72 h, diluted with dichloromethane, washed with 0.3M $KHSO_4$, saturated $NaHCO_3$ then brine, dried and concentrated in vacuo. The residue was purified by flash chromatography on silica gel (eluant; EtOAc to 5% triethyamine: 95% EtOAc) to yield the title compound (424 mg, 46%).

Example E83.2

5-[2-Methyl-4-(3-methyl-4,10-dihydro-3H-2,3,4,9-tetraaza-benzo[f]azulene-9-carbonyl)-phenyl]-pentanoic Acid Lithium hydroxide monohydrate (120 mg, 2.86 mmol) was added to a solution of 5-[2-methyl-4-(3-methyl-4,10-dihydro-3H-2,3,4,9-tetraaza-benzo[f]azulene-9-carbonyl)-phenyl]-pentanoic acid methyl ester from Example E83.1 (410 mg, 0.95 mmol) in THF (10 ml) and water (5 ml). The mixture was stirred for 24 h at room temperature and concentrated in vacuo. The residue was acidified with 1M HCl and extracted with chloroform. The organic layer was washed with brine, dried and concentrated in vacuo. The residue was purified by flash chromatography on silica gel (eluant; 3% acetic acid:7% methanol:90% chloroform) to yield the title compound (105 mg, 26%).

Example E83.3

1-[4-(3,3-Dimethyl-butyl)-piperazin-1-yl]-5-[2-methyl-4-(3-methyl-4,10-dihydro-3H-2,3,4,9-tetraaza-benzo[f]azulene-9-carbonyl)-phenyl]-pentan-1-one HBTU (104 mg, 0.27 mmol) was added to a solution of 5-[2-methyl-4-(3-methyl-4,10-dihydro-3H-2,3,4,9-tetraaza-benzo[f]azulene-9-carbonyl)-phenyl]-pentanoic acid from E83.2 (105 mg, 0.25 mmol) and 1-(3,3-dimethyl-butyl)-piperazine dihydrochloride from Example E4 (69 mg, 0.28 mmol) in DMF (10 ml) and DIEA (0.2 ml, 1.15 mmol). The mixture was stirred for 24 h at room temperature then concentrated in vacuo. The residue was dissolved in di-chloromethane, washed with saturated $NaHCO_3$ then brine, dried and concentrated in vacuo. The residue was purified by flash chromatography on silica gel (eluant; 4% methanol:96% dichloromethane to 8% methanol:92% di-chloromethane) to give a white solid identified as the title compound (88 mg, 62%).

Example E84

1-(4-Hydroxy-piperidin-1-yl)-3-[2-methyl-4-(3-methyl-4,10-dihydro-3H-2,3,4,9-tetraaza-benzo[f]azulene-9-carbonyl)-phenyl]-propan-1-one Sodium borohydride (4 mg, 0.1 mmol) was added to a solution of 1-{3-[2-methyl-4-(3-methyl-4,10-dihydro-3H-2,3,4,9-tetraaza-benzo[f]azulene-9-carbonyl)-phenyl]-propionyl}-piperidin-4-one (Compound number 701) (50 mg, 0.11 mmol) in methanol/acetic acid (99:1, v/v, 100 ml) and the mixture was stirred at room temperature for 1 h. Sodium borohydride (4 mg, 0.11 mmol) was added again and the mixture was stirred for 1 h at room temperature then concentrated in vacuo. The residue was dissolved in di-chloromethane, washed with saturated $NaHCO_3$ then brine, dried and concentrated in vacuo to give a white powder identified as the title compound (28 mg, 56%).

Example E85

1-(4-Cyclobutylmethyl-piperazin-1-yl)-2-[2-methyl-4-(3-methyl-4,10-dihydro-3H-2,3,4,9-tetraaza-benzo[f]azulene-9-carbonyl)-phenyl]-ethanone

Example E85.1

4-[2-(4-Cyclobutylmethyl-piperazin-1-yl)-2-oxo-ethyl]-3-methyl-benzoic Acid Methyl Ester Oxalyl chloride (0.36 ml, 3.3 mmol) was added to a solution of 4-carboxymethyl-3-methyl-benzoic acid methyl ester from Example E32 (687 mg, 3.3 mmol) in dichloromethane (20 ml) and few drops of DMF. The mixture was stirred for 3 h at room temperature, concentrated in vacuo and azeotroped with toluene. The residue was dissolved in dichloromethane (10 ml) and added to a solution of 1-cyclobutylmethyl-piperazine dihydrochloride (750 mg, 3.3 mmol) in dichloromethane (10 ml) and DIEA (1.73 ml, 9.9 mmol) at 0° C. The mixture was stirred for 20 h at room temperature and concentrated in vacuo. The residue was purified by flash chromatography on silica gel (eluant; 3% methanol:97% dichloromethane) to yield the title compound (528 mg, 46%).

Example E85.2

4-[2-(4-Cyclobutylmethyl-piperazin-1-yl)-2-oxo-ethyl]-3-methyl-benzoic Acid

Lithium hydroxide monohydrate (122 mg, 2.9 mmol) was added to a solution of 4-[2-(4-cyclobutylmethyl-piperazin-1-yl)-2-oxo-ethyl]-3-methyl-benzoic acid methyl ester from Example E85.1 (500 mg, 1.4 mmol) in THF (10 ml) and water (5 ml). The mixture was stirred for 20 h at room temperature and concentrated in vacuo. The residue was purified by flash chromatography on silica gel (eluant; 3% acetic acid:7% methanol:90% chloroform) to yield the title compound (300 mg, 63%).

Example E85.3

1-(4-Cyclobutylmethyl-piperazin-1-yl)-2-[2-methyl-4-(3-methyl-4,10-dihydro-3H-2,3,4,9-tetraaza-benzo[f]azulene-9-carbonyl)-phenyl]-ethanone WSCD (76 mg, 0.39 mmol) and DMAP (7 mg, 0.06 mmol) were added to a solution of 4-[2-(4-cyclobutylmethyl-piperazin-1-yl)-2-oxo-ethyl]-3-methyl-benzoic acid from Example E85.2 (100 mg, 0.30 mmol) and 3-methyl-3,4,9,10-tetrahydro-2,3,4,9-tetraaza-benzo[f]azulene from Example E11 (61 mg, 0.30 mmol) in dichloromethane (20 ml) and DIEA (0.16 ml, 0.91 mmol). The mixture was heated at reflux for 20 h and concentrated in vacuo. The residue was purified by flash chromatography on silica gel (eluant; 4% methanol: 96% dichloromethane to 6% methanol:94% dichloromethane to 1% 35% ammonia:7% methanol:92% dichloromethane) to give an off-white solid identified as the title compound (50 mg, 32%).

Example E86

1-(4-Cyclopropylaminomethyl-piperidin-1-yl)-3-[2-methyl-4-(3-methyl-4,10-dihydro-3H-2,3,4,9-tetraaza-benzo[f]azulene-9-carbonyl)-phenyl]-propan-1-one

Example E86.1

4-(3-{4-[(tert-Butoxycarbonyl-cyclopropyl-amino)-methyl]-piperidin-1-yl}-3-oxo-propyl)-3-methyl-benzoic Acid Methyl Ester Oxalyl chloride (1.26 ml, 14.4 mmol) was added to a solution of 4-(2-carboxy-ethyl)-3-methyl-benzoic acid methyl ester from Example E30.3 (1.60 g, 7.2 mmol) in dichloromethane (50 ml) and few drops of DMF. The mixture was stirred for 1 h at room temperature, concentrated in vacuo and azeotroped with toluene. The residue was dissolved in dichloromethane (50 ml) and DIEA (2.5 ml, 14.4 mmol) and cyclopropyl-piperidin-4-ylmethyl-carbamic acid tert-butyl ester from Example E38 (1.83 g, 7.2 mmol) in dichloromethane (5 ml) was added. The mixture was stirred for 2 h at room temperature, diluted with dichloromethane, washed with saturated NaHCO₃ then brine, dried and concentrated in vacuo. The residue was purified by flash chromatography on silica gel (eluant; 50% EtOAc:50% cyclohexane) to yield the title compound (1.42 g, 43%).

Example E86.2

4-(3-{4-[(tert-Butoxycarbonyl-cyclopropyl-amino)-methyl]-piperidin-1-yl}-3-oxo-propyl)-3-methyl-benzoic Acid Lithium hydroxide monohydrate (142 mg, 3.4 mmol) was added to a solution of 4-(3-{4-[(tert-butoxycarbonyl-cyclopropyl-amino)-methyl]-piperidin-1-yl}-3-oxo-propyl)-3-methyl-benzoic acid methyl ester from Example E86.1 (1.41 g, 3.1 mmol) in THF (20 ml) and water (2 ml). The mixture was stirred for 16 h at room temperature then 1M NaOH solution (5 ml) was added. The mixture was heated at 60° C. for 3 h then concentrated in vacuo. The residue was dissolved in EtOAc, washed with 1M HCl then brine, dried and concentrated in vacuo to yield the title compound (1.25 g, 91%).

Example E86.3

Cyclopropyl-(1-{3-[2-methyl-4-(3-methyl-4,10-dihydro-3H-2,3,4,9-tetraaza-benzo[f]azulene-9-carbonyl)-phenyl]-propionyl}-piperidin-4-ylmethyl)-carbamic Acid Tert-butyl Ester WSCD (1.08 g, 5.6 mmol) and DMAP (343 mg, 2.8 mmol) were added to a solution of 4-(3-{4-[(tert-butoxycarbonyl-cyclopropyl-amino)-methyl]-piperidin-1-yl}-3-oxo-propyl)-3-methyl-benzoic acid from Example E86.2 (1.25 g, 2.8 mmol) in dichloromethane (100 ml) and triethylamine (0.783 ml, 5.6 mmol). The mixture was stirred for 1 h at room temperature then 3-methyl-3,4,9,10-tetrahydro-2,3,4,9-tetraaza-benzo[f]azulene from Example E11 (676 mg, 3.4 mmol) was added. The mixture was heated at reflux for 2 days, washed with saturated NaHCO₃ then brine, dried and concentrated in vacuo. The residue was purified by flash chromatography on silica gel (eluant; 2% methanol:98% EtOAc to 5% methanol:95% EtOAc) to yield the title compound (1.1 g, 62%).

Example E86.4

1-(4-Cyclopropylaminomethyl-piperidin-1-yl)-3-[2-methyl-4-(3-methyl-4,10-dihydro-3H-2,3,4,9-tetraaza-benzo[f]azulene-9-carbonyl)-phenyl]-propan-1-one Cyclopropyl-(1-{3-[2-methyl-4-(3-methyl-4,10-dihydro-3H-2,3,4,9-tetraaza-benzo[f]azulene-9-carbonyl)-phenyl]-propionyl}-piperidin-4-ylmethyl)-carbamic acid tert-butyl ester from Example E86.3 (220 mg, 0.35 mmol) was dissolved in methanol (5 ml) and 4M HCl solution in dioxan (5 ml) was added. The mixture was stirred for 2 h at room temperature then concentrated in vacuo to give an off-white solid identified as the title compound (189 mg, 95%).

Example E87

N-Cyclopropyl-3-[2-methyl-4-(3-methyl-4,10-dihydro-3H-2,3,4,9-tetraaza-benzo[f]azulene-9-carbonyl)-phenyl]-N-piperidin-4-ylmethyl-propionamide hydrochloride

Example E87.1

4-[(Cyclopropyl-{3-[2-methyl-4-(3-methyl-4,10-dihydro-3H-2,3,4,9-tetraaza-benzo[f]azulene-9-carbonyl)-phenyl]-propionyl}-amino)-methyl]-piperidine-1-carboxylic Acid Tert-butyl Ester PyBroP (238 mg, 0.51 mmol) was added to a solution of 3-[2-methyl-4-(3-methyl-4,10-dihydro-3H-2,3,4,9-tetraaza-benzo[f]azulene-9-carbonyl)-phenyl]-propionic acid from Example E45 (200 mg, 0.51 mmol) and 4-cyclopropylaminomethyl-piperidine-1-carboxylic acid tert-butyl ester (130 mg, 0.51 mmol) in dichloromethane (10 ml) and DIEA (0.18 ml, 1.02 mmol). The mixture was stirred for 4 days at room temperature, diluted with EtOAc, washed with 5% KHCO₃ then brine, dried and concentrated in vacuo. The residue was purified by flash chromatography on silica gel (eluant; 5% methanol:95% dichloromethane) to yield the title compound (235 mg, 73%).

Example E87.2

N-Cyclopropyl-3-[2-methyl-4-(3-methyl-4,10-dihydro-3H-2,3,4,9-tetraaza-benzo[f]azulene-9-carbonyl)-phenyl]-N-piperidin-4-ylmethyl-propionamide Hydrochloride 4-[(Cyclopropyl-{3-[2-methyl-4-(3-methyl-4,10-dihydro-3H-2,3,4,9-tetraaza-benzo[f]azulene-9-carbonyl)-phenyl]-propionyl}-amino)-methyl]-piperidine-1-carboxylic acid tert-butyl ester from Example E87.1 (235 mg, 0.37 mmol) was dissolved in 4M HCl solution in dioxan (5 ml). The mixture was stirred for 1 h at room temperature, concentrated in vacuo and azeotroped with toluene. The residue was dissolved in 1M HCl, washed twice with dichloromethane and freeze-dried to give an off-white solid identified as the title compound (82 mg, 39%).

Example E88

1-Methyl-5-(3-methyl-2-nitro-phenylamino)-1H-pyrazole-4-carboxylic Acid Ethyl Ester Cesium carbonate (35.2 g, 108 mmol), 4,5-bis(diphenylphosphino)-9,9-dimethylxanthene (0.4 g, 0.7 mmol) and tris(dibenzylideneacetone)dipalladium(0) (0.2 g, 0.2 mmol) were added to a solution of ethyl 5-amino-1-methylpyrazole-4-carboxylate (15.3 g, 90 mmol) in dioxan (50 ml) under an inert atmosphere. A solution of 3-bromo-2-nitrotoluene (16.2 g, 75 mmol) in dioxane (10 ml) was added and the mixture was stirred for 30 min at room temperature then heated at reflux for 72 h. The suspension was filtered through Celite® filter agent, washed with EtOAc and the filtrate was concentrated in vacuo. The residue was purified by flash chromatography on silica gel (eluant; 50% EtOAc:50% pet. ether) then recrystallised from EtOAc/pet. ether to yield the title compound (12.5 g, 45%).

Example E89

5-Amino-1-ethyl-1H-pyrazole-4-carboxylic Acid Ethyl Ester

Triethylamine (19.6 ml, 144 mmol) was added cautiously to a solution of ethyl (ethoxymethylene)cyanoacetate (10.1 g, 60 mmol) and ethyl hydrazine oxalate (9.9 g, 66 mmol) in ethanol (200 ml). The mixture was heated at reflux for 24 h then concentrated in vacuo. The residue was redissolved in EtOAc, washed with 5% $KHCO_3$ solution then brine, dried and concentrated in vacuo. The residue was purified by flash chromatography on silica gel (eluant; 25% pet. ether:75% EtOAc) to yield the title compound (8.8 g, 80%).

Example E90

1-Cyclopropylmethyl-piperidine-4-carboxylic acid 3-fluoro-4-(3-methyl-4,10-dihydro-3H-2,3,4,9-tetraaza-benzo[f]azulene-9-carbonyl)-benzylamide

Example E90.1

[3-Fluoro-4-(3-methyl-4,10-dihydro-3H-2,3,4,9-tetraaza-benzo[f]azulene-9-carbonyl)-benzyl]-carbamic Acid Tert-butyl Ester A mixture of 4-(tert-butoxycarbonylamino-methyl)-2-fluoro-benzoic acid from Example E2 (1.35 g, 5.0 mmol), 3-methyl-3,4,9,10-tetrahydro-2,3,4,9-tetraaza-benzo[f]azulene from Example E11 (11.0 g, 5.0 mmol) and PyBroP (3.03 g, 6.5 mmol) in dichloromethane (25 ml) and DIEA (1.31 ml, 7.5 mmol) was heated at reflux for 18 h. After cooling to room temperature, the mixture was washed with 5% $KHCO_3$, 1M HCl then brine, dried and concentrated in vacuo. The residue was purified by flash chromatography on silica gel (eluant; EtOAc) to yield the title compound (1.25 g, 56%).

Example E90.2

(4-Aminomethyl-2-fluoro-phenyl)-(3-methyl-4,10-dihydro-3H-2,3,4,9-tetraaza-benzo[f]azulen-9-yl)-methanone Hydrochloride

[3-Fluoro-4-(3-methyl-4,10-dihydro-3H-2,3,4,9-tetraaza-benzo[f]azulene-9-carbonyl)-benzyl]-carbamic acid tert-butyl ester from Example E90.1 (1.25 g, 2.8 mmol) was re-acted with 4N HCl/dioxan using an analogous procedure to that described for Example E4.2 to yield the title compound (11.0 g, 97%).

Example E90.3

1-Cyclopropylmethyl-piperidine-4-carboxylic acid 3-fluoro-4-(3-methyl-4,10-dihydro-3H-2,3,4,9-tetraaza-benzo[f]azulene-9-carbonyl)-benzylamide HBTU (227 mg, 0.6 mmol) was added to a solution of 1-cyclopropylmethyl-piperidine-4-carboxylic acid from Example E15a (99 mg, 0.45 mmol) in DMF (5 ml) and DIEA (to pH9). The mixture was stirred at room temperature for 1 h. (4-Aminomethyl-2-fluoro-phenyl)-(3-methyl-4,10-dihydro-3H-2,3,4,9-tetraaza-benzo[f]azulen-9-yl)-methanone hydrochloride from Example E90.2 (116 mg, 0.3 mmol) was added and the mixture was stirred at room temperature for 18 h. Solvents were removed in vacuo and azeotroped with toluene. The residue was redissolved in EtOAc, washed with saturated $NaHCO_3$ then brine, dried and concentrated in vacuo. The residue was purified by flash chromatography on silica gel (eluant; 1% 35% ammonia:19% methanol:80% dichloromethane) to give a white solid identified as the title compound (71.5 mg, 46%).

Example E91

N-[2-Methyl-4-(3-methyl-4,10-dihydro-3H-2,3,4,9-tetraaza-benzo[f]azulene-9-carbonyl)-benzyl]-2-piperidin-4-yl-acetamide Hydrochloride A solution of 4-{[2-methyl-4-(3-methyl-4,10-dihydro-3H-2,3,4,9-tetraaza-benzo[f]azulene-9-carbonyl)-benzylcarbamoyl]-methyl}-piperidine-1-carboxylic acid tert-butyl ester (Compound number 1067) (156 mg, 0.27 mmol) was reacted with 4N HCl/dioxan using an analogous procedure to that described for Example E4.2 to yield the title compound (135 mg, 97%).

Example E92

2-[1-(3,3-Dimethyl-butyl)-piperidin-4-yl]-N-[2-methyl-4-(3-methyl-4,10-dihydro-3H-2,3,4,9-tetraaza-benzo[f]azulene-9-carbonyl)-benzyl]-acetamide 3,3-Dimethylbutyraldehyde (0.048 ml, 0.38 mmol) was added to a solution of N-[2-methyl-4-(3-methyl-4,10-dihydro-3H-2,3,4,9-tetraaza-benzo[f]azulene-9-carbonyl)-benzyl]-2-piperidin-4-yl-acetamide from Example E91 (130 mg, 0.25 mmol) in methanol/acetic acid (49:1, v/v, 2.5 ml) and the mixture was stirred at room temperature for 1 h. Sodium cyanoborohydride (24 mg, 0.38 mmol) was added, and the mixture was stirred at room temperature for 18 h then concentrated in vacuo. The residue was dissolved in dichloromethane, washed with saturated Na—HCO₃ then brine, dried and concentrated in vacuo. The residue was purified by flash chromatography on silica gel through an isolute (eluant; 1.5%:35% ammonia:15% methanol:83.5% dichloromethane) to give a white solid identified as the title compound (107 mg, 75%).

Example E93

1-Propyl-piperidine-4-carboxylic Acid 2-chloro-4-(3-methyl-4,10-dihydro-3H-2,3,4,9-tetraaza-benzo[f]azulene-9-carbonyl)-benzylamide A solution of propionaldehyde (0.29 mg, 0.005 mmol) in 1,2-dichloroethane (0.05 ml) was added to a solution of piperidine-4-carboxylic acid 2-chloro-4-(3-methyl-4,10-dihydro-3H-2,3,4,9-tetraaza-benzo[f]azulene-9-carbonyl)-benzylamide hydrochloride (Compound number 1109) (2.8 mg, 0.005 mmol) in 1,2-dichloroethane (0.05 ml) and DIEA (0.0026 ml). The mixture was stirred at room temperature for 1 h then a solution of sodium triacetoxyborohydride (1.59 mg, 0.0075 mmol) in DMF (0.05 ml) was added. The mixture was stirred for 20 h at room temperature then solvents were removed in vacuo to yield the title compound. (ESI)+: [M+H]+=521.4

Example E94

N-[4-(3,6-Dimethyl-4,10-dihydro-3H-2,3,4,9-tetraaza-benzo[f]azulene-9-carbonyl)-2-fluoro-benzyl]-2-(1-hexyl-piperidin-4-yl)-acetamide A solution of 1-bromohexane (0.83 mg, 0.005 mmol) in DMF (0.05 ml) was added to a solution of N-[4-(3,6-dimethyl-4,10-dihydro-3H-2,3,4,9-tetraaza-benzo[f]azulene-9-carbonyl)-2-fluoro-benzyl]-2-piperidin-4-yl-acetamide hydrochloride (Compound number 1110) (2.82 mg, 0.005 mmol) in DMF (0.05 ml) and triethyl-amine (0.0021 ml). The mixture was stirred for 20 h at room temperature then solvents were removed in vacuo to yield the title compound. (ESI)+: [M+H]+=575.7

Example E95

N-[4-(6-Chloro-3-methyl-4,10-dihydro-3H-2,3,4,9-tetraaza-benzo[f]azulene-9-carbonyl)-3-methyl-benzyl]-3-(1-propionyl-piperidin-4-yl)-propionamide A solution of propionyl chloride (0.46 mg, 0.005 mmol) in dichloromethane (0.05 ml) was added to a solution of N-[4-(6-chloro-3-methyl-4,10-dihydro-3H-2,3,4,9-tetraaza-benzo[f]azulene-9-carbonyl)-3-methyl-benzyl]-3-piperidin-4-yl-propionamide hydrochloride (Compound number 1108) (2.97 mg, 0.005 mmol) in dichloromethane (0.05 ml) and triethylamine (0.0035 ml). The mixture was stirred at room temperature for 1 h then solvents were removed in vacuo to yield the title compound. (ESI)+: [M+H]+=577.4

Example E96

N-[4-(6-Chloro-3-methyl-4,10-dihydro-3H-2,3,4,9-tetraaza-benzo[f]azulene-9-carbonyl)-3-methyl-benzyl]-3-(1-ethanesulfonyl-piperidin-4-yl)-propionamide A solution of ethanesulfonyl chloride (0.64 mg, 0.005 mmol) in dichloromethane (0.05 ml) was added to a solution of N-[4-(6-chloro-3-methyl-4,10-dihydro-3H-2,3,4,9-tetraaza-benzo[f]azulene-9-carbonyl)-3-methyl-benzyl]-3-piperidin-4-yl-propionamide hydrochloride (Compound number 1108) (2.97 mg, 0.005 mmol) in dichloro-methane (0.05 ml) and triethylamine (0.0035 ml). The mixture was stirred at room temperature for 1 h then sol-vents were removed in vacuo to yield the title compound. (ESI)+: [M+H]+=613.4

Example E97

4-{2-[4-(6-Chloro-3-methyl-4,10-dihydro-3H-2,3,4,9-tetraaza-benzo[f]azulene-9-carbonyl)-3-methyl-benzylcarbamoyl]-ethyl}-piperidine-1-carboxylic Acid 4-nitro-benzyl Ester A solution of 4-nitrobenzyl chloroformate (1.08 mg, 0.005 mmol) in dichloromethane (0.05 ml) was added to a solution of N-[4-(6-chloro-3-methyl-4,10-dihydro-3H-2,3,4,9-tetraaza-benzo[f]azulene-9-carbonyl)-3-methyl-benzyl]-3-piperidin-4-yl-propionamide hydrochloride (Compound number 1108) (2.97 mg, 0.005 mmol) in dichloro-methane (0.05 ml) and triethylamine (0.0035 ml). The mixture was stirred at room temperature for 1 h then sol-vents were removed in vacuo to yield the title compound. (ESI)+: [M+H]+=700.5, 702.5

Example E98

Propane-1-sulfonic Acid 4-(3,6-dimethyl-4,10-dihydro-3H-2,3,4,9-tetraaza-benzo[f]azulene-9-carbonyl)-2-fluoro-benzylamide

Example E98.1

[4-(3,6-Dimethyl-4,10-dihydro-3H-2,3,4,9-tetraaza-benzo[f]azulene-9-carbonyl)-2-fluoro-benzyl]-carbamic Acid Tert-butyl Ester A mixture of 4-(tert-butoxycarbonylamino-methyl)-3-fluoro-benzoic acid from Example E3 (1.38 g, 5.1 mmol) and 3,6-dimethyl-3,4,9,10-tetrahydro-2,3,4,9-tetraaza-benzo[f]azulene from Example E2 (11.0 g, 4.7 mmol) in di-chloromethane (20 ml) at room temperature was treated with DIEA (2.44 ml, 14.0 mmol), DMAP (627 mg, 5.1 mmol) and WSCD (1.16 g, 6.1 mmol). The solution was heated at re-flux for 2 days then washed with saturated NaHCO₃ then brine, dried and concentrated in vacuo. The residue was purified by flash chromatography on silica gel through an isolute (eluant; EtOAc) to yield the title compound (1.29 g, 59%).

Example E98.2

(4-Aminomethyl-3-fluoro-phenyl)-(3,6-dimethyl-4,10-dihydro-3H-2,3,4,9-tetraaza-benzo[f]azulen-9-yl)-methanone Hydrochloride

[4-(3,6-Dimethyl-4,10-dihydro-3H-2,3,4,9-tetraaza-benzo[f]azulene-9-carbonyl)-2-fluoro-benzyl]-carbamic acid tert-butyl ester from Example E98.1 (1.29 g, 2.8 mmol) was reacted with 4N HCl/dioxan using an analogous procedure to that described for Example E4.2 to yield the title compound (1.1 g, 99%).

Example E98.3

Propane-1-sulfonic Acid 4-(3,6-dimethyl-4,10-dihydro-3H-2,3,4,9-tetraaza-benzo[f]azulene-9-carbonyl)-2-fluoro-benzylamide 1-Propanesulfonyl chloride (0.016 ml, 0.14 mmol) was added to a solution of (4-aminomethyl-3-fluoro-phenyl)-(3,6-dimethyl-4,10-dihydro-3H-2,3,4,9-tetraaza-benzo[f]azulen-9-yl)-methanone hydrochloride from Example E98.2 (50 mg, 0.12 mmol) in dichloromethane (2 ml) and triethylamine (0.038 ml, 0.27 mmol) at room temperature. The mixture was stirred for 1 h then concentrated in vacuo. The residue was purified by preparative HPLC (eluant; 0.5% 35% ammonia: 9.5% methanol:90% dichloro-methane) to give a white solid identified as the title compound (30 mg, 51%).

Example E99

N-[4-(3,6-Dimethyl-4,10-dihydro-3H-2,3,4,9-tetraaza-benzo[f]azulene-9-carbonyl)-2-fluoro-benzyl]-formamide Formic acid (0.85 ml, 22.5 mmol) and acetic anhydride (1.4 ml, 13.5 mmol) were combined and stirred for 1 h at room temperature. (4-Aminomethyl-3-fluoro-phenyl)-(3,6-dimethyl-4,10-dihydro-3H-2,3,4,9-tetraaza-benzo[f]azulen-9-yl)-methanone hydrochloride from Example E98.2 (113 mg, 0.3 mmol) was added and the mixture was stirred for 1 h. Water (20 ml) was added and the mixture was stirred for 1 h. It was diluted with chloroform, washed with saturated NaHCO$_3$ then brine, dried and concentrated in vacuo to yield a white solid identified as the title compound (48 mg, 40%).

Example E100

Cyclopropanecarboxylic Acid 4-(3,6-dimethyl-4,10-dihydro-3H-2,3,4,9-tetraaza-benzo[f]azulene-9-carbonyl)-2-fluoro-benzylamide DIEA (0.08 ml, 0.46 mmol) and cyclopropanecarbonyl chloride (0.013 ml, 0.14 mmol) were added to a solution of (4-aminomethyl-3-fluoro-phenyl)-(3,6-dimethyl-4,10-dihydro-3H-2,3,4,9-tetraaza-benzo[f]azulen-9-yl)-methanone hydrochloride from Example E98.2 (57 mg, 0.14 mmol) in dichloromethane (10 ml) at 0° C. The mixture was stirred for 90 min at room temperature then diluted with dichloromethane, washed with saturated NaHCO$_3$ then brine, dried and concentrated in vacuo. The residue was purified by preparative HPLC (eluant; 0.5% 35% ammonia:9.5% methanol: 90% dichloromethane) to give a white solid identified as the title compound (33 mg, 54%).

Example E101

Cyclopropanecarboxylic Acid 4-(3,6-dimethyl-4,10-dihydro-3H-2,3,4,9-tetraaza-benzo[f]azulene-9-carbonyl)-2-methyl-benzylamide

Example E101.1

4-(3,6-Dimethyl-4,10-dihydro-3H-2,3,4,9-tetraaza-benzo[f]azulene-9-carbonyl)-2-methyl-benzonitrile A mixture of 4-cyano-3-methyl-benzoic acid from Example E6 (753 mg, 4.7 mmol) and thionyl chloride (1.02 ml, 14.0 mmol) in toluene (50 ml) was heated at reflux for 2 h. After cooling at room temperature, solvents were re-moved in vacuo and azeotroped with toluene. The residue was redissolved in dichloromethane (45 ml) and a solution of 3,6-dimethyl-3,4,9,10-tetrahydro-2,3,4,9-tetraaza-benzo[f]azulene from Example E2 (11.0 g, 4.7 mmol) in dichloromethane (5 ml) and triethylamine (1.3 ml, 9.3 mmol) was added slowly. The mixture was stirred at room temperature for 20 h, washed with brine, dried and concentrated in vacuo. The residue was purified by flash chromatography on silica gel through an isolute (eluant; EtOAc) to yield the title compound (1.42 g, 85%).

Example E101.2

(4-Aminomethyl-3-methyl-phenyl)-(3,6-dimethyl-4,10-dihydro-3H-2,3,4,9-tetraaza-benzo[f]azulen-9-yl)-methanone A solution of 4-(3,6-dimethyl-4,10-dihydro-3H-2,3,4,9-tetraaza-benzo[f]azulene-9-carbonyl)-2-methyl-benzonitrile from Example E101.1 (1.42 g, 4.0 mmol) in methanol (50 ml) at 0° C. was treated with cobalt(II) chloride hexahydrate (1.90 g, 8.0 mmol). The mixture was stirred for 15 min at room temperature then sodium borohydride (1.51 g, 40.0 mmol) was added portionwise. The reaction mixture was stirred for 2 h then saturated NH$_4$Cl was added. The mixture was stirred for 30 min then the solid was filtered off through Celite® filter agent and the filtrate concentrated in vacuo. The residue was re-dissolved in EtOAc and saturated NaHCO$_3$. The layers were partitioned and the aqueous layer was extracted further with chloroform. Organics were combined, dried and concentrated in vacuo. The residue was purified by flash chromatography on silica gel through an isolute (eluant; 1% 35% ammonia:9% methanol:90% dichloro-methane) to yield the title compound (511 mg, 35%).

Example E101.3

Cyclopropanecarboxylic Acid 4-(3,6-dimethyl-4,10-dihydro-3H-2,3,4,9-tetraaza-benzo[f]azulene-9-carbonyl)-2-methyl-benzylamide Triethylamine (0.145 ml, 1.04 mmol) and cyclopropanecarbonyl chloride (0.041 ml, 0.45 mmol) were added to a solution of (4-aminomethyl-3-methyl-phenyl)-(3,6-dimethyl-4,10-dihydro-3H-2,3,4,9-tetraaza-benzo[f]azulen-9-yl)-methanone from Example E101.2 (150 mg, 0.41 mmol) in dichloromethane (10 ml) at room temperature. The mixture was stirred for 20 h then concentrated in vacuo. The residue was purified by preparative HPLC (eluant; 0.5% 35% ammonia:9.5% methanol:90% dichloromethane) to give an off-white solid identified as the title compound (91 mg, 51%).

Example E102

Cyclopropanecarboxylic Acid 4-(6-chloro-3-methyl-4,10-dihydro-3H-2,3,4,9-tetraazabenzo[f]azulene-9-carbonyl)-2-fluoro-benzylamide

Example E102.1

[4-(6-Chloro-3-methyl-4,10-dihydro-3H-2,3,4,9-tetraaza-benzo[f]azulene-9-carbonyl)-2-fluoro-benzyl]-carbamic Acid Tert-butyl Ester A solution of 4-(tert-butoxycarbonylamino-methyl)-3-fluoro-benzoic acid from Example E3 (568 mg, 2.1 mmol) in dichloromethane (25 ml) at room temperature was treated with DMAP (256 mg, 2.1 mmol), DIEA (1.1 ml, 6.3 mmol) then WSCD (520 mg, 2.7 mmol). The mixture was stirred for 3 h then 6-chloro-3-methyl-3,4,9,10-tetrahydro-2,3,4,9-tetraaza-benzo[f]azulene from Example E1 (450 mg, 1.9 mmol) was added. The mixture was stirred for 4 days then washed with saturated NaHCO$_3$ then brine, dried and concentrated in vacuo. The residue was purified by flash chromatography on silica gel (eluant; EtOAc) to yield the title compound (503 mg, 54%).

Example E102.2

(4-Aminomethyl-3-fluoro-phenyl)-(6-chloro-3-methyl-4,10-dihydro-3H-2,3,4,9-tetraaza-benzo[f]azulen-9-yl)-methanone Hydrochloride

[4-(6-Chloro-3-methyl-4,10-dihydro-3H-2,3,4,9-tetraaza-benzo[f]azulene-9-carbonyl)-2-fluoro-benzyl]-carbamic acid tert-butyl ester from Example E102.1 (503 mg, 1.03 mmol) was reacted with 4N HCl/dioxan using an analogous procedure to that described for Example E4.2 to yield the title compound (440 mg, 100%).

Example E102.3

Cyclopropanecarboxylic Acid 4-(6-chloro-3-methyl-4,10-dihydro-3H-2,3,4,9-tetraazabenzo[f]azulene-9-carbonyl)-2-fluoro-benzylamide Cyclopropanecarbonyl chloride (0.045 ml, 0.5 mmol) was added to a solution of (4-aminomethyl-3-fluoro-phenyl)-(6-chloro-3-methyl-4,10-dihydro-3H-2,3,4,9-tetraaza-benzo[f]azulen-9-yl)-methanone hydrochloride from Example E102.2 (210 mg, 0.5 mmol) in dichloromethane (40 ml) and DIEA (0.30 ml, 1.7 mmol) at 0° C. The mixture was stirred for 1 h at room temperature then washed with saturated NaHCO$_3$, brine, dried and concentrated in vacuo. The residue was purified by preparative HPLC (eluant; 0.5% 35% ammonia:9.5% methanol:90% dichloro-methane) to give a white powder identified as the title compound (134 mg, 59%).

Example E103

N-[4-(6-Chloro-3-methyl-4,10-dihydro-3H-2,3,4,9-tetraaza-benzo[f]azulene-9-carbonyl)-2-fluoro-benzyl]-propionamide DIEA (0.27 ml, 1.56 mmol) and propionyl chloride (0.048 ml, 0.55 mmol) were added to a solution of (4-aminomethyl-3-fluoro-phenyl)-(6-chloro-3-methyl-4,10-dihydro-3H-2,3,4,9-tetraaza-benzo[f]azulen-9-yl)-methanone hydrochloride from Example E102.2 (220 mg, 0.52 mmol) in dichloromethane (6 ml) at room temperature. The mixture was stirred for 2 h, washed with saturated NaHCO$_3$ then brine, dried and concentrated in vacuo. The residue was purified by preparative HPLC (eluant; 0.5% 35% ammonia:9.5% methanol:90% dichloromethane) to give a white powder identified as the title compound (129 mg, 56%).

Example E104

N-[4-(6-Chloro-3-methyl-4,10-dihydro-3H-2,3,4,9-tetraaza-benzo[f]azulene-9-carbonyl)-2-fluoro-benzyl]-butyramide DIEA (0.135 ml, 0.78 mmol) and butyryl chloride (0.027 ml, 0.27 mmol) were added to a solution of (4-aminomethyl-3-fluoro-phenyl)-(6-chloro-3-methyl-4,10-dihydro-3H-2,3,4,9-tetraaza-benzo[f]azulen-9-yl)-methanone hydrochloride from Example E102.2 (110 mg, 0.26 mmol) in di-chloromethane (3 ml) at room temperature. The mixture was stirred for 1 h, washed with saturated NaHCO$_3$ then brine, dried and concentrated in vacuo. The residue was purified by preparative HPLC (eluant; 0.5% 35% ammonia:9.5% methanol:90% dichloromethane) to give a white powder identified as the title compound (77 mg, 65%).

Example E105

N-[4-(6-Chloro-3-methyl-4,10-dihydro-3H-2,3,4,9-tetraaza-benzo[f]azulene-9-carbonyl)-2-fluoro-benzyl]-isobutyramide DIEA (0.135 ml, 0.78 mmol) and isobutyryl chloride (0.029 ml, 0.27 mmol) were added to a solution of (4-aminomethyl-3-fluoro-phenyl)-(6-chloro-3-methyl-4,10-dihydro-3H-2,3,4,9-tetraaza-benzo[f]azulen-9-yl)-methanone hydrochloride from Example E102.2 (110 mg, 0.26 mmol) in dichloromethane (3 ml) at room temperature. The mixture was stirred for 1 h, washed with saturated NaHCO$_3$ then brine, dried and concentrated in vacuo. The residue was purified by preparative HPLC (eluant; 0.5% 35% ammonia:9.5% methanol:90% dichloromethane) to give a white powder identified as the title compound (85 mg, 71%).

Example E106

Cyclopropanecarboxylic Acid 2-chloro-4-(6-chloro-3-methyl-4,10-dihydro-3H-2,3,4,9-tetraaza-benzo[f]azulene-9-carbonyl)-benzylamide

Example E106.1

[2-Chloro-4-(6-chloro-3-methyl-4,10-dihydro-3H-2,3,4,9-tetraaza-benzo[f]azulene-9-carbonyl)-benzyl]-carbamic Acid Tert-butyl Ester A solution of 4-(tert-butoxycarbonylamino-methyl)-3-chloro-benzoic acid from Example E2b (568 mg, 2.0 mmol) in dichloromethane (25 ml) at room temperature was treated with DMAP (244 mg, 2.0 mmol), DIEA (11.0 ml, 6.0 mmol) then WSCD (500 mg, 2.6 mmol). The mixture was stirred for 3 h then 6-chloro-3-methyl-3,4,9,10-tetrahydro-2,3,4,9-tetraaza-benzo[f]azulene from Example E1 (430 mg, 1.8 mmol) was added. The mixture was stirred for 4 days then washed with saturated NaHCO$_3$, brine, dried and concentrated in vacuo. The residue was purified by flash chromatography on silica gel (eluant; EtOAc) to yield the title compound (570 mg, 63%).

Example E106.2

(4-Aminomethyl-3-chloro-phenyl)-(6-chloro-3-methyl-4,10-dihydro-3H-2,3,4,9-tetraaza-benzo[f]azulen-9-yl)-methanone Hydrochloride

[2-Chloro-4-(6-chloro-3-methyl-4,10-dihydro-3H-2,3,4,9-tetraaza-benzo[f]azulene-9-carbonyl)-benzyl]-carbamic acid tert-butyl ester from Example E106.1 (570 mg, 1.13 mmol) was reacted with 4N HCl/dioxan using an analogous procedure to that described for Example E4.2 to yield the title compound (490 mg, 100%).

Example E106.3

Cyclopropanecarboxylic Acid 2-chloro-4-(6-chloro-3-methyl-4,10-dihydro-3H-2,3,4,9-tetraaza-benzo[f]azulen-9-carbonyl)-benzylamide Cyclopropanecarbonyl chloride (0.045 ml, 0.5 mmol) was added to a solution of (4-aminomethyl-3-chloro-phenyl)-(6-chloro-3-methyl-4,10-dihydro-3H-2,3,4,9-tetraaza-benzo[f]azulen-9-yl)-methanone hydrochloride from Example E106.2 (220 mg, 0.5 mmol) in dichloromethane (40 ml) and DIEA (0.30 ml, 1.7 mmol) at 0° C. The mixture was stirred for 1 h at room temperature then washed with saturated NaHCO$_3$, brine, dried and concentrated in vacuo. The residue was purified by preparative HPLC (eluant; 0.5% 35% ammonia:9.5% methanol:90% dichloro-methane) to give a white powder identified as the title compound (135 mg, 57%).

Example E107

N-[2-Chloro-4-(6-chloro-3-methyl-4,10-dihydro-3H-2,3,4,9-tetraaza-benzo[f]azulene-9-carbonyl)-benzyl]-butyramide Butyryl chloride (46 mg, 0.4 mmol) was added to a solution of (4-aminomethyl-3-chloro-phenyl)-(6-chloro-3-methyl-4,10-dihydro-3H-2,3,4,9-tetraaza-benzo[f]azulen-9-yl)-methanone hydrochloride from Example E106.2 (161 mg, 0.4 mmol) in dichloromethane (10 ml) and triethylamine (to pH9) at room temperature. The mixture was stirred for 20 h, diluted with EtOAc, washed with saturated NaHCO$_3$ then brine, dried and concentrated in vacuo. The residue was purified by preparative HPLC (eluant; 0.5% 35% ammonia:9.5% methanol:90% dichloro-methane) to give a white solid identified as the title compound (110 mg, 58%).

Example E108

N-[2-Chloro-4-(6-chloro-3-methyl-4,10-dihydro-3H-2,3,4,9-tetraaza-benzo[f]azulene-9-carbonyl)-benzyl]-isobutyramide Isobutyryl chloride (46 mg, 0.4 mmol) was added to a solution of (4-aminomethyl-3-chloro-phenyl)-(6-chloro-3-methyl-4,10-dihydro-3H-2,3,4,9-tetraaza-benzo[f]azulen-9-yl)-methanone hydrochloride from Example E106.2 (161 mg, 0.4 mmol) in dichloromethane (10 ml) and triethylamine (to pH9) at room temperature. The mixture was stirred for 18 h, diluted with EtOAc, washed with saturated NaHCO$_3$ then brine, dried and concentrated in vacuo. The residue was purified by preparative HPLC (eluant; 0.5% 35% ammonia:9.5% methanol:90% dichloromethane) to give a white solid identified as the title compound (75 mg, 40%).

Example E109

{4-[(Cyclopropylmethyl-amino)-methyl]-3-methyl-phenyl}(3-methyl-4,10-dihydro-3H-2,3,4,9-tetraaza-benzo[f]azulen-9-yl)-methanone Cyclopropanecarboxaldehyde (26 mg, 0.34 mmol) was added to a solution of (4-Aminomethyl-3-methyl-phenyl)-(3-methyl-4,10-dihydro-3H-2,3,4,9-tetraaza-benzo[f]azulen-9-yl)-methanone (131 mg, 0.38=mol) in MeOH/AcOH (99:1, ml) and the mixture was stirred at room temperature for 30 min. Sodium cyanoborohydride (31 mg, 0.49 mmol) was added and the mixture was stirred at room temperature for 18 h. The solvents were removed in vacuo and the residue was dissolved in EtOAc. The solution was washed with sat. aq. NaHCO$_3$ and brine, then dried and concentrated in vacuo. The residue was purified by preparative HPLC (eluant; 0.5% 35% ammonia:9.5% methanol:90% dichloromethane to give a white solid identified as the title compound (70 mg, 51%).

Example E110

[4-(6-Chloro-3-methyl-4,10-dihydro-3H-2,3,4,9-tetraaza-benzo[f]azulene-9-carbonyl)-2-fluoro-benzylamino]-acetic Acid Methyl Ester and

Example E111

{[4-(6-Chloro-3-methyl-4,10-dihydro-3H-2,3,4,9-tetraaza-benzo[f]azulene-9-carbonyl)-2-fluoro-benzyl]-methoxycarbonylmethyl-amino}-acetic Acid Methyl Ester Methyl bromoacetate (0.054 ml, 0.58 mmol) was added to a solution of (4-aminomethyl-3-fluoro-phenyl)-(6-chloro-3-methyl-4,10-dihydro-3H-2,3,4,9-tetraaza-benzo[f]azulen-9-yl)-methanone hydrochloride from example E102.2 (107 mg, 0.28 mmol) and DIEA (0.26 ml, 1.53 mmol) in THF (25 ml) and the mixture was stirred at room temperature for 2 h. A further amount of methyl bromoacetate (0.10 ml, 1.11 mmol) was added, and the mixture was stirred overnight at room temperature. The solution was quenched with water and diluted with EtOAc. The organic layer was washed with brine (×3), dried and concentrated in vacuo. The residue was purified by preparative HPLC (eluant; 0.5% 35% ammonia:9.5% methanol:90% dichloromethane) to yield two products. The faster eluting product was isolated as a white solid and identified as E111 (68 mg, 46%).

The slower eluting product was isolated as a white solid and identified as E110 (13 mg, 10%).

Example E112

(6-Chloro-3-methyl-4,10-dihydro-3H-2,3,4,9-tetraaza-benzo[f]azulen-9-yl)-{3-fluoro-4-[(2-hydroxy-ethylamino)-methyl]-phenyl}-methanone Lithium aluminium hydride (14.5 mg, 0.38 mmol) was added to a solution of [4-(6-chloro-3-methyl-4,10-dihydro-3H-2,3,4,9-tetraaza-benzo[f]azulene-9-carbonyl)-2-fluoro-benzylamino]-acetic acid methyl ester from example E110 (58.5 mg, 0.13 mmol) in THF (5 ml), and the mixture was stirred at room temperature for 30 min. Before being quenched with MeOH and extracted with EtOAc. The organic extract was washed with brine, dried and concentrated in vacuo. The residue was purified by flash chromatography on silica gel (eluant; 10% methanol:90% di-chloromethane then 20% methanol:80% dichloromethane) to give a pale yellow solid identified as the title compound (15 mg, 28%).

Example E113

{[4-(6-Chloro-3-methyl-4,10-dihydro-3H-2,3,4,9-tetraaza-benzo[f]azulene-9-carbonyl)-2-fluoro-benzylcarbamoyl]-methyl}-carbamic Acid Tert-butyl Ester HBTU (165 mg, 0.44 mmol) was added to a solution of N-(tert-butoxycarbonyl)glycine (65 mg, 0.37 mmol) in DMF (10 ml) and the mixture was stirred for 30 min at room temperature. (4-Aminomethyl-3-fluoro-phenyl)-(6-chloro-3-methyl-4,10-dihydro-3H-2,3,4,9-tetraaza-benzo[f]azulen-9-yl)-methanone hydrochloride from Example E102.2 (100 mg, 0.22 mmol) and DIEA (0.228 ml, 1.31 mmol) were added and the mixture was stirred for 24 h at room temperature. The solution was diluted with EtOAc, washed with water then brine, dried and concentrated in vacuo. The residue was purified by flash chromatography on silica gel (eluant; 5% methanol:95% dichloromethane then 10% methanol:90% dichloromethane) to give a white solid identified as the title compound (123 mg, 100%).

Example E114

2-Amino-N-[4-(6-chloro-3-methyl-4,10-dihydro-3H-2,3,4,9-tetraaza-benzo[f]azulene-9-carbonyl)-2-fluoro-benzyl]-acetamide Hydrochloride {[4-(6-Chloro-3-methyl-4,10-dihydro-3H-2,3,4,9-tetraaza-benzo[f]azulene-9-carbonyl)-2-fluoro-benzylcarbamoyl]-methyl}-carbamic acid tert-butyl ester from Example E113 (120 mg, 0.22 mmol) was reacted with 4N HCl/dioxan using an analogous procedure to that de-scribed for Example E4.2 to yield the title compound (95 mg, 83%).

Example E115

4-[(3-Chloro-benzoylamino)-methyl]-N-(4-chloro-phenyl)-3,N-dimethyl-benzamide

Example E115.1

N-(4-Chloro-phenyl)-4-cyano-3,N-dimethyl-benzamide

A mixture of 4-cyano-3-methyl-benzoic acid from Example E6 (3.4 g, 21 mmol) and thionyl chloride (10 ml, 137 mmol) in dichloromethane (50 ml) was heated at reflux for 2 h. After cooling at room temperature, solvents were re-moved in vacuo and azeotroped with toluene. The residue was redissolved in dichloromethane (50 ml). (4-Chlorophenyl)-methyl amine (3.0 g, 21 mmol) and triethylamine (to pH9) were added and the mixture was stirred at room temperature for 20 h then concentrated in vacuo. The residue was redissolved in EtOAc, washed with 1M KHSO$_4$, water then brine, dried and concentrated in vacuo. The residue was purified by flash chromatography on silica gel (eluant; 35% EtOAc:65% cyclohexane) to yield the title compound (5.1 g, 85%).

Example E115.2

4-Aminomethyl-N-(4-chloro-phenyl)-3,N-dimethyl-benzamide

A solution of N-(4-Chloro-phenyl)-4-cyano-3,N-dimethyl-benzamide from Example E115.1 (5.1 g, 17.9 mmol) in methanol (250 ml) was treated with cobalt(II) chloride hexahydrate (8.4 g, 35.8 mmol). The mixture was stirred for 15 min at room temperature then cooled down to 0° C. and sodium borohydride (6.7 g, 179 mmol) was added portionwise. The mixture was stirred for 1 h at room temperature, filtered through Celite® filter agent, washed with methanol and the filtrate was concentrated in vacuo. The residue was purified by flash chromatography on silica gel (eluant; 1% 35% ammonia:10% methanol:89% dichloromethane) to yield the title compound (3.6 g, 70%).

Example E115.3

4-[(3-Chloro-benzoylamino)-methyl]-N-(4-chloro-phenyl)-3,N-dimethyl-benzamide

3-Chlorobenzoyl chloride (61 mg, 0.35 mmol) and tri-ethyl-amine (to pH9) were added to a solution of 4-aminomethyl-N-(4-chloro-phenyl)-3,N-dimethyl-benzamide from Example E115.2 (100 mg, 0.35 mmol) in dichloro-methane (5 ml) at room temperature. The mixture was stirred for 1 h then concentrated in vacuo. The residue was purified by preparative HPLC (eluant; 0.5% 35% ammonia:9.5% methanol:90% dichloromethane) to give a white solid identified as the title compound (101 mg, 69%).

Example E116

1-Cyclopropylmethyl-piperidine-4-carboxylic Acid 4-[(4-chloro-phenyl)-methyl-carbamoyl]-2-methyl-benzylamide PyBroP (212 mg, 0.45 mmol) and 1-cyclopropylmethyl-piperidine-4-carboxylic acid from Example E15a (76 mg, 0.42 mmol) were added to a solution of 4-aminomethyl-N-(4-chloro-phenyl)-3,N-dimethyl-benzamide from Example E115.2 (100 mg, 0.35 mmol) in dichloromethane (5 ml) and DMF (1 ml). The mixture was stirred at room temperature for 18 h then solvents were removed in vacuo and azeotroped with toluene. The residue was purified by preparative HPLC (eluant; 0.5% 35% ammonia:9.5% methanol:90% dichloromethane) to give a white powder identified as the title compound (34 mg, 22%).

Example E117

1-(3,3-Dimethyl-butyl)-piperidine-4-carboxylic Acid 4-[(4-chloro-phenyl)-methyl-carbamoyl]-2-methyl-benzylamide HBTU (296 mg, 0.78 mmol) was added to a solution of 1-(3,3-dimethyl-butyl)-piperidine-4-carboxylic acid from Example E15 (182 mg, 0.73 mmol) in DMF (5 ml) and DIEA (0.272 ml, 1.56 mmol). The mixture was stirred at room temperature for 2 h then 4-aminomethyl-N-(4-chloro-phenyl)-3,N-dimethyl-benzamide from Example E115.2 (150 mg, 0.52 mmol) was added. The mixture was stirred for 2 h at room temperature then diluted with EtOAc, washed with saturated NaHCO$_3$ then brine, dried and concentrated in vacuo. The residue was purified by preparative HPLC (eluant; 0.5% 35% ammonia:9.5% methanol:90% dichloromethane) to give a white powder identified as the title compound (209 mg, 83%).

Example E118

1-(3,3-Dimethyl-butyl)-piperidine-4-carboxylic Acid 2-methyl-4-[methyl-(4-trifluoromethyl-phenyl)-carbamoyl]-benzylamide

Example E118.1

4-Cyano-3-methyl-N-(4-trifluoromethyl-phenyl)-benzamide

A mixture of 4-cyano-3-methyl-benzoic acid from Example E6 (750 mg, 4.6 mmol) and thionyl chloride (1.02 ml, 14.0 mmol) in toluene (40 ml) was heated at reflux for 2 h. After cooling at room temperature, solvents were re-moved in vacuo and azeotroped with toluene. The residue was redissolved in dichloromethane (25 ml) then 4-trifluoromethylaniline hydrochloride (1.11 g, 5.6 mmol) in dichloromethane (5 ml) and triethylamine (1.95 ml, 14.0 mmol) was added. The mixture was stirred at room temperature for 2 days, washed with brine, dried and concentrated in vacuo. The residue was purified by flash chromatography on silica gel through an isolute (eluant; 20% EtOAc:80% cyclohexane) to yield the title compound (1.13 g, 80%).

Example E118.2

4-Cyano-3,N-dimethyl-N-(4-trifluoromethyl-phenyl)-benzamide

4-Cyano-3-methyl-N-(4-trifluoromethyl-phenyl)-benzamide from Example E118.1 (1.10 g, 3.6 mmol) was dissolved in DMF (10 ml) and cooled down to 0° C. Sodium hydride (60% dispersion in oil, 174 mg, 4.3 mmol) was added and the mixture was stirred for 30 min at room temperature. Methyl iodide (0.27 ml, 4.3 mmol) was added and the mixture was stirred for 20 h. Solvents were removed in vacuo and azeotroped with toluene. The residue was re-dissolved in EtOAc, washed with brine, dried and concentrated in vacuo to yield the title compound (1.08 g, 94%).

Example E118.3

4-Aminomethyl-3,N-dimethyl-N-(4-trifluoromethyl-phenyl)-benzamide

A solution of 4-cyano-3,N-dimethyl-N-(4-trifluoromethyl-phenyl)-benzamide from Example E118.2 (1.08 g, 3.4 mmol) in methanol (40 ml) at room temperature was treated with cobalt(II) chloride hexahydrate (1.61 g, 6.8 mmol). The mixture was stirred for 10 min then sodium borohydride (1.28 g, 34 mmol) was added portionwise. The mixture was stirred for 20 h then saturated NH$_4$Cl solution (10 ml) was added. The mixture was stirred for 30 min, filtered through glass-fibre paper and the filtrate was concentrated in vacuo. The residue was purified by flash chromatography on silica gel (eluant; 1% 35% ammonia:9% methanol:90% dichloromethane) to yield the title compound (863 mg, 79%).

Example E118.4

1-(3,3-Dimethyl-butyl)-piperidine-4-carboxylic Acid 2-methyl-4-[methyl-(4-trifluoromethyl-phenyl)-carbamoyl]-benzylamide PyBroP (188 mg, 0.40 mmol) and 1-(3,3-dimethyl-butyl)-piperidine-4-carboxylic acid (82 mg, 0.38 mmol) were added to a solution of 4-aminomethyl-3,N-dimethyl-N-(4-trifluoromethyl-phenyl)-benzamide from Example E118.3 (100 mg, 0.31 mmol) in dichloromethane (5 ml) and DIEA (0.081 ml, 0.46 mmol). The mixture was stirred at room temperature for 2 days, washed with saturated NaHCO$_3$ then brine, dried and concentrated in vacuo. The residue was purified by preparative HPLC (eluant; 0.5% 35% ammonia:9.5% methanol: 90% dichloromethane) to give a off-white powder identified as the title compound (22 mg, 14%).

Example E119

Cyclopropanecarboxylic Acid 2-methyl-4-(2-methyl-4,5-dihydro-1-oxa-3,6-diaza-benzo[e]azulene-6-carbonyl)-benzylamide Example E119.1

[2-Methyl-4-(2-methyl-4,5-dihydro-1-oxa-3,6-diaza-benzo[e]azulene-6-carbonyl)-benzyl]-carbamic Acid Tert-butyl Ester A solution of 4-(tert-butoxycarbonylamino-methyl)-3-methyl-benzoic acid from Example E2h (400 mg, 1.5 mmol) in dichloromethane (20 ml) and triethylamine (to pH9) was treated with WSCD (573 mg, 3.0 mmol) and DMAP (183 mg, 1.5 mmol). The solution was stirred for 30 min at room temperature then 2-methyl-5,6-dihydro-4H-1-oxa-3,6-diaza-benzo[e]azulene from Example E6 (300 mg, 1.5 mmol) was added and the mixture was heated at reflux for 3 days. WSCD (287 mg, 1.5 mmol) was added and the mixture was heated at reflux for another 24h then concentrated in vacuo. The residue was dissolved in EtOAc, washed with 1N KHSO$_4$, water then brine, dried and concentrated in vacuo. The residue was purified by flash chromatography on silica gel (eluant; EtOAc) to yield the title compound (62 mg, 9%).

Example E119.2

(4-Aminomethyl-3-methyl-phenyl)-(2-methyl-4,5-dihydro-1-oxa-3,6-diaza-benzo[e]azulen-6-yl)-methanone Hydrochloride

[2-Methyl-4-(2-methyl-4,5-dihydro-1-oxa-3,6-diaza-benzo[e]azulene-6-carbonyl)-benzyl]-carbamic acid tert-butyl ester from Example E119.1 (62 mg, 0.14 mmol) in methanol (0.5 ml) was reacted with 4N HCl/dioxan using an analogous procedure to that described for Example E4.2 to yield the title compound (53 mg, 100%).

Example E119.3

Cyclopropanecarboxylic Acid 2-methyl-4-(2-methyl-4,5-dihydro-1-oxa-3,6-diaza-benzo[e]azulene-6-carbonyl)-benzylamide Cyclopropanecarbonyl chloride (26 mg, 0.25 mmol) was added to a solution of (4-aminomethyl-3-methyl-phenyl)-(2-methyl-4,5-dihydro-1-oxa-3,6-diaza-benzo[e]azulen-6-yl)-methanone hydrochloride from Example E119.2 (85 mg, 0.22 mmol) in dichloromethane (5 ml) and triethylamine (to pH9) at room temperature. The mixture was stirred for 1 h then purified by flash chromatography on silica gel (eluant; 10% methanol:90% dichloromethane) to give a white solid identified as the title compound (62 mg, 67%).

Example E120

1-(3,3-Dimethyl-butyl)-piperidine-4-carboxylic Acid 2-methyl-4-(2-methyl-4,5-dihydro-1-oxa-3,6-diaza-benzo[e]azulene-6-carbonyl)-benzylamide (4-Aminomethyl-3-methyl-phenyl)-(2-methyl-4,5-dihydro-1-oxa-3,6-diaza-benzo[e]azulen-6-yl)-methanone hydrochloride from Example E119.2 (89 mg, 0.225 mmol) was dissolved in dichloromethane (10 ml) and triethylamine (to pH9) at room temperature. 1-(3,3-Dimethyl-butyl)-piperidine-4-carboxylic acid (53 mg, 0.25 mmol), DMAP (27 mg, 0.225 mmol) and PyBroP (165 mg, 0.36 mmol) were added and the mixture was heated at reflux for 18 h. The solution was diluted with EtOAc, washed with saturated NaHCO$_3$ then brine, dried and concentrated in vacuo. The residue was purified by flash chromatography on silica gel (eluant; 1% 35% ammonia:9% methanol:90% dichloro-methane) to give a white solid identified as the title compound (84 mg, 69%).

Example E121

1-(3,3-Dimethyl-butyl)-piperidine-4-carboxylic Acid 4-(1-benzyl-2-methyl-4,5-dihydro-1H-1,3,6-triaza-benzo[e]azulene-6-carbonyl)-2-methyl-benzylamide Example E121.1

4-(1-Benzyl-2-methyl-4,5-dihydro-1H-1,3,6-triaza-benzo[e]azulene-6-carbonyl)-2-methyl-benzonitrile A mixture of 4-cyano-3-methyl-benzoic acid from Example E6 (557 mg, 3.4 mmol) and thionyl chloride (0.755 ml, 10.3 mmol) in toluene (100 ml) was heated at reflux for 2 h. After cooling to room temperature, solvents were re-moved in vacuo and azeotroped with toluene. The residue was redissolved in dichloromethane (100 ml) and triethylamine (0.962 ml, 6.9 mmol) then 1-benzyl-2-methyl-1,4,5,6-tetrahydro-1,3,6-triaza-benzo[e]azulene from Example E5a (1.0 g, 3.4 mmol) was added. The mixture was stirred at room temperature for 2 h, washed with saturated NaHCO$_3$ then brine, dried and concentrated in vacuo. The residue was purified by flash chromatography on silica gel (eluant; 50% EtOAc:50% pet. ether then EtOAc) to yield the title compound (844 mg, 56%).

Example E121.2

(4-Aminomethyl-3-methyl-phenyl)-(1-benzyl-2-methyl-4,5-dihydro-1H-1,3,6-triaza-benzo[e]azulen-6-yl)-methanone A solution of 4-(1-benzyl-2-methyl-4,5-dihydro-1H-1,3,6-triaza-benzo[e]azulene-6-carbonyl)-2-methyl-benzonitrile from Example E121.1 (830 mg, 1.9 mmol) in methanol (10 ml) at room temperature was treated with cobalt(II) chloride hexahydrate (913 mg, 3.8 mmol). The mixture was stirred for 15 min then cooled down to 0° C. Sodium borohydride (726 mg, 19 mmol) was added portion-wise and the reaction mixture was stirred for 2 h at room temperature. 35% Ammonia (5 ml) was added dropwise and the mixture was stirred for 30 min then concentrated in vacuo. The residue was purified by flash chromatography on silica gel (eluant; 1% 35% ammonia:9% methanol:90% dichloromethane) to yield the title compound (680 mg, 81%).

Example E121.3

1-(3,3-Dimethyl-butyl)-piperidine-4-carboxylic Acid 4-(1-benzyl-2-methyl-4,5-dihydro-1H-1,3,6-triaza-benzo[e]azulene-6-carbonyl)-2-methyl-benzylamide HBTU (175 mg, 0.46 mmol) was added to a solution of 1-(3,3-dimethyl-butyl)-piperidine-4-carboxylic acid (86 mg, 0.34 mmol) in DMF (5 ml). The mixture was stirred at room temperature for 2 h then (4-aminomethyl-3-methyl-phenyl)-(1-benzyl-2-methyl-4,5-dihydro-1H-1,3,6-triaza-benzo[e]azulen-6-yl)-methanone from Example E121.2 (100 mg, 0.23 mmol) and DIEA (0.12 ml, 0.69 mmol) were added. The mixture was stirred at room temperature for 18 h then solvents were removed in vacuo and azeotroped with toluene. The residue was purified by flash chromatography on silica gel through an isolute (eluant; 5% methanol:95% dichloromethane then 10% methanol:90% dichloromethane) to give a yellow foam identified as the title compound (114 mg, 79%).

Example E122

1-(3,3-Dimethyl-butyl)-piperidine-4-carboxylic Acid 2-methyl-4-(2-methyl-4,5-dihydro-1H-1,3,6-triaza-benzo[e]azulene-6-carbonyl)-benzylamide 1-(3,3-Dimethyl-butyl)-piperidine-4-carboxylic acid 4-(1-benzyl-2-methyl-4,5-dihydro-1H-1,3,6-triaza-benzo[e]azulene-6-carbonyl)-2-methyl-benzylamide from Example E121 (110 mg, 0.17 mmol) was dissolved in absolute ethanol (5 ml) and placed under an inert atmosphere. 10% Palladium on carbon (110 mg) and cyclo-hexene (0.176 ml, 1.7 mmol) were added and the mixture was heated at 60° C. for 3 h. The catalyst was filtered off through Celite® filter agent and the filtrate was concentrated in vacuo. The residue was purified by preparative HPLC (eluant; 0.5% 35% ammonia:9.5% methanol:90% dichloromethane) to give a white powder identified as the title compound (45 mg, 48%).

Example E123

Cyclopropanecarboxylic Acid 2-methyl-4-(2-methyl-4,5-dihydro-1H-1,3,6-triaza-benzo[e]azulene-6-carbonyl)-benzylamide Example E123.1

Cyclopropanecarboxylic Acid 4-(1-benzyl-2-methyl-4,5-dihydro-1H-1,3,6-triaza-benzo[e]azulene-6-carbonyl)-2-methyl-benzylamide DIEA (0.176 ml, 1.02 mmol) and cyclopropanecarbonyl chloride (0.033 ml, 0.36 mmol) were added to a solution of (4-aminomethyl-3-methyl-phenyl)-(1-benzyl-2-methyl-4,5-dihydro-1H-1,3,6-triaza-benzo[e]azulen-6-yl)-methanone from Example E121.2 (150 mg, 0.34 mmol) in dichloromethane (5 ml) at room temperature. The mixture was stirred for 20 h, washed with saturated NaHCO$_3$ then brine, dried and concentrated in vacuo. The residue was purified by preparative HPLC (eluant; 0.5% 35% ammonia:9.5% methanol:90% dichloromethane) to give the title compound (155 mg, 90%).

Example E123.2

Cyclopropanecarboxylic Acid 2-methyl-4-(2-methyl-4,5-dihydro-1H-1,3,6-triaza-benzo[e]azulene-6-carbonyl)-benzylamide Cyclopropanecarboxylic acid 4-(1-benzyl-2-methyl-4,5-dihydro-1H-1,3,6-triaza-benzo[e]azulene-6-carbonyl)-2-methyl-benzylamide from Example E123.1 (155 mg, 0.31 mmol) was dissolved in absolute ethanol (10 ml) and placed under an inert atmosphere. 10% Palladium on car-bon (155 mg) and cyclohexene (0.311 ml, 3.1 mmol) were added and the mixture was heated at 60° C. for 18 h. The catalyst was filtered off through Celite® filter agent and the filtrate was concentrated in vacuo. The residue was purified by preparative HPLC (eluant; 0.5% 35% ammonia:9.5% methanol:90% dichloromethane) to give a white solid identified as the title compound (67 mg, 53%).

Example E124

Cyclopropanecarboxylic Acid 2-methyl-4-(2-methyl-4,5-dihydro-3-thia-1,6-diaza-benzo[e]azulene-6-carbonyl)-benzylamide

Example E124.1

2-Methyl-4-(2-methyl-4,5-dihydro-3-thia-1,6-diaza-benzo[e]azulene-6-carbonyl)-benzonitrile A mixture of 4-cyano-3-methyl-benzoic acid from Example E6 (147 mg, 0.91 mmol) was dissolved in dichloromethane (25 ml) and 2 drops of DMF and cooled down to 0° C. Oxalyl chloride (0.1 ml) was added slowly and the mixture was stirred for 2 h at room temperature. Solvents were removed in vacuo and azeotroped with toluene. The residue was redissolved in dichloromethane (10 ml) and cooled down to 0° C. Triethylamine (0.5 ml) and 2-methyl-5,6-dihydro-4H-3-thia-1,6-diaza-benzo[e]azulene from Example E7 (165 mg, 0.76 mmol) in dichloromethane (10 ml) were added and the mixture was stirred for 2 days at room temperature. Another 0.91 mmol of acid chloride was formed as previously and added to the mixture. The solution was stirred for 20 h at room temperature, washed with saturated NaHCO₃ then brine, dried and concentrated in vacuo. The residue was purified by flash chromatography on silica gel (eluant; 10% EtOAc:90% cyclohexane then 20% EtOAc:80% cyclohexane) to yield the title compound (220 mg, 80%).

Example E124.2

(4-Aminomethyl-3-methyl-phenyl)-(2-methyl-4,5-dihydro-3-thia-1,6-diaza-benzo[e]azulen-6-yl)-methanone A solution of 2-methyl-4-(2-methyl-4,5-dihydro-3-thia-1,6-diaza-benzo[e]azulene-6-carbonyl)-benzonitrile from Example E124.1 (190 mg, 0.53 mmol) in methanol (15 ml) at room temperature was treated with cobalt(II) chloride hexahydrate (275 mg, 1.15 mmol). The mixture was stirred for 20 min then cooled down to 0° C. Sodium borohydride (200 mg, 5.3 mmol) was added portionwise and the mixture was stirred for 20 h at room temperature. Saturated NH₄Cl (2 ml) was added dropwise and the mixture was stirred for 30 min then concentrated in vacuo. The residue was purified by flash chromatography on silica gel (eluant; 1% 35% ammonia:9% methanol:90% dichloromethane) to yield the title compound (100 mg, 52%).

Example E124.3

Cyclopropanecarboxylic Acid 2-methyl-4-(2-methyl-4,5-dihydro-3-thia-1,6-diaza-benzo[e]azulene-6-carbonyl)-benzylamide DIEA (0.02 ml, 0.115 mmol) and cyclopropanecarbonyl chloride (0.008 ml, 0.088 mmol) were added to a solution of (4-aminomethyl-3-methyl-phenyl)-(2-methyl-4,5-dihydro-3-thia-1,6-diaza-benzo[e]azulen-6-yl)-methanone from E124.2 (20 mg, 0.055 mmol) in dichloromethane (5 ml) at 0° C. The mixture was stirred for 20 h at room temperature then concentrated in vacuo and purified by preparative HPLC (eluant; 0.5% 35% ammonia:9.5% methanol:90% di-chloromethane) to give a white powder identified as the title compound (11 mg, 46%).

Example E125

N-[4-(9-Chloro-2-methyl-4,5-dihydro-1H-1,3,6-triaza-benzo[e]azulene-6-carbonyl)-2-methyl-benzyl]-isobutyramide

Example E125.1

4-[1-(4-Cyano-3-methyl-benzoyl)-9-chloro-2-methyl-4,5-dihydro-1H-1,3,6-triaza-benzo[e]azulene-6-carbonyl]-2-methyl-benzonitrile A mixture of 4-cyano-3-methyl-benzoic acid from Example E6 (262 mg, 1.6 mmol) was dissolved in dichloromethane (20 ml) and 2 drops of DMF and cooled down to 0° C. Oxalyl chloride (0.6 ml) was added and the mixture was stirred for 0.5 h at room temperature. Solvents were removed in vacuo and azeotroped with toluene. The residue was redissolved in dichloromethane (10 ml) and added to a solution of 9-chloro-2-methyl-1,4,5,6-tetrahydro-1,3,6-triaza-benzo[e]azulene from Example E7 (190 mg, 0.8 mmol) and DIEA (0.5 ml) in dichloromethane (10 ml) and the mixture was stirred for 20 h. at room temperature. The sol-vents were removed in vacuo and the residue was taken up in EtOAc, washed with saturated NaHCO₃ then brine, dried and concentrated in vacuo. The residue was purified by flash chromatography on silica gel (eluant; 40% EtOAc:60% cyclohexane) to yield the title compound (124 mg, 30%).

Example E125.2

4-(9-Chloro-2-methyl-4,5-dihydro-1H-1,3,6-triaza-benzo[e]azulene-6-carbonyl)-2-methyl-benzonitrile 4-[1-(4-Cyano-3-methyl-benzoyl)-9-chloro-2-methyl-4,5-dihydro-1H-1,3,6-triaza-benzo[e]azulene-6-carbonyl]-2-methyl-benzonitrile from E125.1 (124 mg, 0.24 mmol) was dissolved in MeOH 5 ml). 2M NaOH (2 ml) was added, and the mixture was stirred for 1 h. at room temperature. The solvents were removed in vacuo, and azeotroped with toluene. The residue was taken up in EtOAc, was with saturated NaHCO₃ then brine, dried and concentrated in vacuo to yield the title compound (80 mg, 89%)

Example E125.3

(4-Aminomethyl-3-methyl-phenyl)-(9-chloro-2-methyl-4,5-dihydro-1H-1,3,6-triaza-benzo[e]azulen-6-yl)-methanone A solution of 4-(9-chloro-2-methyl-4,5-dihydro-1H-1,3,6-triaza-benzo[e]azulene-6-carbonyl)-2-methyl-benzonitrile from E125.2 (80 mg, 0.2 mmol) in methanol (5 ml) at room temperature was treated with cobalt(II) chloride hexahydrate (101 mg, 0.4 mmol). The mixture was cooled to 0° C. then sodium borohydride (80 mg, 2.1 mmol) was added portionwise. The reaction mixture was stirred at 0° C. for 30 min. then for 2 h at room temperature then saturated NH₄Cl was added. The mixture was stirred for 10 min then the solid was filtered off through Celite® filter agent and the filtrate concentrated in vacuo. The residue was purified by flash chroma-

Example E125.4

N-[4-(9-Chloro-2-methyl-4,5-dihydro-1H-1,3,6-triaza-benzo[e]azulene-6-carbonyl)-2-methyl-benzyl]-isobutyramide Isobutyryl chloride (0.07 ml, 0.07 mmol) was added to a solution of (4-aminomethyl-3-methyl-phenyl)-(9-chloro-2-methyl-4,5-dihydro-1H-1,3,6-triaza-benzo[e]azulen-6-yl)-methanone from Example E125.3 (24 mg, 0.07 mmol) in dichloromethane (3 ml) and DIEA (0.10 ml, 0.57 mmol) at 0° C. The mixture was stirred for 20 h at room temperature then solvents were removed in vacuo. The residue was purified by flash chromatography on silica gel (eluant; 5% methanol:95% dichloromethane to 10% methanol:90% di-chloromethane) to give a colourless oil identified as the title compound 24 mg, 85%).

Example A

In Vitro Testing

Compounds were assayed to determine their ability to inhibit the cellular consequences of AVP stimulation on intact cells. In the assay, the compounds of the invention cause significant inhibition of cellular activation at concentrations of 30 μM or less. Preferred compounds cause significant inhibition at concentrations of 300 nM.

Example B

Tablet for Oral Administration

Tablets containing 100 mg of the compound of Example E8 as the active agent may be prepared from the following:

| | |
|---|---|
| Compound of Example E8 | 200.0 g |
| Corn starch | 71.0 g |
| Hydroxypropylcellulose | 18.0 g |
| Carboxymethylcellulose calcium | 13.0 g |
| Magnesium stearate | 3.0 g |
| Lactose | 195.0 g |
| Total | 500.0 g |

The materials are blended and then pressed to give 2000 tablets of 250 mg, each containing 100 mg of the compound of Example E8.

All the cited references are hereby incorporated in their entirety.

Schemes and Structures

Example E1

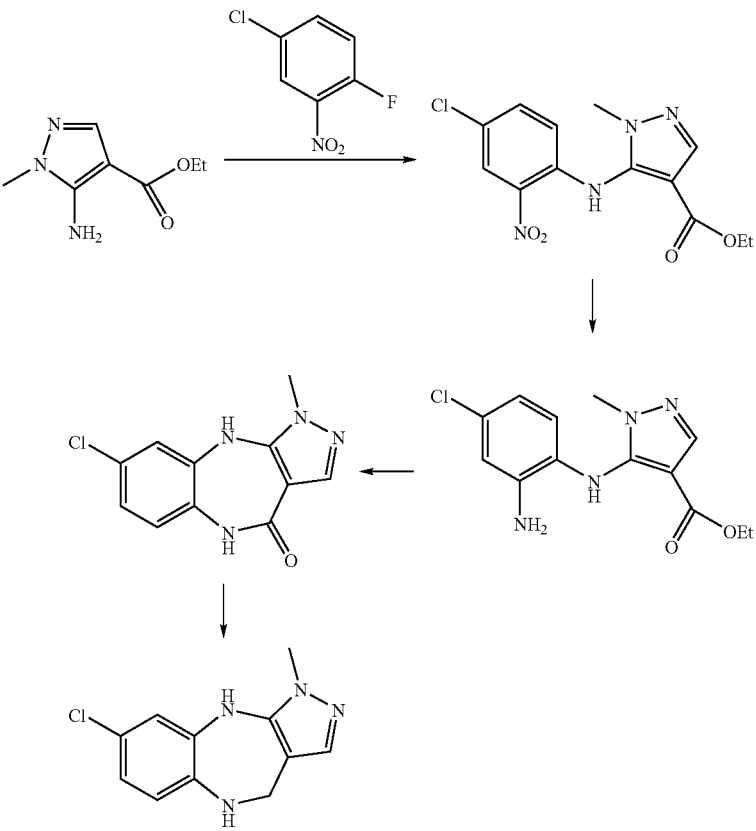

Example E2
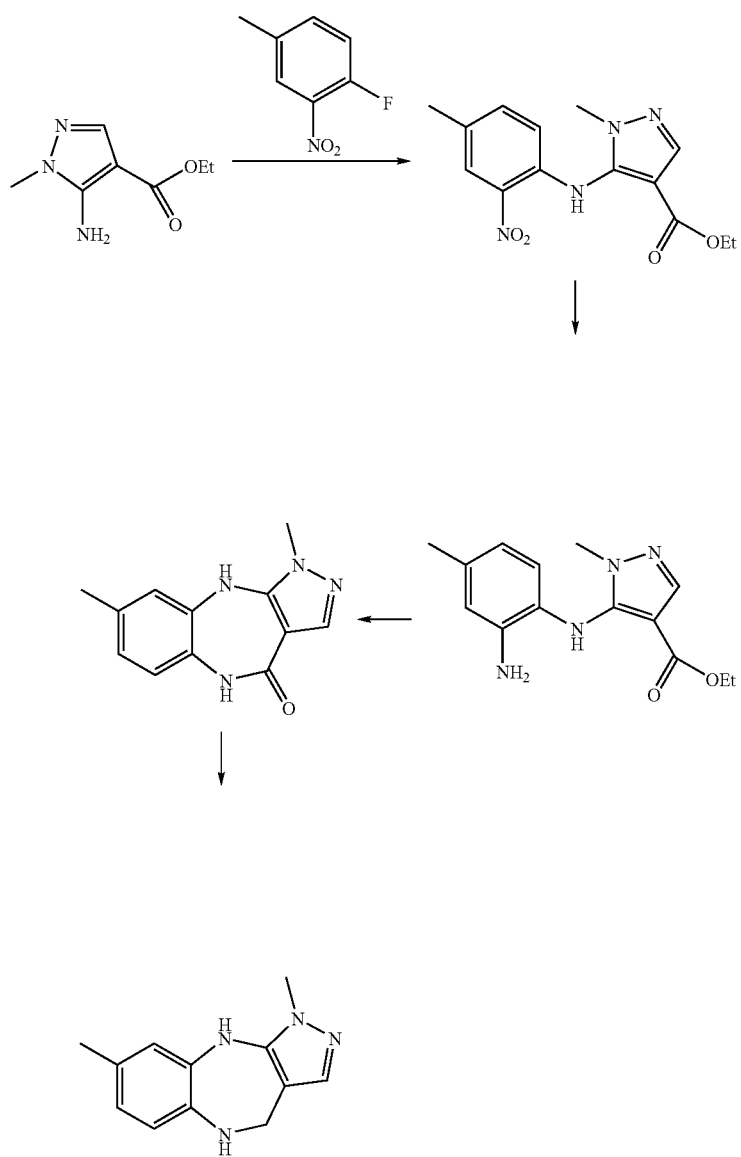
Examples E2a-g
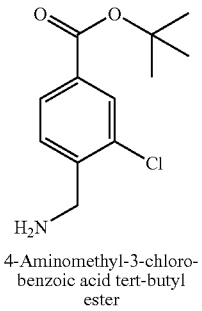
4-Aminomethyl-3-chloro-benzoic acid tert-butyl ester
Example E2a
Example E2b
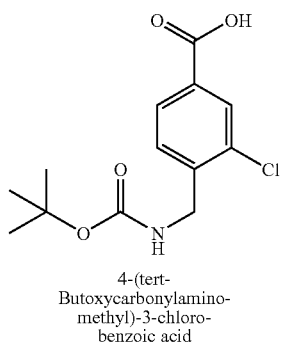
4-(tert-Butoxycarbonylamino-methyl)-3-chloro-benzoic acid

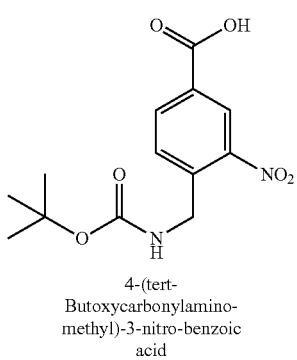
4-(tert-Butoxycarbonylamino-methyl)-3-nitro-benzoic acid
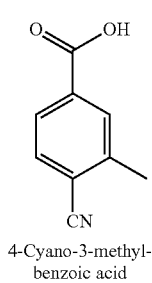
4-Cyano-3-methyl-benzoic acid
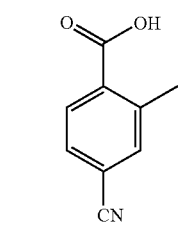
Example E2e
4-Cyano-2-methyl-benzoic acid
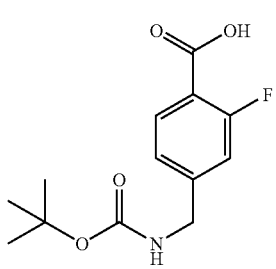
Example E2f
4-(tert-Butoxycarbonylamino-methyl)-2-fluoro-benzoic acid
Example E2c
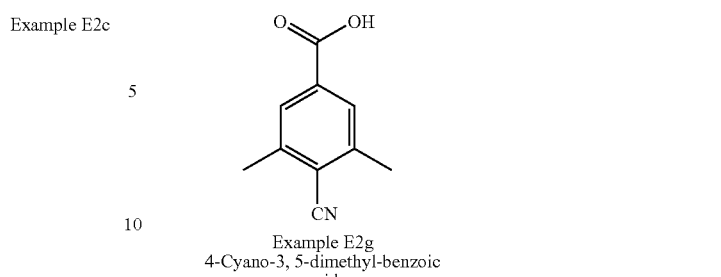
Example E2g
4-Cyano-3,5-dimethyl-benzoic acid
Example E2d
Example E2h
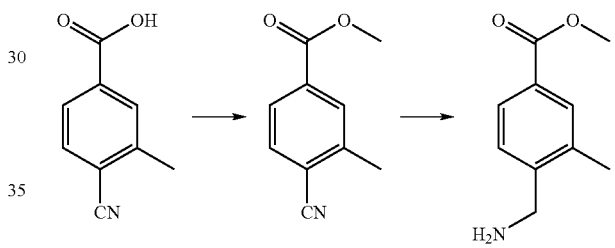
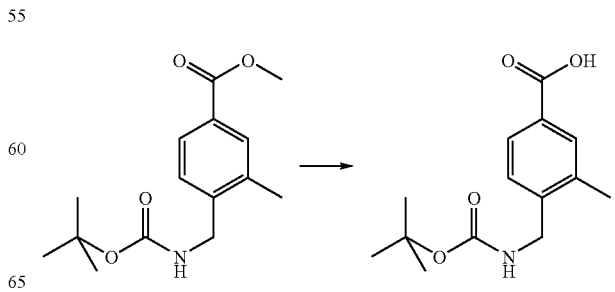

Example E3
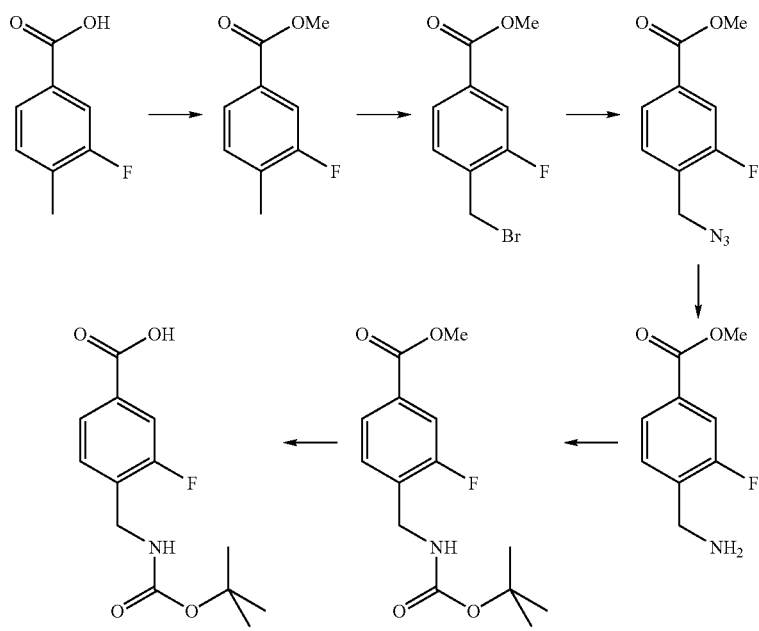
Example E4
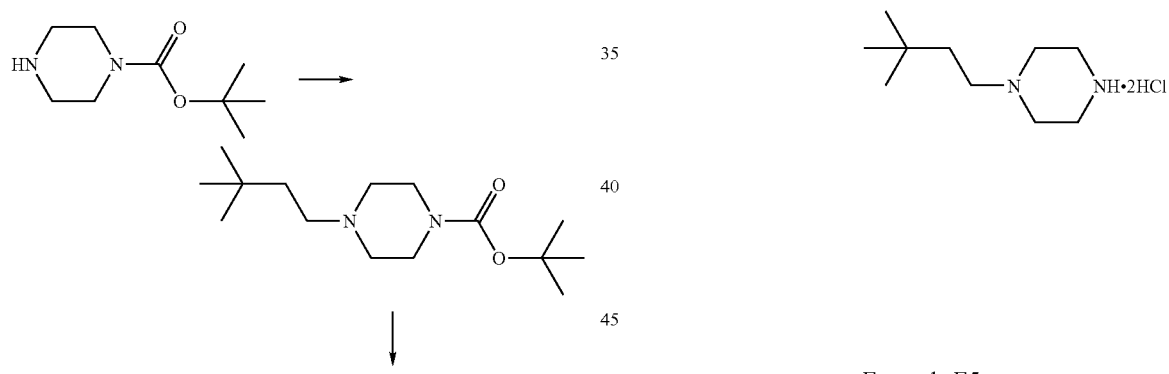
Example E5
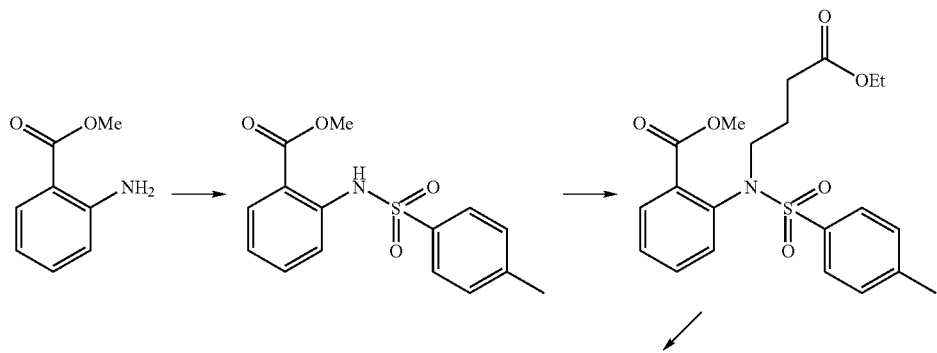

97
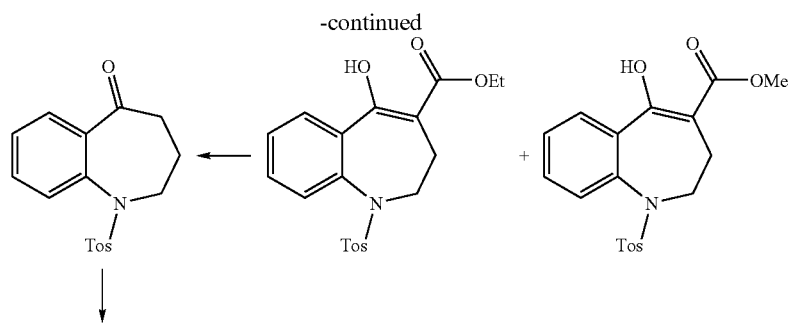
98
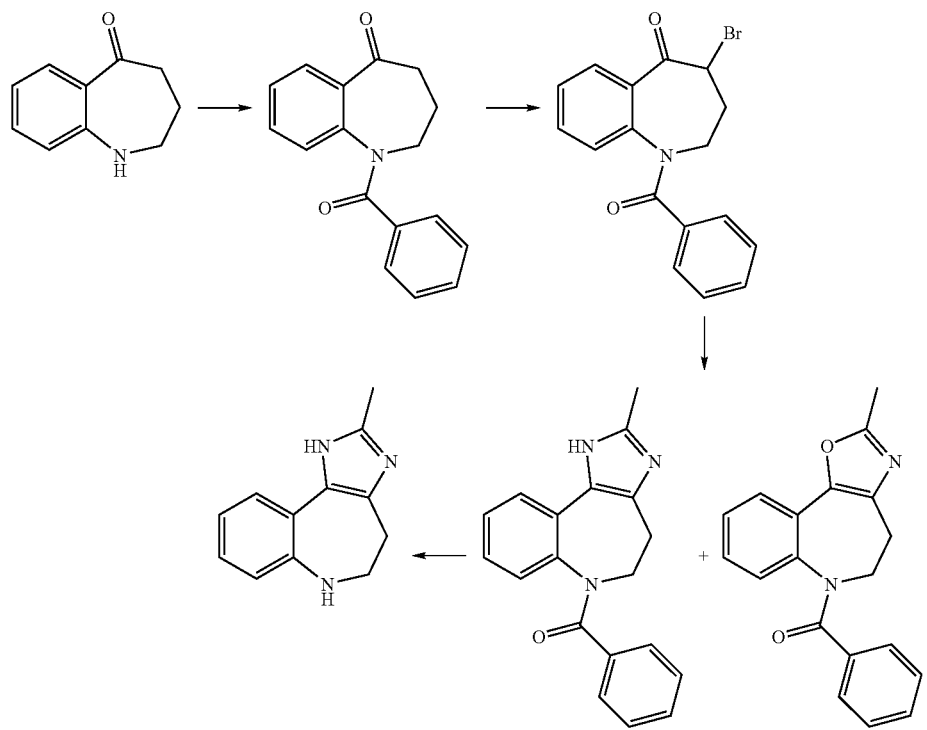
Example E5a
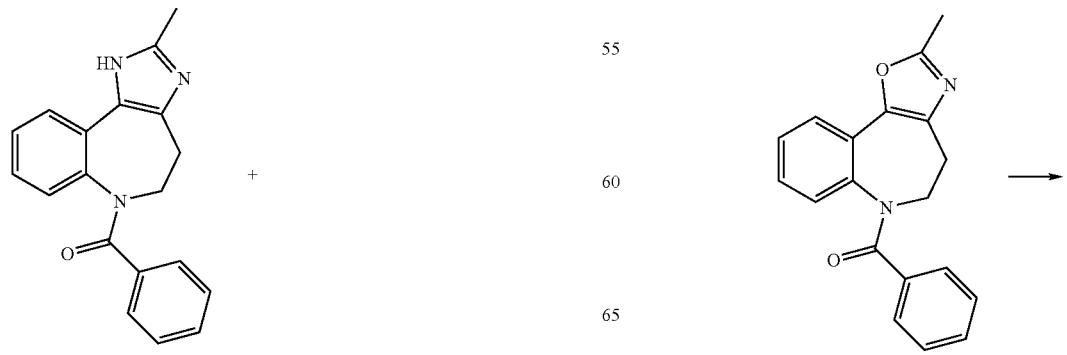
-continued

99
-continued
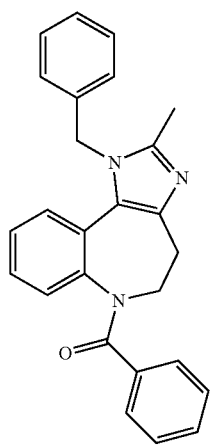
100
Example E7
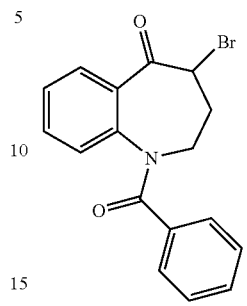
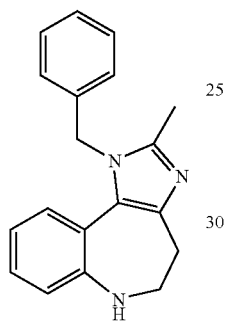
Example E6
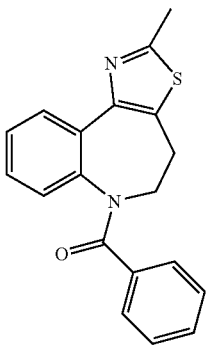
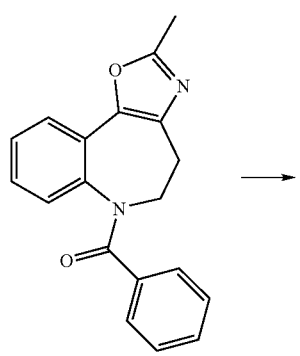
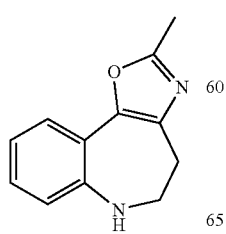
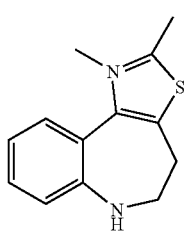

101
Example E8
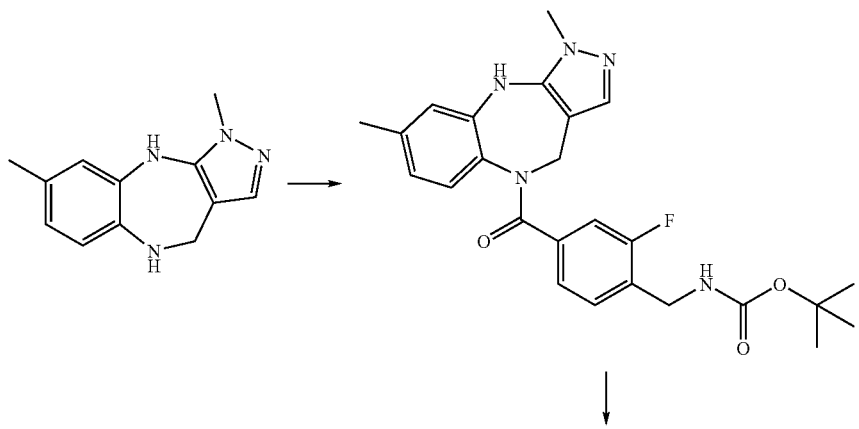
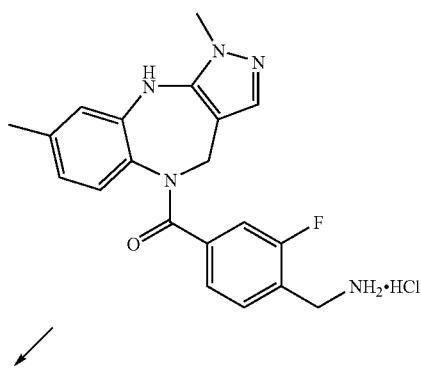
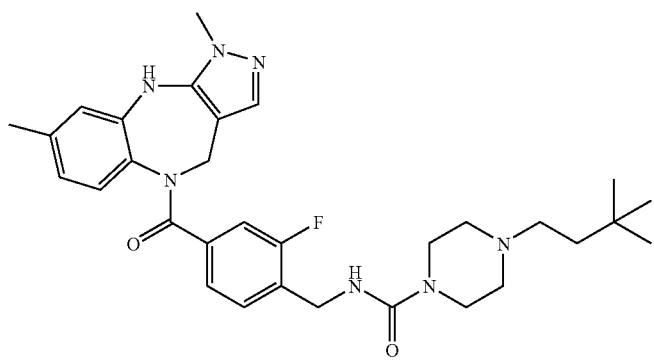

103
Example E9
104
Example E11
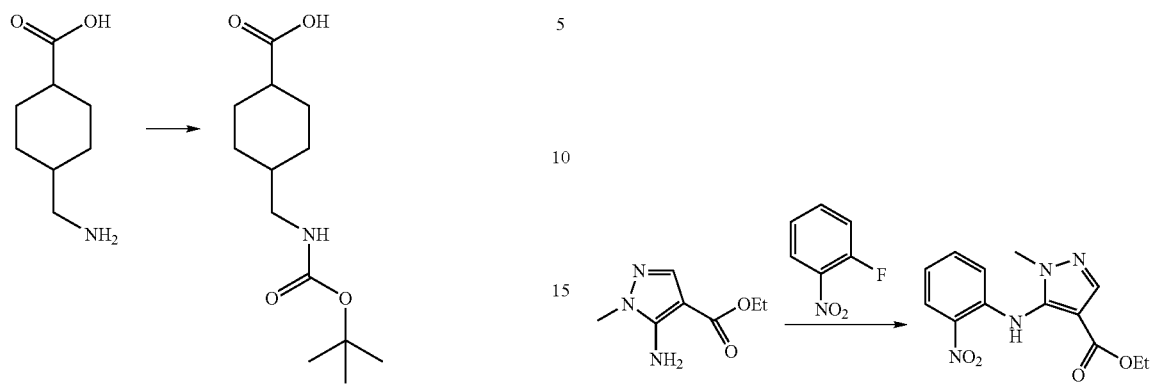
Example E10
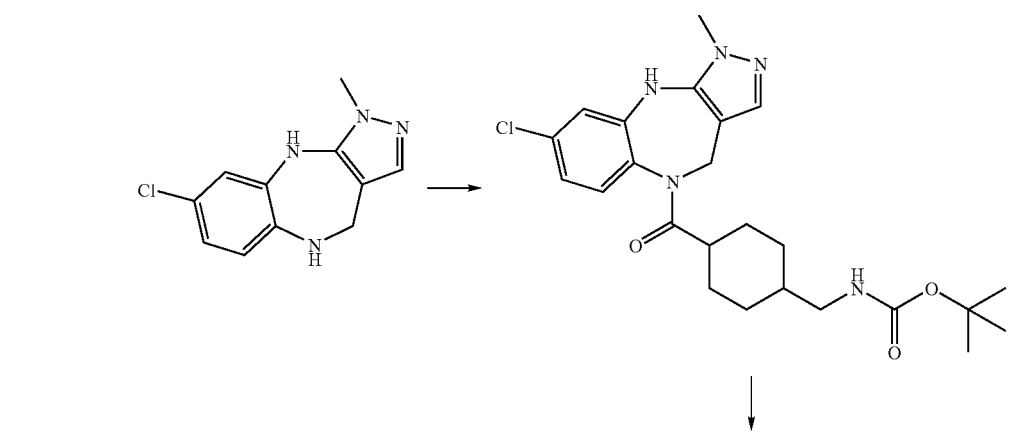
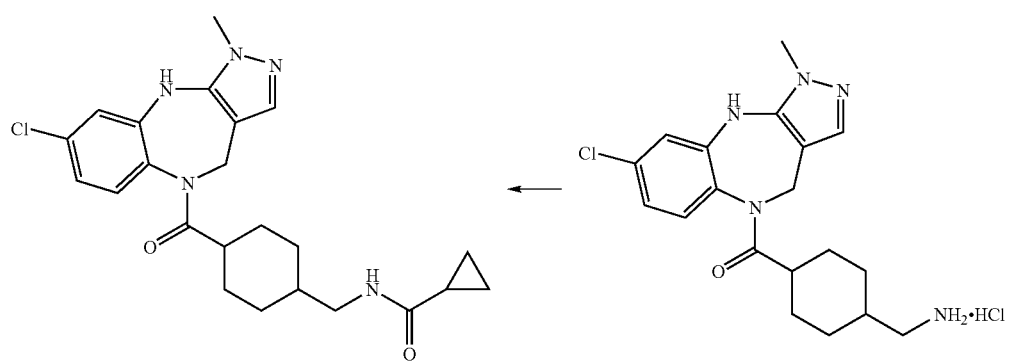

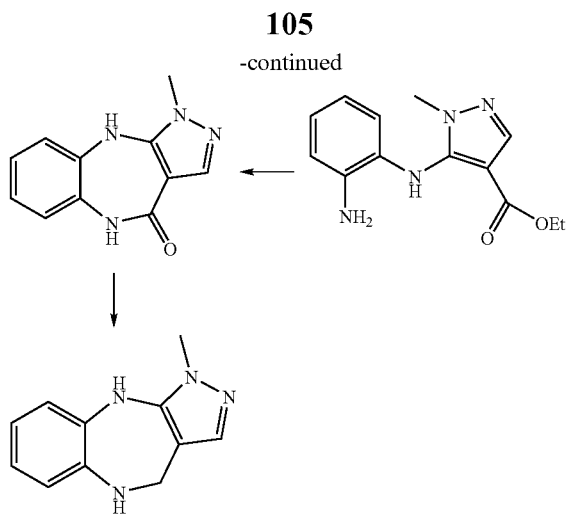
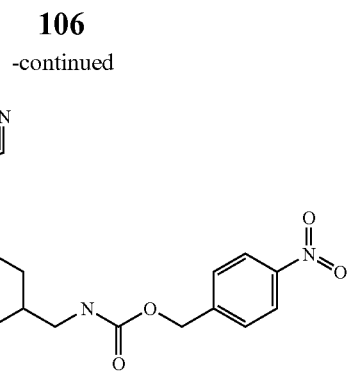
Example E14
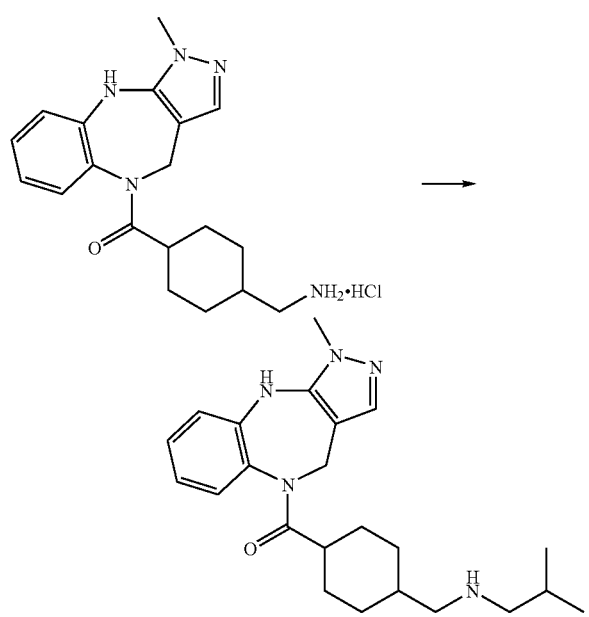
Example E12
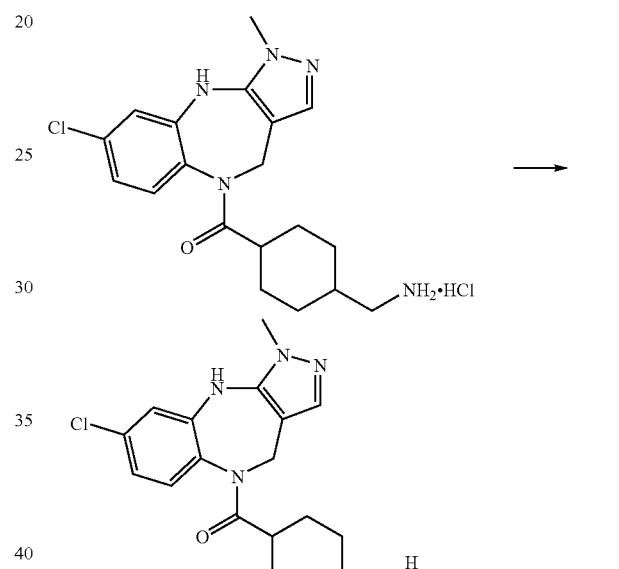
Example E15
Example E13

107
Example E15a
108
Example E16
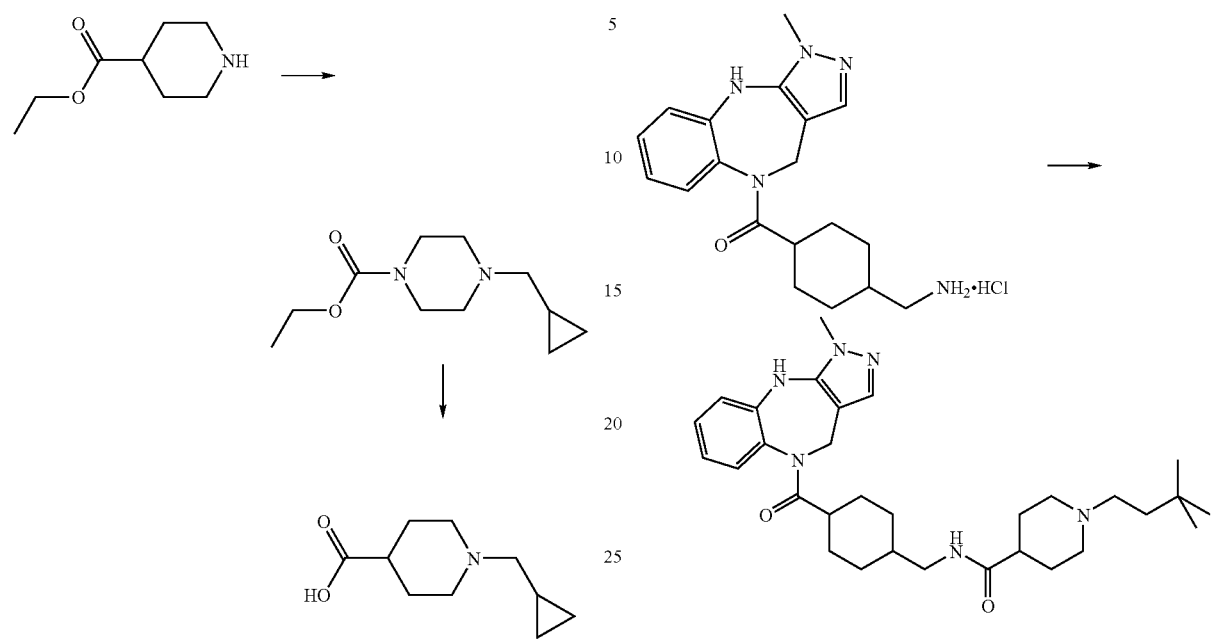
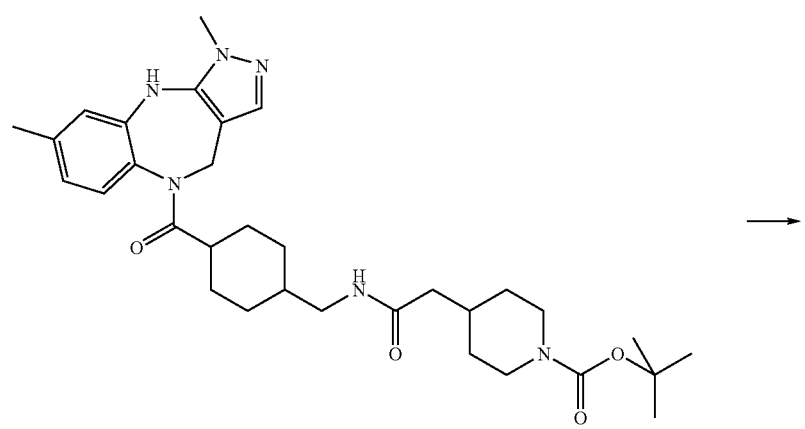
Example E17
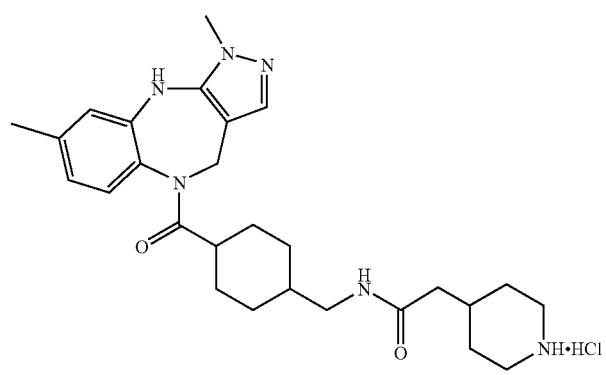

109
Example E18
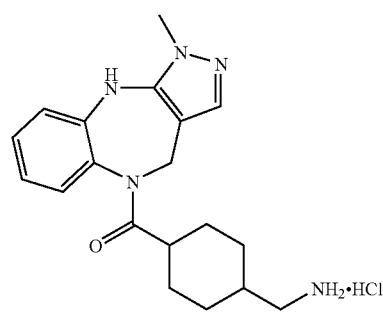
110
Example E20
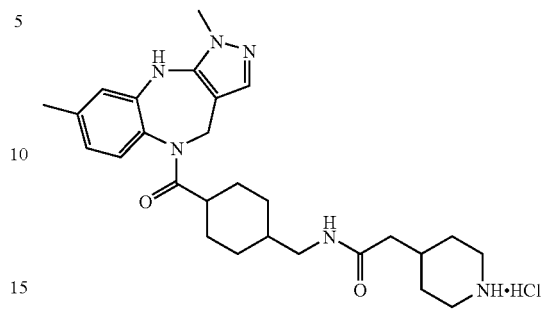
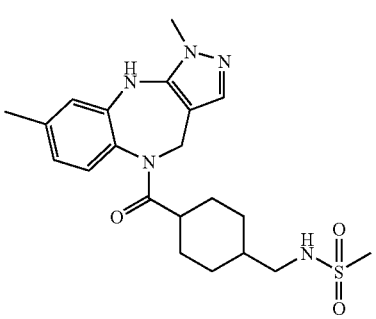
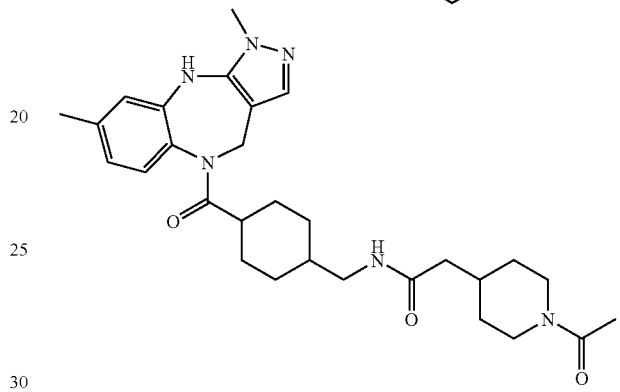
Example E19
Example E21
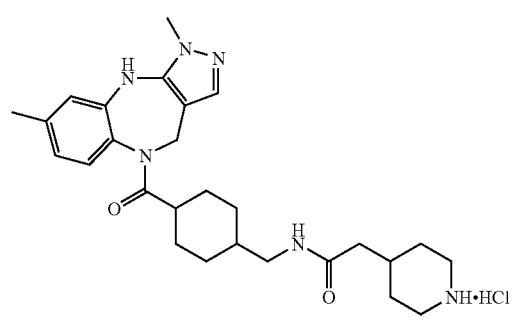
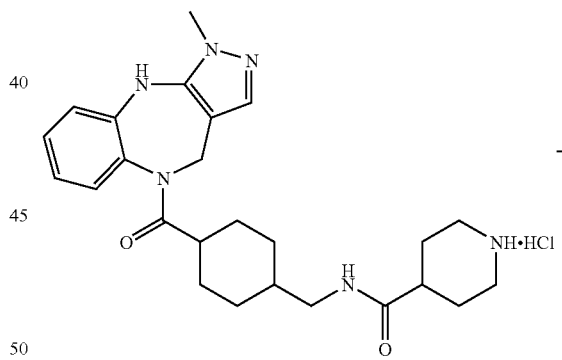
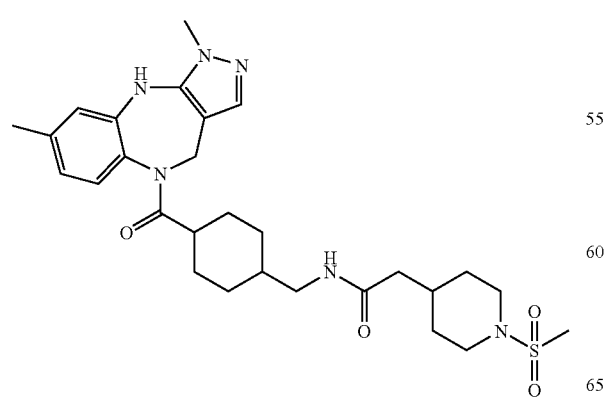
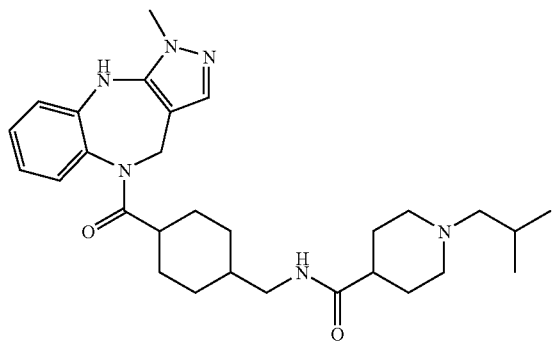

Example E22
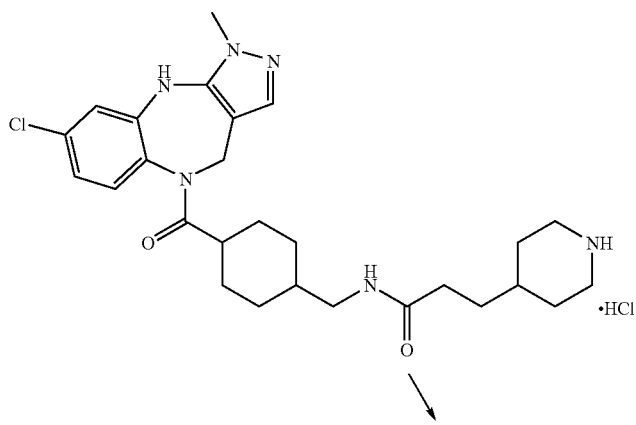
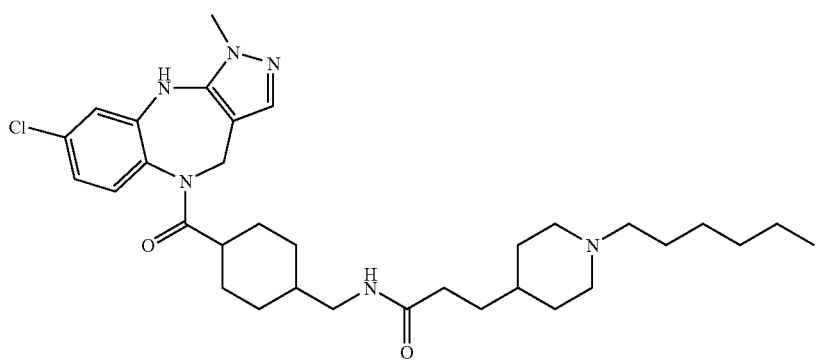
Example E23
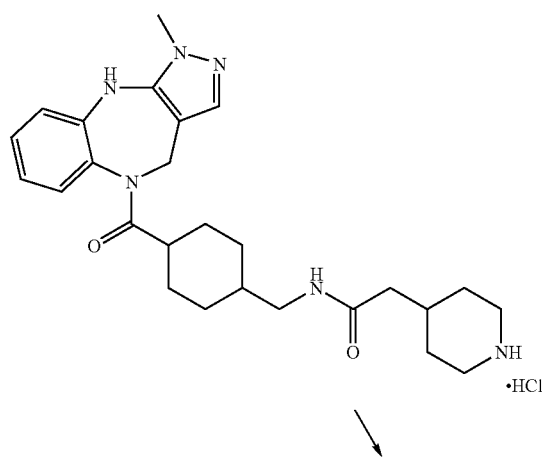

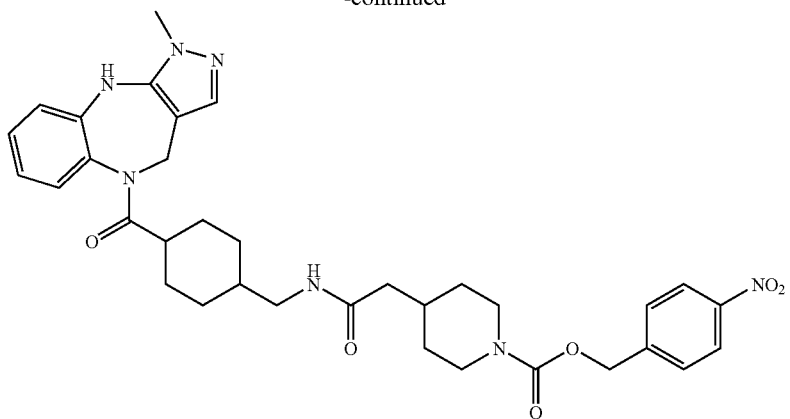
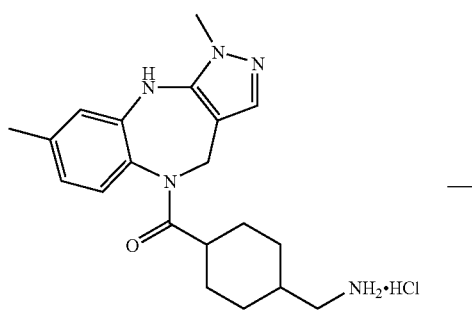
Example E24
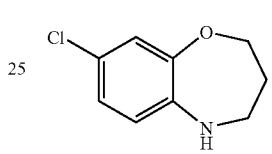
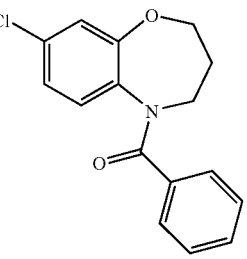
Example E26
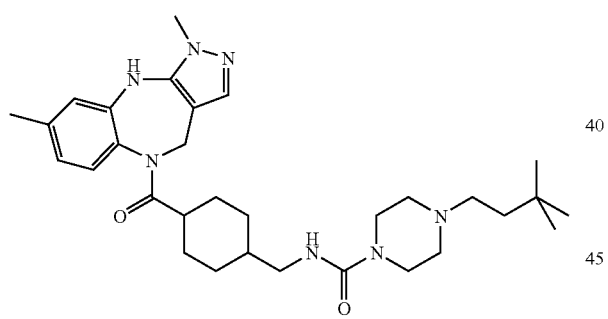
Example E25
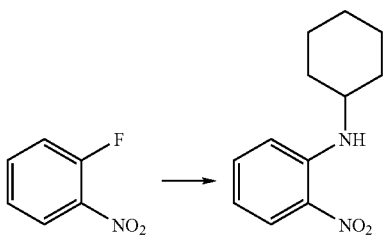
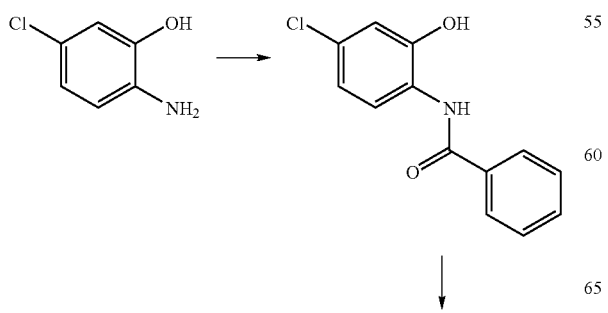
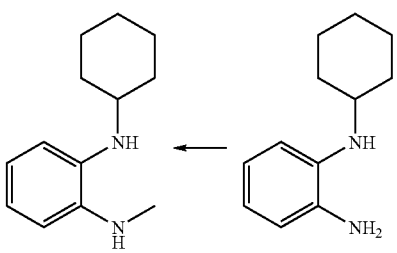

Example E27
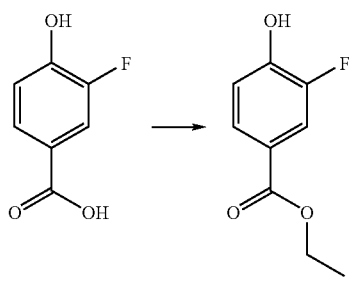
Example E28
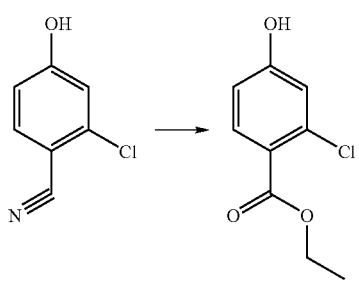
Example E29
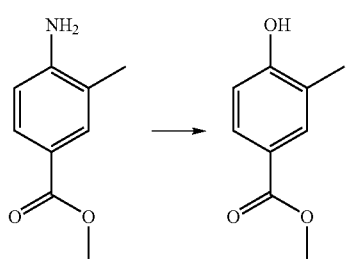
Example E30
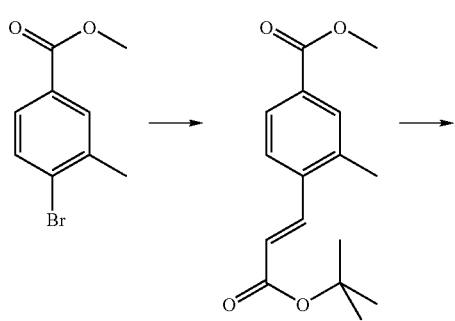
-continued
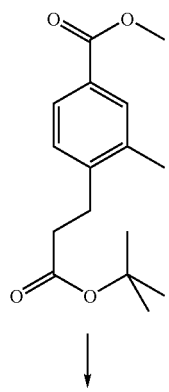
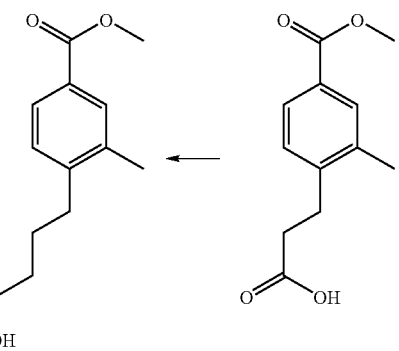
Example E31
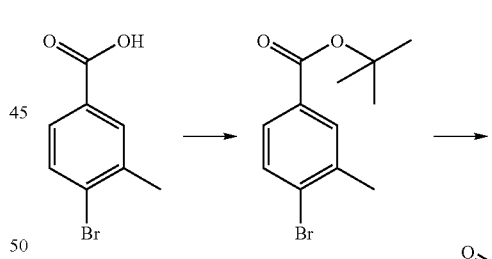
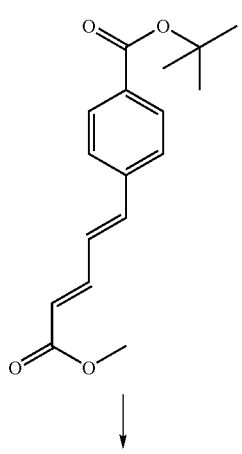

117
-continued
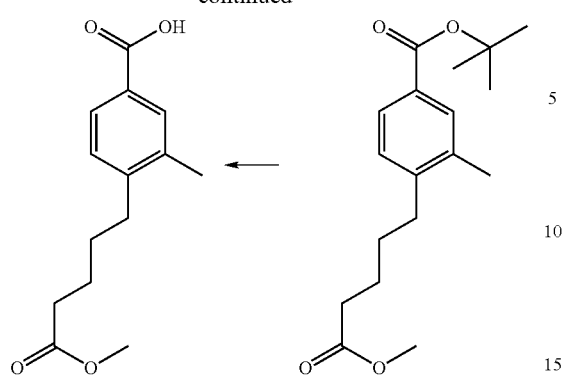
Example E32
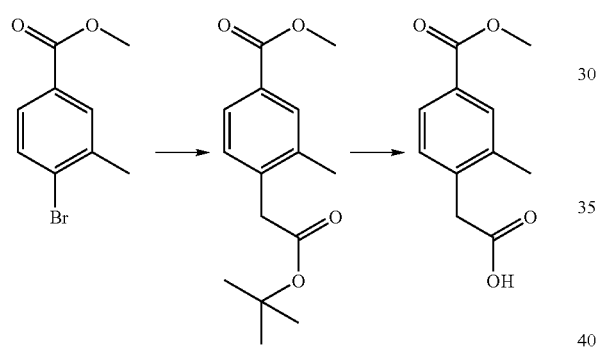
Example E33
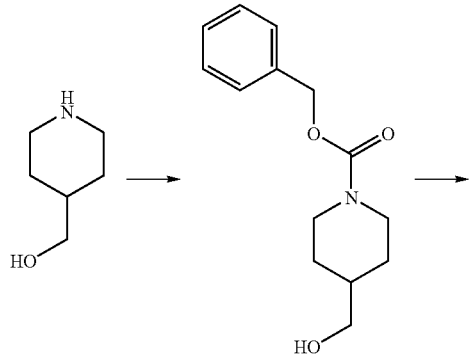
118
-continued
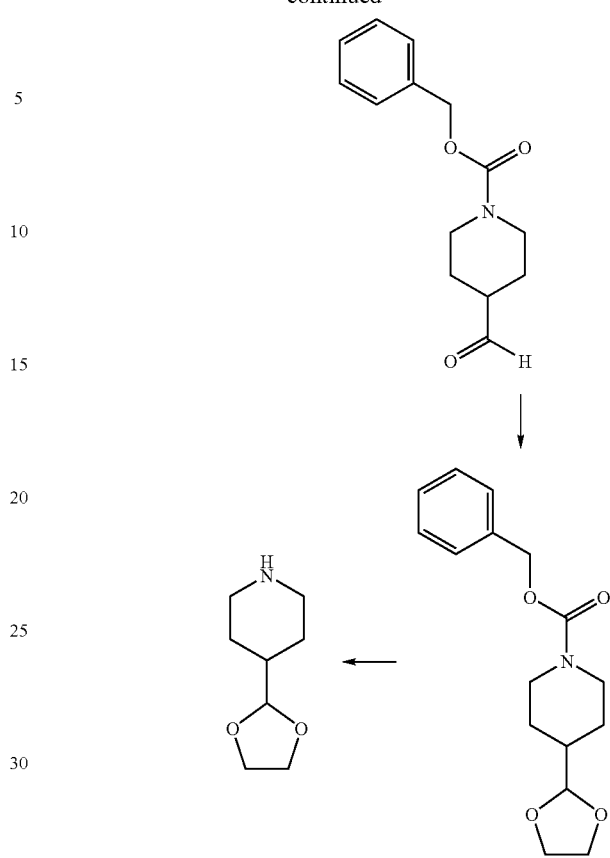
Example E34
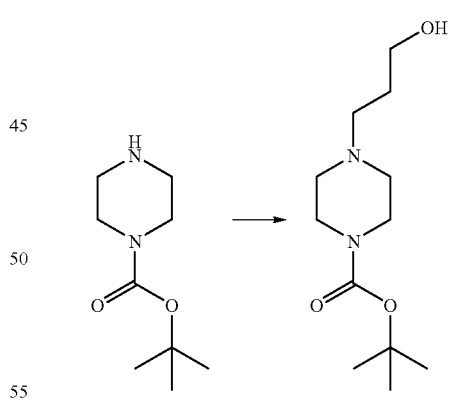
Example E35
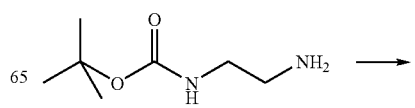

119
-continued
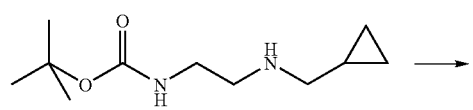
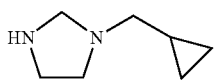
•2TFA
120
Example E38
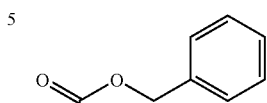
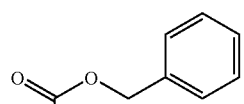
Example E36
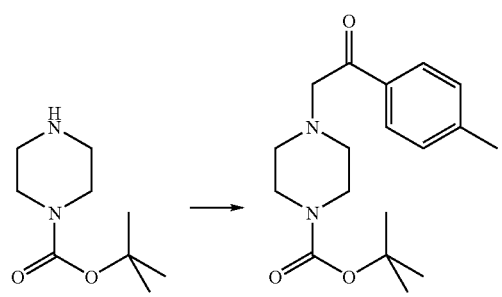
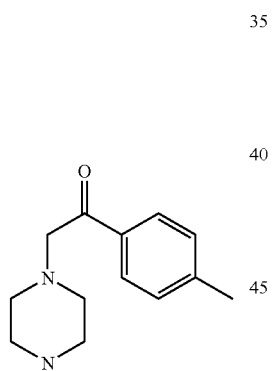
•2HCl
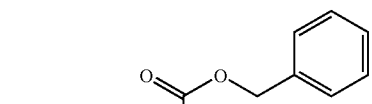
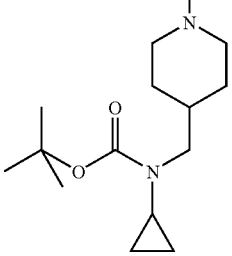
Example E37
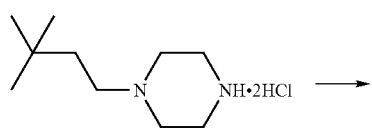
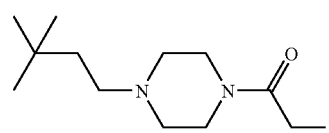
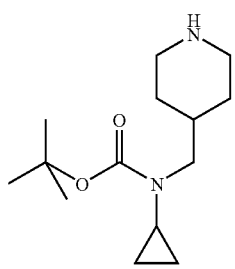

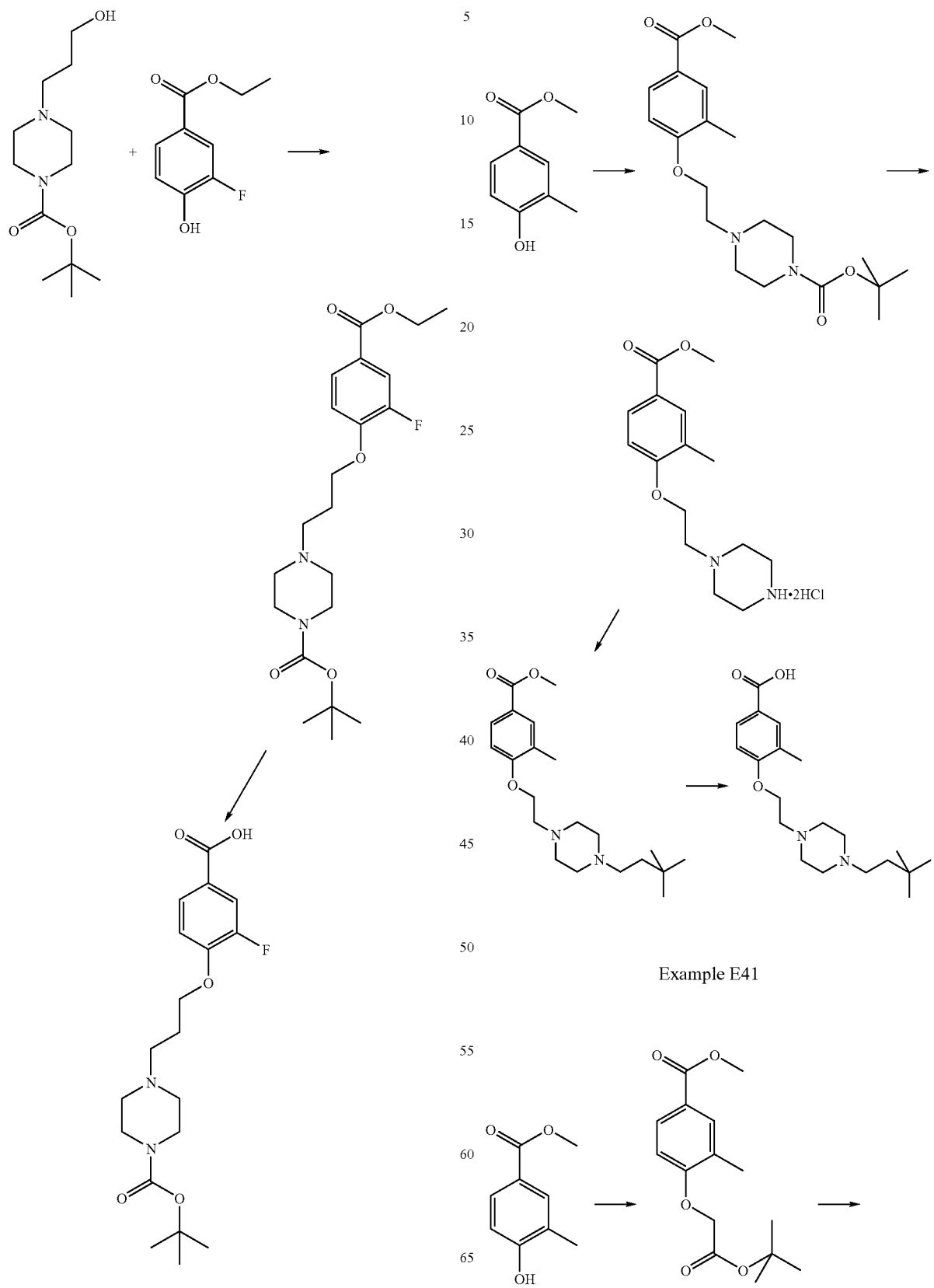

123
-continued
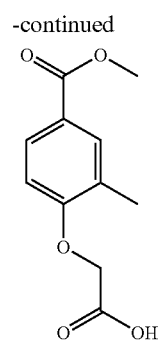
Example E41a
Example E41b
124
-continued
Example E41c
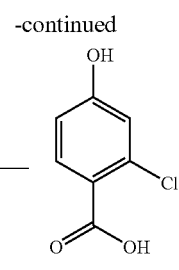
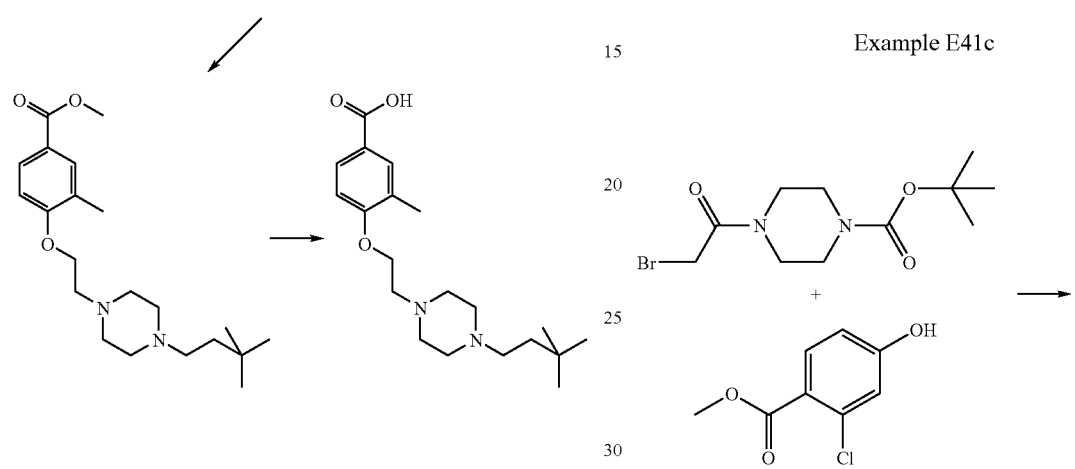
Example E42

125
-continued
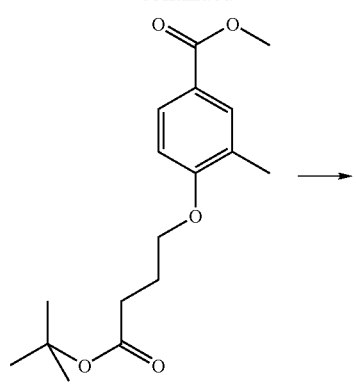
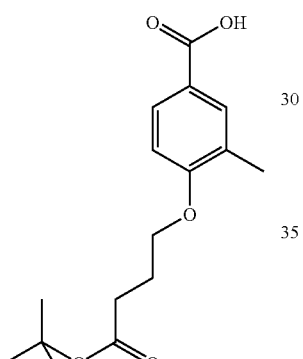
Example E43
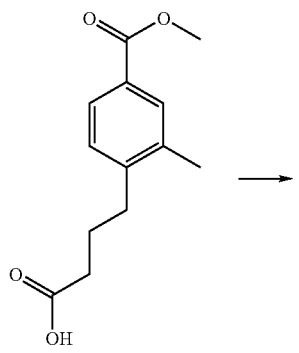
126
-continued
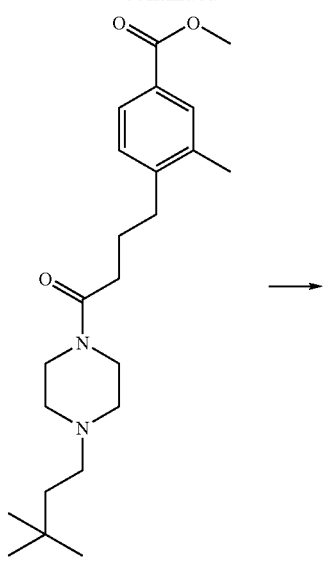
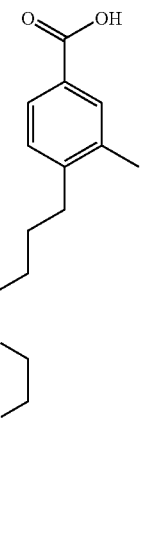
Example E44
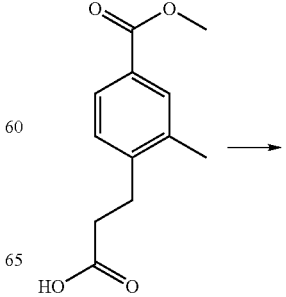

127
-continued
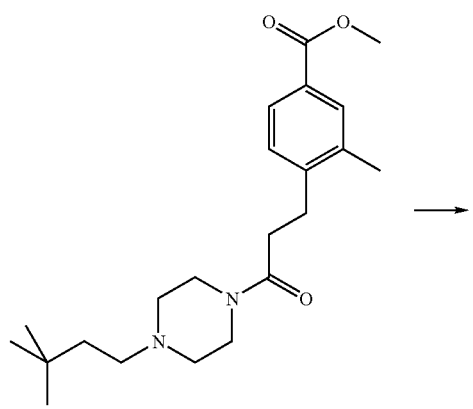
128
-continued
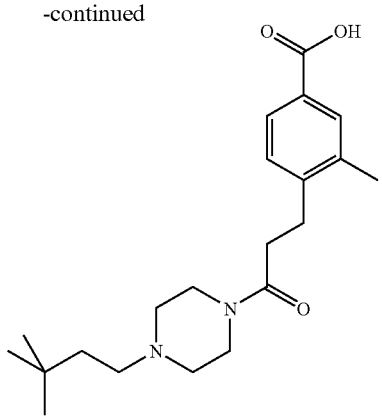
Example E45
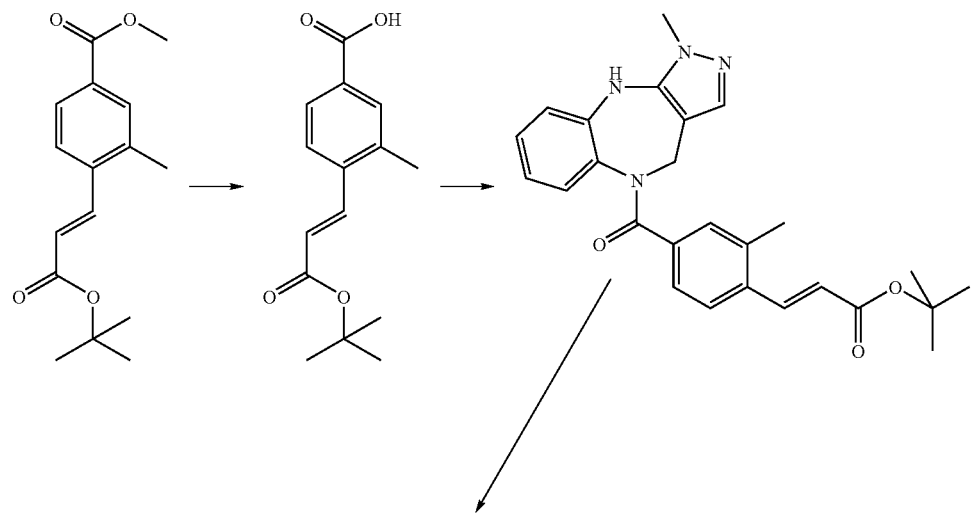
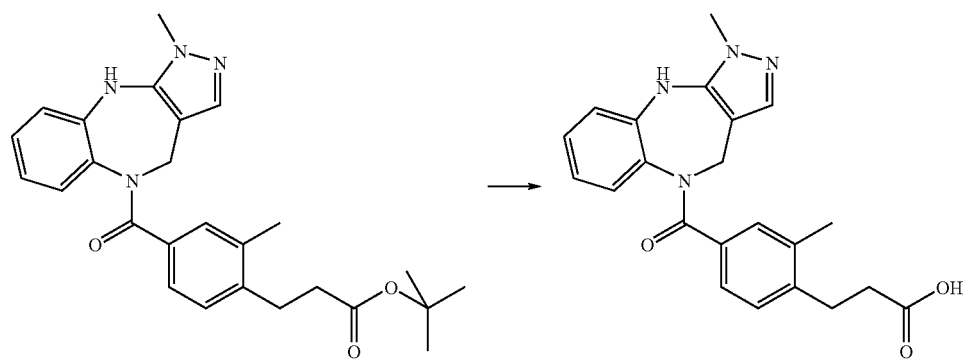

129
Example E46
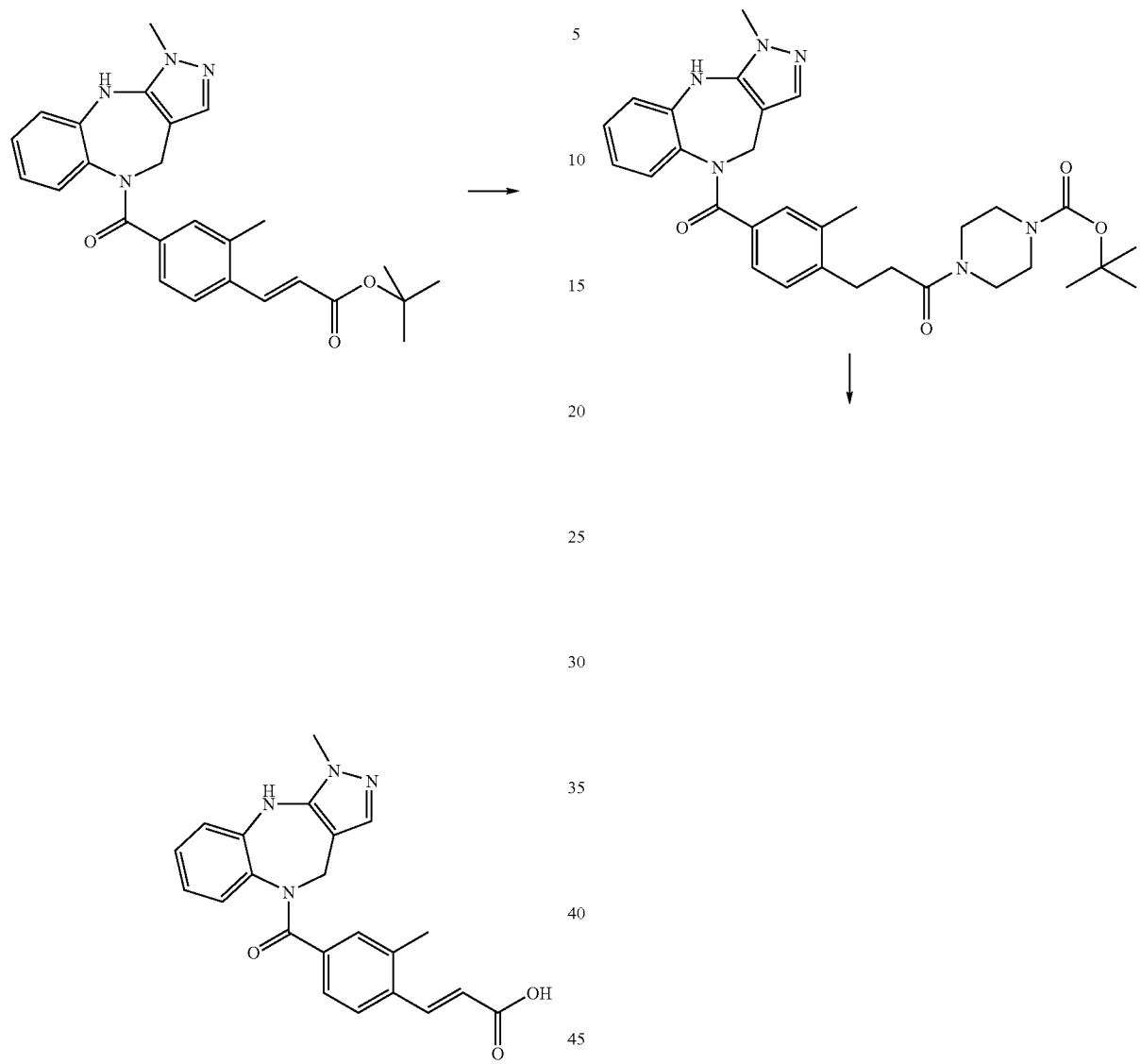
Example E47
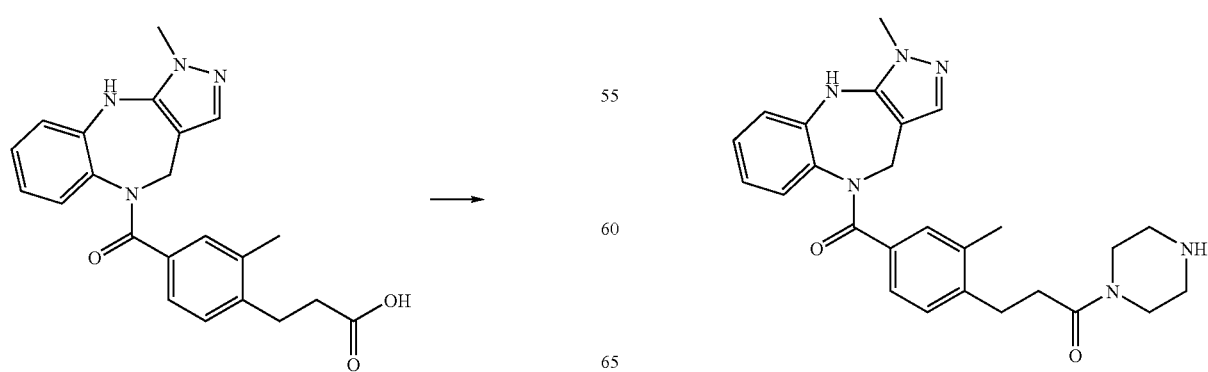

131
Example E48
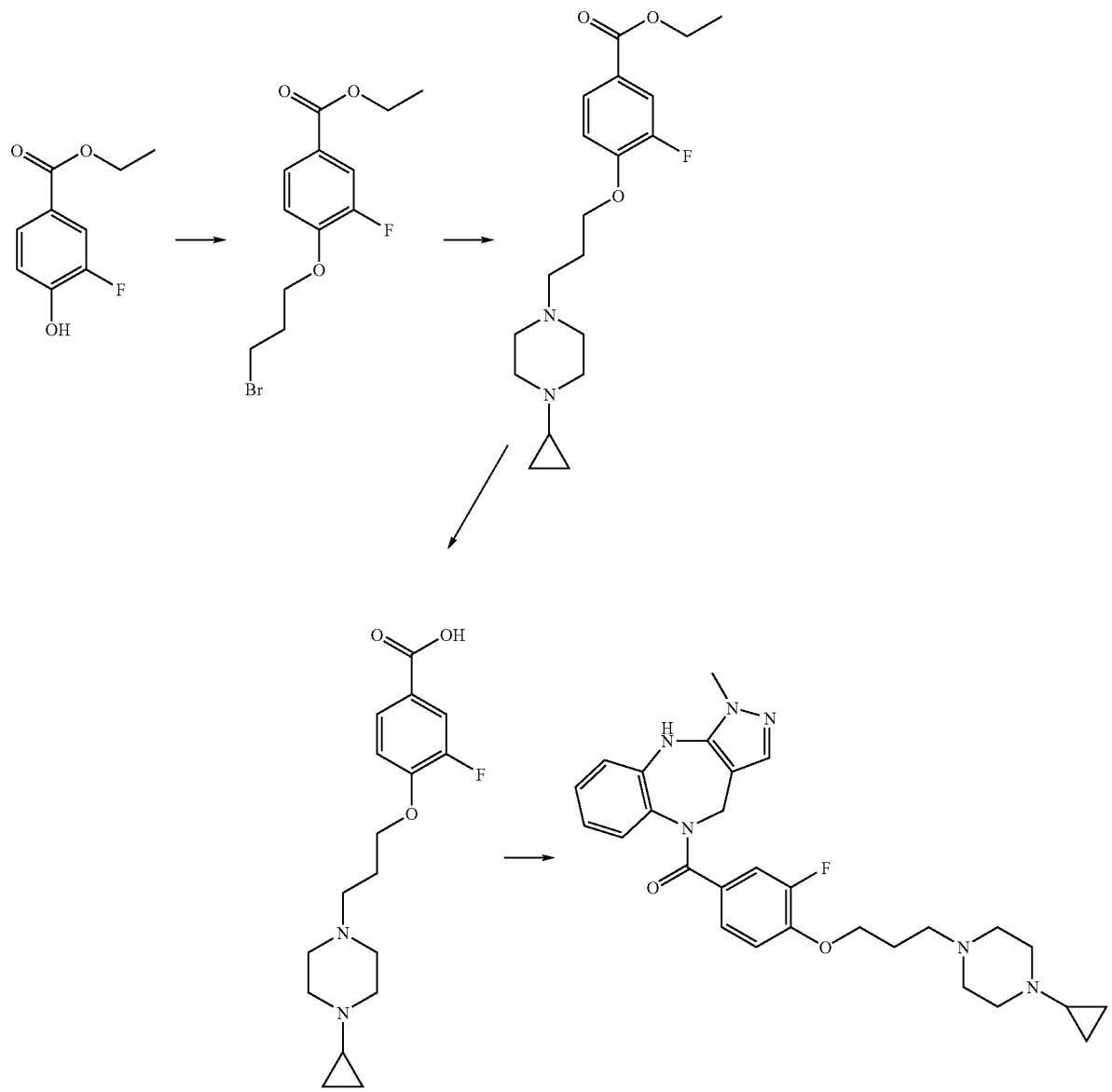
132
Example E49
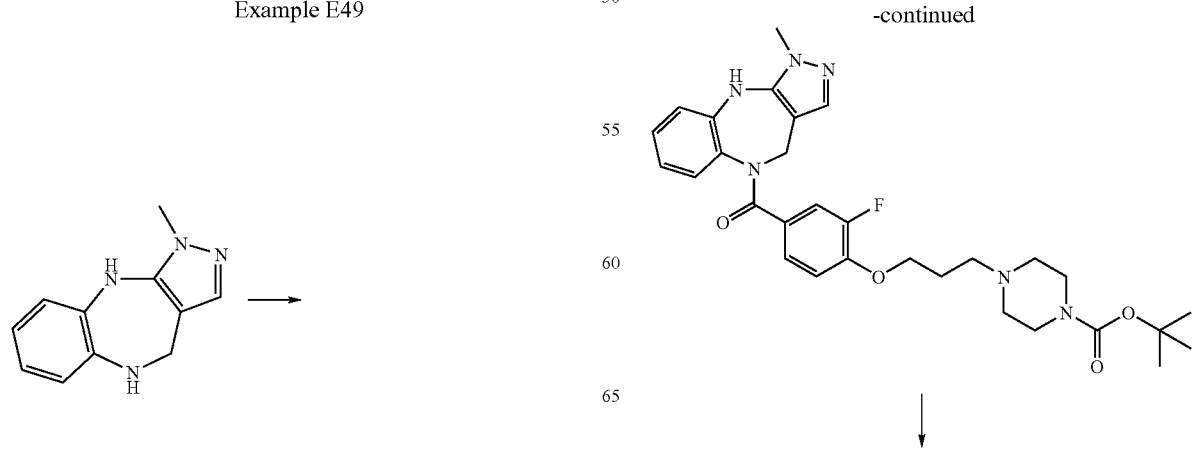
-continued

133
-continued
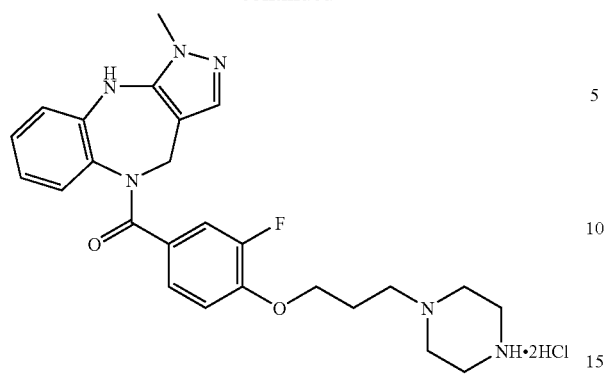
Example E50
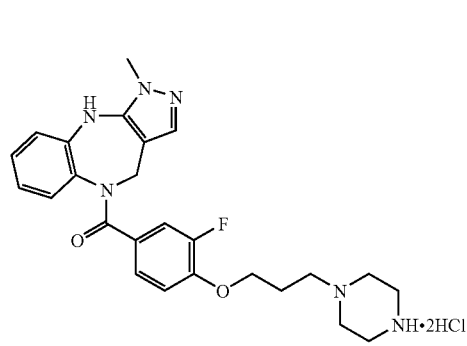
Example E51
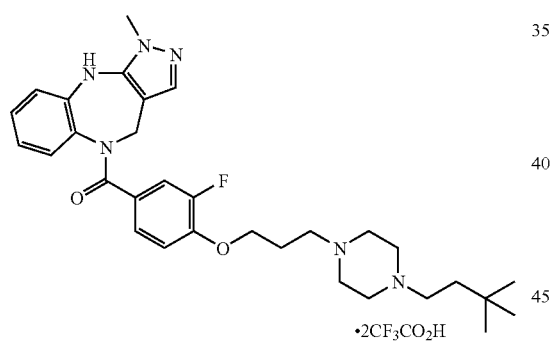
134
-continued
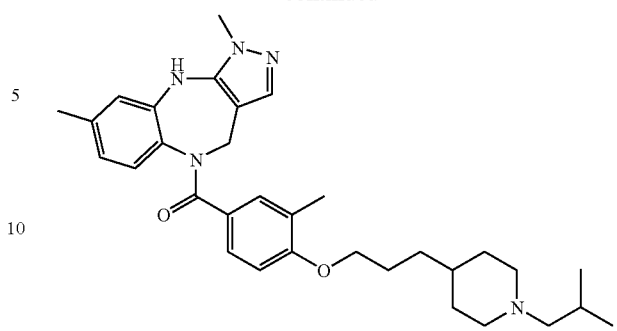
Example E52
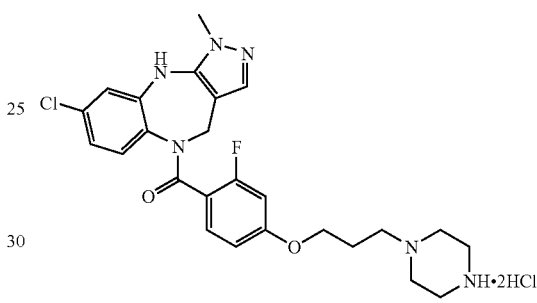
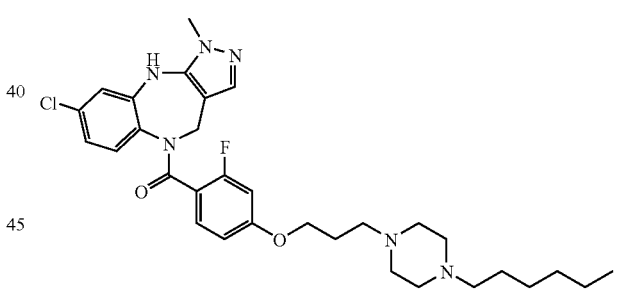
Example E53
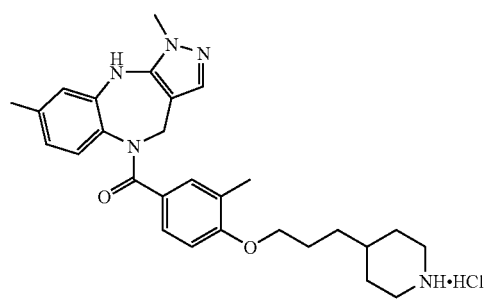
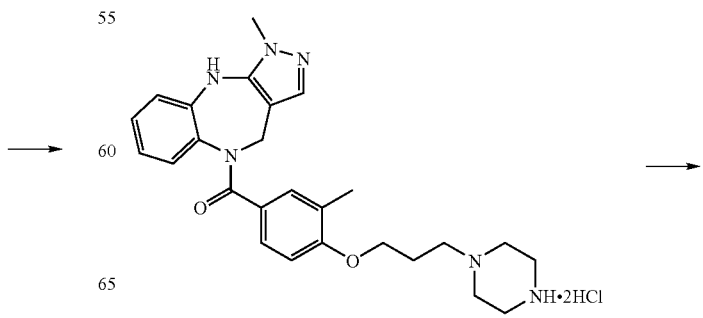

135
-continued
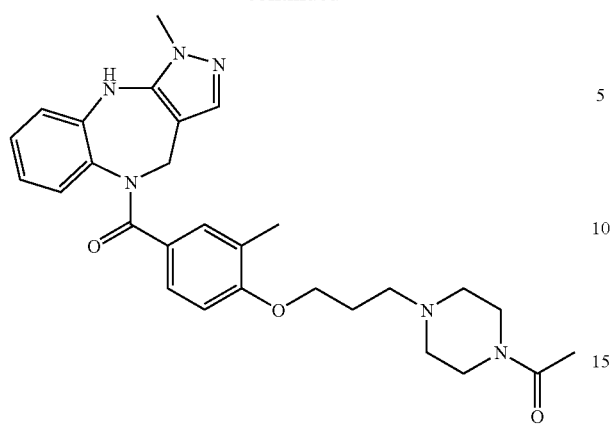
Example E54
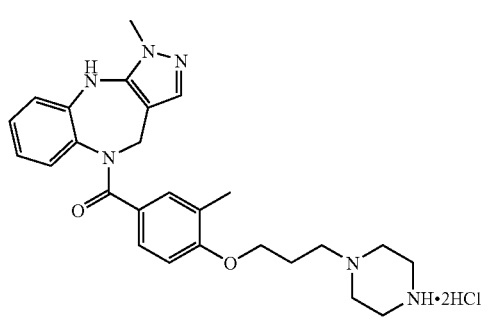
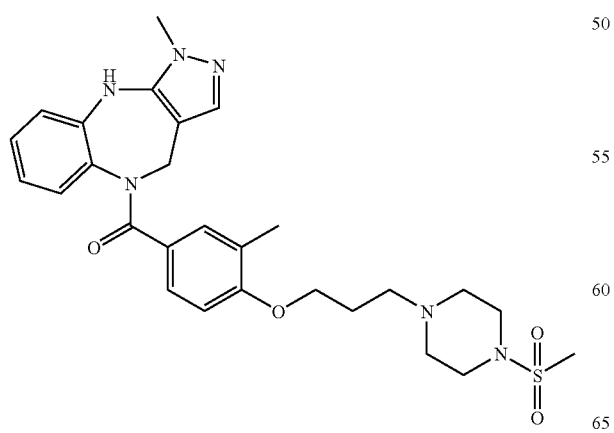
136
Example E55
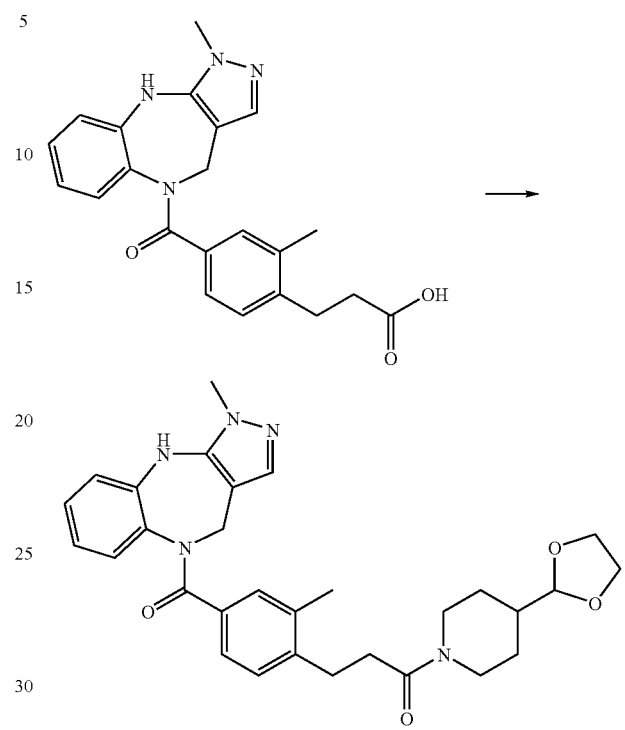
Example E56
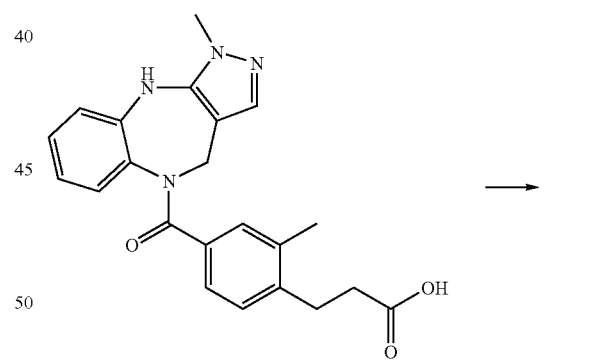
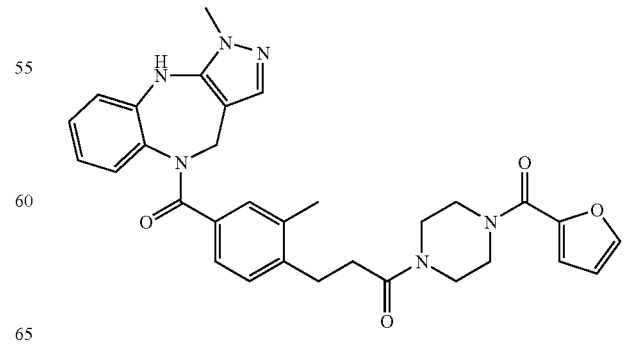

137
Example E57
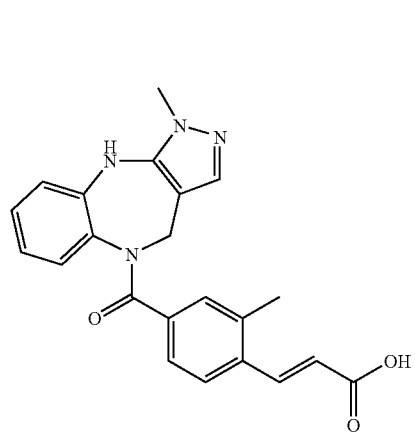
→
138
-continued
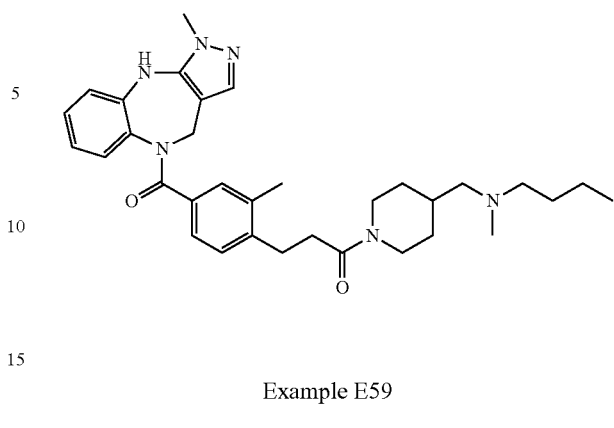
Example E59
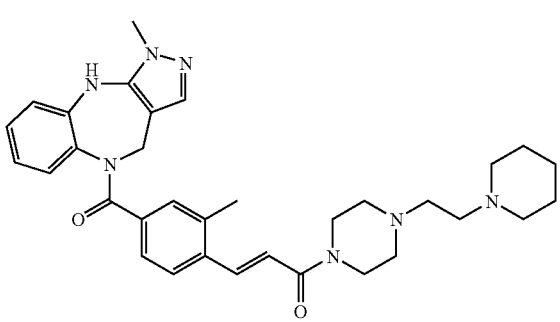
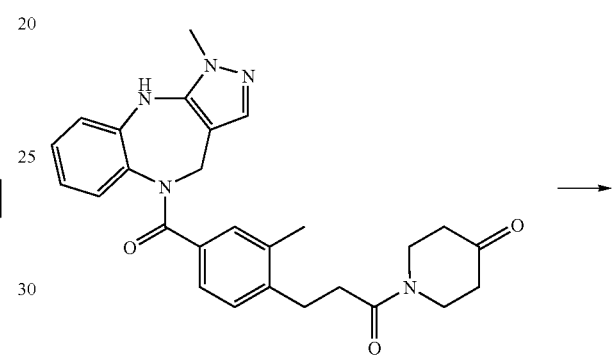
Example E58
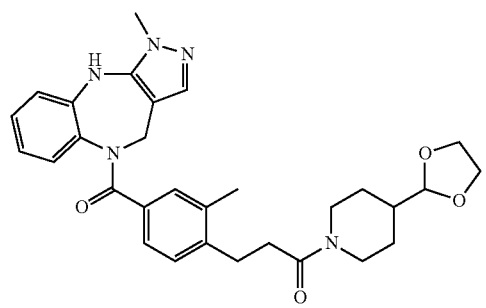
→
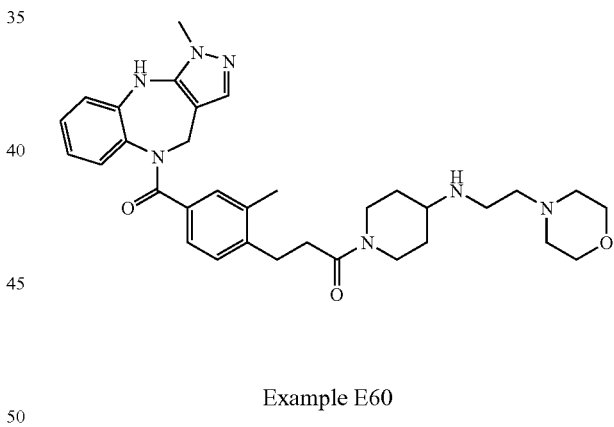
Example E60
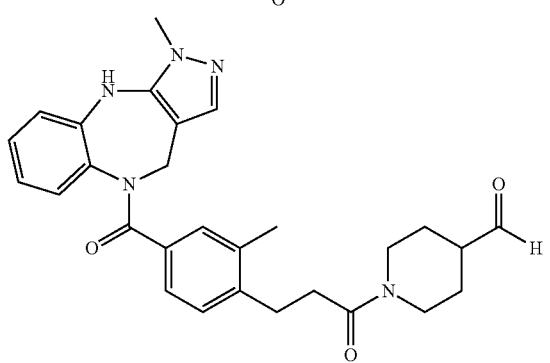
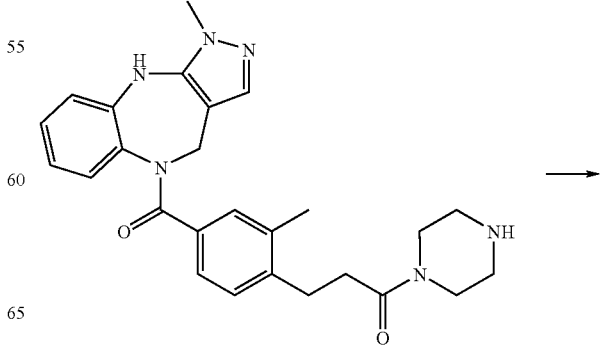
→

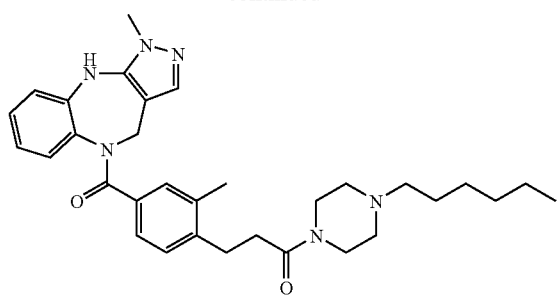
Example E61
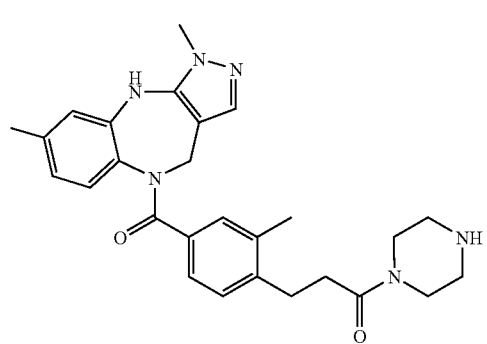 
Example E62
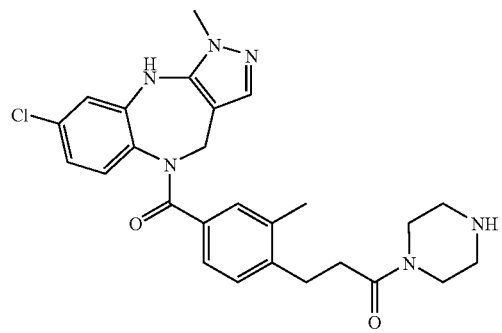 
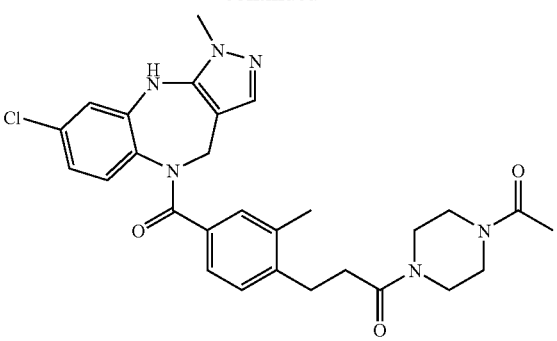
Example E63
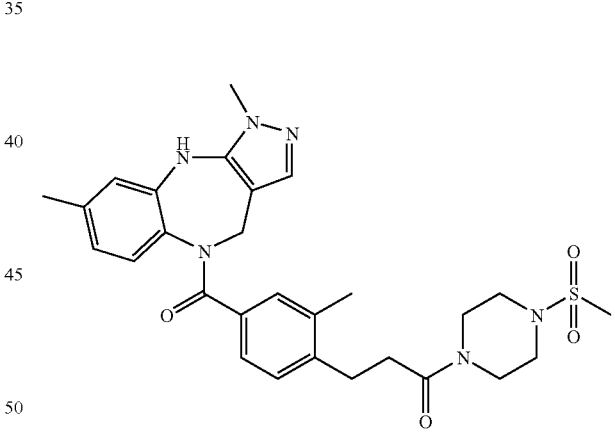
Example E64
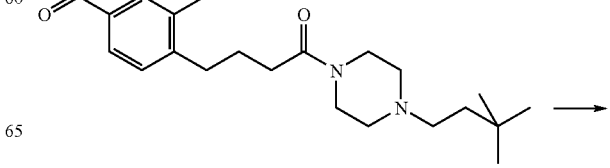

141
-continued
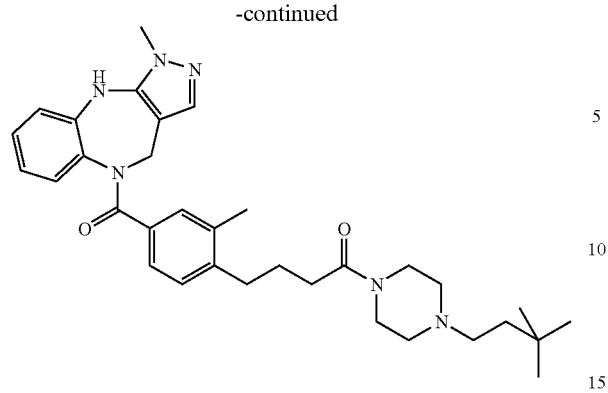
Example E65
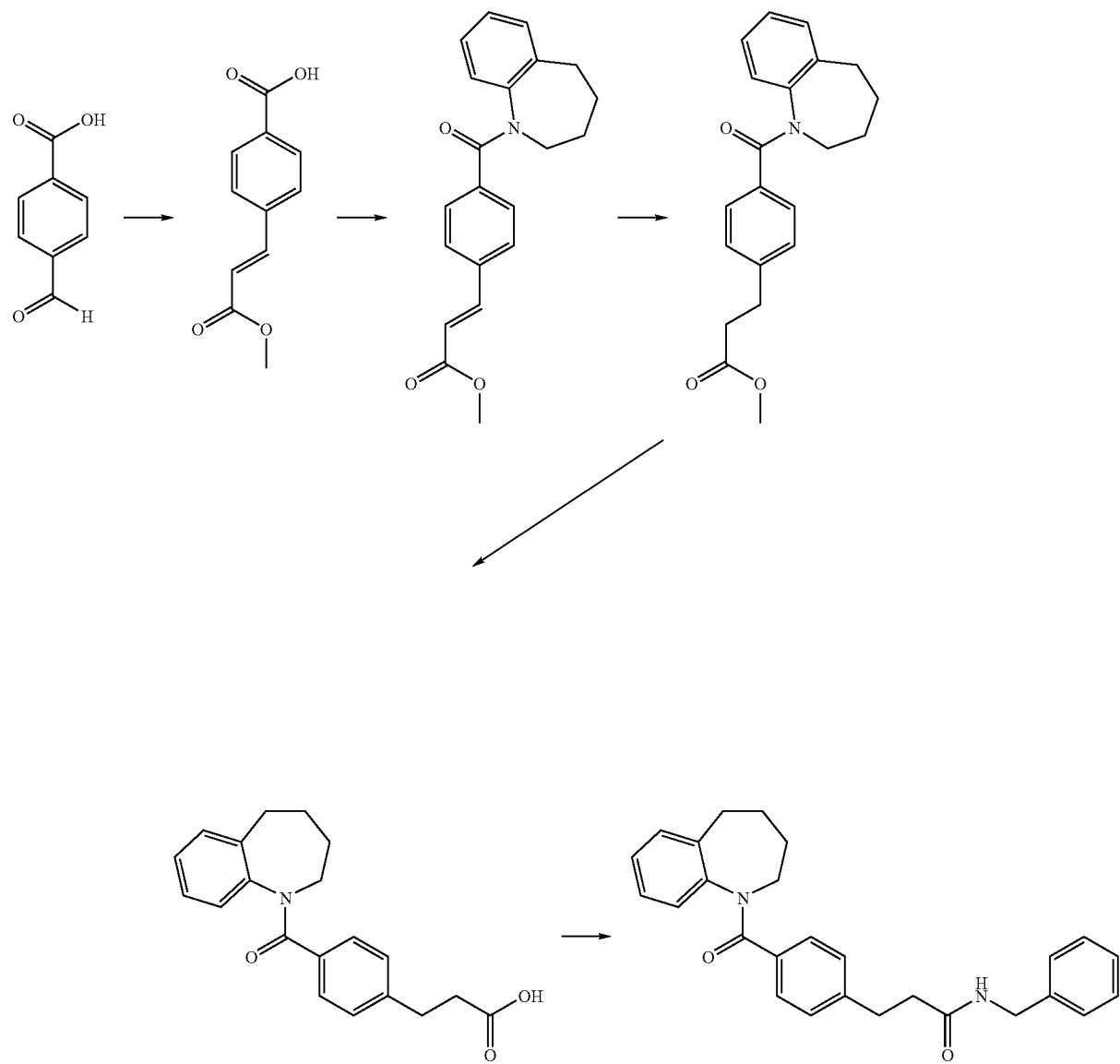

143
Example E66
144
Example E67
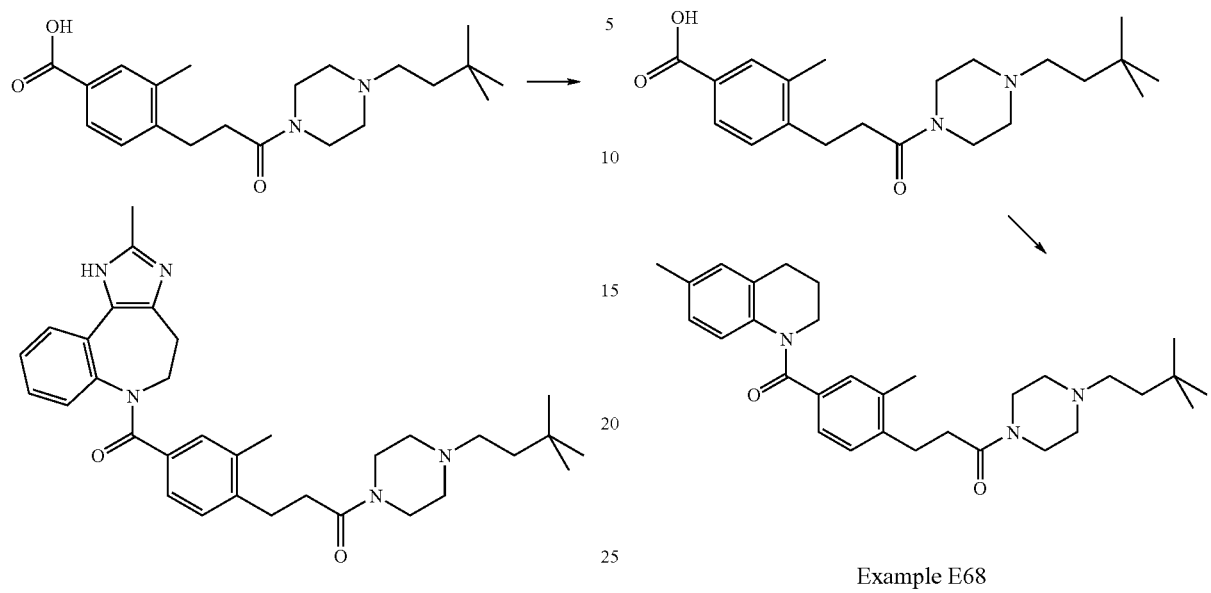
Example E68
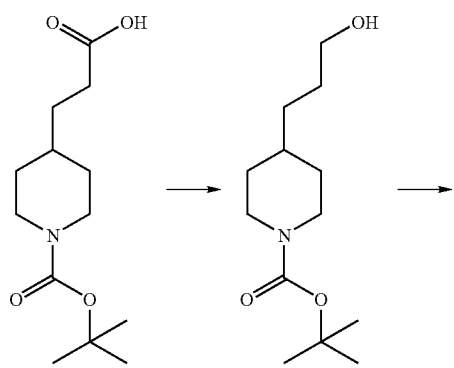
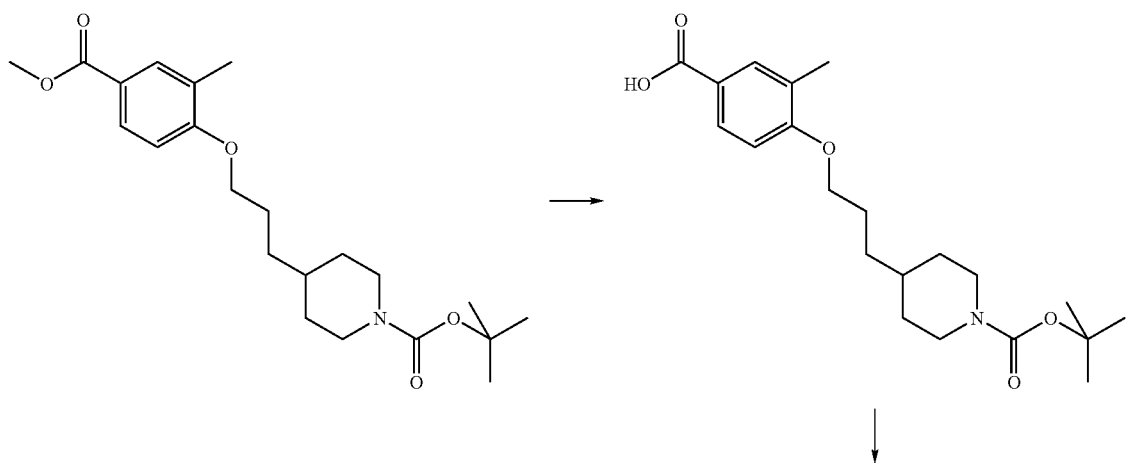

145
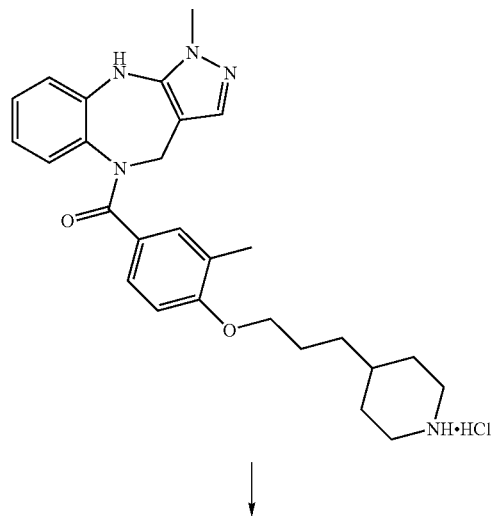
146
-continued
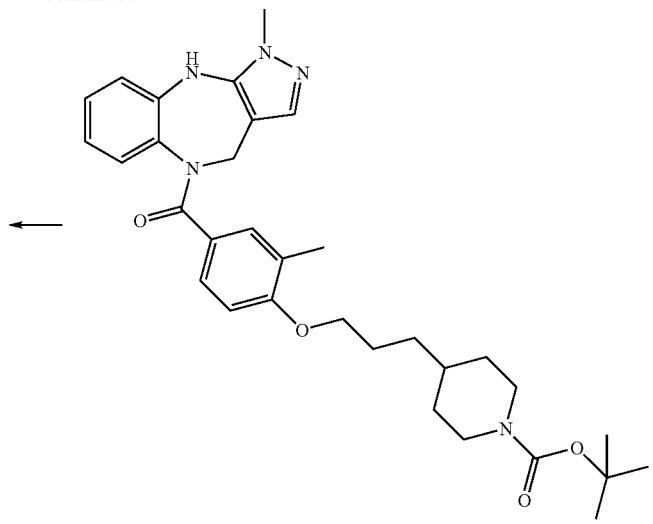
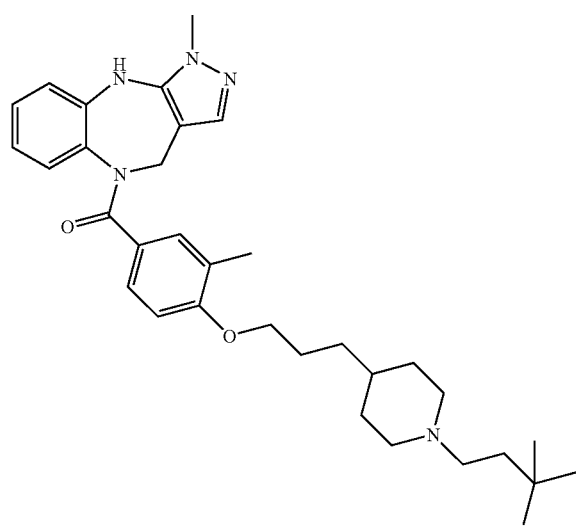

147
Example E69
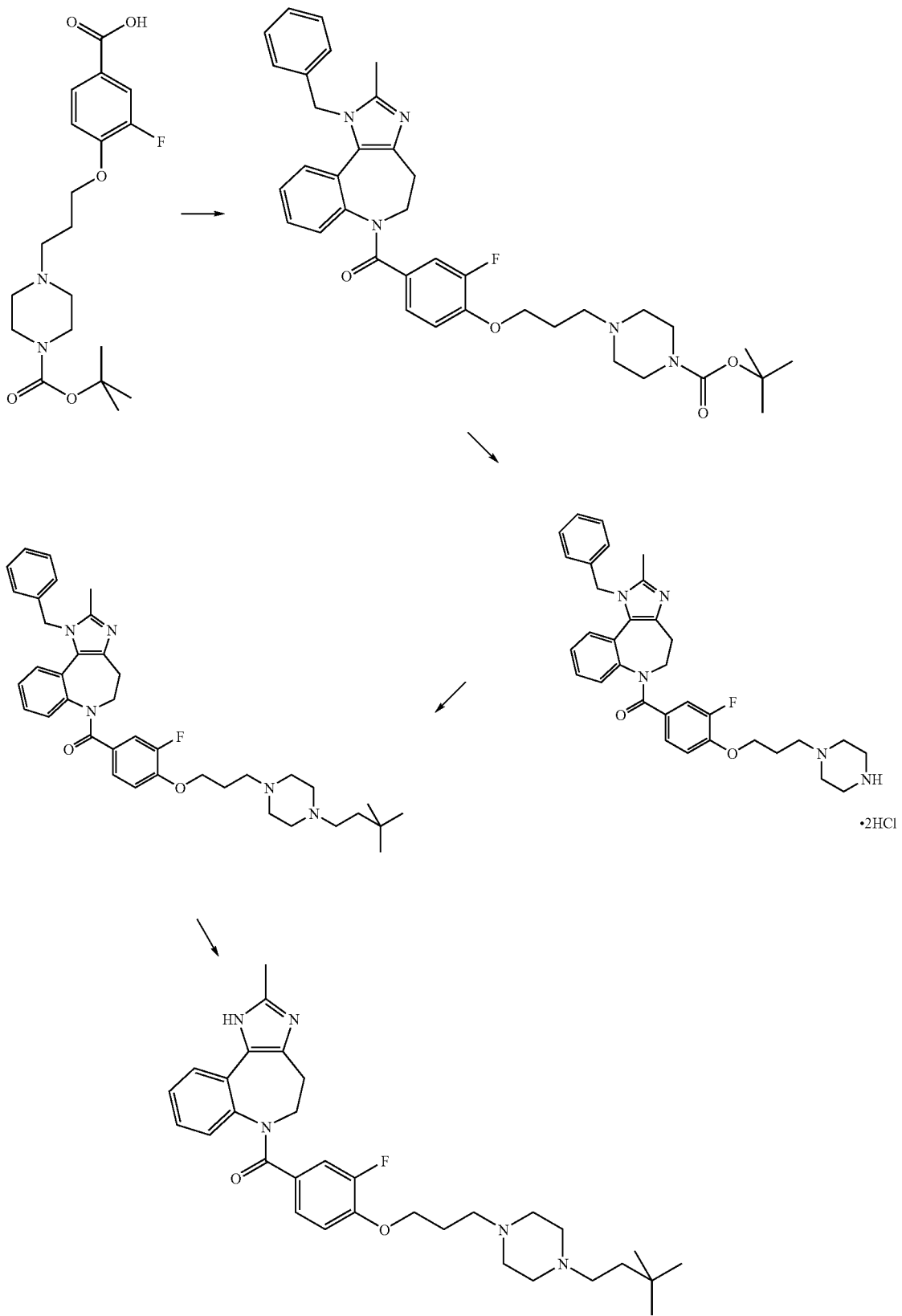

149 150
Example E70
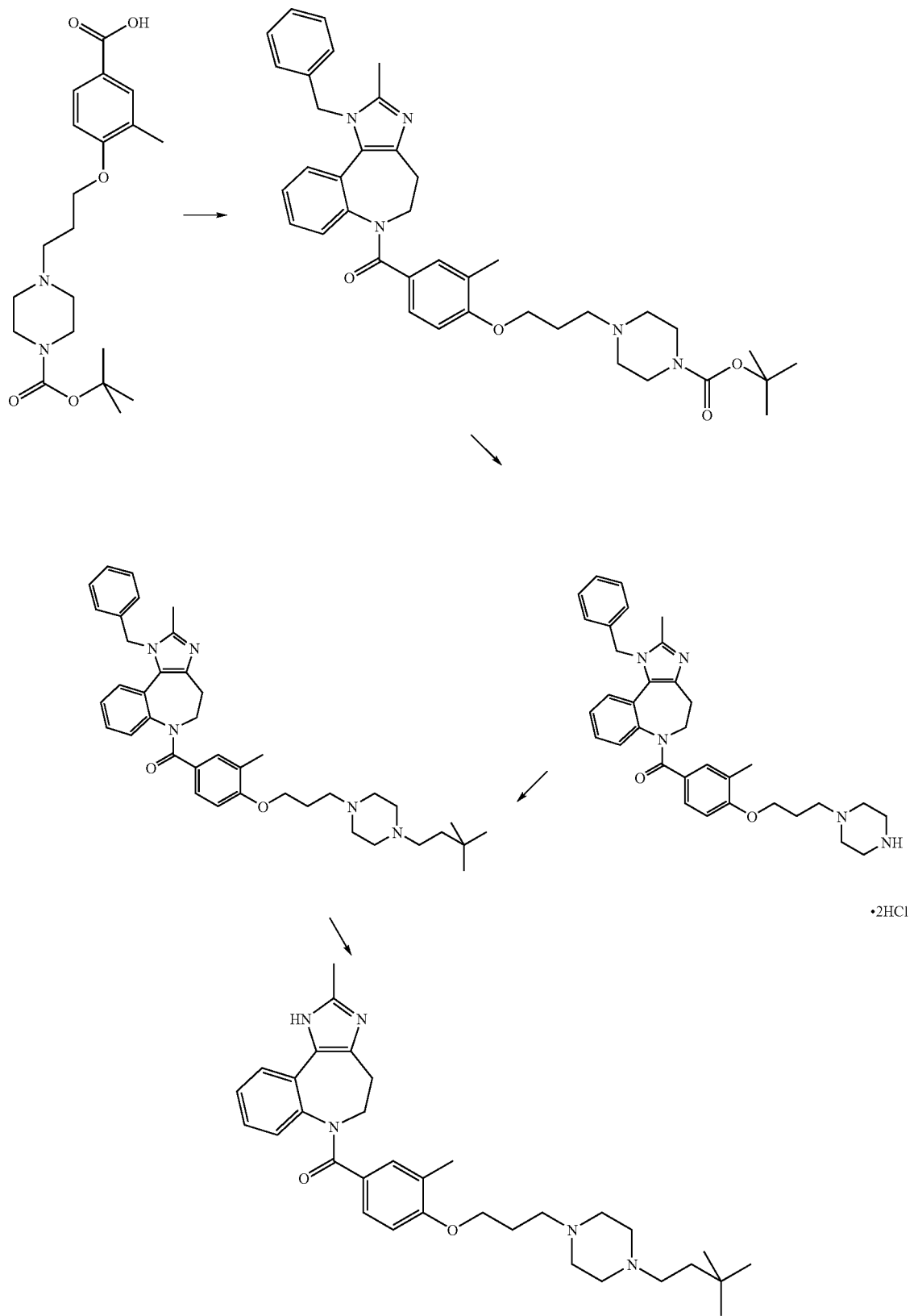

151
Example E71
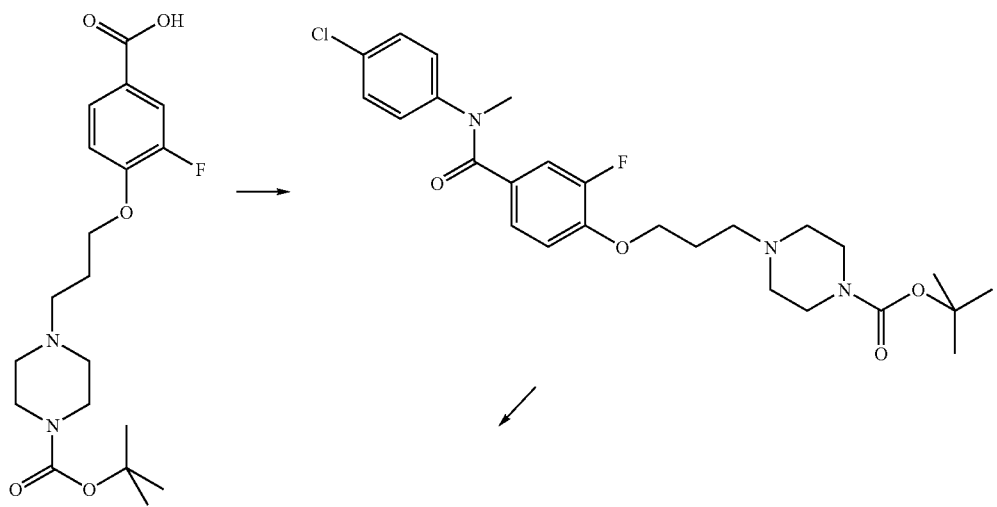
152
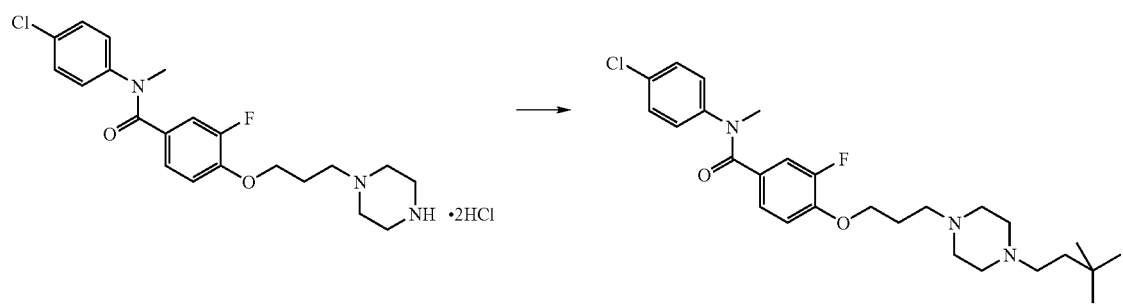
Example E72
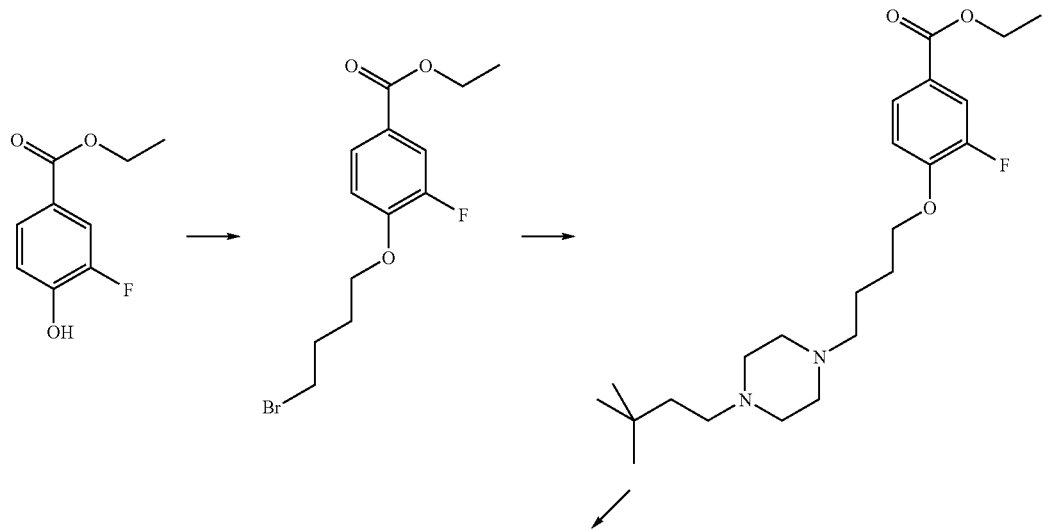

153
-continued
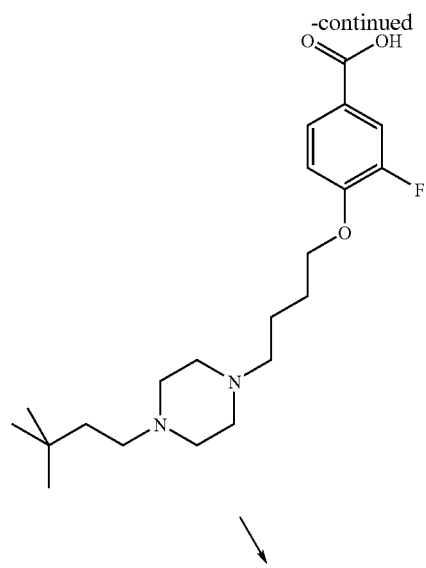
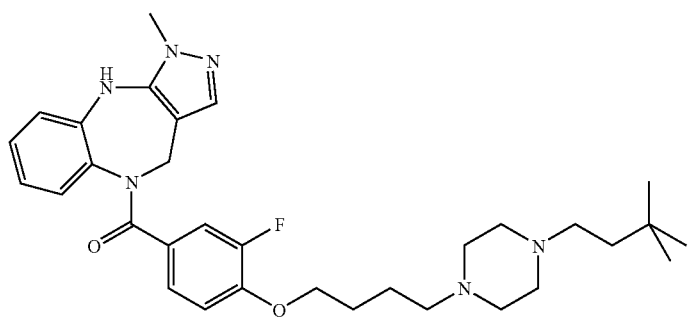
Example E73
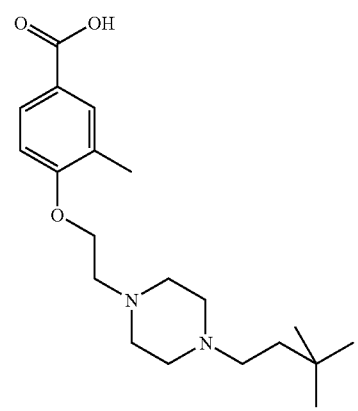  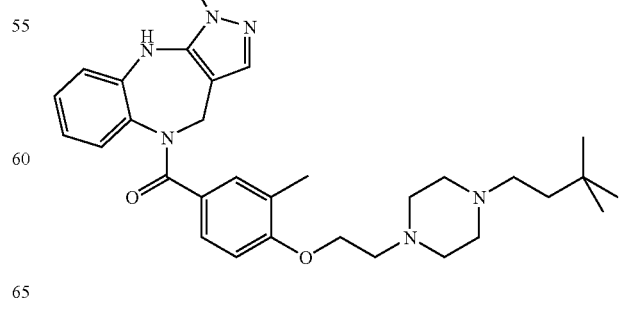

155
Example E74
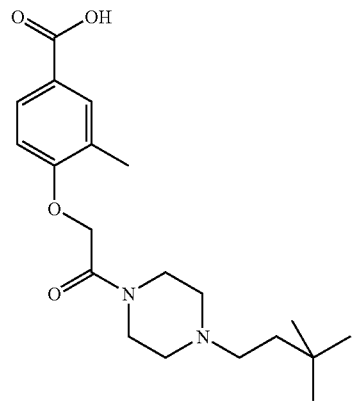
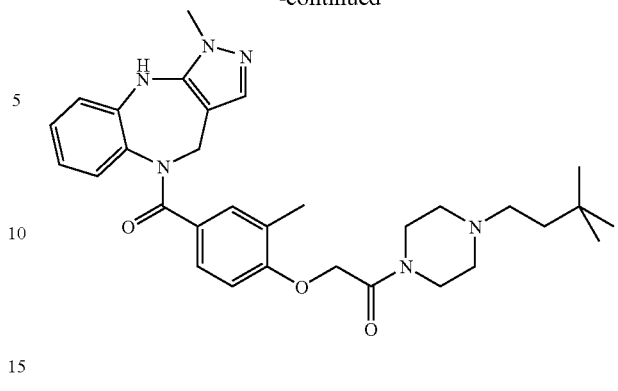
Example E75
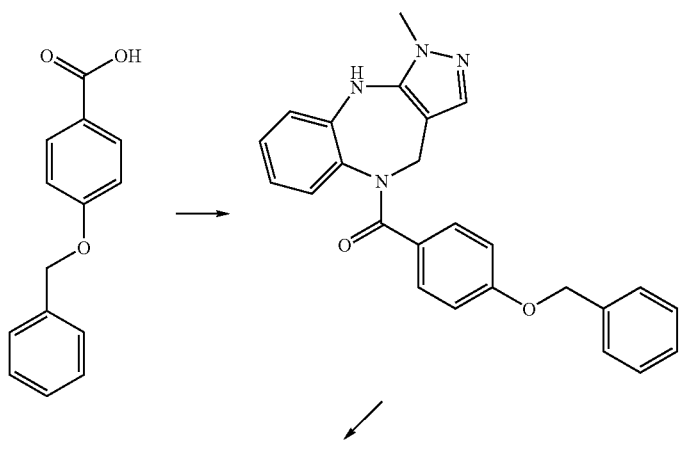
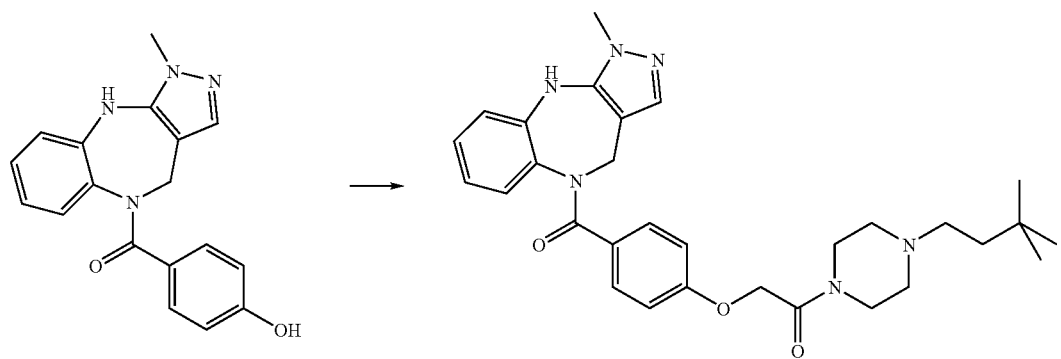

157
Example E76
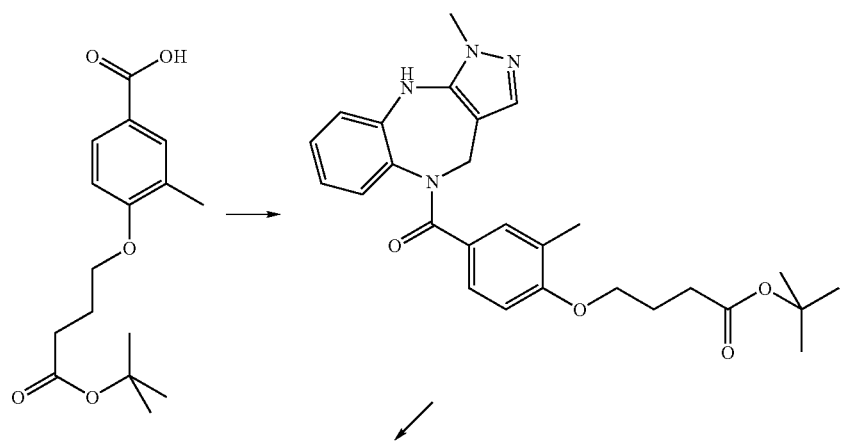
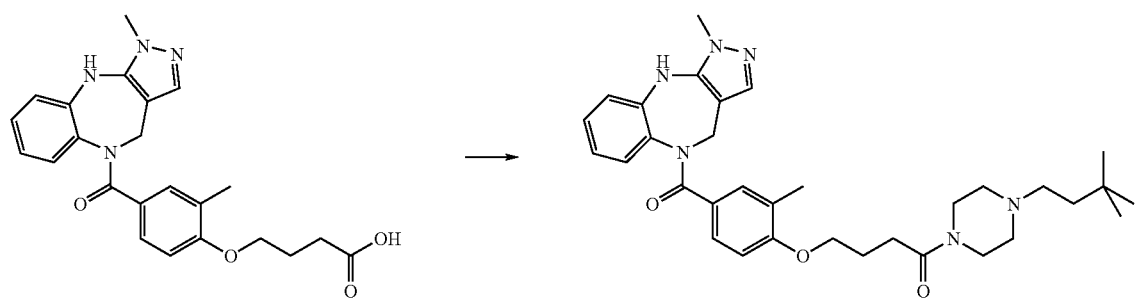
Example E77
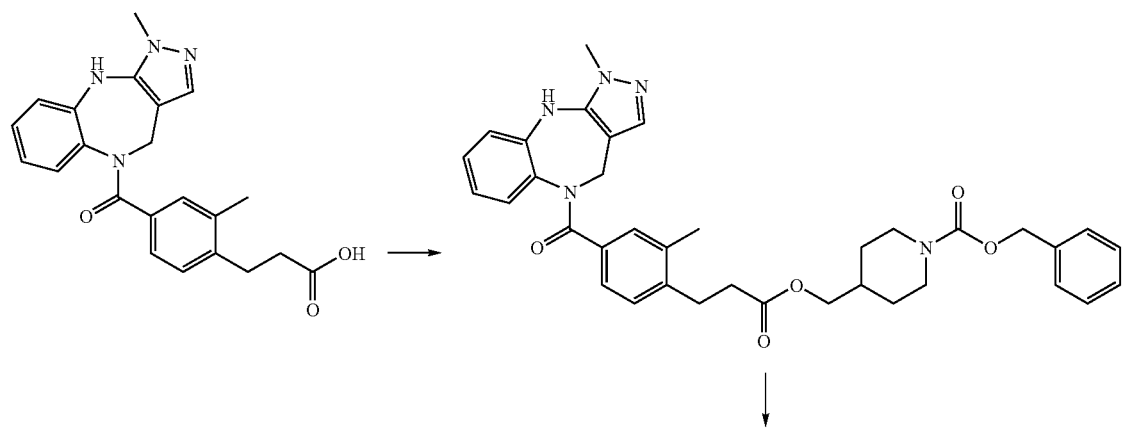

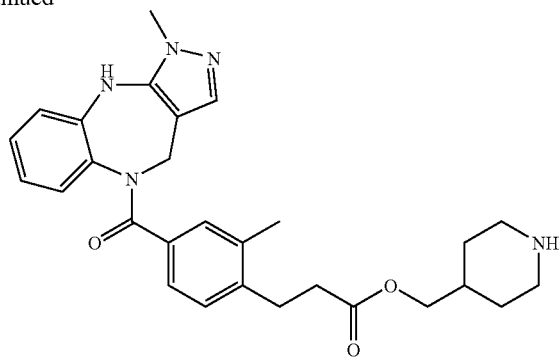
Example E78
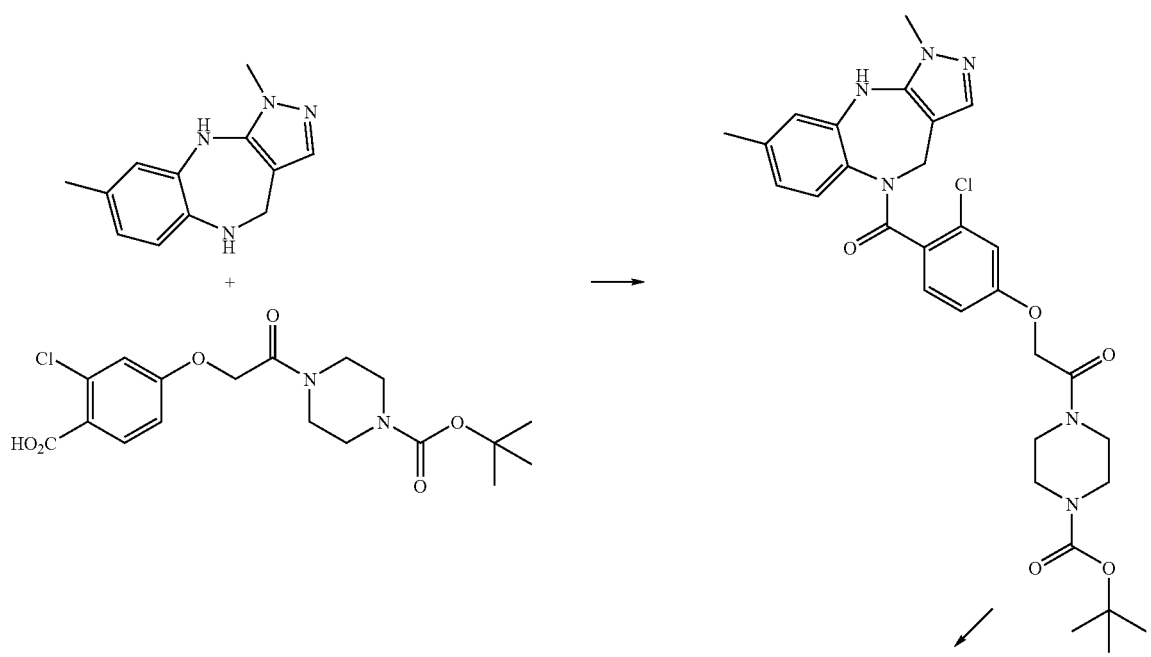
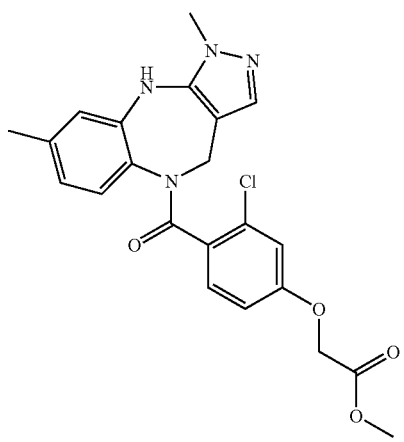

Example E79
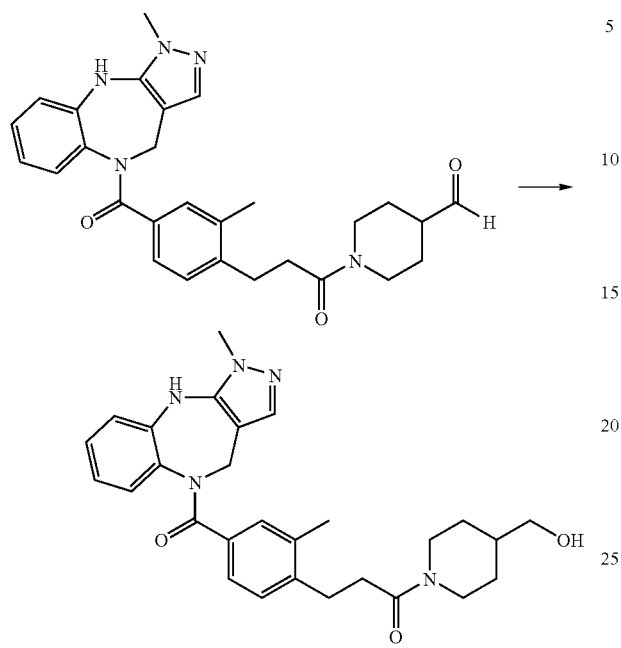
Example E80
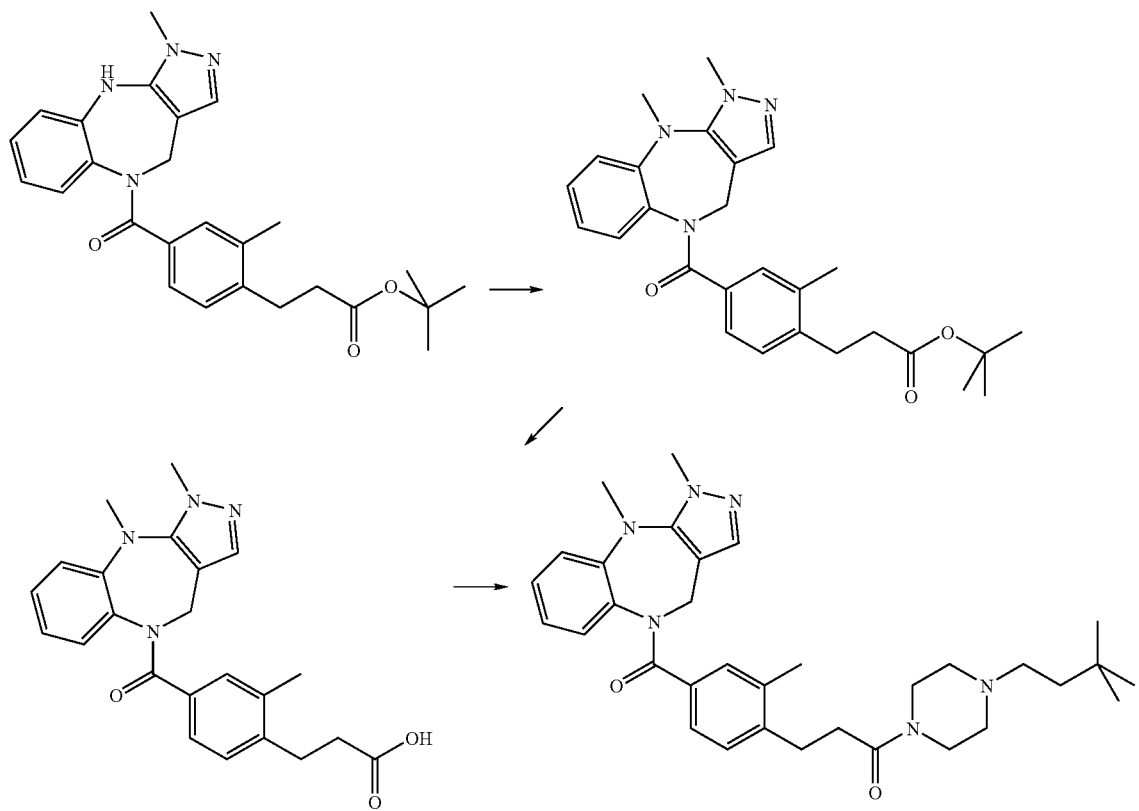

Example E81
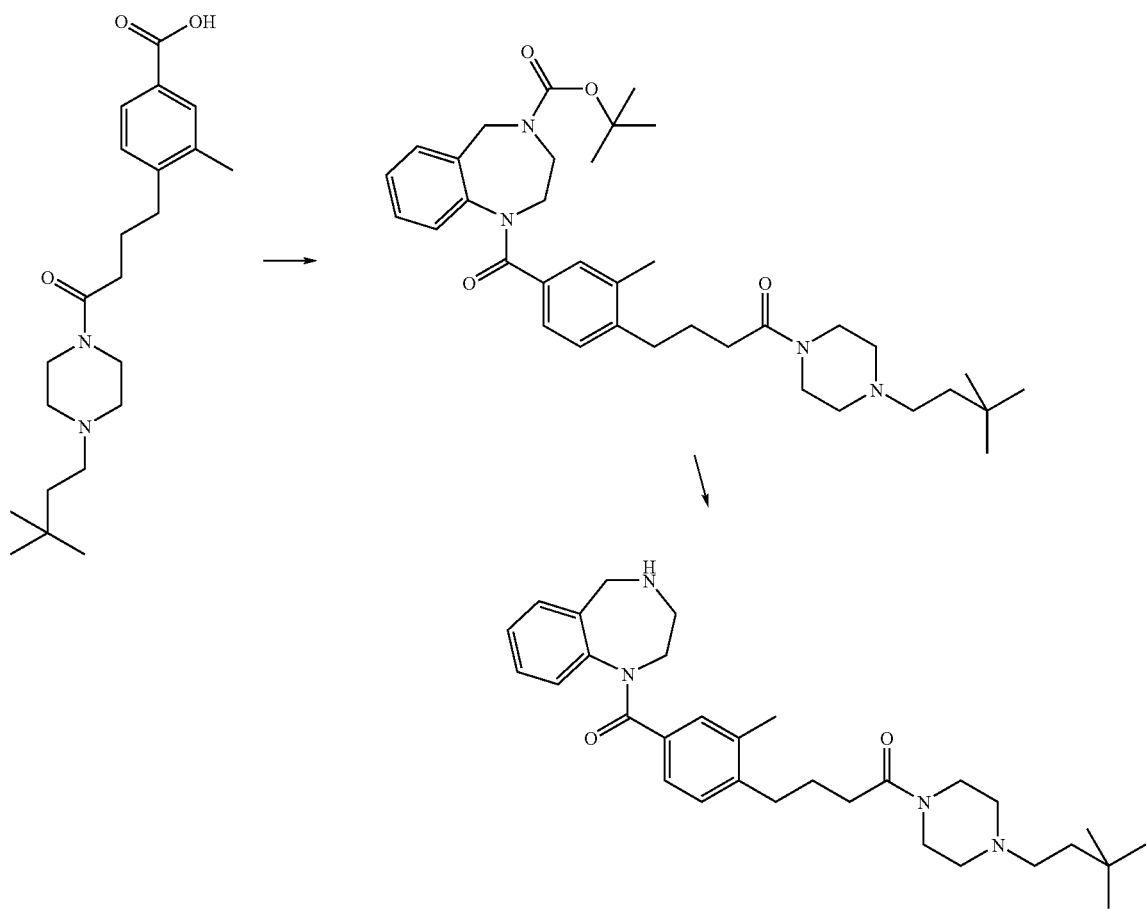
Example E82
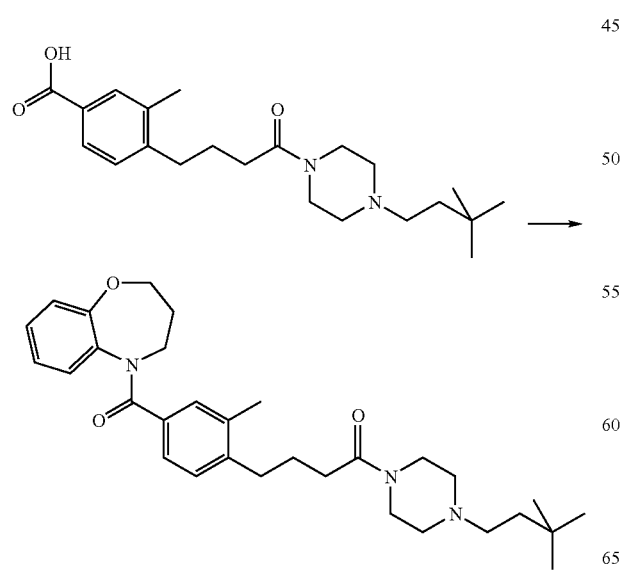

Example E83
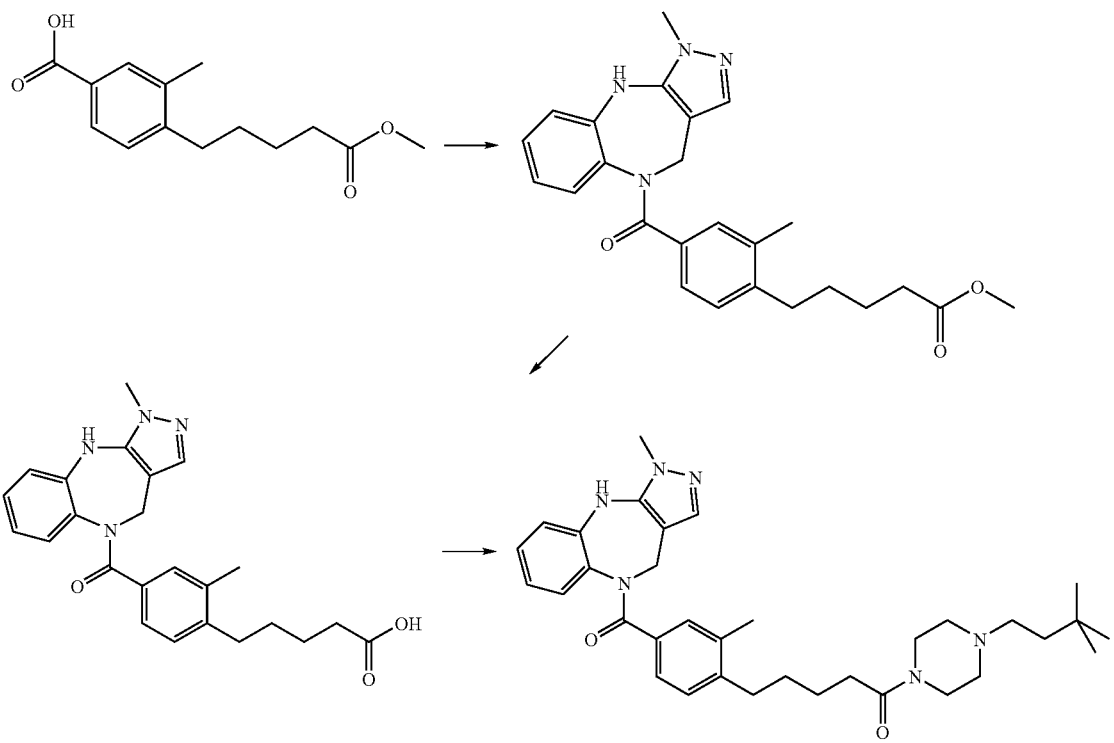
Example E84
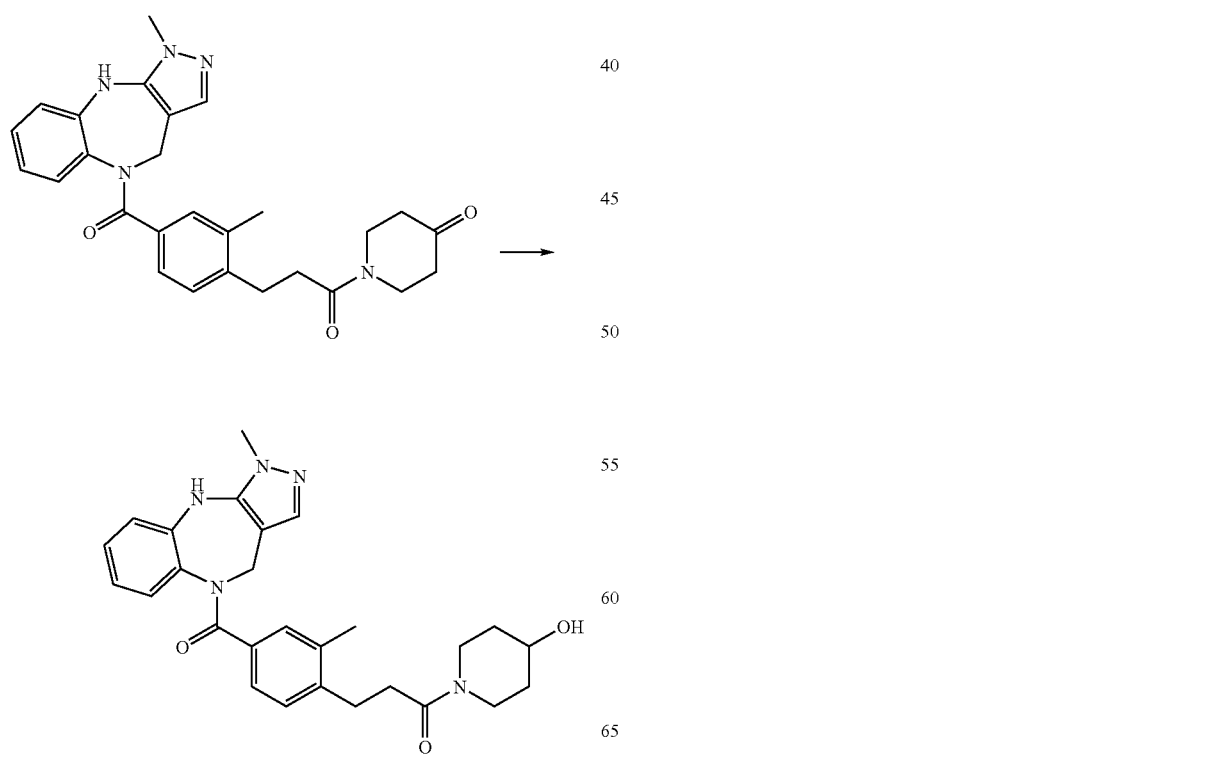

Example E85
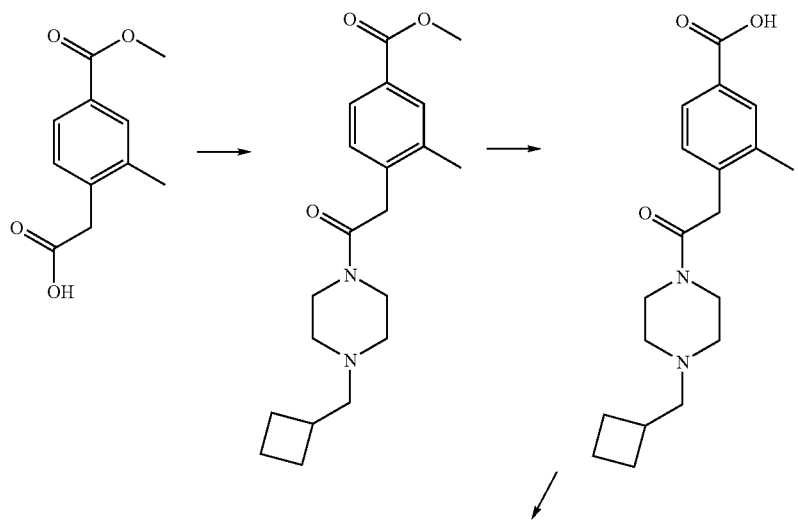
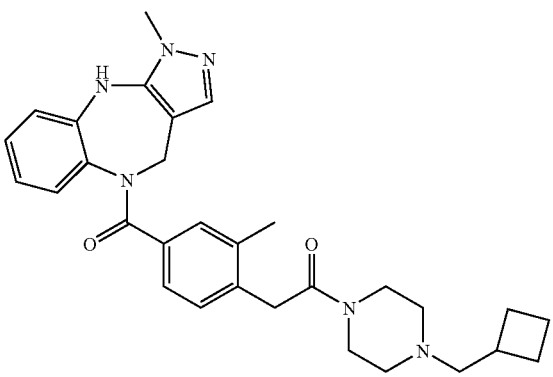
Example E86
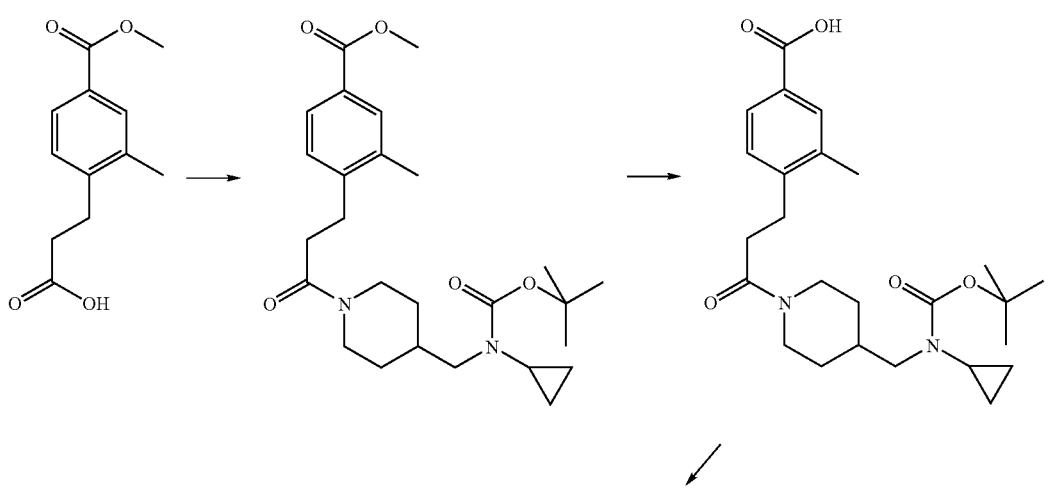

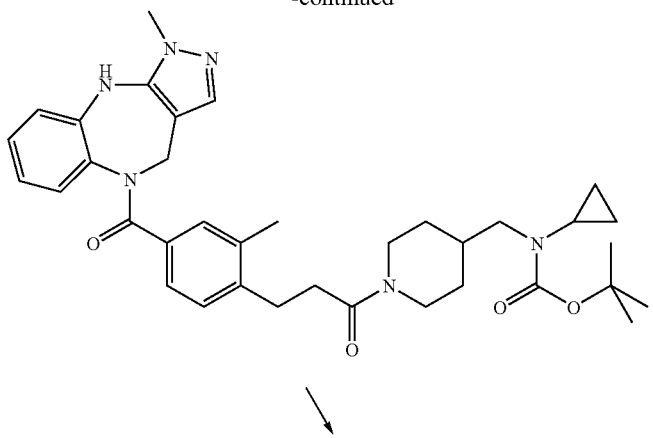
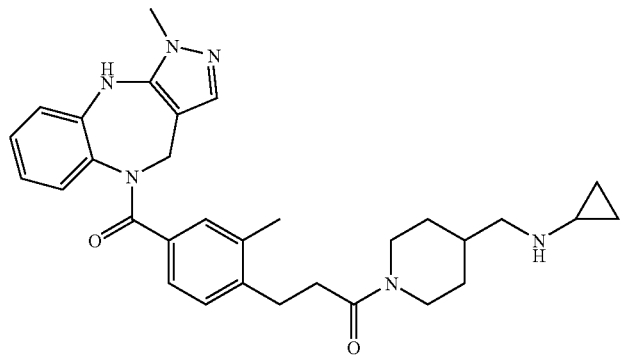
Example E87
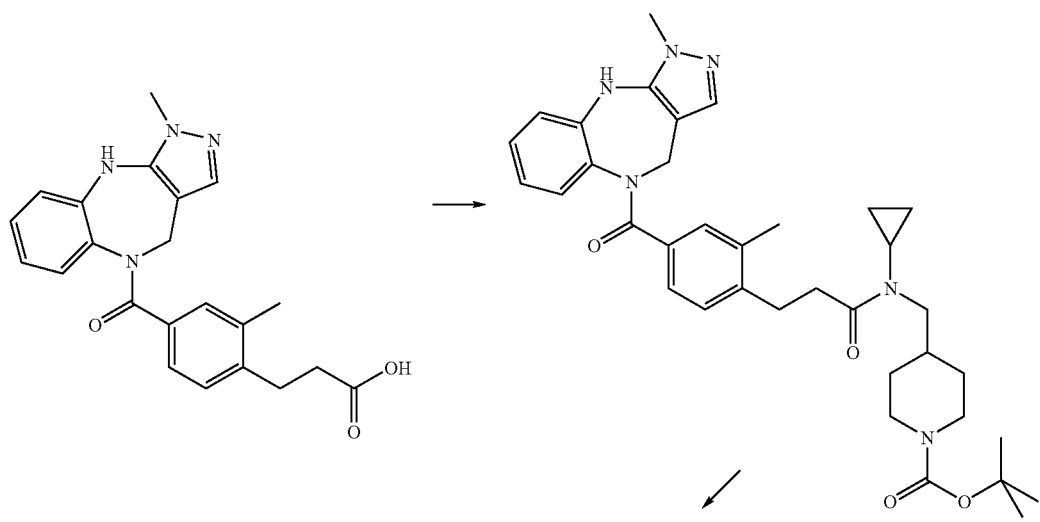

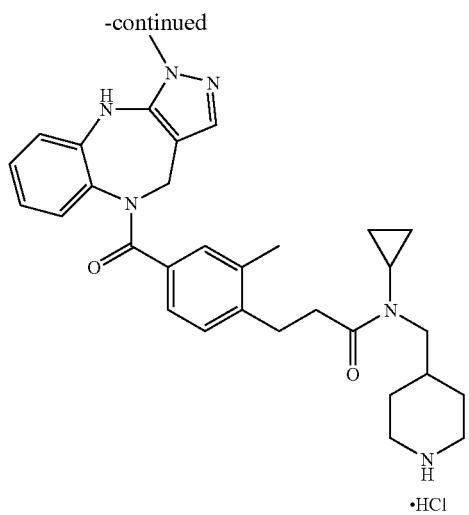
Example E88
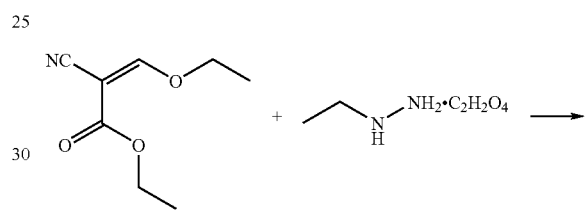
Example E89
Example E90
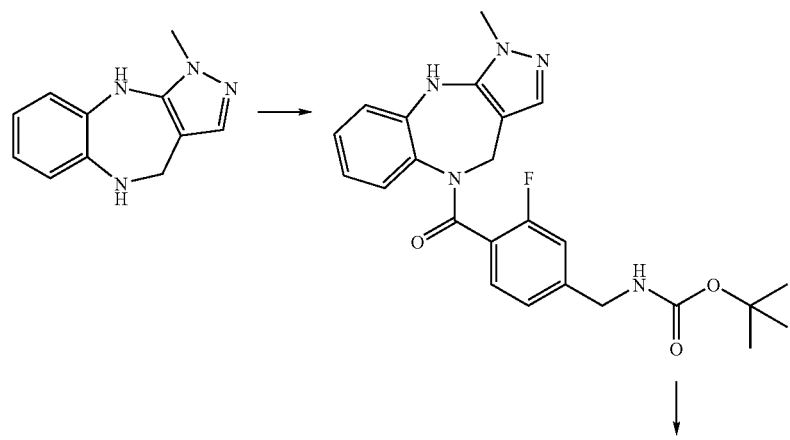

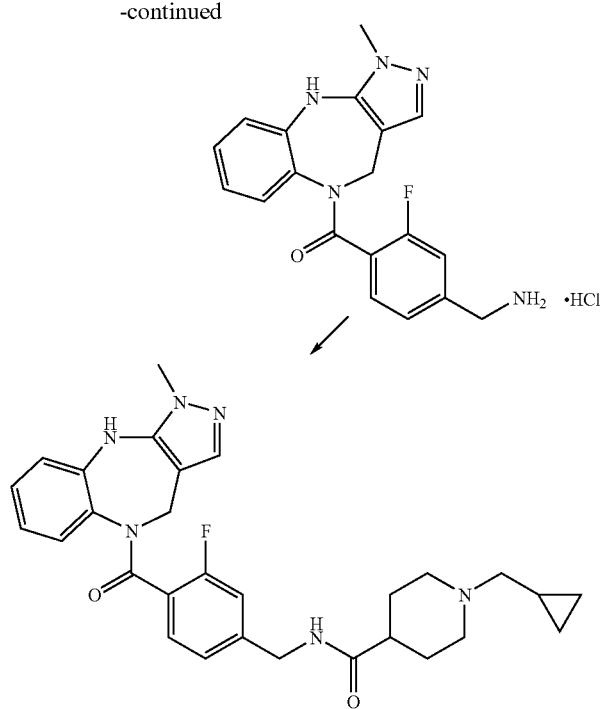
Example E91
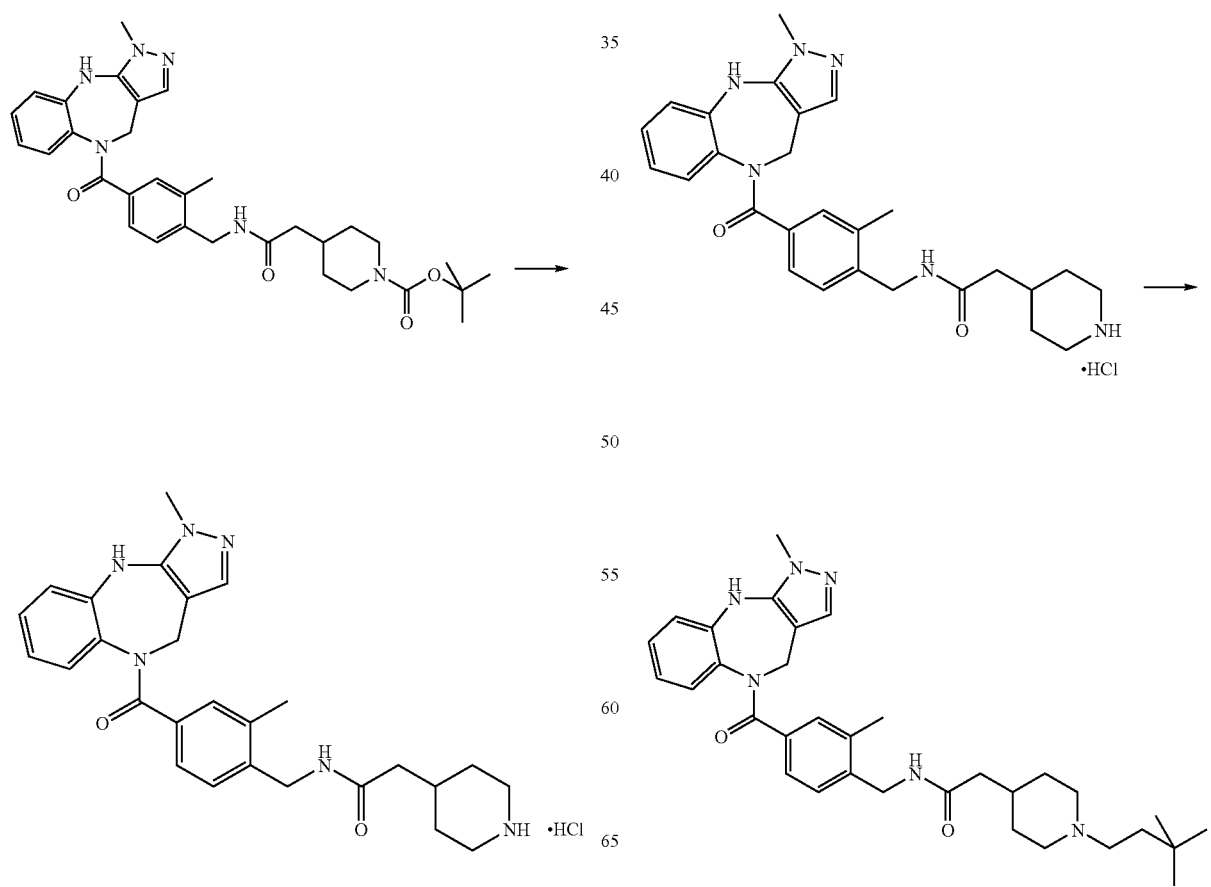
Example E92

175
Example E93
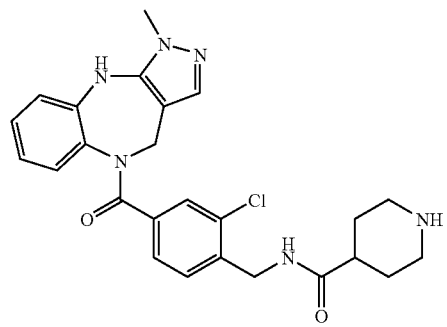
Example E94
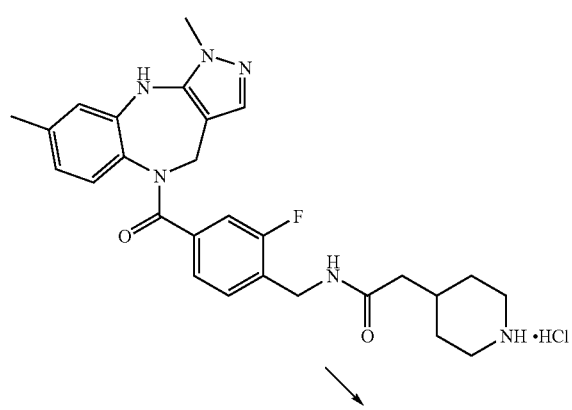
176
Example E95
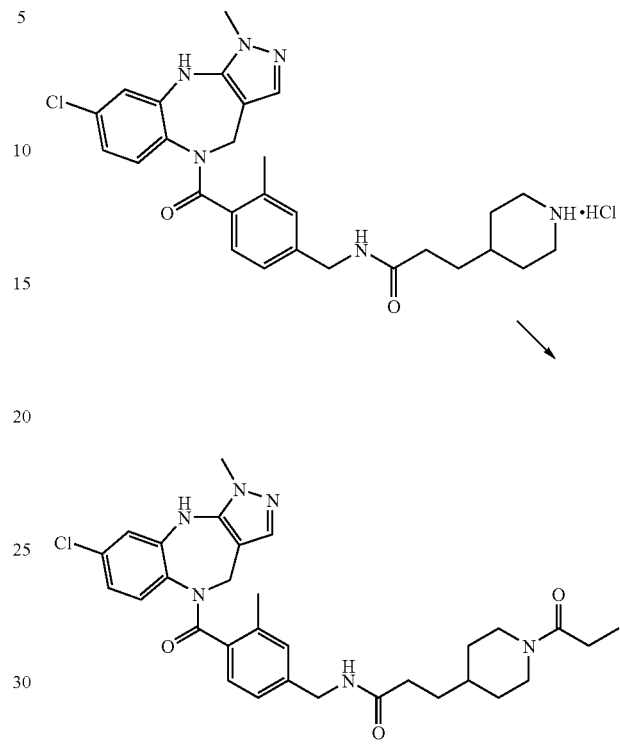
Example E96
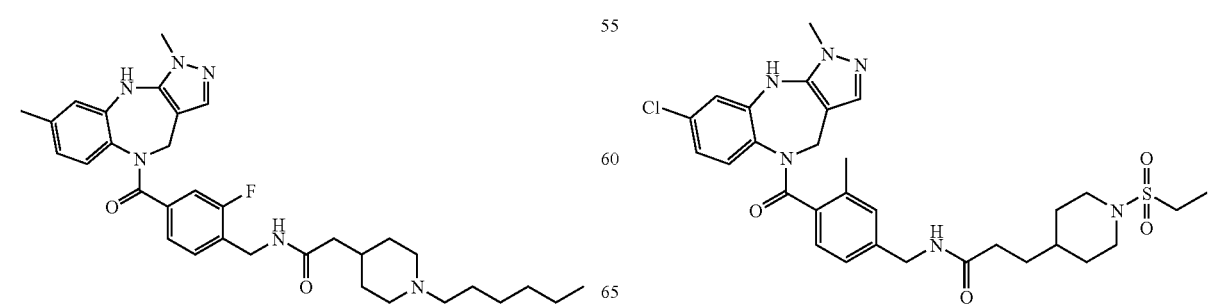

177
Example E97
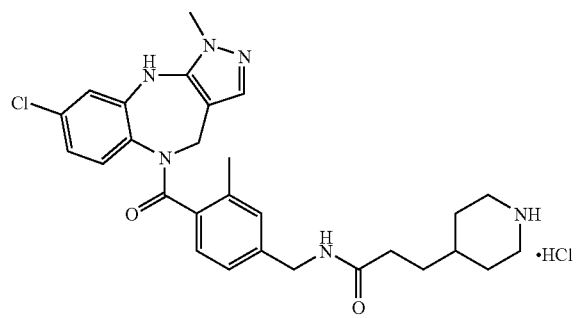
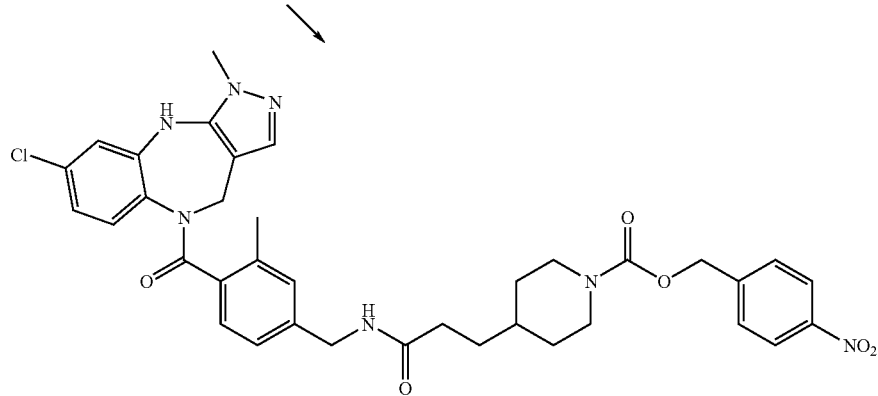
Example E98
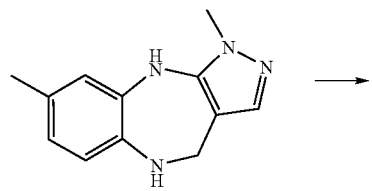
178
-continued
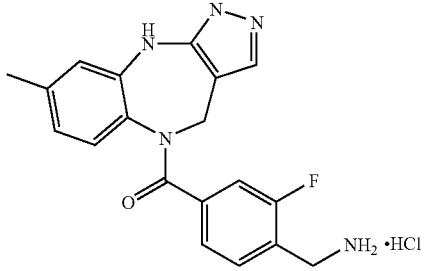
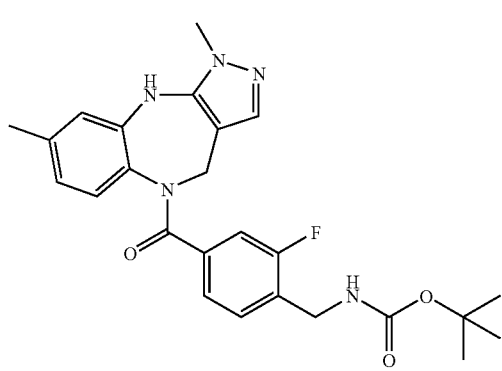
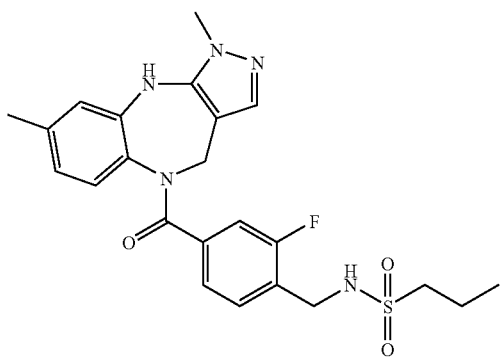

179
Example E99
180
Example E101
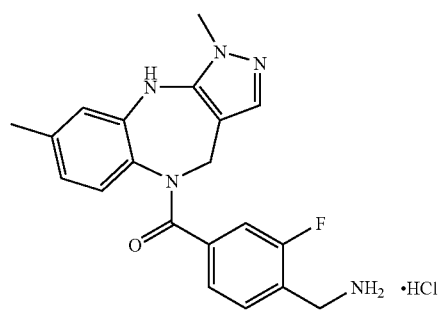
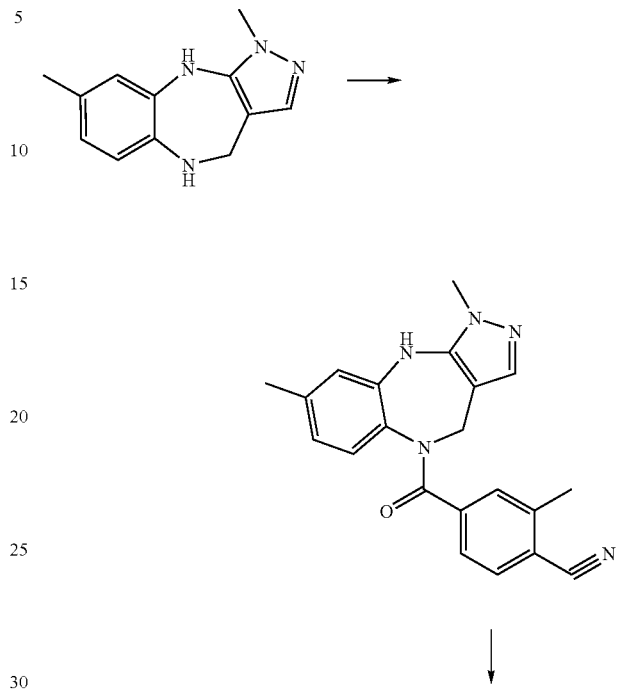
Example E100
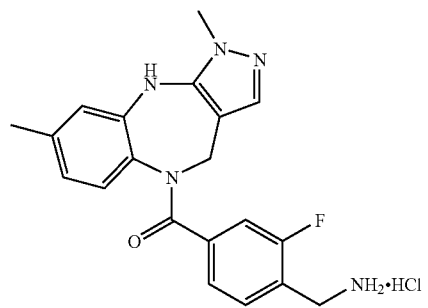
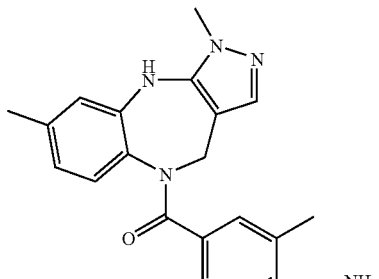
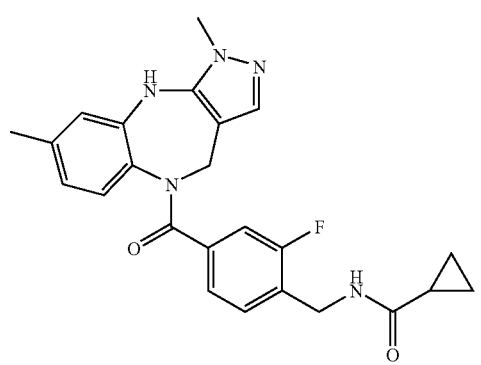
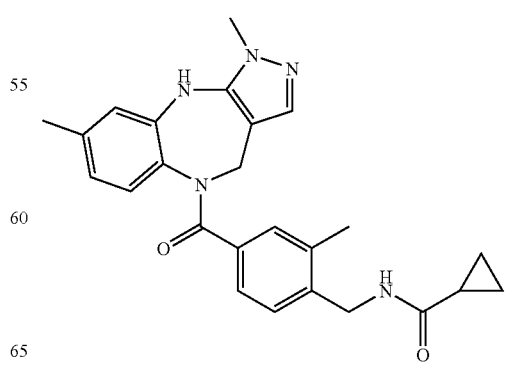

181
Example E102
182
Example E103
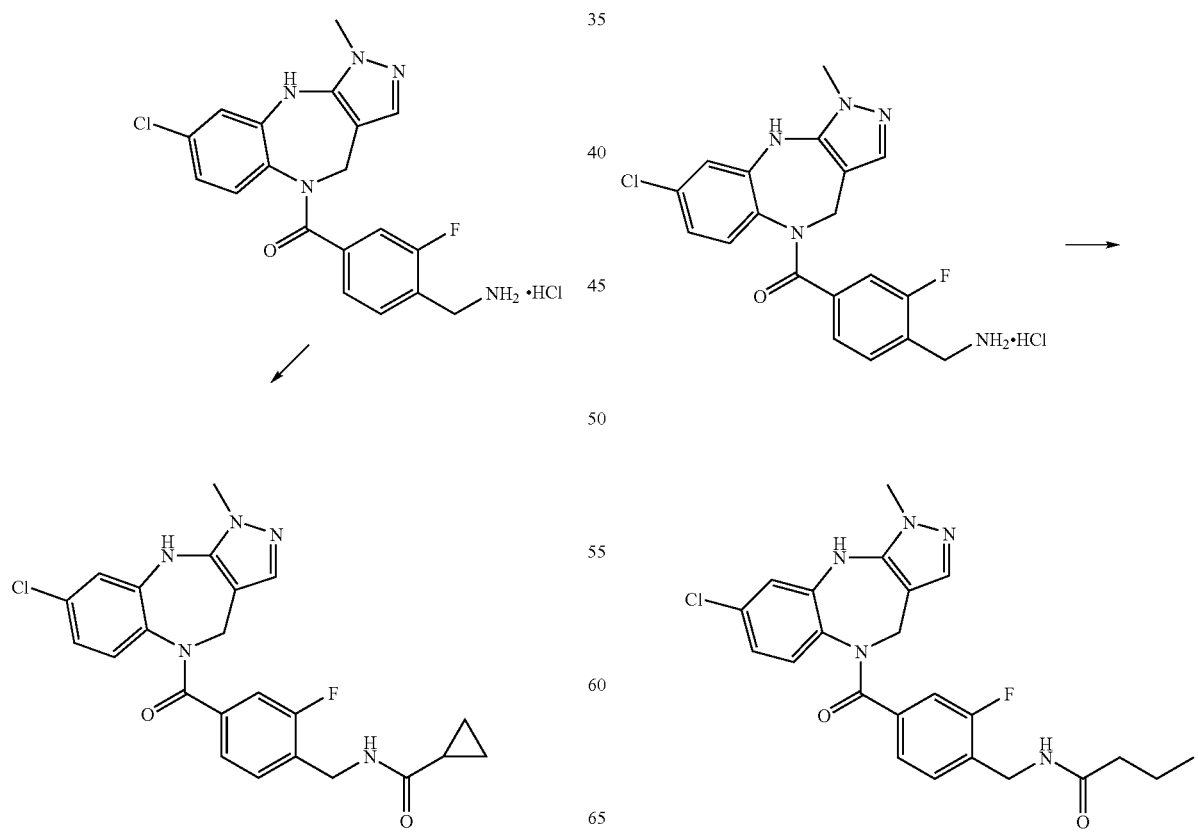
Example E104

183
Example E105
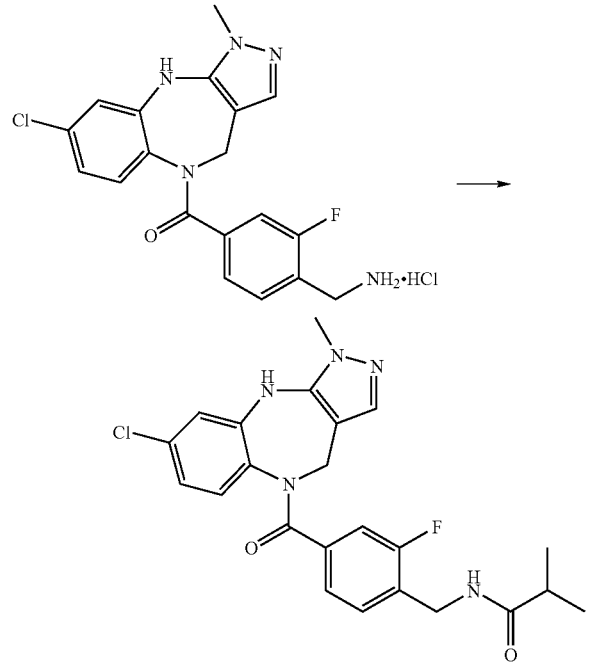
184
-continued
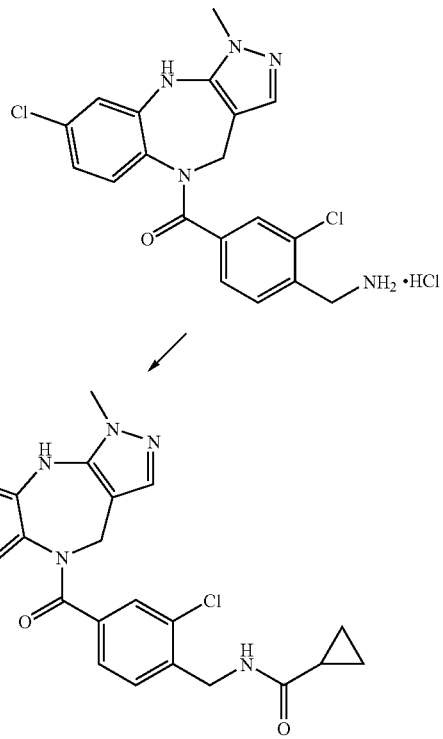
Example E106
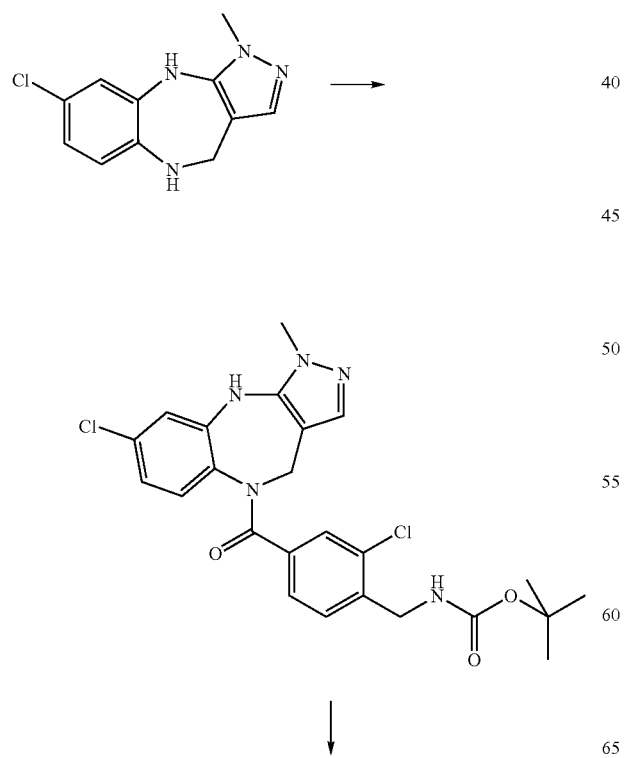
Example E107
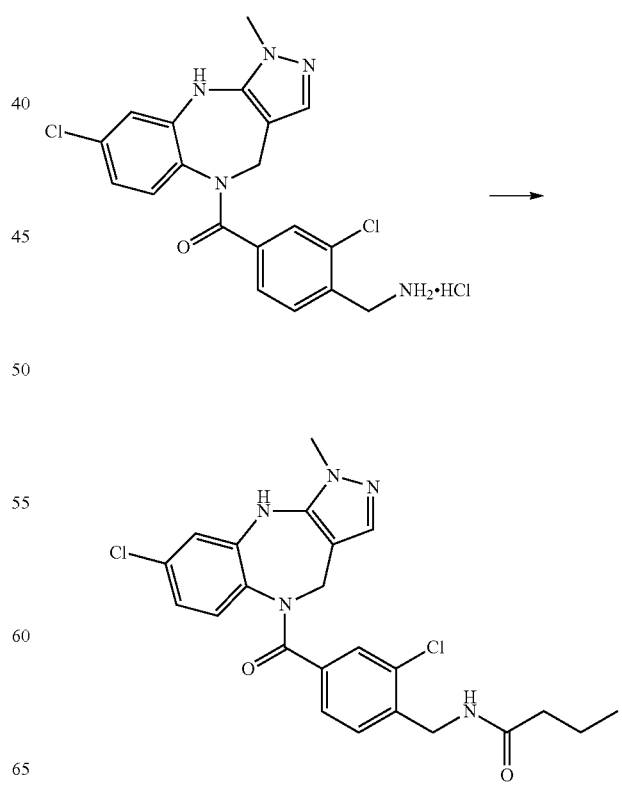

185
Example E108
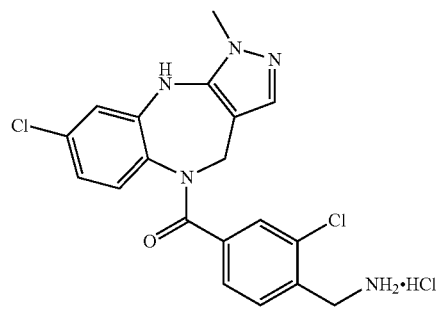
→
186
Example E110 and Example E111
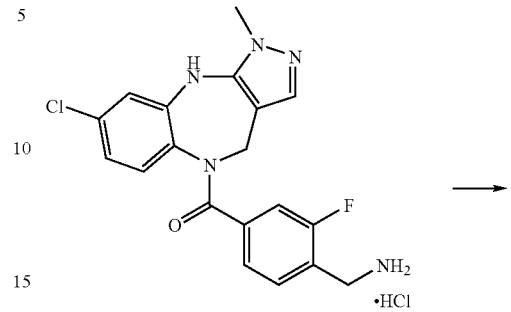
→
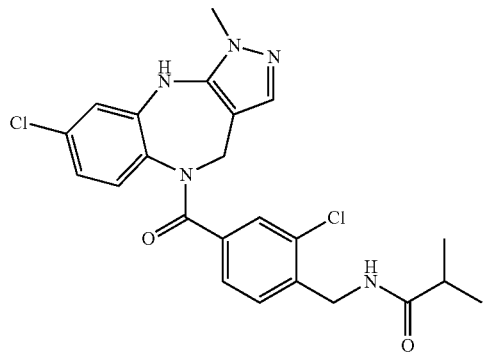
Example E109
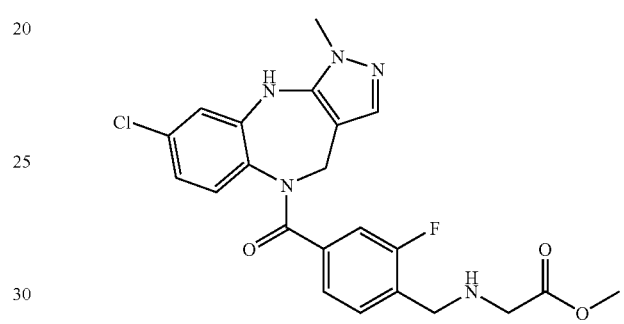
+
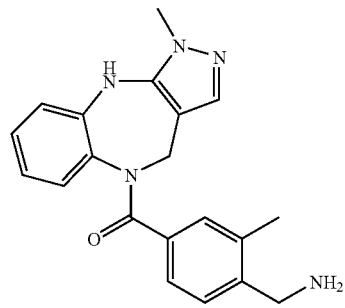
→
Example E112
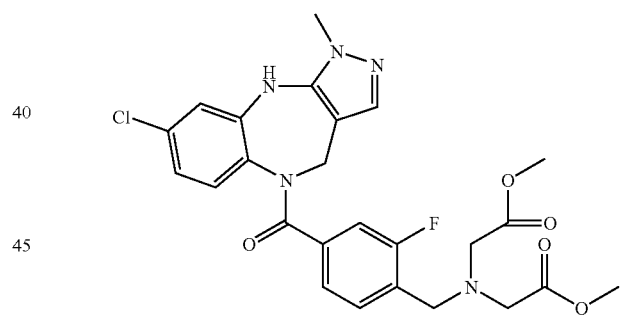
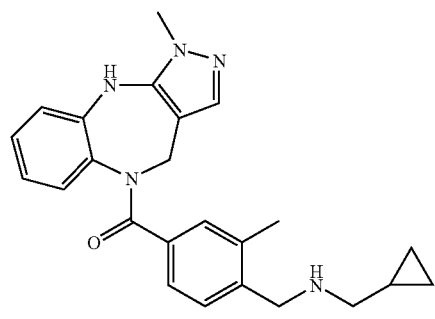
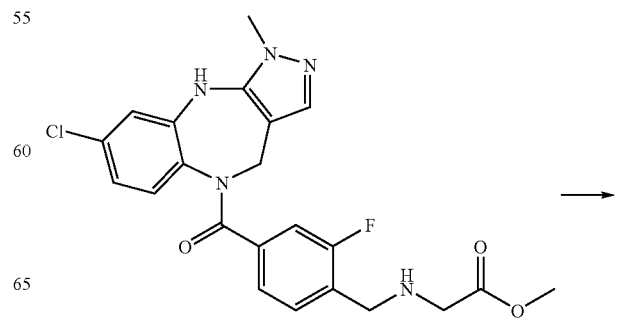
→

187
-continued
Example E113
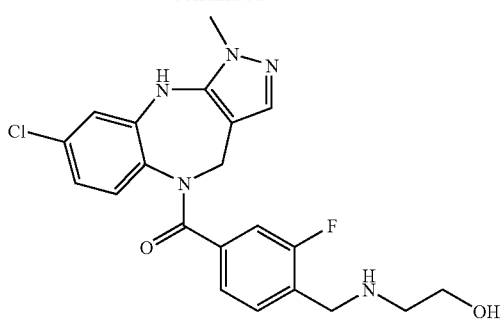
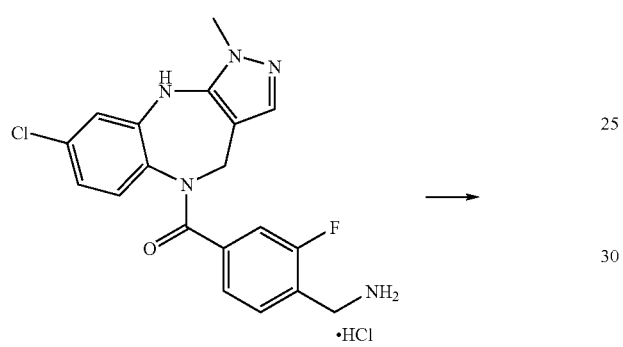
Example E114
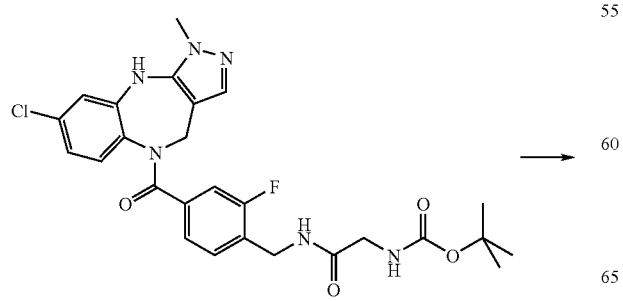
188
-continued
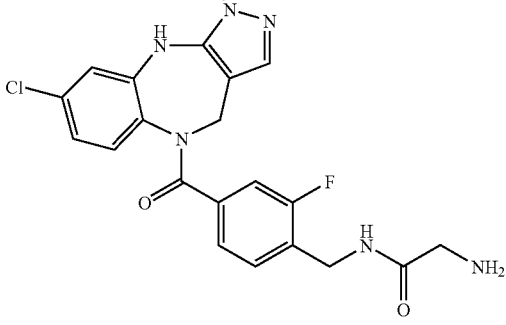
Example E115
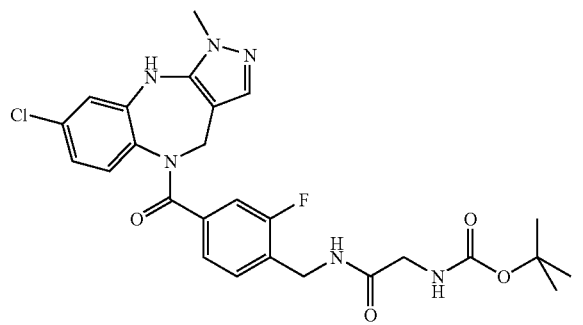

Example E116
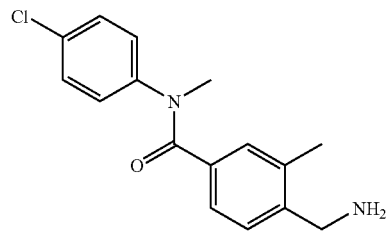
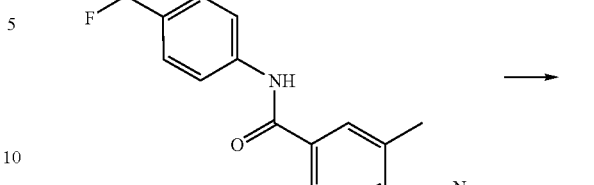
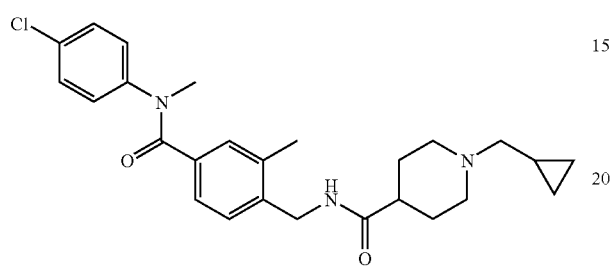
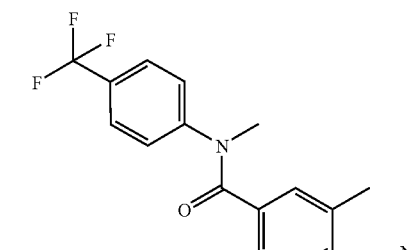
Example E117
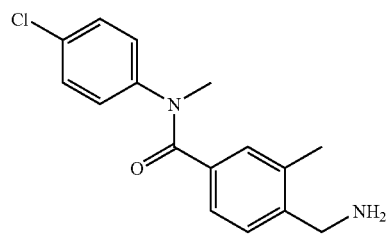
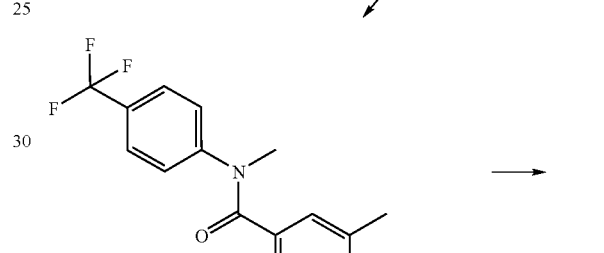
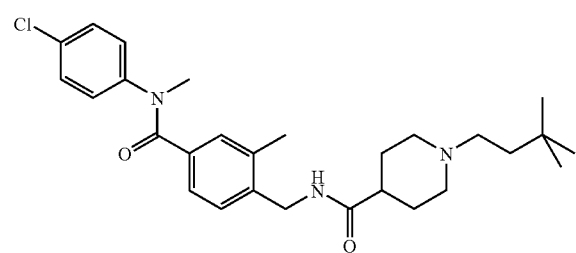
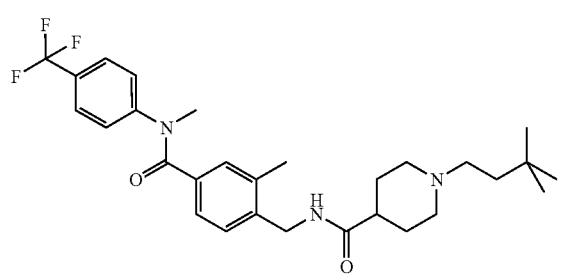
Example E118
Example E119
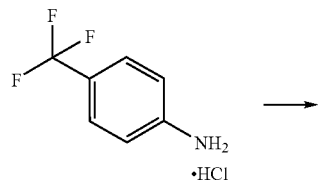
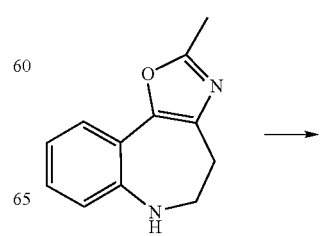

191
-continued
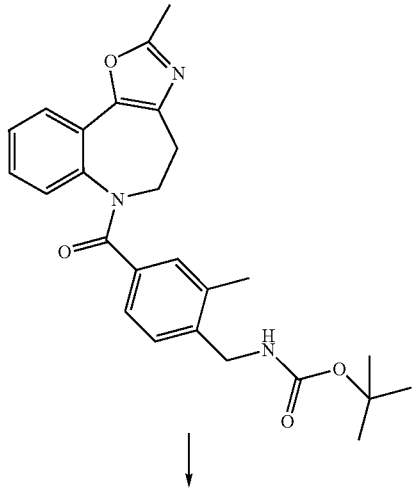
192
Example E120
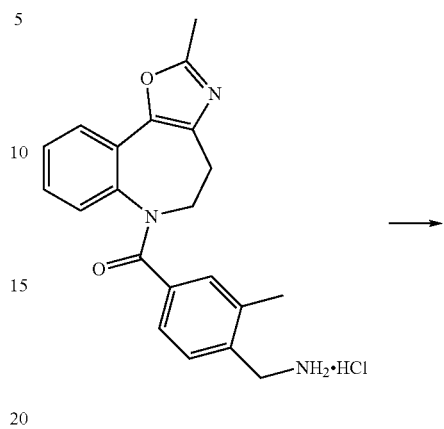
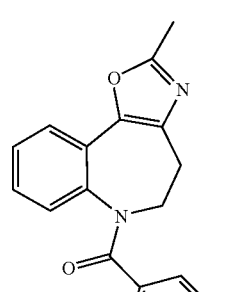
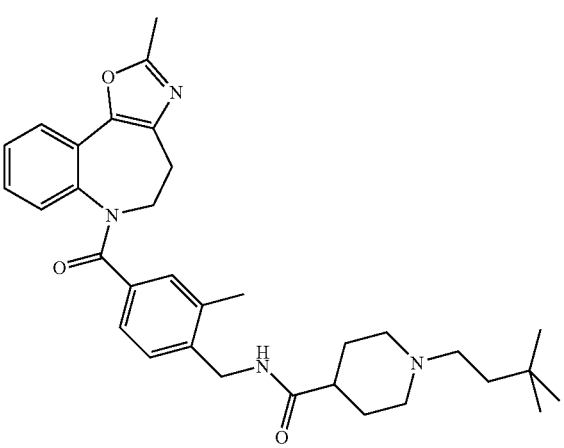
Example E121
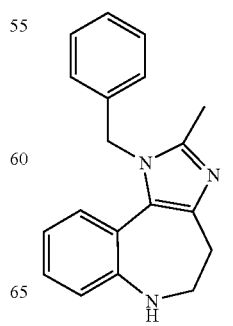

193
-continued
194
Example E122
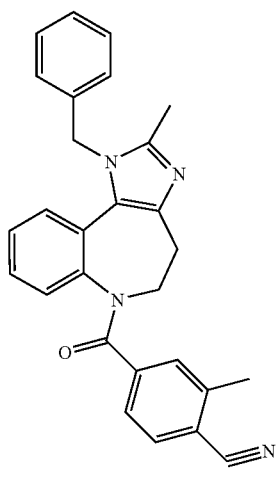
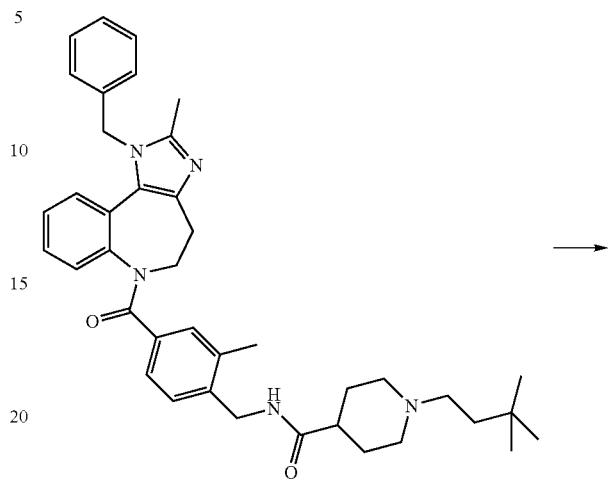
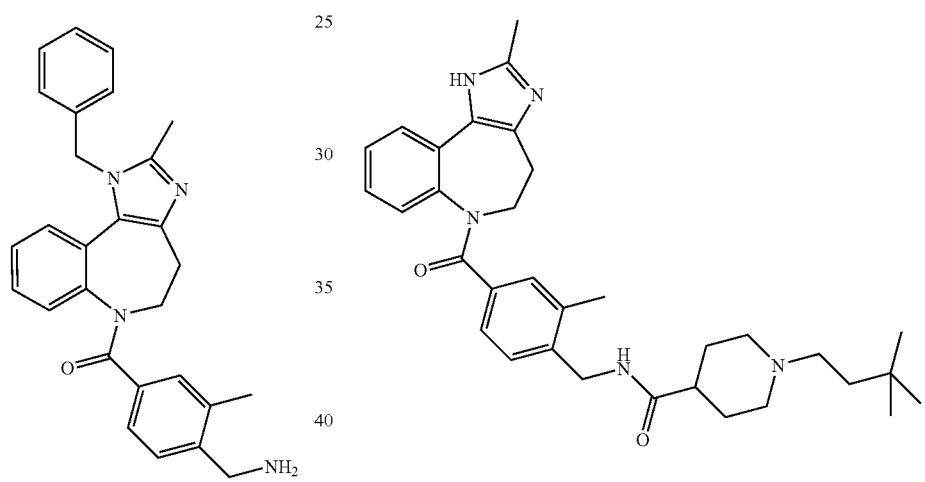
Example E123
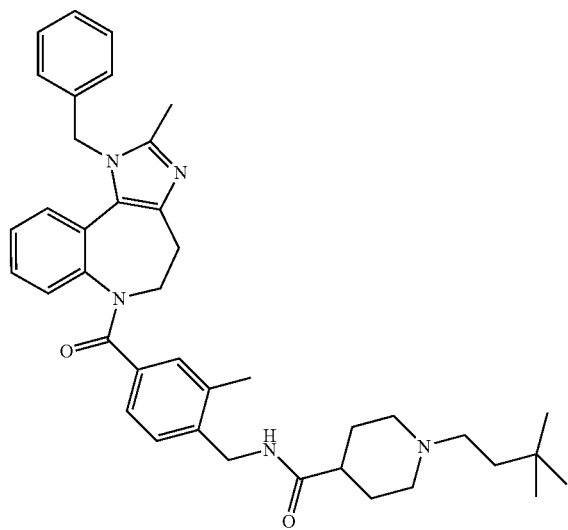
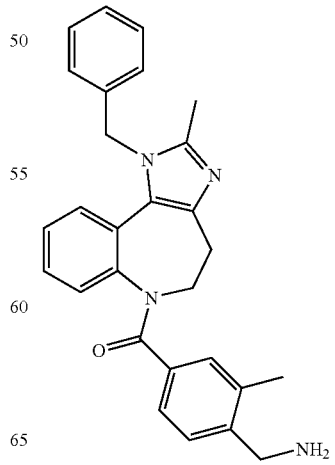

195
-continued
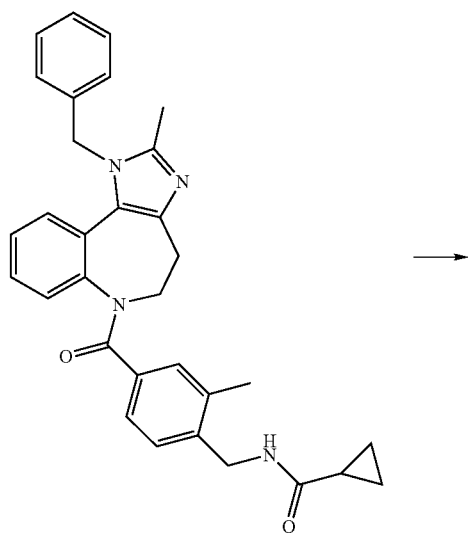
196
-continued
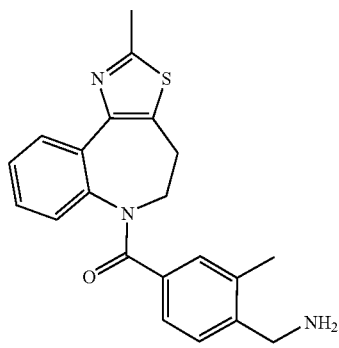
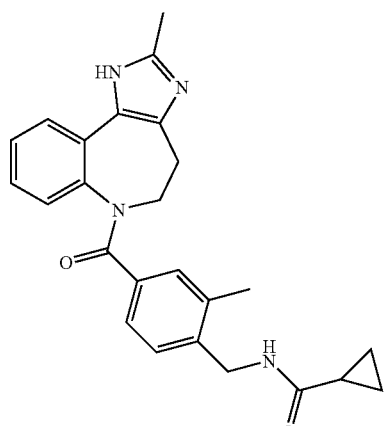
Example E124
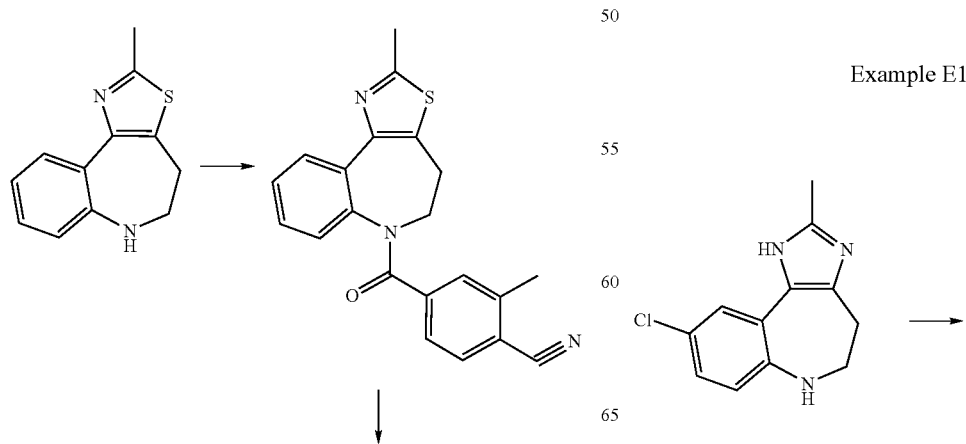
Example E125

-continued
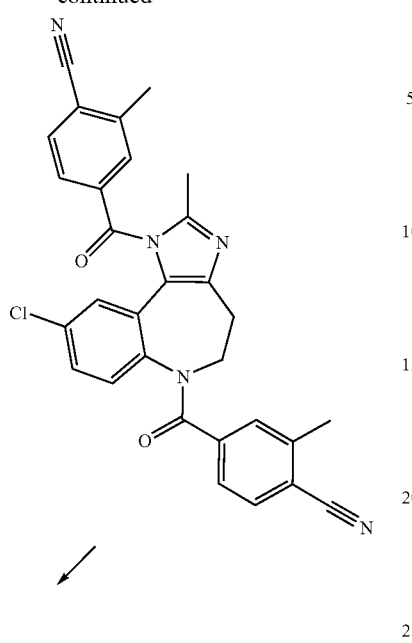
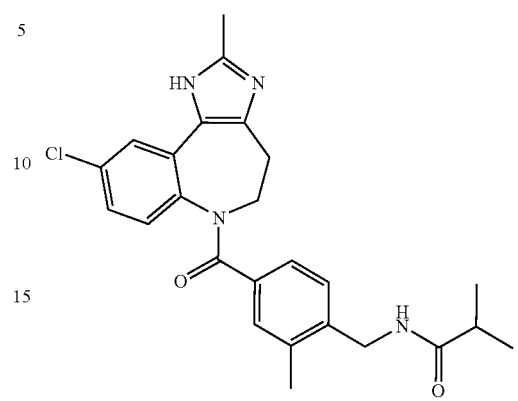
-continued
EXAMPLE TABLES
The following compounds were prepared using methods analogous to those described above.
Example E5 and Compound number 2 have particular utility as intermediates.
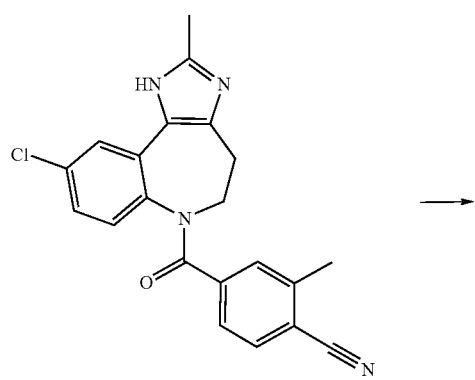
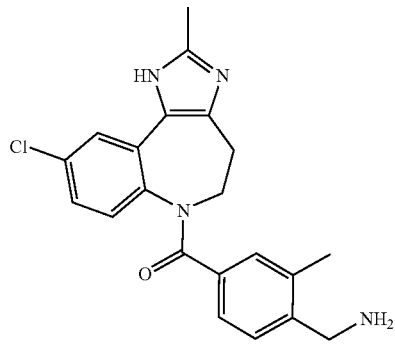
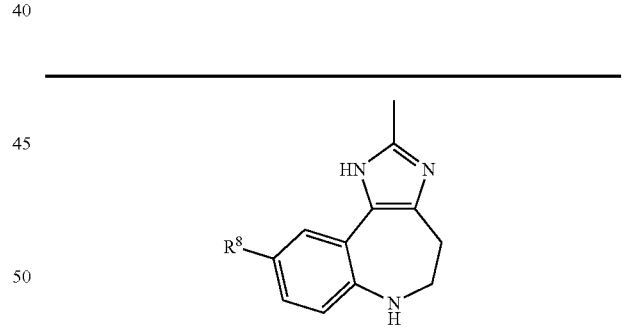
| Compound number | R$^8$ | MS (ESI)+: [M + H]+ = | $^1$H NMR: δ (ppm) |
|---|---|---|---|
| 1 E5 | H | | |
| 2 | Cl | 234.0, 236.0 | 2.43 (3H, s), 2.98 (2H, d, J = 5.2 Hz), 3.34 (2H, t, J = 5.2 Hz), 6.59 (2H, d, J = 8.4 Hz), 6.90-6.95 (1H, m), 7.80-8.10 (1H, m) |

| Compound number | R¹ | R⁴ | R⁷ | MS: [M + H]⁺ |
|---|---|---|---|---|
| 3 E8 | F | neopentyl | Me | 562.4 |
| 4 | Me | neopentyl | Me | 558.4 |
| 5 | Me | cyclopropylmethyl | Me | 528.4 |
| 6 | Me | cyclopropyl | Me | 514.3 |
| 7 | Me | isobutyl | Me | 544.4 |
| 8 | Me | cyclopentylmethyl | Me | 556.6 |
| 9 | Me | neopentyl | Cl | 578.4, 580.4 |
| 10 | Me | cyclopropylmethyl | Cl | 548.3, 550.3 |
| 11 | F | cyclopropylmethyl | Me | 532.3 |
| 12 | F | neopentyl | Cl | 582.4, 584.4 |
| 13 | F | cyclopropyl | Cl | 552.3, 554.3 |
| 14 | F | neopentyl | F | 566.2 |
| 15 | Cl | neopentyl | Cl | 598.3, 600.4 |
| 16 | Cl | cyclopropyl | Cl | 568.1 |
| 17 | Cl | neopentyl | Me | 578.4, 580.4 |
| 18 | Cl | cyclopropylmethyl | Me | 548.3, 550.3 |
| 19 | Me | -CH₂COOH | Me | 532.5 |
| 20 | Me | -CH₂C(O)OCH₂Ph | Me | 622.4 |
| 21 | Me | cyclopentylmethyl | Cl | 576.4, 578.3 |
| 22 | Me | neopentyl | Cl | 564.4, 566.4 |
| 23 | Me | cyclopropyl | Cl | 543.3, 536.3 |
| 24 | Me | isobutyl | Cl | 564.4, 566.4 |
| 25 | Me | isopropyl | Cl | 550.4, 552.4 |
| 26 | Me | propyl | Cl | 536.4, 538.1 |
| 27 | Me | neopentyl | Me | 544.4 |

-continued
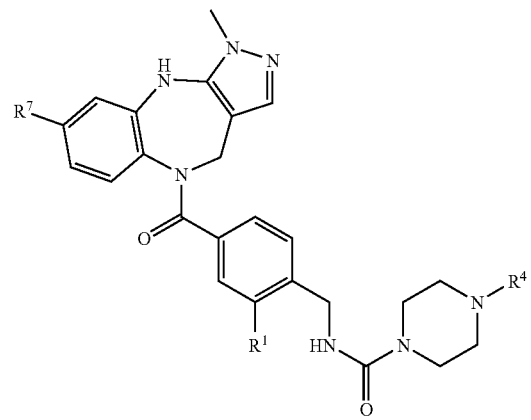
| Compound number | R¹ | R⁴ | R⁷ | MS: [M + H]⁺ |
|---|---|---|---|---|
| 28 | Me | isobutyl | Me | 530.8 |
| 29 | Me | propyl | Me | 516.5 |
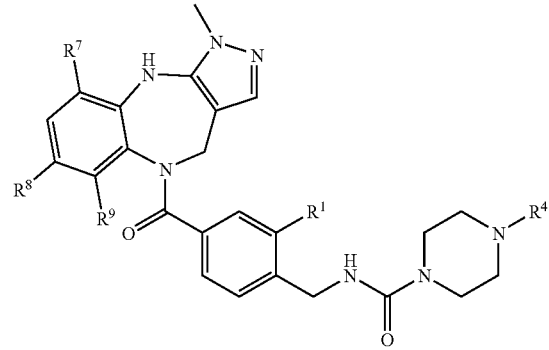
| Compound number | R¹ | R⁴ | R⁷ | R⁸ | R⁹ | MS: [M + H]⁺ |
|---|---|---|---|---|---|---|
| 30 | Me | 3,3-dimethylbutyl | H | Me | H | 558.4 |
| 31 | F | 3,3-dimethylbutyl | Me | H | H | 562.4 |
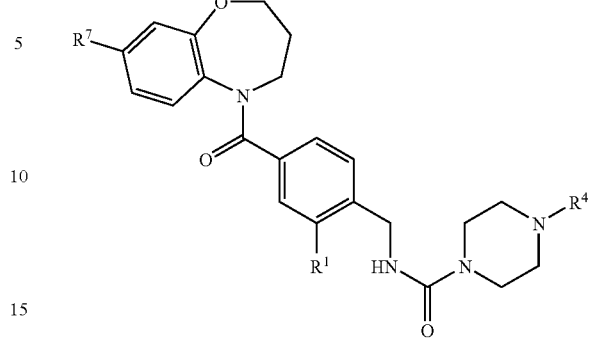
| Compound number | R¹ | R⁴ | R⁷ | MS: [M + H]⁺ |
|---|---|---|---|---|
| 32 | Me | 3,3-dimethylbutyl | Cl | 527.1, 529.1 |
| 33 | Me | 3,3-dimethylbutyl | Me | 507.4 |
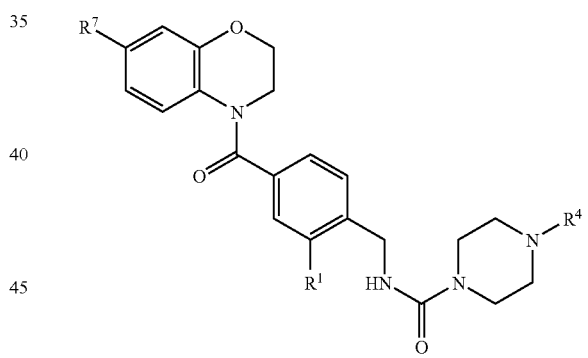
| Compound number | R¹ | R⁴ | R⁷ | MS: [M + H]⁺ |
|---|---|---|---|---|
| 34 | Me | 3,3-dimethylbutyl | Me | 493.4 |
| 35 | Me | 3,3-dimethylbutyl | Cl | 513.1 |

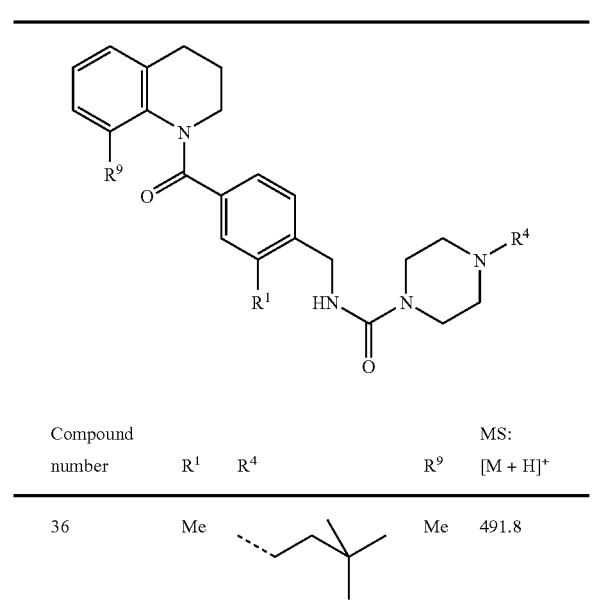
| Compound number | R¹ | R⁴ | R⁹ | MS: [M + H]⁺ |
|---|---|---|---|---|
| 36 | Me | (neopentyl) | Me | 491.8 |
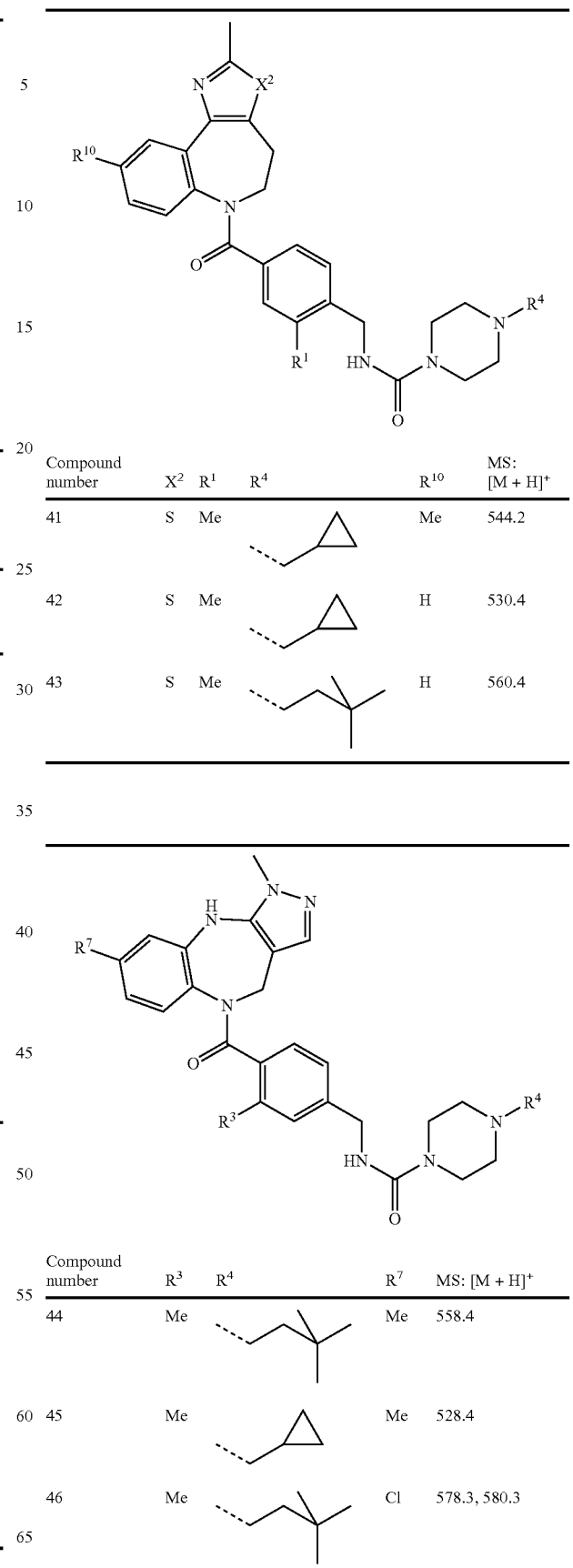
| Compound number | X² | R¹ | R⁴ | R¹⁰ | MS: (ESI)+: [M + H]⁺ |
|---|---|---|---|---|---|
| 37 | NH | Me | (neopentyl) | Cl | 577.4 |
| 38 | NH | Me | (neopentyl) | Me | 557.0 |
| 39 | O | Me | (neopentyl) | H | 544.5 |
| 40 | NH | Me | (neopentyl) | H | 543.4 |
| Compound number | X² | R¹ | R⁴ | R¹⁰ | MS: [M + H]⁺ |
|---|---|---|---|---|---|
| 41 | S | Me | (cyclopropylmethyl) | Me | 544.2 |
| 42 | S | Me | (cyclopropylmethyl) | H | 530.4 |
| 43 | S | Me | (neopentyl) | H | 560.4 |
| Compound number | R³ | R⁴ | R⁷ | MS: [M + H]⁺ |
|---|---|---|---|---|
| 44 | Me | (neopentyl) | Me | 558.4 |
| 45 | Me | (cyclopropylmethyl) | Me | 528.4 |
| 46 | Me | (neopentyl) | Cl | 578.3, 580.3 |

-continued

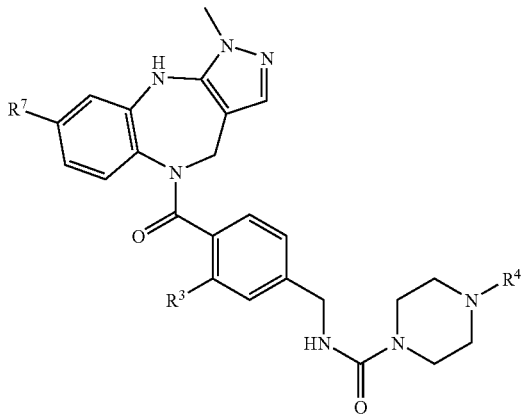

| Compound number | R³ | R⁴ | R⁷ | MS: [M + H]⁺ |
|---|---|---|---|---|
| 47 | Me | cyclopropylmethyl | Cl | 548.3, 550.3 |
| 48 | F | neopentyl | Me | 562.4 |
| 49 | F | cyclopropylmethyl | Me | 532.4 |
| 50 | F | neopentyl | Cl | 582.4, 584.3 |
| 51 | F | cyclopropylmethyl | Cl | 552.3, 554.3 |

-continued

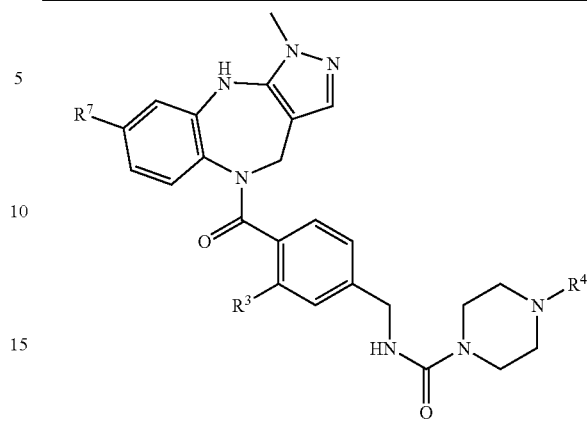

| Compound number | R³ | R⁴ | R⁷ | MS: [M + H]⁺ |
|---|---|---|---|---|
| 52 | Cl | neopentyl | Cl | 598.3, 600.3 |
| 53 | Cl | cyclopropylmethyl | Cl | 568.3 |
| 54 | Cl | neopentyl | Me | 578.3, 580.3 |
| 55 | Cl | cyclopropylmethyl | Me | 548.3, 550.3 |

| Compound number | ¹H NMR: δ (ppm) |
|---|---|
| 3 E8 | 0.86 (9H, s), 1.33-1.39 (2H, m), 2.12 (3H, s), 2.27-2.38 (6H, m), 3.33-3.35 (4H, m), 3.68 (3H, s), 3.92, (1H, d, J = 14.3 Hz), 4.25 (2H, d, J = 5.4 Hz), 5.45 (1H, t, J = 5.4 Hz), 5.79 (1H, d, J = 14.3 Hz), 6.43 (1H, d, J = 8.0 Hz), 6.53 (1H, d, J = 8.0 Hz), 6.79-7.00 (4H, m), 7.17 (1H, s), 7.31 (1H, s) |
| 4 | 0.88 (9H, s), 1.34-1.41 (2H, m), 2.09 (3H, s), 2.18 (3H, s), 2.29-2.36 (2H, m), 2.40 (4H, t, J = 4.7 Hz), 3.37 (4H, t, J = 4.7 Hz), 3.75 (3H, s), 3.94 (1H, d, J = 14.4 Hz), 4.24 (2H, d, J = 5.2 Hz), 4.95 (1H, t), 5.85 (1H, d, J = 14.4 Hz), 6.53 (1H, q, J = 7.9 Hz), 6.76 (1H, d, J = 5.7 Hz), 6.90 (1H, s), 7.02-7.11 (3H, m), 7.58 (1H, s) |
| 5 | 0.05-0.09 (2H, m), 0.47-0.54 (2H, m), 0.81-0.86 (1H, m), 2.08 (3H, s), 2.16 (3H, s), 2.24 (2H, d, J = 6.4 Hz), 2.47-2.49 (4H, m), 3.38-3.44 (4H, m), 3.67 (3H, s), 3.92 (1H, d, J = 14.3 Hz), 4.22 (2H, m), 4.92 (1H, m), 5.85 (1H, d, J = 14.3 Hz), 6.43-6.56 (2H, m), 6.66-6.85 (3H, m), 7.07-7.24 (3H, m) |
| 6 | 0.45-0.47 (4H, m), 1.64 (1H, m), 2.05 (3H, s), 2.13 (3H, s), 2.56 (4H, m), 3.32 (4H, m), 3.65 (3H, s), 3.90 (1H, d, J = 14.6 Hz), 4.18 (2H, m), 5.21 (1H, m), 5.82 (1H, d, J = 14.6 Hz), 6.43 (1H, d, J = 8.0 Hz), 6.53 (1H, d, J = 8.0 Hz), 6.80-6.85 (3H, m), 6.93 (1H, s), 7.04 (1H, s), 7.16 (1H, s) |
| 7 | 0.84 (3H, s), 0.86 (3H, s), 1.28-1.37 (2H, m), 1.48-1.60 (1H, m), 2.01 (3H, s), 2.10 (3H, s), 2.22-2.35 (2H, m), 2.32 (4H, br t), 3.34 (4H, m), 3.59 (3H, s), 3.90 (1H, d, J = 14.6 Hz), 4.16 (2H, d, J = 4.9 Hz), 5.15 (1H, t, J = 5.2 Hz), 5.81 (1H, d, J = 14.6 Hz), 6.40 (1H, d, J = 7.9 Hz), 6.51 (1H, d, J = 7.9 Hz), 6.69-6.83 (3H, m), 7.01 (1H, s), 7.11 (1H, s), 7.14 (1H, s) |
| 8 | 1.06-1.23 (2H, m), 1.38-1.59 (4H, m), 1.63-1.78 (1H, m), 1.98-2.05 (1H, m), 2.07 (3H, s), 2.15 (3H, s), 2.22 (2H, d, J = 7.4 Hz), 2.35 (4H, t, J = 4.7 Hz), 3.33 (4H, t, J = 4.7 Hz), 3.67 (3H, s), 3.91 (1H, d, J = 14.6 Hz), |

| Compound number | ¹H NMR: δ (ppm) |
|---|---|
| | 4.22 (2H, d, J = 5.2 Hz), 4.84 (1H, br t), 5.84 (1H, d, J = 14.6 Hz), 6.43 (1H, d, J = 8.2 Hz), 6.54 (1H, d, J = 8.2 Hz), 6.67 (1H, s), 6.76 (1H, s), 6.77-6.88 (2H, m), 7.07 (1Hs), 7.18 (1H, s) |
| 9 | 0.88 (9H, s), 1.34-1.41 (2H, m), 2.09 (3H, s), 2.25-2.36 (2H, m), 2.36-2.41 (4H, m), 3.35-3.42 (4H, m), 3.72 (3H, s), 3.93 (1H, d, J = 14.6 Hz), 4.24 (2H, d, J = 4.45 Hz), 5.02 (1H, br t), 5.83 (1H, d, J = 14.6 Hz), 6.59 (1H, s), 6.88 (1H, s), 7.01-7.09 (3H, m), 7.56-7.63 (2H, m) |
| 10 | 0.11 (2H, q, J = 4.7 Hz), 0.52 (2H, q, J = 4.7 Hz), 0.76-0.93 (1H, m), 2.10 (3H, s), 2.31 (2H, d, J = 6.4 Hz), 2.45-2.62 (4H, m), 3.39-3.53 (4H, m), 3.79 (3H, s), 3.93 (1H, d, J = 14.6 Hz), 4.23-4.25 (2H, m), 5.27 (1H, s), 5.81 (1H, d, J = 14.6 Hz), 6.58 (2H, s), 6.80-6.90 (2H, m), 7.07 (3H, s), 7.19 (1H, s) |
| 11 | 0.05-0.11 (2H, m), 0.47-0.55 (2H, m), 0.75-0.89 (1H, m), 2.18 (3H, s), 2.24 (2H, d, J = 6.7 Hz), 2.47 (4H, m), 3.38 (4H, m), 3.75 (3H, s), 3.93 (1H, d, J = 14.6 Hz), 4.31 (2H, d, J = 5.7 Hz), 5.13 (1H, t, J = 5.4 Hz), 5.82 (1H, d, J = 14.6 Hz), 6.47-6.58 (2H, m), 6.72-6.80 (2H, m), 6.87-6.95 (2H, m), 7.00-7.04 (1H, m), 7.08-7.17 (1H, m) |
| 12 | 0.86 (9H, s), 1.33-1.39 (2H, m), 2.28-2.38 (6H, m), 3.37 (4H, m), 3.66 (3H, m), 3.94 (1H, d, J = 14.6 Hz), 4.28 (2H, d, J = 5.5 Hz), 5.41 (1H, t, J = 5.5 Hz), 5.78 (1H, d, J = 14.6 Hz), 6.56 (2H, s), 6.84-6.88 (2H, m), 7.00-7.06 (2H, m), 7.18 (1H, s), 7.98 (1H, s) |
| 13 | 0.27-0.29 (2H, m), 0.65-0.67 (2H, m), 0.94-1.10 (1H, m), 1.36-1.56 (2H, m), 2.59 (1H, d, J = 6.4 Hz), 2.76-2.89 (4H, m), 3.54-3.70 (4H, m), 3.83 (3H, s), 3.96 (1H, d, J = 14.6), 4.31-4.35 (2H, m), 5.81 (1H, d, J = 14.6 Hz), 6.63 (1H, s), 6.83-7.00 (1H, m), 7.11 (4H, s), 7.23-7.24 (1H, m), 7.70 (1H, s) |
| 14 | 0.89 (9H, s), 1.37-1.43 (2H, m), 2.33-2.43 (6H, m), 3.35-3.39 (4H, m), 3.74 (3H, s), 3.96 (1H, d, J = 14.6 Hz), 4.34 (2H, d, J = 5.0 Hz), 5.83 (1H, d, J = 14.6 Hz), 6.35-6.41 (1H, m), 6.62-6.73 (2H, m), 6.80 (1H, s), 6.89-6.93 (2H, m), 7.06-7.12 (1H, m) |
| 15 | 0.87 (9H, s), 1.33-1.39 (2H, m), 2.28-2.38 (6H, m), 3.37 (4H, m), 3.66 (3H, m), 3.94 (1H, d, J = 14.6 Hz), 4.31 (2H, d, J = 5.5 Hz), 5.45 (1H, t, J = 5.5 Hz), 5.78 (1H, d, J = 14.6 Hz), 6.91 (1H, m), 7.03 (2H, m), 7.19 (2H, m), 7.84 (1H, s) |
| 16 | (CD3OD): 0.14-0.18 (2H, m), 0.52-0.59 (2H, m), 0.89 (1H, m), 2.28-2.30 (2H, m), 2.52-2.56 (4H, m), 3.43-3.47 (4H, m), 3.80 (3H, s), 3.97 (1H, d, J = 14.6 Hz), 4.34 (2H, d, J = 4.5 Hz), 5.73 (1H, d, J = 14.6 Hz), 6.64-6.77 (2H, m), 7.08-7.17 (2H, m), 7.23-7.28 (3H, m) |
| 17 | 0.87 (9H, s), 1.36 (2H, m), 2.12 (3H, s), 2.32 (6H, m), 3.39 (4H, m), 3.66 (3H, s), 3.92 (1H, d, J = 14.3 Hz), 4.28 (2H, m), 5.43 (1H, m), 5.78 (1H, d, J = 14.3 Hz), 6.48 (1H, d, J = 7.9 Hz), 6.52 (1H, d, J = 7.9 Hz), 6.78 (1H, s), 6.88-6.98 (2H, m), 7.05 (1H, s), 7.17 (1H, m) |
| 18 | 0.06-0.08 (2H, m), 0.48-0.51 (2H, m), 0.76-0.89 (1H, m), 2.15 (3H, s), 2.21-2.29 (2H, m), 2.44-2.48 (4H, m), 3.36-3.38 (4H, m), 3.68 (3H, s), 3.93 (1H, d, J = 14.6 Hz), 4.30 (2H, d, J = 6.0 Hz), 5.33 (1H, m), 5.80 (1H, d, J = 14.6 Hz), 6.48-6.55 (2H, m), 6.77-7.00 (4H, m), 7.19-7.21 (2H, m) |
| 19 | CD3OD: 2.18 (3H, s), 2.22 (3H, s), 3.05-3.09 (4H, m), 3.47 (2H, s), 3.58-3.62 (4H, m), 3.79 (3H, s), 3.93 (1H, d, J = 14.6 Hz), 4.25 (2H, s), 5.75 (1H, d, J = 14.6 Hz), 6.47 (1H, d, J = 8.0 Hz), 6.59 (1H, d, J = 8.0 Hz), 6.97-7.06 (4H, m), 7.21 (1H, s) |
| 20 | 2.02 (3H, s), 2.11 (3H, s), 2.39-2.50 (4H, m), 3.22 (2H, s), 3.32-3.43 (4H, m), 3.60 (3H, s), 3.90 (1H, d, J = 14.6 Hz), 4.16 (2H, d, J = 5.0 Hz), 5.12 (2H, s), 5.25 (1H, t, J = 5.0 Hz), 5.80 (1H, d, J = 14.6 Hz), 6.41 (1H, d, J = 7.9 Hz), 6.51 (1H, d, J = 7.9 Hz), 6.76-6.83 (3H, m), 7.02 (1H, s), 7.12-7.14 (2H, m), 7.28-7.31 (5H, m) |
| 21 | 1.11-1.18 (2H, m), 1.45-1.56 (4H, m), 1.67-1.72 (2H, m), 1.98-2.01, (1H, m), 2.04 (3H, s), 2.22 (2H, d, J = 7.2 Hz), 2.29-2.50 (4H, m), 3.30-3.41 (4H, m), 3.62 (3H, s), 3.91 (1H, d, J = 14.6 Hz), 4.19-4.21 (2H, m), 5.04-5.06 (1H, m), 5.80 (1H, d, J = 14.6 Hz), 6.53-6.54 (2H, m), 6.80-6.84 (2H, m), 7.01-7.03 (2H, m), 7.16 (1H, s), 7.72 (1H, s) |
| 22 | 0.84 (9H, s), 2.05 (2H, m), 2.12 (3H, s), 2.41-2.54 (4H, m), 3.27-3.39 (4H, m), 3.72 (3H, s), 3.92 (1H, d, J = 14.6 Hz), 4.26-4.27 (2H, m), 4.66-4.68 (1H, m), 5.85 (1H, d, J = 14.6 Hz), 6.58-6.59 (2H, m), 6.88-6.92 (2H, m), 6.98-7.00 (2H, m), 7.09 (1H, s), 7.21 (1H, s) |
| 23 | 0.38-0.44 (4H, m), 1.57-1.58 (1H, m), 2.04 (3H, s), 2.53 (4H, m), 3.31 (4H, m), 3.62 (3H, s), 3.91 (1H, d, J = 14.6 Hz), 4.20 (2H, m), 5.08 (1H, m), 5.80 (1H, d, J = 14.6 Hz), 6.54-6.58 (2H, m), 6.80-6.86 (2H, m), 7.01-7.03 (2H, m), 7.16 (1H, s), 7.71 (1H, s) |
| 24 | 0.85 (6H, d, J = 6.4 Hz), 1.23-1.36 (2H, m), 1.49-1.56 (1H, m), 2.01 (3H, s), 2.23-2.35 (6H, m), 3.36 (4H, m), 3.62 (3H, s), 3.91 (1H, d, J = 14.6 Hz), 4.18 (2H, m), 5.29 (1H, m), 5.78 (1H, d, J = 14.6 Hz), 6.48-6.56 (2H, m), 6.80-6.86 (2H, m), 6.98-7.02 (2H, m), 7.15 (1H, s), 8.12 (1H, s) |
| 25 | 0.85 (6H, d, J = 6.4 Hz) 1.73 (1H, m), 2.05 (5H, m), 2.26-2.31 (4H, m), 3.34 (4H, m), 3.62 (3H, s), 3.91 (1H, d, J = 14.6 Hz), 4.21 (1H, m), 5.02 (1H, m), 5.80 (1H, d, J = 14.6 Hz), 6.54 (2H, m), 6.84-6.87 (2H, m), 7.02 (2H, m), 7.16 (1H, s), 7.72 (1H, s) |
| 26 | 0.85 (3H, t, J = 7.2 Hz), 1.40-1.49 (2H, m), 2.01 (3H, s), 2.22-2.28 (2H, m), 2.34 (4H, m) 3.35 (4H, m), 3.58 (3H, s), 3.90 (1H, d, J = 14.6 Hz), 4.18 (2H, |

| Compound number | ¹H NMR: δ (ppm) |
|---|---|
| | m), 5.21 (1H, m), 5.77 (1H, d, J = 14.6 Hz), 6.51-6.55 (2H, m), 6.81-6.85 (2H, m), 7.00 (2H, m), 7.13 (1H, s), 7.88 (1H, s) |
| 27 | 0.84 (9H, s), 2.04 (2H, s), 2.11 (3H, s), 2.18 (3H, s), 2.45 (4H, t, J = 4.7 Hz), 3.30 (4H, t, J = 4.7 Hz), 3.71 (3H, s), 3.92 (1H, d, J = 14.6 Hz), 4.24 (2H, d, J = 5.2 Hz), 4.66 (1H, br t), 5.86 (1H, d, J = 14.6 Hz), 6.41 (1H, s), 6.46 (1H, d, J = 7.9 Hz), 6.56 (1H, d, J = 7.9 Hz), 6.75 (1H, s), 6.88 (2H, s), 7.10 (1H, s), 7.20 (1H, s) |
| 28 | 0.86 (6H, d, J = 6.7 Hz), 1.68-1.81 (1H, m), 2.05 (2H, d, J = 7.4 Hz), 2.09 (3H, s), 2.17 (3H, s), 2.32 (4H, t, J = 4.7 Hz), 3.33 (4H, t, J = 4.7 Hz), 3.69 (3H, s), 3.92 (1H, d, J = 14.6 Hz), 4.23 (2H, d, J = 4.9 Hz), 4.78 (1H, t, J = 4.9 Hz), 5.85 (1H, d, J = 14.6 Hz), 6.46 (1H, d, J = 7.9 Hz), 6.55 (1H, d, J = 7.9 Hz), 6.57 (1H, s), 6.76 (1H, s), 6.86 (2H, s), 7.08 (1H, s), 7.19 (1H, s) |
| 29 | 0.88 (3H, t, J = 7.4 Hz), 1.43-1.54 (2H, m), 2.12 (3H, s), 2.19 (3H, s), 2.28 (2H, t, J = 7.4 Hz), 2.38 (4H, t, J = 4.9 Hz), 3.35 (4H, t, J = 4.9 Hz), 3.73 (3H, s), 3.93 (1H, d, J = 14.6 Hz), 4.25 (2H, d, J = 5.2 Hz), 4.66 (1H, br t), 5.87 (1H, d, J = 14.6 Hz), 6.29 (1H, s), 6.47 (1H, d, J = 7.7 Hz), 6.56 (1H, d, J = 7.7 Hz), 6.74 (1H, s), 6.89 (2H, s), 7.11 (1H, s), 7.21 (1H, s) |
| 30 | 0.88 (9H, s), 1.32-1.42 (2H, m), 2.02 (3H, s), 2.14 (3H, s), 2.28-2.46 (6H, m), 3.30-3.42 (4H, m), 3.75 (3H, s), 3.94 (1H, d, J = 14.4 Hz), 4.26-4.32 (2H, m), 4.48-4.56 (1H, m), 5.87 (1H, d, J = 14.4 Hz), 6.07 (1H, s), 6.52 (1H, s), 6.78-6.97 (4H, m), 7.13 (1H, s) |
| 31 | 0.88 (9H, s), 1.35-1.41 (2H, m), 2.28-2.42 (8H, m), 3.27-3.40 (4H, m), 3.82 (3H, s), 3.96 (1H, d, J = 14.4 Hz), 4.33 (2H, d, J = 5.4 Hz), 4.68-4.79 (1H, m), 5.80 (1H, s), 5.89 (1H, d, J = 14.4 Hz), 6.58-6.70 (2H, m), 6.88-6.95 (2H, m), 6.96-7.12 (3H, m), 7.65 (1H, s) |
| 32 | 0.88 (9H, s), 1.35-1.41 (2H, m), 2.00-2.18 (2H, m), 2.27-2.35 (2H, m), 2.36-2.43 (4H, m), 3.34-3.41 (4H, m), 3.44 (2H, s), 4.29 (2H, d, J = 5.2 Hz), 4.58-4.63 (1H, m), 6.48-6.61 (1H, m), 6.62-6.75 (1H, m), 6.88-7.03 (2H, m), 7.07-7.11 (2H, m) |
| 33 | 0.87 (9H, s), 1.35-1.41 (2H, m), 2.16 (3H, s), 2.22 (3H, s), 2.23-2.36 (2H, m), 2.40 (4H, t, J = 4.7 Hz), 3.35 (4H, t, J = 4.7 Hz), 4.28-4.30 (2H, m), 4.50 (1H, br s), 6.52 (2H, br s), 6.88 (1H, s), 6.95 (2H, s), 7.11 (1H, s) |
| 34 | 0.89 (9H, s), 1.36-1.43 (2H, m), 2.23 (3H, s), 2.31 (3H, s), 2.31-2.41 (2H, m), 2.43 (4H, t, J = 4.9 Hz), 3.40 (4H, t, J = 4.9 Hz), 3.95 (2H, t, J = 4.7 Hz), 4.31 (2H, t, J = 4.7 Hz), 4.41-4.44 (2H, m), 4.55-4.60 (1H, m), 6.47-6.51 (1H, m), 6.70 (1H, s), 6.81-7.00 (1H, m), 7.21-7.27 (2H, m), 7.34 (1H, s) |
| 35 | 0.89 (9H, s), 1.36-1.43 (2H, m), 2.31 (3H, s), 2.32-2.39 (2H, m), 2.44 (4H, t, J = 4.9 Hz), 3.40 (4H, t, J = 4.9 Hz), 3.94 (2H, t, J = 4.4 Hz), 4.31 (2H, t, J = 4.4 Hz), 4.42 (2H, d, J = 5.4 Hz), 4.62 (1H, t, J = 5.2 Hz), 6.64-6.73 (1H, m), 6.91 (1H, d, J = 2.2 Hz), 7.00-7.15 (1H, m), 7.24 (3H, d, J = 3.0 Hz) |
| 36 | 0.88 (9H, s), 0.89 (3H, s), 1.32-1.42 (2H, m), 1.65-2.20 (4H, m), 2.30-2.45 (7H, m), 2.49 (2H, t, J = 5.2 Hz), 2.80-2.90 (1H, m), 3.36 (4H, br s), 3.60 (2H, t, J = 4.9 Hz), 4.25-4.40 (1H, m), 6.80-7.40 (6H, m), 7.84 (1H, s) |
| 37 | 0.92 (9H, s), 1.42-1.49 (2H, m), 2.09 (3H, s), 2.48 (3H, s) 2.50-2.58 (4H, m), 2.80-3.03 (2H, m), 3.13-3.33 (1H, m), 3.40-3.53 (4H, m), 4.17-4.33 (2H, m), 4.90-5.08 (1H, m), 5.67-5.78 (1H, m), 6.54-6.58 (2H, m), 6.79-6.90 (2H, m), 7.10 (2H, s), 7.68 (2H, s), 8.13 (1H, d, J = 2.0 Hz) |
| 38 | 0.89 (9H, s), 1.37-1.43 (2H, m), 2.13 (3H, s), 2.29 (3H, s), 2.30-2.47 (8H, m), 2.49 (3H, s), 2.76-2.88 (1H, m), 2.90-3.07 (1H, m), 3.31-3.42 (4H, m), 4.26 (2H, d, J = 4.2 Hz), 4.70-4.80 (1H, m), 4.96-5.08 (1H, m), 6.51 (1H, d, J = 7.9 Hz), 6.65 (2H, d, J = 7.4 Hz), 6.85 (1H, d, J = 7.7 Hz), 7.06 (1H, m), 7.86-7.97 (1H, m) |
| 39 | 0.87 (9H, s), 1.33-1.39 (2H, m), 2.12 (3H, s), 2.27-2.36 (2H, m), 2.36-2.43 (4H, m), 2.54 (3H, s), 2.82-2.91 (1H, m), 2.91-2.98 (1H, m), 3.20-3.27 (1H, m), 3.31-3.35 (4H, m), 4.27 (2H, t, J = 4.0 Hz), 4.54 (1H, t, J = 4.9 Hz), 5.11-5.16 (1H, m), 6.62-6.72 (2H, m), 6.88-6.98 (2H, m), 6.99 (1H, s), 7.15-7.23 (1H, m), 7.75-7.80 (1H, m) |
| 40 | 0.82 (9H, s), 1.31-1.37 (2H, m), 2.20 (3H, s), 2.25-2.42 (6H, m), 3.32-3.42 (4H, m), 3.55 (3H, s), 3.94 (1H, d, J = 14.6 Hz), 4.06-4.11 (2H, m), 5.53 (1H, m), 5.77 (1H, d, J = 14.6 Hz), 6.49-6.57 (2H, m), 6.64-6.73 (2H, m), 6.80-6.94, (3H, m), 7.16 (1H, s), 7.67 (1H, s) |
| 41 | 0.07-0.13 (2H, m), 0.49-0.55 (2H, m), 0.83-0.88 (1H, m), 2.17 (3H, s), 2.28 (2H, d, J = 6.4 Hz), 2.33 (3H, s), 2.49-2.53 (4H, m), 2.73 (3H, s), 3.02-3.17 (2H, m), 3.36-3.41 (4H, m), 4.27-4.31 (2H, m), 4.51 (1H, s), 5.11-5.18 (1H, m), 6.55 (1H, d, J = 7.9 Hz), 6.67 (1H, d, J = 7.0 Hz), 6.77 (1H, d, J = 7.0 Hz), 6.86 (1H, d, J = 7.9 Hz), 7.15 (1H, s), 8.15 (1H, s) |
| 42 | 0.07-0.09 (2H, m), 0.46-0.54 (2H, m), 0.80-0.85, (1H, m), 2.15 (3H, s), 2.23-2.27 (2H, m), 2.45-2.49 (4H, m), 2.73 (3H, s), 3.10-3.18 (2H, |

| Compound number | $^1$H NMR: δ (ppm) |
|---|---|
| | m), 3.35-3.37 (4H, m), 3.48-3.68 (1H, m), 4.25-4.29 (2H, m), 4.48 (1H, m), 5.16 (1H, m), 6.67 (2H, m), 6.86 (1H, d, J = 7.9 Hz), 6.92-6.98 (1H, m), 7.12 (1H, s) 7.20 (1H, m) 8.36 (1H, d, J = 7.9 Hz) |
| 43 | 0.88 (9H, s), 1.34-1.40 (2H, m), 2.14 (3H, s), 2.29-2.49 (6H, m), 2.72 (3H, s), 3.03-3.18 (2H, m), 3.31-3.35 (4H, m), 3.47-3.67 (1H, m), 4.21-4.31 (2H, m), 4.51-4.54 (1H, m), 5.12-5.19 (1H, m), 6.67 (2H, m), 6.85 (1H, d, J = 7.9 Hz), 6.92-6.97 (1H, m), 7.06-7.22 (2H, m), 8.36 (1H, dd, J = 1.2, 7.9 Hz) |
| 44 | 0.85 (9H, s), 1.31-1.39 (2H, m), 1.99 (3H, s), 2.19 (3H, s), 2.24-2.40 (6H, m), 3.33-3.38 (4H, m), 3.53 (3H, s), 3.90 (1H, d, J = 14.6 Hz), 4.10-4.12 (2H, m), 5.56 (1H, m), 5.75 (1H, d, J = 14.6 Hz), 6.33-6.35 (1H, m), 6.52-6.56 (2H, m), 6.66-7.11 (3H, m), 7.14 (1H, s), 7.48 (1H, s) |
| 45 | 0.01-0.06 (2H, m), 0.42-0.49 (2H, m), 0.75-0.81 (1H, m), 1.98 (3H, s), 2.17-2.25 (5H, m), 2.38-2.48 (4H, m), 3.32-3.41 (4H, m), 3.50 (3H, s), 3.89 (1H, d, J = 14.6 Hz), 4.11 (2H, m), 5.54 (1H, m), 5.75 (1H, d, J = 14.6 Hz), 6.34 (1H, dd, J = 1.0, 8.0 Hz), 6.50-6.54 (2H, m), 6.66-7.07 (3H, m), 7.13 (1H, s) 7.37 (1H, s) |
| 46 | 0.88 (9H, s), 1.33-1.42 (2H, m), 2.24 (3H, s), 2.27-2.45 (6H, m), 3.35-3.43 (4H, m), 3.68 (3H, s), 3.94 (1H, d, J = 14.6 Hz), 4.20 (2H, d, J = 5.4 Hz), 5.01-5.07 (1H, m), 5.79 (1H, d, J = 14.6 Hz), 6.54 (1H, dd, J = 2.2, 8.4 Hz), 6.61-7.02 (5Hm), 7.05 (1H, d, J = 1.0 Hz), 7.53 (1H, d, J = 4.7 Hz) |
| 47 | 0.01-0.06 (2H, m), 0.42-0.47 (2H, m), 0.76-0.80 (1H, m), 2.15-2.23 (5H, m), 2.41-2.46 (4H, m), 3.35-3.48 (4H, m), 3.54 (3H, s), 3.90 (1H, d, J = 14.6 Hz), 4.11 (2H, m), 5.46 (1H, m), 5.72 (1H, d, J = 14.6 Hz), 6.46 (1H, dd, J = 1.5, 8.5 Hz), 6.54-6.61 (2H, m), 6.67-6.73 (1H, m), 6.81-7.09 (2H, m), 7.13 (1H, s), 7.99 (1H, s) |
| 48 | 0.84 (9H, s), 1.31-1.37 (2H, m), 1.99 (3H, s), 2.24-2.33 (6H, m), 3.34 (4H, m), 3.57 (3H, s), 3.90 (1H, d, J = 14.6 Hz), 4.08 (2H, m), 5.70 (1H, d, J = 14.6 Hz), 6.01 (1Hm), 6.34 (1H, m), 6.53-6.60 (2H, m), 6.70 (1H, s), 6.82-6.91 (2H, m), 7.10 (1H, s), 7.49 (1H, s) |
| 49 | 0.02-0.08 (2H, m), 0.44-0.51 (2H, m), 0.77-0.82 (1H, m), 2.02 (3H, s), 2.16-2.24 (2H, m), 2.42-2.44 (4H, m), 3.36-3.42 (4H, m), 3.57 (3H, s), 3.92 (1H, d, J = 14.6 Hz), 4.11 (2H, m), 5.72 (1H, d, J = 14.6 Hz), 5.86 (1H, m), 6.36 (1H, dd, J = 1.0, 8.0 Hz), 6.54-6.89 (5H, m), 7.12 (1H, s), 7.27 (1H, s) |
| 50 | 0.87 (9H, s), 1.33-1.40 (2H, m), 2.27-2.40 (6H, m), 3.34-3.42 (4H, m), 3.60 (3H, s), 3.94 (1H, d, J = 14.6 Hz), 4.16 (2H, d, J = 5.2 Hz), 5.72 (1H, d, J = 14.6 Hz), 5.81 (1H, t, J = 5.4, 11.1 Hz), 6.50 (1H, dd, J = 2.2, 8.4 Hz), 6.60-6.73 (3H, m), 6.91-7.02 (3H, m), 8.00 (1H, s) |
| 51 | 0.02-0.08 (2H, m), 0.44-0.48 (2H, m), 0.77-0.81 (1H, m), 2.20-2.24, (2H, m), 2.43 (4H, m), 3.37-3.47 (4H, m), 3.57 (3H, s), 3.93 (1H, d, J = 14.6 Hz), 4.14 (2H, m), 5.70 (1H, d, J = 14.6 Hz), 5.82 (1H, m), 6.48 (1H, dd, J = 2.0, 8.5 Hz), 6.58-6.72 (3H, m), 6.89-7.00 (2H, m), 7.14 (1H, s), 7.92 (1H, s) |
| 52 | 0.89 (9H, s), 1.34-1.42 (2H, m), 2.29-2.46 (6H, m), 3.35-3.44 (4H, m), 3.66 (3H, s), 3.98 (1H, d, J = 14.6 Hz), 4.21 (2H, d, J = 5.4 Hz), 5.14-5.24 (1H, m), 5.76 (1H, d, J = 14.6 Hz), 6.58 (1H, dd, J = 2.2, 8.4 Hz), 6.74-7.00 (4H, m), 7.07 (1H, s), 7.22 (1H, s) |
| 53 | 0.02-0.07 (2H, m), 0.43-0.48 (2H, m), 0.77-0.81 (1H, m), 2.19-2.24 (2H, m), 2.42-2.47 (4H, m), 3.37-3.41 (4H, m), 3.56 (3H, s), 3.95 (1H, d, J = 14.6 Hz), 4.10 (2H, m), 5.68 (1H, d, J = 14.6 Hz), 5.89 (1H, m), 6.49 (1H, dd, J = 2.0, 8.5 Hz), 6.68-6.96 (5H, m), 7.14 (1H, s), 7.93 (1H, s) |
| 54 | 0.82 (9H, s), 1.33-1.41 (2H, m), 1.99 (3H, s), 2.28-2.38 (6H, m), 3.36-3.37 (4H, m), 3.60 (3H, s), 3.95 (1H, d, J = 14.6 Hz), 4.07 (2H, m), 5.69 (1H, d, J = 14.6 Hz), 6.06 (1H, m), 6.37 (1H, m), 6.61-6.82 (3H, m), 6.94 (2H, m), 7.14 (1H, s), 7.46 (1H, s) |
| 55 | 0.02-0.07 (2H, m), 0.43-0.50 (2H, m), 0.76-0.81 (1H, m), 1.97 (3H, s), 2.16-2.23 (2H, m), 2.41-2.45 (4H, m), 3.36-3.44, (4H, m), 3.54 (3H, s), 3.93 (1H, d, J = 14.6 Hz), 4.05 (2H, m), 5.68 (1H, d, J = 14.6 Hz), 6.00 (1H, m), 6.34 (1H, m), 6.58-6.79 (4H, m), 6.90 (1H, s), 7.11 (1H, s), 7.35 (1H, s) |

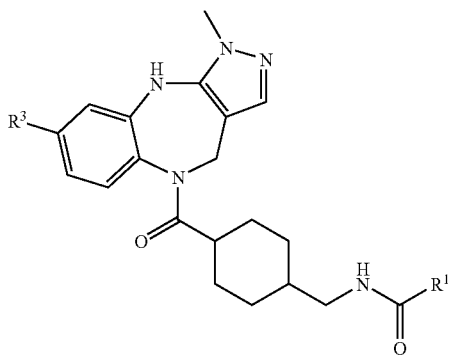
| Compound number | R³ | R¹ | ¹H NMR: δ (ppm) | MS |
|---|---|---|---|---|
| 109 E10 | Cl | cyclopropyl | 0.42-0.90 (6H, m), 1.28 (6H, m), 1.78-1.80 (2H, m), 2.08 (1H, m), 2.95-3.01 (2H, m), 3.66 (3H, s), 3.76 (1H, d, J = 14.6 Hz), 5.55 (1H, d, J = 14.6 Hz), 5.95 (1H, m), 6.97 (1H, dd, J = 8.4, 2.1 Hz), 7.03 (1H, s), 7.07 (1H, d, J = 8.4 Hz), 7.09 (1H, d, J = 2.1 Hz), 7.14 (1H, s) | (ESI)+: [M + H]+ = 442.3, 444.3 |
| 110 | Me | cyclopropyl | 0.58-0.90 (6H, m), 1.23-2.13 (9H, m), 2.33 (3H, s), 2.95-3.03 (2H, m), 3.68 (3H, s), 3.76 (1H, d, J = 14.6 Hz), 5.59 (1H, d, J = 14.6 Hz), 5.80 (1H, m), 6.15 (1H, s), 6.81-6.83 (2H, m), 6.97-7.00 (1H, m), 7.14 (1H, s) | (ESI)+: [M + H]+ = 422.4 |
| 111 | H | cyclopropyl | 0.58-0.81 (6H, m), 1.31-1.74 (6H, m), 1.69-1.80 (2H, m), 2.09-2.16 (1H, m), 2.89-2.98 (2H, m), 3.64 (3H, s), 3.80 (1H, d, J = 14.6 Hz), 5.58 (1H, d, J = 14.6 Hz), 6.49 (1H, m), 6.95-7.23 (5H, m), 7.39 (1H, s) | (APCI)+: [M + H]+ = 408.3 |
| 112 | Me | CH₃ | | |
| 113 | Me | phenyl | | (ESI)+: [M + H]+ = 458.7 |
| 114 | Me | 3-chlorophenyl | | (ESI)+: [M + H]+ = 492.2, 494.2 |
| 115 | Me | 4-chlorophenyl | | (ESI)+: [M + H]+ = 492.6, 494.2 |
| 116 | Me | 2-chlorophenyl | | (ESI)+: [M + H]+ = 492.2, 494.2 |

-continued
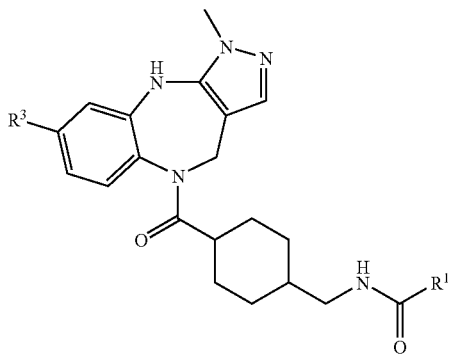
| Compound number | R³ | R¹ | ¹H NMR: δ (ppm) | MS |
|---|---|---|---|---|
| 117 | Me | 4-methoxyphenyl | | (ESI)+: [M + H]+ = 488.7 |
| 118 | Me | 3-methylphenyl | | (ESI)+: [M + H]+ = 472.7 |
| 119 | Me | 2-methylphenyl | | (ESI)+: [M + H]+ = 472.7 |
| 120 | Me | 2-chloropyridin-3-yl | | (ESI)+: [M + H]+ = 493.2 |
| 121 | Me | pyridin-3-yl | | (ESI)+: [M + H]+ = 459.2 |
| 122 | Me | pyridin-4-yl | | (ESI)+: [M + H]+ = 459.2 |
| 123 | Me | thiophen-2-yl | | (ESI)+: [M + H]+ = 464.6 |
| 124 | Me | 3-chlorothiophen-2-yl | | (ESI)+: [M + H]+ = 498.1 |
| 125 | Me | thiophen-3-yl | | (ESI)+: [M + H]+ = 464.2 |
| 126 | Me | 2,5-dimethylfuran-3-yl | | (ESI)+: [M + H]+ = 476.6 |

-continued
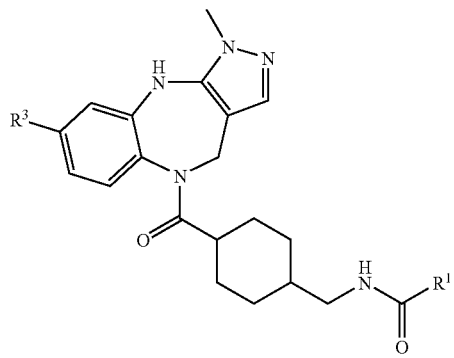
| Compound number | R³ | R¹ | ¹H NMR: δ (ppm) | MS |
|---|---|---|---|---|
| 127 | Me | furan-2-yl | | (ESI)+: [M + H]+ = 448.6 |
| 128 | Me | isoxazol-5-yl | | (ESI)+: [M + H]+ = 449.6 |
| 129 | Me | 4-methyl-2-phenyl-2H-1,2,3-triazol-5-yl | | (ESI)+: [M + H]+ = 539.3 |
| 130 | Me | CH₂CH₃ | | (ESI)+: [M + H]+ = 410.7 |
| 131 | Me | CH₂CH₂CH₃ | | (ESI)+: [M + H]+ = 424.7 |
| 132 | Me | C(CH₃)₃ | | (ESI)+: [M + H]+ = 438.3 |
| 133 | Me | CH₂-cyclopentyl | | (ESI)+: [M + H]+ = 464.7 |
| 134 | Me | CH₂(CH₂)₃CH₃ | | (ESI)+: [M + H]+ = 452.8 |
| 135 | Me | CH(CH₂CH₃)CH₂CH₂CH₂CH₃ | | (ESI)+: [M + H]+ = (ESI)+: [M + H]+ = 480.8 |
| 136 | Me | 2,5-dimethoxyphenyl | | (ESI)+: [M + H]+ = 523.3 |
| 137 | Me | CH₂-phenyl | | (ESI)+: [M + H]+ = 472.7 |

-continued
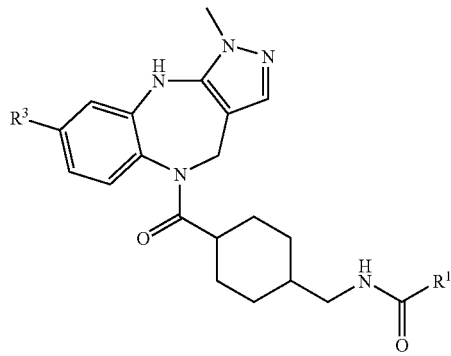
| Compound number | R³ | R¹ | ¹H NMR: δ (ppm) | MS |
|---|---|---|---|---|
| 138 | Me | (CH₂CH₂-phenyl) | | (ESI)+: [M + H]+ = 486.7 |
| 139 | Me | (cyclopropyl-phenyl) | | (ESI)+: [M + H]+ = 498.7 |
| 140 | Me | (CH₂-thiophen-2-yl) | | (ESI)+: [M + H]+ = 478.6 |
| 141 | Me | (CH₂-O-phenyl) | | (ESI)+: [M + H]+ = 488.7 |
| 142 | Me | (CH₂-O-CH₂-phenyl) | | (ESI)+: [M + H]+ = 502.7 |
| 143 | Me | CH₂CO₂CH₂CH₃ | | (ESI)+: [M + H]+ = 468.2 |
| 144 | Me | CH₂CH₂CO₂CH₃ | | (ESI)+: [M + H]+ = 468.2 |
| 145 | Me | CH₂(CH₂)₂CO₂CH₂CH₃ | | (ESI)+: [M + H]+ = 496.7 |

| Compound number | R¹ | R³ | X | MS (ESI)+: [M + H]+ = | ¹H NMR: δ (ppm) |
|---|---|---|---|---|---|
| 146 |  | Cl | S | 458.4, 460.4 | 0.51-0.98 (6H, m), 1.11-1.99 (7H, m), 2.30-2.41 (1H, m), 2.67 (3H, s), 2.83-3.08 (4H, m), 3.42-3.62 (1H, m), 5.55 (1H, s), 7.10 (1H, d, J = 8.4 Hz), 7.25 (1H, dd, J = 2.5, 8.4 Hz), 8.38 (1H, d, J = 2.5 Hz) |
| 147 |  | Me | S | 438.2 | 0.55-0.62 (1H, m), 0.62-0.72 (2H, m), 0.72-0.85 (1H, m), 0.85-1.00 (2H, m), 1.10-1.45 (4H, m), 1.45-1.95 (4H, m), 2.35-2.50 (1H, m), 2.43 (3H, s), 2.68 (3H, s), 2.85-3.10 (4H, m), 3.45-3.65 (1H, m), 4.75-4.85 (1H, m), 5.45-5.65 (1H, m), 7.00-7.15 (2H, m), 8.14 (1H, s) |
| Compound number | R³ | MS (ESI)+: [M + H]+ = |
|---|---|---|
| 148 E10.2 | Cl | |
| 149 | Me | 354.2 |
| 150 | H | 340.2 |
| Compound number | R⁸ | MS (ESI)+: [M + H]+ = |
|---|---|---|
| 151 E12 | CH(CH₃)₂ | 396.4 |
| 152 | CH₂CH₃ | 396.4 |
| 153 | 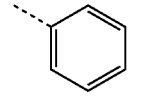 | 430.4 |
| 154 | 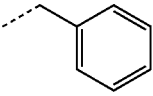 | 444.4 |
| 155 | 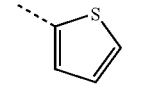 | 436.1 |
| 156 | 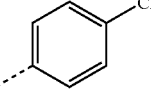 | 464.2, 466.2 |
| 157 | 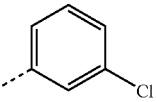 | 464.3, 466.3 |
| 158 | CH₂CH₂CH₂CH₃ | 410.4 |
| 159 |  | 394.4 |
| 160 | 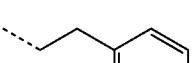 | 458.4 |
| 161 | CH₂CH(CH₃)₂ | 410.4 |
| 162 | 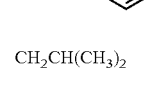 | 410.3 |
| 163 | 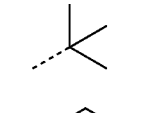 | 431.1 |

-continued
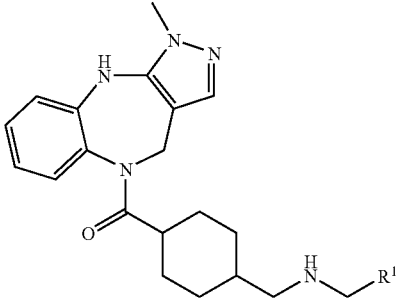
| Compound number | R⁸ | MS (ESI)+: [M + H]+ = |
|---|---|---|
| 164 | 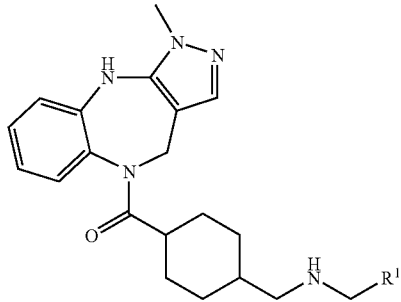 4-isopropylphenyl | 472.4 |
| 165 | 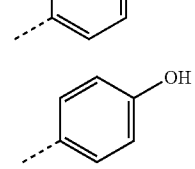 4-hydroxyphenyl | 446.4 |
| 166 | 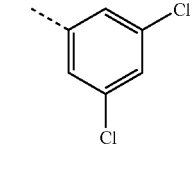 2-pyridyl | 431.4 |
| 167 | 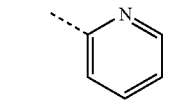 3-thienyl | 436.3 |
| 168 | CH₂CF₃ | 436.3 |
| 169 | 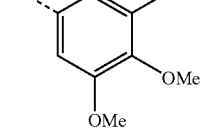 cyclohexenyl | 434.4 |
| 170 | 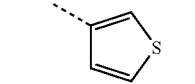 4-methylphenyl | 444.4 |
| 171 | 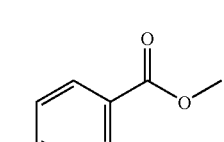 3-methylphenyl | 444.3 |
| 172 | 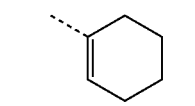 2-methylphenyl | 444.2 |
| 173 | 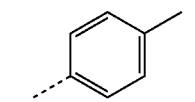 2-cyanophenyl | 454.2 |
-continued
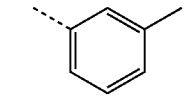
| Compound number | R⁸ | MS (ESI)+: [M + H]+ = |
|---|---|---|
| 174 | 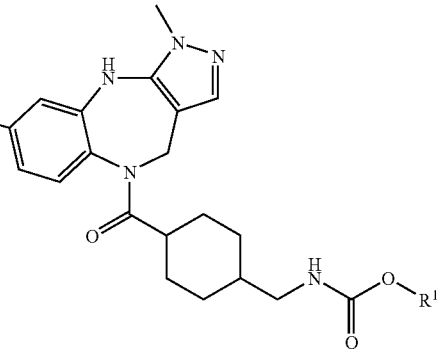 3-cyanophenyl | 454.4 |
| 175 | 3,5-dichlorophenyl | 498.3 |
| 176 | 3,4,5-trimethoxyphenyl | 520.4 |
| 177 | 4-(methoxycarbonyl)phenyl | 488.4 |
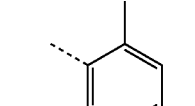
| Compound number | R¹ | MS (ESI)+: [M + H]+ = |
|---|---|---|
| 178 E13 | 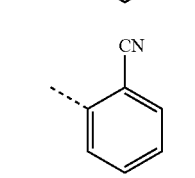 benzyl | 533.3 |

225
-continued
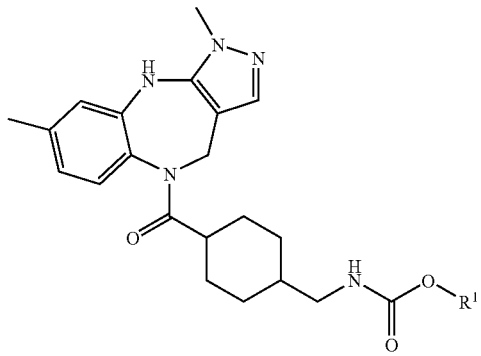
| Compound number | R¹ | MS (ESI)+: [M + H]+ = |
|---|---|---|
| 179 | 2-Cl-C₆H₄-CH₂- | 522.2, 524.2 |
| 180 | isopropyl-methyl-cyclohexyl | 536.4 |
| 181 | 4-NO₂-C₆H₄- | 519.7 |
| 182 | allyl | 438.2 |
| 183 | 4-MeO-C₆H₄- | 504.7 |
| 184 | propargyl | 436.7 |
| 185 | pyridyl | 474.7 |
| 186 | 4-Cl-C₆H₄- | 508.6 |
| 187 | benzyl | 488.7 |
| 188 | isobutyl | 454.7 |
| 189 | ethyl | 426.2 |
226
-continued
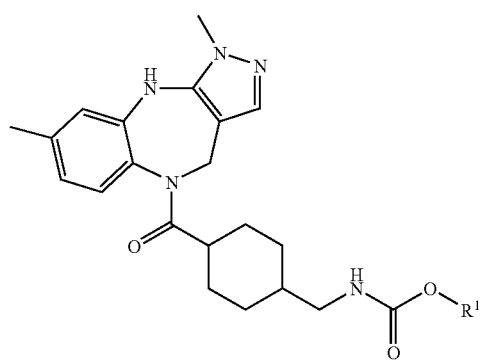
| Compound number | R¹ | MS (ESI)+: [M + H]+ = |
|---|---|---|
| 190 | C(Cl)₃C(CH₃)₂- | 556.2, 558.2 |
| 191 | CH₃ | 412.2 |
| 192 | vinyl | 424.2 |
| 193 | -CH₂CH₂-O-CH₂-C₆H₅ | 532.3 |
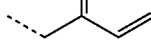
| Compound number | R¹ | MS (ESI)+: [M + H]+ = |
|---|---|---|
| 194 E14 | CH₂CH₂CH₂CH₂CH₃ | 458.4 |
| 195 | CH₂CH₃ | 416.4, 418.4 |
| 196 | (CH₂)₂CN | 441.5, 443.5 |
| 197 | cyclohexylmethyl | 484.4, 486.4 |
| 198 | 3-F-C₆H₄- | 482.4, 484.4 |

227-continued

| Compound number | R¹ | MS (ESI)+: [M + H]+ = |
|---|---|---|
| 199 | 4-tert-butylphenyl | 520.6, 522.6 |
| 200 | 4-(OCF₃)phenyl | 548.5, 550.5 |
| 201 | 4-(CO₂Me)phenyl | 522.6, 524.6 |
| 202 | phenyl | 464.5, 466.5 |
| 203 | cyclohexyl | 470.5, 472.5 |
| 204 | CH₂OH | 418.3, 420.3 |
| 205 | CO₂CH(CH₃)₂ | 474.4, 476.4 |
| 206 | 4-(Boc)piperazin-1-ylcarbonyl | 600.6, 602.6 |
| 207 | CH₂CH(CH₃)₂ | 444.5, 446.5 |
| 208 | CH₂CH₂OH | 432.5 |
| 209 | CN | 413.4, 415.5 |
| 210 | CH₂OEt | 446.5, 448.5 |
| 211 | CH₂CH₂F | 434.3, 436.3 |
| 212 | 3-nitrophenyl | 509.5, 511.5 |

228-continued

| Compound number | R¹ | MS (ESI)+: [M + H]+ = |
|---|---|---|
| 213 | cyclopropyl | 428.4, 430.4 |
| 214 | 2-naphthyl | 514.6, 516.6 |
| 215 | vinyl | 414.4, 416.5 |
| 216 | styryl | 490.6, 492.6 |
| 217 | 2-biphenyl | 540.6, 542.6 |
| 218 | (E)-CH=CHCO₂Me | 472.3, 474.4 |
| 219 | 2-cyanophenyl | 489.4, 491.4 |
| 220 | (Z)-C(OEt)=CHCO₂Et | 530.5, 532.5 |
| 221 | COC(CH₃)₃ | 472.5, 474.5 |
| 222 | CONH₂ | 431.5, 433.5 |
| 223 | 5-nitrofuran-2-yl | 499.5, 501.5 |
| 224 | benzofurazan-5-yl | 506.6, 508.6 |

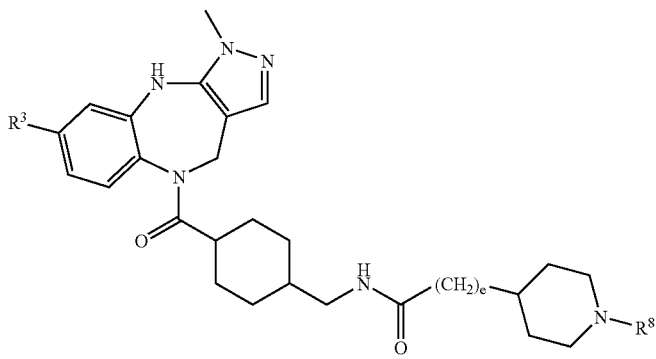

| Compound number | R³ | e | R⁸ | MS | ¹H NMR: δ (ppm) |
|---|---|---|---|---|---|
| 225 E16 | H | 0 | CH₂CH₂C(CH₃)₃ | (ESI)+: [M + H]+ = 535.5 | 0.45-0.80 (2H, m), 0.88 (9H, s), 1.20-1.62 (7H, m), 1.62-2.19 (10H, m), 2.33-2.46 (2H, m), 3.72 (3H, s), 3.79 (1H, d, J = 14.6 Hz), 5.61 (1H, d, J = 14.6 Hz), 5.63-5.70 (1H, m), 6.10 (1H, s), 7.02 (2H, t, J = 8.4 Hz), 7.10-7.19 (3H, m), 7.26-7.28 (2H, m) |
| 226 | Cl | 2 | CO₂C(CH₃)₃ | (ESI)+: [M + H]+ = 613.4, 615.4 | 0.43-0.62 (1H, m), 0.64-0.83 (1H, m), 0.91-1.14 (2H, m), 1.22-1.81 (11H, m), 1.44 (9H, s), 1.98-2.07 (2H, m), 2.16 (2H, t, J = 7.7 Hz), 2.61 (2H, brs), 2.98 (2H, d, J = 5.4 Hz), 3.70 (3H, s), 3.75 (1H, d, J = 14.6 Hz), 4.02 (2H, d, J = 12.4 Hz), 5.55 (1H, d, J = 14.6 Hz), 5.95 (1H, t, J = 5.2 Hz), 6.96 (1H, dd, J = 2.0, 8.4 Hz), 7.04 (1H, d, J = 8.4 Hz), 7.09-7.13 (2H, m), 7.35 (1H, s) |
| 227 | H | 0 | CO₂C(CH₃)₃ | — | d4-MeOH δ 0.46-0.80 (2H, m), 1.13-1.84 (11H, m), 1.44 (9H, s), 2.13-2.37 (2H, m), 2.74 (2H, brs), 2.89 (2H, t, J = 6.2 Hz), 3.72 (3H, s), 3.80 (1H, d, J = 14.6 Hz), 4.07 (2H, d, J = 13.4 Hz), 5.47 (1H, d, J = 14.6 Hz), 7.01-7.09 (1H, m), 7.14 (1H, s), 7.16-7.22 (1H, m), 7.26-7.37 (2H, m), 7.82-7.92 (2H, m) |
| 228 | Me | 1 | CO₂C(CH₃)₃ | | 0.48-0.61 (1H, m), 0.63-1.81 (1H, m), 0.92-1.14 (2H, m), 1.16-1.30 (2H, m), 1.42 (9H, s), 1.50-2.21 (10H, m), 2.31 (3H, s), 2.53-2.72 (2H, m), 2.95 (2H, t, J = 5.9 Hz), 3.31-3.53 (1H, m), 3.67 (3H, s), 3.75 (1H, d, J = 14.6 Hz), 3.98-4.03 (2H, m), 5.53 (1H, d, J = 14.6 Hz), 6.10 (1H, brt), 6.71 (1H, s), 6.80 (1H, d, J = 7.9 Hz), 6.86 (1H, s), 6.97 (1H, d, J = 7.9 Hz), 7.10 (1H, s) |

-continued

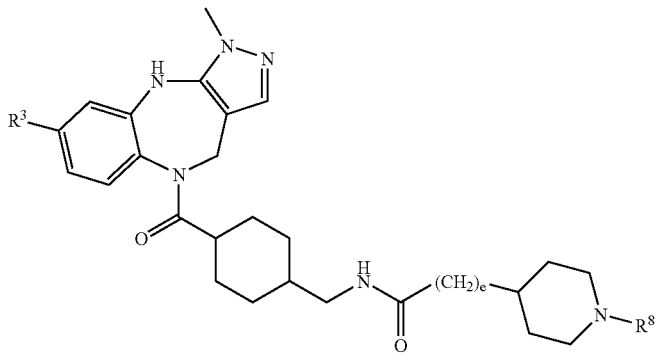

| Compound number | R³ | e | R⁸ | MS | ¹H NMR: δ (ppm) |
|---|---|---|---|---|---|
| 229 | H | 0 | cyclopropylmethyl | (ESI)+: [M + H]+ = 505.5 | 0.19 (2H, d, J = 4.7 Hz), 0.41-0.80 (4H, m), 0.80-0.99 (2H, m), 1.06-1.60 (6H, m), 1.61-1.93 (4H, m), 2.18-2.30 (2H, m), 2.30-2.45 (2H, m), 2.48 (2H, d, J = 6.7 Hz), 2.91 (2H, t, J = 6.4 Hz), 3.16-3.30 (2H, m), 3.68 (3H, s), 3.78 (1H, d, J = 14.6 Hz), 5.54 (1H, d, J = 14.6 Hz), 6.42-6.74 (1H, m), 6.95-7.18 (4H, m), 7.20-7.30 (2H, m) |
| 230 | Cl | 0 | $CH_2CH_2C(CH_3)_3$ | (APCI)+: [M + H]+ = 569.5 | 0.42-0.82 (2H, m), 0.86 (9H, s), 1.19-2.14 (17H, m), 2.28-2.34 (2H, m), 2.86-3.00 (4H, m), 3.65 (3H, s), 3.76 (1H, d, J = 14.6 Hz), 5.52 (1H, d, J = 14.6 Hz), 6.01-6.03 (1H, m), 6.94 (1H, dd, J = 2.2, 8.4 Hz), 7.03 (1H, d, J = 8.4 Hz), 7.10-7.11 (2H, m), 7.72 (1H, s) |
| 231 | Cl | 0 | cyclopropylmethyl | (APCI)+: [M + H]+ = 539.4, 541.4 | d4-MeOH: 0.37-0.43 (2H, m), 0.57-0.80 (4H, m), 1.05-2.01 (12H, m), 2.15-2.24 (1H, m), 2.44-2.52 (1H, m), 2.91-3.04 (6H, m), 3.61-3.69 (2H, m), 3.71 (3H, s), 3.80 (1H, d, J = 14.6 Hz), 5.43 (1H, d, J = 14.6 Hz), 7.03 (1H, dd, J = 2.2, 8.4 Hz), 7.15 (1H, s), 7.20 (1H, d, J = 8.4 Hz), 7.33 (1H, d, J = 2.2 Hz) |
| 232 | Me | 0 | $CH_2CH_2C(CH_3)_3$ | (APCI)+: [M + H]+ = 549.5 | 0.51-0.82 (2H, m), 0.86 (9H, s), 1.12-1.84 (13H, m), 1.91-2.11 (4H, m), 2.20-2.36 (5H, m), 2.94-3.02 (4H, m), 3.66 (3H, s), 3.75 (1H, d, J = 14.6 Hz), 5.55 (1H, d, J = 14.6 Hz), 6.53 (1H, s), 6.80 (1H, d, J = 7.9 Hz), 6.85 (1H, s), 6.97 (1H, d, J = 7.9 Hz), 7.12 (1H, s) |
| 233 | Me | 0 | cyclopropylmethyl | (APCI)+: [M + H]+ = 519.4 | d4-MeOH: 0.39-0.76 (6H, m), 1.05-2.02 (16H, m), 2.20-2.26 (1H, m), 2.34 (3H, s), 2.44-2.50 (1H, m), 2.88-3.00 (4H, m), 3.69 (3H, s), 3.75 (1H, d, J = 14.6 Hz), 5.43 (1H, d, J = 14.6 Hz), 6.86-6.89 (1H, m), 7.03-7.13 (3H, m), 7.79 (1H, t, J = 5.9 Hz), 7.85 (1H, s) |

233

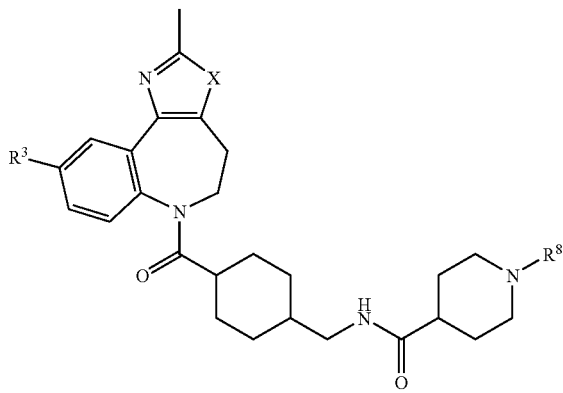

| Compound number | R³ | R⁸ | X | MS | ¹H NMR: δ (ppm) |
|---|---|---|---|---|---|
| 234 | Cl | CH₂CH₂C(CH₃)₃ | S | 585.5, 587.6 | 0.50-0.56 (1H, m), 0.88 (9H, s), 1.11-1.19 (2H, m), 1.35-1.49 (4H, m), 1.56-2.10 (9H, m), 2.28-2.34 (3H, m), 2.67 (3H, s), 2.83-3.12 (6H, m), 3.42-3.60 (2H, m), 4.76-4.83 (1H, m), 5.39-5.44 (1H, m), 7.10 (1H, d, J = 8.4 Hz), 7.26 (1H, dd, J = 2.5, 8.4 Hz), 8.38 (1H, d, J = 2.5 Hz) |

234
-continued

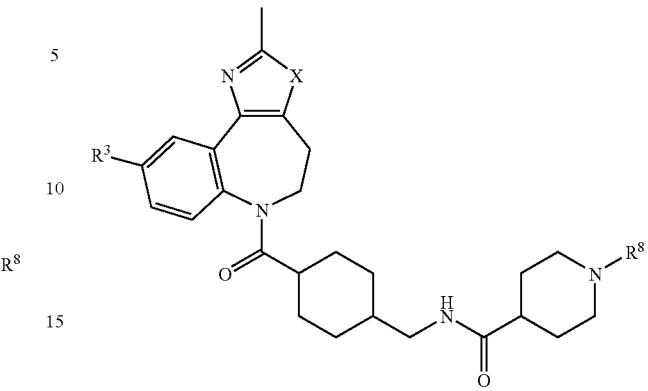

| Compound number | R³ | R⁸ | X | MS | ¹H NMR: δ (ppm) |
|---|---|---|---|---|---|
| 235 | Me | CH₂CH₂C(CH₃)₃ | S | 565.4 | 0.42-0.62 (1H, m), 0.72-0.84 (1H, m), 0.87 (9H, s), 1.08-1.20 (2H, m), 1.30-1.50 (4H, m), 1.56-1.75 (6H, m), 1.75-1.95 (5H, m), 1.96-2.10 (1H, m), 2.25-2.35 (1H, m), 2.43 (3H, s), 2.69 (3H, s), 2.85-3.05 (6H, m), 3.40-3.65 (1H, m), 4.75-4.85 (1H, m), 5.35-5.45 (1H, m), 7.00-7.15 (2H, m), 8.15 (1H, s) |

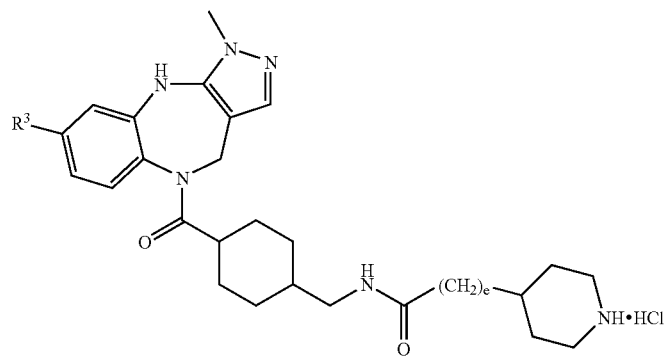

| Compound number | R³ | e | MS | ¹H NMR: δ (ppm) |
|---|---|---|---|---|
| 236 E17 | Me | 1 | (APCI)+: [M + H]+ = 579.5 | 0.44-0.68 (1H, m), 0.69-0.87 (1H, m), 1.19-2.32 (15H, m), 2.40 (3H, s), 2.88-3.03 (4H, m), 3.28-3.43 (4H, m), 3.52-3.75 (1H, m), 3.84 (1H, d, J = 14.6 Hz), 3.96 (3H, s), 5.50 (1H, d, J = 14.6 Hz), 7.07 (1H, d, J = 7.9 Hz), 7.22 (1H, d, J = 7.9 Hz), 7.28 (1H, s), 7.96 (1H, s) |
| 237 | Cl | 2 | (ESI)+: [M + H]+ = 513.4, 515.4 | CD₃OD δ 0.54-0.70 (1H, m), 0.72-0.89 (1H, m), 1.12-1.98 (14H, m), 2.20-2.29 (3H, m), 2.89-2.98 (4H, m), 3.30-3.39 (2H, m), 3.87 (1H, d, J = 14.6 Hz), 3.98 (3H, s), 5.51 (1H, d, J = 14.6 Hz), 7.24 (1H, dd, J = 2.2, 8.4 Hz), 7.37 (1H, d, J = 8.4 Hz), 7.56 (1H, d, J = 2.2 Hz), 7.91 (1H, s), 8.00 (1H, s) |

-continued
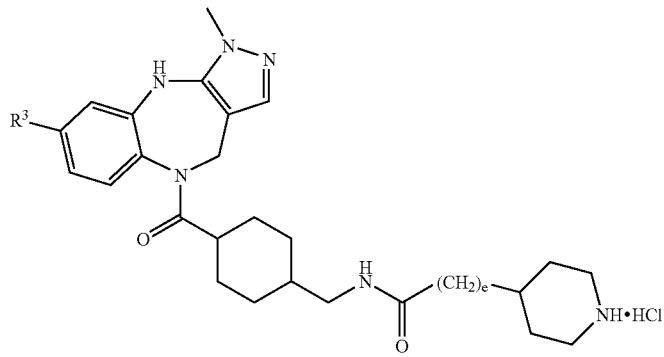
| Compound number | R³ | e | MS | ¹H NMR: δ (ppm) |
|---|---|---|---|---|
| 238 | H | 0 | (ESI)+: [M + H]+ = 451.3 | CD₃OD δ 0.44-0.63 (1H, m), 0.66-0.83 (1H, m), 1.10-2.03 (11H, m), 2.21-2.31 (1H, m), 2.47-2.61 (1H, m), 2.89-2.92 (2H, m), 2.98-3.14 (2H, m), 3.34-3.42 (2H, m), 3.87 (1H, d, J = 14.6 Hz), 3.99 (3H, s), 5.53 (1H, d, J = 14.6 Hz), 7.24 (1H, dd, J = 2.0, 8.4 Hz), 7.32 (1H, d, J = 8.4 Hz), 7.38-7.53 (2H, m), 7.98 (1H, s) |
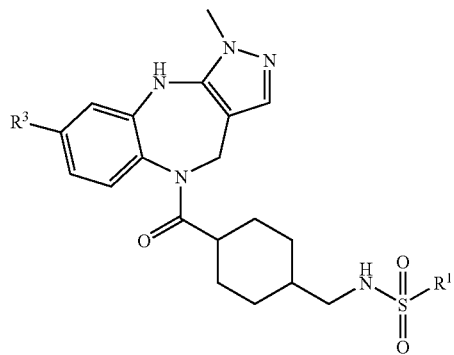
| Compound number | R¹ | R³ | MS (ESI)+: [M + H]+ = | ¹H NMR: δ (ppm) |
|---|---|---|---|---|
| 239 E18 | Me | Me | 432.1 | |
| 240 | CH(CH₃)₂ | Me | 460.2 | |
| 241 | benzyl | Me | 508.2 | |
| 242 | phenyl | Me | (494.2 | |
| 243 | 2,4-dichlorophenyl | Me | 562.2 | |

-continued
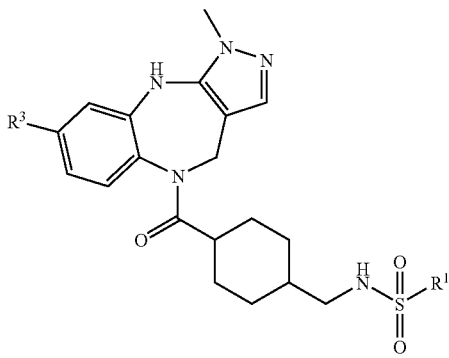
| Compound number | R¹ | R³ | MS (ESI)+: [M + H]+ = | ¹H NMR: δ (ppm) |
|---|---|---|---|---|
| 244 | 4-Cl-C₆H₄ | Me | 528.2, 530.2 | |
| 245 | 3-Cl-C₆H₄ | Me | 528.2, 530.2 | |
| 246 | 2-Cl-C₆H₄ | Me | 528.2, 530.2 | |
| 247 | 4-MeO-C₆H₄ | Me | 524.2 | |
| 248 | 4-Me-C₆H₄ | Me | 508.7 | 0.50-0.80 (2H, m), 1.20-1.80 (7H, m), 2.05-2.20 (1H, m), 2.35 (3H, s), 2.40 (3H, s), 2.67 (2H, t, J = 6.4 Hz), 3.71 (3H, s), 3.75 (1H, d, J = 14.5 Hz), 4.29 (1H, t, J = 6.5 Hz), 6.59 (1H, d, J = 14.5 Hz), 5.71 (1H, s), 6.79 (1H, s), 6.79-6.89 (1H, m), 6.99 (1H, d, J = 7.9 Hz), 7.23-7.31 (2H, m), 7.66 (2H, d, J = 8.2 Hz) |
| 249 | 4-CN-C₆H₄ | Me | 519.7 | |
| 250 | 4-CF₃-C₆H₄ | Me | 562.2 | |
| 251 | 4-AcNH-C₆H₄ | Me | 551.3 | |

-continued

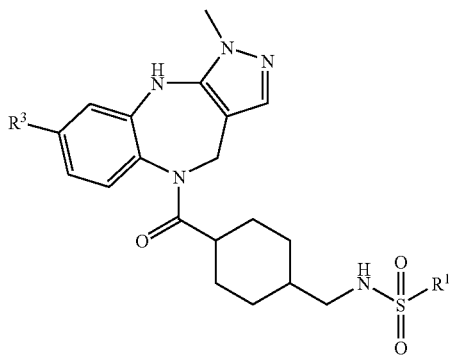

| Compound number | R¹ | R³ | MS (ESI)+: [M + H]+ = | ¹H NMR: δ (ppm) |
|---|---|---|---|---|
| 252 | (5-chloro-thien-2-yl) | Me | 534.1, 536.1 | |
| 253 | (1-methyl-imidazol-4-yl) | Me | 498.2 | |
| 254 | CH₂CF₃ | Me | 500.2 | |
| 255 | (2-chloro-3-bromo-pyridin-5-yl) | Me | 607.1, 609.1 | |
| 256 | (5-methoxycarbonyl-furan-2-yl) | Me | 542.2 | |
| 257 | CH₂CH₃ | Me | 446.1 | 0.55-0.90 (2H, m), 1.20-1.90 (10H, m) 2.08-2.20 (1H, m), 2.36 (3H, s), 2.86 (2H, t J = 6.0 Hz) 2.95-3.15 (2H, m), 3.71 (3H, s), 3.75 (1H, d, J = 14.6 Hz), 4.12-4.16 (1H, m), 5.60 (1H, d, J = 14.6 Hz), 5.77 (1H, s), 6.80 (1H, s), 6.83 (1H, d, J = 7.9 Hz), 7.01 (61H, d, J = 7.9 Hz), 7.17 (1H, s) |
| 258 | CH₂CH₂CH₃ | Me | 460.6 | |
| 259 | CH₂CH₂CH₂CH₃ | Me | 474.2 | |
| 260 | CH₂CH₂CH₂CH₃ | Cl | 494.2, 496.2 | 0.55-0.85 (2H, m), 0.92 (3H, t, J = 7.3 Hz), 1.25-1.85 (11H, m), 2.05-2.20 (1H, m), 2.80-3.00 (4H, m), 3.72 (3H, s), 3.76 (1H, d, J = 14.6 Hz), 4.10-4.20 (1H, m), 5.59 (1H, d, J = 14.6 Hz), 5.91 (1H, s), 7.00-7.10 (3H, m), 7.19 (1H, s) |
| 261 | (4-methylphenyl) | Cl | 528.1, 530.1 | 0.50-0.80 (2H, m), 1.20-1.80 (7H, m), 2.00-2.15 (1H, m), 2.40 (3H, s), 2.60-2.75 (2H, m), 3.71 (3H, s), 3.75 (1H, d, J = 14.6 Hz), 4.64 (1H, t, J = 6.5 Hz), 5.57 (1H, d, J = 14.6 Hz), 6.29 (1H, s), 6.95-7.10 (3H, m), 7.16 (1H, s), 7.25-7.35 (2H, m), 7.71 (2H, d, J = 8.2 Hz) |

-continued
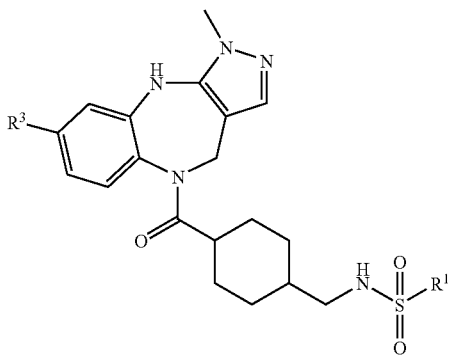
| Compound number | R¹ | R³ | MS (ESI)+: [M + H]+ = | ¹H NMR: δ (ppm) |
|---|---|---|---|---|
| 262 | isobutyl | H | 446.2 | 0.50-0.80 (1H, m), 1.30 (6H, d, J = 6.7 Hz), 1.32-1.48 (4H, m), 1.50-1.90 (5H, m), 2.10-2.20 (1H, m)2.75-3.00 (2H, m), 3.72 (3H, s), 3.81 (1H, d, J = 14.6 Hz), 4.25-4.45 (1H, m), 5.62 (1H, d, J = 14.6 Hz), 6.21 (1H, s), 6.95-7.10 (2H, m), 7.10-7.20 (2H, m), 7.25-7.30 (1H, m) |
| 263 | 4-methoxyphenyl | H | 510.1 | 0.45-0.75 (1H, m), 1.20-1.85 (8H, m), 2.00-2.15 (1H, m), 2.60-2.70 (2H, m), 3.73 (3H, s), 3.79 (1H, d, J = 14.6 Hz), 3.84 (3H, s), 4.30-4.40 (1H, m), 5.60 (1H, d, J = 14.6 Hz), 5.90 (1H, s), 6.90-7.10 (4H, m), 7.10-7.20 (2H, m), 7.25-7.30 (1H, m), 7.70-7.80 (2H, m) |
| Compound number | R¹² | MS |
|---|---|---|
| 264 E19 | Me | (ESI)+: [M + H]+ = 557.4 |
| 265 | CH(CH₃)₂ | (ESI)+: [M + H]+ = 585.4 |
| 266 | benzyl | (ESI)+: [M + H]+ = 633.6 |
-continued
| Compound number | R¹² | MS |
|---|---|---|
| 267 | phenyl | (ESI)+: [M + H]+ = 619.5 |

TABLE 243-continued

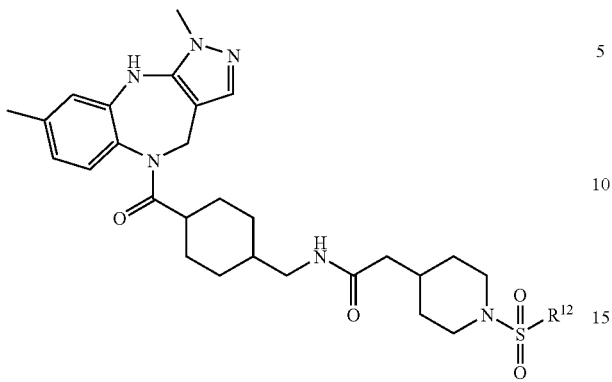

| Compound number | R12 | MS |
|---|---|---|
| 268 | 2,4-dichlorophenyl | (ESI)+: [M + H]+ = 687.4, 689.4 |
| 269 | 4-chlorophenyl | (ESI)+: [M + H]+ = 653.4, 655.4 |
| 270 | 3-chlorophenyl | (ESI)+: [M + H]+ = 653.5, 655.5 |
| 271 | 2-chlorophenyl | (ESI)+: [M + H]+ = 653.5, 655.5 |
| 272 | 4-methoxyphenyl | (ESI)+: [M + H]+ = 649.6 |
| 273 | 4-methylphenyl | (ESI)+: [M + H]+ = 633.5 |
| 274 | 4-cyanophenyl | (ESI)+: [M + H]+ = 644.5 |
| 275 | 4-trifluoromethylphenyl | (ESI)+: [M + H]+ = 687.5 |
| 276 | 4-acetamidophenyl | (ESI)+: [M + H]+ = 676.5 |

TABLE 244-continued

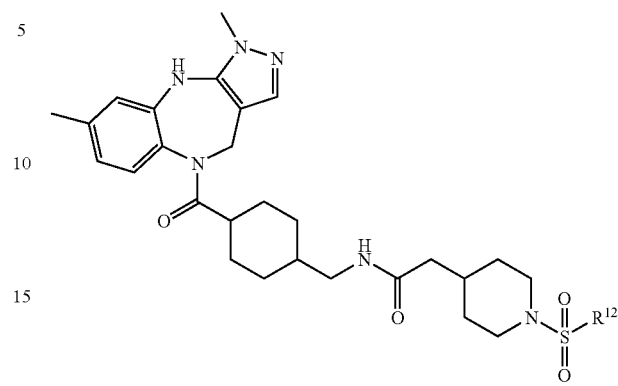

| Compound number | R12 | MS |
|---|---|---|
| 277 | 5-chlorothien-2-yl | (ESI)+: [M + H]+ = 659.4, 661.4 |
| 278 | 1-methylimidazol-4-yl | (ESI)+: [M + H]+ = 623.5 |
| 279 | $CH_2CF_3$ | (ESI)+: [M + H]+ = 625.5 |
| 280 | 2-chloro-3-bromopyridin-5-yl | (ESI)+: [M + H]+ = 732.4, 734.4 |
| 281 | 5-(methoxycarbonyl)furan-2-yl | (ESI)+: [M + H]+ = 667.5 |
| 282 | $CH_2CH_3$ | (ESI)+: [M + H]+ = 571.4 |
| 283 | $CH_2CH_2CH_3$ | (ESI)+: [M + H]+ = 585.5 |
| 284 | $CH_2CH_2CH_2CH_3$ | (ESI)+: [M + H]+ = 599.5 |

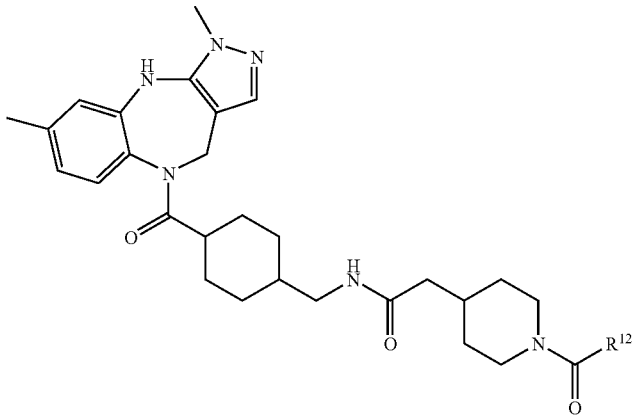
| Compound number | R¹² | MS |
|---|---|---|
| 285 E20 | Me | (ESI)+: [M + H]+ = 521.5 |
| 286 | phenyl | (ESI)+: [M + H]+ = 583.4 |
| 287 | 3-chlorophenyl | (ESI)+: [M + H]+ = 617.5, 619.5 |
| 288 | 4-chlorophenyl | (ESI)+: [M + H]+ = 617.5, 619.5 |
| 289 | 2-chlorophenyl | (ESI)+: [M + H]+ = 617.3, 619.3 |
| 290 | 4-methoxyphenyl | (ESI)+: [M + H]+ = 613.5 |
| 291 | 2-methylphenyl | (ESI)+: [M + H]+ = 597.5 |
| 292 | 2-chloropyridin-3-yl | (ESI)+: [M + H]+ = 618.5, 620.5 |
| 293 | pyridin-4-yl | (ESI)+: [M + H]+ = 584.4 |
| 294 | thiophen-2-yl | (ESI)+: [M + H]+ = 589.3 |

-continued
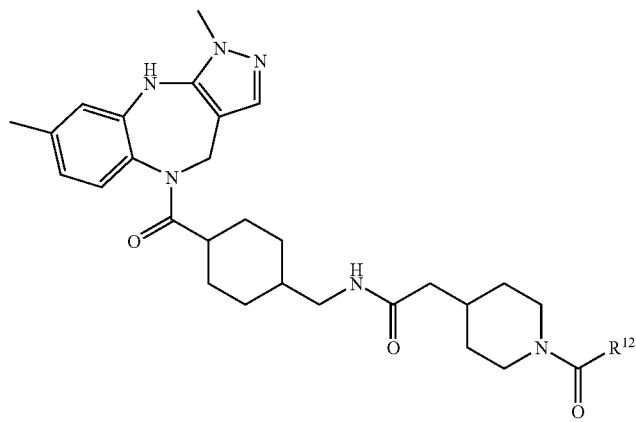
| Compound number | R¹² | MS |
|---|---|---|
| 295 | 3-chloro-thiophen-2-yl | (ESI)+: [M + H]+ = 623.5, 625.5 |
| 296 | thiophen-3-yl | (ESI)+: [M + H]+ = 589.2 |
| 297 | 2,5-dimethylfuran-3-yl | (ESI)+: [M + H]+ = 601.5 |
| 298 | furan-2-yl | (ESI)+: [M + H]+ = 573.4 |
| 299 | isoxazol-5-yl | (ESI)+: [M + H]+ = 574.4 |
| 300 | 5-methyl-2-phenyl-2H-1,2,3-triazol-4-yl | (ESI)+: [M + H]+ = 664.6 |
| 301 | $CH_2CH_3$ | (ESI)+: [M + H]+ = 535.3 |
| 302 | $CH_2CH_2CH_3$ | (ESI)+: [M + H]+ = 549.4 |
| 303 | cyclopropyl | (ESI)+: [M + H]+ = 547.4 |
| 304 | $C(CH_3)_3$ | (ESI)+: [M + H]+ = 563.5 |
| 305 | cyclopentylmethyl | (ESI)+: [M + H]+ = 589.5 |
| 306 | $CH_2(CH_2)_3CH_3$ | (ESI)+: [M + H]+ = 577.5 |
| 307 | $CH(CH_2CH_3)CH_2CH_2CH_3$ | (ESI)+: [M + H]+ = 605.6 |

-continued
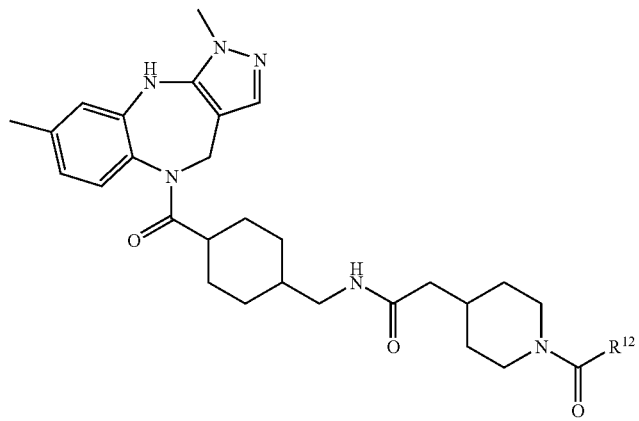
| Compound number | R$^{12}$ | MS |
|---|---|---|
| 308 | 2,5-dimethoxyphenyl | (ESI)+: [M + H]+ = 657.6 |
| 309 | benzyl | (ESI)+: [M + H]+ = 597.4 |
| 310 | phenethyl | (ESI)+: [M + H]+ = 611.5 |
| 311 | 2-phenylcyclopropyl | (ESI)+: [M + H]+ = 623.6 |
| 312 | 2-thienylmethyl | (ESI)+: [M + H]+ = 603.5 |
| 313 | phenoxymethyl | (ESI)+: [M + H]+ = 613.5 |
| 314 | benzyloxymethyl | (ESI)+: [M + H]+ = 627.6 |
| 315 | CH$_2$CH$_2$CO$_2$CH$_3$ | (ESI)+: [M + H]+ = 593.4 |
| 316 | CH$_2$(CH$_2$)$_2$CO$_2$CH$_2$CH$_3$ | (ESI)+: [M + H]+ = 621.6 |

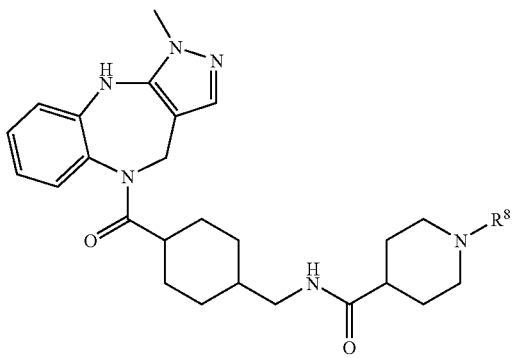
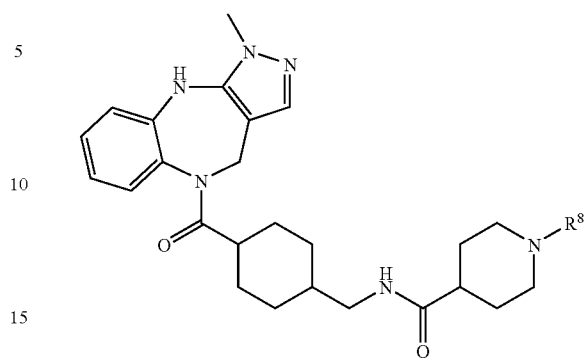

| Compound number | R⁸ | MS |
|---|---|---|
| 317 E21 | | (ESI)+: [M + H]+ = 507.4 |
| 318 | CH₂CH₂CH₃ | (ESI)+: [M + H]+ = 493.5 |
| 319 | benzyl | (ESI)+: [M + H]+ = 541.5 |
| 320 | phenethyl | (ESI)+: [M + H]+ = 555.5 |
| 321 | 2-thienylmethyl | (ESI)+: [M + H]+ = 547.4 |
| 322 | CH₂CH₂CH₂CH₂CH₃ | (ESI)+: [M + H]+ = 521.5 |
| 323 | 3-phenylpropyl | (ESI)+: [M + H]+ = 569.4 |
| 324 | CH₂CH₂CH(CH₃)₂ | (ESI)+: [M + H]+ = 521.5 |
| 325 | 2-pyridylmethyl | (ESI)+: [M + H]+ = 542.4 |
| 326 | 3-thienylmethyl | (ESI)+: [M + H]+ = 547.4 |
| 327 | CH₂CH₂CF₃ | (ESI)+: [M + H]+ = 547.3 |
| 328 | cyclohexenylmethyl | (ESI)+: [M + H]+ = 545.5 |
| 329 | CH₂CH₂OH | (ESI)+: [M + H]+ = 495.6 |
| 330 | 3-methylbenzyl | (ESI)+: [M + H]+ = 555.5 |

| Compound number | R⁸ | MS |
|---|---|---|
| 331 | 2-methylbenzyl | (ESI)+: [M + H]+ = 555.3 |
| 332 | 2-cyanobenzyl | (ESI)+: [M + H]+ = 566.4 |
| 333 | 3-cyanobenzyl | (ESI)+: [M + H]+ = 566.4 |
| 334 | 4-cyanobenzyl | (ESI)+: [M + H]+ = 566.5 |
| 335 | pentafluorobenzyl | (ESI)+: [M + H]+ = 631.5 |
| 336 | 3,5-dichlorobenzyl | (ESI)+: [M + H]+ = 609.5 |
| 337 | 3,4,5-trimethoxybenzyl | (ESI)+: [M + H]+ = 631.6 |

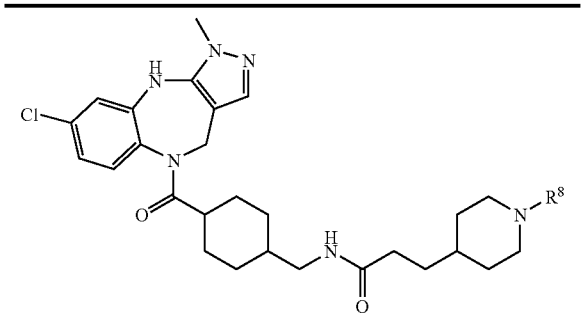

| Compound | R⁸ | MS |
|---|---|---|
| 338 E22 | | (ESI)+: [M + H]+ = 597.6, 599.6 |
| 339 | CH₂CH₂CH₃ | (ESI)+: [M + H]+ = 555.6, 557.6 |
| 340 | CH₂(CH₂)₂CN | (ESI)+: [M + H]+ = 580.7, 582.7 |
| 341 | phenyl C(O)CH₂CH₂- | (ESI)+: [M + H]+ = 631.8, 633.8 |
| 342 | cyclohexyl-CH₂CH₂- | (ESI)+: [M + H]+ = 623.6, 625.6 |
| 343 | 3-F-benzyl | (ESI)+: [M + H]+ = 621.6, 623.6 |
| 344 | 4-tBu-benzyl | (ESI)+: [M + H]+ = 659.8, 661.8 |
| 345 | 4-OCF₃-benzyl | (ESI)+: [M + H]+ = 687.7, 689.7 |
| 346 | 4-CO₂Me-benzyl | (ESI)+: [M + H]+ = 661.8, 663.8 |
| 347 | benzyl | (ESI)+: [M + H]+ = 603.7, 605.7 |
| 348 | CH₂CH₂OH | (ESI)+: [M + H]+ = 557.5, 559.5 |
| 349 | CH₂CO₂CH(CH₃)₂ | (ESI)+: [M + H]+ = 613.6, 615.6 |
| 350 | CH₂CH₂CH(CH₃)₂ | (ESI)+: [M + H]+ = 571.6, 573.6 |
| 351 | CH₂CH₂CH₂OH | (ESI)+: [M + H]+ = 571.6, 573.6 |
| 352 | CH₂CN | (ESI)+: [M + H]+ = 552.6, 554.6 |
| 353 | 3-NO₂-benzyl | (ESI)+: [M + H]+ = 648.7, 650.7 |

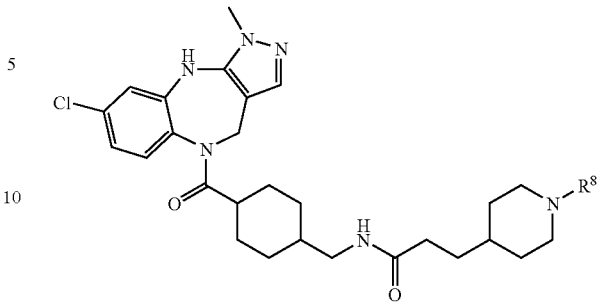

-continued

| Compound | R⁸ | MS |
|---|---|---|
| 354 | cyclopropylmethyl | (ESI)+: [M + H]+ = 567.7, 569.6 |
| 355 | naphthalen-2-ylmethyl | (ESI)+: [M + H]+ = 653.8, 655.8 |
| 356 | allyl | (ESI)+: [M + H]+ = 553.6, 555.6 |
| 357 | cinnamyl | (ESI)+: [M + H]+ = 629.8, 631.8 |
| 358 | biphenyl-2-ylmethyl | (ESI)+: [M + H]+ = 679.8, 681.8 |
| 359 | (E)-CH₂CH=CHCO₂Me | (ESI)+: [M + H]+ = 611.6, 613.6 |
| 360 | 2-CN-benzyl | (ESI)+: [M + H]+ = 628.7, 630.7 |
| 361 | CH₂COC(CH₃)₃ | (ESI)+: [M + H]+ = 611.7, 613.7 |
| 362 | CH₂CONH₂ | (ESI)+: [M + H]+ = 570.6, 572.6 |
| 363 | (5-NO₂-furan-2-yl)methyl | (ESI)+: [M + H]+ = 638.8, 640.8 |
| 364 | benzo[c][1,2,5]oxadiazol-5-ylmethyl | (ESI)+: [M + H]+ = 645.8, 647.8 |

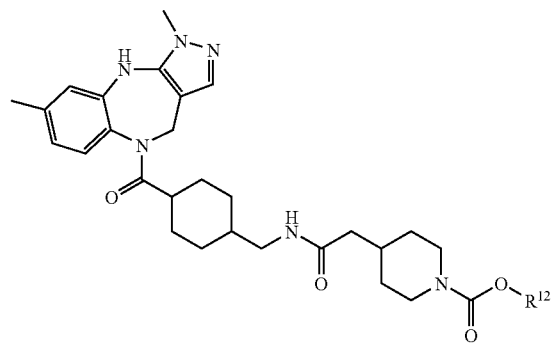

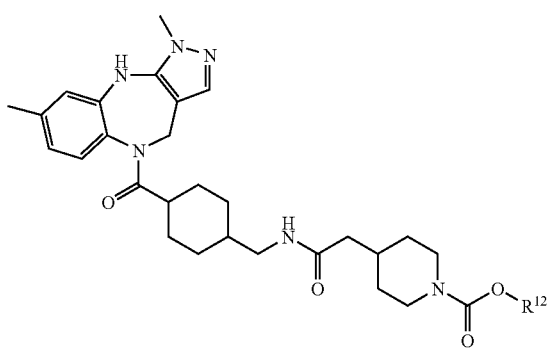

| Compound number | R12 | MS |
|---|---|---|
| 365 E23 | 4-nitrobenzyl | (ESI)+: [M + H]+ = 658.5 |
| 366 | 2-chlorobenzyl | (ESI)+: [M + H]+ = 647.5 |
| 367 | menthyl (isopropyl-methylcyclohexyl) | (ESI)+: [M + H]+ = 661.7 |
| 368 | 4-nitrophenyl | (ESI)+: [M + H]+ = 644.5 |
| 369 | allyl | (ESI)+: [M + H]+ = 563.5 |
| 370 | 4-methoxyphenyl | (ESI)+: [M + H]+ = 629.6 |
| 371 | propargyl | (ESI)+: [M + H]+ = 561.4 |
| 372 | phenyl | (ESI)+: [M + H]+ = 599.4 |

| Compound number | R12 | MS |
|---|---|---|
| 373 | 4-chlorophenyl | (ESI)+: [M + H]+ = 633.5 |
| 374 | benzyl | (ESI)+: [M + H]+ = 613.5 |
| 375 | isobutyl | (ESI)+: [M + H]+ = 579.5 |
| 376 | ethyl | (ESI)+: [M + H]+ = 551.5 |
| 377 | 2,2-dimethyl-1,1,1-trichloroethyl | (ESI)+: [M + H]+ = 683.5 |
| 378 | CH3 | (ESI)+: [M + H]+ = 683.5 |
| 379 | vinyl | (ESI)+: [M + H]+ = 549.4 |
| 380 | 2-(benzyloxy)ethyl | (ESI)+: [M + H]+ = 657.6 |

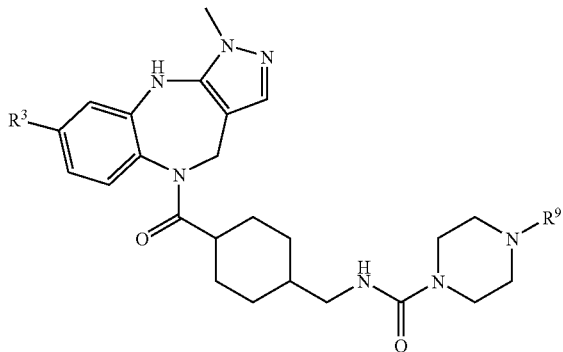

| Compound number | R³ | R⁹ | MS | ¹H NMR: δ(ppm) |
|---|---|---|---|---|
| 381 E24 | Me | CH₂CH₂C(CH₃)₃ | (APCI)+: [M + H]+ = 550.4 | 0.41-0.82(2 H, m), 0.86 (9 H, s), 1.33-1.50(7 H, m), 1.73(2 H, m), 2.12(1 H, m), 2.27-2.39(6 H, m), 2.29 (3 H, s), 2.90-2.93(2 H, m), 3.31-3.35(4 H, m), 3.64 (3 H, s), 3.74(1 H, d, J = 14.6 Hz), 4.78(1 H, m), 5.54(1 H, d, J = 14.6 Hz), 6.77(1 H, dd, J = 1.0, 8.0 Hz), 6.88(1 H, s), 6.95 (1 H, d, J = 8.0 Hz), 7.03(1 H, d, J = 1.0 Hz), 7.11(1 H, s) |
| 382 | Me | CH₂CH₂CH₂SCH₃ | (ESI)+: [M + H]+ = 554.6 | — |
| 383 | Me | CH₂CH₂OCH₃ | (ESI)+: [M + H]+ = 524.7 | — |
| 384 | Me | CH₂CH₂CH₂CF₃ | (ESI)+: [M + H]+ = 576.6 | — |
| 385 | Me | CH₂CH₂N(CH₂CH₃)₂ | (ESI)+: [M + H]+ = 565.6 | — |
| 386 | Me | CH₂CH₂CH₂F | (ESI)+: [M + H]+ = 526.6 | — |
| 387 | Me | CH₂CH₂CH₂OH | (ESI)+: [M + H]+ = 524.6 | — |
| 388 | Me | CH₂C(CH₃)₃ | (ESI)+: [M + H]+ = 536.5 | 0.55-0.84(2 H, m), 0.84 (9 H, s), 1.18-1.75(7 H, m), 2.04-2.16(3 H, m), 2.34 (3 H, s), 2.44-2.48(4 H, m), 2.93-2.97(2 H, m), 3.26-3.29(4 H, m), 3.70(3 H, s), 3.75(1 H, d, J = 14.6 Hz), 4.35-4.39(1 H, bs), 5.58 (1 H, d, J = 14.6 Hz), 5.84 (1 H, s), 6.79-6.83(2 H, m), 6.98(1 H, m), 7.16(1 H, s) |
| 389 | Me | CH₂-cyclopentyl | (APCI)+: [M + H]+ = 548.5 | 0.46-0.71(2 H, m), 1.11-1.27(4 H, m), 1.37-1.59 (7 H, m), 1.69-1.78(4 H, m), 1.95-2.17(2 H, m), 2.21 (2 H, d, J = 7.4 Hz), 2.30(3 H, s), 2.32-2.36(4 H, m), 2.85-2.98(2 H, m), 3.29-3.32 (4 H, m), 3.64(3 H, s), 3.74 (1 H, d, J = 14.6 Hz), 4.67-4.71(1 H, m), 5.55(1 H, d, J = 14.6 Hz), 6.78(1 H, d, J = 8.0 Hz), 6.87-6.88(2 H, m), 6.95(1 H, d, J = 8.0 Hz), 7.11(1 H, s) |

-continued
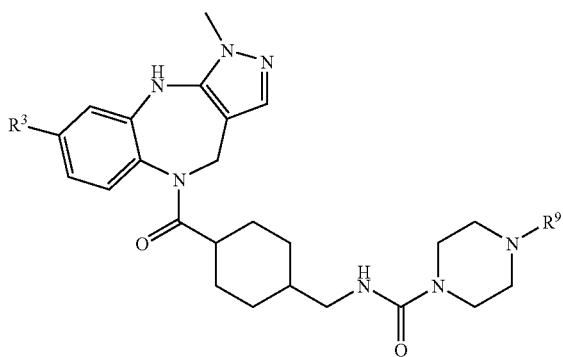
| Compound number | R³ | R⁹ | MS | ¹H NMR: δ(ppm) |
|---|---|---|---|---|
| 390 | Me | CH₂CH₂CH(CH₃)₂ | (APCI)+: [M + H]+ = 536.5 | 0.48-0.72(2 H, m), 0.86 (6 H, t, J = 6.4 Hz), 1.18-1.38 (5 H, m), 1.46-1.60(3 H, m), 1.68-1.79(2 H, m), 2.07-2.18(1 H, m), 2.28-2.38 (9 H, m), 2.88-2.96(2 H, m), 3.31-3.34(4 H, m), 3.65 (3 H, s), 3.75(1 H, d, J = 14.6 Hz), 4.71-4.75(1 H, m), 5.55(1 H, d, J = 14.6 Hz), 6.78(1 H, d, J = 7.9 Hz), 6.88 (1 H, s), 6.96(1 H, d, J = 7.9 Hz), 7.04(1 H, dd, J = 1.2, 7.9 Hz), 7.12(1 H, s) |
| 391 | Me | CH₂CH(CH₃)₂ | (APCI)+: [M + H]+ = 522.4 | 0.46-0.71(2 H, m), 0.85 (6 H, t, J = 6.4 Hz), 1.19-1.27 (2 H, m), 1.37-1.54(3 H, m), 1.68-1.78(3 H, m), 2.04 (2 H, d, J = 7.4 Hz), 2.05-2.17 (1 H, m) 2.29(3 H, s), 2.29-2.33(4 H, m), 2.87-2.98 (2 H, m), 3.28-3.32(4 H, m), 3.64(3 H, s), 3.74(1 H, d, J = 14.6 Hz), 4.68-4.72(1 H, m), 5.55(1 H, d, J = 14.6 Hz), 6.78(1 H, d, J = 8.0 Hz), 6.88 (1 H, s), 6.93(1 H, s), 6.95 (1 H, d, J = 8.0 Hz), 7.11(1 H, s) |
| 392 | Me | CH₂CH₂CH₃ | (APCI)+: [M + H]+ = 508.4 | 0.47-0.89(2 H, m), 0.87 (3 H, t, J = 7.2 Hz), 1.18-1.27 (2 H, m), 1.37-1.54(5 H, m), 1.68-1.78(2 H, m), 2.07-2.17(1 H, m), 2.23-2.26 (2 H, m), 2.29(3 H, s), 2.34-2.38(4 H, m), 2.87-2.97 (2 H, m), 3.30-3.34(4 H, m), 3.64(3 H, s), 3.74(1 H, d, J = 14.6 Hz), 4.72-4.76(1 H, m), 5.54(1 H, d, J = 14.6 Hz), 6.78(1 H, d, J = 8.0 Hz) 6.87-6.88(2 H, m), 6.95(1 H, d, J = 8.0 Hz), 7.11(1 H, s) |

-continued

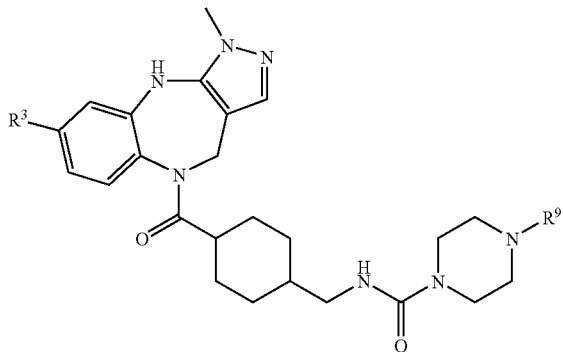

| Compound number | R³ | R⁹ | MS | ¹H NMR: δ(ppm) |
|---|---|---|---|---|
| 393 | Cl | cyclopentylmethyl | (APCI)+: [M + H]+ = 568.4, 570.4 | 0.41-0.56(1 H, m), 0.60-0.75(1 H, m), 0.78(1 H, d, J = 6.4 Hz), 0.94-1.14(2 H, m), 1.14-1.55(9 H, m), 1.57-1.72(4 H, m), 1.83-2.00(2 H, m), 2.18(2 H, d, J = 6.9 Hz), 2.29(4 H, t, J = 4.9 Hz), 2.70-2.90(2 H, m), 3.22(4 H, t, J = 4.9 Hz), 3.58(3 H, s), 3.66(1 H, d, J = 14.6 Hz), 5.17(1 H, t, J = 5.4 Hz), 5.38(1 H, d, J = 14.6 Hz), 6.86(1 H, d, J = 2.2 Hz), 6.91(1 H, s), 7.03(1 H, s), 7.12(1 H, d, J = 2.2 Hz) |
| 394 | Cl | CH₂CH₂CH(CH₃)₂ | (APCI)+: [M + H]+ = 556.4, 558.4 | 0.40-0.59(1 H, m), 0.60-0.80(1 H, m), 0.86(6 H, d, J = 6.7 Hz), 1.09-1.65(9 H, m), 1.65-1.81(2 H, m), 2.01-2.17(1 H, m), 2.30-2.41(2 H, m), 2.41(4 H, t, J = 4.9 Hz) 2.92(2 H, t, J = 5.9 Hz), 3.38(4 H, t, J = 4.9 Hz), 3.70(3 H, s), 3.77(1 H, d, J = 14.6 Hz), 5.07(1 H, t, J = 5.4 Hz) 5.52 (1 H, d, J = 14.6 Hz), 6.94 (1 H, d, J = 2.2 Hz), 7.02(1 H, s), 7.12(1 H, s), 7.32(1 H, d, J = 2.2 Hz) |
| 395 | Cl | CH₂CH(CH₃)₂ | (APCI)+: [M + H]+ = 542.4, 544.4 | 0.38-0.60(1 H, m), 0.60-0.78(1 H, m), 0.82(6 H, d, J = 6.7 Hz), 1.10-1.40(2 H, m), 1.40-1.56(2 H, m), 1.63-1.80(4 H,m ), 2.03 (2 H, d, J = 7.4 Hz), 2.12(2 H, s), 2.31(4 H, t, J = 4.9 Hz), 2.85-2.94(2 H, m), 3.30 (4 H, t, J = 4.9 Hz), 3.64(3 H, s), 3.72(1 H, d, J = 14.6 Hz), 4.75(1 H, t, J = 5.7 Hz), 5.49 (1 H, d, J = 14.6 Hz), 6.93 (1 H, d, J = 2.2 Hz), 6.98(1 H, s), 7.11(1 H, s), 7.15(1 H, d, J = 2.2 Hz) |
| 396 | Cl | CH₂CH₂CH₃ | (APCI)+: [M + H]+ = 528.3, 530.3 | 0.39-0.60(1 H, m), 0.60-0.83(1 H, m), 0.88(3 H, t, J = 7.4 Hz), 1.17-1.63(9 H, m), 1.64-1.83(2 H, m), 2.00-2.15(1 H, m), 2.25-2.35(2 H, m), 2.40(4 H, t, J = 4.9 Hz), 2.90-3.00(2 H, m), 3.35(4 H, t, J = 4.9 Hz), 3.72(3 H, s), 4.59(1 H, t, J = 5.7 Hz), 5.54(1 H, d, J = 14.6 Hz), 6.90-7.04(2 H, m), 7.10-7.19(2 H, m) |

-continued

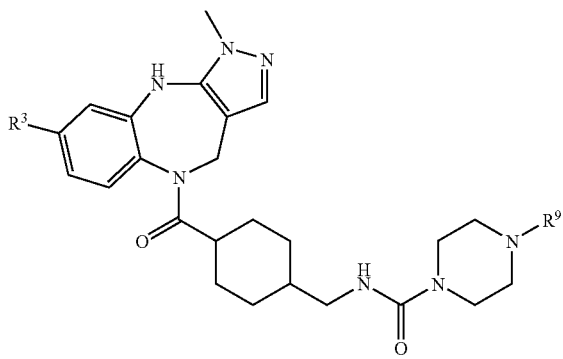

| Compound number | R³ | R⁹ | MS | ¹H NMR: δ(ppm) |
|---|---|---|---|---|
| 397 | Cl | cyclopropylmethyl | (APCI)+: [M + H]+ = 540.3, 542.3 | d₆-DMSO: 0.02-0.04(2 H, m), 0.41-0.47(2 H, m), 0.80-1.75(10 H, m), 2.03 (1 H, m), 2.14(2 H, d, J = 6.5 Hz), 2.30-2.34(4 H, m), 2.74(2 H, m), 3.20-3.28 (4 H, m), 3.67(3 H, s), 3.70 (1 H, d, J = 14.6 Hz), 5.34 (1 H, d, J = 14.6 Hz), 6.29 (1 H, m), 7.02(1 H, dd, J = 2.5, 8.0 Hz), 7.08(1 H, s), 7.25(1 H, d, J = 8.0 Hz), 7.42 (1 H, d, J = 2.5 Hz) |
| 398 | Me | cyclopropylmethyl | (APCI)+: [M + H]+ = 520.4 | 0.06-0.08(2 H, m), 0.46-0.53(2 H, m), 0.81(1 H, m), 1.13-1.79(9 H, m), 2.09 (1 H, m), 2.23(2 H, m), 2.30 (3 H, s), 2.45-2.49(4 H, m), 2.92(2 H, m), 3.33-3.37 (4 H, m), 3.65(3 H, s), 3.74 (1 H, d, J = 14.6 Hz), 4.69 (1 H, m), 5.54(1 H, d, J = 14.6 Hz), 6.67(1 H, s), 6.78(1 H, dd, J = 1.0, 8.0 Hz), 6.86(1 H, d, J = 1.0 Hz), 6.96(1 H, d, J = 8.0 Hz), 7.11(1 H, s) |
| 399 | Cl | CH₂CH₂C(CH₃)₃ | (APCI)+: [M + H]+ = 570.3, 572.3 | 0.42-0.81(2 H, m), 0.87 (9 H, s), 1.22-1.40(7 H, m), 1.74-1.78(2 H, m), 2.08 (1 H, m), 2.28-2.40(6 H, m), 2.87-2.92(2 H, m), 3.33-3.37(4 H, m), 3.63(3 H, s), 3.74(1 H, d, J = 14.6 Hz), 4.89(1 H, m), 5.51(1 H, d, J = 14.6 Hz), 6.93(1 H, dd, J = 2.2, 8.4 Hz), 7.03(1 H, d, J = 8.4 Hz), 7.10(1 H, s), 7.20(1 H, d, J = 2.2 Hz), 8.10 (1 H, s) |
| 400 | H | CH₂CH₂C(CH₃)₃ | (APCI)+: [M + H]+ = 536.4 | 0.40-0.46(1 H, m), 0.63-0.68(1 H, m), 0.82(9 H, s), 1.26-1.67(7 H, m), 1.73-1.79(2 H, m), 2.03-2.08 (1 H, m), 2.34-2.37(6 H, m), 2.82-2.94(2 H, m), 3.32 (4 H, m), 3.63(3 H, s), 3.77 (1 H, d, J = 14.6 Hz), 4.80 (1 H, t, J = 5.4 Hz), 5.56(1 H, d, J = 14.6 Hz), 6.95(1 H, m), 7.05-7.12(3 H, m), 7.19 (1 H, m), 7.32(1 H, s) |

-continued
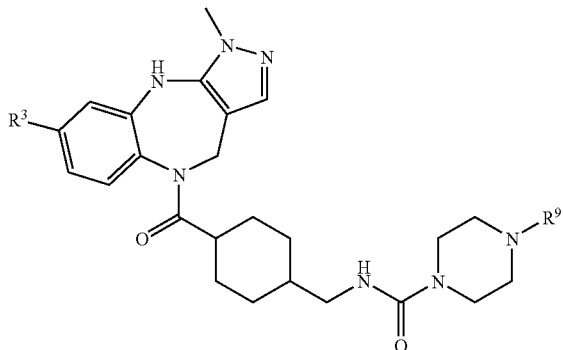
| Compound number | R³ | R⁹ | MS | ¹H NMR: δ(ppm) |
|---|---|---|---|---|
| 401 | H | ‑‑CH₂-cyclopropyl | (ESI)+: [M + H]+ = 506.3 | 0.04-0.11(2 H, m), 0.46-0.53(2 H, m), 0.61-0.72 (1 H, m), 0.72-0.89(1 H, m), 1.20-1.59(6 H, m), 1.69-1.81(2 H, m), 2.04-2.17 (1 H, m), 2.23(2 H, d, J = 6.4 Hz), 2.46(4 H, t, J = 4.9 Hz), 2.81-3.05(2 H, m), 3.35(4 H, t, J = 4.9 Hz), 3.69(3 H, s), 3.79(1 H, d, J = 14.6 Hz), 4.56(1 H, t, J = 5.6 Hz), 5.60(1 H, d, J = 14.6 Hz), 6.67(1 H, s), 6.96-7.26(4 H, m), 7.15 (1 H, s) |
| 402 | H | ‑‑CH₂-cyclobutyl | (ESI)+: [M + H]+ = 520.3 | — |
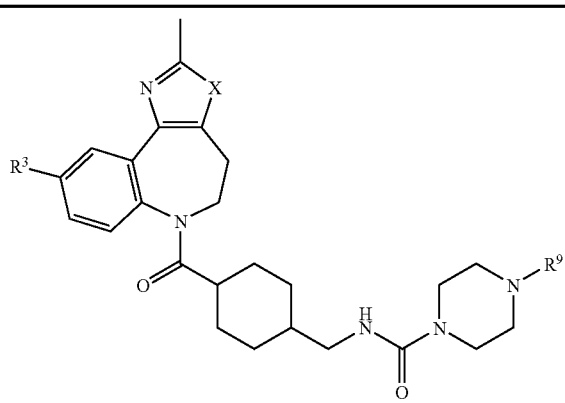
| Compound number | R³ | R⁹ | X | MS | ¹H NMR: δ(ppm) |
|---|---|---|---|---|---|
| 403 | Cl | CH₂CH₂C(CH₃)₃ | S | (ESI)⁺: [M + H]⁺ = 586.6, 588.6 | 0.49-0.60(1 H, m), 0.88(9 H, s), 1.11-1.24(2 H, m), 1.34-1.41(4 H, m), 1.47-1.87(5 H, m), 2.28-2.41(5 H, m), 2.67 (3 H, s), 2.82-3.18(4 H, m), 3.29-3.33(4 H, m), 3.37-3.59 (1 H, m), 4.34-4.38(1 H, m), 4.76-4.83(1 H, m), 7.10(1 H, dJ, =8.4 Hz), 7.25(1 H, dd, J = 2.5, 8.4 Hz), 8.38(1 H, d, J = 2.5 Hz) |

-continued

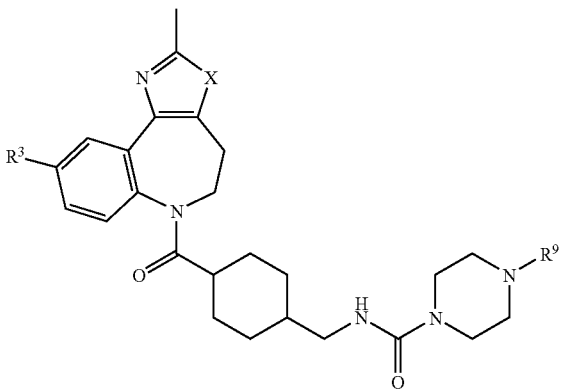

| Compound number | R³ | R⁹ | X | MS | ¹H NMR: δ(ppm) |
|---|---|---|---|---|---|
| 404 | Me | CH₂-cyclopropyl | S | (ESI)+: [M + H]+ = 536.3 | 0.05-0.15(2 H, m), 0.40-0.60 (3 H, m), 0.70-0.90(2 H, m), 1.10-1.20(2 H, m), 1.45-1.95 (5 H, m), 2.24(2 H, d, J = 6.7 Hz), 2.35-2.55(8 H, m), 2.69(3 H, s), 2.85-3.05(4 H, m), 3.30-3.40(4 H,m), 3.46-3.65(1 H, m), 4.32-4.38(1 H, m), 4.74-4.86(1 H, m), 7.00-7.15(2 H, m), 8.14(1 H, s) |

| Compound number | R³ | R⁹ | X | MS | ¹H NMR: δ(ppm) |
|---|---|---|---|---|---|
| 405 | Me | CH₂CH₂C(CH₃)₃ | NH | | 0.45-0.55(1 H, m), 0.75-0.90(10 H, m), 1.10-1.20 (1 H, m), 1.20-1.90(8 H, m), 2.30-2.45(13 H,m), 2.65-3.00(4 H,m ), 3.30-3.40(5 H, m), 4.35-4.45 (1 H, m), 4.70-4.80(1 H, m), 6.95-7.15(2 H, m), 7.95-8.05(1 H, m) |

| Compound number | R¹ | R³ | R⁸ | MS | ¹H NMR: δ(ppm) |
|---|---|---|---|---|---|
| 406 E49 | F | H | H | (APCI)+: [M + H]+ = 465.3 | d4 MeOH 2.29-2.36(2 H, m), 3.47(2 H, t, J = 7.7 Hz), 3.50-3.78(8 H, m), 4.02(3 H, s), 4.03(1 H, d), 4.16(2 H, t, J = 5.4 Hz), 5.87(1 H, d, J = 15.0 Hz), 6.88-7.05(4 H, m), 7.24-7.31(1 H, m), 7.39-7.43 (1 H, m), 8.02(1 H, s) |
| 407 | H | F | Cl | (APCI)+: [M + H]+ = 499.4, 501.4 | — |
| 408 | Me | H | H | (APCI)+: [M + H]+ = 461.4 | d4-MeOH 2.07(3 H, s), 2.25-2.35(2 H, m), 3.43-3.49(2 H, m), 3.52-3.73(8 H, m), 4.03 (3 H, s), 3.98-4.07(3 H, m), 5.90(1 H, d, J = 14.6 Hz), 6.71 (1 H, d, J = 8.9 Hz), 6.81-6.88 (2 H, m), 7.04-7.07(2 H, m), 7.22-7.29(1 H, m), 7.40(1 H, d, J = 7.7 Hz), 8.02(1 H, s) |

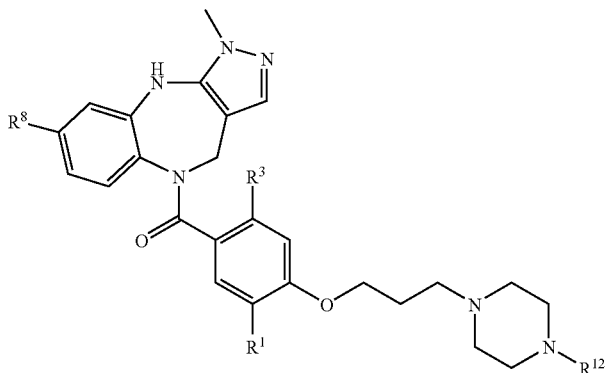
| Compound number | R¹ | R³ | R⁸ | R¹² | MS | ¹H NMR): δ(ppm) |
|---|---|---|---|---|---|---|
| 409 E50 | F | H | H | CH₂CH₂C(CH₃)₃ | (APCI)⁺: [M + H]⁺ = 549.4 | (9 H, s), 1.35-1.46 (2 H, m), 1.90-1.95 (2 H, m), 2.42-2.70 (11 H, m), 2.95-3.08(1 H, m), 3.47-3.59(1 H, m), 3.79 (3 H, s), 3.90-4.03 (2 H, m), 5.87(1 H, d, J = 1.48 Hz), 6.31 (1 H, s), 6.70(3 H, s), 6.89-7.04(3 H, m), 7.04-7.13(1 H, m), 7.21(1 H, s) |
| 410 | H | Cl | H | CH₂CH(CH₃)₂ | (APCI)+: [M + H]+ = 537.4, 539.3 | 0.84-0.88(6 H, m), 1.69-2.08(5 H, m), 2.37-2.53(10 H, m), 3.68(3 H, s), 3.83-4.03(3 H, m), 4.33-4.42(1 H, brs), 5.81( H, d, J = 14.6 Hz), 6.40-6.44(2 H, m), 6.54-7.34(5 H, m), 7.21 (1 H, s) |
| 411 | H | Cl | H | CH₂CH₂CH₃ | (APCI)+: [M + H]+ = 523.3, 525.4 | 0.84-0.90(3 H, m), 1.41-1.54(2 H, m), 1.80-2.00(2 H, m), 2.24-2.54(12 H, m), 3.68(3 H, s), 3.81-4.01(3 H,m), 4.33-4.42(1 H, brs), 5.80(1 H, d, J = 14.6 Hz), 6.40-7.34(7 H, m), 7.21 (1 H, s) |
| 412 | Me | H | Me | cyclopentylmethyl | (APCI)+: [M + H]+ = 557.5 | 1.06-1.26(3 H, m), 1.40-1.63(6 H, m), 1.63-1.78(2 H, m), 1.78-1.96(1 H, m), 1.96-2.10(4 H, m), 2.10-2.29(6 H, m), 2.30-2.60(8 H, m), 3.76(3 H, s), 3.81-4.00(3 H, m), 5.89 (1 H, d, J = 14.6 Hz), 6.00(1 H, s), 6.40-6.62(2 H, m), 6.73 (1 H, s), 6.98(1 H, d, J = 7.9 Hz), 7.12 (1 H, brs), 7.20 (1 H, brs) |
| 413 | Me | H | Me | CH₂C(CH₃)₃ | (ESI)+: [M + H]+ = 545.4 | 0.85(9 H, s), 1.95-2.01(3 H, m), 2.01-2.11(1 H, m), 2.16 (2 H, s), 2.19(3 H, s), 2.70-2.82(6 H, |

-continued
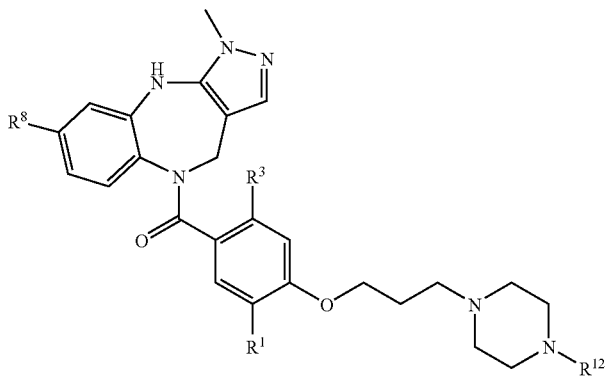
| Compound number | R¹ | R³ | R⁸ | R¹² | MS | ¹H NMR): δ(ppm) |
|---|---|---|---|---|---|---|
| | | | | | | m), 2.85-3.07(6 H, m), 3.73-3.85(5 H, m), 3.90(1 H, d, J = 14.6 Hz), 5.83 (1 H, d, J = 14.6 Hz), 6.39(1 H, d, J = 8.7 Hz), 6.43-6.56(2 H, m), 6.88 (1 H, s), 6.92(1 H, s), 6.95-7.10(1 H, m), 7.12(1 H, s), 7.18(1 H, s) |
| 414 | Me | H | Me | CH₂CH(CH₂CH₃)₂ | (ESI)+: [M + H]= 559.5 | 0.83(6 H,t, J = 7.4 Hz), 1.20-1.40(7 H, m), 1.40-1.52(1 H, m), 1.90-2.10(8 H, m), 2.19 (3 H, s), 2.41(2 H, d, J = 6.7 Hz), 2.70-2.85(3 H, m), 2.85-2.92(3 H, m), 3.79 (3 H, s), 3.80-3.90 (2 H, m), 5.83(1 H, d, J = 14.6 Hz), 6.37-6.60(2 H, m), 6.80(1 H, s), 6.87-6.97(2 H, m), 7.13 (2 H, d, J = 16.1 Hz) |
| 415 | Me | H | Me | CH₂CH₂CH(CH₃)₂ | (APCI)+: [M + H]+ = 545.5 | 0.86(6 H, d, J = 6.7 Hz), 1.33-1.45(2 H, m), 1.46-1.62(1 H, m), 1.82-1.93(2 H, m), 2.01 (3 H, s), 2.10-2.25 (2 H, m), 2.29-2.40 (2 H, m), 2.40-2.59 (8 H, m), 2.79-2.91 (1 H, m), 3.48-3.60 (1 H, m), 3.60-3.80 (3 H, m), 3.80-3.96 (3 H, m), 3.98-4.10 (1 H, m), 5.88(1 H, d, J = 14.6 Hz), 6.19 (1 H, s), 6.41-6.52 (2 H, m), 6.52-6.60 (1 H, m), 6.75(1 H, s), 6.97(1 H, d, J = 7.7 Hz) 7.12(1 H, s), 7.19(1 H, s) |
| 416 | Me | H | Me | CH₂CH(CH₃)₂ | (APCI)+: [M + H]+ = 531.2 | 0.90(6 H, d, J = 6.7 Hz), 1.28 (2 H, t, J = 7.4 Hz), 1.72-1.88(1 H, m), 1.90-2.07(7 H, m), 2.19(3 H, s), 2.26 (2 H, d, J = 7.2 Hz), 2.61-2.88(8 H, m), 3.45(1 H, s), 3.78 |

-continued
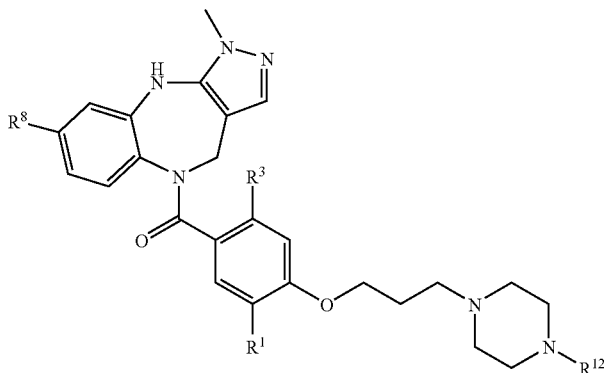
| Compound number | R¹ | R³ | R⁸ | R¹² | MS | ¹H NMR): δ(ppm) |
|---|---|---|---|---|---|---|
| | | | | | | (2 H, s), 3.81-3.91 (2 H, m), 5.86(1 H, d, J = 14.6 Hz), 6.40-6.60(3 H, m), 6.83(1 H, s), 6.95 (1 H, d, J = 8.2 Hz), 7.13-7.19(2 H, m) |
| 417 | Me | H | Me | CH₂CH₂CH₃ | (APCI)+: [M + H]+ = 517.4 | 0.88(3 H, t, J = 7.4 Hz), 1.39-1.60(2 H, m), 1.80-1.95(2 H, m), 1.96-2.06(2 H, m), 2.19 (3 H, s), 2.29-2.38 (2 H, m), 2.39-2.64 (12 H, m), 3.75 (3 H, s), 3.80-3.96 (3 H, m), 5.88(1 H, d, J = 14.6 Hz), 6.23 (1 H, s), 6.40-6.60 (2 H, m), 6.76(1 H, s), 6.98(1 H, d, J = 7.7 Hz), 7.04-7.20(2 H, m) |
| 418 | F | H | H | CH₂CH(CH₃)₂ | (APCI)+: [M + H]+ = 521.4 | 0.85(6 H, d, J = 6.4 Hz), 1.71-1.76(1 H, m), 1.89-1.95( 2 H, m), 2.04 (2 H, d, J = 7.2 Hz), 2.43(10 H, m), 3.74 (3 H, s), 3.93-3.98 (3 H, m), 5.86 (1 H, d, J = 14.6 Hz), 6.67-6.72(4 H, m), 6.91-7.08(4 H, m), 7.20(1 H, s) |
| 419 | F | H | H | ![cyclopentylmethyl] | (APCI)+: [M + H]+ = 547.5 | 1.10-1.17(2 H, m), 1.44-1.58(4 H, m), 1.64-1.73(2 H, m), 1.87-2.03(3 H, m), 2.22(2 H, d, J = 7.2 Hz), 2.42 (10 H, m), 3.72 (3 H, s), 3.92-3.97 (3 H, m), 5.86(1 H, d, J = 14.6 Hz), 6.66-6.72(3 H, m), 6.76(1 H, s), 6.87-7.07(4 H, m), 7.19 (1 H, s) |
| 420 | F | H | H | CH₂CH(CH₂CH₃)₂ | (APCI)+: [M + H]+ = 549.5 | 0.81(6 H, t, J = 7.3 Hz), 1.21-1.37(5 H, m), 1.88-1.93(2 H, m), 2.10 (2 H, d, J = 6.7 Hz), 2.41(10 H, m), 3.73(3 H, s), 3.93- |

-continued
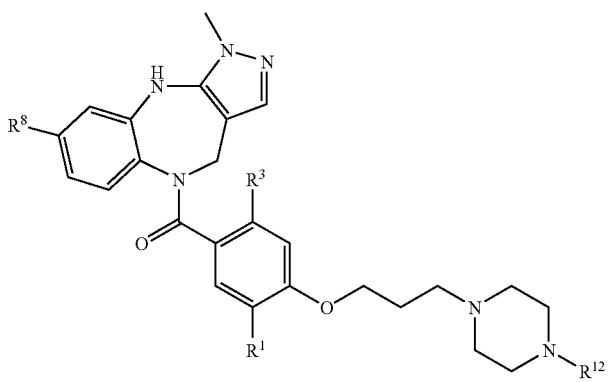
| Compound number | R¹ | R³ | R⁸ | R¹² | MS | ¹H NMR): δ(ppm) |
|---|---|---|---|---|---|---|
|  |  |  |  |  |  | 3.98(3 H, m), 5.87 (1 H, d, J = 14.6 Hz), 6.67-6.72(4 H, m), 6.87-7.07(4 H, m), 7.20(1 H, s) |
| 421 | F | H | H | CH₂CH₂CH(CH₃)₂ | (APCI)+: [M + H]+ = 535.4 | 0.83(6 H, d, J = 6.4 Hz), 1.27-1.35(2 H, m), 1.50 (1 H, m), 1.85-1.94 (2 H, m), 2.24-2.40 (12 H, m), 3.69 (3 H, s), 3.90-3.95 (3 H, m), 5.84(1 H, d, J = 14.6 Hz), 6.63-6.69(3 H, m), 6.86(1 H, d, J = 11.9 Hz), 6.97-7.02(4 H, m), 7.16 (1 H, s) |
| 422 | F | H | H | CH₂C(CH₃)₃ | (ESI)+: [M + H]+ = 535.4 | 0.83(9 H, s), 1.92-2.00(2 H, m), 2.03 (2 H, s), 2.47-2.54 (10 H, m), 3.79 (3 H, s), 3.93-3.98 (3 H, m), 5.88(1 H, d, J = 14.6 Hz), 6.20 (1 H, s), 6.67-6.70 (3 H, m), 6.91-6.96 (2 H, m), 7.03-7.13 (2 H, m), 7.21-7.22 (1 H, m) |
| 423 | F | H | H | CH₂CH₂CH₃ | (APCI)+: [M + H]+ = | 0.85(3 H, t, J = 7.4 Hz), 1.47 (2 H, m), 1.90(2 H, m), 2.25(2 H, m), 2.43(10 H, m), 3.73(3 H, s), 3.95 (3 H, m), 5.86(1 H, d, J = 14.6 Hz), 6.67-6.72(4 H, m), 6.87-7.08(4 H, m), 7.20(1 H, s) |

-continued

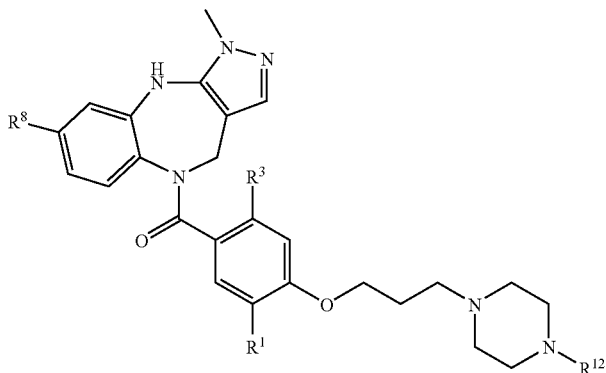

| Compound number | R¹ | R³ | R⁸ | R¹² | MS | ¹H NMR): δ(ppm) |
|---|---|---|---|---|---|---|
| 424 | Me | H | H | CH₂-cyclopropyl | (ESI)+: [M + H]+ = 515.3 | 0.07-0.13(2 H, m), 0.47-0.54(2 H, m), 0.81-0.92(1 H, m), 1.87-1.96(3 H, brt), 2.01(3 H, s), 2.27(2 H, d, J = 6.7 Hz), 2.42-2.64(10 H, m), 3.78(3 H, s), 3.86-4.01(3 H, m), 5.92 (1 H, d, J = 14.8 Hz), 6.06(1 H, s), 6.48 (1 H, brd J = 9.6 Hz), 6.70 (2 H, s), 6.92(1 H, d, J = 7.4 Hz), 6.94-7.11 (3 H, m), 7.22 (1 H, s) |
| 425 | F | H | H | CH₂-cyclopropyl | (ESI)+: [M + H]+ = 519.3 | 0.05-0.12(2 H, m), 0.46-0.53(2 H, m), 0.81-0.87(1 H, m), 1.87-1.98(2 H, m), 2.25(2 H, d, J = 6.7 Hz), 2.38-2.62(10 H, m), 3.78(3 H, s), 3.98 (2 H, t, J = 5.7 Hz), 3.96(1 H, d, J = 14.6 Hz), 5.88 (1 H, d, J = 14.6 Hz), 6.21(1 H, s), 6.68-6.74(3 H, m), 6.89-6.96(2 H, m), 7.03-7.13(2 H, m), 7.22 (1 H, s) |
| 426 | H | Cl | Me | CH₂CH₂C(CH₃)₃ | (APCI)+: [M + H]+ = 579.4, 581.4 | 0.89(9 H, s), 1.38-1.50(2 H, m), 1.79-1.91(2 H, m), 2.16 (3 H, s), 2.43-2.60 (8 H, m), 2.60-2.79 (4 H, m), 3.46(3 H, s), 3.74(2 H, s), 3.86(2 H, t, J = 5.9 Hz), 5.78 (1 H, d, J = 14.6 Hz), 6.26(1 H, s), 6.47 (1 H, d, J = 6.7 Hz), 6.67-6.84(4 H, m), 7.21(1 H, s) |
| 427 | H | Cl | Cl | CH₂CH₂C(CH₃)₃ | (APCI)+: [M + H]+ = 599.3 | 0.88(9 H, s), 1.35 (1 H, d, J = 6.7 Hz), 1.37-1.47(2 H, m), 1.83-1.90(1 H, m), 2.42-2.78(10 H, m), 3.46(3 H, s), 3.74(2 H, s), 3.88 |

-continued
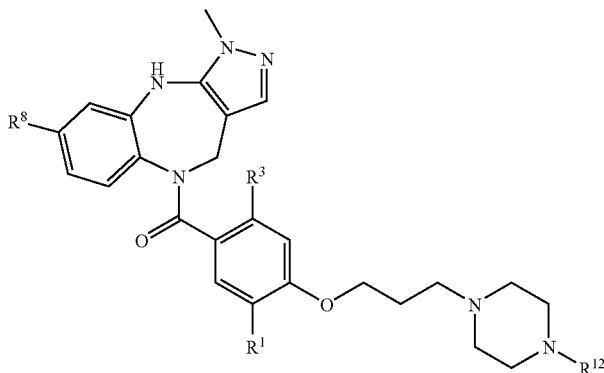
| Compound number | R¹ | R³ | R⁸ | R¹² | MS | ¹H NMR): δ(ppm) |
|---|---|---|---|---|---|---|
| | | | | | | (2 H, t, J = 6.2 Hz), 3.94-4.00(1 H, m), 5.77(1 H, d, J = 14.6 Hz), 6.50 (1 H, dd, J = 2.2, 8.7 Hz), 6.61(1 H, dd, J = 2.2, 8.7 Hz), 6.73(1 H, d, J = 2.2 Hz), 6.81 (1 H, s), 6.83(1 H, s), 6.84-7.00(2 H, m), 7.22(1 H, s) |
| 428 | H | F | Cl | CH₂CH₂C(CH₃)₃ | (APCI)+: [M + H]+ = 583.4, 585.4 | 0.87(9 H, s), 1.26 (1 H, d, J = 5.2 Hz), 1.32-1.41(2 H, m), 1.88-1.91(1 H, m), 2.30-2.41(2 H, m), 2.42-2.63(8 H, m), 3.44(3 H, s), 3.69 (2 H, s), 3.82-3.93 (2 H, m), 5.78(1 H, d, J = 14.8 Hz), 6.33 (1 H, dd, J = 2.2, 14.1 Hz), 6.43-6.51 (1 H, m), 6.54-6.70 (2 H, m), 6.86(1 H, s), 6.97(1 H, d, J = 2.2 Hz), 7.02-7.10(2 H, m), 7.19 (1 H, s) |
| 429 | Cl | H | Cl | CH₂CH₂C(CH₃)₃ | (ESI)+: [M + H]+ = 599.4 | 0.88(9 H, s), 1.35-1.41(2 H, m), 1.88-2.12(4 H, m), 2.29-2.35(2 H, m), 2.38-2.57(8 H, m), 3.46 (3 H, s), 3.72-3.76 (2 H, m), 3.92-4.08 (2 H, m), 5.85(1 H, d, J = 14.6 Hz), 6.43 (1 H, s), 6.56-6.74 (2 H, m), 6.98(1 H, s), 7.08(1 H, d, J = 8.7 Hz), 7.21 (1 H, s), 7.27(1 H, s) |
| 430 | F | H | Cl | CH₂CH₂C(CH₃)₃ | (APCI)+: [M + H]+ = 583.4, 585.4 | 0.88(9 H, s), 1.36-1.42(2 H, m), 1.84-2.03(4 H, m), 2.31-2.39(2 H, m), 2.40-2.62(8 H, m), 3.46 (3 H, s), 3.76(2 H, s), 3.92-4.04(2 H, m), 5.85( 1 H, d, J = 14.1 Hz), 6.52 (1 H, s), 6.57-6.80 (3 H, m), 6.95-7.06 (2 H, m), 7.21(1 H, s) |

-continued
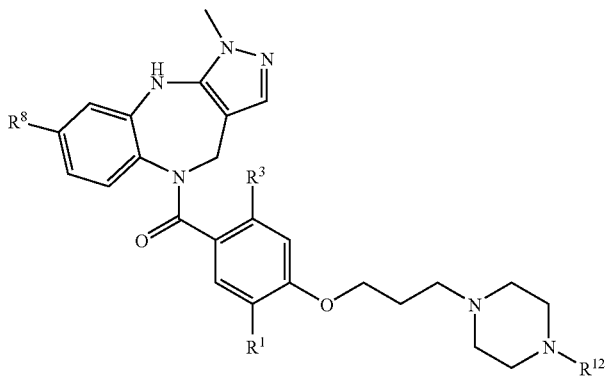
| Compound number | R¹ | R³ | R⁸ | R¹² | MS | ¹H NMR): δ(ppm) |
|---|---|---|---|---|---|---|
| 431 | H | F | Me | CH₂CH₂C(CH₃)₃ | (APCI)+: [M + H]+ = 563.5 | 0.89(9 H, s), 1.35-1.41(2 H, m), 1.88-1.97(2 H, m), 2.05-2.13(1 H, m), 2.21(3 H, s), 2.28-2.34(2 H, m), 2.34-2.54(9 H, m), 3.37(3 H, s), 3.68(3 H, s), 3.91(2 H, t, J = 6.4 Hz), 5.96-6.01(1 H, m), 6.24-6.28(1 H, m), 6.33-6.42(1 H, m), 6.42-6.48(1 H, m), 6.54-6.60( H, m), 6.72(1 H, d, J = 7.9 Hz), 7.48-7.51(1 H, m) |
| 432 | Me | H | Me | CH₂CH₂C(CH₃)₃ | (ESI)+: [M + H]+ = 559.5 | 0.88(9 H, t, J = 12.9 Hz), 1.35-1.42(2 H, m), 1.72-2.00(2 H, m), 2.02(3 H, s), 2.22(3 H, s), 2.28-2.35(2 H, m), 2.37-2.62(10 H, m), 3.77(3 H, s), 3.88-3.96(3 H, m), 5.89(1 H, d, J = 11.6 Hz), 6.45-6.62(3 H, m), 6.73(1 H, s), 6.94-7.01(1 H, m), 7.13(1 H, s), 7.19-7.22(1 H, m) |
| 433 | Me | H | Cl | CH₂CH₂C(CH₃)₃ | (ESI)+: [M + H]+ = 579.4, 581.5 | 0.88(9 H, t, J = 12.9 Hz), 1.36-1.43(2 H, m), 1.91-2.02(2 H, m), 2.05(3 H, s), 2.30-2.37(2 H, m), 2.39-2.63(10 H, m), 3.75(3 H, s), 3.82-3.98(3 H, m), 5.87(1 H, d, J = 14.6 Hz), 6.25(1 H, s), 6.53-6.70(2 H, m), 6.96(2 H, s), 7.13-7.23(2 H, m) |
| 434 | Cl | H | Me | CH₂CH₂C(CH₃)₃ | (APCI)+: [M + H]+ = 579.4, 581.4 | 0.88(9 H, s), 1.32-1.43(2 H, m), 1.61-1.82(1 H, m), 1.89-2.02(2 H, m), 2.23(3 H, s), 2.28-2.37(2 H, m), 2.37-2.68(9 H, m), 3.78(3 H, s), 3.96-4.01(3 H, m), 5.86(1 H, d, J = 14.6 Hz), 6.00(1 H, s), 6.48-6.61 |

-continued

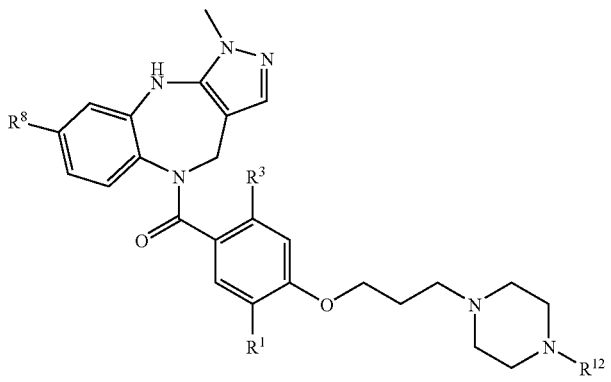

| Compound number | R¹ | R³ | R⁸ | R¹² | MS | ¹H NMR): δ(ppm) |
|---|---|---|---|---|---|---|
| | | | | | | (2 H, m), 6.61-6.70 (2 H, m), 6.75(1 H, s), 7.14(1 H, d, J = 8.2 Hz), 6.22 (1 H, s) |
| 435 | F | H | Me | CH₂CH₂C(CH₃)₃ | (APCI)+: [M + H]+ = 563.4 | 0.87(9 H, s), 1.35-1.41(2 H, m), 1.88-1.97(2 H, m), 2.05-2.13(1 H, m), 2.21 (3 H, s), 2.28-2.34 (2 H, m), 2.34-2.54 (9 H, m), 3.76(3 H, s), 3.90-4.04(3 H, m), 5.85(1 H, d, J = 12.1 Hz), 6.18 (1 H, s), 6.47-6.60 (2 H, m), 6.67-6.79 (2 H, m), 6.91(1 H, d, J = 9.3 Hz), 7.05 (1 H, d, J = 9.3 Hz), 7.20(1 H, s) |
| 436 | Cl | H | H | CH₂CH₂C(CH₃)₃ | (APCI)+: [M + H]+ = 565.4, 567.4 | 0.88(9 H, s), 1.29 (2 H, d, J = 6.7 Hz), 1.31-1.42(2 H, m), 1.59-1.82(2 H, m), 1.92-1.97(2 H, m), 2.29-2.35(2 H, m), 2.35.2.67(9 H, m), 3.80(3 H, s), 3.91-4.04(2 H, m), 5.89 (1 H, d, J = 15 Hz), 6.03(1 H, s), 6.60-6.80(2 H, m), 6.94 (1 H, d, J = 7.9 Hz), 7.07-7.19(2 H, m), 7.23(1 H, s) |
| 437 | H | Cl | H | CH₂CH₂C(CH₃)₃ | (APCI)+: [M + H]+ = 565.5, 567.4 | 0.88(9 H, s), 1.32-1.43(2 H, m), 1.80-1.93(2 H, m), 2.27-2.38(2 H, m), 2.38-2.58(9 H, m), 3.61 (1 H, s), 3.77(3 H, s), 3.86(1 H, t, J = 6.2 Hz), 4.02 (1 H, s), 5.85(1 H, d, J = 14.8 Hz), 6.02 (1 H, s), 6.45(1 H, dd, J = 2.2, 8.4 Hz), 6.67-6.69(1 H, m), 6.69-6.91(2 H, m), 6.91-7.12(2 H, m) |
| 438 | H | F | H | CH₂CH₂C(CH₃)₃ | (APCI)+: [M + H]+ = 549.4 | 0.88(9 H, s), 1.35-1.46(2 H, m), 1.80-1.94(2 H, m), 2.30-2.41(2 H, m), 2.41-2.62(9 H, m), 3.57 (1 H, s), 3.76(3 H, s), 3.87(2 H, t, |

-continued
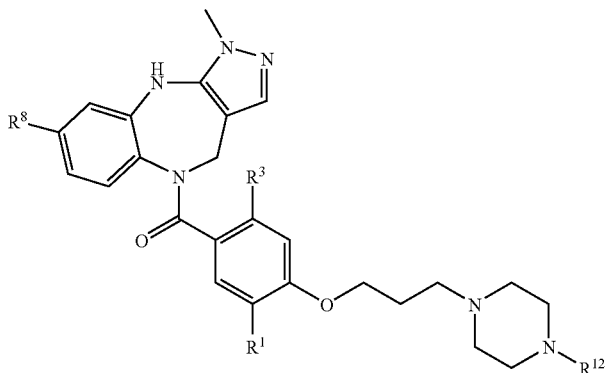
| Compound number | R¹ | R³ | R⁸ | R¹² | MS | ¹H NMR: δ(ppm) |
|---|---|---|---|---|---|---|
| | | | | | | J = 6.4 Hz), 3.99 (1 H, d, J = 14.6 Hz), 5.85(1 H, d, J = 14.6 Hz), 6.16 (1 H, s), 6.39(1 H, dd, J = 2.2, 21.8 Hz), 6.62-6.75 (1 H, m), 6.77(1 H, d, J = 6.7 Hz), 6.87 (1 H, d, J = 6.7 Hz), 6.97-7.12 (2 H, m), 7.23 (1 H, s) |
| 439 | Me | H | H | CH₂CH₂C(CH₃)₃ | (ESI)+: [M + H]+ = 545.4 | 0.88(9 H, s), 1.38-1.53 (2 H, m), 1.82-1.96(2 H, m), 1.96-2.06(3 H, s), 2.53-2.69(4 H, m), 2.69-2.80(2 H, m), 2.80-2.96(2 H, m), 3.73 (3 H, s), 3.82-3.93 (2 H, m), 5.90(1 H, d, J = 14.3 Hz), 6.37 (1 H, s), 6.46(1 H, d, J = 7.7 Hz), 6.69 (2 H, s), 6.90-7.01 (2 H, m), 7.02-7.13 (2 H, m), 7.14-7.27 (2 H, m), 7.83-8.13 (3 H, m) |
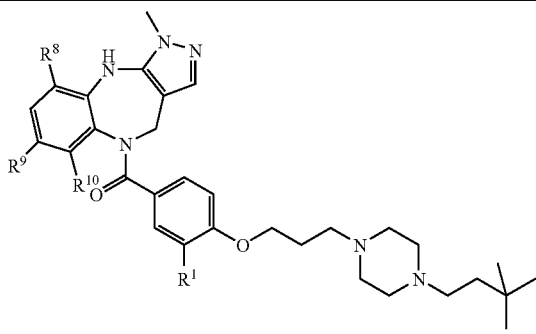
| Compound number | R¹ | R⁸ | R⁹ | R¹⁰ | MS | ¹H NMR: δ(ppm) |
|---|---|---|---|---|---|---|
| 440 | Me | H | H | Me | (APCI)+: [M + H]+ = 559.6 | 0.88(9 H, s), 1.35-1.50 (2 H, m), 1.60-1.85(2 H, m), 1.90-2.05(8 H, m), 2.35-2.40(2 H, m), 2.40- |
-continued
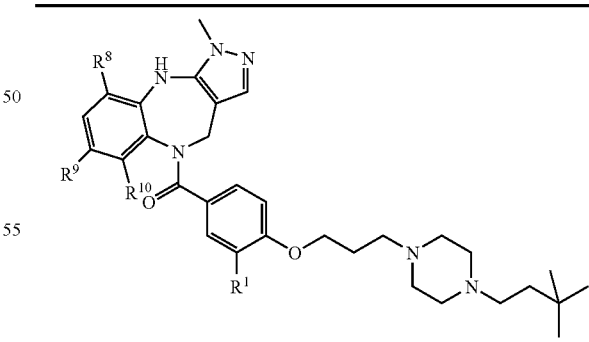
| Compound number | R¹ | R⁸ | R⁹ | R¹⁰ | MS | ¹H NMR: δ(ppm) |
|---|---|---|---|---|---|---|
| | | | | | | 2.70(8 H, m), 3.79(3 H, s), 3.85-3.95(2 H, m), 4.00-4.10(2 H, m), 5.85- |

287
-continued

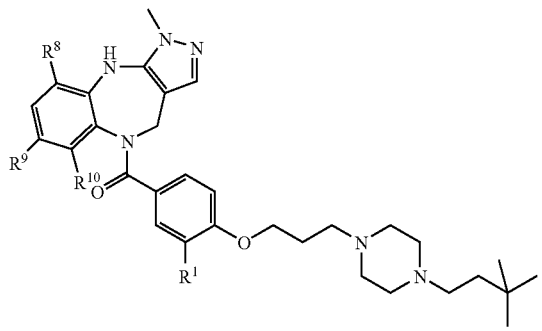

| Compound number | R¹ | R⁸ | R⁹ | R¹⁰ | MS | ¹H NMR: δ(ppm) |
|---|---|---|---|---|---|---|
| 441 | Me | H | Me | H | (APCI)+: [M + H]+ = 559.6 | 5.96(1 H, m), 6.41-7.28 (7 H, m) 0.88(9 H, s), 1.36-1.42 (2 H, m), 1.60-1.70(2 H, m), 1.85-2.15(10 H, m), 2.25-2.60(8 H, m), 3.77 (3 H, s), 3.90-3.92(3 H, m), 5.80-6.00(2 H, m), 6.45-6.55(2 H, m), 6.75-7.22(5 H, m) |

288
-continued

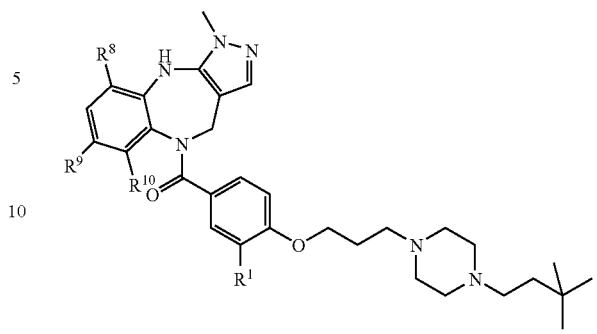

| Compound number | R¹ | R⁸ | R⁹ | R¹⁰ | MS | ¹H NMR: δ(ppm) |
|---|---|---|---|---|---|---|
| 442 | F | Me | H | H | (ESI)+: [M + H]+ = 563.4 | 0.92( 9 H, s), 1.49-1.56 (2 H, m), 1.85-2.03(2 H, m), 2.41(3 H, s), 2.50-2.97(13 H, m), 3.83(3 H, s), 3.88-4.03(3 H, m), 5.78-5.99(2 H, m), 6.57-6.75(3 H, m), 6.92-7.08 (3 H, m) |

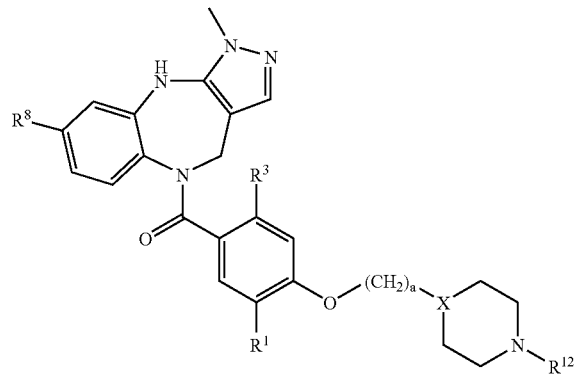

| Compound number | R¹ | R³ | R⁸ | R¹² | X | a | MS |
|---|---|---|---|---|---|---|---|
| 443 E51 | Me | H | Me | CH₂CH(CH₃)₂ | CH | 3 | (ESI)+: [M + H]+ = 530.5 |
| 444 | Me | H | Me | CH₂CH₂CH₃ | CH | 3 | (ESI)+: [M + H]+ = 516.5 |
| 445 | Me | H | Me | ⌬CH₂-phenyl | CH | 3 | (ESI)+: [M + H]+ = 564.5 |
| 446 | Me | H | Me | CH₂-cyclohexyl | CH | 3 | (ESI)+: [M + H]+ = 570.5 |
| 447 | Me | H | Me | CH₂CH₂-phenyl | CH | 3 | (ESI)+: [M + H]+ = 578.5 |

-continued

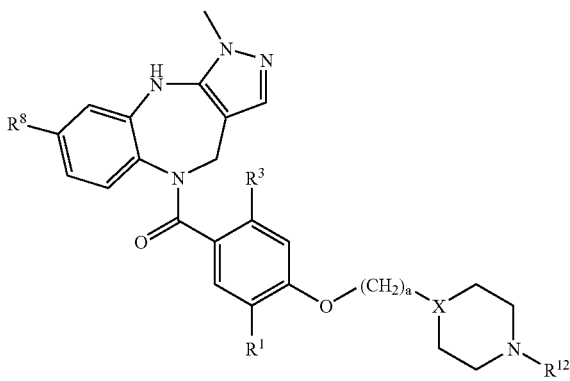

| Compound number | R¹ | R³ | R⁸ | R¹² | X | a | MS |
|---|---|---|---|---|---|---|---|
| 448 | Me | H | Me | (CH₂-thiophene) | CH | 3 | (ESI)+: [M + H]+ = 570.5 |
| 449 | Me | H | Me | (CH₂-4-Cl-phenyl) | CH | 3 | (ESI)+: [M + H]+ = 598.4 |
| 450 | Me | H | Me | (CH₂-3-Cl-phenyl) | CH | 3 | (ESI)+: [M + H]+ = 598.5 |
| 451 | Me | H | Me | (CH₂-2-Cl-phenyl) | CH | 3 | (ESI)+: [M + H]+ = 598.5 |
| 452 | Me | H | Me | CH₂CH₂CH₂CH₂CH₃ | CH | 3 | (ESI)+: [M + H]+ = 544.5 |
| 453 | Me | H | Me | (CH₂-cyclopropyl) | CH | 3 | (ESI)+: [M + H]+ = 528.5 |
| 454 | Me | H | Me | (CH₂CH₂-phenyl) | CH | 3 | (ESI)+: [M + H]+ = 592.5 |
| 455 | Me | H | Me | CH₂CH₂CH(CH₃)₂ | CH | 3 | (ESI)+: [M + H]+ = 544.5 |
| 456 | Me | H | Me | (CH₂-furan) | CH | 3 | (ESI)+: [M + H]+ = 554.4 |
| 457 | Me | H | Me | (CH₂-furan-CH₂OH) | CH | 3 | (ESI)+: [M + H]+ = 584.5 |
| 458 | Me | H | Me | (CH₂-pyridine) | CH | 3 | (ESI)+: [M + H]+ = 565.5 |

-continued

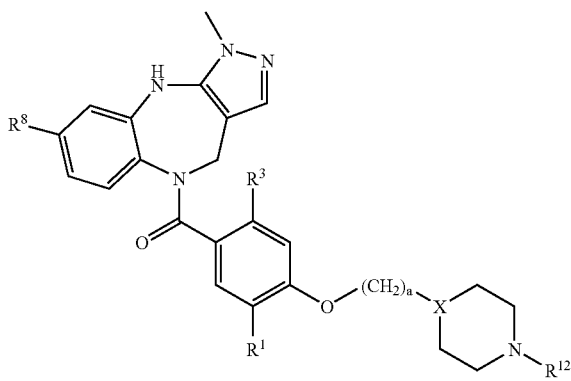

| Compound number | R¹ | R³ | R⁸ | R¹² | X | a | MS |
|---|---|---|---|---|---|---|---|
| 459 | Me | H | Me | (2-pyrrolyl-methyl, NH) | CH | 3 | (ESI)+: [M + H]+ = 553.4 |
| 460 | Me | H | Me | (4-isopropylbenzyl) | CH | 3 | (ESI)+: [M + H]+ = 606.6 |
| 461 | Me | H | Me | (4-hydroxybenzyl) | CH | 3 | (ESI)+: [M + H]+ = 580.5 |
| 462 | Me | H | Me | (2-pyridylmethyl) | CH | 3 | (ESI)+: [M + H]+ = 565.4 |
| 463 | Me | H | Me | (4-pyridylmethyl) | CH | 3 | (ESI)+: [M + H]+ = 565.4 |
| 464 | Me | H | Me | (isothiazolylmethyl) | CH | 3 | (ESI)+: [M + H]+ = 570.4 |
| 465 | Me | H | Me | CH₂CH₂CF₃ | CH | 3 | (ESI)+: [M + H]+ = 570.4 |
| 466 | Me | H | Me | (cyclohexenylmethyl) | CH | 3 | (ESI)+: [M + H]+ = 568.5 |
| 467 | Me | H | Me | (N-methylpyrrol-2-ylmethyl) | CH | 3 | (ESI)+: [M + H]+ = 567.5 |
| 468 | Me | H | Me | (4-methylbenzyl) | CH | 3 | (ESI)+: [M + H]+ = 578.5 |

-continued
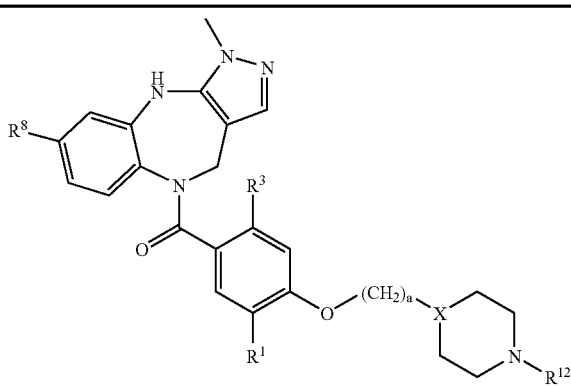
| Compound number | R[1] | R[3] | R[8] | R[12] | X | a | MS |
|---|---|---|---|---|---|---|---|
| 469 | Me | H | Me | 3-methylbenzyl | CH | 3 | (ESI)+: [M + H]+ = 578.5 |
| 470 | Me | H | Me | 2-methylbenzyl | CH | 3 | (ESI)+: [M + H]+ = 578.5 |
| 471 | Me | H | Me | 2-cyanobenzyl | CH | 3 | (ESI)+: [M + H]+ = 589.5 |
| 472 | Me | H | Me | 3-cyanobenzyl | CH | 3 | (ESI)+: [M + H]+ = 589.5 |
| 473 | Me | H | Me | 4-cyanobenzyl | CH | 3 | (ESI)+: [M + H]+ = 589.5 |
| 474 | Me | H | Me | 3,5-dichlorobenzyl | CH | 3 | (ESI)+: [M + H]+ = 632.5 |
| 475 | Me | H | Me | 3,4,5-trimethoxybenzyl | CH | 3 | (ESI)+: [M + H]+ = 654.6 |
| 476 | Me | H | Me | 4-(methoxycarbonyl)benzyl | CH | 3 | (ESI)+: [M + H]+ = 622.6 |
| 477 | Me | H | Me | $CH_2CH(CH_3)_2$ | N | 2 | (ESI)+: [M + H]+ = 517.5 |

-continued

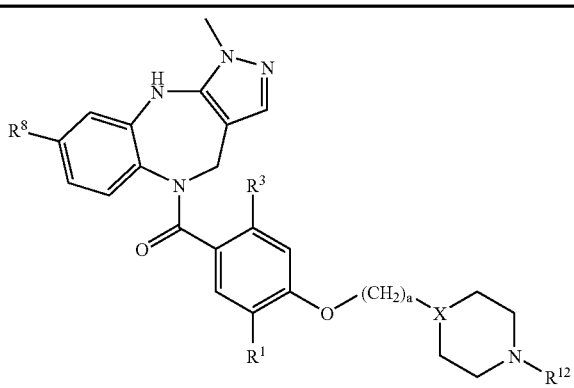

| Compound number | R¹ | R³ | R⁸ | R¹² | X | a | MS |
|---|---|---|---|---|---|---|---|
| 478 | Me | H | Me | CH₂CH₂CH₃ | N | 2 | (ESI)+: [M + H]+ = 503.5 |
| 479 | Me | H | Me | (benzyl) | N | 2 | (ESI)+: [M + H]+ = 551.4 |
| 480 | Me | H | Me | (phenethyl) | N | 2 | (ESI)+: [M + H]+ = 565.5 |
| 481 | Me | H | Me | (2-thienylmethyl) | N | 2 | (ESI)+: [M + H]+ = 557.3 |
| 482 | Me | H | Me | (4-chlorobenzyl) | N | 2 | (ESI)+: [M + H]+ = 585.4 |
| 483 | Me | H | Me | (3-chlorobenzyl) | N | 2 | (ESI)+: [M + H]+ = 585.4 |
| 484 | Me | H | Me | (2-chlorobenzyl) | N | 2 | (ESI)+: [M + H]+ = 585.4 |
| 485 | Me | H | Me | CH₂CH₂CH₂CH₂CH₃ | N | 2 | (ESI)+: [M + H]+ = 531.4 |
| 486 | Me | H | Me | (cyclopropylmethyl) | N | 2 | (ESI)+: [M + H]+ = 515.5 |
| 487 | Me | H | Me | (3-phenylpropyl) | N | 2 | (ESI)+: [M + H]+ = 579.5 |
| 488 | Me | H | Me | CH₂CH₂CH(CH₃)₂ | N | 2 | (ESI)+: [M + H]+ = 531.5 |
| 489 | Me | H | Me | CH₂C(CH₃)₃ | N | 2 | (ESI)+: = 531.4 |

-continued

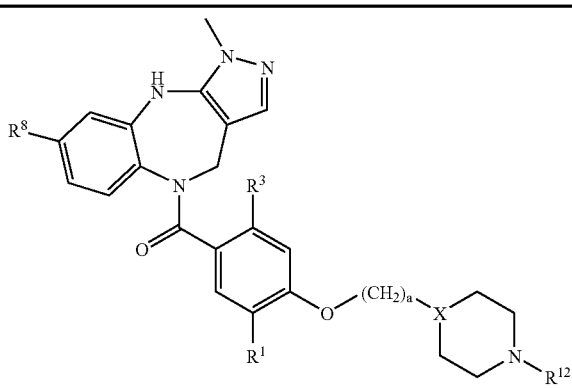

| Compound number | R¹ | R³ | R⁸ | R¹² | X | a | MS |
|---|---|---|---|---|---|---|---|
| 490 | Me | H | Me | (furan-2-ylmethyl) | N | 2 | (ESI)+: [M + H]+ = 541.4 |
| 491 | Me | H | Me | (5-(hydroxymethyl)furan-2-ylmethyl) | N | 2 | (ESI)+: [M + H]+ = 571.5 |
| 492 | Me | H | Me | (pyridin-3-ylmethyl) | N | 2 | (ESI)+: [M + H]+ = 552.4 |
| 493 | Me | H | Me | (1H-pyrrol-2-ylmethyl) | N | 2 | (ESI)+: [M + H]+ = 540.4 |
| 494 | Me | H | Me | (4-isopropylbenzyl) | N | 2 | (ESI)+: [M + H]+ = 593.5 |
| 495 | Me | H | Me | (4-hydroxybenzyl) | N | 2 | (ESI)+: [M + H]+ = 567.4 |
| 496 | Me | H | Me | (pyridin-2-ylmethyl) | N | 2 | (ESI)+: [M + H]+ = 552.4 |
| 497 | Me | H | Me | (pyridin-4-ylmethyl) | N | 2 | (ESI)+: [M + H]+ = 552.5 |
| 498 | Me | H | Me | (thiophen-3-ylmethyl) | N | 2 | (ESI)+: [M + H]+ = 557.4 |
| 499 | Me | H | Me | $CH_2CH_2CF_3$ | N | 2 | (ESI)+: [M + H]+ = 557.4 |
| 500 | Me | H | Me | (cyclohex-1-enylmethyl) | N | 2 | (ESI)+: [M + H]+ = 555.5 |

-continued
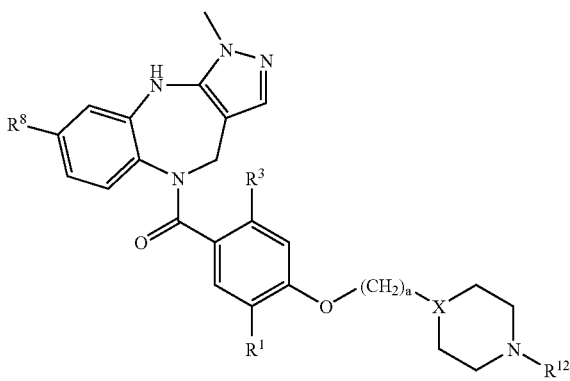
| Compound number | R¹ | R³ | R⁸ | R¹² | X | a | MS |
|---|---|---|---|---|---|---|---|
| 501 | Me | H | Me | 4-methylbenzyl | N | 2 | (ESI)+: [M + H]+ = 565.4 |
| 502 | Me | H | Me | 3-methylbenzyl | N | 2 | (ESI)+: [M + H]+ = 565.4 |
| 503 | Me | H | Me | 2-methylbenzyl | N | 2 | (ESI)+: [M + H]+ = 565.4 |
| 504 | Me | H | Me | 2-cyanobenzyl | N | 2 | (ESI)+: [M + H]+ = 576.5 |
| 505 | Me | H | Me | 3-cyanobenzyl | N | 2 | (ESI)+: [M + H]+ = 576.4 |
| 506 | Me | H | Me | 4-cyanobenzyl | N | 2 | (ESI)+: [M + H]+ = 576.4 |
| 507 | Me | H | Me | 3,5-dichlorobenzyl | N | 2 | (ESI)+: [M + H]+ = 619.4 |
| 508 | Me | H | Me | 3,4,5-trimethoxybenzyl | N | 2 | (ESI)+: [M + H]+ = 641.5 |

-continued

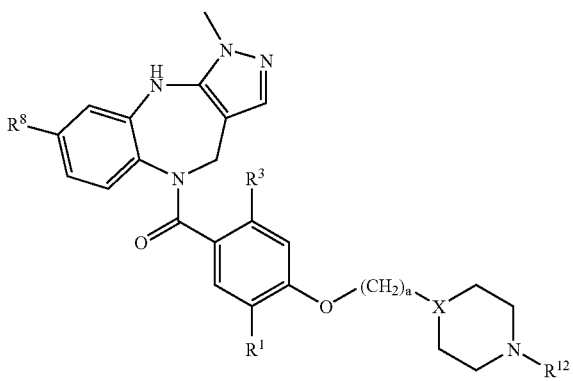

| Compound number | R¹ | R³ | R⁸ | R¹² | X | a | MS |
|---|---|---|---|---|---|---|---|
| 509 | Me | H | Me | (CH₂-C₆H₄-COOMe, para) | N | 2 | (ESI)+: [M + H]+ = 609.5 |
| 510 | H | F | H | CH₂CH(CH₃)₂ | N | 2 | (ESI)+: [M + H]+ = 507.4 |
| 511 | H | F | H | CH₂CH₂CH₃ | N | 2 | (ESI)+: [M + H]+ = 493.4 |
| 512 | H | F | H | CH₂-phenyl | N | 2 | (ESI)+: [M + H]+ = 541.4 |
| 513 | H | F | H | CH₂CH₂-phenyl | N | 2 | (ESI)+: [M + H]+ = 555.4 |
| 514 | H | F | H | CH₂-(2-thienyl) | N | 2 | (ESI)+: [M + H]+ = 547.3 |
| 515 | H | F | H | CH₂-(4-Cl-phenyl) | N | 2 | (ESI)+: [M + H]+ = 575.3 |
| 516 | H | F | H | CH₂-(3-Cl-phenyl) | N | 2 | (ESI)+: [M + H]+ = 575.3 |
| 517 | H | F | H | CH₂-(2-Cl-phenyl) | N | 2 | (ESI)+: [M + H]+ = 575.3 |
| 518 | H | F | H | CH₂CH₂CH₂CH₂CH₃ | N | 2 | (ESI)+: [M + H]+ = 521.4 |
| 519 | H | F | H | CH₂-cyclopropyl | N | 2 | (ESI)+: [M + H]+ = 505.4 |

-continued

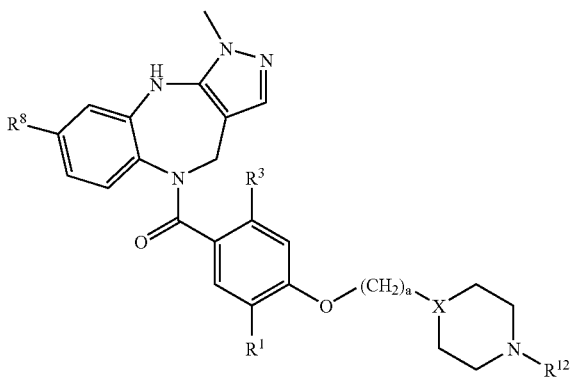

| Compound number | R¹ | R³ | R⁸ | R¹² | X | a | MS |
|---|---|---|---|---|---|---|---|
| 520 | H | F | H | 3-phenylpropyl | N | 2 | (ESI)+: [M + H]+ = 569.4 |
| 521 | H | F | H | furan-2-ylmethyl | N | 2 | (ESI)+: [M + H]+ = 531.3 |
| 522 | H | F | H | (5-(hydroxymethyl)furan-2-yl)methyl | N | 2 | (ESI)+: [M + H]+ = 561.4 |
| 523 | H | F | H | 4-isopropylbenzyl | N | 2 | (ESI)+: [M + H]+ = 583.4 |
| 524 | H | F | H | 4-hydroxybenzyl | N | 2 | (ESI)+: [M + H]+ = 557.3 |
| 525 | H | F | H | thiophen-3-ylmethyl | N | 2 | (ESI)+: [M + H]+ = 547.3 |
| 526 | H | F | H | CH₂CH₂OH | N | 2 | (ESI)+: [M + H]+ = 495.3 |
| 527 | H | F | H | 4-methylbenzyl | N | 2 | (ESI)+: [M + H]+ = 555.3 |
| 528 | H | F | H | 2-cyanobenzyl | N | 2 | (ESI)+: [M + H]+ = 566.3 |
| 529 | H | F | H | 3-cyanobenzyl | N | 2 | (ESI)+: [M + H]+ = 566.4 |

-continued
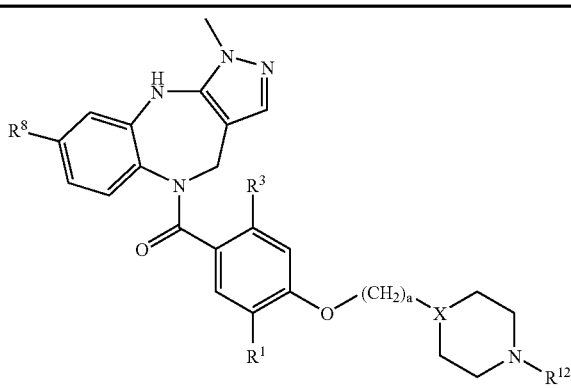
| Compound number | R¹ | R³ | R⁸ | R¹² | X | a | MS |
|---|---|---|---|---|---|---|---|
| 530 | H | F | H | 4-cyanobenzyl | N | 2 | (ESI)+: [M + H]+ = 566.3 |
| 531 | H | F | H | pentafluorobenzyl | N | 2 | (ESI)+: [M + H]+ = 629.4 |
| 532 | H | F | H | 3,5-dichlorobenzyl | N | 2 | (ESI)+: [M + H]+ = 609.3 |
| 533 | H | F | H | 4-(methoxycarbonyl)benzyl | N | 2 | (ESI)+: [M + H]+ = 599.4 |
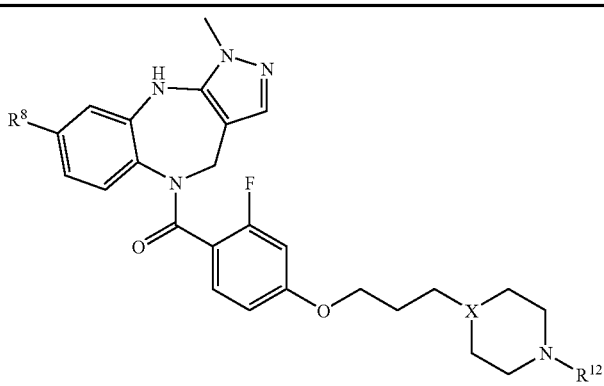
| Compound number | R⁸ | R¹² | X | MS |
|---|---|---|---|---|
| 534 E52 | Cl | CH₂CH₂CH₂CH₂CH₂CH₃ | N | (ESI)+: [M + H]+ = 583.6 |
| 535 | Cl | CH₂(CH₂)₂CH₃ | N | (ESI)+: [M + H]+ = 555.6 |

-continued

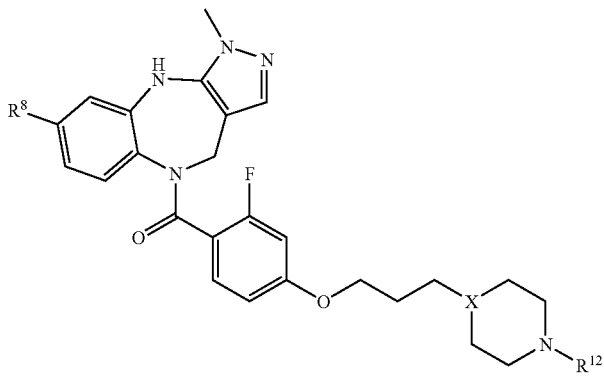

| Compound number | R⁸ | R¹² | X | MS |
|---|---|---|---|---|
| 536 | Cl | $CH_2(CH_2)_2CN$ | N | (ESI)+: [M + H]+ = 566.5 |
| 537 | Cl | phenacyl (–CH₂C(O)Ph) | N | (ESI)+: [M + H]+ = 617.7 |
| 538 | Cl | 2-cyclohexylethyl | N | (ESI)+: [M + H]+ = 609.8 |
| 539 | Cl | 3-fluorobenzyl | N | (ESI)+: [M + H]+ = 607.7 |
| 540 | Cl | 4-tert-butylbenzyl | N | (ESI)+: [M + H]+ = 645.8 |
| 541 | Cl | 4-(trifluoromethoxy)benzyl | N | (ESI)+: [M + H]+ = 673.7 |
| 542 | Cl | 4-(methoxycarbonyl)benzyl | N | (ESI)+: [M + H]+ = 647.7 |
| 543 | Cl | benzyl | N | (ESI)+: [M + H]+ = 589.6 |
| 544 | Cl | cyclohexylmethyl | N | (ESI)+: [M + H]+ = 595.6 |
| 545 | Cl | $CH_2CO_2CH(CH_3)_2$ | N | (ESI)+: [M + H]+ = 599.7 |
| 546 | Cl | $CH_2CH_2CH(CH_3)_2$ | N | (ESI)+: [M + H]+ = 569.6 |
| 547 | Cl | $CH_2CH_2CN$ | N | (ESI)+: [M + H]+ = 552.5 |
| 548 | Cl | $CH_2CH_2CH_2OH$ | N | (ESI)+: [M + H]+ = 557.6 |
| 549 | Cl | $CH_2CN$ | N | (ESI)+: [M + H]+ = 538.5 |

-continued

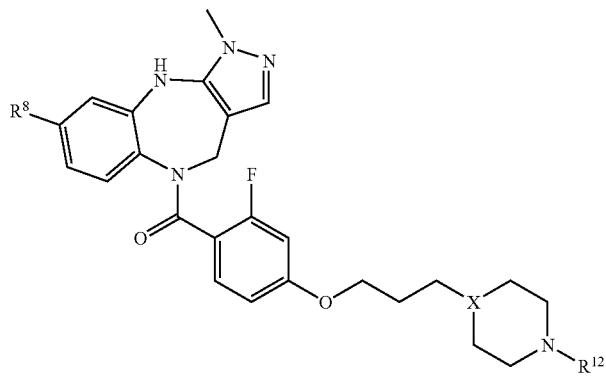

| Compound number | R⁸ | R¹² | X | MS |
|---|---|---|---|---|
| 550 | Cl | $CH_2CH_2OCH_2CH_3$ | N | (ESI)+: [M + H]+ = 571.5 |
| 551 | Cl | $CH_2CH_2CH_2F$ | N | (ESI)+: [M + H]+ = 559.6 |
| 552 | Cl | 3-nitrobenzyl | N | (ESI)+: [M + H]+ = 634.8 |
| 553 | Cl | cyclopropylmethyl | N | (ESI)+: [M + H]+ = 553.5 |
| 554 | Cl | 2-naphthylmethyl | N | (ESI)+: [M + H]+ = 639.8 |
| 555 | Cl | allyl | N | (ESI)+: [M + H]+ = 539.6 |
| 556 | Cl | cinnamyl | N | (ESI)+: [M + H]+ = 615.7 |
| 557 | Cl | 2-biphenylmethyl | N | (ESI)+: [M + H]+ = 665.6 |
| 558 | Cl | methyl (E)-but-2-enoate | N | (ESI)+: [M + H]+ = 597.6 |
| 559 | Cl | 2-cyanobenzyl | N | (ESI)+: [M + H]+ = 614.7 |
| 560 | Cl | $CH_2COC(CH_3)_3$ | N | (ESI)+: [M + H]+ = 597.6 |
| 561 | Cl | $CH_2CONH_2$ | N | (ESI)+: [M + H]+ = 556.5 |
| 562 | Cl | (5-nitrofuran-2-yl)methyl | N | (ESI)+: [M + H]+ = 624.6 |

-continued

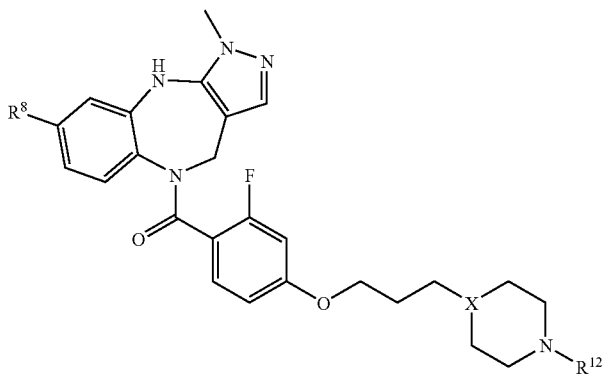

| Compound number | R⁸ | R¹² | X | MS |
|---|---|---|---|---|
| 563 | Cl | 5-benzofurazanylmethyl | N | (ESI)+: [M + H]+ = 631.6 |
| 564 | H | $CH_2(CH_2)_4CH_3$ | CH | (ESI)+: [M + H]+ = 548.6 |
| 565 | H | $CH_2(CH_2)_2CH_3$ | CH | (ESI)+: [M + H]+ = 520.6 |
| 566 | H | $CH_2(CH_2)_3OH$ | CH | (ESI)+: [M + H]+ = 536.6 |
| 567 | H | 2-oxo-2-phenylethyl | CH | (ESI)+: [M + H]+ = 582.5 |
| 568 | H | 2-cyclohexylethyl | CH | (ESI)+: [M + H]+ = 574.6 |
| 569 | H | 3-fluorobenzyl | CH | (ESI)+: [M + H]+ = 572.5 |
| 570 | H | 4-tert-butylbenzyl | CH | (ESI)+: [M + H]+ = 610.7 |
| 571 | H | 4-(trifluoromethoxy)benzyl | CH | (ESI)+: [M + H]+ = 638.7 |
| 572 | H | 4-(methoxycarbonyl)benzyl | CH | (ESI)+: [M + H]+ = 612.6 |
| 573 | H | benzyl | CH | (ESI)+: [M + H]+ = 554.5 |

-continued

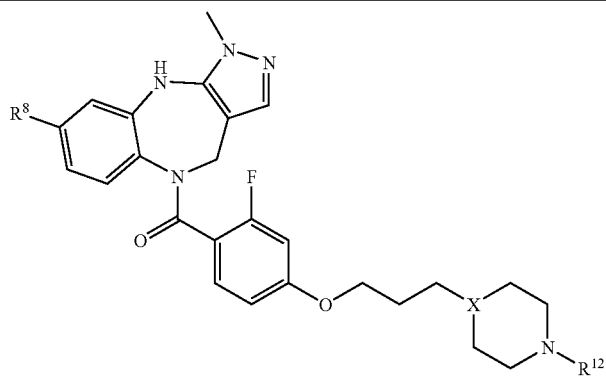

| Compound number | R[8] | R[12] | X | MS |
|---|---|---|---|---|
| 574 | H | ![cyclohexylmethyl] | CH | (ESI)+: [M + H]+ = 560.1 |
| 575 | H | CH$_2$CO$_2$CH(CH$_3$)$_2$ | CH | (ESI)+: [M + H]+ = 564.6 |
| 576 | H | CH$_2$CH$_2$CH(CH$_3$)$_2$ | CH | (ESI)+: [M + H]+ = 534.6 |
| 577 | H | CH$_2$CH$_2$CN | CH | (ESI)+: [M + H]+ = 517.5 |
| 578 | H | CH$_2$CN | CH | (ESI)+: [M + H]+ = 503.5 |
| 579 | H | CH$_2$CH$_2$OCH$_2$CH$_3$ | CH | (ESI)+: [M + H]+ = 536.6 |
| 580 | H | CH$_2$CH$_2$CH$_2$F | CH | (ESI)+: [M + H]+ = 524.6 |
| 581 | H | 3-nitrobenzyl | CH | (ESI)+: [M + H]+ = 599.6 |
| 582 | H | cyclopropylmethyl | CH | (ESI)+: [M + H]+ = 518.6 |
| 583 | H | 2-naphthylmethyl | CH | (ESI)+: [M + H]+ = 604.6 |
| 584 | H | allyl | CH | (ESI)+: [M + H]+ = 504.5 |
| 585 | H | cinnamyl | CH | (ESI)+: [M + H]+ = 580.5 |
| 586 | H | 2-biphenylmethyl | CH | (ESI)+: [M + H]+ = 630.7 |
| 587 | H | CH$_2$CH=CHCO$_2$Me | CH | (ESI)+: [M + H]+ = 562.5 |
| 588 | H | 2-cyanobenzyl | CH | (ESI)+: [M + H]+ = 579.5 |
| 589 | H | CH$_2$COC(CH$_3$)$_3$ | CH | (ESI)+: [M + H]+ = 562.6 |

-continued
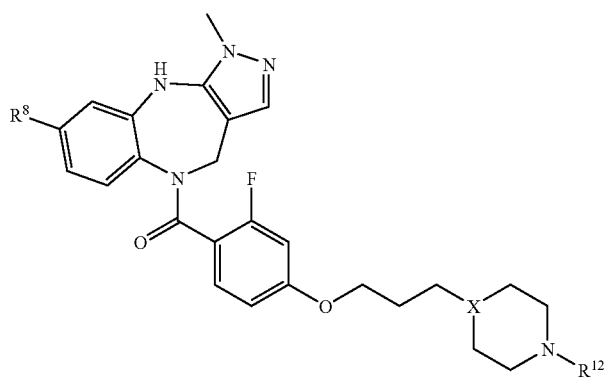
| Compound number | R⁸ | R¹² | X | MS |
|---|---|---|---|---|
| 590 | H | CH₂CONH₂ | CH | (ESI)+: [M + H]+ = 521.5 |
| 591 | H | ⸺CH₂-(5-nitrofuran-2-yl) | CH | (ESI)+: [M + H]+ = 589.5 |
| 592 | H | ⸺CH₂-(benzo[c][1,2,5]oxadiazol-5-yl) | CH | (ESI)+: [M + H]+ = 596.6 |
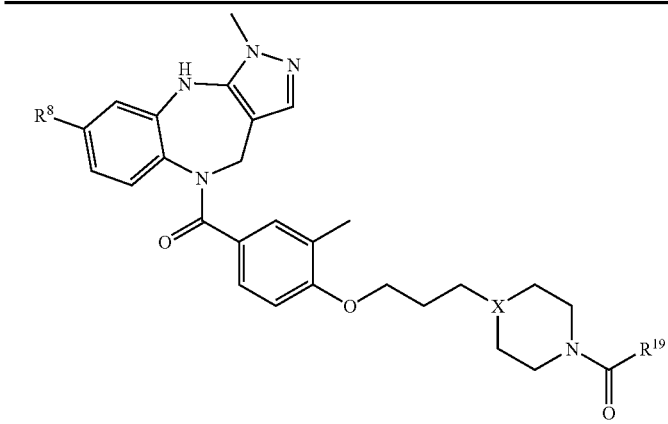
| Compound number | X | R⁸ | R¹⁹ | MS |
|---|---|---|---|---|
| 593 E53 | N | H | Me | (ESI)+: [M + H]+ = 503.2 |
| 594 | N | H | phenyl | (ESI)+: [M + H]+ = 565.3 |
| 595 | N | H | 3-chlorophenyl | (ESI)+: [M + H]+ = 599.3 |

-continued
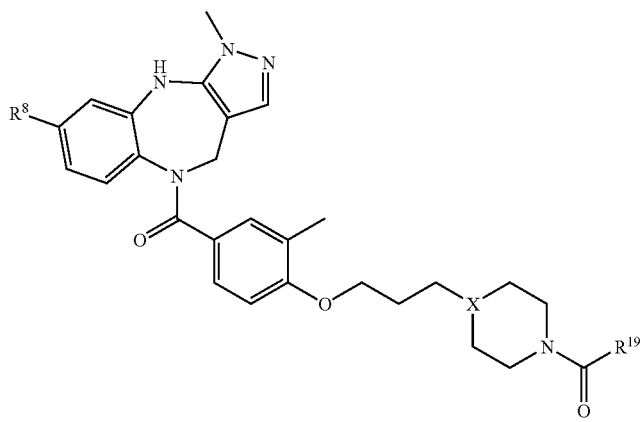
| Compound number | X | R⁸ | R¹⁹ | MS |
|---|---|---|---|---|
| 596 | N | H | 4-Cl-phenyl | (ESI)+: [M + H]+ = 599.3 |
| 597 | N | H | 2-Cl-phenyl | (ESI)+: [M + H]+ = 599.3 |
| 598 | N | H | 4-OMe-phenyl | (ESI)+: [M + H]+ = 595.3 |
| 599 | N | H | 3-Me-phenyl | (ESI)+: [M + H]+ = 579.3 |
| 600 | N | H | 2-Me-phenyl | (ESI)+: [M + H]+ = 579.3 |
| 601 | N | H | 3-Cl-pyridin-2-yl | (ESI)+: [M + H]+ = 600.3 |
| 602 | N | H | pyridin-3-yl | (ESI)+: [M + H]+ = 566.3 |
| 603 | N | H | thiophen-2-yl | (ESI)+: [M + H]+ = 571.3 |
| 604 | N | H | thiophen-3-yl | (ESI)+: [M + H]+ = 571.3 |

-continued

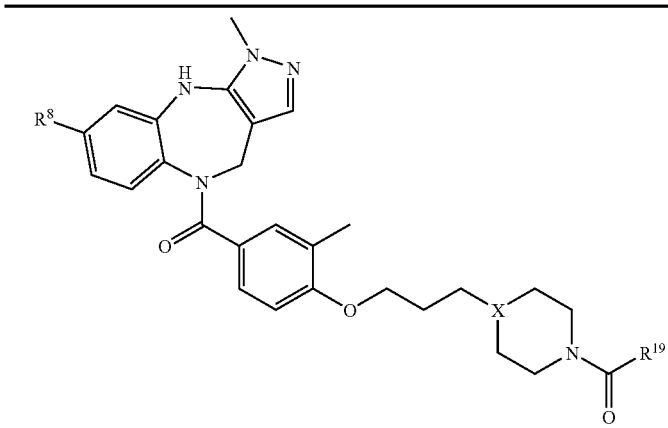

| Compound number | X | R⁸ | R¹⁹ | MS |
|---|---|---|---|---|
| 605 | N | H | 2,5-dimethylfuran-3-yl | (ESI)+: [M + H]+ = 583.3 |
| 606 | N | H | furan-2-yl | (ESI)+: [M + H]+ = 555.3 |
| 607 | N | H | isoxazol-5-yl | (ESI)+: [M + H]+ = 556.3 |
| 608 | N | H | 5-methyl-2-phenyl-2H-1,2,3-triazol-4-yl | (ESI)+: [M + H]+ = 646.4 |
| 609 | N | H | CH₂CH₃ | (ESI)+: [M + H]+ = 517.3 |
| 610 | N | H | CH₂CH₂CH₃ | (ESI)+: [M + H]+ = 531.3 |
| 611 | N | H | cyclopropyl | (ESI)+: [M + H]+ = 529.3 |
| 612 | N | H | C(CH₃)₃ | (ESI)+: [M + H]+ = 545.3 |
| 613 | N | H | cyclopentylmethyl | (ESI)+: [M + H]+ = 571.3 |
| 614 | N | H | CH₂(CH₂)₃CH₃ | (ESI)+: [M + H]+ = 559.3 |
| 615 | N | H | CH(CH₂CH₃)CH₂CH₂CH₂CH₃ | (ESI)+: [M + H]+ = 587.4 |
| 616 | N | H | 2,5-dimethoxyphenyl | (ESI)+: [M + H]+ = 639.4 |
| 617 | N | H | benzyl | (ESI)+: [M + H]+ = 579.3 |

-continued
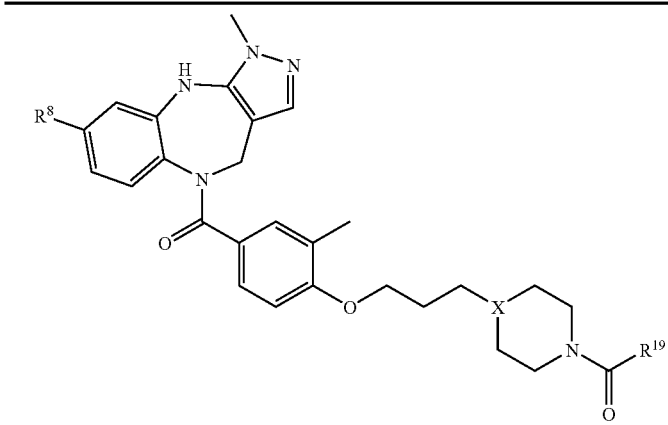
| Compound number | X | R⁸ | R¹⁹ | MS |
|---|---|---|---|---|
| 618 | N | H | (CH₂CH₂-phenyl) | (ESI)+: [M + H]+ = 593.3 |
| 619 | N | H | (cyclopropyl-phenyl) | (ESI)+: [M + H]+ = 605.4 |
| 620 | N | H | (CH₂-thiophene) | (ESI)+: [M + H]+ = 585.3 |
| 621 | N | H | (CH₂-O-phenyl) | (ESI)+: [M + H]+ = 595.3 |
| 622 | N | H | (CH₂-O-CH₂-phenyl) | (ESI)+: [M + H]+ = 609.4 |
| 623 | N | H | $CH_2CH_2CO_2CH_3$ | (ESI)+: [M + H]+ = 575.3 |
| 624 | N | H | $CH_2CH_2CH_2CO_2CH_2CH_3$ | (ESI)+: [M + H]+ = 603.4 |
| 625 | CH | Me | $CH_3$ | (ESI)+: [M + H]+ = 516.4 |
| 626 | CH | Me | (phenyl) | (ESI)+: [M + H]+ = 578.4 |
| 627 | CH | Me | (3-Cl-phenyl) | (ESI)+: [M + H]+ = 612.4 |
| 628 | CH | Me | (4-Cl-phenyl) | (ESI)+: [M + H]+ = 612.4 |
| 629 | CH | Me | (2-Cl-phenyl) | (ESI)+: [M + H]+ = 612.4 |

-continued
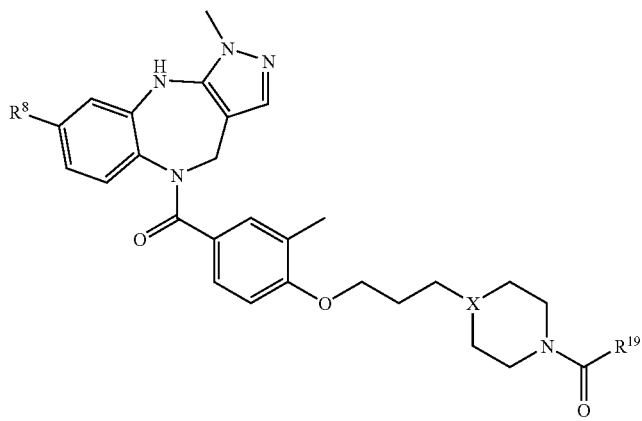
| Compound number | X | R⁸ | R¹⁹ | MS |
|---|---|---|---|---|
| 630 | CH | Me | 4-methoxyphenyl | (ESI)+: [M + H]+ = 608.5 |
| 631 | CH | Me | 3-methylphenyl | (ESI)+: [M + H]+ = 592.4 |
| 632 | CH | Me | 2-methylphenyl | (ESI)+: [M + H]+ = 592.4 |
| 633 | CH | Me | 2-chloropyridin-3-yl | (ESI)+: [M + H]+ = 613.4 |
| 634 | CH | Me | pyridin-3-yl | (ESI)+: [M + H]+ = 579.4 |
| 635 | CH | Me | pyridin-4-yl | (ESI)+: [M + H]+ = 579.4 |
| 636 | CH | Me | thiophen-2-yl | (ESI)+: [M + H]+ = 584.4 |
| 637 | CH | Me | thiophen-3-yl | (ESI)+: [M + H]+ = 584.4 |
| 638 | CH | Me | 2,5-dimethylfuran-3-yl | (ESI)+: [M + H]+ = 596.4 |

-continued

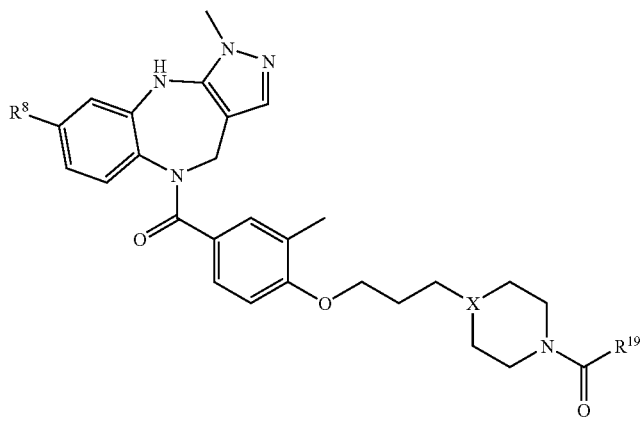

| Compound number | X | R⁸ | R¹⁹ | MS |
|---|---|---|---|---|
| 639 | CH | Me | (2-furyl) | (ESI)+: [M + H]+ = 568.4 |
| 640 | CH | Me | (isoxazolyl) | (ESI)+: [M + H]+ = 569.4 |
| 641 | CH | Me | (methyl-phenyl-triazolyl) | (ESI)+: [M + H]+ = 659.5 |
| 642 | CH | Me | CH₂CH₂CH₃ | (ESI)+: [M + H]+ = 544.4 |
| 643 | CH | Me | (cyclopropyl) | (ESI)+: [M + H]+ = 542.4 |
| 644 | CH | Me | C(CH₃)₃ | (ESI)+: [M + H]+ = 558.4 |
| 645 | CH | Me | (CH₂-cyclopentyl) | (ESI)+: [M + H]+ = 584.4 |
| 646 | CH | Me | CH₂(CH₂)₃CH₃ | (ESI)+: [M + H]+ = 572.4 |
| 647 | CH | Me | CH(CH₂CH₃)CH₂CH₂CH₃ | (ESI)+: [M + H]+ = 600.5 |
| 648 | CH | Me | (dimethoxyphenyl) | (ESI)+: [M + H]+ = 652.5 |
| 649 | CH | Me | (benzyl) | (ESI)+: [M + H]+ = 592.5 |
| 650 | CH | Me | (phenethyl) | (ESI)+: [M + H]+ = 606.5 |

-continued
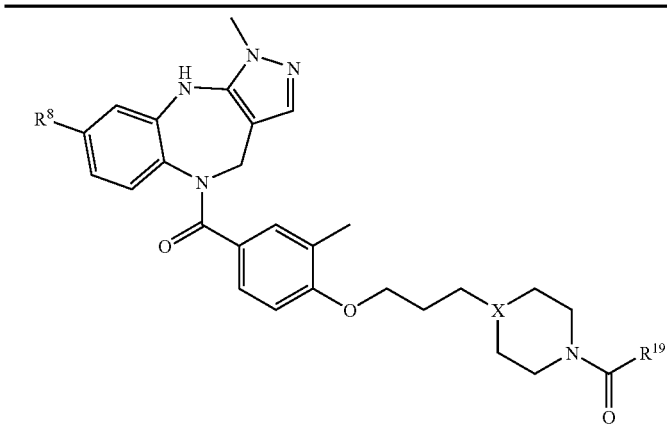
| Compound number | X | R⁸ | R¹⁹ | MS |
|---|---|---|---|---|
| 651 | CH | Me | (phenylcyclopropyl) | (ESI)+: [M + H]+ = 618.5 |
| 652 | CH | Me | (thiophen-2-ylmethyl) | (ESI)+: [M + H]+ = 598.4 |
| 653 | CH | Me | (phenoxymethyl) | (ESI)+: [M + H]+ = 608.5 |
| 654 | CH | Me | (benzyloxymethyl) | (ESI)+: [M + H]+ = 622.5 |
| 655 | CH | Me | CH₂CH₂CH₂CO₂CH₂CH₃ | (ESI)+: [M + H]+ = 616.5 |
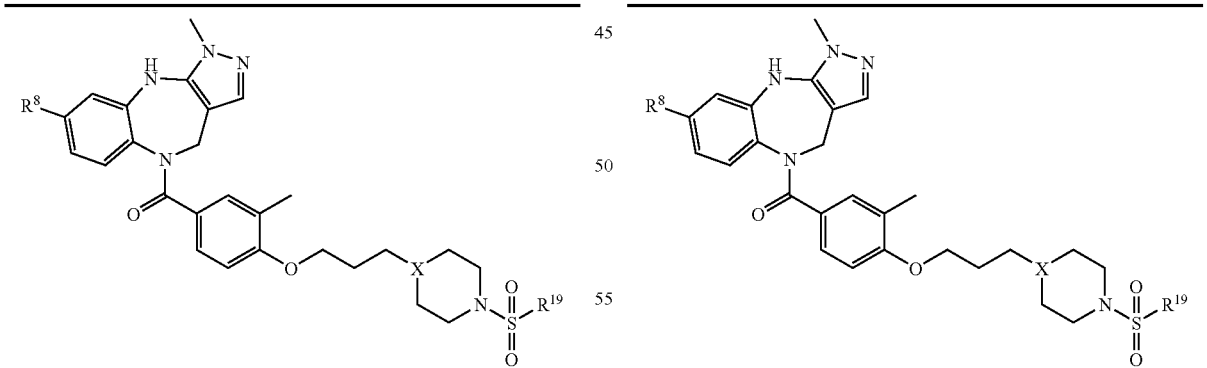
| Compound number | X | R⁸ | R¹⁹ | MS |
|---|---|---|---|---|
| 656 E54 | N | H | Me | (ESI)+: [M + H]+ = 539.2 |
| 657 | N | H | CH(CH₃)₂ | (ESI)+: [M + H]+ = 567.3 |
| 658 | N | H | (benzyl) | (ESI)+: [M + H]+ = 615.3 |

329
-continued

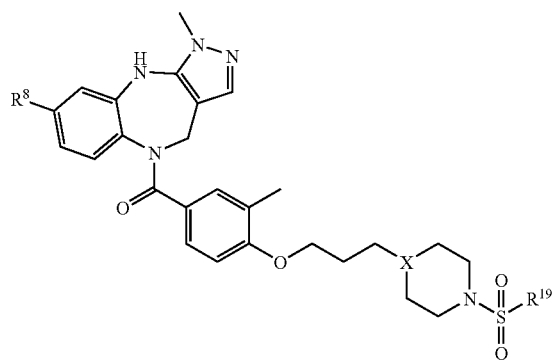

| Compound number | X | R8 | R19 | MS |
|---|---|---|---|---|
| 659 | N | H | phenyl | (ESI)+: [M + H]+ = 601.3 |
| 660 | N | H | 2,4-dichlorophenyl | (ESI)+: [M + H]+ = 669.3 |
| 661 | N | H | 4-chlorophenyl | (ESI)+: [M + H]+ = 635.3 |
| 662 | N | H | 3-chlorophenyl | (ESI)+: [M + H]+ = 635.3 |
| 663 | N | H | 2-chlorophenyl | (ESI)+: [M + H]+ = 635.3 |
| 664 | N | H | 4-methoxyphenyl | (ESI)+: [M + H]+ = 631.3 |
| 665 | N | H | 4-methylphenyl | (ESI)+: [M + H]+ = 615.3 |
| 666 | N | H | 4-cyanophenyl | (ESI)+: [M + H]+ = 626.3 |
| 667 | N | H | 4-trifluoromethylphenyl | (ESI)+: [M + H]+ = 669.3 |

330
-continued

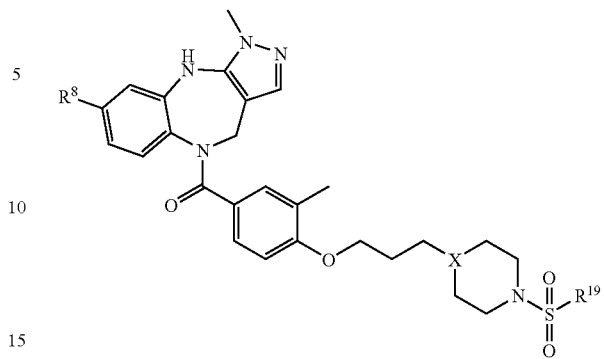

| Compound number | X | R8 | R19 | MS |
|---|---|---|---|---|
| 668 | N | H | 4-acetamidophenyl | (ESI)+: [M + H]+ = 658.4 |
| 669 | N | H | 5-chlorothiophen-2-yl | (ESI)+: [M + H]+ = 641.3 |
| 670 | N | H | 1-methylimidazol-4-yl | (ESI)+: [M + H]+ = 605.3 |
| 671 | N | H | $CH_2CF_3$ | (ESI)+: [M + H]+ = 607.3 |
| 672 | N | H | 3-bromo-2-chloropyridin-5-yl | (ESI)+: [M + H]+ = 716.2 |
| 673 | N | H | 5-(methoxycarbonyl)furan-2-yl | (ESI)+: [M + H]+ = 649.3 |
| 674 | N | H | $CH_2CH_3$ | (ESI)+: [M + H]+ = 553.3 |
| 675 | N | H | $CH_2CH_2CH_3$ | (ESI)+: [M + H]+ = 567.3 |
| 676 | N | H | $CH_2CH_2CH_2CH_3$ | (ESI)+: [M + H]+ = 581.3 |
| 677 | CH | Me | $CH_3$ | (ESI)+: [M + H]+ = 552.3 |
| 678 | CH | Me | $CH(CH_3)_2$ | (ESI)+: [M + H]+ = 580.4 |
| 679 | CH | Me | benzyl | (ESI)+: [M + H]+ = 628.5 |
| 680 | CH | Me | phenyl | (ESI)+: [M + H]+ = 614.4 |

| | | | | |
|---|---|---|---|---|
| | | | | 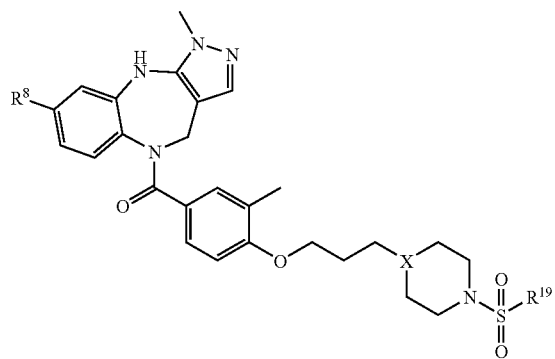 |

| Compound number | X | R⁸ | R¹⁹ | MS |
|---|---|---|---|---|
| 681 | CH | Me | 2,4-dichlorophenyl | (ESI)+: [M + H]+ = 682.4 |
| 682 | CH | Me | 4-chlorophenyl | (ESI)+: [M + H]+ = 648.4 |
| 683 | CH | Me | 3-chlorophenyl | (ESI)+: [M + H]+ = 648.4 |
| 684 | CH | Me | 2-chlorophenyl | (ESI)+: [M + H]+ = 648.4 |
| 685 | CH | Me | 4-methoxyphenyl | (ESI)+: [M + H]+ = 644.5 |
| 686 | CH | Me | 4-methylphenyl | (ESI)+: [M + H]+ = 628.5 |
| 687 | CH | Me | 4-cyanophenyl | (ESI)+: [M + H]+ = 639.5 |
| 688 | CH | Me | 4-(trifluoromethyl)phenyl | (ESI)+: [M + H]+ = 682.4 |

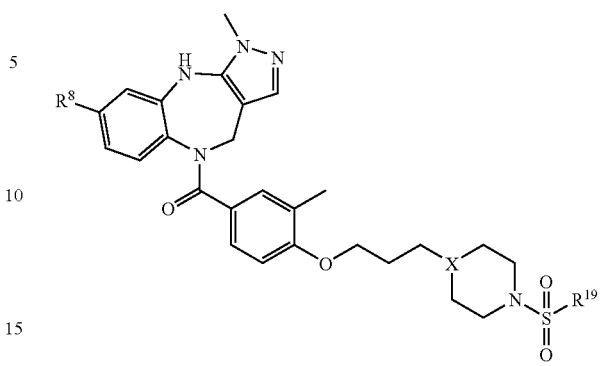

| Compound number | X | R⁸ | R¹⁹ | MS |
|---|---|---|---|---|
| 689 | CH | Me | 4-acetamidophenyl | (ESI)+: [M + H]+ = 671.5 |
| 690 | CH | Me | 5-chlorothien-2-yl | (ESI)+: [M + H]+ = 654.4 |
| 691 | CH | Me | 1-methylimidazol-4-yl | (ESI)+: [M + H]+ = 618.5 |
| 692 | CH | Me | 2-chloro-3-bromopyridin-5-yl | (ESI)+: [M + H]+ = 729.2 |
| 693 | CH | Me | 5-(methoxycarbonyl)furan-2-yl | (ESI)+: [M + H]+ = 662.4 |
| 694 | CH | Me | $CH_2CH_3$ | (ESI)+: [M + H]+ = 566.3 |
| 695 | CH | Me | $CH_2CH_2CH_3$ | (ESI)+: [M + H]+ = 580.4 |
| 696 | CH | Me | $CH_2CH_2CH_2CH_3$ | (ESI)+: [M + H]+ = 594.4 |

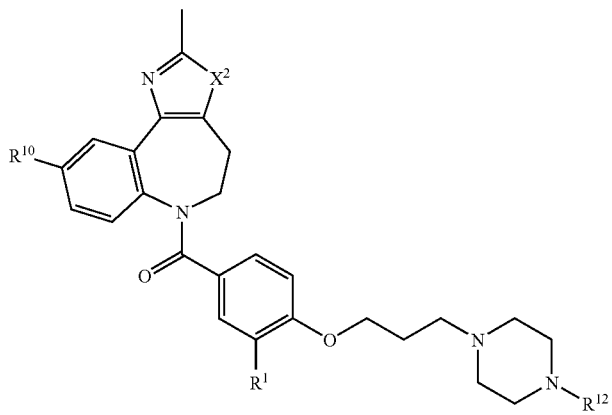
| Compound number | R¹ | R¹⁰ | R¹² | X² | MS | 1H NMR |
|---|---|---|---|---|---|---|
| 697 | F | Cl | cyclopropylmethyl | S | (ESI)+: [M + H]+ = 569.5, 571.3 | 0.05-0.15 (2H, m), 0.45-0.55 (2H, m), 0.80-0.90 (1H, m), 1.90-2.00 (2H, m), 2.24 (2H, d, J = 6.4 Hz), 2.35-2.70 (10H, m), 2.73 (3H, s), 2.95-3.25 (2H, m), 3.45-3.55 (1H, m), 3.99 (2H, t, J = 6.4 Hz), 5.15-5.25 (1H, m), 6.60-6.75 (3H, m), 6.90-7.05 (2H, m), 8.41 (1H, d, J = 2.5 Hz) |
| 698 | Cl | Me | 4-isobutylbenzyl | S | (ESI)+: [M + H]+ = 643.3, 645.4 | 1.22 (6H, d, J = 6.9 Hz), 1.87-1.99 (2H, m), 2.34 (3H, s), 2.45-2.52 (10H, m), 2.74 (3H, s), 2.87 (1H, septet, J = 6.9 Hz), 3.03-3.18 (2H, m), 3.45 (2H, s), 3.45-3.54 (1H, m), 3.95 (2H, t, J = 6.2 Hz), 5.13-5.19 (1H, m), 6.52 (1H, d, J = 8.6 Hz), 6.57 (1H, d, J = 8.2 Hz), 6.75 (1H, dd, J = 2.2, 8.6 Hz), 6.81 (1H, d, J = 8.2 Hz), 7.15 (2H, d, J = 8.2 Hz), 7.21 (2H, d, J = 8.2 Hz), 7.38 (1H, d, J = 2.2 Hz), 8.18 (1H, s) |
| 699 | Cl | Me | 3,3-dimethylbutyl | S | (ESI)+: [M + H]+ = 595.4, 597.4 | 0.89 (9H, s), 1.38-1.44 (2H, m), 1.89-1.99 (2H, m), 2.34 (3H, s), 2.35-2.41 (2H, m), 2.47-2.56 (10H, m), 2.73 (3H, s), 3.01-3.18 (2H, m), 3.45-3.57 (1H, m), 3.95 (2H, t, J = 6.4 Hz), 5.12-5.19 (1H, m), 6.52 (1H, d, J = 8.6 Hz), 6.57 (1H, d, J = 8.4 Hz), 6.75 (1H, dd, J = 2.2, 8.4 Hz), 6.80 (1H, d, J = 8.6 Hz), 7.38 (1H, d, J = 2.2 Hz), 8.17 (1H, s) |

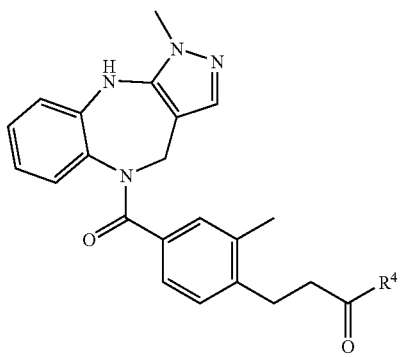
| Compound number | R⁴ | | ¹H NMR: δ (ppm) |
|---|---|---|---|
| 700 | piperazine-CH₂CH₂-C(CH₃)₃ | (ESI)+: [M + H]+ = 543.6 | 0.85 (9H, s), 1.30-1.41 (4H, m), 2.10 (3H, s), 2.28-2.45 (6H, m), 2.71-2.82 (2H, m), 3.25-3.34 (2H, m), 3.52-3.65 (2H, m), 3.71 (3H, s), 3.93 (1H, d, J = 14.6 Hz), 5.85 (1H, d, J = 14.6 Hz), 6.65 (1H, s), 6.75-7.01 (5H, m), 7.07-7.17 (3H, m) |
| 701 | 4-oxopiperidin-1-yl | (ESI)+: [M + H]+ = 472.7 | 2.17 (3H, s), 2.29 (2H, t, J = 5.7 Hz), 2.40 (2H, t, J = 5.7 Hz), 2.53 (2H, t, J = 7.2 Hz), 2.87 (2H, t, J = 7.2 Hz), 3.52 (2H, brs), 3.79 (3H, s), 3.77-3.83 (2H, m), 3.95 (1H, d, J = 14.6 Hz), 5.89 (1H, d, J = 14.6 Hz), 6.19 (1H, s), 6.62-6.74 (2H, m), 6.81-6.94 (3H, m), 7.02-7.08 (1H, m), 7.16 (1H, s) |
| 702 | piperazine-CH₂-cyclobutyl | (ESI)+: [M + H]+ = 527.7 | 1.61-1.68 (2H, m), 1.68-1.91 (3H, m), 1.92-2.08 (2H, m), 2.14 (3H, s), 2.28-2.51 (4H, m), 2.72-2.89 (2H, m), 2.93-3.08 (2H, m), 3.21-3.34 (2H, m), 3.46-3.69 (4H, m), 3.80 (3H, s), 3.98 (1H, d, J = 14.6 Hz), 5.87 (1H, d, J = 14.6 Hz), 6.51 (1H, s), 6.68 (2H, s), 6.74-6.89 (2H, m), 6.94-7.08 (2H, m), 7.13 (1H, s) |
| 703 | imidazolidine-CH₂-cyclopropyl | (ESI)+: [M + H]+ = 499.7 | — |

-continued
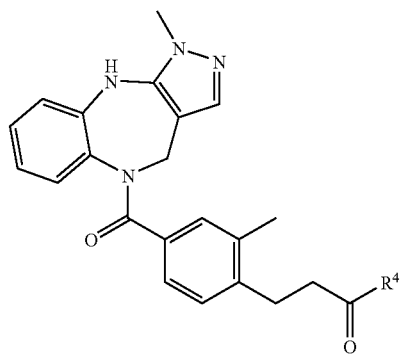
| Compound number | R⁴ | ¹H NMR: δ (ppm) | |
|---|---|---|---|
| 704 | (pyrrolidinylethyl-piperazinyl) | (ESI)+: [M + H]+ = 556.7 | — |
| 705 | (4-methylphenacyl-piperazinyl) | (ESI)+: [M + H]+ = 632.0 (MeCN adduct) | — |
| 706 | (pyrrolidinyl) | (ESI)+: [M + H]+ = 444.3 | — |
| 707 | (2-methoxycarbonyl-piperidinyl) | (ESI)+: [M + H]+ = 516.4 | — |
| 708 | (1,2,3,4-tetrahydroisoquinolin-2-yl) | (ESI)+: [M + H]+ = 506.3 | — |
| 709 | (2,6-dimethylpiperidinyl) | (ESI)+: [M + H]+ = 486.4 | — |
| 710 E56 | (4-(furan-2-carbonyl)piperazinyl) | (ESI)+: [M + H]+ = 553.4 | — |
| 711 | (piperidinyl) | (ESI)+: [M + H]+ = 458.3 | — |

-continued
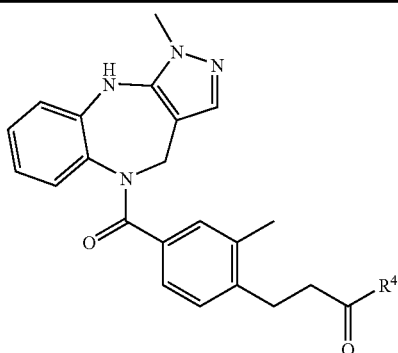
| Compound number | R⁴ | ¹H NMR: δ (ppm) | |
|---|---|---|---|
| 712 | azepan-1-yl | (ESI)+: [M + H]+ = 472.4 | — |
| 713 | morpholin-4-yl | (ESI)+: [M + H]+ = 406.4 | — |
| 714 | 4-(2-(isopropylamino)-2-oxoethyl)piperazin-1-yl | (ESI)+: [M + H]+ = 558.4 | — |
| 715 | 4-methylpiperazin-1-yl | (ESI)+: [M + H]+ = 473.3 | — |
| 716 | decahydroquinolin-1-yl | (ESI)+: [M + H]+ = 512.4 | — |
| 717 | decahydroisoquinolin-2-yl | (ESI)+: [M + H]+ = 512.4 | — |
| 718 | thiomorpholin-4-yl | (ESI)+: [M + H]+ = 476.3 | — |
| 719 | thiazolidin-3-yl | (ESI)+: [M + H]+ = 462.3 | — |
| 720 | 3-(methoxycarbonyl)-4-oxopiperidin-1-yl | (ESI)+: [M + H]+ = 530.4 | — |

-continued
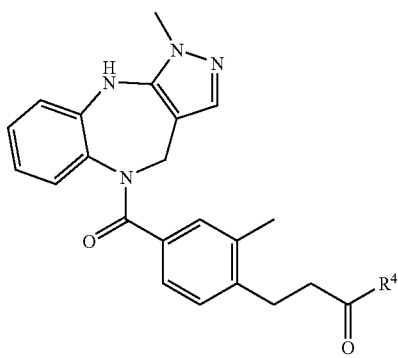
| Compound number | R⁴ | ¹H NMR: δ (ppm) | |
|---|---|---|---|
| 721 | piperidine-CH₂CH₂OH | (ESI)+: [M + H]+ = 502.4 | — |
| 722 | piperidine-CH₂CH₂OH (2-position) | (ESI)+: [M + H]+ = 502.4 | — |
| 723 | N-methylhomopiperazine | (ESI)+: [M + H]+ = 487.3 | — |
| 724 | piperazine-CH₂-(benzo[1,3]dioxole) | (ESI)+: [M + H]+ = 593.4 | — |
| 725 | 4-(4-fluorophenyl)piperazine | (ESI)+: [M + H]+ = 553.4 | — |
| 726 | 4-(CO₂Et)piperidine | (ESI)+: [M + H]+ = 530.4 | — |
| 727 | 4-(3,4-dichlorophenyl)piperazine | (ESI)+: [M + H]+ = 603.4 | — |
| 728 | 4-(3-trifluoromethylphenyl)piperazine | (ESI)+: [M + H]+ = 603.4 | — |

-continued
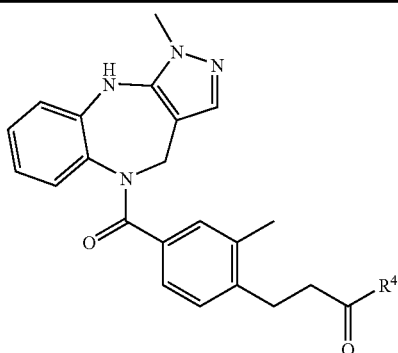
| Compound number | R⁴ | ¹H NMR: δ (ppm) | |
|---|---|---|---|
| 729 | ![2-methoxyphenyl piperazine] | (ESI)+: [M + H]+ = 565.4 | — |
| 730 | ![4-benzylpiperidine] | (ESI)+: [M + H]+ = 548.4 | — |
| 731 | ![4-pyrrolidinylpiperidine] | (ESI)+: [M + H]+ = 527.5 | — |
| 732 | ![7-methoxy-tetrahydrobenzazepine] | (ESI)+: [M + H]+ = 550.3 | — |
| 733 | ![indoline] | (ESI)+: [M + H]+ = 492.4 | — |
| 734 | ![1,2,3,4-tetrahydroquinoline] | (ESI)+: [M + H]+ = 506.4 | — |
| 735 | ![3,4-dihydro-2H-1,4-benzoxazine] | (ESI)+: [M + H]+ = 508.4 | — |

-continued
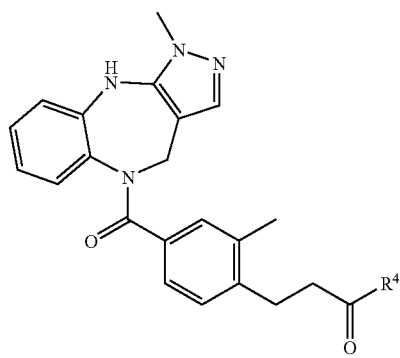
| Compound number | R⁴ | ¹H NMR: δ (ppm) | |
|---|---|---|---|
| 736 | ![pyrido-oxazine] | (ESI)+: [M + H]+ = 509.3 | — |
| 737 | ![piperazinyl-pyridine] | (ESI)+: [M + H]+ = 536.4 | — |
| 738 | ![acetyl-diazepane] | (ESI)+: [M + H]+ = 515.4 | — |
| 739 | ![piperidine-3-CONH₂] | (ESI)+: [M + H]+ = 501.4 | — |
| 740 | ![piperidine-4-CONH₂] | (ESI)+: [M + H]+ = 501.4 | — |
| 741 | ![piperidine-3-CON(Et)₂] | (ESI)+: [M + H]+ = 557.5 | — |
| 742 | ![2,6-dimethylmorpholine] | (ESI)+: [M + H]+ = 488.4 | — |

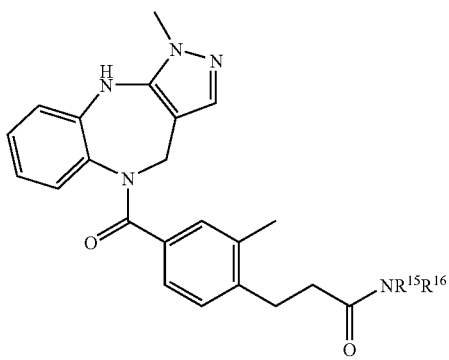
| Compound number | R¹⁵ | R¹⁶ | |
|---|---|---|---|
| 743 | H | phenyl | (ESI)+: [M + H]+ = 466.1 |
| 744 | H | 3,5-dimethylphenyl | (ESI)+: [M + H]+ = 494.2 |
| 745 | H | 4-OCF₃-phenyl | (ESI)+: [M + H]+ = 550.3 |
| 746 | H | 4-(1-hydroxyethyl)phenyl | (ESI)+: [M + H]+ = 510.3 |
| 747 | H | 4-CO₂C(CH₃)₃-phenyl | (ESI)+: [M + H]+ = 566.3 |
| 748 | H | 4-NMe₂-phenyl | (ESI)+: [M + H]+ = 509.3 |
| 749 | H | 2-pyridyl | (ESI)+: [M + H]+ = 467.2 |
| 750 | H | 3-pyridyl | (ESI)+: [M + H]+ = 467.2 |
| 751 | H | 4-methyl-5-(4-methoxyphenyl)thiazol-2-yl | (ESI)+: [M + H]+ = 593.3 |

-continued

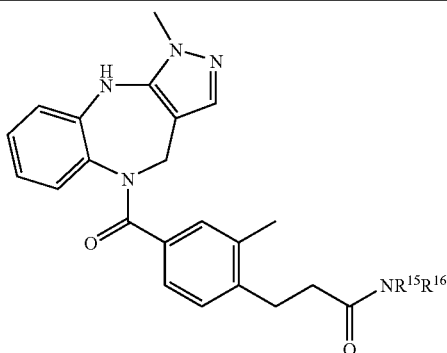

| Compound number | R15 | R16 | |
|---|---|---|---|
| 752 | H | (2-thiazolyl, 4-phenyl) | (ESI)+: [M + H]+ = 549.3 |
| 753 | H | (propyl-imidazole) | (ESI)+: [M + H]+ = 498.3 |
| 754 | H | CH$_3$ | (ESI)+ [M + H]+ = 404.2 |
| 755 | H | CH$_2$CH$_3$ | (ESI)+ [M + H]+ = 418.2 |
| 756 | H | CH$_2$CH(CH$_3$)$_3$ | (ESI)+ [M + H]+ = 446.2 |
| 757 | H | CH$_2$CH$_2$CH$_3$ | (ESI)+ [M + H]+ = 432.2 |
| 758 | H | cyclopropyl | (ESI)+: [M + H]+ = 430.2 |
| 759 | H | CH$_2$(CH$_2$)$_4$CH$_3$ | (ESI)+ [M + H]+ = 474.3 |
| 760 | H | cyclopentyl | (ESI)+: [M + H]+ = 458.2 |
| 761 | H | cycloheptyl | (ESI)+: [M + H]+ = 486.3 |
| 762 | H | C(CH$_3$)$_2$CH$_2$CH$_3$ | (ESI)+ [M + H]+ = 460.2 |
| 763 | H | CH$_2$(CH$_2$CH$_3$)$_2$ | (ESI)+ [M + H]+ = 460.3 |
| 764 | H | CH$_2$CH$_2$CH(CH$_3$)$_2$ | (ESI)+ [M + H]+ = 460.2 |
| 765 | H | 1-indanyl | (ESI)+: [M + H]+ = 506.3 |
| 766 | H | 2-indanyl | (ESI)+: [M + H]+ = 506.3 |

-continued
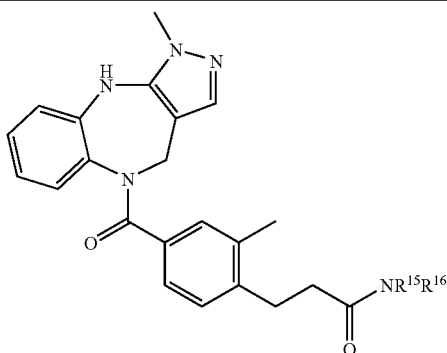
| Compound number | R$^{15}$ | R$^{16}$ | |
|---|---|---|---|
| 767 | H | cyclohexylmethyl | (ESI)+: [M + H]+ = 486.3 |
| 768 | H | benzyl | (ESI)+: [M + H]+ = 480.2 |
| 769 | H | 2-OCF$_3$-benzyl | (ESI)+: [M + H]+ = 564.2 |
| 770 | H | 3-CF$_3$-benzyl | (ESI)+: [M + H]+ = 548.2 |
| 771 | H | 4-OMe-benzyl | (ESI)+: [M + H]+ = 510.3 |
| 772 | H | 2,3-diCl-benzyl | (ESI)+: [M + H]+ = 548.2 |
| 773 | H | 2-phenylethyl | (ESI)+: [M + H]+ = 494.3 |
| 774 | H | 2-(4-Cl-phenyl)ethyl | (ESI)+: [M + H]+ = 528.2 |
| 775 | H | 3-phenylpropyl | (ESI)+: [M + H]+ = 508.2 |
| 776 | H | 1-hydroxymethyl-2-phenylethyl | (ESI)+: [M + H]+ = 524.3 |

-continued

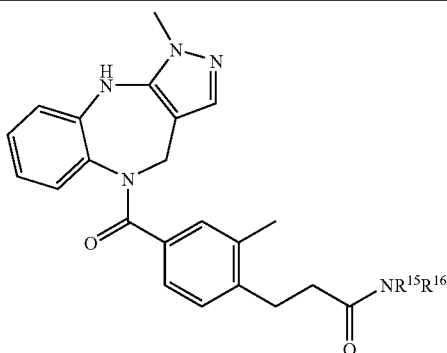

| Compound number | R15 | R16 | |
|---|---|---|---|
| 777 | H | 2-pyridylmethyl | (ESI)+: [M + H]+ = 481.2 |
| 778 | H | 4-pyridylmethyl | (ESI)+: [M + H]+ = 481.2 |
| 779 | H | 2-(2-pyridyl)ethyl | (ESI)+: [M + H]+ = 495.3 |
| 780 | H | 2-thienylmethyl | (ESI)+: [M + H]+ = 486.2 |
| 781 | H | 2-furylmethyl | (ESI)+: [M + H]+ = 470.2 |
| 782 | H | $CH_2CH_2F$ | (ESI)+ [M + H]+ = 436.2 |
| 783 | H | $CH_2CH_2OH$ | (ESI)+ [M + H]+ = 434.2 |
| 784 | H | $CH_2CH_2CH_2OH$ | (ESI)+ [M + H]+ = 448.2 |
| 785 | H | $CH_2(CH_2)_3OH$ | (ESI)+ [M + H]+ = 462.2 |
| 786 | H | $CH_2(CH_2)_4OH$ | (ESI)+ [M + H]+ = 476.2 |
| 787 | H | CH(CH3)CH2OMe | (ESI)+: [M + H]+ = 462.2 |
| 788 | H | methacrylate ester | (ESI)+: [M + H]+ = 502.2 |
| 789 | H | $CH_2(CH_2)_2SCH_3$ | (ESI)+ [M + H]+ = 478.2 |
| 790 | H | 2-morpholinoethyl | (ESI)+: [M + H]+ = 503.2 |

-continued

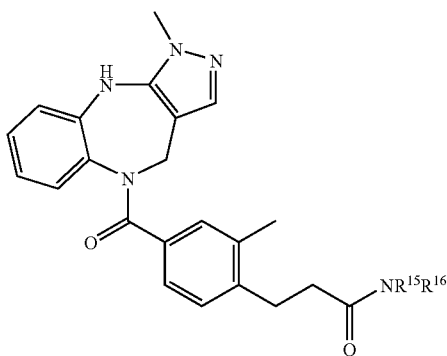

| Compound number | R¹⁵ | R¹⁶ | |
|---|---|---|---|
| 791 | H | CH₂CH₂N(CH₃)₂ | (ESI)+ [M + H]+ = 461.2 |
| 792 | H | ⋯⋯CH(CH₃)CH₂CH₂CH₂N(Et)₂ | (ESI)+: [M + H]+ = 531.4 |
| 793 | H | CH₂(CH₂)₂N(CH₃)₂ | (ESI)+ [M + H]+ = 475.2 |
| 794 | H | 4-(N-benzyl)piperidinyl | (ESI)+: [M + H]+ = 563.3 |
| 795 | H | CH₂CH₂NHCOCH₃ | (ESI)+ [M + H]+ = 475.2 |
| 796 | H | 4-(N-CO₂Et)piperidinyl | (ESI)+: [M + H]+ = 545.3 |
| 797 | H | CH₂CO₂CH₃ | (ESI)+ [M + H]+ = 462.2 |
| 798 | H | ⋯⋯CH(CO₂Me)CH₂-cyclohexyl | (ESI)+: [M + H]+ = 558.4 |
| 799 | H | CH₂CO₂CH(CH₃)₂ | (ESI)+ [M + H]+ = 490.3 |
| 800 | H | ⋯⋯CH(CO₂CH₃)CH₂CH₂CO₂C(CH₃)₃ | (ESI)+: [M + H]+ = 590.3 |
| 801 | H | CH₂CONH₂ | (ESI)+ [M + H]+ = 447.1 |
| 802 | H | CH₂CN | (ESI)+ [M + H]+ = 429.2 |
| 803 | H | CH₂CH₂CN | (ESI)+ [M + H]+ = 443.2 |
| 804 | H | CH₂(CH₂)₄CN | (ESI)+ [M + H]+ = 485.3 |
| 805 | H | CH₂CF₃ | (ESI)+ [M + H]+ = 472.2 |

-continued

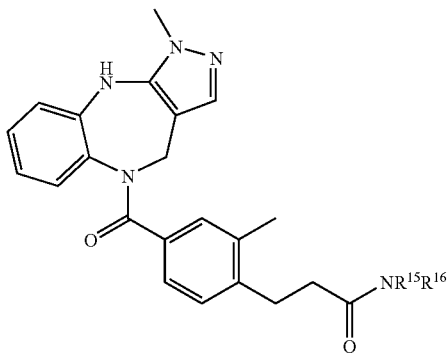

| Compound number | R15 | R16 | |
|---|---|---|---|
| 806 | CH3 | benzyl | (ESI)+: [M + H]+ = 494.4 |
| 807 | CH2CH2CH3 | 4-nitrobenzyl | (ESI)+: [M + H]+ = 567.4 |
| 808 | CH3 | CH2CH3 | (ESI)+ [M + H]+ = 432.3 |
| 809 | CH2CH3 | (pyridin-4-yl)methyl | (ESI)+: [M + H]+ = 509.4 |
| 810 | CH2CH2CN | (pyridin-4-yl)methyl | (ESI)+: [M + H]+ = 534.3 |
| 811 | CH2CO2CH2CH3 | benzyl | (ESI)+: [M + H]+ = 566.4 |
| 812 | CH3 | naphthalen-1-ylmethyl | (ESI)+: [M + H]+ = 544.4 |
| 813 | CH3 | CH2CH2CH2CH3 | (ESI)+ [M + H]+ = 460.3 |
| 814 | CH3 | CH2(CH2)4CH3 | (ESI)+ [M + H]+ = 488.4 |
| 815 | CH(CH3)2 | cyclohexyl | (ESI)+: [M + H]+ = 514.5 |
| 816 | CH2CH3 | CH2CH3 | (ESI)+ [M + H]+ = 446.2 |
| 817 | CH(CH3)2 | CH(CH3)2 | (ESI)+ [M + H]+ = 474.4 |
| 818 | CH3 | 2-(pyridin-4-yl)ethyl | (ESI)+: [M + H]+ = 509.4 |

-continued
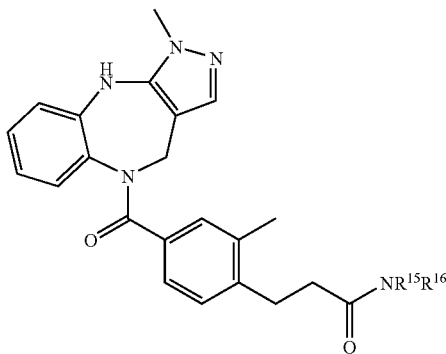
| Compound number | R[15] | R[16] | |
|---|---|---|---|
| 819 | CH₂CH₃ | (2-oxo-1-phenylpropyl, branched) | (ESI)+: [M + H]+ = 550.4 |
| 820 | CH(CH₃)₂ | CH₂CH₂OCH₃ | (ESI)+ [M + H]+ = 490.4 |
| 821 | CH₃ | CH₂CH₂-phenyl | (ESI)+: [M + H]+ = 508.4 |
| 822 | CH₂CH₂OCH₃ | CH₂CH₂OCH₃ | (ESI)+ [M + H]+ = 506.3 |
| 823 | CH₃ | C₆H₅ | (ESI)+ [M + H]+ = 480.3 |
| 824 | CH₂CH₂OH | C₆H₅ | (ESI)+ [M + H]+ = 510.4 |
| 825 | CH₃ | 4-chlorophenyl | (ESI)+: [M + H]+ = 514.4 |
| 826 | CH₃ | 2-pyridyl | (ESI)+: [M + H]+ = 481.4 |
| 827 | CH₃ | 4-pyridyl | (ESI)+: [M + H]+ = 481.3 |
| 828 | CH₂CH₃ | 1,3,4-thiadiazol-2-yl | (ESI)+: [M + H]+ = 502.4 |

-continued
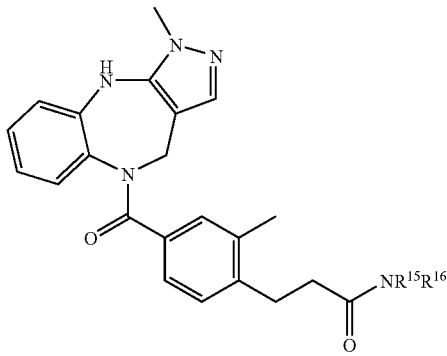
| Compound number | R[15] | R[16] | |
|---|---|---|---|
| 829 | $CH_3$ | $CH_3$ | (ESI)+ [M + H]+ = 418.3 |
| 830 | $CH_3$ | ⋯CH(OH)CH₂CH(Ph) (1-phenyl-3-hydroxybutyl group) | (ESI)+: [M + H]+ = 538.3 |
| 831 | $CH_3$ | furan-2-ylmethyl | (ESI)+: [M + H]+ = 484.3 |
| 832 | $CH_3$ | $CH_2CO_2H$ | (ESI)+ [M − H]+ = 460.4 |
| 833 | $CH_3$ | $CH_2CH_2CH_2CO_2H$ | (ESI)+ [M + H]+ = 490.4 |
| 834 | $CH_3$ | $CH_2CN$ | (ESI)+ [M + H]+ = 443.3 |
| 835 | $CH_3$ | $CH_2CH_2CN$ | (ESI)+ [M + H]+ = 457.3 |
| 836 | $CH_2CH_2N(CH_3)_2$ | benzyl | (ESI)+: [M + H]+ = 551.5 |
| 837 | $CH_2CH_2OH$ | benzyl | (ESI)+: [M + H]+ = 524.4 |
| 838 | $CH_2CN$ | benzyl | (ESI)+: [M + H]+ = 519.4 |

| 363 | 364 |
|---|---|
| 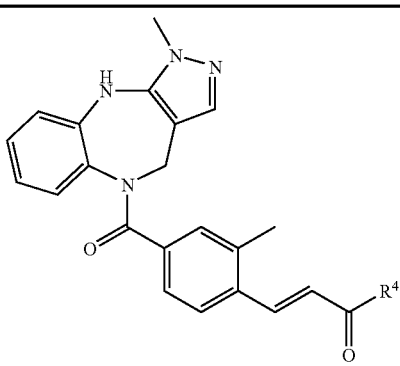 | -continued<br/>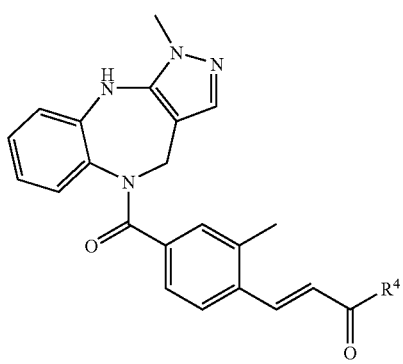 |
| Compound number | R4 | MS |
|---|---|---|
| 839 E57 | (methylpiperazinyl-ethyl-piperidine) | |
| 840 | (methylpiperidinyl-methyl-NH-cyclopropyl) | |
| Compound number | R4 | MS |
|---|---|---|
| 841 | (methylpiperazinyl-methyl-cyclobutyl) | |
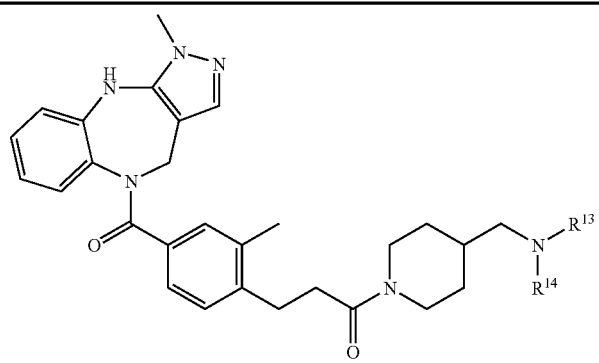
| Compound number | R13 | R14 | MS | 1H NMR |
|---|---|---|---|---|
| 842 E58 | Me | CH2CH2CH2CH3 | (ESI)+: [M + H]+ = 557.6 | |
| 843 | H | (methylpiperidinyl-N-benzyl) | (ESI)+: [M + H]+ = 660.7 | — |
| 844 | H | CH2C6H5 | (ESI)+: [M + H]+ = 577.6 | — |
| 845 | H | CH2CH2C6H5 | (ESI)+: [M + H]+ = 591.7 | — |
| 846 | H | (propyl-imidazolyl) | (ESI)+: [M + H]+ = 595.7 | — |

-continued
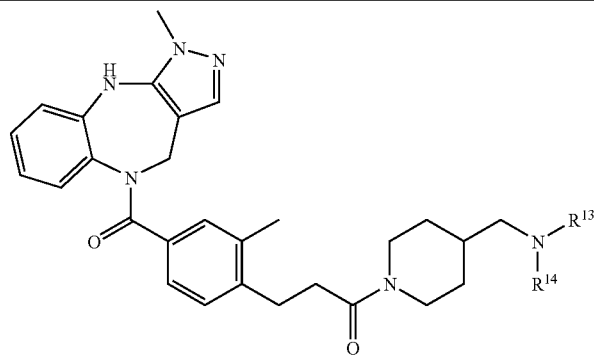
| Compound number | R¹³ | R¹⁴ | MS | ¹H NMR |
|---|---|---|---|---|
| 847 | H | cyclopentyl | (ESI)+: [M + H]+ = 555.6 | — |
| 848 | H | CH₂CH(CH₃)₂ | (ESI)+: [M + H]+ = 543.6 | — |
| Compound number | R⁴ | MS | ¹H NMR |
|---|---|---|---|
| 849 | (1-methylpiperidin-4-yl)methyl-1,2,3,4-tetrahydroisoquinolin-2-yl | (ESI)+: [M + H]+ = 603.7 | — |
| 850 | (1-methylpiperidin-4-yl)methyl-thiomorpholin-4-yl | (ESI)+: [M + H]+ = 573.6 | — |

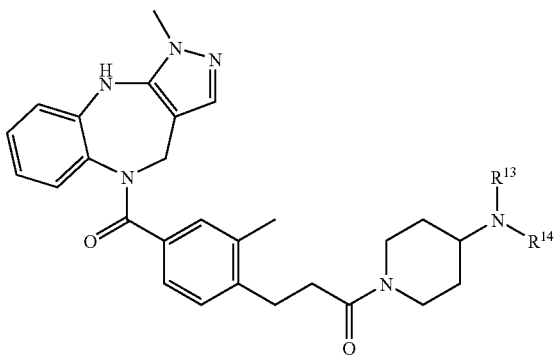

| Compound number | R<sup>13</sup> | R<sup>14</sup> | MS | <sup>1</sup>H NMR |
|---|---|---|---|---|
| 851 E59 | H | ⋯CH$_2$CH$_2$-morpholine | (ESI)+: [M + H]+ = 586.6 | — |
| 852 | H | CH$_2$C$_6$H$_5$ | (ESI)+: [M + H]+ = 563.6 | — |
| 853 | H | ⋯CH$_2$-cyclohexyl | (ESI)+: [M + H]+ = 569.6 | — |
| 854 | H | ⋯-cyclopentyl | (ESI)+: [M + H]+ = 541.5 | — |
| 855 | H | CH$_2$CH(CH$_3$)$_2$ | (ESI)+: [M + H]+ = 529.8 | — |
| 856 | CH$_2$C$_6$H$_5$ | CH$_2$CH$_2$CH$_3$ | (ESI)+: [M + H]+ = 619.6 | — |
| 857 | H | ⋯-cyclobutyl | (ESI)+: [M + H]+ = 527.6 | — |
| 858 | CH$_2$C$_6$H$_5$ | CH$_2$CH$_2$N(CH$_3$)$_2$ | (ESI)+: [M + H]+ = 634.6 | — |
| 859 | H | ⋯CH$_2$CH$_2$-pyrrolidinyl | (ESI)+: [M + H]+ = 570.6 | — |
| 860 | H | CH$_2$CH$_2$OH | (ESI)+: [M + H]+ = 517.6 | — |
| 861 | H | ⋯CH$_2$CH$_2$-(N-methylpyrrolidin-2-yl) | (ESI)+: [M + H]+ = 584.6 | — |
| 862 | H | CH$_2$CH$_2$CH$_2$OH | (ESI)+: [M + H]+ = 531.6 | — |
| 863 | H | ⋯CH$_2$CH$_2$CH$_2$-imidazolyl | (ESI)+: [M + H]+ = 581.6 | — |
| 864 | H | CH$_2$CH$_2$C$_6$H$_5$ | (ESI)+: [M + H]+ = 577.6 | — |

-continued
| | | | MS | |
|---|---|---|---|---|
| 865 | H | 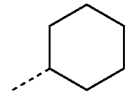 | (ESI)+:<br>[M + H]+ = 555.6 | — |
| 866 | H | CH$_2$(CH$_2$)$_4$CH$_3$ | (ESI)+:<br>[M + H]+ = 557.6 | — |
| 867 | H | 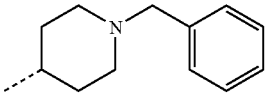 | (ESI)+:<br>[M + H]+ = 646.6 | — |
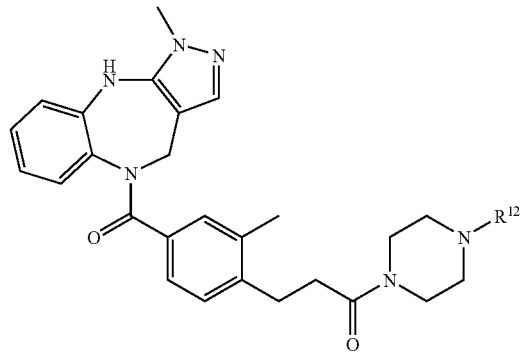
| Compound<br>number | R$^{12}$ | MS |
|---|---|---|
| 868<br>E60 | CH$_2$CH$_2$CH$_2$CH$_2$CH$_2$CH$_3$ | (ESI)+:<br>[M + H]+ = 543.4 |
| 869 | CH$_2$CH$_2$CH$_3$ | (ESI)+:<br>[M + H]+ = 501.4 |
| 870 | CH$_2$(CH$_2$)$_3$OH | (ESI)+:<br>[M + H]+ = 531.3 |
| 871 | CH$_2$(CH$_2$)$_2$CN | (ESI)+:<br>[M + H]+ = 526.4 |
| 872 | 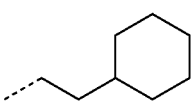 | (ESI)+:<br>[M + H]+ = 569.4 |
| 873 | 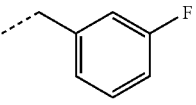 | (ESI)+:<br>[M + H]+ = 567.3 |
| 874 | 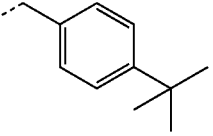 | (ESI)+:<br>[M + H]+ = 605.5 |
| 875 | 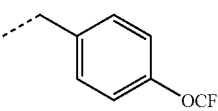 | (ESI)+:<br>[M + H]+ = 633.5 |
| 876 | 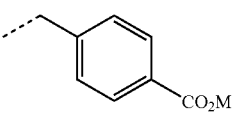 | (ESI)+:<br>[M + H]+ = 607.4 |
| 877 | 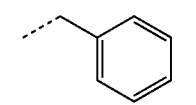 | (ESI)+:<br>[M + H]+ = 549.4 |

-continued
| | | |
|---|---|---|
| 878 | CH₂CH₂OH | (ESI)+:<br>[M + H]+ = 503.3 |
| 879 | CH₂CO₂CH(CH₃)₂ | (ESI)+:<br>[M + H]+ = 559.3 |
| 880 | CH₂CH₂CH(CH₃)₂ | (ESI)+:<br>[M + H]+ = 529.4 |
| 881 | CH₂CH₂CH₂OH | (ESI)+:<br>[M + H]+ = 517.4 |
| 882 | CH₂CN | (ESI)+:<br>[M + H]+ = 498.4 |
| 883 | CH₂CH₂OCH₂CH₃ | (ESI)+:<br>[M + H]+ = 531.4 |
| 884 | 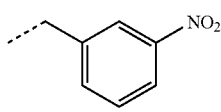 | (ESI)+:<br>[M + H]+ = 594.4 |
| 885 | 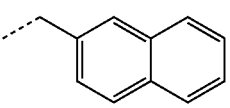 | (ESI)+:<br>[M + H]+ = 599.4 |
| 886 | 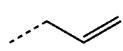 | (ESI)+:<br>[M + H]+ = 499.4 |
| 887 | 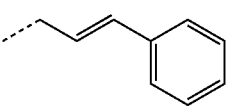 | (ESI)+:<br>[M + H]+ = 575.4 |
| 888 | 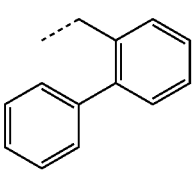 | (ESI)+:<br>[M + H]+ = 625.5 |
| 889 | CH₂COC(CH₃)₃ | (ESI)+:<br>[M + H]+ = 557.4 |
| 890 | CH₂CONH₂ | (ESI)+:<br>[M + H]+ = 516.4 |
| 891 | 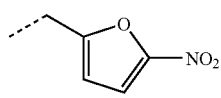 | (ESI)+:<br>[M + H]+ = 584.4 |
| 892 | 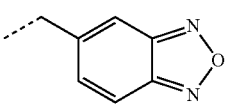 | (ESI)+:<br>[M + H]+ = 591.4 |

373

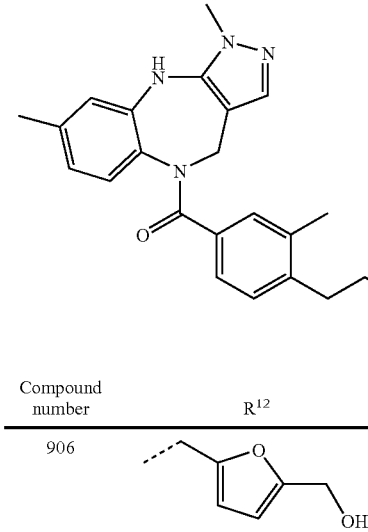

| Compound number | R12 | MS |
|---|---|---|
| 893 | CH₂CH₂CH₃ | (ESI)+: [M + H]+ = 515.5 |
| 894 | CH₂CH(CH₃)₂ | (ESI)+: [M + H]+ = 529.5 |
| 895 | 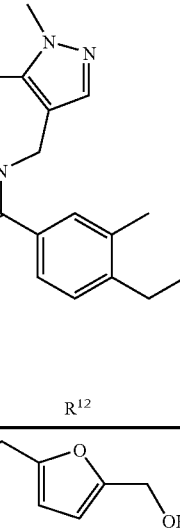 | (ESI)+: [M + H]+ = 563.4 |
| 896 | 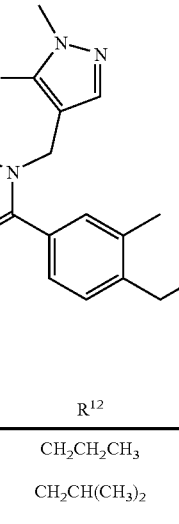 | (ESI)+: [M + H]+ = 569.4 |
| 897 | 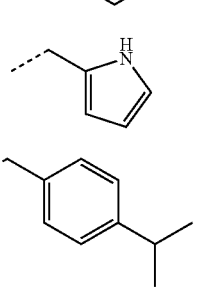 | (ESI)+: [M + H]+ = 577.5 |
| 898 | 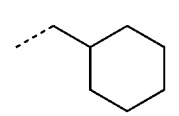 | (ESI)+: [M + H]+ = 597.4 |
| 899 | 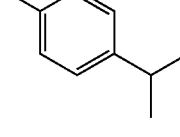 | (ESI)+: [M + H]+ = 597.4 |
| 900 | 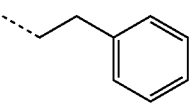 | (ESI)+: [M + H]+ = 597.5 |
| 901 | CH₂CH₂CH₂CH₃ | (ESI)+: [M + H]+ = 543.4 |
| 902 | 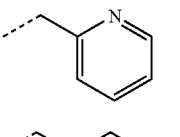 | (ESI)+: [M + H]+ = 527.4 |
| 903 | 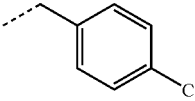 | (ESI)+: [M + H]+ = 591.5 |
| 904 | CH₂CH₂CH(CH₃)₂ | (ESI)+: [M + H]+ = 543.5 |
| 905 | 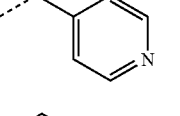 | (ESI)+: [M + H]+ = 553.4 |

374
-continued

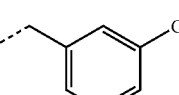

| Compound number | R12 | MS |
|---|---|---|
| 906 | 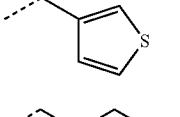 | (ESI)+: [M + H]+ = 583.5 |
| 907 | 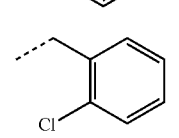 | (ESI)+: [M + H]+ = 564.4 |
| 908 | 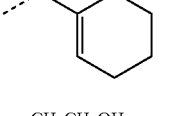 | (ESI)+: [M + H]+ = 552.4 |
| 909 |  | (ESI)+: [M + H]+ = 605.5 |
| 910 | 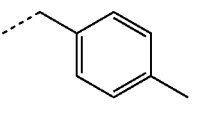 | (ESI)+: [M + H]+ = 564.4 |
| 911 | 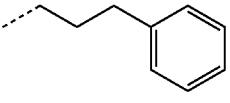 | (ESI)+: [M + H]+ = 564.4 |
| 912 | 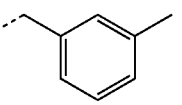 | (ESI)+: [M + H]+ = 569.3 |
| 913 | 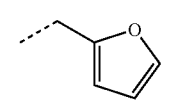 | (ESI)+: [M + H]+ = 567.5 |
| 914 | CH₂CH₂OH | (ESI)+: [M + H]+ = 517.4 |
| 915 |  | (ESI)+: [M + H]+ = 577.5 |
| 916 |  | (ESI)+: [M + H]+ = 577.5 |

375
-continued

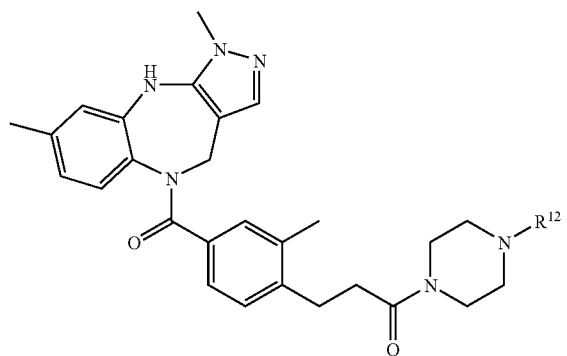

| Compound number | R¹² | MS |
|---|---|---|
| 917 | 2-methylphenyl-CH₂ | (ESI)+: [M + H]+ = 577.4 |
| 918 | 2-cyanophenyl-CH₂ | (ESI)+: [M + H]+ = 588.5 |
| 919 | 3-cyanophenyl-CH₂ | (ESI)+: [M + H]+ = 588.5 |
| 920 | 4-cyanophenyl-CH₂ | (ESI)+: [M + H]+ = 588.5 |
| 921 | pentafluorophenyl-CH₂ | (ESI)+: [M + H]+ = 653.5 |
| 922 | 3,5-dichlorophenyl-CH₂ | (ESI)+: [M + H]+ = 631.5 |
| 923 | 3,4,5-trimethoxyphenyl-CH₂ | (ESI)+: [M + H]+ = 653.6 |
| 924 | 4-(methoxycarbonyl)phenyl-CH₂ | (ESI)+: [M + H]+ = 621.6 |

376

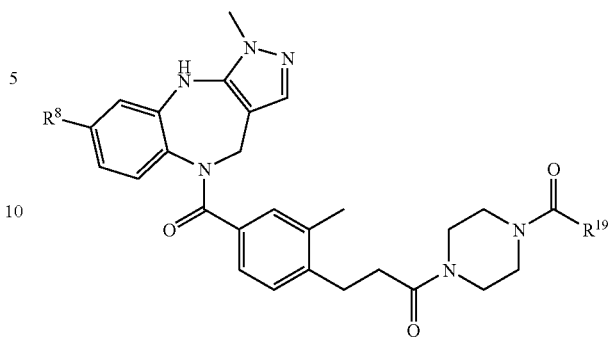

| Compound number | R⁸ | R¹⁹ | MS |
|---|---|---|---|
| 925 E62 | Cl | Me | (ESI)+: [M + H]+ = 535.5 |
| 926 | Cl | phenyl | (ESI)+: [M + H]+ = 597.5 |
| 927 | Cl | 3-chlorophenyl | (ESI)+: [M + H]+ = 631.5 |
| 928 | Cl | 4-chlorophenyl | (ESI)+: [M + H]+ = 631.5 |
| 929 | Cl | 2-chlorophenyl | (ESI)+: [M + H]+ = 631.5 |
| 930 | Cl | 4-methoxyphenyl | (ESI)+: [M + H]+ = 627.6 |
| 931 | Cl | 3-methylphenyl | (ESI)+: [M + H]+ = 611.5 |
| 932 | Cl | 2-methylphenyl | (ESI)+: [M + H]+ = 611.6 |
| 933 | Cl | 2-chloropyridin-3-yl | (ESI)+: [M + H]+ = 632.5 |
| 934 | Cl | pyridin-3-yl | (ESI)+: [M + H]+ = 598.5 |

377
-continued

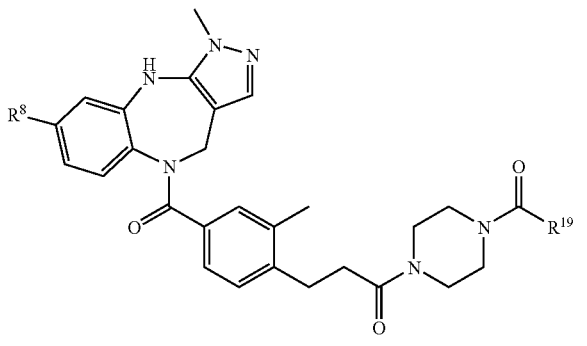

| Compound number | R⁸ | R¹⁹ | MS |
|---|---|---|---|
| 935 | Cl | 4-pyridyl | (ESI)+: [M + H]+ = 598.5 |
| 936 | Cl | 2-thienyl | (ESI)+: [M + H]+ = 603.5 |
| 937 | Cl | 3-thienyl | (ESI)+: [M + H]+ = 603.4 |
| 938 | Cl | 2,5-dimethylfuran-3-yl | (ESI)+: [M + H]+ = 615.6 |
| 939 | Cl | 2-furyl | (ESI)+: [M + H]+ = 587.5 |
| 940 | Cl | isoxazol-5-yl | (ESI)+: [M + H]+ = 588.5 |
| 941 | Cl | 5-methyl-2-phenyl-2H-1,2,3-triazol-4-yl | (ESI)+: [M + H]+ = 678.6 |
| 942 | Cl | $CH_2CH_3$ | (ESI)+: [M + H]+ = 549.4 |
| 943 | Cl | $CH_2CH_2CH_3$ | (ESI)+: [M + H]+ = 563.5 |
| 944 | Cl | cyclopropyl | (ESI)+: [M + H]+ = 561.5 |
| 945 | Cl | $C(CH_3)_3$ | (ESI)+: [M + H]+ = 577.5 |
| 946 | Cl | cyclopentylmethyl | (ESI)+: [M + H]+ = 603.6 |
| 947 | Cl | $CH_2(CH_2)_3CH_3$ | (ESI)+: [M + H]+ = 591.5 |

378
-continued

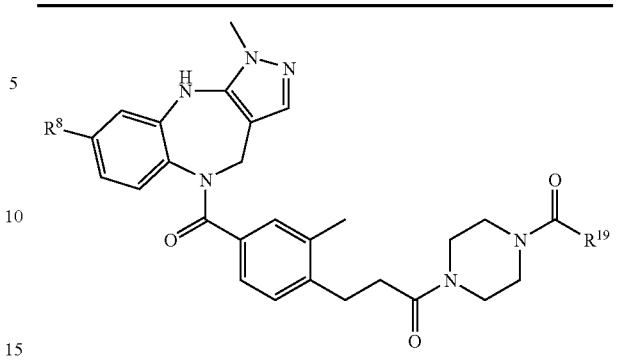

| Compound number | R⁸ | R¹⁹ | MS |
|---|---|---|---|
| 948 | Cl | $CH(CH_2CH_3)CH_2CH_2CH_3$ | (ESI)+: [M + H]+ = 619.6 |
| 949 | Cl | 2,5-dimethoxyphenyl | (ESI)+: [M + H]+ = 671.6 |
| 950 | Cl | benzyl | (ESI)+: [M + H]+ = 611.6 |
| 951 | Cl | phenethyl | (ESI)+: [M + H]+ = 625.6 |
| 952 | Cl | 2-phenylcyclopropyl | (ESI)+: [M + H]+ = 637.6 |
| 953 | Cl | 2-thienylmethyl | (ESI)+: [M + H]+ = 617.5 |
| 954 | Cl | phenoxymethyl | (ESI)+: [M + H]+ = 627.6 |
| 955 | Cl | benzyloxymethyl | (ESI)+: [M + H]+ = 641.6 |
| 956 | Cl | $CH_2CH_2CH_2CO_2CH_2CH_3$ | (ESI)+: [M + H]+ = 635.6 |
| 957 | Me | phenyl | (ESI)+: [M + H]+ = 577.4 |

379
-continued

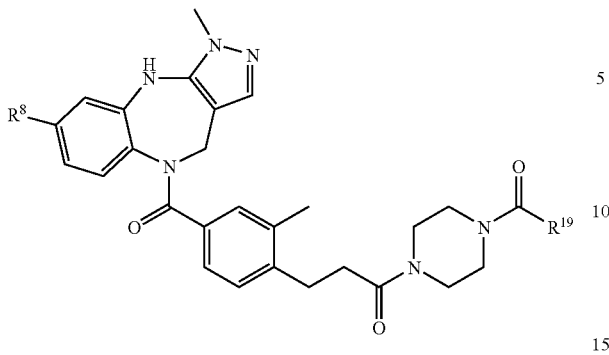

| Compound number | R⁸ | R¹⁹ | MS |
|---|---|---|---|
| 958 | Me | 3-Cl-phenyl | (ESI)+: [M + H]+ = 611.3 |
| 959 | Me | 4-Cl-phenyl | (ESI)+: [M + H]+ = 611.3 |
| 960 | Me | 2-Cl-phenyl | (ESI)+: [M + H]+ = 611.3 |
| 961 | Me | 4-OMe-phenyl | (ESI)+: [M + H]+ = 607.4 |
| 962 | Me | 3-Me-phenyl | (ESI)+: [M + H]+ = 591.4 |
| 963 | Me | 2-Me-phenyl | (ESI)+: [M + H]+ = 591.3 |
| 964 | Me | 2-Cl-pyridin-3-yl | (ESI)+: [M + H]+ = 612.3 |
| 965 | Me | pyridin-3-yl | (ESI)+: [M + H]+ = 578.3 |
| 966 | Me | thien-2-yl | (ESI)+: [M + H]+ = 583.3 |
| 967 | Me | 3-Cl-thien-2-yl | (ESI)+: [M + H]+ = 617.3 |

380
-continued

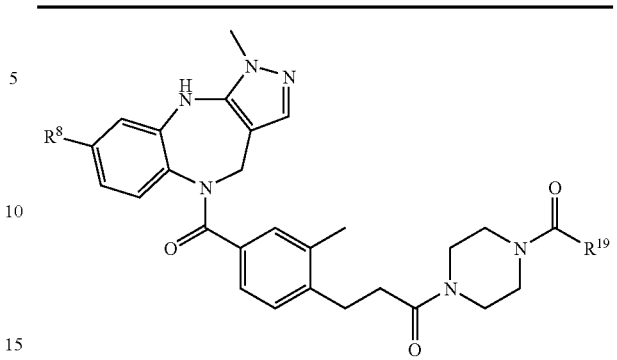

| Compound number | R⁸ | R¹⁹ | MS |
|---|---|---|---|
| 968 | Me | thien-3-yl | (ESI)+: [M + H]+ = 583.3 |
| 969 | Me | 2,5-dimethylfuran-3-yl | (ESI)+: [M + H]+ = 595.3 |
| 970 | Me | furan-2-yl | (ESI)+: [M + H]+ = 567.3 |
| 971 | Me | isoxazol-5-yl | (ESI)+: [M + H]+ = 568.3 |
| 972 | Me | 5-methyl-2-phenyl-2H-1,2,3-triazol-4-yl | (ESI)+: [M + H]+ = 658.4 |
| 973 | Me | $CH_2CH_3$ | (ESI)+: [M + H]+ = 529.3 |
| 974 | Me | $CH_2CH_2CH_3$ | (ESI)+: [M + H]+ = 543.4 |
| 975 | Me | cyclopropyl | (ESI)+: [M + H]+ = 541.3 |
| 976 | Me | $C(CH_3)_3$ | (ESI)+: [M + H]+ = 557.3 |
| 977 | Me | cyclopentylmethyl | (ESI)+: [M + H]+ = 583.4 |

381

-continued

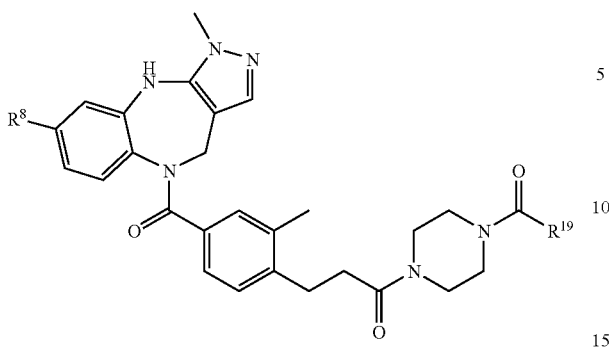

| Compound number | R⁸ | R¹⁹ | MS |
|---|---|---|---|
| 978 | Me | CH₂(CH₂)₃CH₃ | (ESI)+: [M + H]+ = 571.4 |
| 979 | Me | CH(CH₂CH₃)CH₂CH₂CH₃ | (ESI)+: [M + H]+ = 599.5 |
| 980 | Me | 2,5-dimethoxyphenyl | (ESI)+: [M + H]+ = 651.4 |
| 981 | Me | benzyl | (ESI)+: [M + H]+ = 591.3 |
| 982 | Me | phenethyl | (ESI)+: [M + H]+ = 605.4 |
| 983 | Me | phenylcyclopropyl | (ESI)+: [M + H]+ = 617.4 |
| 984 | Me | 2-thienyl | (ESI)+: [M + H]+ = 597.3 |
| 985 | Me | CH₂OPh | (ESI)+: [M + H]+ = 607.4 |
| 986 | Me | CH₂OCH₂Ph | (ESI)+: [M + H]+ = 621.4 |
| 987 | Me | CH₂N(CH₃)₂ | (ESI)+: [M + H]+ = 558.3 |
| 988 | Me | CH₂CH₂CH₂CO₂CH₂CH₃ | (ESI)+: [M + H]+ = 615.4 |

382

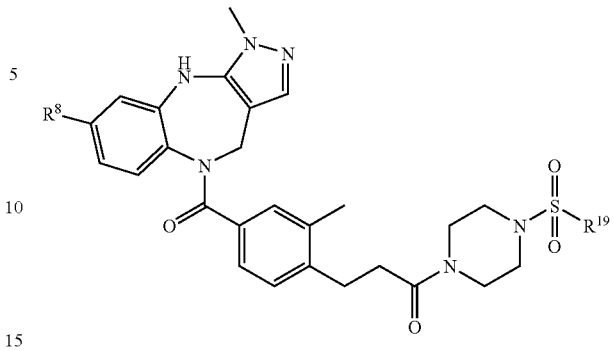

| Compound number | R⁸ | R¹⁹ | MS |
|---|---|---|---|
| 989 E63 | Me | Me | (ESI)+: [M + H]+ = 551.3 |
| 990 | Me | CH(CH₃)₂ | (ESI)+: [M + H]+ = 579.4 |
| 991 | Me | benzyl | (ESI)+: [M + H]+ = 627.4 |
| 992 | Me | phenyl | (ESI)+: [M + H]+ = 613.3 |
| 993 | Me | 2,4-dichlorophenyl | (ESI)+: [M + H]+ = 681.3 |
| 994 | Me | 3-chlorophenyl | (ESI)+: [M + H]+ = 647.3 |
| 995 | Me | 2-chlorophenyl | (ESI)+: [M + H]+ = 647.3 |
| 996 | Me | 4-methoxyphenyl | (ESI)+: [M + H]+ = 643.3 |
| 997 | Me | 4-methylphenyl | (ESI)+: [M + H]+ = 627.4 |
| 998 | Me | 4-cyanophenyl | (ESI)+: [M + H]+ = 638.4 |
| 999 | Me | 4-trifluoromethylphenyl | (ESI)+: [M + H]+ = 681.3 |

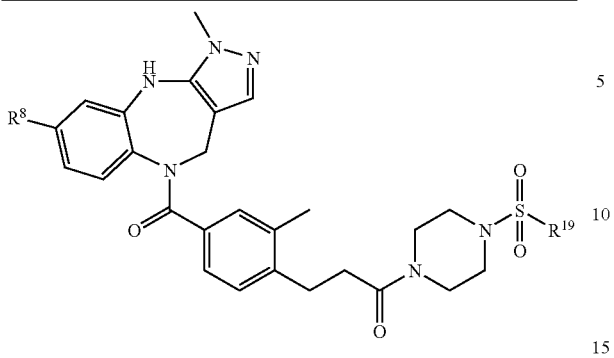

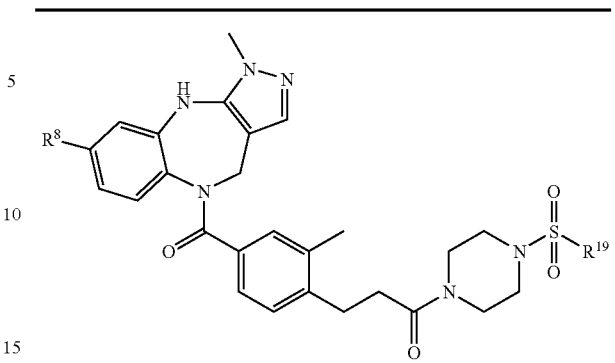

| Compound number | R⁸ | R¹⁹ | MS |
|---|---|---|---|
| 1000 | Me | 4-(NHC(O)CH₃)-C₆H₄- | (ESI)+: [M + H]+ = 670.4 |
| 1001 | Me | 5-Cl-thiophen-2-yl | (ESI)+: [M + H]+ = 653.3 |
| 1002 | Me | CH₂CF₃ | (ESI)+: [M + H]+ = 619.3 |
| 1003 | Me | 2-Cl-3-Br-pyridin-5-yl | (ESI)+: [M + H]+ = 728.3 |
| 1004 | Me | 5-(CO₂Me)-furan-2-yl | (ESI)+: [M + H]+ = 661.3 |
| 1005 | Me | CH₂CH₃ | (ESI)+: [M + H]+ = 565.3 |
| 1006 | Me | CH₂CH₂CH₃ | (ESI)+: [M + H]+ = 579.3 |
| 1007 | Me | CH₂CH₂CH₂CH₃ | (ESI)+: [M + H]+ = 593.3 |
| 1008 | Cl | CH₃ | (ESI)+: [M + H]+ = 571.4 |
| 1009 | Cl | CH(CH₃)₂ | (ESI)+: [M + H]+ = 599.5 |
| 1010 | Cl | CH₂-C₆H₅ | (ESI)+: [M + H]+ = 647.6 |
| 1011 | Cl | C₆H₅ | (ESI)+: [M + H]+ = 633.6 |
| 1012 | Cl | 2,4-diCl-C₆H₃- | (ESI)+: [M + H]+ = 701.4 |
| 1013 | Cl | 4-Cl-C₆H₄- | (ESI)+: [M + H]+ = 667.5 |

| Compound number | R⁸ | R¹⁹ | MS |
|---|---|---|---|
| 1014 | Cl | 3-Cl-C₆H₄- | (ESI)+: [M + H]+ = 667.5 |
| 1015 | Cl | 2-Cl-C₆H₄- | (ESI)+: [M + H]+ = 667.5 |
| 1016 | Cl | 4-OMe-C₆H₄- | (ESI)+: [M + H]+ = 663.6 |
| 1017 | Cl | 4-Me-C₆H₄- | (ESI)+: [M + H]+ = 647.6 |
| 1018 | Cl | 4-CN-C₆H₄- | (ESI)+: [M + H]+ = 658.5 |
| 1019 | Cl | 4-CF₃-C₆H₄- | (ESI)+: [M + H]+ = 701.5 |
| 1020 | Cl | 4-(NHC(O)CH₃)-C₆H₄- | (ESI)+: [M + H]+ = 690.5 |

-continued

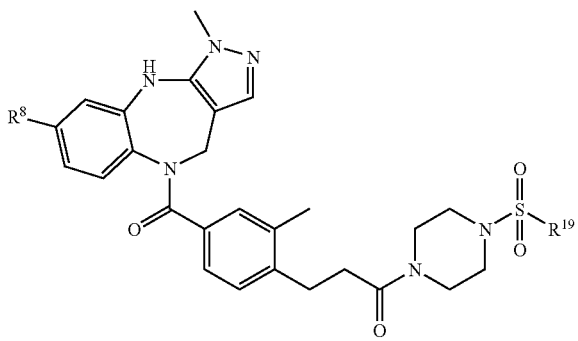

| Compound number | R⁸ | R¹⁹ | MS |
|---|---|---|---|
| 1021 | Cl | 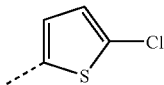 | (ESI)+: [M + H]+ = 673.4 |
| 1022 | Cl | 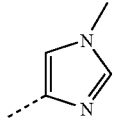 | (ESI)+: [M + H]+ = 637.5 |
| 1023 | Cl | CH₂CF₃ | (ESI)+: [M + H]+ = 639.5 |
| 1024 | Cl | 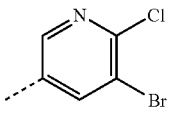 | (ESI)+: [M + H]+ = 748.5 |
| 1025 | Cl | 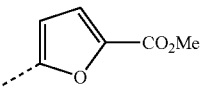 | (ESI)+: [M + H]+ = 687.5 |
| 1026 | Cl | CH₂CH₃ | (ESI)+: [M + H]+ = 585.4 |
| 1027 | Cl | CH₂CH₂CH₃ | (ESI)+: [M + H]+ = 599.5 |
| 1028 | Cl | CH₂CH₂CH₂CH₃ | (ESI)+: [M + H]+ = 613.6 |

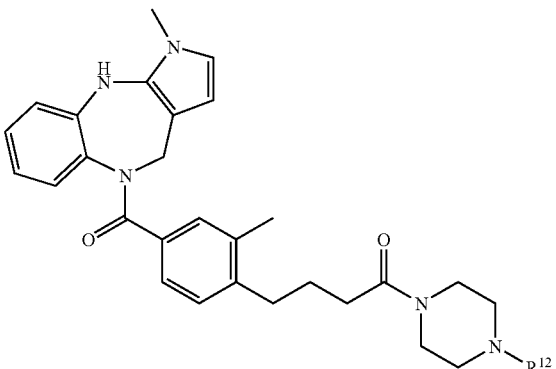

| Compound number | R¹² | | ¹H NMR: δ (ppm) |
|---|---|---|---|
| 1029 | CH₂CH₂C(CH₃)₃ | (ESI)+: [M + H]+ = 557.6 | 0.88 (9 H, s), 1.33-1.41 (2 H, m), 1.74-1.82 (2 H, m), 2.14 (3 H, s), 2.15-2.28 (2 H, m), 2.29-2.38 (6 H, m), 2.42-2.54 (2 H, m), 3.31-3.39 (2 H, m), 3.54-3.63 (2 H, m), 3.79 (3 H, s), 3.95 (1 H, d, J = 14.6 Hz), 5.91 (1 H, d, J = 14.6 Hz), 6.16 (1 H, s), 6.62-6.71 (2 H, m), 6.79-6.91 (3 H, m), 7.01-7.13 (2 H, m) |
| 1030 | *cyclobutylmethyl* | (ESI)+: [M + H]+ = 541.5 | 1.61-2.11 (8 H, m), 2.12 (3 H, s), 2.14-2.26 (1 H, m), 2.27-2.41 (8 H, m), 2.50 (2 H, t, J = 7.0 Hz), 3.32 (2 H, brs), 3.56 (2 H, brs), 3.76 (3 H, s), 3.94 (1 H, d, J = 14.6 Hz), 5.90 (1 H, d, J = 14.6 Hz), 6.42 (1 H, s), 6.63-6.67 (2 H, m), 6.74-7.23 (5 H, m) |

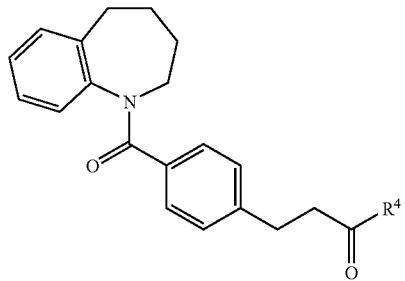
| Compound number | R⁴ | MS | ¹H NMR |
|---|---|---|---|
| 1031 E65 | (benzyl) | (APCl)+: [M + H]+ = 413.4 | 1.38-1.60 (1 H, m), 1.84-2.00 (2 H, m), 2.00-2.14 (1 H, m), 2.38 (2 H, t, J = 7.7 Hz), 2.64-2.77 (1 H, m), 2.77-2.91 (1 H, m), 2.87 (2 H, t, J = 7.7 Hz), 2.95-3.08 (1 H, m), 4.32-4.36 (2 H, m), 4.99 (1 H, d, J = 13.6 Hz), 5.61 (1 H, s), 6.58 (1 H, d, J = 7.7 Hz), 6.80-6.87 (1 H, m), 6.91-6.95 (2 H, m), 7.01-7.12 (3 H, m), 7.14-7.21 (3 H, m), 7.25-7.35 (3 H, m) |
| 1032 | NHCH₂(CH₂)₃OH | — | — |
| 1033 | (thiazolidine) | — | — |
| 1034 | (4-pyrrolidinopiperidine) | — | — |
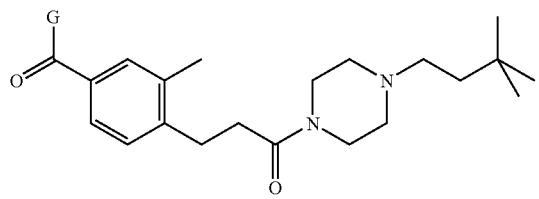
| Compound number | G | ¹H NMR: δ (ppm) |
|---|---|---|
| 1035 E66 | (2-methyl-imidazo-fused benzazepine) | (ESI)+: [M + H]+ = 542.5 | 0.88 (9 H, s), 1.34-1.40 (2 H, m), 2.13 (3 H, s), 2.28-2.40 (8 H, m), 2.44 (3 H, s), 2.77-2.87 (3 H, m), 2.87-3.05 (2 H, m), 3.28-3.41 (3 H, m), 3.52-3.67 (2 H, m), 5.08 (1 H, dd, J = 4.2, 12.9 Hz), 6.64 (2 H, d, J = 7.9 Hz), 6.75 (1 H, d, J = 7.9 Hz), 6.85 (1 H, t, J = 7.4 Hz), 7.06 (1 H, s), 7.17 (1 H, t, J = 7.6 Hz), 8.00-8.17 (1 H, m) |

-continued

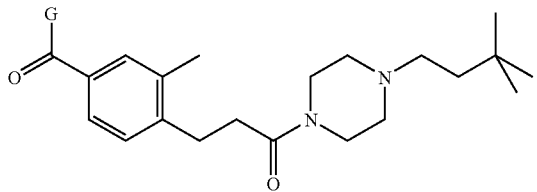

| Compound number | G | $^1$H NMR: δ (ppm) | |
|---|---|---|---|
| 1036 | 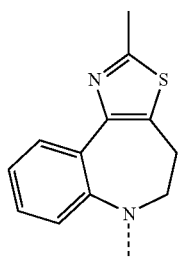 | (APCl)+:<br>[M + H]+ =<br>559.4 | 0.88 (9 H, s), 1.23-1.40 (4H, m), 2.16 (3 H, s), 2.34-2.37 (6 H, m), 2.73 (3 H, s), 2.78-2.84 (2 H, m), 3.09-3.57 (7 H, m), 5.15-5.20 (1 H, m), 6.67 (2 H, m), 6.77 (1 H, d, J = 7.9 Hz), 6.96 (1 H, m), 7.12 (1 H, s), 7.23 (1 H, m), 8.37 (1 H, dd, J = 1.5, 8.2 Hz) |
| 1037 | 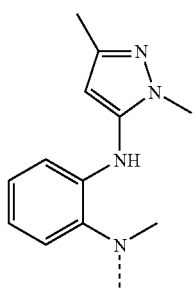 | (ESI)+:<br>[M + H]+ =<br>559.4 | 0.88 (9 H, s), 1.36-1.43 (2 H, m), 2.15 (3 H, s), 2.23 (3 H, s), 2.35-2.46 (8 H, m), 2.83 (2 H, t, J = 7.4 Hz), 3.31-3.39 (2 H, m), 3.37 (3 H, s), 3.48 (3 H, s), 3.63 (2 H, t, J = 4.4 Hz), 5.70 (1 H, s), 5.74 (1 H, s), 6.49-6.56 (1 H, m), 6.65-6.72 (1 H, m), 6.83-6.94 (2 H, m), 7.01-7.08 (2 H, m), 7.19 (1 H, s) |
| 1038 | 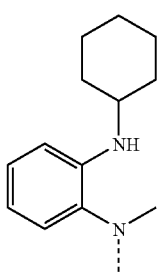 | (ESI)+:<br>[M + H]+ =<br>547.5 | 0.88 (9 H, s), 1.03-1.40 (8 H, m), 1.58-1.83 (3 H, m), 1.94-2.08 (2 H, m), 2.15 (3 H, s), 2.26-2.45 (8 H, m), 2.81 (2 H, t, J = 7.4 Hz), 3.24 (3 H, s), 3.29 (2 H, t, J = 4.4 Hz), 3.58 (2 H, t, J = 4.4 Hz), 3.91 (1 H, d, J = 8.2 Hz), 6.37-6.43 (1 H, m), 6.61-6.70 (2 H, m), 6.85 (1 H, d, J = 7.9 Hz), 7.01-7.06 (2 H, m), 7.20 (1 H, s) |
| 1039 | 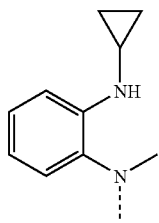 | (APCl)+:<br>[M + H]+ =<br>505.2 | 0.28-0.38 (2 H, m), 0.49-0.59 (2 H, m), 0.73-0.81 (1 H, m), 0.88 (9 H, s), 1.34-1.40 (2 H, m), 2.15 (3 H, s), 2.25-2.45 (8 H, m), 2.82 (2 H, t, J = 7.7 Hz), 3.24 (3 H, s), 3.31 (2 H, t, J = 5.2 Hz), 3.59 (2 H, t, J = 5.2 Hz), 4.44 (1 H, s), 6.49-6.55 (1 H, m), 6.73 (1 H, d, J = 6.7 Hz), 6.84 (1 H, d, J = 7.9 Hz), 6.94-7.02 (2 H, m), 7.07-7.15 (2 H, m) |
| 1040 | 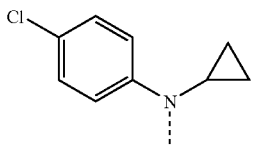 | (ESI)+:<br>[M + H]+ =<br>510.3,<br>512.4 | 0.51-0.54 (2 H, m), 0.80-0.89 (2 H, m), 0.88 (9 H, s), 1.35-1.41 (2 H, m), 1.53-1.62 (1 H, m), 2.23 (3 H, s), 2.29-2.43 (5 H, m), 2.44-2.50 (2 H, m), 2.85-2.91 (2 H, m), 3.14-3.24 (1 H, m), 3.31-3.38 (2 H, m), 3.56-3.63 (2 H, m), 6.93-7.02 (4 H, m), 7.18-7.25 (3 H, m) |

-continued

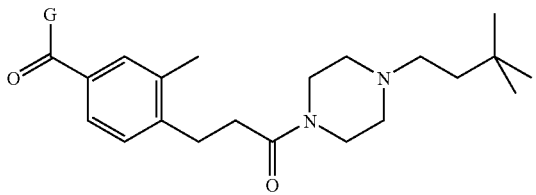

| Compound number | G | ¹H NMR: δ (ppm) |
|---|---|---|
| 1041 | 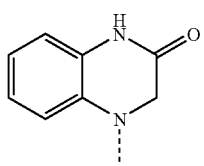 | (ESI)+: [M + H]+ = 491.5 | 0.88 (9 H, s), 1.99 (1 H, d, J = 6.4 Hz), 1.34-1.40 (2 H, m), 1.80 (1 H, s), 2.26 (3 H, s), 2.28-2.40 (4 H, m), 2.49-2.55 (2 H, m), 2.90-2.97 (2 H, m), 3.39 (2 H, t, J = 4.7 Hz), 3.62 (2 H, t, J = 4.7 Hz), 4.55 (2 H, s), 6.72-6.83 (2 H, m), 6.90-6.96 (1 H, m), 7.01-7.12 (3 H, m), 7.25 (1 H, s), 9.20 (1 H, s) |
| 1042 | 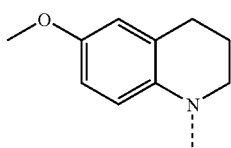 | (ESI)+: [M + H]+ = 506.8 | 0.89 (9 H, s), 1.34-1.40 (2 H, m), 1.93-2.08 (2 H, m), 2.26 (3 H, s), 2.26-2.43 (6 H, m), 2.46-2.53 (2 H, m), 2.79 (2 H, t, J = 6.7 Hz), 2.88-2.94 (2 H, m), 3.37 (2 H, t, J = 4.9 Hz), 3.62 (2 H, t, J = 4.9 Hz), 3.73 (3 H, s), 3.83 (2 H, t, J = 6.4 Hz), 6.40-6.48 (1 H, m), 6.66 (1 H, d, J = 3.0 Hz), 6.67-6.81 (1 H, m), 6.99 (2 H, s), 7.23 (1 H, s) |
| 1043 | 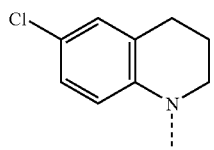 | (ESI)+: [M + H]+ = 510.8 | 0.89 (9 H, m), 1.36-1.42 (2 H, m), 1.97-2.07 (2 H, m), 2.28 (3 H, s), 2.28-2.44 (6 H, m), 2.46-2.54 (2 H, m), 2.80 (2 H, t, J = 6.7 Hz), 3.33-3.42 (2 H, m), 3.58-3.70 (2 H, m), 3.84 (2 H, t, J = 6.7 Hz), 6.76 (1 H, d, J = 8.9 Hz), 6.87 (1 H, dd, J = 2.2, 8.7 Hz), 7.02 (2 H, s), 7.12 (1 H, d, J = 2.2 Hz), 7.25 (1 H, s) |
| 1044 | 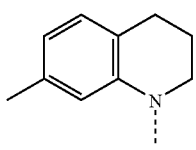 | (ESI)+: [M + H]+ = 490.8 | 0.89 (9 H, s), 1.34-1.41 (2 H, m), 1.92-1.99 (2 H, m), 2.06 (3 H, m), 2.25 (3 H, s), 2.28-2.43 (6 H, m), 2.43-2.52 (2 H, m), 2.70-2.81 (2 H, m), 2.88-2.96 (2 H, m), 3.35-3.43 (2 H, m), 3.56-3.68 (2 H, m), 3.80-3.90 (2 H, m), 6.64 (1 H, s), 6.77-6.89 (2 H, m), 6.92-7.06 (3 H, m) |
| 1045 | 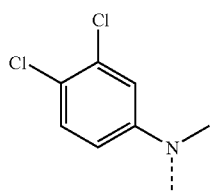 | (ESI)+: [M + H]+ = 518.4 | 0.88 (9 H, s), 1.34-1.41 (2 H, m), 2.23 (3 H, s), 2.28-2.42 (6 H, m), 2.43-2.51 (2 H, m), 2.85-2.91 (2 H, m), 3.36 (2 H, t, J = 4.9 Hz), 3.43 (3 H, s), 3.61 (2 H, t, J = 4.9 Hz), 6.83 (1 H, dd, J = 2.5, 8.7 Hz), 6.94 (2 H, s), 7.20-7.27 (3 H, m) |
| 1046 | 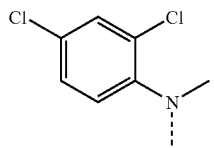 | (ESI)+: [M + H]+ = 518.4 | 0.88 (9 H, s), 1.34-1.40 (2 H, m), 2.20 (3 H, s), 2.26-2.39 (6 H, m), 2.45 (2 H, t, J = 7.9 Hz), 2.85 (2 H, t, J = 7.9 Hz), 3.31 (3 H, s), 3.24-3.33 (2 H, m), 3.59 (2 H, d, J = 3.2 Hz), 6.82-7.03 (3 H, m), 7.06-7.14 (1 H, m), 7.19 (1 H, s), 7.38 (1 H, s) |
| 1047 | 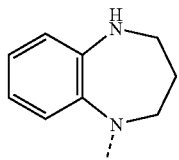 | (ESI)+: [M + H]+ = 491.6 | 0.88 (9 H, s), 1.34-1.40 (2 H, m), 2.15 (3 H, s), 2.28-2.46 (8 H, m), 2.82 (2 H, t, J = 7.9 Hz), 3.31 (2 H, t, J = 4.7 Hz), 3.59 (2 H, t, J = 4.7 Hz), 6.48-6.62 (2 H, m), 6.75 (1 H, d, J = 7.2 Hz), 6.83 (1 H, d, J = 7.2 Hz), 6.90-6.98 (2 H, m), 7.11 (1 H, s) |

-continued

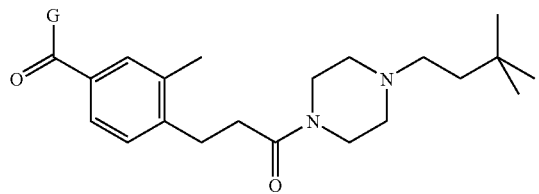

| Compound number | G | $^1$H NMR: δ (ppm) |
|---|---|---|
| 1048 | 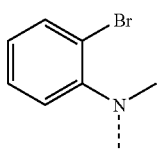 | (APCl)+: [M + H]+ = 528.1, 530.3 | 0.87 (9 H, s), 1.32-1.39 (2 H, m), 2.16 (3 H, s), 2.24-2.46 (8 H, m), 2.81 (2 H, t, J = 7.2 Hz), 3.28 (2 H, t, J = 4.4 Hz), 3.33 (3 H, s), 3.57 (2 H, t, J = 4.4 Hz), 6.85 (1 H, d), 6.94-7.07 (3 H, m), 7.11-7.19 (2 H, m), 7.52 (1 H, d, J = 7.7 Hz) |
| 1049 | 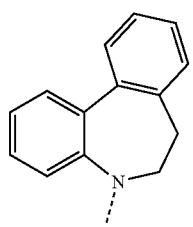 | (ESI)+: [M + H]+ = 538.7 | 0.87 (9 H, s), 1.33-1.39 (2 H, m), 2.11 (3 H, s), 2.25-2.43 (8 H, m), 2.75-2.88 (4 H, m), 3.28 (2 H, t, J = 4.9 Hz), 3.58 (2 H, t, J = 4.9 Hz), 3.83-3.91 (1 H, m), 4.60-4.71 (1 H, m), 6.69-6.82 (3 H, m), 6.90 (1 H, s), 7.06 (1 H, t, J = 7.2 Hz), 7.25-7.52 (6 H, m) |
| 1050 | 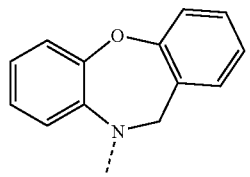 | (ESI)+: [M + H]+ = 540.7 | 0.87 (9 H, s), 1.33-1.40 (2 H, m), 2.19 (3 H, s), 2.26-2.49 (8 H, m), 2.85 (2 H, t, J = 7.7 Hz), 3.32 (2 H, t, J = 4.7 Hz), 3.59 (2 H, t, J = 4.7 Hz), 5.07-5.23 (2 H, m), 6.71-6.81 (2 H, m), 6.83-6.93 (2 H, m), 6.98-7.09 (2 H, m), 7.11-7.28 (5 H, m) |
| 1051 | 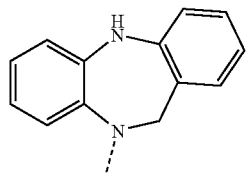 | (ESI)+: [M + H]+ = 539.7 | 0.87 (9 H, s), 1.33-1.40 (2 H, m), 2.15 (3 H, s), 2.24-2.46 (8 H, m), 2.81 (2 H, t, J = 8.2 Hz), 3.30 (2 H, t, J = 4.4 Hz), 3.59 (2 H, t, J = 4.4 Hz), 4.08-4.24 (2 H, m), 5.68-5.89 (1 H, m), 6.48-6.59 (3 H, m), 6.72-6.93 (4 H, m), 6.95-7.23 (4 H, m) |
| 1052 | 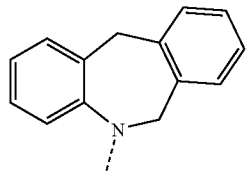 | (ESI)+: [M + H]+ = 538.7 | 0.87 (9 H, s), 1.33-1.40 (2 H, m), 2.20 (3 H, s), 2.27-2.39 (6 H, m), 2.42-2.47 (2 H, m), 2.85 (2 H, t, J = 7.4 Hz), 3.32 (2 H, t, J = 4.7 Hz), 3.59 (2 H, t, J = 4.7 Hz), 4.02-4.48 (4 H, m), 6.78-7.34 (11 H, m) |
| 1053 E67 | 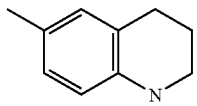 | (ESI)+: [M + H]+ = 490.7 | 0.89 (9 H, 2), 1.34-1.41 (2 H, m), 1.94-2.03 (2 H, m), 2.23 (3 H, s), 2.26 (3 H, s), 2.28-2.40 (6 H, m), 2.47-2.53 (2 H, m), 2.78 (2 H, t, J = 6.7 Hz), 2.88-2.94 (2 H, m), 3.36 (2 H, t, J = 4.7 Hz), 3.61 (2 H, t, J = 4.7 Hz), 3.84 (2 H, t, J = 6.4 Hz), 6.68 (2 H, s), 6.93 (1 H, s), 6.99 (3 H, s) |
| 1054 | 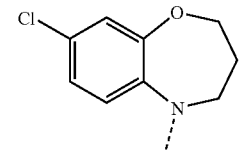 | (APCl)+: [M + H]+ = 526.1, 528.2 | 0.92 (9 H, s), 1.34-1.45 (5 H, m), 1.47-1.54 (5 H, m), 1.55-1.78 (2 H, m), 2.00-2.13 (1 H, m), 2.20 (3 H, s), 2.42-2.53 (2 H, m), 2.70-2.81 (1 H, m), 2.82-2.93 (2 H, m), 3.03-3.13 (2 H, m), 3.58-3.72 (2 H, m), 6.51-6.61 (1 H, m), 6.68-6.77 (1 H, m), 6.90 (2 H, s), 7.09 (2 H, d, J = 2.2 Hz) ppm. |

-continued

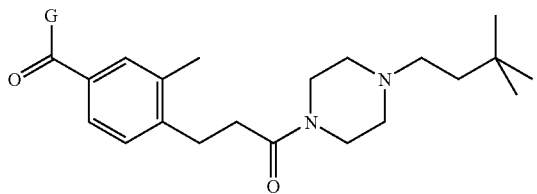

| Compound number | G | | ¹H NMR: δ (ppm) |
|---|---|---|---|
| 1055 | [structure: benzoxazine carboxamide linked to methyl-oxadiazole] | (ESI)+:<br>[M + H]+ =<br>617.5 | 0.88 (9 H, s), 1.29-1.42 (2 H, m), 2.24-2.43 (12 H, m), 2.47-2.60 (2 H, m), 2.88-3.02 (2 H, m), 3.37-3.58 (2 H, m), 3.59-3.71 (2 H, m), 3.93 (1 H, dd, J = 7.2, 13.4 Hz), 4.31 (1 H, dd, J = 3.2, 13.4 Hz), 4.51-4.78 (2 H, m), 4.79-4.82 (1 H, m), 6.80-6.90 (1 H, m), 7.01-7.06 (2 H, m), 7.12-7.16 (1 H, m), 7.17-7.23 (1 H, m), 7.28-7.39 (2 H, m) ppm. |
| 1056 | [structure: 7-fluoro-benzoxazine] | (ESI)+:<br>[M + H]+ =<br>496.5 | 0.89 (9 H, s), 1.35-1.41 (2 H, m), 2.32 (3 H, s), 2.36-2.42 (6 H, m), 2.51-2.57 (2 H, m), 2.93-3.00 (2 H, m), 3.40 (2 H, t, J = 4.7 Hz), 3.63 (2 H, t, J = 4.4 Hz), 3.95 (2 H, t, J = 4.4 Hz), 4.31 (2 H, t, J = 4.4 Hz), 6.42-6.48 (1 H, m), 6.62 (1 H, dd, J = 3.0, 9.6 Hz), 7.11-7.19 (1 H, m), 7.22-7.24 (1 H, m), 7.31 (1 H, s) ppm. |

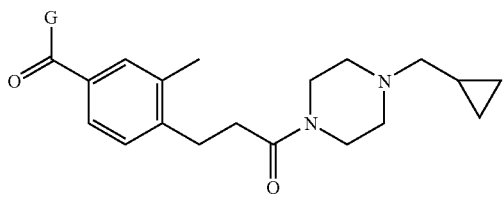

| Compound number | G | | ¹H NMR |
|---|---|---|---|
| 1057 | [structure: pyrazolo-benzodiazepine with N-methyl] | (ESI)+:<br>[M + H]+ =<br>513.6 | CDCl₃ δ 0.05-0.09 (2 H, m), 0.42-0.52 (2 H, m), 0.71-0.89 (1 H, m), 2.13 (3 H, s), 2.17-2.22 (2 H, m), 2.28-2.52 (6 H, m), 2.79-2.86 (2 H, m), 3.22-3.35 (2 H, m), 3.56-3.72 (2 H, m), 3.74 (3 H, s), 3.94 (1 H, d, J = 14.6 Hz), 5.89 (1 H, d, J = 14.6 Hz), 6.58-6.71 (2 H, m), 6.75-6.90 (2 H, m), 6.91-7.06 (2 H, m), 7.08-7.22 (2 H, m) ppm. |
| 1058 | [structure: dibenzoxazepine] | (ESI)+:<br>[M + H]+ =<br>510.7 | CDCl₃ δ 0.03-0.08 (2 H, m), 0.43-0.50 (2 H, m), 0.77-0.86 (1 H, m), 2.19 (3 H, s), 2.18-2.21 (2 H, m), 2.36-2.47 (6 H, m), 2.84 (2 H, t, J = 7 4 Hz), 3.32 (2 H, t, J = 4.9 Hz), 3.60 (2 H, t, J = 4.9 Hz), 5.03-5.26 (2 H, m), 6.74-6.78 (1 H, m), 6.82-6.91 (2 H, m), 6.98-7.07 (2 H, m), 7.11-7.18 (2 H, m), 7.19-7.24 (4 H, m) ppm. |

-continued
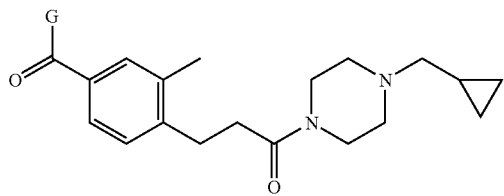
| Compound number | G | | ¹H NMR |
|---|---|---|---|
| 1059 | 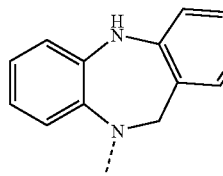 | (ESI)+: [M + H]+ = 509.7 | CDCl₃ δ 0.03-0.08 (2 H, m), 0.45-0.50 (2 H, m), 0.71-0.89 (1 H, m), 2.15 (3 H, s), 2.19-2.22 (2 H, m), 2.34-2.45 (6 H, m), 2.83 (2 H, t, J = 7.2 Hz), 3.31 (2 H, brs), 3.60 (2 H, brs), 4.03-4.34 (2 H, m), 5.62-5.97 (1 H, m), 6.48-6.59 (3 H, m), 6.72-6.93 (5 H, m), 6.97-7.03 (1 H, m), 7.07-7.16 (2 H, m) ppm. |
| 1060 | 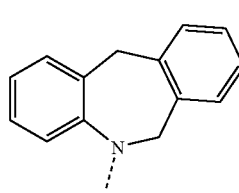 | (ESI)+: [M + H]+ = 508.7 | CDCl₃ δ 0.06-0.10 (2 H, m), 0.47-0.54 (2 H, m), 0.72-0.89 (1 H, m), 2.21 (3 H, s), 2.19-2.24 (2 H, m), 2.38-2.49 (6 H, m), 2.85 (2 H, t, J = 7.4 Hz), 3.34 (2 H, t, J = 4.9 Hz), 3.62 (2 H, t, J = 4.9 Hz), 4.00-4.50 (4 H, m), 6.73-7.31 (11 H, m) ppm. |
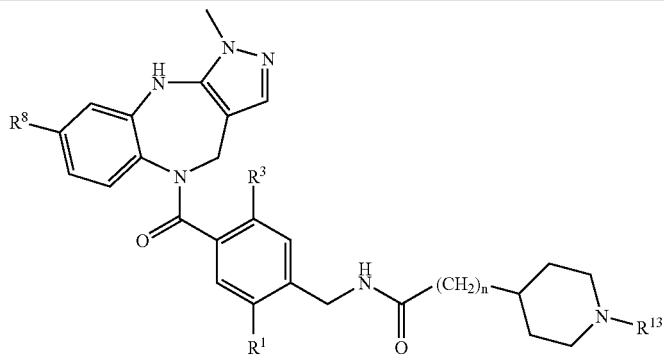
| Compound number | R¹ | R³ | R⁸ | R¹³ | n | MS | ¹H NMR: δ (ppm) |
|---|---|---|---|---|---|---|---|
| 1061 E90 | H | F | H |  | 0 | (APCl)+: [M + H]+ = 517.4 | 0.03-0.12 (3 H, m), 0.45-0.54 (3 H, m), 0.77-0.91 (2 H, m), 1.70-1.82 (3 H, m), 1.88-2.03 (2 H, m), 2.03-2.17 (1 H, m), 2.22 (2 H, d, J = 4.9 Hz), 2.98-3.17 (2 H, m), 3.65 (3 H, s), 3.98 (1 H, d, J = 14.6 Hz), 4.10-4.30 (2 H, m), 5.80 (1 H, d, J = 14.6 Hz), 6.53-6.79 (4 H, m), 6.88-7.00 (3 H, m), 7.21 (1 H, s) |
| 1062 | F | H | F | CH₂CH₂CH₃ | 0 | (ESI)+: [M + H]+ = 565.3 | d4-MeOH 0.95 (9 H, s), 1.50-1.56 (2 H, m), 1.80-1.91 (4 H, m), 2.35-2.41 (1 H, m), 2.52-2.58 |

-continued
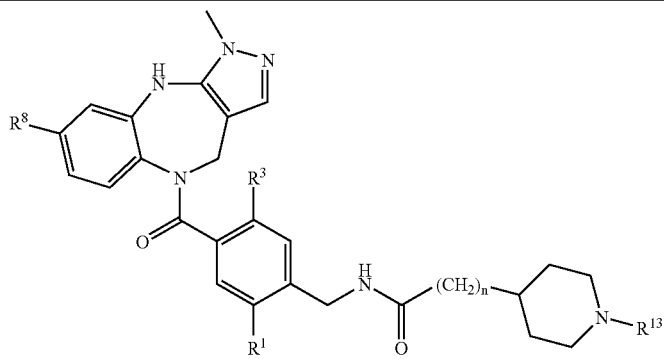
| Compound number | R¹ | R³ | R⁸ | R¹³ | n | MS | ¹H NMR: δ (ppm) |
|---|---|---|---|---|---|---|---|
| | | | | | | | (1 H, m), 2.74-2.81 (2 H, m), 3.30-3.33 (3 H, m), 3.81 (3 H, s), 4.00 (1 H, d, J = 14.6 Hz), 4.32 (2 H, s), 5.73 (1 H, d, J = 14.6 Hz), 6.39-6.46 (1 H, m), 6.77-6.83 (1 H, m), 6.93-7.01 (3 H, m), 7.12-7.18 (1 H, m), 7.24 (1 H, s) |
| 1063 | H | Me | Cl | CO₂C(CH₃)₃ | 2 | (APCl)+: [M + H]+ = 621.5, 623.5 | 1.44 (9 H, s), 1.34-1.71 (5 H, m), 2.12-2.30 (2 H, m), 2.32 (3 H, s), 2.53-2.72 (4 H, m), 3.80 (3 H, s), 3.94 (1 H, d, J = 14.6 Hz), 3.93-4.04 (2 H, m), 4.19-4.42 (2 H, m), 5.81 (1 H, d, J = 14.6 Hz), 6.17 (1 H, s), 6.57-7.20 (7 H, m), 7.38 (1 H, s) |
| 1064 | Cl | H | H | CO₂C(CH₃)₃ | 0 | (APCl)+: [M − Boc + H]+ = 479.4, 481.4 | 1.43 (9 H, s), 1.47-1.62 (2 H, m), 1.65-1.78 (2 H, m), 2.16-2.31 (1 H, m), 2.57-2.72 (2 H, m), 3.77 (3 H, s), 3.98 (1 H, d, J = 14.6 Hz), 4.00-4.13 (2 H, m), 4.33-4.36 (2 H, m), 5.86 (1 H, d, J = 14.6 Hz), 6.18-6.24 (1 H, m), 6.51 (1 H, s), 6.67-6.70 (2 H, m), 6.89-6.98 (3 H, m), 7.04-7.11 (1 H, m), 7.21-7.27 (2 H, m) |
| 1065 | F | H | Me | CO₂C(CH₃)₃ | 1 | (APCl)+: [M − Boc + H]+ = 492.2 | 1.43 (9 H, s), 1.50-1.63 (2 H, m), 1.82-2.00 (2 H, m), 2.01-2.11 (2 H, m), 2.13-2.23 (1 H, m), 2.20 (3 H, s), 2.53-2.71 (3 H, m), 3.79 (3 H, s), 3.94 (1 H, d, J = 14.6 Hz), 3.96-4.04 (3 H, m), 4.19-4.42 (1 H, m), 5.83 (1 H, d, J = 14.6 Hz), 6.31-6.42 (1 H, m), 6.43-6.58 (2 H, m), 6.78-6.83 (2 H, m), |

-continued
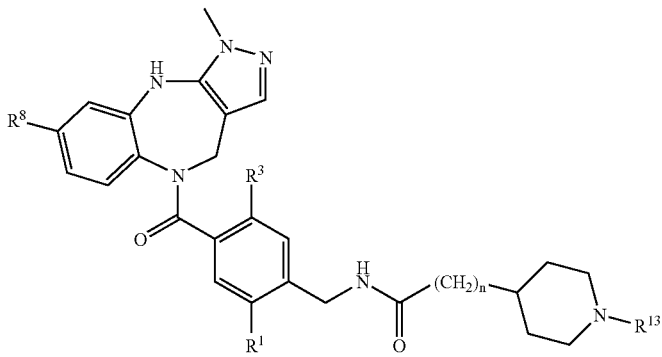
| Compound number | R¹ | R³ | R⁸ | R¹³ | n | MS | ¹H NMR: δ (ppm) |
|---|---|---|---|---|---|---|---|
| 1066 | Me | H | H | CO₂C(CH₃)₃ | 2 | (APCl)+: [M − Boc + H]+ = 487.5 | 0.91-1.12 (2 H, m), 1.30-1.64 (6 H, m), 1.43 (9 H, s), 2.11 (3 H, s), 2.22 (2 H, t, J = 7.2 Hz), 2.48-2.64 (2 H, m), 3.79 (3 H, s), 3.93-4.09 (3 H, m), 4.29-4.44 (1 H, m), 5.87 (1 H, d, J = 14.6 Hz), 6.11 (1 H, brs), 6.65-6.68 (2 H, m), 6.70-6.84 (3 H, m), 6.85-6.92 (1 H, m), 6.99-7.05 (1 H, m) 7.15 (1 H, s), 7.21 (1 H, s) |
| 1067 | Me | H | H | CO₂C(CH₃)₃ | 1 | (APCl)+: [M − Boc + H]+ = 473.5 | 0.91-1.11 (2 H, m), 1.44 (9 H, s), 1.49-1.72 (4 H, m), 1.84-2.06 (2 H, m), 2.09 (3 H, s), 2.58-2.74 (2 H, m), 3.76 (3 H, s), 3.93-4.06 (3 H, m), 4.17-4.31 (1 H, m), 5.87 (1 H, d, J = 14.6 Hz), 6.25 (1 H, brs), 6.64-6.67 (2 H, m), 6.74-6.76 (3 H, m), 6.94-6.98 (1 H, m), 7.01-7.08 (1 H, m), 7.12 (1 H, s), 7.21 (1 H, s) |
| 1068 | Cl | H | H | CH₂CH₂C(CH₃)₃ | 0 | (APCl)+: [M + H]+ = 563.4, 565.4 | 0.87 (9 H, s), 1.34-1.40 (2 H, m), 1.65-1.95 (5 H, m), 2.08-2.14 (2 H, m), 2.27-2.33 (2 H, m), 2.93-2.97 (2 H, m), 3.73 (3 H, s), 3.97 (1 H, d, J = 14.6 Hz), 4.33 (1 H, d, J = 5.9 Hz), 5.85 (1 H, d, J = 14.6 Hz), 6.20-6.22 (1 H, m), 6.66-6.71 (3 H, m), 6.91-6.98 (4 H, m), 7.03-7.07 (1 H, m), 7.22 (1 H, s) |
6.85-6.96 (2 H, m), 7.21 (1 H, s)

-continued

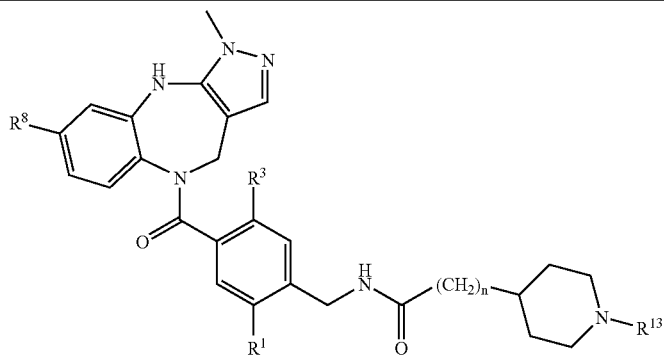

| Compound number | R¹ | R³ | R⁸ | R¹³ | n | MS | ¹H NMR: δ (ppm) |
|---|---|---|---|---|---|---|---|
| 1069 | Cl | H | H | ![cyclopropylmethyl] | 0 | (APCl)+: [M + H]+ = 533.4, 535.2 | 0.04-0.10 (2 H, m), 0.46-0.53 (4 H, m), 0.78-0.85 (1 H, m), 1.64-1.77 (4 H, m), 1.93-2.16 (2 H, m), 2.23 (2 H, d, J = 6.7 Hz), 2.33-2.40 (1 H, m), 3.05-3.10 (2 H, m), 3.73 (3 H, s), 3.98 (1 H, d, J = 14.6 Hz), 4.33 (2 H, d, J = 5.9 Hz), 5.85 (1 H, d, J = 14.6 Hz), 6.30-6.32 (1 H, m), 6.66-6.67 (2 H, m), 6.83 (1 H, s), 6.90-7.08 (3 H, m), 7.22 (1 H, s) |
| 1070 | H | F | Cl | CH₂CH₂C(CH₃)₃ | 0 | (APCl)+: [M + H]+ = 581.4, 583.4 | 0.86 (9 H, s), 1.34-1.40 (2 H, m), 1.72-1.76 (4 H, m), 1.88-1.95 (2 H, m), 2.10-2.14 (1 H, m), 2.28-2.34 (2 H, m), 2.94-2.98 (2 H, m), 3.64 (3 H, s), 3.97 (1 H, d, J = 14.6 Hz), 4.22 (2 H, d, J = 5.7 Hz), 5.76 (1 H, d, J = 14.6 Hz), 6.54 (1 H, dd, J = 2.2, 8.4 Hz), 6.58-6.76 (4 H, m), 6.96-7.03 (2 H, m), 7.20 (1 H, s) |
| 1071 | H | F | Cl | ![cyclopropylmethyl] | 0 | (APCl)+: [M + H]+ = 551.3, 553.3, 553.3 | 0.07-0.09 (2 H, m), 0.46-0.51 (2 H, m), 0.80-0.84 (1 H, m), 1.73-1.78 (4 H, m), 1.93-1.99 (2 H, m), 2.10-2.15 (1 H, m), 2.24 (2 H, d, J = 6.4 Hz), 2.51-2.53 (1 H, brs), 3.07-3.11 (2 H, m), 3.66 (3 H, s), 3.97 (1 H, d, J = 14.6 Hz), 4.24 (2 H, d, J = 5.9 Hz), 5.77 (1 H, d, J = 14.6 Hz), 6.55-6.77 (5 H, m), 6.96-7.04 (2 H, m), 7.21 (1 H, s) |
| 1072 | H | F | Me | CH₂CH₂C(CH₃)₃ | 0 | (APCl)+: [M + H]+ = | 0.87 (9 H, s), 1.35-1.41 (2 H, m), |

-continued
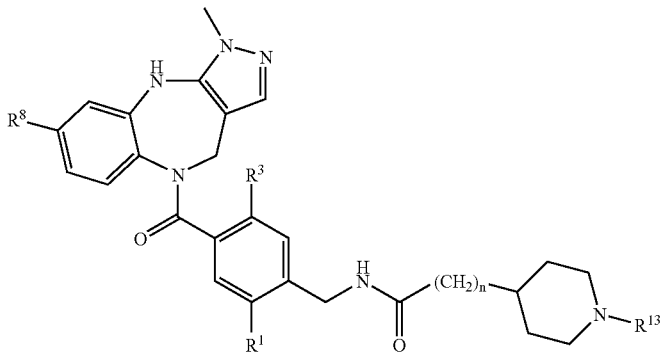
| Compound number | R¹ | R³ | R⁸ | R¹³ | n | MS | ¹H NMR: δ (ppm) |
|---|---|---|---|---|---|---|---|
| | | | | | | 561.4 | 1.73-1.81 (4 H, m), 1.89-2.02 (2 H, m), 2.10-2.14 (4 H, m), 2.29-2.35 (2 H, m), 2.94-2.98 (2 H, m), 3.68 (3 H, s), 3.95 (1 H, d, J = 14.6 Hz), 4.20-4.25 (2 H, m), 5.79 (1 H, d, J = 14.6 Hz), 6.42 (1 H, dd, J = 1.2, 8.2 Hz), 6.52-7.00 (6 H, m), 7.20 (1 H, s) |
| 1073 | H | F | Me | cyclopropylmethyl | 0 | (APCl)+: [M + H]+ = 531.4 | 0.05-0.10 (2 H, m), 0.46-0.53 (2 H, m), 0.79-0.83 (1 H, m), 1.72-1.79 (4 H, m), 1.95-2.04 (2 H, m), 2.08-2.14 (4 H, m), 2.22-2.26 (2 H, m), 2.90-2.92 (1 H, brs), 3.06-3.10 (2 H, m), 3.66 (3 H, s), 3.95 (1 H, d, J = 14.6 Hz), 4.18-4.23 (2 H, m), 5.76 (1 H, d, J = 14.6 Hz), 6.43 (1 H, dd, J = 1.2, 8.2 Hz), 6.57-6.97 (6 H, m), 7.18 (1 H, s) |
| 1074 | F | H | Me | cyclopropylmethyl | 0 | (APCl)+: [M + H]+ = 531.4 | 0.09-0.15 (2 H, m), 0.49-0.57 (2 H, m), 0.79-0.92 (1 H, m), 1.72-1.84 (4 H, m), 1.99-2.19 (3 H, m), 2.21 (3 H, s), 2.26-2.33 (2 H, m), 3.10-3.16 (2 H, m), 3.77 (3 H, s), 3.95 (1 H, d, J = 14.6 Hz), 4.33 (2 H, d, J = 5.9 Hz), 5.83 (1 H, d, J = 14.6 Hz), 6.24 (1 H, brs), 6.36 (1 H, s), 6.48-6.58 (2 H, m), 6.79 (1 H, s), 6.87-7.01 (3 H, m), 7.21 (1 H, s) |
| 1075 | F | H | Me | CH₂CH₂C(CH₃)₃ | 0 | (APCl)+: [M + H]+ = 561.4 | 0.87 (9 H, s), 1.36-1.43 (2 H, m), 1.62-1.81 (4 H, m), 1.96-1.17 (3 H, m), 2.20 (3 H, s), |

-continued
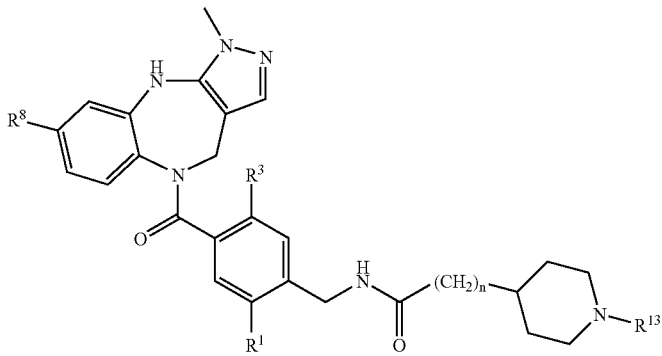
| Compound number | R¹ | R³ | R⁸ | R¹³ | n | MS | ¹H NMR: δ (ppm) |
|---|---|---|---|---|---|---|---|
| | | | | | | | 2.33-2.40 (2 H, m), 2.97-3.02 (2 H, m), 3.76 (3 H, s), 3.94 (1 H, d, J = 14.6 Hz), 4.32 (2 H, d, J = 5.7 Hz), 5.83 (1 H, d, J = 14.6 Hz), 6.19 (1 H, brs), 6.39 (1 H, s), 6.47-6.57 (2 H, m), 6.78 (1 H, s), 6.86-7.00 (3 H, m), 7.21 (1 H, s) |
| 1076 | H | F | H | CH₂CH₂C(CH₃)₃ | 0 | (APCl)+: [M + H]+ = 547.4 | 0.87 (9 H, s), 1.34-1.40 (2 H, m), 1.68-1.77 (4 H, m), 1.97-2.03 (2 H, m), 2.03-2.19 (1 H, m), 2.28-2.38 (2 H, m), 2.52 (2 H, s), 2.90-3.00 (2 H, m), 3.65 (3 H, s), 3.98 (1 H, d, J = 14.6 Hz), 4.18 (1 H, t, J = 6.2 Hz), 5.79 (1 H, d, J = 14.6 Hz), 6.57-6.72 (4 H, m), 6.75 (1 H, s), 6.90-7.02 (4 H, m) |
| 1077 | H | Cl | H | ![cyclopropylmethyl] | 0 | (ESI)+: [M + H]+ = 533.5, 535.5 | 0.35-0.45 (3 H, m), 0.68-0.80 (3 H, m), 0.98-1.15 (2 H, m), 1.81-2.10 (4 H, m), 2.46-2.55 (1 H, m), 2.91-3.00 (4 H, m), 3.60-3.75 (3 H, m), 3.78 (3 H, s), 4.02 (1 H, d, J = 14.6 Hz), 5.69 (1 H, d, J = 14.6 Hz), 6.59-6.70 (1 H, m), 6.91-7.20 (6 H, m), 7.25 (1 H, s) |
| 1078 | H | Cl | H | CH₂CH₂C(CH₃)₃ | 0 | (ESI)+: [M + H]+ = 565.7 | 0.87 (9 H, s), 1.31-1.48 (3 H, m), 1.67-1.82 (4 H, m), 1.93-2.22 (2 H, m), 2.28-2.47 (3 H, m), 2.90-3.10 (3 H, m), 3.67 (3 H, s), 4.03 (1 H, d, J = 14.6 Hz), 4.10-4.21 (2 H, m), 5.78 (1 H, d, J = 14.6 Hz), 6.56-6.70 (2 H, m), |

-continued
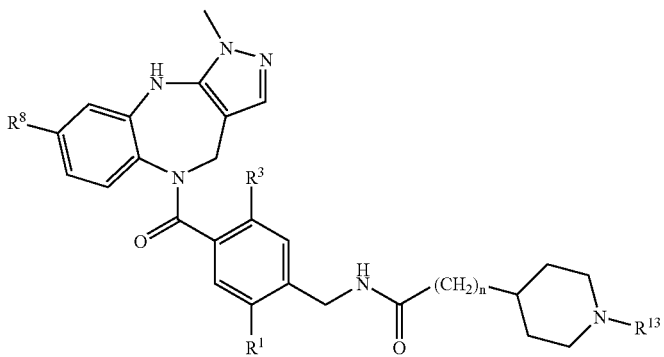
| Compound number | R¹ | R³ | R⁸ | R¹³ | n | MS | ¹H NMR: δ (ppm) |
|---|---|---|---|---|---|---|---|
| | | | | | | | 6.70-6.85 (1 H, m), 6.85-6.95 (4 H, m), 7.22 (1 H, s) |
| 1079 | H | Me | H | -CH₂-cyclopropyl | 0 | (ESI)+: [M + H]+ = 513.5 | 0.05-0.07 (3 H, m), 0.48-0.51 (3 H, m), 0.83-0.85 (2 H, m), 1.61-2.00 (7 H, m), 2.22 (2 H, d, J = 6.4 Hz), 2.31 (3 H, s), 3.00-3.15 (2 H, m), 3.71 (3 H, s), 4.03 (1 H, d, J = 14.6 Hz), 4.22 (2 H, d, J = 5.7 Hz), 5.85 (1 H, d, J = 14.6 Hz), 6.42 (1 H, s), 6.60-6.87 (4 H, m), 6.90-7.10 (2 H, m) ppm. |
| 1080 | H | Me | H | CH₂CH₂C(CH₃)₃ | 0 | (ESI)+: [M + H]+ = 543.5 | δ 0.93 (9 H, s), 1.28-1.37 (5 H, m), 1.43-1.52 (2 H, m), 1.71-1.91 (3 H, m), 2.29 (3 H, s), 2.30-2.40 (2 H, m), 2.60-2.68 (2 H, m), 3.12-3.23 (2 H, m), 3.62-3.73 (1 H, m), 3.78 (3 H, s), 4.00 (1 H, d, J = 14.6 Hz), 5.73 (1 H, d, J = 14.6 Hz), 6.59-6.66 (1 H, m), 6.78-6.85 (2 H, m), 6.90-7.00 (2 H, m), 7.01-7.15 (1 H, m), 7.24 (1 H, s), 7.25-7.30 (1 H, m) |

-continued
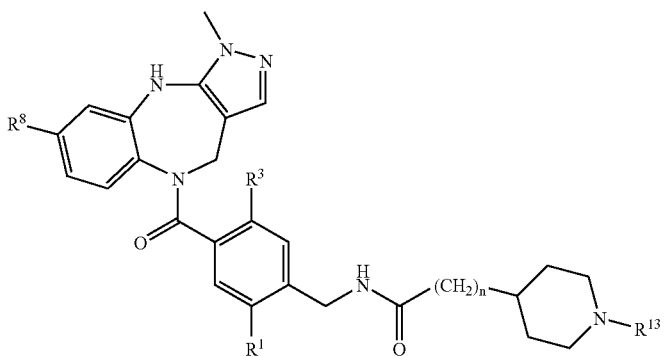
| Compound number | R¹ | R³ | R⁸ | R¹³ | n | MS | ¹H NMR: δ (ppm) |
|---|---|---|---|---|---|---|---|
| 1081 | H | Cl | Cl | (cyclopropylmethyl) | 0 | (APCI)+: [M + H]+ = 567.3 | 0.04-0.09 (2 H, m), 0.46-0.51 (2 H, m), 0.74-0.89 (1 H, m), 1.63-1.84 (2 H, m), 1.89-2.04 (2 H, m), 2.05-2.21 (1 H, m), 2.23 (2 H, d, J = 6.4 Hz), 3.04-3.15 (4 H, m), 3.61 (3 H, s), 3.98 (1 H, d, J = 14.6 Hz), 4.10-4.19 (2 H, m), 4.31-4.38 (1 H, m), 5.71 (1 H, d, J = 14.6 Hz), 6.53 (1 H, dd, J = 2.0, 8.4 Hz), 6.70-6.84 (3 H, m), 6.96-7.11 (2 H, m), 7.17 (1 H, s), 7.73 (1 H, s) |
| 1082 | H | Me | Cl | (cyclopropylmethyl) | 0 | (APCI)+: [M + H]+ = 547.4, 549.4 | 0.03-0.09 (2 H, m), 0.44-0.49 (2 H, m), 0.78-0.84 (1 H, m), 1.68-1.85 (4 H, m), 1.94-2.10 (2 H, m), 2.10-2.24 (1 H, m), 2.22 (3 H, s), 2.23 (2 H, d, J = 8.2 Hz), 3.04-3.13 (2 H, m), 3.61 (3 H, s), 3.94 (1 H, d, J = 14.6 Hz), 4.17 (2 H, d, J = 5.7 Hz), 4.38 (1 H, d, J = 5.7 Hz), 5.76 (1 H, d, J = 14.6 Hz), 6.49-6.65 (3 H, m), 6.71-6.83 (2 H, m), 6.87-7.02 (1 H, m), 7.19 (1 H, s), 7.57 (1 H, s) |

-continued

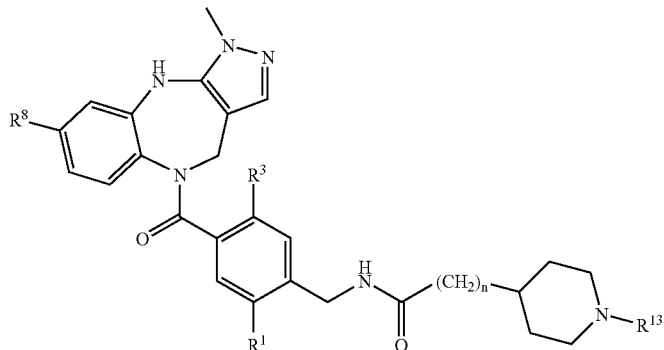

| Compound number | R¹ | R³ | R⁸ | R¹³ | n | MS | ¹H NMR: δ (ppm) |
|---|---|---|---|---|---|---|---|
| 1083 | H | Cl | Me | cyclopropylmethyl | 0 | (APCl)+: [M + H]+ = 547.3, 549.3 | d4-MeOH: 0.30-0.36 (2 H, m), 0.65-0.71 (2 H, m), 0.96-1.10 (1 H, m), 1.82-2.04 (4 H, m), 2.15 (3 H, s), 2.38-2.49 (1 H, m), 2.68-2.84 (4 H, m), 3.49 (2 H, brd, J = 12.6 Hz), 3.76 (3 H, s), 3.98 (1 H, d, J = 14.6 Hz), 4.22 (2 H, s), 5.67 (1 H, d, J = 14.6 Hz), 6.46 (1 H, dd, J = 1.5, 8.2 Hz), 6.83 (1 H, d, J = 8.2 Hz), 6.94-7.11 (3 H, m), 7.16 (1 H, s), 7.22 (1 H, s) |
| 1084 | H | Me | Me | cyclopropylmethyl | 0 | (APCl)+: [M + H]+ = 527.4 | 0.05-0.09 (2 H, m), 0.45-0.52 (2 H, m), 0.72-0.86 (1 H, m), 1.62-1.84 (4 H, m), 1.97-2.11 (2 H, m), 2.05 (3 H, s), 2.11-2.24 (1 H, m), 2.25 (2 H, d, J = 5.7 Hz), 2.26 (3 H, s), 3.06-3.17 (2 H, m), 3.66 (3 H, s), 3.94 (1 H, d, J = 14.6 Hz), 4.17 (2 H, d, J = 5.7 Hz), 4.37 (1 H, d, J = 5.7 Hz), 5.78 (1 H, d, J = 14.6 Hz), 6.31-6.83 (7 H, m), 7.19 (1 H, s) |
| 1085 | H | Cl | Cl | CH₂CH₂C(CH₃)₃ | 0 | (APCl)+: [M + H]+ = 597.3 | 0.87 (9 H, s), 1.33-1.41 (2 H, m), 1.63-1.98 (6 H, m), 2.07-2.17 (1 H, m), 2.26-2.32 (2 H, m), 2.92-2.96 (2 H, m), 3.61 (3 H, s), 3.98 (1 H, d, J = 14.6 Hz), 4.08-4.23 (2 H, m), 4.34-4.37 (1 H, m), 5.71 (1 H, d, J = 14.6 Hz), 6.52 (1 H, dd, J = 2.0, 8.4 Hz), 6.70-6.98 (5 H, m), 7.17 (1 H, s), 7.73 (1 H, s) |
| 1086 | H | Me | Cl | CH₂CH₂C(CH₃)₃ | 0 | (APCl)+: [M + H]+ = | 0.87 (9 H, s), 1.33-1.41 (2 H, m), |

-continued
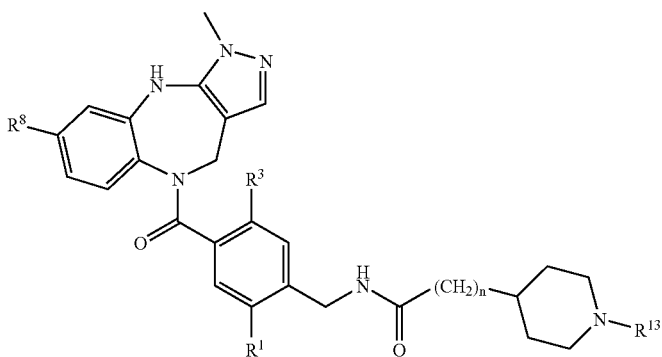
| Compound number | R¹ | R³ | R⁸ | R¹³ | n | MS | ¹H NMR: δ (ppm) |
|---|---|---|---|---|---|---|---|
| | | | | | | 577.4, 579.3 | 1.68-1.98 (6 H, m), 2.03-2.17 (1 H, m), 2.22 (3 H, s), 2.27-2.33 (2 H, m), 2.93-2.97 (2 H, m), 3.61 (3 H, s), 3.95 (1 H, d, J = 14.6 Hz), 4.17-4.19 (2 H, m), 4.37-4.39 (1 H, m), 5.77 (1 H, d, J = 14.6 Hz), 6.40-7.17 (6 H, m), 7.19 (1 H, s), 7.47 (1 H, s) ppm. |
| 1087 | H | Cl | Me | CH₂CH₂C(CH₃)₃ | 0 | (APCl)+: [M + H]+ = 577.4, 579.4 | δ 0.88 (9 H, s), 1.34-1.42 (2 H, m), 1.67-2.22 (7 H, m), 2.07 (3 H, s), 2.27-2.33 (2 H, m), 2.93-2.97 (2 H, m), 3.65 (3 H, s), 3.98 (1 H, d, J = 14.6 Hz), 4.13-4.20 (2 H, m), 4.34-4.37 (1 H, m), 5.75 (1 H, d, J = 14.6 Hz), 6.43 (1 H, dd, J = 1.2, 8.2 Hz), 6.67-6.80 (5 H, m), 6.92-6.93 (1 H, m), 7.19 (1 H, s) |
| 1088 | H | Me | Me | CH₂CH₂C(CH₃)₃ | 0 | (APCl)+: [M + H]+ = 557.4 | 0.87 (9 H, s), 1.33-1.41 (2 H, m), 1.65-2.04 (7 H, m), 2.07 (3 H, s), 2.22-2.34 (5 H, m), 2.92-3.00 (2 H, m), 3.62 (3 H, s), 3.94 (1 H, d, J = 14.6 Hz), 4.16-4.19 (2 H, m), 4.36-4.39 (1 H, m), 5.80 (1 H, d, J = 14.6 Hz), 6.34-7.14 (7 H, m), 7.19 (1 H, s) |

-continued
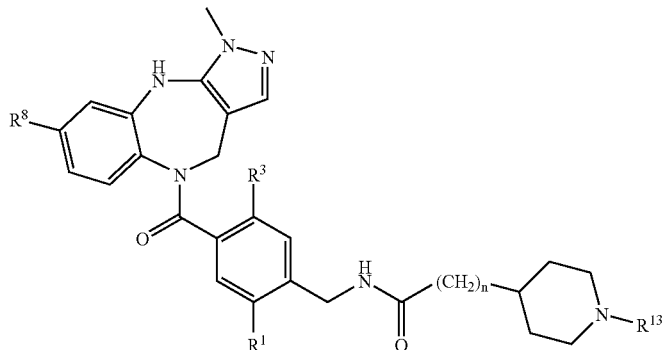
| Compound number | R¹ | R³ | R⁸ | R¹³ | n | MS | ¹H NMR: δ (ppm) |
|---|---|---|---|---|---|---|---|
| 1089 | F | H | H | (cyclopropylmethyl) | 0 | (ESI)+: [M + H]+ = 517.5 | d4-MeOH: 0.14-0.19 (2 H, m), 0.53-0.59 (2 H, m), 0.87-0.90 (1 H, m), 1.73-1.81 (4 H, m), 2.14-2.24 (3 H, m), 2.35-2.37 (2 H, m), 3.16-3.21 (2 H, m), 3.79 (3 H, s), 3.97 (1 H, d, J = 14.6 Hz), 4.29 (2 H, s), 5.75 (1 H, d, J = 14.6 Hz), 6.65-6.77 (2 H, m), 6.90-7.00 (2 H, m), 7.07-7.15 (2 H, m), 7.20-7.24 (2 H, m) |
| 1090 | F | H | H | $CH_2CH_2C(CH_3)_3$ | 0 | (ESI)+: [M + H]+ = 547.5 | 0.86 (9 H, s), 1.32-1.39 (2 H, m), 1.69-1.92 (3 H, m), 2.04-2.10 (2 H, m), 2.25-2.31 (1 H, m), 2.58 (1 H, m), 2.90-2.94 (2 H, m), 3.67 (3 H, s), 3.97 (1 H, d, J = 14.6 Hz), 4.25-4.28 (2 H, m), 5.83 (1 H, d, J = 14.6 Hz), 6.37-6.39 (1 H, m), 6.65 (2 H, m), 6.83-7.03 (5 H, m), 7.14 (1 H, s), 7.20 (1 H, s) |
| 1091 | Cl | H | Me | (cyclopropylmethyl) | 0 | (ESI)+: [M + H]+ = 547.4, 549.4 | d4-MeOH: 0.14-0.20 (2 H, m), 0.52-0.60 (2 H, m), 0.90 (1 H, m), 1.76-1.84 (4 H, m), 2.16-2.32 (6 H, m), 2.36-2.39 (2 H, m), (3.18-3.22 (2 H, m), 3.78 (3 H, s), 3.93 (1 H, d, J = 14.6 Hz), 4.32 (2 H, s), 5.73 (1 H, d, J = 14.6 Hz), 6.50 (1 H, dd, J = 1.0 8.0 Hz), 6.62 (1 H, d, J = 8.0 Hz), 7.04 7.11 (2 H, s), 7.20-7.23 (2 H, m) |
| 1092 | Cl | H | Me | $CH_2CH_2C(CH_3)_3$ | 0 | (APCl)+: [M + H]+ = 577.3, 579.3 | 0.86 (9 H, s), 1.33-1.40 (2 H, m), 1.70-1.92 (6 H, m), 2.12-2.14 (4 H, m), 2.28-2.34 (2 H, m), 2.93-2.96 (2 H, m), |

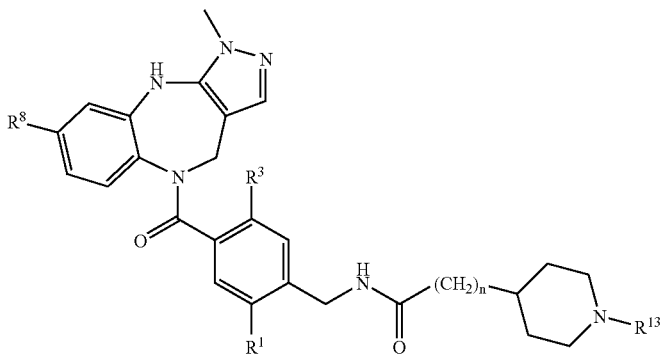
| Compound number | R¹ | R³ | R⁸ | R¹³ | n | MS | ¹H NMR: δ (ppm) |
|---|---|---|---|---|---|---|---|
| | | | | | | | 3.70 (3 H, s), 3.93 (1 H, d, J = 14.6 Hz), 4.28-4.32 (2 H, m), 5.79 (1 H, d, J = 14.6 Hz), 6.45-6.54 (2 H, m), 6.79-6.89 (4 H, m), 7.17 (1 H, s), 7.22 (1 H, s) |
| 1093 | Cl | H | Cl | CH₂CH₂C(CH₃)₃ | 0 | (APCl)+: [M + H]+ = 597.2 | 0.86 (9 H, s), 1.33-1.39 (2 H, m), 1.68-1.90 (6 H, m), 2.13 (1 H, m), 2.26-2.32 (2 H, m), 2.93-2.97 (2 H, m), 3.67 (3 H, s), 3.94 (1 H, d, J = 14.6 Hz), 4.32 (d, J = 14.6 Hz), (2 H, m), 5.78 (1 H, d, J = 14.6 Hz), 6.56 (2 H, s), 6.87-6.97 (2 H, m), 7.02 (1 H, s), 7.18 (1 H, s), 7.21 (1 H, d, J = 1.2 Hz), 7.64 (1 H, s) |
| 1094 | F | H | Cl | CH₂CH₂C(CH₃)₃ | 0 | (APCl)+: [M + H]+ = 581.3, 583.3 | 0.85 (9 H, s), 1.35-1.41 (2 H, m), 1.76 (4 H, m), 2.01-2.14 (3 H, m), 2.34-2.40 (2 H, m), 2.97-3.01 (2 H, m), 3.68 (3 H, s), 3.94 (1 H, d, J = 1 4.6 Hz), 4.27 (2 H, m), 5.76 (1 H, d, J = 14.6 Hz), 6.54 (2 H, s), 6.81-6.97 (3 H, m), 7.05 (1 H, s), 7.17 (1 H, s), 8.08 (1 H, s) |

-continued
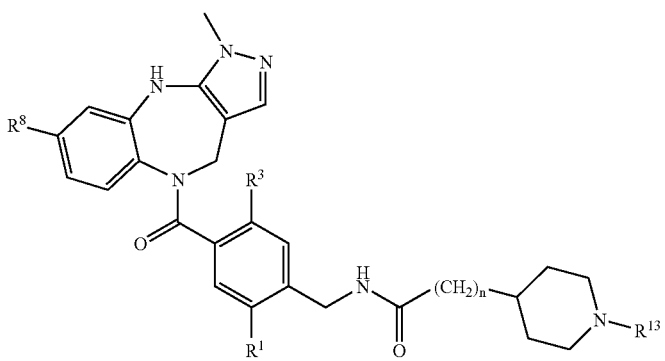
| Compound number | R¹ | R³ | R⁸ | R¹³ | n | MS | ¹H NMR: δ (ppm) |
|---|---|---|---|---|---|---|---|
| 1095 | Me | H | Cl | ...cyclopropylmethyl | 0 | (APCl)+: [M + H]+ = 547.4, 549.4 | d6-DMSO: 0.15-0.24 (2 H, m), 0.48-0.59 (2 H, m), 0.84-1.03 (1 H, m), 1.61-1.88 (4 H, m), 2.14 (3 H, s), 2.20-2.80 (4 H, m), 3.16-3.46 (3 H, m), 3.77 (3 H, s), 3.90 (1 H, d, J = 14.6 Hz), 4.06-4.23 (2 H, m), 5.63 (1 H, d, J = 14.6 Hz), 6.67 (1 H, dd, J = 2.0, 8.4 Hz), 6.74 (1 H, d, J = 8.4 Hz), 6.84 (1 H, d, J = 7.8 Hz), 6.94 (1 H, d, J = 7.8 Hz), 7.05 (1 H, s), 7.18 (1 H, s), 7.40 (1 H, d, J = 2.0 Hz), 8.26 (1 H, s), 8.82 (1 H, s) |
| 1096 | Cl | H | Cl | ...cyclopropylmethyl | 0 | (ESI)+: [M + H]+ = 567.2 | d6-DMSO: 0.15-0.22 (2 H, m), 0.50-0.52 (2 H, m), 0.89 (1 H, m), 1.60-1.82 (6 H, m), 2.13-2.34 (3 H, m), 3.09-3.18 (2 H, m), 3.76 (3 H, s), 3.93 (1 H, d, J = 14.6 Hz), 4.25 (2 H, m), 5.62 (1 H, d, J = 14.6 Hz), 6.71 (1 H, dd, J = 2.2, 8.4 Hz), 6.84 (1 H, d, J = 8.4 Hz), 7.03-7.11 (2 H, m), 7.20 (2 H, s), 7.38 (1 H, d, J = 2.2 Hz), 8.34 (1 H, m), 8.82 (1 H, s) |

-continued
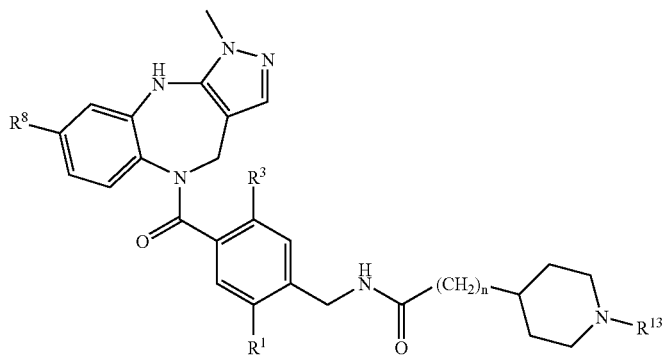
| Compound number | R¹ | R³ | R⁸ | R¹³ | n | MS | ¹H NMR: δ (ppm) |
|---|---|---|---|---|---|---|---|
| 1097 | F | H | Cl | (cyclopropylmethyl) | 0 | (ESI)+: [M + H]+ = 551.3, 553.3 | d6-DMSO: 0.04-0.06 (2 H, m), 0.43-0.45 (2 H, m), 0.78-0.81 (1 H, m), 1.53-1.66 (5 H, m), 1.90 (1 H, m), 2.07-2.16 (3 H, m), 2.98 (2 H, m), 3.76 (3 H, s), 3.93 (1 H, d, J = 14.6 Hz), 4.19 (2 H, m), 5.61 (1 H, d, J = 14.6 Hz), 6.69 (1 H, dd, J = 2.2, 8.4 Hz), 6.82 (1 H, d, J = 8.4 Hz), 6.90-6.94 (2 H, m), 7.05-7.11 (1 H, m), 7.19 (1 H, s), 7.37 (1 H, d, J = 2.2 Hz), 8.25 (1 H, m), 8.80 (1 H, s) |
| 1098 | Me | H | Me | (cyclopropylmethyl) | 0 | (APCl)+: [M + H]+ = 527.4 | d4-MeOH: 0.32-0.45 (2 H, m), 0.68-0.80 (2 H, m), 101-1.19 (1 H, m), 1.78-2.15 (4 H, m), 2.17 (3 H, s), 2.24 (3 H, s), 2.81-3.20 (4 H, m), 3.51-3.78 (3 H, m), 3.93 (1 H, d, J = 14.6 Hz), 3.96 (3 H, s), 4.26 (2 H, s), 5.78 (1 H, d, J = 14.6 Hz), 6.52-6.71 (2 H, m), 6.99-7.13 (4 H, m), 7.61 (1 H, s) |
| 1099 | Me | H | Cl | CH₂CH₂C(CH₃)₃ | 0 | (APCl)+: [M + H]+ = 577.4, 579.4 | 0.88 (9 H, s), 1.38-1.45 (2 H, m), 1.72-1.94 (4 H, m), 2.01-2.18 (2 H, m), 2.11 (3 H, s), 2.39-2.45 (2 H, m), 2.96-3.05 (2 H, m), 3.09-3.22 (1 H, m), 3.76 (3 H, s), 3.93 (1 H, d, J = 14.6 Hz), 4.26 (2 H, d, J = 4.5 Hz), 5.83 (1 H, d, J = 14.6 Hz), 6.13 (1 H, brs), 6.57-6.61 (2 H, m), 6.80-6.84 (3 H, m), 7.03 (1 H, s), 7.08 (1 H, s), 7.21 (1 H, s) |

-continued
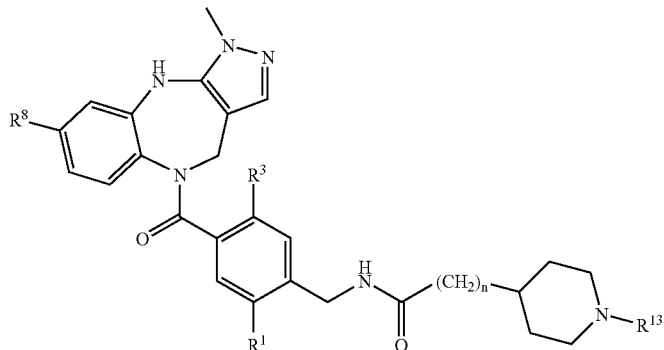
| Compound number | R¹ | R³ | R⁸ | R¹³ | n | MS | ¹H NMR: δ (ppm) |
|---|---|---|---|---|---|---|---|
| 1100 | Me | H | Me | CH₂CH₂C(CH₃)₃ | 0 | (APCl)+: [M + H]+ = 577.5 | 0.88 (9 H, s), 1.38-1.45 (2 H, m), 1.67-1.83 (4 H, m), 1.94-2.23 (2 H, m), 2.07 (3 H, s), 2.19 (3 H, s), 2.35-2.44 (2 H, m), 2.93-3.15 (3 H, m), 3.74 (3 H, s), 3.93 (1 H, d, J = 14.6 Hz), 4.19-4.25 (2 H, m), 5.83 (1 H, d, J = 14.6 Hz) 6.19 (1 H, brs), 6.45-6.55 (3 H, m), 6.77-6.83 (3 H, m), 7.06 (1 H, s), 7.19 (1 H, s) |
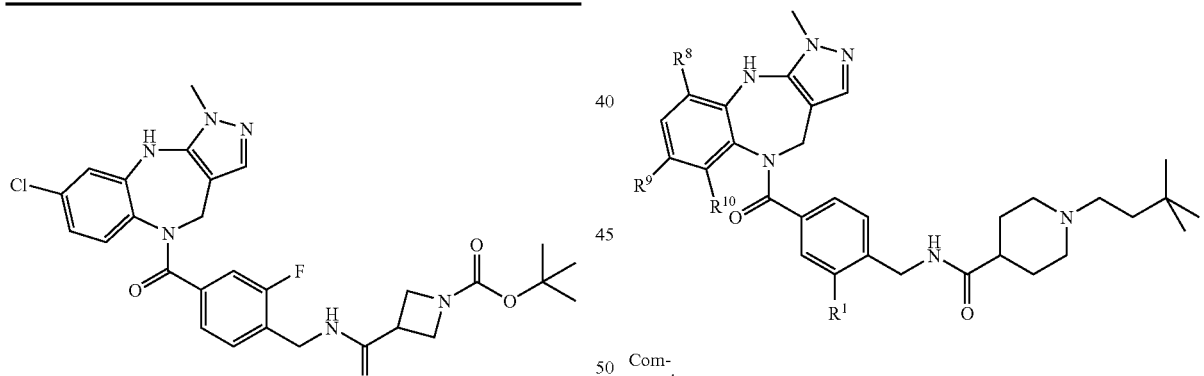
| Compound number | MS | ¹H NMR: δ (ppm) |
|---|---|---|
| 1101 | (ESI)+: [M + H]+ = 569.2 | 1.41 (9 H, s), 3.13-3.30 (2 H, m), 3.73 (2 H, s), 3.80-4.15 (6 H, m), 4.18-4.34 (2 H, m), 5.77 (1 H, m), 6.58 (2 H, s), 6.73-6.87 (2 H, m), 6.87-6.99 (1 H, m), 7.08 (1 H, s), 7.19 (1 H, s), 7.82 (1 H, s) |
| Compound number | R¹ | R⁸ | R⁹ | R¹⁰ | MS | ¹H NMR: δ (ppm) |
|---|---|---|---|---|---|---|
| 1102 | Me | Me | H | H | (ESI)+: [M + H]+ = 557.6 | 0.89 (9 H, s), 1.46-1.56 (2 H, m), 1.78-2.06 (7 H, m), 2.20-2.62 (8 H, m), 3.10-3.20 (2 H, m), 3.88 (3 H, s), 3.95 (1 H, d, J = 14.6 Hz), 4.22 (2 H, m), 5.90 (1 H, d, J = 14.6 Hz), 6.28-6.40 (1 H, m), 6.55-6.68 (2 H, m), 6.79-6.88 (2 H, m), 6.90-7.04 (2 H, m), 7.25 |

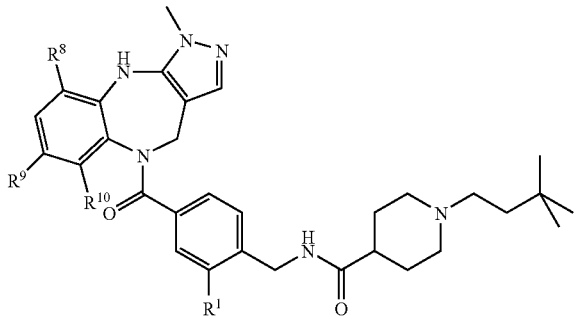
| Compound number | R¹ | R⁸ | R⁹ | R¹⁰ | MS | ¹H NMR: δ (ppm) |
|---|---|---|---|---|---|---|
| 1103 | Me | H | Me | H | (ESI)+: [M + H] + = 557.4 | (1 H, s) 0.88 (9 H, s), 1.36-1.46 (2 H, m), 1.68-1.90 (4 H, m), 2.03 (3 H, s), 2.12 (3 H, s), 2.26-2.43 (4 H, m), 2.95-3.05 (2 H, m), 3.65-3.75 (1 H, m), 3.78 (3 H, s), 3.95 (1 H, d, J = 14.7 Hz), 4.25-4.35 (2 H, m), 5.86 (1 H, d, J = 14.7 Hz), 6.02-6.12 (1 H, m), 6.51 (1 H, s), 6.82 (1 H, s), 6.82-6.94 (4 H, m), 7.12 (1 H, s) |
| 1104 | F | Me | H | H | (ESI)+: [M + H] + = 561.4 | 0.91 (9 H, s), 1.79-2.00 (2 H, m), 2.10-2.34 (1 H, m), 2.42 (3 H, s), 2.50-2.73 (1 H, m), 2.83-2.97 (2 H, m), 2.98-3.12 (3 H, m), 3.13-3.33 (1 H, m), 3.35-3.52 (1 H, m), 3.53-3.70 (2 H, m), 3.85 (3 H, s), 3.95 (1 H, d, J = 14.6 Hz), 4.14-4.42 (2 H, m), 5.81 (1 H, d, J = 14.6 Hz), 6.08 (1 H, s), 6.40-6.70 (2 H, m), 6.72-7.06 (4 H, m), 7.43 (1 H, s) |
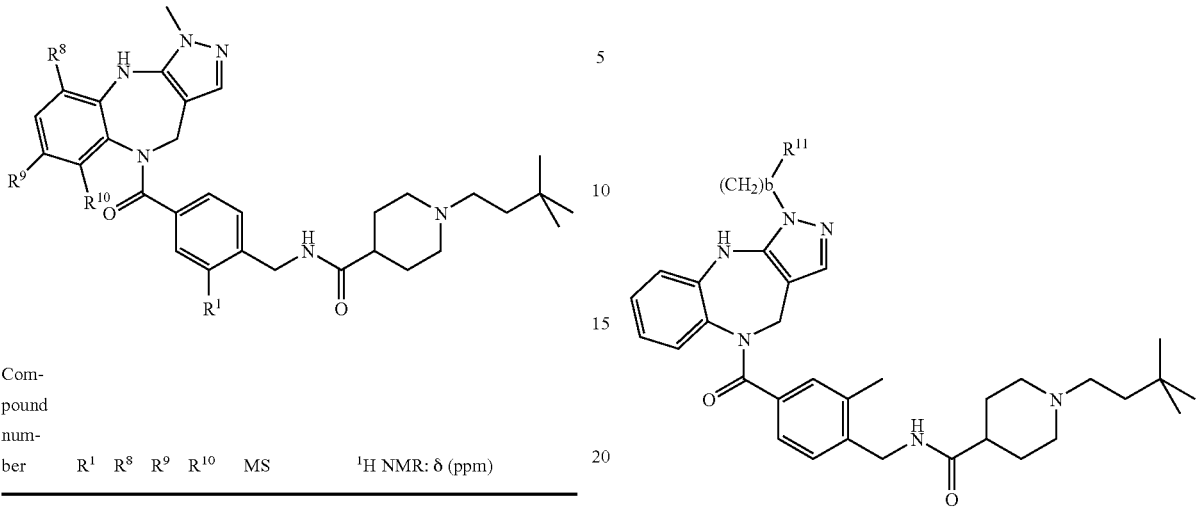
| Compound number | b | R¹¹ | MS | ¹H NMR: δ (ppm) |
|---|---|---|---|---|
| 1105 | 3 | Me | 585.4 | 0.88 (9 H, s), 0.97 (3 H, t, J = 7.3 Hz), 1.03-1.05 (4 H, m), 1.07-1.95 (6 H, m), 2.00-2.25 (5 H, m), 2.35-2.50 (2 H, m), 3.00-3.12 (3 H, m), 3.97 (1 H, d, J = 14.6 Hz), 4.06 (2 H, t, J = 6.8 Hz), 4.26 (2 H, d, J = 4.7 Hz) 5.90 (1 H, d, J = 14.6 Hz) 5.95-6.05 (1 H, m) 6.24, (1 H, s), 6.67-6.73 (2 H, m), 6.80-6.98 (3 H, m), 7.05-7.15 (2 H, m) |
| 1106 | 1 | Me | 557.4 | 0.87 (9 H, s), 1.36-1.52 (5 H, m), 1.68-1.90 (4 H, m), 1.92-2.16 (6 H, m), 2.32-2.42 (2 H, m), 2.96-3.06 (2 H, m), 3.97 (1 H, d, J = 14.5 Hz), 4.09 (2 H, q, J = 7.0 Hz), 4.46 (2 H, d, J = 4.9 Hz), 5.80-5.90 (1 H, m), 5.90 (1 H, d, J = 14.5 Hz), 6.63-6.74 (2 H, m), 6.79-7.00 (3 H, m), 7.02-7.12 (2 H, m), 7.13 (1 H, s), 7.24 (1 H, s) |

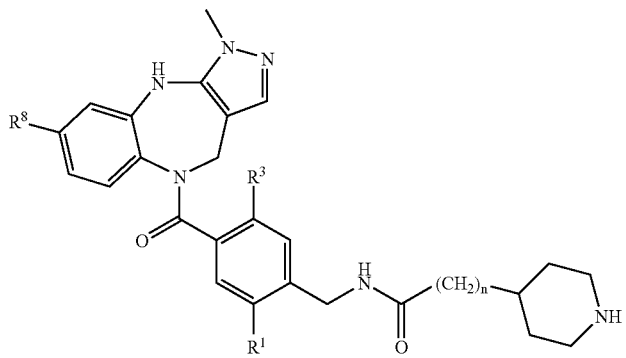

| Compound number | R¹ | R³ | R⁸ | n | MS | ¹H NMR: δ (ppm) |
|---|---|---|---|---|---|---|
| 1107 E91 | Me | H | H | 1 | (APCl)+: [M + H]+ = 473.5 | d4-MeOH 1.35-1.54 (3 H, m), 1.89 (2 H, d, J = 13.6 Hz), 1.92-2.11 (1 H, m), 2.18 (3 H, s), 2.18-2.24 (1 H, m), 2.92-3.02 (2 H, m), 3.29-3.39 (2 H, m), 3.99-4.04 (1 H, m), 4.04 (3 H, s), 4.27 (2 H, s), 5.88 (1 H, d, J = 14.6 Hz), 6.84-6.86 (2 H, m), 6.98-7.07 (3 H, m), 7.20-7.27 (1 H, m), 7.40 (1 H, d, J = 8.2 Hz), 8.03 (1 H, s) |
| 1108 | H | Me | Cl | 2 | (APCl)+: [M + H]+ = 521.6, 523.5 | d4-MeOH 1.28-1.41 (1 H, m), 1.42-1.67 (2 H, m), 1.85-1.91 (2 H, m), 2.20-2.33 (1 H, m), 2.27 (3 H, s), 2.78-2.94 (1 H, m), 3.27-3.39 (5 H, m), 3.79 (3 H, s), 3.99 (1 H, d, J = 14.6 Hz), 4.22 (2 H, s), 5.71 (1 H, d, J = 14.6 Hz), 6.53-6.61 (1 H, m), 6.74-6.81 (1 H, m), 6.83-6.94 (2 H, m), 7.00-7.04 (1 H, m), 7.22-7.25 (2 H, m) |
| 1109 | Cl | H | H | 0 | (APCl)+: [M + H]+ = 479.4, 481.4 | d4-MeOH 1.78-2.07 (2 H, m), 2.52-2.71 (1 H, m), 2.96-3.12 (2 H, m), 3.19-3.32 (2 H, m), 3.35-3.43 (2 H, m), 4.04 (1 H, d, J = 14.6 Hz), 4.05 (3 H, s), 4.35 (2 H, s), 5.87 (1 H, d, J = 14.6 Hz), 6.86-6.90 (2 H, m), 7.11-7.19 (2 H, m), 7.22-7.28 (2 H, m), 7.42-7.45 (1 H, m), 8.05 (1 H, s) |
| 1110 | F | H | Me | 1 | (ESI)+: [M + H]+ = 491.6 | d4-MeOH 1.34-1.53 (2 H, m), 1.85-1.91 (2 H, m), 1.93-2.17 (1 H, m), 2.20-2.23 (2 H, m), 2.28 (3 H, s), 2.91-3.02 (2 H, m), 3.30-3.38 (2 H, m), 3.99 (1 H, d, J = 14.6 Hz), 4.02 (3 H, s), 4.32 (2 H, s), 5.84 (1 H, d, J = 14.6 Hz), 6.67-6.78 (2 H, m), 6.95-7.03 (2 H, m), 7.12-7.23 (2 H, m), 8.01 (1 H,s) |
| 1111 | Me | H | H | 2 | (APCl)+: [M + H]+ = 487.4 | d4-MeOH: 1.29-1.48 (2 H, m), 1.50-1.64 (3 H, m), 1.82-1.98 (2 H, m), 2.18 (3 H, s), 2.18-2.31 (2 H, m), 2.85-2.99 (2 H, m), 3.30-3.38 (2 H, m), 3.94-4.05 (1 H, m), 4.05 (3 H, s), 4.26 (2 H, s), 5.88 (1 H, d, J = 14.6 Hz), 6.85 (2 H, s), 7.00-7.09 (3 H, m), 7.19-7.28 (1 H, m), 7.40-7.43 (1 H, m), 8.04 (1 H, s) |

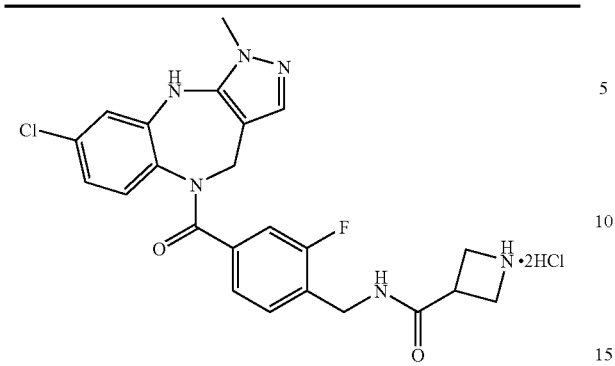
| Compound number | MS | ¹H NMR: δ (ppm) |
|---|---|---|
| 1112 | (ESI)+: [M + H]+ = 469.2, 471.2 | d4-MeOH 3.57-3.72 (1 H, m), 3.98 (3 H, s), 4.04 (1 H, d, J = 15.3 Hz), 4.17 (4 H, d, J = 8.2 Hz), 4.36-4.42 (2 H, m), 5.83 (1 H, d, J = 15.3 Hz), 6.82-6.92 (2 H, m), 6.96-7.08 (2 H, m), 7.18-7.32 (1 H, m), 7.41 (1 H, s), 7.92 (1 H, s), 8.56-8.64 |
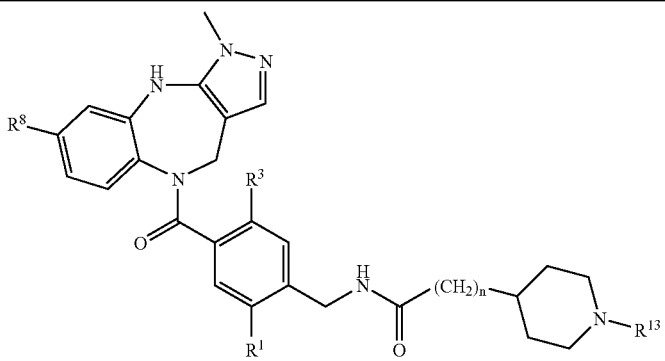
| Compound number | R¹ | R³ | R⁸ | R¹³ | n | MS | ¹H NMR: δ (ppm) |
|---|---|---|---|---|---|---|---|
| 1113 E92 | Me | H | H | $CH_2CH_2C(CH_3)_3$ | 1 | (APCl)+: [M+ H]+ = 557.5 | 0.86 (9H, s), 1.11-1.29 (2 H, m), 1.34-1.41 (2 H, m), 1.58-1.64 (2 H, m), 1.65-1.86 (1 H, m), 1.89-2.01 (2 H, m), 2.04 (3 H, s), 2.29-2.36 (2 H, m), 2.80-2.91 (4 H, m), 3.64 (3 H, s), 3.94 (1 H, d, J = 14.6 Hz), 4.19 (2 H, d, J = 4.0 Hz), 5.83 (1 H, d, J = 14.6 Hz), 6.51-6.68 (3 H, m), 6.75-6.81 (2 H, m), 6.91-7.02 (3 H, m), 7.10-7.17 (2 H, m) |
| 1114 | Me | H | H | $CH_2CH_2C(CH_3)_3$ | 2 | (APCl)+: [M+ H]+ = 571.5 | 0.87 (9H, s), 1.13-1.28 (3 H, m), 1.34-1.40 (2 H, m), 1.43-1.68 (2 H, m), 1.78-1.89 (4 H, m), 2.06 (2 H, m), 2.15 (3 H, s), 2.23-2.30 (2 H, t, J = 7.4 Hz), 2.88 (2 H, m) |

-continued
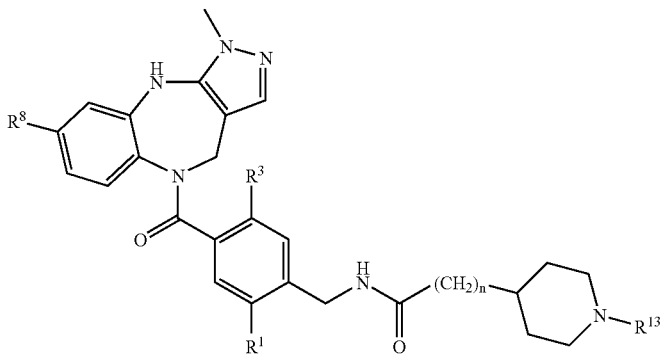
| Compound number | R¹ | R³ | R⁸ | R¹³ | n | MS | ¹H NMR: δ (ppm) |
|---|---|---|---|---|---|---|---|
| | | | | | | | (2 H, d, J = 10.9 Hz), 3.66 (3 H, s), 3.95 (1 H, d, J = 14.6 Hz), 4.22 (2 H, d, J = 5.2 Hz), 5.87 (1 H, d, J = 14.6 Hz), 6.08 (1 H, t, J = 5.2 Hz), 6.61-6.68 (2 H, m), 6.76-6.87 (3 H, m), 6.95-7.05 (2 H, m), 7.07 (1 H, s), 7.20 (1 H, s) |
| 1115 | Me | H | H | $CH_2CH_2C(CH_3)_3$ | 0 | (ESI)+: [M+ H]+ = 543.4 | 0.88 (9H, s), 1.35-1.42 (2 H, m), 1.57-2.00 (6 H, m), 2.12 (3 H, s), 2.29-2.32 (2 H, m), 2.92-3.03 (2 H, m), 3.14-3.15 (1 H, m), 3.80 (3 H, s), 3.97 (1 H, d, J = 14.6 Hz), 4.28 (2 H, d, J = 5.2 Hz), 5.58-5.72 (1 H, m), 5.90 (1 H, d, J = 14.6 Hz), 6.11 (1 H, s), 6.70 (2 H, d, J = 4.2 Hz), 6.82-6.96 (3 H, m), 7.03-7.14 (1 H, m), 7.14 (1 H, s) |
| 1116 | Me | H | H | ![cyclopropylmethyl] | 0 | (ESI)+: [M+ H]+ = 513.3 | 0.12-0.14 (2 H, m), 0.53-0.56 (2 H, m), 0.78-0.97 (1 H, m), 1.48-2.01 (6 H, m), 2.17 (3 H, s), 2.18-2.24 (2 H, m), 2.32 (2 H, d, J = 6.7 Hz), 3.12-3.16 (2 H, m), 3.80 (3 H, s), 3.96 (1 H, d, J = 15.1 Hz) 5.88 (1 H, d, J = 15.1 Hz), 6.05-6.18 (1 H, m), 6.42-6.43 (1 H, m), 6.68 (2 H, d, J = 4.0 Hz), 6.80-6.89 (2 H, m), 6.97-7.02 (1 H, m), 7.03-7.13 (2 H, m) |

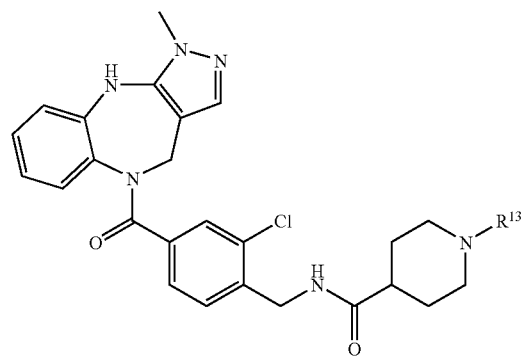

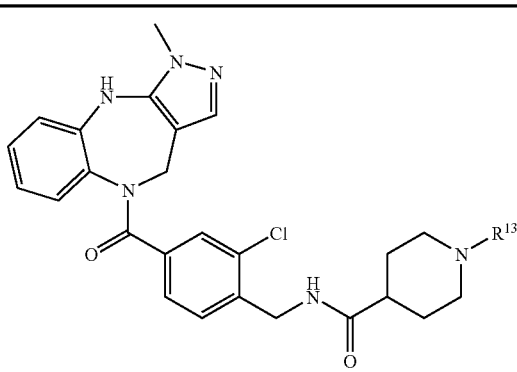

| Compound number | R13 | MS |
|---|---|---|
| 1117 E93 | CH₂CH₂CH₃ | (ESI)+: [M + H]+ = 521.4 |
| 1118 | benzyl | (ESI)+: [M + H]+ = 569.3 |
| 1119 | phenethyl | (ESI)+: [M + H]+ = 583.4 |
| 1120 | 3-chlorobenzyl | (ESI)+: [M + H]+ = 603.3 |
| 1121 | 2-chlorobenzyl | (ESI)+: [M + H]+ = 603.4 |
| 1122 | CH₂CH₂CH₂CH₂CH₃ | (ESI)+: [M + H]+ = 549.4 |
| 1123 | 3-phenylpropyl | (ESI)+: [M + H]+ = 597.4 |
| 1124 | CH₂CH₂CH(CH₃)₂ | (ESI)+: [M + H]+ = 549.4 |
| 1125 | CH₂C(CH₃)₃ | (ESI)+: [M + H]+ = 549.4 |
| 1126 | (5-hydroxymethylfuran-2-yl)methyl | (ESI)+: [M + H]+ = 589.4 |
| 1127 | (pyridin-2-yl)methyl | (ESI)+: [M + H]+ = 570.3 |
| 1128 | (thiophen-3-yl)methyl | (ESI)+: [M + H]+ = 575.3 |

| Compound number | R13 | MS |
|---|---|---|
| 1129 | cyclohex-1-enylmethyl | (ESI)+: [M + H]+ = 573.4 |
| 1130 | 4-methylbenzyl | (ESI)+: [M + H]+ = 583.3 |
| 1131 | 3-methylbenzyl | (ESI)+: [M + H]+ = 583.4 |
| 1132 | 2-methylbenzyl | (ESI)+: [M + H]+ = 583.4 |
| 1133 | 2-cyanobenzyl | (ESI)+: [M + H]+ = 594.4 |
| 1134 | 3-cyanobenzyl | (ESI)+: [M + H]+ = 594.4 |
| 1135 | 4-cyanobenzyl | (ESI)+: [M + H]+ = 594.2 |
| 1136 | pentafluorobenzyl | (ESI)+: [M + H]+ = 659.4 |

437
-continued

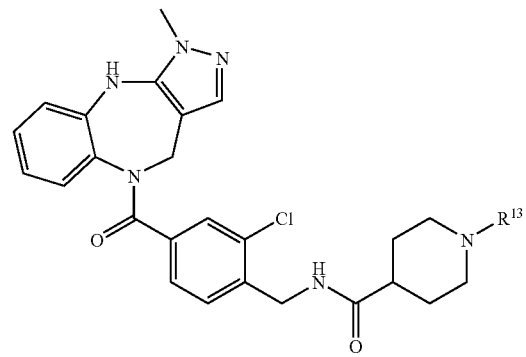

| Compound number | R13 | MS |
|---|---|---|
| 1137 | (3,4,5-trimethoxybenzyl) | (ESI)+: [M + H]+ = 659.5 |

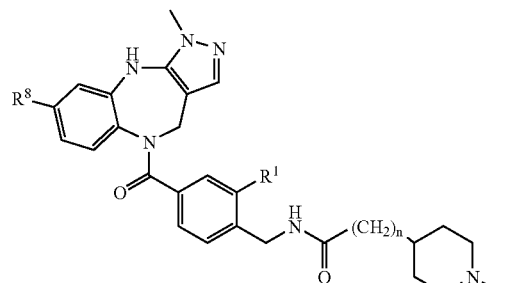

| Compound number | R1 | R8 | R13 | n | MS |
|---|---|---|---|---|---|
| 1138 E94 | F | Me | CH2(CH2)4CH3 | 1 | (ESI)+: [M + H]+ = 575.7 |
| 1139 | Cl | H | CH2(CH2)4CH3 | 0 | (ESI)+: [M + H]+ = 563.3 |
| 1140 | Cl | H | CH2(CH2)2CH3 | 0 | (ESI)+: [M + H]+ = 535.3 |
| 1141 | Cl | H | CH2(CH2)3OH | 0 | (ESI)+: [M + H]+ = 551.3 |
| 1142 | Cl | H | CH2(CH2)2CN | 0 | (ESI)+: [M + H]+ = 546.3 |
| 1143 | Cl | H | (phenacyl) | 0 | (ESI)+: [M + H]+ = 597.3 |
| 1144 | Cl | H | (2-cyclohexylethyl) | 0 | (ESI)+: [M + H]+ = 589.3 |

438
-continued

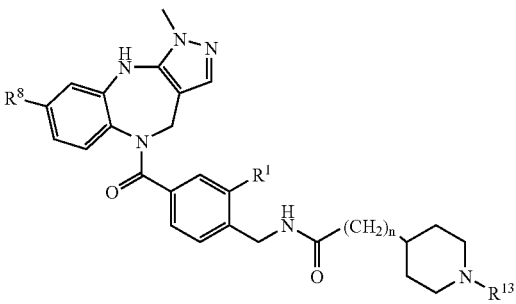

| Compound number | R1 | R8 | R13 | n | MS |
|---|---|---|---|---|---|
| 1145 | Cl | H | (3-fluorobenzyl) | 0 | (ESI)+: [M + H]+ = 587.3 |
| 1146 | Cl | H | (4-tert-butylbenzyl) | 0 | (ESI)+: [M + H]+ = 625.4 |
| 1147 | Cl | H | (4-trifluoromethoxybenzyl) | 0 | (ESI)+: [M + H]+ = 653.3 |
| 1148 | Cl | H | (4-methoxycarbonylbenzyl) | 0 | (ESI)+: [M + H]+ = 627.3 |
| 1149 | Cl | H | (cyclohexylmethyl) | 0 | (ESI)+: [M + H]+ = 575.3 |
| 1150 | Cl | H | CH2CO2CH(CH3)2 | 0 | (ESI)+: [M + H]+ = 579.3 |
| 1151 | Cl | H | CH2CH2CN | 0 | (ESI)+: [M + H]+ = 532.2 |
| 1152 | Cl | H | CH2CH2CH2OH | 0 | (ESI)+: [M + H]+ = 537.3 |
| 1153 | Cl | H | CH2CN | 0 | (ESI)+: [M + H]+ = 518.2 |
| 1154 | Cl | H | (3-nitrobenzyl) | 0 | (ESI)+: [M + H]+ = 614.3 |
| 1155 | Cl | H | (2-naphthylmethyl) | 0 | (ESI)+: [M + H]+ = 619.3 |
| 1156 | Cl | H | (allyl) | 0 | (ESI)+: [M + H]+ = 519.2 |

439

-continued

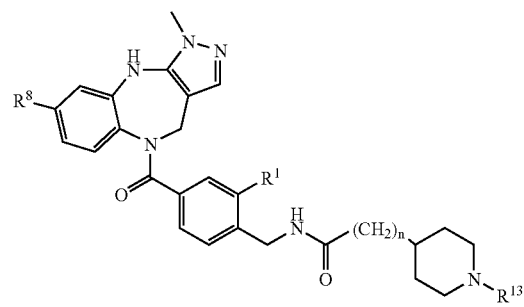

| Compound number | R¹ | R⁸ | R¹³ | n | MS |
|---|---|---|---|---|---|
| 1157 | Cl | H | 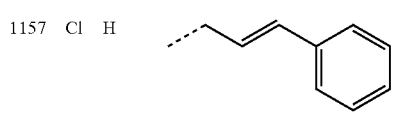 | 0 | (ESI)+: [M + H]+ = 595.3 |
| 1158 | Cl | H | 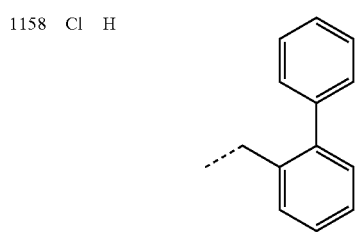 | 0 | (ESI)+: [M + H]+ = 645.4 |
| 1159 | Cl | H |  | 0 | (ESI)+: [M + H]+ = 577.3 |
| 1160 | Cl | H | $CH_2COC(CH_3)_3$ | 0 | (ESI)+: [M + H]+ = 577.3 |
| 1161 | Cl | H | $CH_2CONH_2$ | 0 | (ESI)+: [M + H]+ = 536.2 |
| 1162 | Cl | H |  | 0 | (ESI)+: [M + H]+ = 604.3 |
| 1163 | Cl | H | 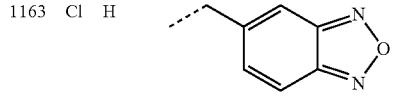 | 0 | (ESI)+: [M + H]+ = 611.3 |
| 1164 | F | Me | $CH_2(CH_2)_2CH_3$ | 1 | (ESI)+: [M + H]+ = 547.6 |
| 1165 | F | Me | $CH_2(CH_2)_3OH$ | 1 | (ESI)+: [M + H]+ = 563.7 |
| 1166 | F | Me | $CH_2(CH_2)_2CN$ | 1 | (ESI)+: [M + H]+ = 558.8 |
| 1167 | F | Me | 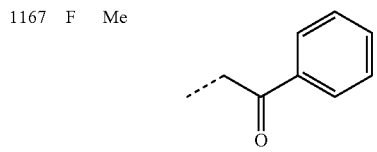 | 1 | (ESI)+: [M + H]+ = 609.8 |

440

-continued

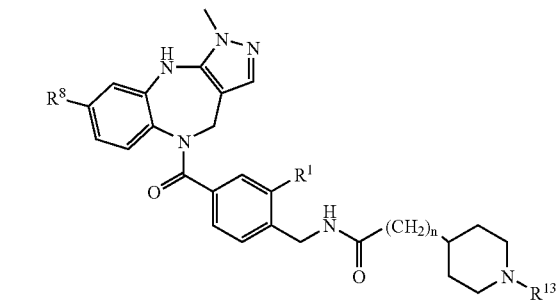

| Compound number | R¹ | R⁸ | R¹³ | n | MS |
|---|---|---|---|---|---|
| 1168 | F | Me |  | 1 | (ESI)+: [M + H]+ = 601.8 |
| 1169 | F | Me | 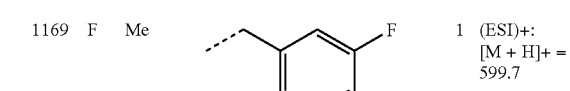 | 1 | (ESI)+: [M + H]+ = 599.7 |
| 1170 | F | Me | 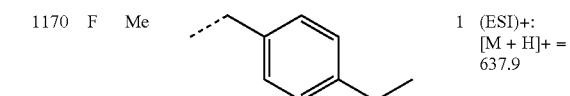 | 1 | (ESI)+: [M + H]+ = 637.9 |
| 1171 | F | Me | 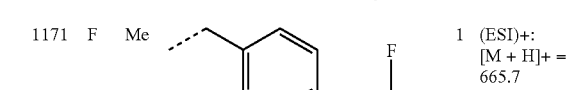 | 1 | (ESI)+: [M + H]+ = 665.7 |
| 1172 | F | Me | 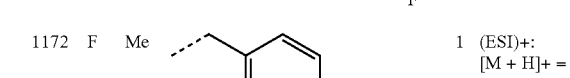 | 1 | (ESI)+: [M + H]+ = 639.8 |
| 1173 | F | Me | 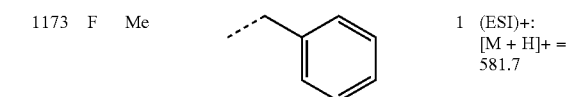 | 1 | (ESI)+: [M + H]+ = 581.7 |
| 1174 | F | Me | 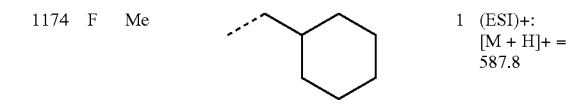 | 1 | (ESI)+: [M + H]+ = 587.8 |
| 1175 | F | Me | $CH_2CO_2CH(CH_3)_2$ | 1 | (ESI)+: [M + H]+ = 591.7 |
| 1176 | F | Me | $CH_2CH_2CH(CH_3)_2$ | 1 | (ESI)+: [M + H]+ = 561.6 |
| 1177 | F | Me | $CH_2CH_2CH_2OH$ | 1 | (ESI)+: [M + H]+ = 549.6 |
| 1178 | F | Me | $CH_2CH_2OCH_2CH_3$ | 1 | (ESI)+: [M + H]+ = 563.5 |
| 1179 | F | Me | $CH_2CH_2CH_2F$ | 1 | (ESI)+: [M + H]+ = 551.5 |

-continued

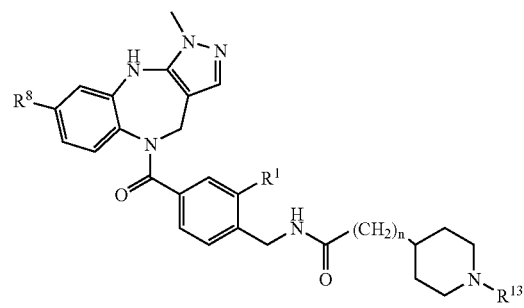

| Compound number | R¹ | R⁸ | R¹³ | n | MS |
|---|---|---|---|---|---|
| 1180 | F | Me | 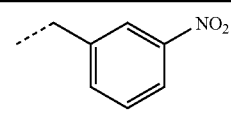 3-NO₂-benzyl | 1 | (ESI)+: [M + H]+ = 626.8 |
| 1181 | F | Me | 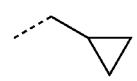 cyclopropyl | 1 | (ESI)+: [M + H]+ = 545.6 |
| 1182 | F | Me | 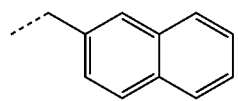 2-naphthylmethyl | 1 | (ESI)+: [M + H]+ = 631.8 |
| 1183 | F | Me | 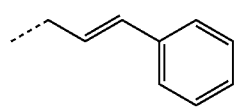 cinnamyl | 1 | (ESI)+: [M + H]+ = 607.7 |
| 1184 | F | Me | 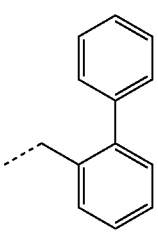 biphenylmethyl | 1 | (ESI)+: [M + H]+ = 657.7 |
| 1185 | F | Me | 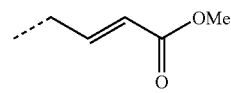 | 1 | (ESI)+: [M + H]+ = 589.7 |
| 1186 | F | Me | 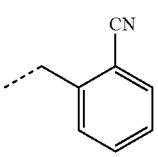 2-CN-benzyl | 1 | (ESI)+: [M + H]+ = 606.8 |
| 1187 | F | Me | CH₂COC(CH₃)₃ | 1 | (ESI)+: [M + H]+ = 589.7 |
| 1188 | F | Me | CH₂CONH₂ | 1 | (ESI)+: [M + H]+ = 548.5 |
| 1189 | F | Me | 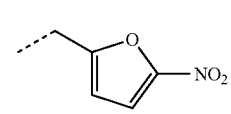 | 1 | (ESI)+: [M + H]+ = 616.7 |

-continued

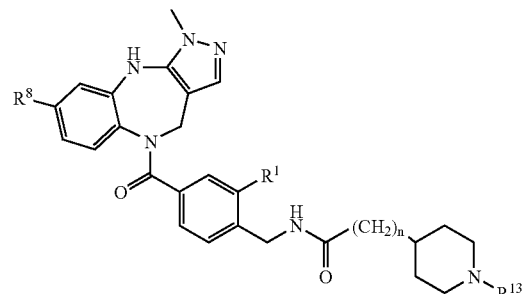

| Compound number | R¹ | R⁸ | R¹³ | n | MS |
|---|---|---|---|---|---|
| 1190 | F | Me | 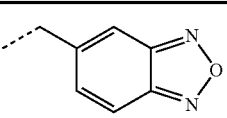 benzofurazan-5-ylmethyl | 1 | (ESI)+: [M + H]+ = 623.6 |

| Compound number | R¹⁶ | MS |
|---|---|---|
| 1191 E95 | CH₂CH₃ | (ESI)+: [M + H]+ = 577.4 |
| 1192 | 3-Cl-phenyl | (ESI)+: [M + H]+ = 660.7 |
| 1193 | 4-Cl-phenyl | (ESI)+: [M + H]+ = 660.4 |
| 1194 | 2-Cl-phenyl | (ESI)+: [M + H]+ = 659.5 |
| 1195 | 4-OMe-phenyl | (ESI)+: [M + H]+ = 655.5 |

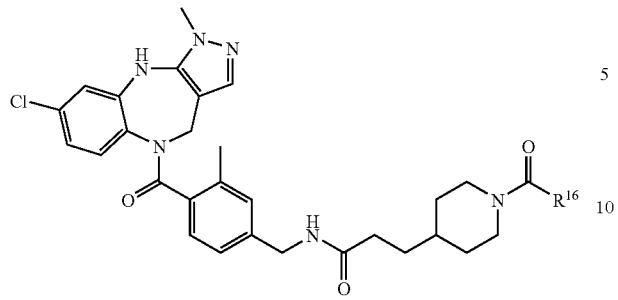

| Compound number | R16 | MS |
|---|---|---|
| 1196 | 2-chloropyridin-3-yl | (ESI)+: [M + H]+ = 660.6 |
| 1197 | pyridin-3-yl | (ESI)+: [M + H]+ = 626.3 |
| 1198 | thiophen-2-yl | (ESI)+: [M + H]+ = 631.4 |
| 1199 | 2,5-dimethylfuran-3-yl | (ESI)+: [M + H]+ = 643.3 |
| 1200 | $CH_2CH_2CH_3$ | (ESI)+: [M + H]+ = 591.3 |
| 1201 | cyclopropyl | (ESI)+: [M + H]+ = 589.4 |
| 1202 | $C(CH_3)_3$ | (ESI)+: [M + H]+ = 605.2 |
| 1203 | $CH_2(CH_2)_3CH_3$ | (ESI)+: [M + H]+ = 619.3 |
| 1204 | $CH(CH_2CH_3)CH_2CH_2CH_3$ | (ESI)+: [M + H]+ = 648.7 |
| 1205 | benzyl | (ESI)+: [M + H]+ = 639.4 |
| 1206 | 2-phenylcyclopropyl | (ESI)+: [M + H]+ = 665.5 |
| 1207 | (thiophen-2-yl)methyl | (ESI)+: [M + H]+ = 645.3 |

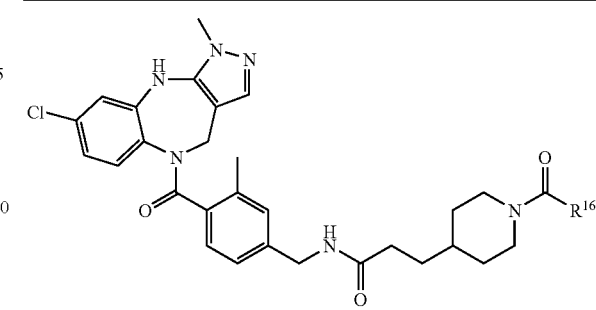

| Compound number | R16 | MS |
|---|---|---|
| 1208 | phenoxymethyl | (ESI)+: [M + H]+ = 655.4 |
| 1209 | $CH_2CH_2CH_2CO_2CH_2CH_3$ | (ESI)+: [M + H]+ = 663.5 |

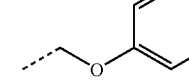

| Compound number | R16 | MS |
|---|---|---|
| 1210 E96 | $CH_2CH_3$ | |
| 1211 | phenyl | (ESI)+: [M + H]+ = 661.2 |
| 1212 | 4-cyanophenyl | (ESI)+: [M + H]+ = 686.2 |
| 1213 | 4-(trifluoromethyl)phenyl | (ESI)+: [M + H]+ = 729.3 |
| 1214 | 4-acetamidophenyl | (ESI)+: [M + H]+ = 718.4 |

445
-continued

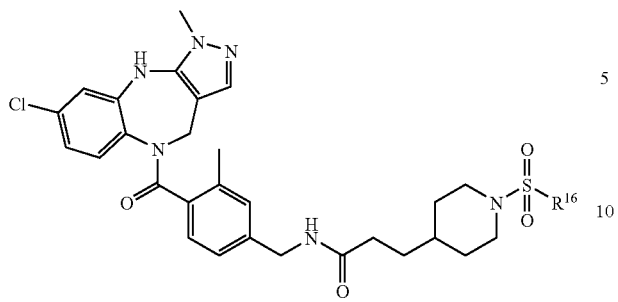

| Compound number | R16 | MS |
|---|---|---|
| 1215 | 2-chloro-thiophen-5-yl | (ESI)+: [M + H]+ = 701.2 |
| 1216 | 2-chloro-3-bromo-pyridin-5-yl | (ESI)+: [M + H]+ = 776.4 |
| 1217 | CH₂CH₂CH₃ | (ESI)+: [M + H]+ = 641.4 |

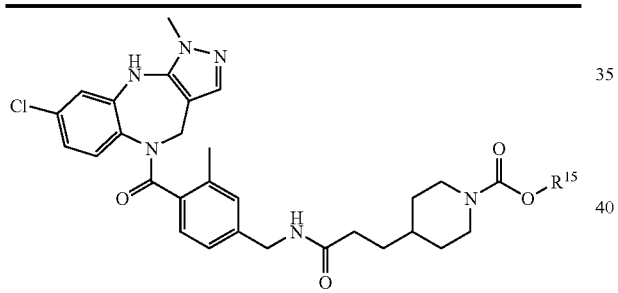

| Compound number | R16 | MS |
|---|---|---|
| 1218 E97 | 4-nitrobenzyl | |
| 1219 | 2-chlorobenzyl | (ESI)+: [M + H]+ = 689.4, 691.4 |
| 1220 | 2-isopropyl-5-methylcyclohexyl | (ESI)+: [M + H]+ = 703.6, 705.6 |
| 1221 | 4-nitrophenyl | (ESI)+: [M + H]+ = 686.3, 688.3 |

446
-continued

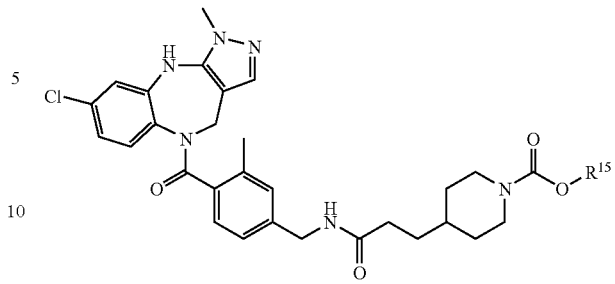

| Compound number | R16 | MS |
|---|---|---|
| 1222 | allyl | (ESI)+: [M + H]+ = 605.4, 607.4 |
| 1223 | 4-methoxyphenyl | (ESI)+: [M + H]+ = 671.3 |
| 1224 | propargyl | (ESI)+: [M + H]+ = 603.4, 605.4 |
| 1225 | phenyl | (ESI)+: [M + H]+ = 641.5 |
| 1226 | 4-chlorophenyl | (ESI)+: [M + H]+ = 675.4, 677.4 |
| 1227 | benzyl | (ESI)+: [M + H]+ = 655.5, 657.5 |
| 1228 | isobutyl | (ESI)+: [M + H]+ = 621.3, 623.3 |
| 1229 | ethyl | (ESI)+: [M + H]+ = 593.4 |
| 1230 | 2,2,2-trichloro-1,1-dimethylethyl | (ESI)+: [M + H]+ = 725.4, |
| 1231 | CH₃ | (ESI)+: [M + H]+ = 579.4, 581.4 |
| 1232 | propenyl | (ESI)+: [M + H]+ = 591.1 |
| 1233 | 2-benzyloxyethyl | (ESI)+: [M + H]+ = 699.5, 701.5 |

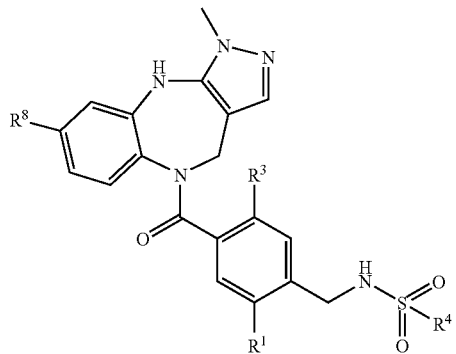
| Compound number | R¹ | R³ | R⁴ | R⁸ | MS | ¹H NMR: δ (ppm) |
|---|---|---|---|---|---|---|
| 1234 E98 | F | H | CH₂CH₂CH₃ | Me | (APCl)+: [M + H]+ = 472.4 | 0.96 (3 H, t, J = 7.4 Hz), 1.65-1.78 (2 H, m), 2.21 (3 H, s), 2.83 (2 H, t, J = 7.7 Hz), 3.75 (3 H, s), 3.95 (1 H, d, J = 14.6 Hz), 4.21 (2 H, d, J = 6.2 Hz), 4.90 (1 H, brs), 5.83 (1 H, d, J = 14.6 Hz), 6.24 (1 H, s), 6.48-6.58 (2 H, m), 6.77 (1 H, s), 6.93-7.02 (2 H, m), 7.06-7.12 (1 H, m), 7.21 (1 H, s) |
| 1235 | Cl | H | CH₂CH₂CH₃ | Cl | (APCl)+: [M + H]+ = 508.3 | 0.97 (3 H, t, J = 7.4 Hz), 1.68-1.83 (2 H, m), 2.86 (2 H, t, J = 7.4 Hz), 3.69 (3 H, s), 3.95 (1 H, d, J = 14.6 Hz), 4.26 (2 H, d, J = 6.4 Hz), 5.56 (1 H, t, J = 6.4 Hz), 5.80 (1 H, d, J = 14.6 Hz), 6.58-6.62 (2 H, m), 6.94 (1 H, dd, J = 1.5, 7.9 Hz), 7.04 (1 H, s), 7.09 (1 H, s), 7.16-7.20 (2 H, m), 7.33 (1 H, d, J = 1.5 Hz) |
| 1236 | F | H | CH₂CH₂CH₃ | Cl | (APCl)+: [M + H]+ = 492.3, 494.3 | 0.97 (3 H, t, J = 7.4 Hz), 1.68-1.79 (2 H, m), 2.85, (2 H, t, J = 7.4 Hz), 3.77 (3 H, s), 3.95 (1 H, d, J = 14.6 Hz), 4.25 (2 H, d, J = 6.2 Hz), 4.80 (1 H, t, J = 6.2 Hz), 5.84 (1 H, d, J = 14.6 Hz), 6.38 (1 H, s), 6.60-6.66 (2 H, m), 6.94-7.03 (3 H, m), 7.17-7.24 (2 H, m) |

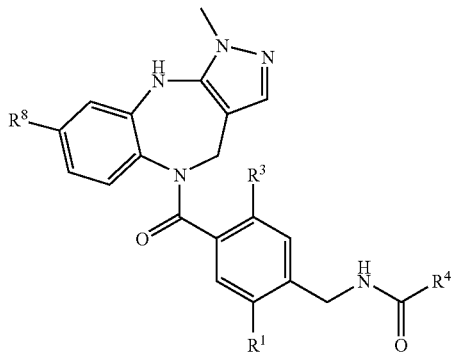
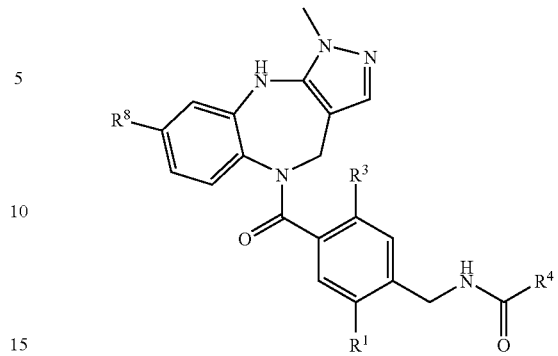
| Compound number | R¹ | R³ | R⁴ | R⁸ | MS | ¹H NMR: δ (ppm) |
|---|---|---|---|---|---|---|
| 1237 E99 | F | H | H | Me | (ESI)+: [M + H]+ = 394.2 | 2.20 (3 H, s), 3.75 (3 H, s), 3.94 (1 H, d, J = 14.6 Hz), 4.30-4.40 (2 H, m), 5.82 (1 H, d, J = 14.6 Hz), 6.31-6.42 (1 H, m), 6.46 (1 H, s), 6.47-6.59 (2 H, m), 6.78 (1 H, s), 6.88-7.03 (3 H, m), 7.21 (1 H, s), 8.16 (1 H, s) |
| 1238 | Cl | H | H | Cl | (ESI)+: [M + H]+ = 430.2 | 3.69 (3 H, s), 3.95 (1 H, d, J = 14.6 Hz), 4.40-4.55 (2 H, m), 5.83 (1 H, d, J = 14.6 Hz), 6.28-6.41 (1 H, m), 6.56-6.68 (2 H, m), 6.78 (1 H, s), 6.90-7.14 (3 H, m), 7.23 (1 H, s), 7.30 (1 H, s), 8.20 (1 H, s) |
| 1239 | F | H | H | Cl | (APCl)+: [M + H]+ = 414.2, 416.2 | 3.72 (3 H, s), 3.96 (1 H, d, J = 14.6 Hz), 4.33-4.40 (2 H, m), 5.81 (1 H, d, J = 14.6 Hz), 6.52-6.56 (1 H, m), 6.61 (2 H, s), 6.87-6.94 (2 H, m), 7.01-7.07 (2 H, m), 7.13 (1 H, s), 7.21 (1 H, s), 8.16 (1 H, s) |
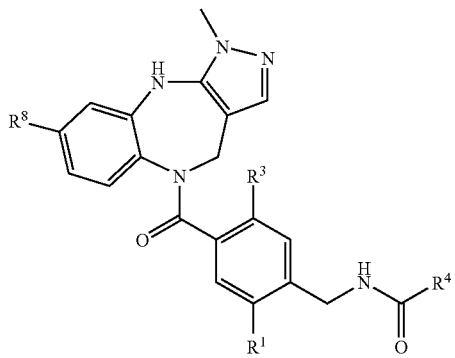
| Compound number | R¹ | R³ | R⁴ | R⁸ | MS | ¹H NMR: δ (ppm) |
|---|---|---|---|---|---|---|
| 1240 E100 | F | H |  | Me | (APCl)+: [M + H]+ = 434.2 | 0.65-0.69 (2 H, m), 0.85-0.88 (2 H, m), 1.37-1.43 (1 H, m), 2.08 (3 H, s), 3.64 (3 H, s), 3.94 (1 H, d, J = 14.6 Hz), 4.28-4.31 (2 H, m), 5.81 (1 H, d, J = 14.6 Hz), 6.46 (1 H, d, J = 8.4 Hz), 6.53 (1 H, d, J = 7.9 Hz), 6.78-6.96 (4 H, m), 7.15 (1 H, s), 7.17 (1 H, s) |

-continued

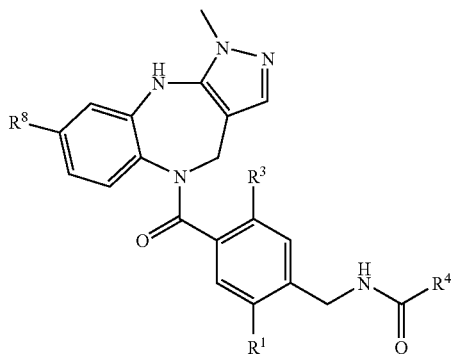

| Compound number | R¹ | R³ | R⁴ | R⁸ | MS | ¹H NMR: δ (ppm) |
|---|---|---|---|---|---|---|
| 1241 E101 | Me | H | cyclopropyl | Me | (ESI)+: [M + H]+ = 430.4 | 0.62-0.71 (2 H, m), 0.81-0.89 (2 H, m), 1.39-1.50 (1 H, m), 2.04 (3 H, s), 2.12 (3 H, s), 3.66 (3 H, s), 3.91 (1 H, d, J = 14.6 Hz), 4.22 (2 H, d, J = 2.0 Hz), 5.82 (1 H, d, J = 14.6 Hz), 6.46 (2 H, q, J = 7.9 Hz), 6.68-6.87 (4 H, m), 7.06 (2 H, s) |
| 1242 E102 | F | H | cyclopropyl | Cl | (APCl)+: [M + H]+ = 454.2, 456.2 | 0.62-0.80 (2 H, m), 0.88-1.00 (2 H, m), 1.31-1.47 (1 H, m), 3.69 (3 H, s), 3.95 (1 H, d, J = 14.6 Hz), 4.35 (2 H, d, J = 5.4 Hz), 5.82 (1 H, d, J = 14.6 Hz), 6.51 (1 H, t, J = 5.4 Hz), 6.61 (2 H, s), 6.82-7.08 (4 H, m), 7.17 (1 H, s), 7.21 (1 H, s) |
| 1243 E103 | F | H | CH₂CH₃ | Cl | (ESI)+: [M + H]+ = 442.1, 444.2 | 1.12 (3 H, t, J = 7.7 Hz), 2.21 (2 H, q, J = 7.7 Hz), 3.76 (3 H, s), 3.95 (1 H, d, J = 14.6 Hz), 4.37 (2 H, d, J = 5.7 Hz), 5.83 (1 H, d, J = 14.6 Hz), 5.94 (1 H, t, J = 5.7 Hz), 6.58-6.67 (3 H, m), 6.89-7.00 (3 H, m), 7.07 (1 H, t, J = 7.4 Hz), 7.23 (1 H, s) |
| 1244 E104 | F | H | CH₂CH₂CH₃ | Cl | (APCl)+: [M + H]+ = 456.3, 458.3 | 0.88 (3 H, t, J = 7.4 Hz), 1.56-1.69 (2 H, m), 2.15 (2 H, t, J = 7.2 Hz), 3.71 (3 H, s), 3.96 (1 H, d, 14.6 Hz), 4.35 (2 H, d, J = 5.7 Hz), 5.83 (1 H, d, J = 14.6 Hz), 6.23 (1 H, t, J = 5.7 Hz), 6.59-6.64 (2 H, m), 6.87-6.94 (2 H, m), 7.01-7.06 (2 H, m), 7.19 (1 H, s), 7.22 (1 H, s) |
| 1245 E105 | F | H | CH(CH₃)₂ | Cl | (APCl)+: [M + H]+ = 456.3, 458.2 | 1.11 (6 H, d, J = 6.9 Hz), 2.29-2.42 (1 H, m), 3.73 (3 H, s), 3.95 (1 H, d, J = 14.6 Hz), 4.35 (2 H, d, J = 5.7 Hz), 5.83 (1 H, d, J = 14.6 Hz), 6.06 (1 H, t, J = 5.7 Hz), 6.60-6.63 (2 H, m), 6.88-7.08 (5 H, m), 7.22 (1 H, s) |

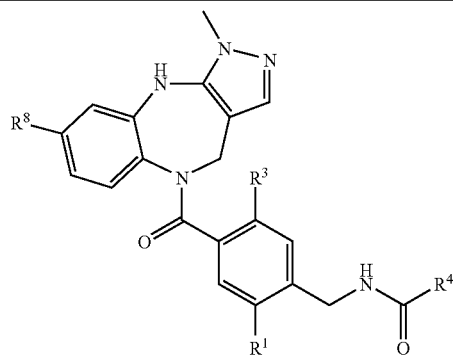

| Compound number | R¹ | R³ | R⁴ | R⁸ | MS | ¹H NMR: δ (ppm) |
|---|---|---|---|---|---|---|
| 1246 E106 | Cl | H | (cyclopropyl) | Cl | (APCl)+: [M + H]+ = 470.2 | 0.71-0.74 (2 H, m), 0.90-0.91 (2 H, m), 1.40-1.43 (1 H, m), 3.67 (3 H, s), 3.94 (1 H, d, J = 14.6 Hz), 4.38 (2 H, d, J = 5.4 Hz), 5.81 (1 H, d, J = 14.6 Hz), 6.56 (3 H, m), 6.90-7.04 (4 H, m), 7.21 (1 H, s), 7.26 (1 H, s) |
| 1247 E107 | Cl | H | CH₂CH₂CH₃ | Cl | (APCl)+: [M + H]+ = 472.3 | 0.87 (3 H, t, J = 7.4 Hz), 1.60-1.65 (2 H, m), 2.16 (2 H, t, J = 7.7 Hz), 3.67 (3 H, s), 3.95 (1 H, d, J = 14.6 Hz), 4.36 (2 H, t, J = 3.5 Hz), 5.79 (1 H, d, J = 14.6 Hz), 6.59 (2 H, s), 6.91 (1 H, d, J = 7.7 Hz), 6.98 (1 H, d, J = 7.7 Hz), 7.03 (2 H, s), 7.20 (1 H, s), 7.23 (1 H, s), 7.60 (1 H, s) |
| 1248 E108 | Cl | H | CH(CH₃)₂ | Cl | (APCl)+: [M + H]+ = 472.3 | 1.09-1.13 (6 H, m), 2.30-2.50 (1 H, m), 3.70 (3 H, s), 3.95 (1 H, d, J = 14.6 Hz), 4.37 (2 H, d, J = 4.0 Hz), 5.81 (1 H, d, J = 14.6 Hz), 6.25 (1 H, t, J = 5.9 Hz), 6.60 (2 H, s), 6.85-7.04 (3 H, m), 7.22 (1 H, s), 7.26 (2 H, s) |
| 1249 | Me | H | CH(CH₃)₂ | Cl | (ESI)+: [M + H]+ = 452.2, 454.2 | 1.14 (6 H, d, J = 6.7 Hz), 2.14 (3 H, s), 2.27-2.42 (1 H, m), 3.74 (3 H, s), 3.94 (1 H, d, J = 14.5 Hz), 4.30 (2 H, d, J = 5.2 Hz), 5.70 (1 H, s), 5.87 (1 H, d, J = 14.5 Hz), 6.57-6.67, (3 H, m), 6.88 (2 H, s), 6.98 (2 H, s), 7.13 (1 H, s) |
| 1250 | Me | H | CH₂CH₂CH₃ | Cl | (ESI)+: [M + H]+ = 452.2, 454.2 | 0.92 (3 H, t, J = 7.3 Hz), 1.64 (2 H, q, J = 7.3 Hz), 2.12-2.24 (5 H, m), 3.75 (3 H, s), 3.94 (1 H, d, J = 14.6 Hz), 4.32 (2 H, d, J = 5.0 Hz), 5.64 (1 H, s), 5.87 (1 H, d, J = 14.6 Hz), 6.40 (1 H, s), 6.62 (2 H, s), 6.89 (2 H, s), 6.97 (2 H, s), 7.14 (1 H, s) |
| 1251 | Me | H | CH₂CH₃ | Cl | (ESI)+: [M + H]+ = 438.2, 440.2 | 1.14 (3 H, t, J = 7.3 Hz), 2.15 (3 H, s), 2.23 (2 H, q, J = 7.3 Hz), 3.74 (3 H, s), 3.93 (1 H, d. J = 14.9 Hz), 4.31 (2 H, d, J = 5.2 Hz), 5.71 (1 H, s), 5.87 (1 H, d, J = 14.9 Hz), 6.55 (1 H, s), 6.62 (2 H, s), 6.88 (2 H, s), 6.98 (2 H, s), 7.13 (1 H, s) |

-continued

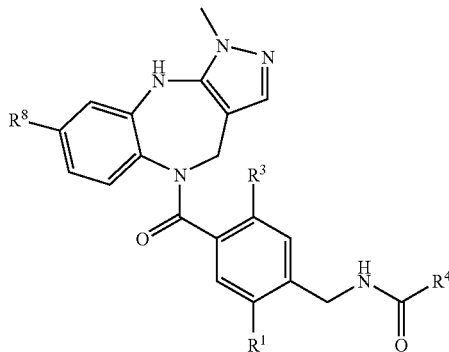

| Compound number | R¹ | R³ | R⁴ | R⁸ | MS | ¹H NMR: δ (ppm) |
|---|---|---|---|---|---|---|
| 1252 | Me | H | CH$_2$CH$_2$CH$_3$ | Me | (ESI)+: [M + H]+ = 433.2 | 0.91 (3 H, t, J = 7.4 Hz), 1.65 (2 H, q, J = 7.4 Hz), 2.13 (3 H, s), 2.11-2.30 (2 H, m), 2.21 (3 H, s), 3.76 (3 H, s), 3.93 (1 H, d, J = 14.6 Hz), 4.29 (2 H, d, J = 5.2 Hz), 5.55-5.70 (1 H, m), 5.87 (1 H, d, J = 14.6 Hz), 6.09 (1 H, s), 6.52 (2 H, q, J = 7.7 Hz), 6.74 (1 H, s), 6.80-6.93 (2 H, m), 7.14 (1 H, s), 7.23 (1 H, s) |
| 1253 | Me | H | CH(CH$_3$)$_2$ | Me | (ESI)+: [M + H]+ = 433.2 | 1.12 (6 H, d, J = 6.7 Hz), 2.13 (3 H, s), 2.21 (3 H, s), 2.25-2.42 (1 H, m), 3.76 (3 H, s), 3.93 (1 H, d, J = 14.6 Hz), 4.29 (2 H, d, J = 5.4 Hz), 5.55-5.70 (1 H, m), 5.88 (1 H, d, J = 14.6 Hz), 6.10 (1 H, s), 6.52 (2 H, q, J = 7.9 Hz), 6.74 (1 H, s), 6.75-6.93 (2 H, m), 7.14 (1 H, s), 7.23 (1 H, s) |
| 1254 | Me | H | CH$_2$CH$_3$ | Me | (ESI)+: [M + H]+ = 418.2 | 1.13 (3 H, t, J = 7.4 Hz), 2.12 (3 H, s), 2.18-2.28 (5 H, m), 3.76 (3 H, s), 3.93 (1 H, d, J = 14.6 Hz), 4.29 (2 H, d, J = 5.2 Hz), 5.57-5.70 (1 H, m), 5.87 (1 H, d, J = 14.6 Hz), 6.07 (1 H, s), 6.52 (2 H, q, J = 7.9 Hz), 6.74 (1 H, s), 6.80-6.92 (2 H, m), 7.14 (1 H, s), 7.23 (1 H, s) |
| 1255 | Me | H | CH$_2$CH$_3$ | F | (APCl)+: [M + H]+ = 422.4 | 1.13 (3 H, t, J = 7.4 Hz), 2.12 (3 H, s), 2.20 (2 H, q, J = 7.4 Hz), 3.70 (3 H, s), 3.94 (1 H, d, J = 14.6 Hz), 4.28 (1 H, d, J = 5.2 Hz), 5.83 (1 H, s), 5.85 (1 H, d, J = 14.6 Hz), 6.33-6.39 (1 H, m), 6.61-6.70 (2 H, m), 6.77-6.86 (3 H, m), 7.10 (1 H, s), 7.23 (1 H, s) |
| 1256 | Me | H | CH$_2$CH$_2$CH$_3$ | F | (APCl)+: [M + H]+ = 436.4 | 0.91 (3 H, t, J = 7.4 Hz), 1.59-1.68 (2 H, m), 2.10-2.20 (5 H, m), 3.71 (3 H, s), 3.94 (1 H, d, J = 14.6 Hz), 4.29 (2 H, d, J = 5.2 Hz), 5.79 (1 H, s), 5.86 (1 H, d, J = 14.6 Hz), 6.33-6.42 (1 H, m), 6.61-6.72 (3 H, m), 6.83-6.88 (2 H, m), 7.11 (1 H, s), 7.23 (1 H, s) |
| 1257 | Me | H | CH(CH$_3$)$_2$ | F | (APCl)+: [M + H]+ = 436.4 | 1.12 (6 H, d, J = 6.4 Hz), 2.12 (3 H, s), 2.30-2.41 (1 H, m), 3.71 (3 H, s), 3.94 |

-continued

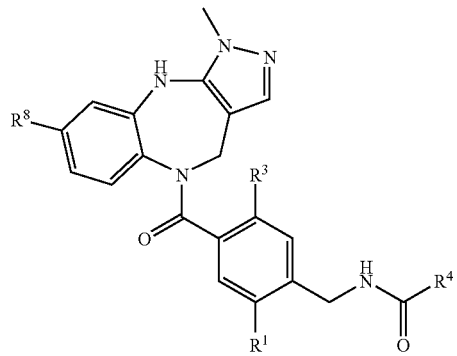

| Compound number | R¹ | R³ | R⁴ | R⁸ | MS | ¹H NMR: δ (ppm) |
|---|---|---|---|---|---|---|
| | | | | | | (1 H, d, J = 14.6 Hz), 4.28 (2 H, d, J = 5.2 Hz), 5.75 (1 H, s), 5.86 (1 H, d, J = 14.6 Hz), 6.33-6.39 (1 H, m), 6.62-6.73 (3 H, m), 6.80-6.92 (2 H, m), 7.10 (1 H, s), 7.23 (1 H, s) |
| 1258 | Me | H | cyclopropyl | F | (APCl)+: [M + H]+ = 434.4 | 0.71-0.74 (2 H, m), 0.91-0.96 (2 H, m), 1.35-1.37 (1 H, m), 2.13 (3 H, s), 3.70 (3 H, s), 3.94 (1 H, d, J = 14.6 Hz), 4.30 (2 H, d, J = 5.2 Hz), 5.86 (1 H, d, J = 14.6 Hz), 5.99 (1 H, s), 6.34-6.40 (1 H, m), 6.62-6.70 (3 H, m), 6.83-6.91 (2 H, m), 7.11 (1 H, s) |
| 1259 | F | H | cyclopropyl | F | (APCl)+: [M + H]+ = 438.4 | 0.71-0.75 (2 H, m), 0.91-0.95 (2 H, m), 1.31-1.37 (1 H, m), 3.74 (3 H, s), 3.96 (1 H, d, J = 14.6 Hz), 4.38 (2 H, d, J = 5.7 Hz), 5.84 (1 H, d, J = 14.6 Hz), 6.14 (1 H, s), 6.37-6.43 (1 H, m), 6.64-6.69 (3 H, m), 6.89-6.95 (2 H, m), 7.04-7.10 (1 H, m) |
| 1260 | F | H | CH(CH₃)₂ | F | (APCl)+: [M + H]+ = 440.4 | 1.11 (6 H, d, J = 6.7 Hz), 2.34 (1 H, septet, J = 6.7 Hz), 3.76 (3 H, s), 3.96 (1 H, d, J = 14.6 Hz), 4.36 (2 H, d, J = 5.9 Hz), 5.84 (1 H, d, J = 14.6 Hz), 5.87 (1 H, s), 6.37-6.43 (1 H, m), 6.51 (1 H, s), 6.64-6.69 (2 H, m), 6.91-6.95 (2 H, m), 7.04-7.10 (1 H, m) |
| 1261 | F | H | CH₂CH₂CH₃ | F | (APCl)+: [M + H]+ = 440.4 | 0.88 (3 H, t, J = 7.2 Hz), 1.58-1.66 (2 H, m), 2.14 (2 H, t, J = 7.4 Hz), 3.74 (3 H, s), 3.96 (1 H, d, J = 14.6 Hz), 4.36 (2 H, d, J = 5.2 Hz), 5.83 (1 H, d, J = 14.6 Hz), 6.01 (1 H, s), 6.36-6.41 (1 H, m), 6.63-6.71 (2 H, m), 6.79 (1 H, s), 6.91-6.94 (2 H, m), 7.03-7.09 (1 H, m) |
| 1262 | F | H | CH₂CH₃ | F | (APCl)+: [M + H]+ = 426.4 | 1.12 (3 H, t, J = 7.4 Hz), 2.20 (2 H, q, J = 7.4 Hz), 3.76 (3 H, s), 3.96 (1 H, d, J = 14.6 Hz), 4.37 (2 H, d, J = 5.4 Hz), 5.83 (1 H, d, J = 14.6 Hz), 5.87 (1 H, s), 6.37-6.47 (2 H, m), |

-continued

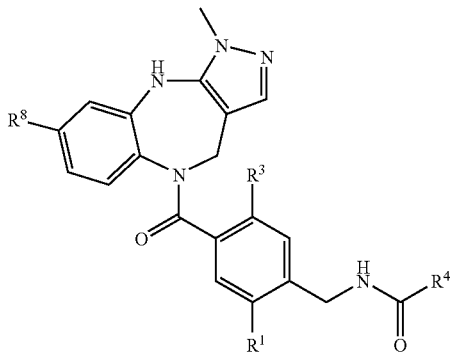

| Compound number | R¹ | R³ | R⁴ | R⁸ | MS | ¹H NMR: δ (ppm) |
|---|---|---|---|---|---|---|
| | | | | | | 6.64-6.69 (2 H, m), 6.92-6.95 (2 H, m), 7.05-7.11 (1 H, m) |
| 1263 | F | H | cyclobutyl | Me | (APCl)+: [M + H]+ = 448.4 | 1.72-1.91 (3 H, m), 2.05-2.28 (4 H, m), 2.92-3.06 (1 H, m), 3.46 (2 H, s), 3.72 (3 H, s), 3.94 (1 H, d, J = 14.6 Hz), 4.31 (2 H, d, J = 5.7 Hz), 5.83 (1 H, d, J = 14.6 Hz), 6.05 (1 H, t, J = 5.7 Hz), 6.47 (1 H, d, J = 7.7 Hz), 6.54 (1 H, d, J = 7.7 Hz), 6.68 (1 H, s), 6.78 (1 H, s), 6.82-7.00 (3 H, m), 7.20 (1 H, s) |
| 1264 | F | H | cyclohexyl | Me | (APCl)+: [M + H]+ = 476.4 | 1.10-1.48 (5 H, m), 1.60-1.70 (1 H, m), 1.70-1.84 (4 H, m), 2.00-2.14 (1 H, m), 2.19 (3 H, s), 3.74 (3 H, s), 3.94 (1 H, d, J = 14.6 Hz), 4.32 (2 H, d, J = 5.9 Hz), 5.83 (1 H, d, J = 14.6 Hz), 6.03 (1 H, t, J = 6.0 Hz), 6.44-6.59 (3 H, m), 6.77 (1 H, s), 6.88-7.02 (3 H, m), 7.21 (1 H, s) |
| 1265 | F | H | CH₂CH₂CH₃ | Me | (APCl)+: [M + H]+ = 436.4 | 0.86 (3 H, t, J = 7.4 Hz), 1.53-1.68 (2 H, m), 2.13 (2 H, q, J = 7.4 Hz), 2.17 (3 H, s), 3.71 (3 H, s), 3.94 (1 H, d, J = 14.6 Hz), 4.31 (2 H, d, J = 5.4 Hz), 5.83 (1 H, d, J = 14.6 Hz), 6.29 (1 H, t, J = 6.7 Hz), 6.47 (1 H, d, J = 8.2 Hz), 6.55 (1 H, d, J = 8.2 Hz), 6.76 (2 H, d, J = 6.4 Hz), 6.87-6.97 (3 H, m), 7.20 (1 H, s) |
| 1266 | F | H | Me | Me | (APCl)+: [M + H]+ = 408.4 | 1.92 (3 H, s), 2.17 (3 H, s), 3.70 (3 H, s), 3.94 (1 H, d, J = 14.6 Hz), 4.29 (2 H, d, J = 5.4 Hz), 5.81 (1 H, d, J = 14.6 Hz), 6.42-6.61 (3 H, m), 6.85 (2 H, d, J = 6.9 Hz), 6.87-7.00 (3 H, m), 7.20 (1 H, s) |
| 1267 | F | H | CH(CH₃)₂ | Me | (APCl)+: [M + H]+ = 436.4 | 1.08-1.11 (6 H, m), 2.16 (3 H, s), 2.28-2.42 (1 H, m), 3.71 (3 H, s), 3.94 (1 H, d, J = 14.6 Hz), 4.31 (2 H, d, J = 4.2 Hz), 5.82 (1 H, d, J = 14.6 Hz), 6.23 (1 H, t, J = 5.9 Hz), 6.47 (1 H, d, J = 7.9 Hz), 6.55 (1 H, d, J = 7.9 Hz), 6.77 (2 H, d, |

-continued

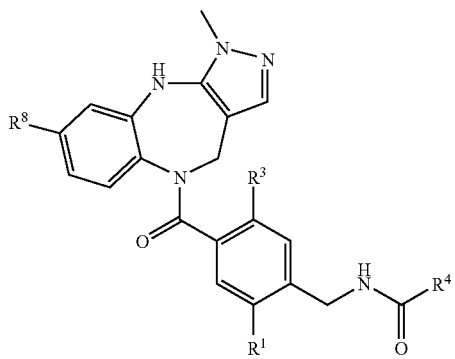

| Compound number | R¹ | R³ | R⁴ | R⁸ | MS | ¹H NMR: δ (ppm) |
|---|---|---|---|---|---|---|
| 1268 | F | H | C(CH₃)₃ | Me | (APCl)+: [M + H]+ = 450.4 | J = 2.5 Hz), 6.85-7.03 (3 H, m), 7.20 (1 H, s) 1.15 (9 H, s), 2.16 (3 H, s), 3.71 (3 H, s), 3.94 (1 H, d, J = 14.6 Hz), 4.32 (2 H, d, J = 5.7 Hz), 5.83 (1 H, d, J = 14.6 Hz), 6.10-6.23 (1 H, m,) 6.46 (1 H, d, J = 7.9 Hz), 6.55 (1 H, d, J = 7.9 Hz), 6.68 (1 H, s), 6.76 (1 H, s), 6.85-7.05 (3 H, m), 7.20 |
| 1269 | Cl | H | cyclobutyl | Cl | (APCl)+: [M + H]+ = 484.3 | 7.78-2.04 (2 H, m), 2.04-2.32 (4 H, m), 2.92-3.10 (1 H, m), 3.73 (3 H, s), 3.95 (1 H, d, J = 14.6 Hz), 4.39 (2 H, d, J = 3.2 Hz), 5.83 (1 H, d, J = 14.6 Hz), 6.01 (1 H, t, J = 5.7 Hz), 6.62 (2 H, s), 6.85-7.10 (4 H, m), 7.23 (1 H, s), 7.27 (1 H, s) |
| 1270 | Cl | H | cyclohexyl | Cl | (APCl)+: [M + H]+ = 512.4 | 1.23 (2 H, t, J = 7.2 Hz), 1.26-1.50 (3 H, m), 1.59-1.71 (1 H, m), 1.71-1.83 (5 H, m), 2.12-2.28 (1 H, m), 3.79 (3 H, s), 3.97 (1 H, d, J = 14.6 Hz), 4.33 (2 H, d, J = 1.5 Hz), 5.74 (1 H, d, J = 14.6 Hz), 6.63-6.68 (2 H, m), 7.08-7.13 (2 H, m), 7.20 (1 H, s), 7.21-7.23 (2 H, m) |
| 1271 | Cl | H | cyclopentyl | Cl | (APCl)+: [M + H]+ = 498.3 | 1.43-1.58 (1 H, m), 1.58-1.78 (5 H, m), 1.58-1.90 (2 H, m), 2.46-2.60 (1 H, m), 3.72 (3 H, s), 3.95 (1 H, d, J = 14.6 Hz), 4.30-4.50 (2 H, m), 5.83 (1 H, d, J = 14.6 Hz), 6.12 (1 H, t, J = 5.9 Hz), 6.61 (2 H, s), 6.84-7.11 (4 H, m), 7.22 (1 H, s), 7.27 (1 H, s) |
| 1272 | Cl | H | Me | Cl | (APCl)+: [M + H]+ = 444.3 | 1.97 (3 H, s), 3.67 (3 H, s), 3.94 (1 H, d, J = 14.6 Hz), 4.33 (2 H, t, J = 5.2 Hz), 5.79 (1 H, d, J = 14.6 Hz), 6.59 (2 H, s), 6.60-6.70 (1 H, m), 6.90 (1 H, d, J = 7.9 Hz), 6.97 (1 H, d, J = 7.9 Hz), 7.04 (1 H, s), 7.19 (1 H, s), 7.23 (1 H, s), 7.58 (1 H, s) |

-continued

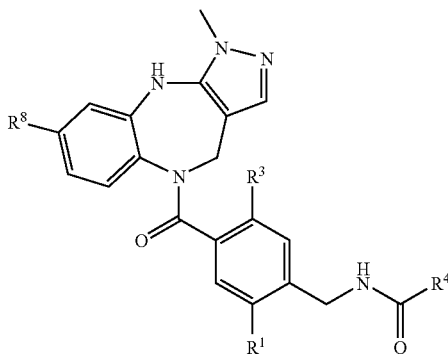

| Compound number | R¹ | R³ | R⁴ | R⁸ | MS | ¹H NMR: δ (ppm) |
|---|---|---|---|---|---|---|
| 1273 | F | H | cyclopentyl | Me | (APCl)+: [M + H]+ = 462.4 | 1.41-1.84 (8 H, m), 2.13 (3 H, s), 2.46-2.57 (1 H, m), 3.67 (3 H, s), 3.94 (1 H, d, J = 14.6 Hz), 4.28 (2 H, d, J = 5.2 Hz), 5.81 (1 H, d, J = 14.6 Hz), 6.43-6.55 (3 H, m), 6.79 (1 H, s), 6.83-6.96 (3 H, m), 7.12 (1 H, s), 7.17 (1 H, s) |
| 1274 | F | H | $CH_2CH_3$ | Me | (APCl)+: [M + H]+ = 422.4 | 1.08 (3 H, t, J = 7.7 Hz), 2.15 (3 H, s), 2.17 (2 H, q, J = 7.7 Hz), 3.69 (3 H, s), 3.93 (1 H, d, J = 14.6 Hz), 4.30 (2 H, d, J = 5.2 Hz), 5.81 (1 H, d, J = 14.6 Hz), 6.38-6.57 (3 H, m), 6.80-6.98 (5 H, m), 7.19 (1 H, s) |
| 1275 | Cl | H | $C(CH_3)_3$ | Cl | (APCl)+: [M + H]+ = 486.3 | 1.17 (9 H, s), 3.72 (3 H, s), 3.95 (1 H, d, J = 14.6 Hz), 4.38 (2 H, d, J = 5.9 Hz), 5.82 (1 H, d, J = 14.6 Hz), 6.21 (1 H, t, J = 5.7 Hz), 6.61 (2 H, s), 6.85-7.08 (4 H, m), 7.22-7.27 (2 H, m) |
| 1276 | Cl | H | $CH_2CH_3$ | Cl | (APCl)+: [M + H]+ = 458.2 | 1.11 (3 H, t, J = 7.7 Hz), 2.22 (2 H, q, J = 7.7 Hz), 3.45 (1 H, d, J = 5.2 Hz), 3.67 (3 H, s), 3.95 (1 H, d, J = 14.6 Hz), 4.23-4.45 (2 H, m), 5.80 (1 H, d, J = 14.6 Hz), 6.53 (1 H, t, J = 5.9 Hz), 6.59 (2 H, s), 6.85-6.92 (1 H, m), 6.98 (1 H, s), 6.99-7.04 (1 H, m), 7.20 (1 H, s), 7.59 (1 H, s) |
| 1277 | F | H | cyclohexyl | Cl | (APCl)+: [M + H]+ = 496.3, 498.3 | 1.17-1.25 (2 H, m), 1.25-1.42 (2 H, m), 1.65-1.81 (6 H, m), 2.02-2.18 (1 H, m), 3.73 (3 H, s), 3.96 (1 H, d, J = 14.6 Hz), 4.34 (2 H, d, J = 5.7 Hz), 5.83 (1 H, d, J = 14.6 Hz), 6.08 (1 H, t, J = 5.7 Hz), 6.59-6.64 (2 H, m), 6.87-6.94 (2 H, m), 7.00-7.04 (2 H, m), 7.06 (1 H, s), 7.22 (1 H, s) |

-continued

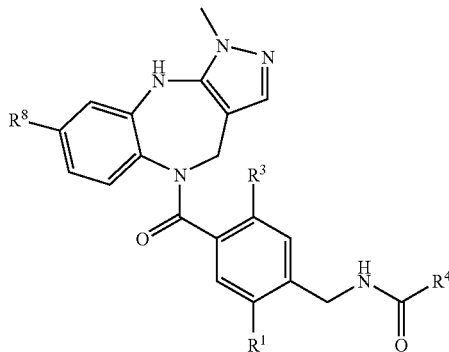

| Compound number | R¹ | R³ | R⁴ | R⁸ | MS | ¹H NMR: δ (ppm) |
|---|---|---|---|---|---|---|
| 1278 | F | H | cyclobutyl | Cl | (APCl)+: [M + H]+ = 468.3, 470.3 | 1.80-2.02 (2 H, m), 2.03-2.31 (4 H, m), 2.95-3.08 (1 H, m), 3.71 (3 H, s), 3.95 (1 H, d, J = 14.6 Hz), 4.34 (2 H, d, J = 5.7 Hz), 5.83 (1 H, d, J = 14.6 Hz), 6.06 (1 H, t, J = 5.7 Hz), 6.59-6.63 (2 H, m), 6.87-6.94 (2 H, m), 6.99-7.06 (2 H, m), 7.22 (2 H, s) |
| 1279 | F | H | Me | Cl | (APCl)+: [M + H]+ = 428.2, 430.2 | 1.96 (3 H, s), 3.73 (3 H, s), 3.95 (1 H, d, J = 14.6 Hz), 4.35 (2 H, d, J = 5.7 Hz), 5.83 (1 H, d, J = 14.6 Hz), 6.23 (1 H, t, J = 5.7 Hz), 6.58-6.66 (2 H, m), 6.87-7.05 (5 H, m), 7.22 (1 H, s) |
| 1280 | F | H | C(CH₃)₃ | Cl | (APCl)+: [M + H]+ = 470.3, 472.3 | 1.16 (9 H, s), 3.74 (3 H, s), 3.95 (1 H, d, J = 14.6 Hz), 4.36 (2 H, d, J = 5.7 Hz), 5.84 (1 H, d, J = 14.6 Hz), 6.07 (1 H, t, J = 5.7 Hz), 6.60-6.64 (2 H, m), 6.79 (1 H, s), 6.90-6.98 (3 H, s), 7.02-7.08 (1 H, m), 7.23 (1 H, s) |
| 1281 | F | H | cyclopentyl | Cl | (APCl)+: [M + H]+ = 482.2, 484.2 | 1.31-1.88 (8H, m), 2.48-2.58 (1 H, m), 3.72 (3 H, s), 3.95 (1 H, d, J = 14.6 Hz), 4.34 (2 H, d, J = 5.7 Hz), 5.81 (1 H, d, J = 14.6 Hz), 6.25 (1 H, t, J = 5.7 Hz), 6.59 (2 H, s), 6.87-6.93 (2 H, m), 7.01 (1 H, t, J = 7.4 Hz), 7.08 (1 H, s), 7.21 (1 H, s), 7.44 (1 H, s) |
| 1282 | H | Cl | cyclopropyl | Me | (APCl)+: [M + H]+ = 450.2, 452.3 | 0.70-0.74 (2 H, m), 0.91-0.94 (2 H, m), 1.39 (1 H, m), 2.13 (3 H, s), 3.70 (3 H, s), 3.98 (1 H, d, J = 14.6 Hz), 4.25 (2 H, m), 5.79 (1 H, d, J = 14.6 Hz), 6.32 (1 H, s), 6.45-6.49 (2 H, m), 6.65 (1 H, s), 6.74-6.83 (3 H, m), 7.04 (1 H, s), 7.23 (1 H, s) |
| 1283 | H | Me | cyclopropyl | Cl | (APCl)+: [M + H]+ = 450.2, 452.2 | 0.68-0.73 (2 H, m), 0.90-0.94 (2 H, m) 1.31-1.43 (1 H, m), 2.25 (3 H, s), 3.63 (3 H, s), 3.95 (1 H, d, J = 14.6 Hz), 4.23 (2 H, d, J = 5.6 Hz), 4.41 (1 H, d, J = 5.6 Hz), 5.80 (1 H, d, J = 14.6 Hz), 6.39-6.46 (1 H, m), 6.56-7.23 (7 H, m) |

-continued

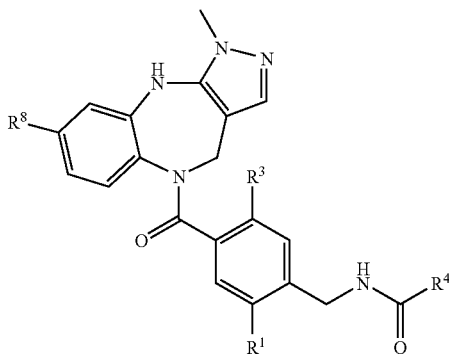

| Compound number | R¹ | R³ | R⁴ | R⁸ | MS | ¹H NMR: δ (ppm) |
|---|---|---|---|---|---|---|
| 1284 | H | Me |  | Me | (APCl)+: [M + H]+ = 430.2 | 0.69-0.74 (2 H, m), 0.93-0.96 (2 H, m), 1.28-1.36 (1 H, m), 2.15 (3 H, s), 2.31 (3 H s), 3.47 (2 H, d, J = 5.6 Hz), 3.72 (3 H, s), 3.94 (1 H, d, J = 14.6 Hz), 4.27 (1 H, d, J = 5.6 Hz), 5.83 (1 H, d, J = 14.6 Hz), 6.11 (1 H, s), 6.41-6.46 (1 H, m), 6.58-6.91 (6 H, m) |
| 1285 | H | Cl |  | Cl | (APCl)+: [M + H]+ = 470.2 | 0.68-0.76 (2 H, m), 0.88-0.97 (2 H, m), 1.42 (1 H, m), 3.60 (3 H, s), 3.98 (1 H, d, J = 14.6 Hz), 4.19 (2 H, m), 4.38 (1 H, m), 5.73 (1 H, d, J = 14.6 Hz), 6.52-6.56 (1 H, m), 6.71-7.18 (6 H, m), 7.60 (1 H, brs) |
| 1286 | H | F |  | Cl | (APCl)+: [M + H]+ = 454.2, 456.3 | 0.69-0.75 (2 H, m), 0.91-0.94 (2 H, m), 1.32-1.44 (1 H, m), 3.66 (3 H, s), 3.96 (1 H, d, J = 14.6 Hz), 4.28 (2 H d, J = 5.9 Hz), 5.80 (1 H, d, J = 14.6 Hz), 6.51-6.62 (2 H, m), 6.69 (2 H, t, J = 8.4, 18.3 Hz), 6.79 (1 H, d, J = 6.4 Hz), 6.92 (2 H, s), 6.98-7.09 (1 H, m), 7.22 (1 H, s) |
| 1287 | H | F |  | Me | (APCl)+: [M + H]+ = 434.2 | 0.69-0.74 (2 H, m), 0.91-0.96 (2 H, m), 1.31-1.42 (1 H, m), 2.15 (3 H, s), 3.69 (3 H, s), 3.96 (1 H, d, J = 14.6 Hz), 4.27 (2 H, t, J = 5.7, 11.1 Hz), 5.81 (1 H, d, J = 14.6 Hz), 6.32 (1 H, s), 6.42-6.47 (2 H, m), 6.62-6.79 (3 H, m), 7.02 (1 H, t, J = 7.4, 14.8 Hz), 7.21 (1 H, s) |
| 1288 | Cl | H |  | Me | (APCl)+: [M + H]+ = 450.3, 452.4 | 0.63-0.75 (2 H, m), 0.83-0.94 (2 H, m), 1.37-1.46 (1 H, m), 2.15 (3 H, s), 3.68 (3 H, s), 3.95 (1 H, d, J = 14.6 Hz), 4.24-4.42 (2 H, m), 5.81 (1 H, d, J = 14.6 Hz), 6.47 (1 H, d, J = 8.2 Hz), 6.54 (1 H, d, J = 8.2 Hz), 6.74-6.79 (2 H, m), 6.90-6.96 (2 H, m), 7.19-7.23 (1 H, m) |

-continued
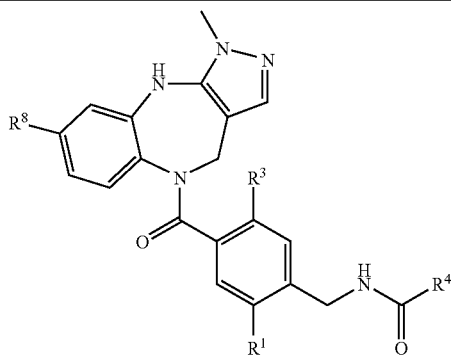
| Compound number | R¹ | R³ | R⁴ | R⁸ | MS | ¹H NMR: δ (ppm) |
|---|---|---|---|---|---|---|
| 1289 | Me | H | cyclopropyl | Cl | (ESI)+: [M + H]+ = 450.3, 452.4 | 0.66-0.78 (2 H, m), 0.82-0.94 (2 H, m), 1.34-1.46 (1 H, m), 2.08 (3 H, s), 3.63 (3 H, s), 3.93 (1 H, d, J = 14.6 Hz), 4.26 (2 H, d, J = 4.0 Hz), 5.83 (1 H, d, J = 14.6 Hz), 6.47-6.62 (2 H, m), 6.78-6.86 (2 H, m), 7.01-7.08 (1 H, m), 7.19 (1 H, s), 7.39 (1 H, s) |
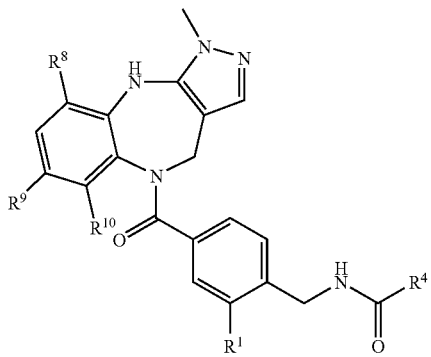
| Compound number | R¹ | R⁴ | R⁸ | R⁹ | R¹⁰ | MS | ¹H NMR: δ (ppm) |
|---|---|---|---|---|---|---|---|
| 1290 | Me | CH(CH₃)₂ | Me | H | H | (ESI)+: [M + H]+ = 433.2 | 1.13 (6H, d, J = 6.5 Hz), 2.15 (3H, s), 2.26-2.38 (1H, m), 2.39 (3H, s), 3.82 (3H, s), 3.95 (1H, d, J = 14.6 Hz), 4.29 (2H, d, J = 5.2 Hz), 5.43 (1H, s), 5.77 (1H, s), 5.93 (1H, d, J = 14.6 Hz), 6.62 (2H, s), 6.87 (2H, s), 6.96-7.06 (1H, m), 7.16 (1H, s), 7.25 (1H, s) |
| 1291 | Me | CH₂CH₂CH₃ | Me | H | H | (ESI)+: [M + H]+ = 433.2 | 0.91 (3H, t, J = 7.2 Hz), 1.56-1.74 (2H, m), 2.09 (3H, s), 2.10-2.20 (2H, m), 2.39 (3H, s), 3.81 (3H, s), 3.94 (1H, d, J = 14.6 Hz), 4.25 (2H, d, J = 4.7 Hz), 5.65 (1H, s), 5.85-6.05 (2H, m), 6.60-6.63 (2H, m), 6.82 (2H, s), 7.00 (1H, |

-continued

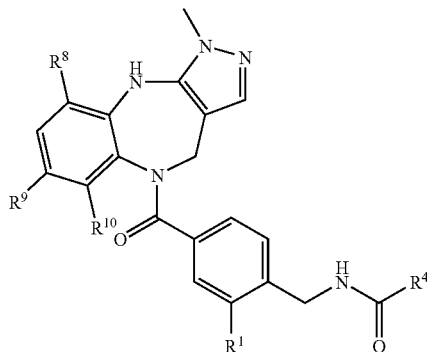

| Compound number | R¹ | R⁴ | R⁸ | R⁹ | R¹⁰ | MS | ¹H NMR: δ (ppm) |
|---|---|---|---|---|---|---|---|
| 1292 | Me | CH₂CH₃ | Me | H | H | (ESI)+: [M + H]+ = 418.2 | d, J = 5.7 Hz), 7.07 (1H, s), 7.20 (1H, s) 1.34 (3H, t, J = 7.4 Hz), 2.12 (3H, s), 2.20 (2H, q, J = 7.4 Hz), 2.39 (3H, s), 3.82 (3H, s), 3.94 (1H, d, J = 14.7 Hz), 4.27 (2H, d, J = 5.2 Hz), 5.52 (1H, s), 5.85 (1H, s), 5.92 (1H, d, J = 14.7 Hz), 6.56-6.68 (2H, m), 6.86 (2H, s), 7.00 (1H, d, J = 5.7 Hz), 7.12 (1H, s), 7.25 (1H, s) |
| 1293 | Me | CH(CH₃)₂ | H | Me | H | (ESI)+: [M + H]+= 433.2 | 1.08-1.24 (6H, m), 2.02 (3H, s), 2.13 (3H, s), 2.26-2.44 (1H, m), 3.74 (3H, s), 3.94 (1H, d, J = 14.4 Hz), 4.28 (2H, d, J = 5.2 Hz), 5.62 (1H, s), 5.88 (1H, d, J = 14.4 Hz), 6.12 (1H, s), 6.52 (1H, s), 6.78-6.96 (4H, m), 7.14 (1H, s), 7.22 (1H, s) |
| 1294 | Me | CH₂CH₂CH₃ | H | Me | H | (ESI)+: [M + H]+ = 433.2 | 0.88-1.02 (3H, m), 2.02 (3H, s), 2.08-2.22 (7H, m), 3.72 (3H, s), 3.93 (1H, d, J = 14.5 Hz), 4.28 (2H, d, J = 5.2 Hz), 5.73 (1H, s), 5.86 (1H, d, J = 14.5 Hz), 6.21 (1H, s), 6.51 (1H, s), 6.79-6.96 (4H, m), 7.12 (1H, s), 7.22 (1H, s) |
| 1295 | Me | CH₂CH₃ | H | Me | H | (ESI)+: [M + H]+ = 418.2 | 1.12 (3H, t, J = 7.4 Hz), 2.02 (3H, s), 2.12 (3H, s), 2.19 (2H, q, J = 7.4 Hz), 3.73 (3H, s), 3.94 (1H, d, J = 14.4 Hz), 4.28 (2H, d, J = 5.0 Hz), 5.68 (1H, s), 5.87 (1H, d, J = 14.4 Hz), 6.15 (1H, s), 6.51 (1H, s), 6.78-6.98 (4H, m), 7.13 (1H, s), 7.22 (1H, s) |

-continued

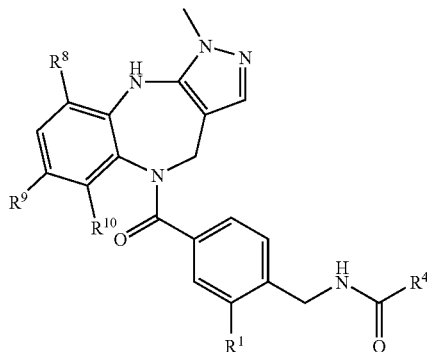

| Compound number | R¹ | R⁴ | R⁸ | R⁹ | R¹⁰ | MS | ¹H NMR: δ (ppm) |
|---|---|---|---|---|---|---|---|
| 1296 | Me | cyclopropyl | H | H | Me | (ESI)+: [M + H]+ = 430.1 | 0.69-0.79 (2H, m), 0.91-1.03 (2H, m), 1.32-1.41 (1H, m), 1.97 (3H, s), 2.07 (3H, s), 3.71 (3H, s), 3.86 (1H, d, J = 14.6 Hz), 4.26 (2H, d, J = 5.5 Hz), 5.89 (1H, d, J = 14.6 Hz), 5.99-6.08 (1H, m), 6.64 (1H, d, J = 7.4 Hz), 6.69-6.83 (2H, m), 6.90-7.03 (2H, m), 7.13 (1H, s), 7.23 (1H, s) |
| 1297 | Me | CH(CH₃)₂ | H | H | Me | (ESI)+: [M + H]+ = 432.2 | 1.10-1.21 (6H, m), 1.99 (3H, s), 2.10 (3H, s), 2.33-2.42 (1H, m), 3.76 (3H, s), 3.86 (1H, d, J = 14.6 Hz), 4.27 (2H, d, J = 5.5 Hz), 5.61 (1H, s), 5.89 (1H, d, J = 14.6 Hz), 6.65 (1H, d, J = 7.4 Hz), 6.76-6.85 (2H, m), 6.94-7.04 (2H, m), 7.17 (1H, s), 7.22 (1H, s) |
| 1298 | Me | CH₂CH₂CH₃ | H | H | Me | (ESI)+: [M + H]+ = 432.2 | 0.87-0.99 (3H, m), 1.56-1.72 (2H, m), 1.98 (3H, s), 2.10 (3H, s), 2.13-2.25 (2H, m), 3.76 (3H, s), 3.86 (1H, d, J = 14.6 Hz), 4.27 (2H, d, J = 5.7 Hz), 5.66 (1H, s), 5.90 (1H, d, J = 14.6 Hz), 6.65 (1H, d, J = 7.4 Hz), 6.76-6.85 (3H, m), 6.94-7.04 (3H, m), 7.16 (1H, s) |
| 1299 | Me | CH₂CH₃ | H | H | Me | (ESI)+ [M + H]+ = 418.2 | 1.09-1.22 (3H, m), 1.98 (3H, s), 2.08 (3H, s), 2.14-2.29 (2H, m), 3.74 (3H, s), 3.86 (1H, d, J = 14.6 Hz), 4.26 (2H, d, J = 5.5 Hz), 5.75 (1H, s), 5.89 (1H, d, J = 14.6 Hz), 6.61-6.66 (1H, m), 6.74-6.83 (2H, m), 6.94-7.04 (2H, m), 7.15 (1H, s), 7.22 (1H, s) |

-continued
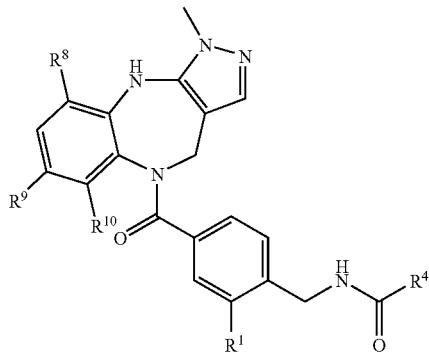
| Compound number | R¹ | R⁴ | R⁸ | R⁹ | R¹⁰ | MS | ¹H NMR: δ (ppm) |
|---|---|---|---|---|---|---|---|
| 1300 | Me | cyclopropyl | H | Me | H | (ESI)+: [M + H]+ = 430.2 | 0.68-0.79 (2H, m), 0.90-0.98 (2H, m), 1.30-1.40 (1H, m), 2.03 (3H, s), 2.12 (3H, s), 3.73 (3H, s), 3.94 (1H, d, J = 14.6 Hz), 4.27-4.33 (2H, m), 5.87 (1H, d, J = 14.6 Hz), 5.90-5.97 (1H, m), 6.24 (1H, s), 6.51 (1H, s), 6.79-6.94 (4H, m), 7.13 (1H, s) |
| 1301 | Me | cyclopropyl | Me | H | H | (ESI)+: [M + H+ = 430.3 | 0.68-0.80 (2H, m), 0.90-1.02 (2H, m), 1.28-1.40 (1H, m), 2.14 (3H, s), 2.39 (3H, s), 3.82 (3H, m), 3.95 (1H, d, J = 14.6 Hz), 4.30 (2H, d, J = 5.4 Hz), 5.69 (1H, brs), 5.82 (1H, s), 5.93 (1H, d, J = 14.6 Hz), 6.58-6.70 (2H, m), 6.85-6.96 (2H, m), 6.96-7.08 (1H, m), 7.14 (1H, s) |
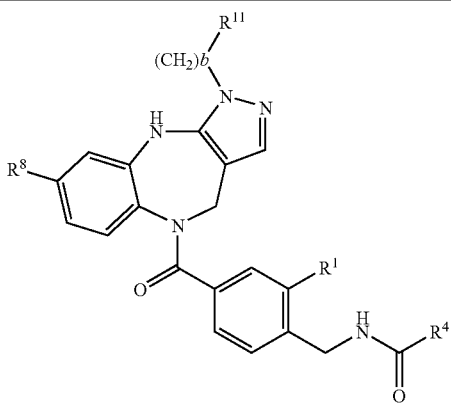
| Compound number | R¹ | R⁴ | R⁸ | b | R¹¹ | MS |
|---|---|---|---|---|---|---|
| 1302 | F | CH2CH2CH3 | F | 0 | phenyl | (ESI)+: [M + H]+ = 502.4 |

-continued

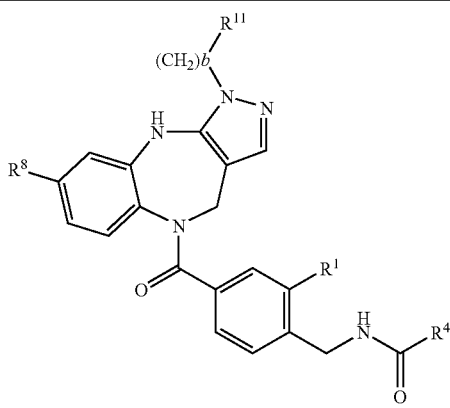

| Compound number | R¹ | R⁴ | R⁸ | b | R¹¹ | MS |
|---|---|---|---|---|---|---|
| 1303 | F | CH(CH3)2 | F | 0 | phenyl | (ESI)+: [M + H]+ = 502.2 |
| 1304 | F | cyclopropyl | F | 0 | phenyl | (ESI)+: [M + H]+ = 500.2 |
| 1305 | F | CH2CH3 | F | 0 | phenyl | (ESI)+: [M + H]+ = 488.2 |
| 1306 | F | CH2CH2CH3 | F | 1 | CH3 | (ESI)+: [M + H]+ = 454.3 |
| 1307 | F | CH(CH3)2 | F | 1 | CH3 | (ESI)+: [M + H]+ = 454.3 |
| 1308 | F | cyclopropyl | F | 1 | CH3 | (ESI)+: [M + H]+ = 452.3 |
| 1309 | F | CH2CH3 | F | 1 | CH3 | (ESI)+: [M + H]+ = 440.3 |
| 1310 | Me | CH2CH2CH3 | F | 0 | C(CH3)3 | (ESI)+: [M + H]+ = 478.4 |
| 1311 | Me | CH2CH3 | F | 0 | C(CH3)3 | (ESI)+: [M + H]+ = 464.4 |
| 1312 | Me | CH(CH3)2 | F | 0 | C(CH3)3 | (ESI)+: [M + H]+ = 478.4 |
| 1313 | Me | cyclopropyl | F | 0 | C(CH3)3 | (ESI)+: [M + H]+ = 476.4 |
| 1314 | F | CH2CH2CH3 | F | 0 | cyclohexyl | (ESI)+: [M + H]+ = 508.3 |
| 1315 | F | CH2CH3 | F | 0 | cyclohexyl | (ESI)+: [M + H]+ = 494.2 |
| 1316 | F | CH(CH3)2 | F | 0 | cyclohexyl | (ESI)+: [M + H]+ = 508.3 |
| 1317 | F | cyclopropyl | F | 0 | cyclohexyl | (ESI)+: [M + H]+ = 506.2 |
| 1318 | F | CH2CH2CH3 | F | 0 | C(CH3)3 | (ESI)+: [M + H]+ = 482.2 |

-continued

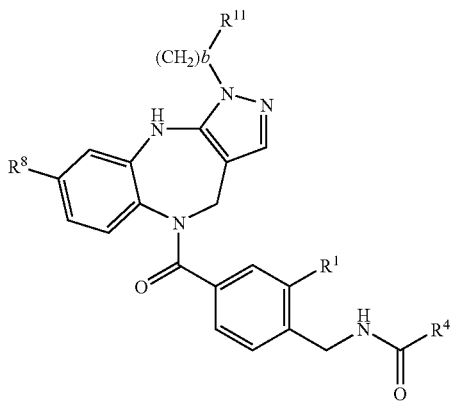

| Compound number | R¹ | R⁴ | R⁸ | b | R¹¹ | MS |
|---|---|---|---|---|---|---|
| 1319 | F | CH2CH3 | F | 0 | C(CH3)3 | (ESI)+: [M + H]+ = 468.2 |
| 1320 | F | CH(CH3)2 | F | 0 | C(CH3)3 | (ESI)+: [M + H]+ = 482.2 |
| 1321 | F | △ | F | 0 | C(CH3)3 | (ESI)+: [M + H]+ = 480.2 |
| 1322 | F | CH(CH₃)₂ | Cl | 1 | CH₃ | (ESI)+: [M + H]+ = 436.4 |
| 1323 | F | CH₂CH₂CH₃ | Cl | 1 | CH₃ | (ESI)+: [M + H]+ = 436.4 |
| 1324 | F | CH₂CH₃ | Cl | 1 | CH₃ | (ESI)+: [M + H]+ = 422.4 |
| 1325 | F | △ | Cl | 1 | CH₃ | (ESI)+: [M + H]+ = 434.4 |
| 1326 | Me | CH₂CH₃ | H | 2 | CH₂CH₃ | (ESI)+: [M + H]+ = 446.3 |
| 1327 | Me | CH₂CH₂CH₃ | H | 2 | CH₂CH₃ | (ESI)+: [M + H]+ = 460.3 |
| 1328 | Me | CH(CH₃)₂ | H | 2 | CH₂CH₃ | (ESI)+: [M + H]+ = 460.2 |
| 1329 | Me | △ | H | 2 | CH₂CH₃ | (ESI)+: [M + H]+ = 458.2 |
| 1330 | F | CH₂CH₃ | H | 2 | CH₂CH₃ | (ESI)+: [M + H]+ = 450.2 |
| 1331 | F | CH₂CH₂CH₃ | H | 2 | CH₂CH₃ | (ESI)+: [M + H]+ = 464.2 |
| 1332 | F | CH(CH₃)₂ | H | 2 | CH₂CH₃ | (ESI)+: [M + H]+ = 464.2 |
| 1333 | F | △ | H | 2 | CH₂CH₃ | (ESI)+: [M + H]+ = 462.4 |
| 1334 | F | △ | Cl | 0 | 2-pyridyl | (ESI)+: [M + H]+ = 517.2, 519.2 |
| 1335 | F | CH(CH₃)₂ | Cl | 0 | 2-pyridyl | (ESI)+: [M + H]+ = 519.2, 521.2 |
| 1336 | F | CH₂CH₂CH₃ | Cl | 0 | 2-pyridyl | (ESI)+: [M + H]+ = 519.2, 521.2 |
| 1337 | F | CH₂CH₃ | Cl | 0 | 2-pyridyl | (ESI)+: [M + H]+ = 505.2, 507.2 |
| 1338 | Me | CH(CH₃)₂ | H | 1 | CH₃ | (ESI)+: [M + H]+ = 433.2 |
| 1339 | Me | CH₂CH₂CH₃ | H | 1 | CH₃ | (ESI)+: [M + H]+ = 433.2 |

-continued

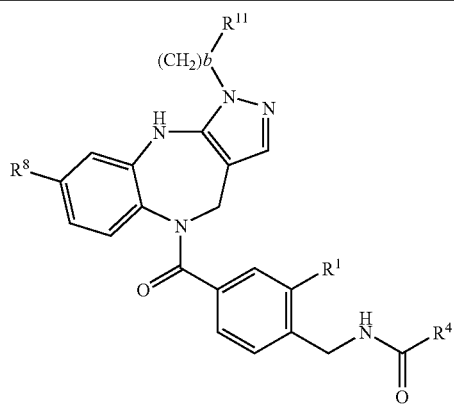

| Compound number | R¹ | R⁴ | R⁸ | b | R¹¹ | MS |
|---|---|---|---|---|---|---|
| 1340 | Me | CH₂CH₃ | H | 1 | CH₃ | (ESI)+: [M + H]+ = 418.2 |
| 1341 | Me | cyclopropyl | H | 1 | CH₃ | (ESI)+: [M + H]+ = 430.2 |
| 1342 | F | CH₂CH₂CH₃ | Cl | 0 | cyclohexyl | (ESI)+: [M + H]+ = 524.3, 526.3 |
| 1343 | F | CH(CH₃)₂ | Cl | 0 | cyclohexyl | (ESI)+: [M + H]+ = 524.3, 526.3 |
| 1344 | F | cyclopropyl | Cl | 0 | cyclohexyl | (ESI)+: [M + H]+ = 522.2, 524.2 |
| 1345 | F | CH₂CH₃ | Cl | 0 | cyclohexyl | (ESI)+: [M + H]+ = 510.3, 512.3 |
| 1346 | F | CH₂CH₂CH₃ | Cl | 0 | phenyl | (ESI)+: [M + H]+ = 518.3, 520.3 |
| 1347 | F | cyclobutyl | Cl | 0 | phenyl | (ESI)+: [M + H]+ = 530.2, 532.2 |
| 1348 | F | CH₂CH₃ | Cl | 0 | phenyl | (ESI)+: [M + H]+ = 504.2, 506.2 |
| 1349 | F | CH(CH₃)₂ | Cl | 0 | phenyl | (ESI)+: [M + H]+ = 518.2, 520.2 |
| 1350 | F | CH₂CH₂CH₃ | Cl | 0 | C(CH₃)₃ | (ESI)+: [M + H]+ = 498.2, 500.2 |
| 1351 | F | cyclobutyl | Cl | 0 | C(CH₃)₃ | (ESI)+: [M + H]+ = 510.4, 512.4 |

-continued

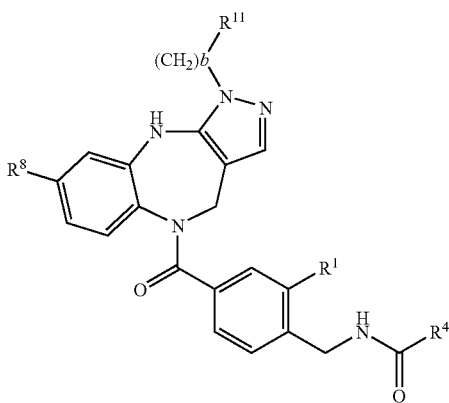

| Compound number | R¹ | R⁴ | R⁸ | b | R¹¹ | MS |
|---|---|---|---|---|---|---|
| 1352 | F | CH₂CH₃ | Cl | 0 | C(CH₃)₃ | (ESI)+: [M + H]+ = 484.4, 486.4 |
| 1353 | F | CH(CH₃)₂ | Cl | 0 | C(CH₃)₃ | (ESI)+: [M + H]+ = 498.4, 500.4 |
| 1354 | F | CH₂CH₂CH₃ | Cl | 1 | CH₃ | (ESI)+: [M + H]+ = 470.3, 472.3 |
| 1355 | F | cyclobutyl | Cl | 1 | CH₃ | (ESI)+: [M +H]+ = 482.3, 484.3 |
| 1356 | F | CH₂CH₃ | Cl | 1 | CH₃ | (ESI)+: [M + H]+ = 456.2, 458.2 |
| 1357 | F | CH(CH₃)₂ | Cl | 1 | CH₃ | (ESI)+: [M + H]+ = 470.2, 472.2 |
| 1358 | F | CH₂CH₂CH₃ | Cl | 2 | CH₂CH₃ | (ESI)+: [M + H]+ = 498.3, 500.3 |
| 1359 | F | cyclobutyl | Cl | 2 | CH₂CH₃ | (ESI)+: [M + H]+ = 510.3, 512.3 |
| 1360 | F | CH₂CH₃ | Cl | 2 | CH₂CH₃ | (ESI)+: [M + H]+ = 484.3, 486.3 |
| 1361 | F | CH(CH₃)₂ | Cl | 2 | CH₂CH₃ | (ESI)+: [M + H]+ = 498.3, 500.3 |
| 1362 | F | cyclopropyl | Cl | 0 | phenyl | (ESI)+: [M + H]+ = 516.2, 518.2 |
| 1363 | F | cyclopropyl | Cl | 0 | C(CH₃)₃ | (ESI)+: [M + H]+ = 496.2, 498.2 |
| 1364 | F | cyclopropyl | Cl | 1 | CH₃ | (ESI)+: [M + H]+ = 468.1, 470.2 |
| 1365 | F | cyclopropyl | Cl | 2 | CH₂CH₃ | (ESI)+: [M + H]+ = 496.3, 498.3 |

485
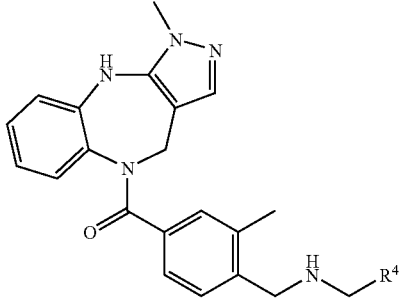
| Compound number | R⁴ | MS |
|---|---|---|
| 1366 E109 | 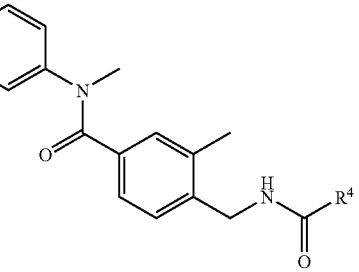 | (ESI)+: [M + H]+ = 402.4 |
| 1367 |  | (APCl)+: [M + H]+ = 522.3 |
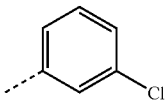
| Compound number | c | R¹² | MS |
|---|---|---|---|
| 1368 E113 | 1 | NHCO₂C(CH₃)₃ | (ESI)+: [M + H]+ = 543.2, 545.2 |
| 1369 | 1 | N(CH₃)₂ | (ESI)+: [M + H]+ = 471.2 |
| 1370 | 1 | N(CH₃)CO₂C(CH₃)₃ | (ESI)+: [M + H]+ = 557.1, 559.1 |
| 1371 E114 | 1 | NH₂ | (ESI)+: [M + H]+ = 443.0 |
| 1372 | 1 | NHCH₃ | (ESI)+: [M + H]+ = 457.1 |
486
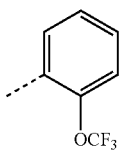
| Compound number | R⁴ | MS |
|---|---|---|
| 1373 E115 |  | (ESI)+: [M + H]+ = 427.2 |
| 1374 | 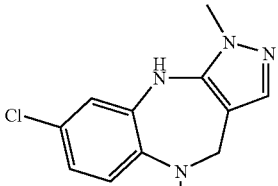 | (APCl)+: [M + H]+ = 357.3, 359.3 |
| 1375 | 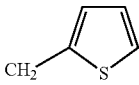 | (APCl)+: [M + H]+ = 413.2, 415.2 |
| 1376 | 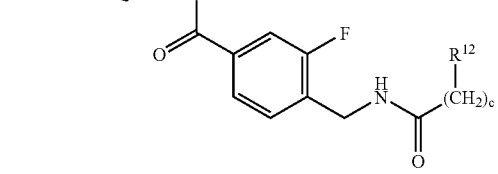 | (APCl)+: [M + H]+ = 399.2, 401.2 |
| 1377 | CH₂CH₂CH₂CH₂CH₃ | (APCl)+: [M + H]+ = 387.2, 389.2 |
| 1378 | 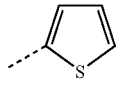 | (APCl)+: [M + H]+ = 427.1, 429.1 |
| 1379 |  | (APCl)+: [M + H]+ = 427.1, 429.1 |
| 1380 | 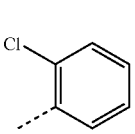 | (APCl)+: [M + H]+ = 393.2, 395.2 |

487

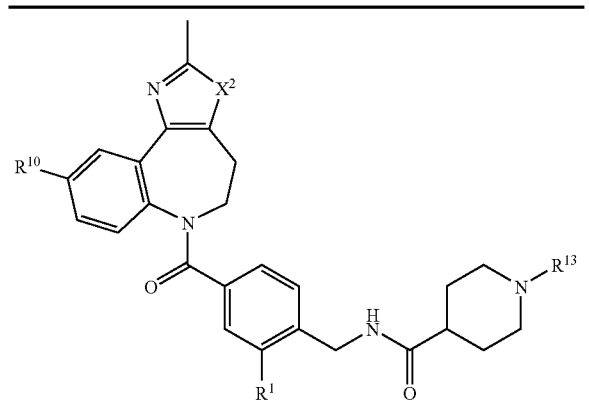

| Compound number | R¹ | R¹⁰ | R¹³ | X² | MS |
|---|---|---|---|---|---|
| 1381 | Me | Me | (neopentyl-like) | S | (ESI)+: [M + H]+ = 573.3 |

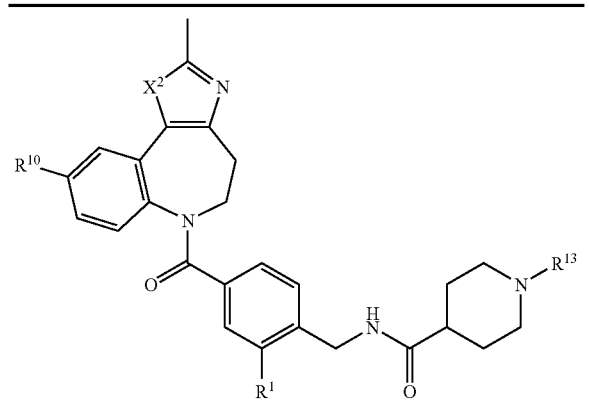

| Compound number | R¹ | R¹⁰ | R¹³ | X² | MS |
|---|---|---|---|---|---|
| 1382 E122 | Me | H | (neopentyl-like) | NH | (APCI)+: [M + H]+ = 542.4 |
| 1383 | Me | Cl | (neopentyl-like) | NH | (ESI)+: [M + H]+ = 576.4 |
| 1384 | Me | Me | (neopentyl-like) | NH | (ESI)+: [M + H]+ = 556.4 |

488

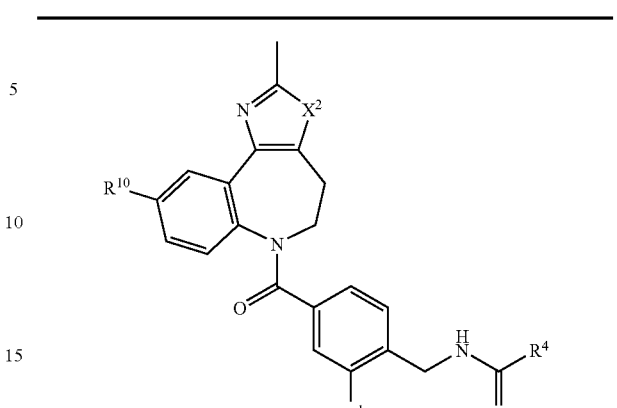

| Compound number | R¹ | R⁴ | R¹⁰ | X² | MS |
|---|---|---|---|---|---|
| 1385 E124 | Me | cyclopropyl | H | S | (APCI)+: [M + H]+ = 432.3 |
| 1386 | Cl | cyclopropyl | Me | S | (ESI)+: [M + H]+ = 446.2 |

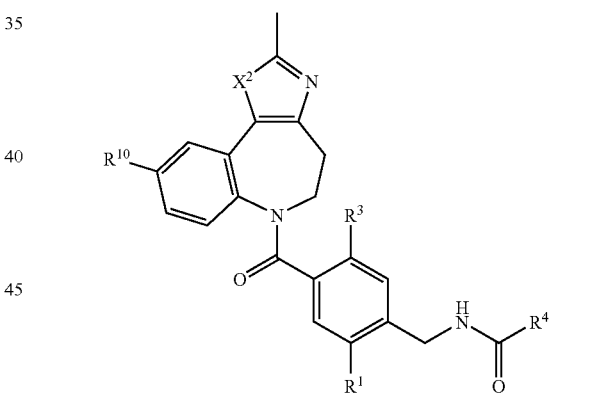

| Compound number | R¹ | R³ | R⁴ | R¹⁰ | X² | MS |
|---|---|---|---|---|---|---|
| 1387 | H | F | CH₂CH₂CH₃ | Me | NH | (ESI)+: [M + H]+ = 435.2 |

| Compound number | ¹H NMR: δ (ppm) |
|---|---|
| 1314 | 0.89 (3H, t, J = 7.4 Hz), 1.20-1.53 (3H, m), 1.54-1.70 (2H, m), 1.71-1.82 (1H, m), 1.80-2.10 (6H, m), 2.14 (2H, t, J = 7.4 Hz), 2.77-3.93 (1H, m), 3.97 (1H, d, J = 14.6 Hz), 4.38 (2H, d, J = 6.2 Hz), 5.70-5.79 (1H, m), 5.86 (1H, d, J = 14.6 Hz), 6.10 (1H, s), 6.34-6.46 (1H, m), |

-continued

| Compound number | ¹H NMR: δ (ppm) |
|---|---|
| | 6.62-6.75 (2H, m), 6.95 (2H, d, J = 8.6 Hz), 7.11 (1H, t, J = 7.4 Hz), 7.28 (1H, s) |
| 1315 | 1.13 (3H, t, J = 7.4 Hz), 1.30-1.54 (3H, m), 1.72-1.80 (1H, m), 1.89-2.11 (6H, m), 2.19 (2H, q, J = 7.4 Hz), 3.78-3.92 (1H, m), 3.97 (1H, d, J = 14.6 Hz), 4.38 (2H, d, J = 5.7 Hz), 5.69-5.80 (1H, m), 5.87 (1H, d, J = 14.6 Hz), 6.07 (1H, s), 6.38-6.48 (1H, m), 6.62-6.71 (2H, m), 6.94 (2H, d, J = 8.6 Hz), 7.11 (1H, t, J = 7.2 Hz), 7.28 (1H, s) |
| 1316 | 1.11 (6H, d, J = 6.9 Hz), 1.30-1.49 (3H, m), 1.74-1.80 (1H, m), 1.94-1.99 (6H, m), 2.31-2.36 (1H, m), 3.79-3.92 (1H, m), 3.97 (1H, d, J = 14.8 Hz), 4.37 (2H, d, J = 5.9 Hz), 5.70-5.81 (1H, m), 5.87 (1H, d, J = 14.8 Hz), 6.10 (1H, s), 6.36-6.43 (1H, m), 6.62-6.70 (2H, m), 6.95 (2H, d, J = 8.9 Hz), 7.10 (1H, t, J = 7.4 Hz), 7.28 (1H, s) |
| 1317 | 0.72-0.77 (2H, m), 0.92-1.00 (2H, m), 1.25-1.50 (4H, m), 1.74-1.80 (1H, m), 1.95-2.00 (6H, m), 3.78-3.90 (1H, m), 3.97 (1H, d, J = 14.8 Hz), 4.40 (2H, d, J = 5.7 Hz), 5.84-5.94 (2H, m), 6.04 (1H, s), 6.36-6.45 (1H, m), 6.64-6.70 (2H, m), 6.95 (2H, d, J = 8.9 Hz), 7.12 (1H, t, J = 7.7 Hz), 7.28 (1H, s) |
| 1318 | 0.89 (3H, t, J = 7.4 Hz), 1.59-1.64 (2H, m), 1.74 (9H, s), 2.14 (2H, t, J = 7.7 Hz), 3.97 (1H, d, J = 14.6 Hz), 4.38 (2H, d, J = 5.7 Hz), 5.62-5.77 (1H, m), 5.85 (1H, d, J = 14.6 Hz), 6.36-6.48 (2H, m), 6.58-6.70 (2H, m), 6.92-7.00 (2H, m), 7.13 (1H, t, J = 7.7 Hz), 7.21 (1H, s) |
| 1319 | 1.13 (3H, t, J = 7.4 Hz), 1.74 (9H, s), 2.18 (2H, q, J = 7.4 Hz), 3.97 (1H, d, J = 14.6 Hz), 4.39 (2H, d, J = 5.9 Hz), 5.63-5.75 (1H, m), 5.85 (1H, d, J = 14.6 Hz), 6.37-6.45 (2H, m), 6.60-6.70 (2H, m), 6.90-7.00 (2H, m), 7.12 (1H, t, J = 7.4 Hz), 7.22 (1H, s) |
| 1320 | 1.11 (6H, d, J = 6.7 Hz), 1.74 (9H, s), 2.22-2.40 (1H, m), 3.97 (1H, d, J = 14.8 Hz), 4.38 (2H, d, J = 5.7 Hz), 5.65-5.73 (1H, m), 5.85 (1H, d, J = 14.8 Hz), 6.34-6.48 (2H, m), 6.56-6.70 (2H, m), 6.90-7.00 (2H, m), 7.12 (1H, t, J = 7.7 Hz), 7.22 (1H, s) |
| 1321 | 0.68-0.81 (2H, m), 0.92-1.01 (2H, m), 1.24-1.35 (1H, m), 1.74 (9H, s), 3.97 (1H, d, J = 14.4 Hz), 4.40 (2H, d, J = 6.2 Hz), 5.77-5.95 (2H, m), 6.36 (1H, s), 6.37-6.48 (1H, m), 6.58-6.70 (2H, m), 6.90-7.03 (2H, m), 7.13 (1H, t, J = 7.2 Hz), 6.22 (1H, s) |
| 1322 | 1.11 (6H, d, J = 6.9 Hz), 1.47 (3H, t, J = 7.2 Hz), 2.32 (1H, septet, J = 6.9 Hz), 3.99 (1H, d, J = 14.6 Hz), 4.09 (2H, q, J = 7.2 Hz), 4.34 (2H, d, J = 5.9 Hz) 5.79 (1H, s), 5.88 (1H, d, J = 14.6 Hz), 6.14 (1H, s), 6.69-6.71, (2H, m), 6.91-7.11 (5H, m), 7.25-7.26 (1H, m) |
| 1323 | 0.89 (3H, t, J = 7.4 Hz), 1.48 (3H, t, J = 7.2 Hz), 1.57-1.60, (2H, m), 2.13 (2H, q, J = 7.6 Hz), 3.99 (1H, d, J = 14.6 Hz), 4.09 (2H, q, J = 7.2 Hz), 4.36 (2H, d, J = 5.9 Hz), 5.74 (1H, s), 5.87 (1H, d, J = 14.6 Hz), 6.05 (1H, s), 6.69-6.71 (2H, m), 6.90-6.97 (3H, m), 7.03-7.12 (2H, m), 7.25-7.26 (1H, m) |
| 1324 | 1.11 (3H, t, J = 7.7 Hz), 1.46 (3H, t, J = 7.2 Hz), 2.18 (2H, q, J = 7.7 Hz), 3.99 (1H, d, J = 14.6 Hz), 4.09 (2H, q, J = 7.2 Hz), 4.35 (2H, d, J = 5.9 Hz), 5.82 (1H, s), 5.88 (1H, d, J = 14.6 Hz), 6.19 (1H, s), 6.69-6.71 (2H, m), 6.91-7.13 (5H, m), 7.25-7.26 (1H, m) |
| 1325 | 0.70-0.74 (2H m), 0.91-0.95 (2H, m), 1.25-1.35 (1H, m), 1.48 (3H, t, J = 7.2 Hz), 3.98 (1H, d. J = 14.6 Hz), 4.09 (2H, q, J = 7.2 Hz), 4.37 (2H, d. J = 5.9 Hz), 5.89 (1H, d, J = 14.6 Hz), 5.96 (1H, s), 6.10 (1H, s), 6.70-6.72, (2H, m), 6.90-7.12 (5H, m), 7.25-7.26 (1H, m) |
| 1326 | 0.96 (3H, t, J = 7.4 Hz), 1.12 (3H, t, J = 7.4 Hz), 1.33-1.44 (2H, m), 1.79-1.88 (2H, m), 2.10-2.25 (5H, m), 3.95-4.04 (3H, m), 4.27 (2H, d, J = 5.4 Hz), 5.67 (1H, s), 5.90 (1H, d, J = 14.6 Hz), 6.21 (1H, s), 6.68-6.70 (2H, m), 6.83-7.12 (5H, m), 7.24 (1H, s) |
| 1327 | 0.87-0.99 (6H, m), 1.33-1.44 (2H, m), 1.58-1.67 (2H, m), 1.77-1.87 (2H, m), 2.10-2.16 (5H, m), 3.95-4.04 (3H, m), 4.27 (2H, d, J = 5.7 Hz), 5.65 (1H, s), 5.90 (1H, d, J = 14.6 Hz), 6.18 (1H, s), 6.68-6.70 (2H, m), 6.86-7.12 (5H, m), 7.24 (1H, s) |
| 1328 | 0.97 (3H, t, J = 7.2 Hz), 1.12 (6H, d, J = 6.2 Hz), 1.37-1.45 (2H, m), 1.78-1.87 (2H, m), 2.13 (3H, s), 2.30-2.36 (1H, m), 3.95-4.06 (3H, m), 4.28 (2H, d, J = 5.4 Hz), 5.53 (1H, s), 5.91 (1H, d, J = 14.6 Hz), 6.05 (1H, s), 6.68-6.70 (2H, m), 6.85-7.14 (5H, m), 7.24 (1H, s) |
| 1329 | 0.70-0.74 (2H, m), 0.94-1.00 (5H, m), 1.30-1.45 (3H, m), 1.81-1.87 (2H, m), 2.13 (3H, s), 3.95-4.05 (3H, m), 4.30 (2H, d, J = 5.7 Hz), 5.74 (1H, s), 5.91 (1H, d, J = 14.6 Hz), 6.06 (1H, s), 6.70-6.72 (2H, m), 6.89-6.93 (3H, m), 7.03-7.14 (2H, m), 7.24 (1H, s) |
| 1330 | 0.96 (3H, t, J = 7.4 Hz), 1.10 (3H, t, J = 7.4 Hz), 1.35-1.44 (2H, m), 1.77-1.85 (2H, m), 2.17 (2H, q, J = 7.4 Hz), 3.96-4.06 (3H, m), 4.33 (2H, d, J = 5.4 Hz), 5.87 (1H, d, J = 14.6 Hz), 5.90 (1H, s), 6.26 (1H, s), 6.68-6.70 (2H, m), 6.86-7.10 (5H, m), 7.24 (1H, s) |
| 1331 | 0.87 (3H, t, J = 7.4 Hz), 0.95 (3H, t, J = 7.4 Hz), 1.35-1.43 (2H, m), 1.56-1.64 (2H, m), 1.76-1.84 (2H, m), 2.09-2.15 (2H, m), 3.96-4.05 (3H, m), 4.33 (2H, d, J = 5.7 Hz), 5.87 (1H, d, J = 14.6 Hz), 5.93 (1H, s), 6.28 (1H, s), 6.68-6.70 (2H, m), 6.86-7.10 (5H, m), 7.24 (1H, s) |
| 1332 | 0.96 (3H, t, J = 7.2 Hz), 1.09 (6H, d, J = 6.2 Hz), 1.32-1.46 (2H, m), 1.77-1.88 (2H, m), 2.27-2.37 (1H, m), 3.96-4.06 (3H, m), 4.32 (2H, |

| Compound number | $^1$H NMR: δ (ppm) |
|---|---|
|  | d, J = 5.4 Hz), 5.87 (1H, d, J = 14.6 Hz), 5.90 (1H, s), 6.27 (1H, s), 6.68-6.70 (2H, m), 6.85-7.10 (5H, m), 7.24 (1H, s) |
| 1333 | 0.70-0.74 (2H, m), 0.94-1.01 (5H, m), 1.29-1.45 (3H, m), 1.78-1.87 (2H, m), 3.96-4.05 (3H, m), 4.36 (2H, d, J = 5.7 Hz), 5.88 (1H, d, J = 14.6 Hz), 5.97 (1H, s), 6.06 (1H, s), 6.70-6.72 (2H, m), 6.89-6.97 (3H, m), 7.03-7.09 (2H, m), 7.24 (1H, s) |
| 1334 | 0.63-0.80 (2H, m), 0.80-1.08 (2H, m), 1.21-1.45 (1H, m), 4.00 (1H, d, J = 15.1 Hz), 4.40 (2H, d, J = 5.7 Hz), 5.80-5.94 (2H, m), 6.55-6.70 (2H, m), 6.89-7.21 (5H, m), 7.46 (1H, s), 7.80-7.90 (1H, m), 8.04 (1H, d, J = 8.7 Hz), 8.44 (1H, d, J = 4.5 Hz), 11.26 (1H, s) |
| 1335 | 1.11 (6H, d, J = 6.7 Hz), 2.32 (1H, sept, J = 6.7 Hz), 4.00 (1H, d, J = 14.6 Hz), 4.38 (2H, d, J = 5.7 Hz), 5.62-5.78 (1H, m), 5.92 (1H, d, J = 14.6 Hz), 6.50-6.70 (2H, m), 6.90-7.21 (5H, m), 7.46 (1H, s), 7.83-7.89 (1H, m), 8.04 (1H, d, J = 8.4 Hz), 8.44 (1H, d, J = 4.2 Hz), 11.26 (1H, s) |
| 1336 | 0.89 (3H, t, J = 7.4 Hz), 1.62 (2H, m), 2.14 (2H, t, J = 7.7 Hz), 4.00 (1H, d, J = 14.6 Hz), 4.39 (2H, d, J = 5.7 Hz), 5.50-5.65 (1H, m), 5.92 (1H, d, J = 14.6 Hz), 6.50-6.70 (2H, m), 6.91-7.21 (5H, m), 7.46 (1H, s), 7.82-7.91 (1H, m), 8.05 (1H, d, J = 8.4 Hz), 8.44 (1H, d, J = 4.2 Hz), 11.26 (1H, s) |
| 1337 | 1.12 (3H, t, J = 7.5 Hz), 2.18 (2H, q, J = 7.5 Hz), 4.00 (1H, d, J = 14.8 Hz), 4.39 (2H, d, J = 5.7 Hz), 5.60-5.85 (1H, m), 5.92 (1H, d, J = 14.8 Hz), 6.58-6.69 (2H, m), 6.98-7.20 (5H, m), 7.46 (1H, s), 7.83-7.90 (1H, m), 8.04 (1H, d, J = 8.7 Hz), 8.44 (1H, d, J = 4.7 Hz), 11.26 (1H, s) |
| 1338 | 1.12 (6H, d, J = 6.7 Hz), 1.47 (3H, t, J = 7.0 Hz), 2.13 (3H, s), 2.33 (1H, sept, J = 6.7 Hz), 3.98 (1H, d, J = 14.9 Hz), 4.08 (2H, q, J = 7.0 Hz), 4.28 (2H, d, J = 5.2 Hz), 5.50-5.60 (1H, m), 5.92 (1H, d, J = 14.9 Hz), 6.10 (1H, s), 6.62-6.76 (2H, m), 6.82-7.00 (3H, m), 7.02-7.10 (1H, m), 7.14 (1H, s) |
| 1339 | 0.90 (3H, t, J = 7.3 Hz), 1.46 (3H, t, J = 7.2 Hz), 1.54-1.71 (2H, m), 2.06-2.20 (5H, m), 3.97 (1H, d, J = 14.6 Hz), 4.07 (2H, q, J = 7.2 Hz), 4.28 (2H, d, J = 4.9 Hz), 5.56-5.66 (1H, m), 5.86 (1H, d, J = 14.6 Hz), 6.17 (1H, s), 6.62-6.74 (2H, m), 6.84-6.98 (3H, m), 7.02-7.12 (1H, m), 7.13 (1H, s) |
| 1340 | 1.13 (3H, t, J = 7.7 Hz), 1.47 (3H, t, J = 7.1 Hz), 2.13 (3H, s), 2.19 (2H, q, J = 7.7 Hz), 3.97 (1H, d, J = 14.9 Hz), 4.08 (2H, q, J = 7.1 Hz), 4.28 (2H, d, J = 5.4 Hz), 5.54-5.64 (1H, m), 5.91 (1H, d, J = 14.9 Hz), 6.14 (1H, s), 6.66-6.76 (2H, m), 6.82-6.98 (3H, m), 7.02-7.12 (1H, m), 7.14 (1H, s) |
| 1341 | 0.68-0.78 (2H, m), 0.94 (2H, s), 1.26-1.38 (1H, m), 1.46 (3H, t, J = 7.2 Hz), 2.13 (3H, s), 3.97 (1H, d, J = 14.6 Hz), 4.07 (2H, q, J = 7.2 Hz), 4.29 (2H, d, J = 5.2 Hz), 5.76-5.86 (1H, m), 5.92 (1H, d, J = 14.6 Hz), 6.18 (1H, s), 6.64-6.74 (2H, m), 6.86-6.96 (3H, m), 7.02-7.12 (1H, m), 7.14 (1H, s) |
| 1342 | 0.90 (3H, t, J = 7.4 Hz), 1.20-1.71 (5H, m), 1.70 (1H, m), 1.81-2.10 (6H, m), 2.15 (2H, t, J = 7.4 Hz), 3.76-3.90 (1H, m), 3.95 (1H, d, J = 14.4 Hz), 4.39 (2H, d, J = 5.9 Hz), 5.65-5.79 (1H, m), 5.87 (1H, d, J = 14.4 Hz), 6.64 (2H, q, J = 7.2 Hz), 6.58-6.70 (3H, m), 7.12 (1H, t, J = 7.7 Hz), 7.27 (1H, s) |
| 1343 | 1.12 (6H, d, J = 6.7 Hz), 1.14-1.50 (3H, m), 1.77 (1H, m), 1.81-2.11 (6H, m), 2.28-2.40 (1H, m), 3.73-3.91 (1H, m), 3.95 (1H, d, J = 14.6 Hz), 4.38 (2H, d, J = 6.2 Hz), 5.64-5.76 (1H, m), 5.98 (1H, d, J = 14.6 Hz), 6.64 (2H, q, J = 6.9 Hz), 6.95-6.98 (3H, m), 7.12 (1H, t, J = 7.9 Hz), 7.28 (1H, s) |
| 1344 | 0.60-0.81 (2H, m), 0.90-1.00 (2H, m), 1.20-1.48 (4H, m), 1.76 (1H, m), 1.82-2.10 (6H, m), 3.73-3.90 (1H, m), 3.95 (1H, d, J = 14.6 Hz), 4.41 (2H, d, J = 6.2 Hz), 5.84-5.90 (2H, m), 6.60-6.72 (2H, m), 6.88-7.03 (3H, m), 7.12 (1H, t, J = 7.2 Hz), 7.28 (1H, s) |
| 1345 | 1.13 (3H, t, J = 7.5 Hz), 1.16-1.63 (3H, m), 1.76 (1H, m), 1.85-2.13 (6H, m), 2.22 (2H, q, J = 7.5 Hz), 3.72-3.90 (1H, m), 3.95 (1H, d, J = 15.1 Hz), 4.39 (2H, d, J = 5.9 Hz), 5.66-5.80 (1H, m), 5.86 (1H, d, J = 15.1 Hz), 6.60-6.87 (2H, m), 6.92-7.05 (3H, m), 7.12 (1H, t, J = 7.2 Hz), 7.27 (1H, s) |
| 1346 | 0.88-0.98 (3H, m), 1.60-1.71 (2H, m), 2.10-2.21 (2H, m), 4.08 (1H, d, J = 14.6 Hz), 4.40 (2H, d, J = 5.4 Hz), 5.70 (1H, brs), 5.95 (1H, d, J = 14.6 Hz), 6.27 (1H, s), 6.62-6.70 (2H, m), 6.80 (1H, s), 6.85-7.08 (2H, m), 7.12-7.19 (1H, m), 7.45-7.65 (6H, m) |
| 1347 | 1.80-2.02 (2H, m), 2.08-2.30 (4H, m), 2.97 (1H, t, J = 9.2 Hz), 4.01 (1H, d, J = 14.9 Hz), 4.39 (2H, d, J = 6.2 Hz), 5.60 (1H, brs), 5.96 (1H, d, J = 14.9 Hz), 6.27 (1H, s), 6.62-6.72 (2H, m), 6.80 (1H, s), 6.96-7.06 (2H, m), 7.10-7.20 (1H, m), 7.45-7.65 (6H, m) |
| 1348 | 1.13 (3H, t, J = 7.5 Hz), 2.19 (2H, q, J = 7.5 Hz), 4.04 (1H, d, J = 14.9 Hz), 4.39 (2H, d, J = 5.9 Hz), 5.69 (1H, brs), 5.96 (1H, d, J = 14.9 Hz), 6.27 (1H, s), 6.61-6.71 (2H, m), 6.80 (1H, s), 6.96-7.02 (2H, m), 7.10-7.18 (1H, m), 7.42-7.66 (6H, m) |

| Compound number | ¹H NMR: δ (ppm) |
|---|---|
| 1349 | 1.20 (6H, d, J = 6.7 Hz), 2.30-2.40 (1H, m), 4.05 (1H, d, J = 14.6 Hz), 4.39 (1H, d, J = 5.7 Hz), 5.72 (1H, brs), 5.96 (1H, d, J = 14.6 Hz), 6.29 (1H, s), 6.61-6.72 (2H, m), 6.72 (1H, s), 6.95-7.15 (2H, m), 7.10-7.20 (1H, m), 7.45-7.70 (6H, m) |
| 1350 | 0.88-1.00 (3H, m), 1.59-1.71 (2H, m), 1.74 (9H, s), 2.12-2.20 (2H, m), 3.95 (1H, d, J = 14.6 Hz), 4.39 (2H, d, J = 5.2 Hz), 5.70 (1H, brs), 5.84 (1H, d, J = 14.6 Hz), 6.36 (1H, s), 6.58-6.62 (2H, m), 6.88-7.02 (3H, m), 7.10-7.20 (1H, m), 7.20-7.22 (1H, s) |
| 1351 | 1.74 (9H, s), 1.82-2.03 (2H, m), 2.04-2.35 (4H, m), 2.90-3.05 (1H, m), 3.95 (1H, d, J = 14.6 Hz), 4.39 (2H, d, J = 5.9 Hz), 5.59 (1H, brs), 5.85 (1H, d, J = 14.6 Hz), 6.36 (1H, s), 6.60-6.72 (2H, m), 6.90-7.08 (3H, m), 7.10-7.20 (1H, m), 7.25 (1H, s) |
| 1352 | 1.13 (3H, t, J = 7.4 Hz), 1.74 (9H, s), 2.19 (2H, q, J = 7.4 Hz), 3.98 (1H, d, J = 14.6 Hz), 4.40 (2H, d, J = 5.4 Hz), 5.70 (1H, brs), 5.88 (1H, d, J = 14.6 Hz), 6.36 (1H, s), 6.58-6.70 (2H, m), 6.89-7.04 (3H, m), 7.10-7.20 (1H, m), 7.25 (1H, s) |
| 1353 | 1.12 (6H, d, J = 6.7 Hz), 1.74 (9H, s), 2.33 (1H, q, J = 6.9 Hz), 3.95 (1H, d, J = 14.9 Hz), 4.39 (2H, d, J = 5.9 Hz), 5.70 (1H, brs), 5.85 (1H, d, J = 14.9 Hz), 6.36 (1H, s), 6.59-6.71 (2H, m), 6.90-7.05 (3H, m), 7.21 (1H, s), 7.25 (1H, s) |
| 1354 | 0.89 (3H, t, J = 7.4 Hz), 1.48 (3H, t, J = 7.2 Hz), 1.56-1.68 (2H, m), 2.15 (2H, t, J = 7.4 Hz), 3.95 (1H, d, J = 14.8 Hz), 4.06 (2H, q, J = 7.2 Hz), 4.39 (2H, d, J = 5.9 Hz), 5.72-5.80 (1H, m), 5.85 (1H, d, J = 14.8 Hz), 6.11 (1H, s), 6.65 (2H, dd, J = 8.4, 14.1 Hz), 6.89-6.98 (3H, m), 7.12 (1H, t, J = 7.7 Hz), 7.27 (1H, s) |
| 1355 | 1.45 (3H, t, J = 7.2 Hz), 1.75-2.03 (2H, m), 2.04-2.31 (4H, m), 2.88-3.07 (1H, m), 3.95 (1H, d, J = 14.6 Hz), 4.07 (2H, q, J = 7.4 Hz), 4.38 (2H, d, J = 5.9 Hz), 5.58-5.72 (1H, m), 5.85 (1H, d, J = 14.6 Hz), 6.17 (1H, s), 6.65 (2H, dd, J = 8.4, 13.6 Hz), 6.88-6.98 (3H, m), 7.10 (1H, t, J = 8.2 Hz), 7.26 (1H, s) |
| 1356 | 1.13 (3H, t, J = 7.7 Hz), 1.47 (3H, t, J = 7.4 Hz), 2.21 (2H, q, J = 7.7 Hz), 3.98 (1H, d, J = 14.6 Hz), 4.07 (2H, q, J = 7.4 Hz), 4.39 (2H, d, J = 7.4 Hz), 5.70-5.91 (2H, m), 6.17 (1H, s), 6.65 (2H, dd, J = 8.4, 14.1 Hz), 6.88-7.00 (3H, m), 7.11 (1H, t, J = 7.7 Hz), 7.26 (1H, s) |
| 1357 | 1.12 (6H, d, J = 6.9 Hz), 1.47 (3H, t, J = 7.2 Hz), 2.25-2.43 (1H, m), 3.95 (1H, d, J = 14.6 Hz), 4.06 (2H, q, J = 7.2 Hz), 4.38 (2H, d, J = 5.9 Hz), 5.73-5.92 (2H, m), 6.22 (1H, s), 6.64 (2H, dd, J = 8.1, 12.4 Hz), 6.88-6.99 (3H, m), 7.09 (1H, t, J = 7.7 Hz), 7.26 (1H, s) |
| 1358 | 0.90 (3H, t, J = 7.4 Hz), 0.98 (3H, t, J = 7.4 Hz), 1.33-1.52 (1H, m), 1.56-1.70 (2H, m), 1.73-1.90 (2H, m), 2.15 (2H, t, J = 7.7 Hz), 3.88-4.04 (3H, m), 4.39 (2H, d, J = 7.2 Hz), 5.69-5.80 (1H, m), 5.85 (1H, d, J = 14.6 Hz), 6.06 (1H, s), 6.59-6.72 (2H, m), 6.89-7.01 (3H, m), 7.12 (1H, t, J = 7.4 Hz), 7.25 (1H, s) |
| 1359 | 0.98 (3H, t, J = 7.2 Hz), 1.33-1.48 (2H, m), 1.56 (2H, s), 1.78-2.00 (4H, m), 2.03-2.30 (3H, m), 2.90-3.06 (1H, m), 3.88-4.05 (3H, m), 4.38 (2H, d, J = 5.7 Hz), 5.58-5.68 (1H, m), 5.85 (1H, d, J = 14.6 Hz) 6.06 (1H, s), 6.57-6.70 (2H, m), 6.90-7.02 (3H, m), 7.11 (1H, t, J = 7.7 Hz) |
| 1360 | 0.97 (3H, t, J = 7.4 Hz), 1.13 (3H, t, J = 7.4 Hz), 1.31-1.49 (2H, m), 1.72-1.91 (2H, m), 2.13-2.28 (2H, m), 3.00-3.15 (1H, m), 3.90-4.10 (3H, m), 4.38 (2H, d, J = 6.2 Hz), 5.83-5.90 (2H, m), 6.20 (1H, s), 6.56-6.70 (2H, m), 6.90-7.03 (3H, m), 7.07-7.14 (1H, m) |
| 1361 | 0.98 (3H, t, J = 7.4 Hz), 1.12 (6H, d, J = 6.9 Hz), 1.33-1.48 (2H, m), 1.77-1.91 (2H, m), 2.28-2.41 (1H, m), 3.90-4.10 (3H, m), 4.38 (2H, d, J = 5.9 Hz), 5.70-5.90 (2H, m), 6.14 (1H, s), 6.64 (2H, dd, J = 7.9, 12.1 Hz), 6.90-7.00 (3H, m), 7.10 (1H, t, J = 7.2 Hz), 7.25 (1H, s) |
| 1362 | 0.66-0.78 (2H, m), 0.90-0.99 (2H, m), 1.28-1.52 (2H, m), 4.03 (1H, d, J = 14.6 Hz), 4.40 (2H, d, J = 5.9 Hz), 5.90-6.00 (2H, m), 6.29 (1H, s), 6.60-6.74 (2H, m), 6.80 (1H, d, J = 1.7 Hz), 6.91-7.03 (2H, m), 7.13 (1H, t, J = 7.7 Hz), 7.42-7.66 (5H, m) |
| 1363 | 0.66-0.78 (2H, m), 0.91-1.00 (2H, m), 1.21-1.46 (2H, m), 1.74 (9H, s), 3.95 (1H, d, J = 14.8 Hz), 4.40 (2H, d, J = 5.7 Hz), 5.85 (1H, d, J = 14.8 Hz), 5.92-6.00 (1H, m), 6.39 (1H, s), 6.59-6.69 (2H, m), 6.89-7.02 (2H, m), 7.13 (1H, t, J = 7.4 Hz), 7.25 (1H, s) |
| 1364 | 0.67-0.85 (2H, m), 0.94 (2H, s), 1.25-1.55 (5H, m), 3.95 (1H, d, J = 14.6 Hz), 4.07 (2H, q, J = 7.2 Hz), 4.39 (2H, d, J = 5.7 Hz), 5.85 (1H, d, J = 14.6 Hz), 6.11 (1H, s), 6.52 (1H, s), 6.65 (2H, dd, J = 8.6, 13.3 Hz), 6.80-7.00 (3H, m), 7.09 (1H, t, J = 7.2 Hz) |
| 1365 | 0.67-0.80 (2H, m), 0.86-1.06 (5H, m), 1.28-1.46 (4H, m), 1.75-1.90 (2H, m), 3.89-4.08 (3H, m), 4.39 (2H, d, J = 7.2 Hz), 5.85 (1H, d, J = 14.6 Hz), 5.95-6.07 (1H, m), 6.25 (1H, s), 6.64 (2H, dd, J = 8.4, 13.1 Hz), 6.85-7.00 (3H, m), 7.05-7.15 (1H, m) |
| 1366 | 0.37-0.11 (2H, m), 0.42-0.47 (2H, m), 0.87-1.10 (1H, m), 1.32-1.69 (1H, m), 2.16 (3H, s), 2.37-2.43 (2H, m), 3.64 (2H, s), 3.77 (3H, s), 3.99 (1H, d, J = 14.6 Hz), 5.90 (1H, d, J = 14.6 Hz), 6.20-6.34 (1H, m), 6.58-6.72 (2H, m), 6.80-7.09 (4H, m), 7.16 (1H, s), 7.24 (1H, d, J = 4.7 Hz) |

| Compound number | ¹H NMR: δ (ppm) |
|---|---|
| 1367 | 1.46-1.63 (2H, m), 2.15 (3H, s), 3.64 (2H, s), 3.79 (4H, s), 3.96 (1H, d, J = 14.6 Hz), 5.92 (1H, d, J = 14.6 Hz), 6.07 (1H, s), 6.61-6.73 (2H, m), 6.87-6.96 (2H, m), 6.99-7.10 (2H, m), 7.17 (1H, s), 7.20-7.30 (4H, m), 7.36-7.48 (1H, m) |
| 1368 | 1.38 (9H, s), 3.66 (3H, s), 3.70-3.80 (2H, m), 3.94 (1H, d, J = 14.6 Hz), 4.28-4.38 (2H, m), 5.52-5.61 (1H, m), 5.78 (1H, d, J = 14.6 Hz), 6.58 (2H, s), 6.82-7.20 (6H, m), 7.62 (1H, s) |
| 1369 | 2.23 (6H, s), 2.96 (2H, s), 3.78 (3H, s), 3.95 (1H, d, J = 14.5 Hz), 4.41 (2H, d, J = 5.9 Hz), 5.85 (1H, d, J = 14.5 Hz), 6.44 (1H, s), 6.58-6.70 (2H, m), 6.90-7.10 (3H, m), 7.11 (1H, t, J = 7.0 Hz), 7.51 (1H, s) |
| 1370 | 1.38 (9H, s), 2.85 (3H, s), 3.68 (3H, s), 3.84 (2H, s), 3.93 (1H, d, J = 14.6 Hz), 4.30-4.41 (2H, m), 5.78 (1H, d, J = 14.6 Hz), 6.57 (2H, s), 6.75-7.25 (6H, m), 7.70 (1H, s) |
| 1371 | 3.30 (1H, s), 3.68 (2H, s), 4.00 (3H, s), 4.00-4.10 (1H, m), 4.41 (2H, s), 5.84 (1H, d, J = 15.1 Hz), 6.82-6.92 (2H, m), 7.00 (1H, d, J = 8.9 Hz), 7.26 (1H, t, J = 7.5 Hz), 7.43 (1H, s), 7.95 (1H, s), 8.55-8.65 (1H, m) |
| 1372 | 2.70 (3H, s), 3.30 (1H, s), 3.79 (2H, s), 4.01 (3H, s), 4.01-4.10 (1H, m), 4.41 (2H, s), 5.84 (1H, d, J = 15.1 Hz), 6.82-6.96 (2H, m), 6.98-7.06 (2H, m), 7.26 (1H, t, J = 7.7 Hz), 7.44 (1H, s), 7.98 (1H, s), 8.70-8.80 (1H, m) |
| 1373 | 2.21 (3H, s), 3.43 (3H, s), 4.51 (2H, d, J = 5.7 Hz), 6.40-6.52 (1H, m), 6.87-6.98 (4H, m), 7.17-7.21 (3H, m), 7.28-7.38 (1H, m), 7.42-7.48 (1H, m), 7.61-7.67 (1H, m), 7.76 (1H, s) |
| 1374 | 0.68-0.79 (2H, m), 0.92-1.00 (2H, m), 1.27-1.40 (1H, m), 2.21 (3H, s), 3.44 (3H, s), 4.36 (2H, d, J = 5.7 Hz), 5.61-5.68 (1H, m), 6.95-7.04 (4H, m), 7.18-7.25 (3H, m) |
| 1375 | 2.12 (3H, s), 3.42 (3H, s), 3.85 (2H, s), 4.31 (2H, d, J = 5.7 Hz), 5.72-5.77 (1H, m), 6.84-6.99 (6H, m), 7.12-7.25 (4H, m) |
| 1376 | 2.27 (3H, s), 3.44 (3H, s), 4.52 (2H, d, J = 5.7 Hz), 6.00-6.16 (1H, m), 6.92-6.99 (3H, m), 7.04-7.11 (2H, m), 7.21-7.30 (3H, m), 7.45-7.48 (2H, m) |
| 1377 | 0.85 (3H, t, J = 7.2 Hz), 1.20-1.37 (4H, m), 1.53-1.70 (2H, m), 2.12-2.29 (2H, m), 2.21 (3H, s), 3.43 (3H, s), 4.34 (2H, d, J = 5.4 Hz), 5.44-5.54 (1H, m), 6.91-6.99 (4H, m), 7.17-7.24 (3H, m) |
| 1378 | 2.28 (3H, s), 3.44 (3H, s), 4.57 (2H, d, J = 5.4 Hz), 6.19-6.30 (1H, m), 6.92-7.01 (2H, m), 7.09-7.11 (1H, m), 7.11-7.29 (4H, m), 7.31-7.42 (3H, m), 7.62-7.70 (1H, m) |
| 1379 | 2.21 (3H, s), 3.42 (3H, s), 4.50 (2H, d, J = 5.4 Hz), 6.41-6.51 (1H, m), 6.87-7.03 (4H, m), 7.13-7.22 (3H, m), 7.37 (2H, d, J = 6.7 Hz), 7.69 (2H, d, J = 6.7 Hz) |
| 1380 | 2.23 (3H, s), 3.43 (3H, s), 4.53 (2H, d, J = 5.7 Hz), 6.29-6.42 (1H, m), 6.89-7.07 (4H, m), 7.13-7.25 (3H, m), 7.37-7.50 (3H, m), 7.74-7.77 (2H, m) |
| 1381 | 0.87 (9H, s), 1.34-1.41 (2H, m), 1.68-2.10 (7H, m), 2.14 (3H, s), 2.27-2.32 (2H, m), 2.33 (3H, s), 2.74 (3H, s), 2.94-3.18 (4H, m), 3.48-3.55 (1H, m), 4.30 (2H, d, J = 5.4 Hz), 5.12-5.18 (1H, m), 5.51 (1H, s), 6.55 (1H, d, J = 7.9 Hz), 6.67 (1H, d, J = 7.9 Hz), 6.76-6.81 (2H, m), 7.16 (1H, s), 8.16 (1H, s) |
| 1382 | 0.86 (9H, s), 1.33-1.40 (2H, m), 1.66-1.92 (6H, m), 2.04-2.11 (1H, m), 2.08 (3H, s), 2.24-2.32 (2H, m), 2.45 (3H, s), 2.69-3.43 (5H, m), 4.25 (2H, d, J = 4.4 Hz), 4.98-5.06 (1H, brd), 5.76-5.84 (1H, brd), 6.62 (2H, t, J = 6.4, 13.6 Hz), 6.76-6.85 (2H, m), 7.06 (1H, s), 7.07-7.24 (1H, m), 8.11-8.23 (1H, m), 10.04-10.19 (1H, m) |
| 1383 | (CD₃OD): 0.89-0.99 (10H, m), 1.48-1.54 (2H, m), 1.77-1.80 (1H, m), 1.80-1.91 (4H, m), 2.15 (3H, s), 2.30-2.43 (1H, m), 2.43 (3H, s), 2.44-2.50 (1H, m), 2.64-2.73 (1H, m), 2.91-3.10 (2H, m), 3.22-3.39 (4H, m), 4.26 (2H, s), 4.95-5.08 (1H, m), 6.63-6.75 (2H, m), 6.78-6.87 (2H, m), 6.90-7.00 (2H, m), 7.95 (1H, s) |
| 1384 | 0.75-0.98 (11H, m), 1.33-1.50 (2H, m), 1.51-1.67 (1H, m), 1.68-1.90, (4H, m), 2.09 (3H, s), 2.11-2.33 (6H, m), 2.36-2.58 (4H, m), 2.77-2.92 (1H, m), 2.93-3.16 (2H, m), 3.17-3.30 (1H, m), 4.14-4.30 (2H, m), 4.90-5.09 (1H, m), 6.36-6.53 (1H, m), 6.53-6.70 (1H, m), 6.70-6.78 (1H, m), 7.04 (1H, s), 7.20-7.30 (2H, m), 7.88 (1Hs) |
| 1385 | 0.69-0.73 (2H, m), 0.81-0.97 (2H, m), 1.23-1.28 (1H, m), 2.14 (3H, s), 2.73 (3H, s), 3.09-3.19 (2H, m), 3.48-3.60 (1H, m), 4.30 (2H, d, J = 5.4 Hz), 5.13-5.23 (1H, m), 5.72 (1H, brs), 6.67 (2H, m), 6.86 (1H, d, J = 7.9 Hz), 6.95 (1H, m), 7.12-7.24 (2H, m), 8.37 (1H, dd, J = 1.5, 8.1 Hz) |
| 1386 | 0.68-0.75 (2H, m), 0.93-0.98 (2H, m), 1.25-1.42 (1H, m), 2.16 (3H, s), 2.33 (3H, s), 2.74 (3H, s), 3.04-3.18 (2H, m), 3.48-3.57 (1H, m), 4.32 (2H, d, J = 5.4 Hz), 5.12-5.19 (1H, m), 5.64 (1H, s), 6.55 (1H, d, J = 7.9 Hz), 6.69 (1H, d, J = 7.6 Hz), 6.77 (1H, d, J = 7.6 Hz), 6.86 (1H, d, J = 7.9 Hz), 7.16 (1H, s), 8.16 (1H, s) |

-continued

| Compound number | ¹H NMR: δ (ppm) | |
|---|---|---|
| 1387 | 0.90 (3H, t, J = 7.4 Hz), 1.56-1.70 (2H, m), 2.14 (2H, t, J = 7.2 Hz), 2.25 (3H, s), 2.46 (3H, s), 2.81-2.87 (1H, m), 2.98-3.10 (1H, m), 3.25-3.34 (1H, m), 4.28 (2H, d, J = 5.9 Hz), 4.93-5.00 (1H, m), 6.06 (1H, bs), 6.57-6.84 (6H. m), 7.82 (1H, bs) | |

| Compound number | ¹H NMR: δ (ppm) | MS |
|---|---|---|
| 1388 E48 | δ 0.32-0.47 (4H, m), 1.50-1.61 (1H, m), 1.83-2.00 (2H, m), 2.31-2.52 (4H, m), 2.52-2.73 (4H, m), 3.45 (2H, s), 3.76 (3H, s), 3.89-4.06 (3H, m), 5.87 (1H, d, J = 14.3 Hz), 6.37 (1H, s), 6.61-6.80 (3H, m), 6.86-7.00 (2H, m), 7.00-7.13 (2H, m), 7.20 (1H, s) ppm. | (APCI)+: [M + H]+ = 505.4 |
| 1389 E55 | δ 1.10-1.35 (4H, m), 1.62-1.82 (4H, m), 2.11 (3H, s), 2.36-2.50 (2H, m), 2.70-2.90 (2H, m), 3.73 (3H, s), 3.80-4.00 (5H, m), 4.50-4.65 (2H, m), 5.87 (1H, d, J = 14.6 Hz), 6.60-7.25 (9H, m) ppm. | (ESI)⁺: [M + H]⁺ = 530.3 |
| 1390 E68 | δ 0.88 (9H, s), 1.22-1.46 (7H, m), 1.64-1.77 (4H, m), 1.93 (2H, t, J = 10.9 Hz), 2.02 (3H, s), 2.31-2.38 (2H, m), 2.95-2.99 (2H, m), 3.78 (3H, s), 3.78-3.92 (2H, m), 3.95 (1H, d, J = 14.6 Hz), 5.91 (1H, d, J = 14.6 Hz), 6.16 (1H, s), 6.43-6.49 (1H, m), 6.68-6.73 (2H, m), 6.92-7.11 (4H, m), 7.21 (1H, s) ppm. | (APCI)+: [M + H]+ = 544.6 |
| 1391 E69 | δ 0.86 (9H, s), 1.33-1.40 (2H, m), 1.84-1.94 (2H, m), 2.26-2.33 (2H, m), 2.42 (3H, s), 2.33-2.51 (10H, m), 2.85 (1H, d, J = 15.6 Hz), 2.91-3.05 (1H, m), 3.26-3.42 (1H, m), 3.91 (2H, t, J = 6.2 Hz), 5.06 (1H, dd, J = 4.2, 12.6 Hz), 6.56 (1H, t, J = 8.2 Hz), 6.62-6.73 (2H, m), 6.83-6.94 (2H, m), 7.18 (1H, t, J = 7.4 Hz), 8.08-8.22 (1H, brs), 10.25-10.55 (1H, brs) ppm. | (APCI)+: [M + H]+ = 548.4 |
| 1392 E70 | δ 0.87 (9H, s), 1.37-1.45 (2H, m), 1.83-1.94 (2H, m), 2.00 (3H, s), 2.29-2.40 (2H, m), 2.43 (3H, s), 2.44-2.63 (10H, m), 2.83 (1H, d, J = 15.3 Hz), 2.91-3.08 (1H, m), 3.22-3.41 (1H, m), 3.83 (2H, t, J = 5.9 Hz), 5.09 (1H, dd, J = 4.2, 12.9 Hz), 6.35 (1H, d, J = 8.4 Hz), 6.63-6.69 (2H, m), 6.85 (1H, t, J = 7.4 Hz), 7.07 (1H, s), 7.16 (1H, t, J = 7.4 Hz), 8.10 (1H, d, J = 6.4 Hz) ppm. | (APCI)+: [M + H]+ = 544.5 |
| 1393 E71 | δ 0.89 (9H, s), 1.42-1.49 (2H, m), 1.88-2.02 (2H, m), 2.46-2.58 (4H, m), 2.58-2.78 (8H, m), 3.42 (3H, s), 4.01 (2H, t, J = 6.2 Hz), 6.72 (1H, t, J = 8.4 Hz), 6.93-6.99 (3H, m), 7.04 (1H, dd, J = 2.0, 11.6 Hz), 7.19-7.25 (2H, m) ppm. | (APCI)+: [M + H]+ = 490.3/ 492.3 |
| 1394 E72 | δ 0.89 (9H, s), 1.42-1.53 (2H, m), 1.58-1.82 (4H, m), 2.40-2.58 (3H, m), 2.58-2.79 (4H, m), 3.46 (3H, s), 3.81 (3H, s), 3.88-3.97 (3H, m), 5.87 (1H, d, J = 14.8 Hz), 6.55 (1H, s), 6.60-6.69 (4H, m), 6.93 (1H, d, J = 11.4 Hz) 6.99-7.12 (4H, m), 7.21 (1H, s) ppm. | (APCI)+: [M + H]+ = 563.4 |
| 1395 E73 | δ 0.88 (9H, s), 1.32-1.46 (2H, m), 1.47-1.83 (2H, m), 2.03 (3H, s), 2.30-2.40 (2H, m), 2.40-2.57 (2H, m), 2.57-2.69 (2H, m), 2.80 (2H, t, J = 4.9 Hz), 3.80 (3H, s), 3.95-4.08 (2H, m), 5.91-6.01 (2H, m), 6.50 (1H, d, J = 7.7 Hz), 6.63-7.78 (2H, m), 6.92 (1H, d, J = 7.9 Hz), 6.92-7.01 (1H, m), 7.06-7.18 (2H, m), 7.21-7.28 (3H, m) ppm. | (ESI)+: [M + H]+ = 531.4 |
| 1396 E74 | δ 0.86 (9H, s), 1.33-1.39 (2H, m), 2.09 (3H, s), 2.24-2.37 (6H, m), 3.50-3.60 (4H, m), 3.75 (3H, s), 3.95 (1H, d, J = 14.6 Hz), 4.60 (2H, s), 5.91 (1H, d, J = 14.6 Hz), 6.10 (1H, s), 6.51 (1H, d, J = 8.1 Hz), 6.70 (2H, s), 6.88-6.99 (2H, m), 7.01-7.10 (1H, m), 7.20-7.24 (2H, m) ppm. | (ESI)+: [M + H]+ = 545.4 |
| 1397 E75 | δ 0.88 (9H, s), 1.37 (2H, t, J = 8.4 Hz), 2.24-2.37 (6H, m), 3.50-3.60 (4H, m), 3.75 (3H, s), 3.95 (1H, d, J = 14.6 Hz), 4.60 (2H, s), 5.93 (1H, d, J = 14.6 Hz), 6.39 (1H, s), 6.61-6.73 (4H, m), 6.93 (1H, d, J = 7.9 Hz), 7.01-7.10 (1H, m), 7.20-7.24 (2H, m) ppm. | (ESI)+: [M + H]+ = 531.5 |
| 1398 E76 | δ 0.87 (9H, s), 1.30-1.36 (2H, m), 1.86-1.91 (2H, m), 1.99 (3H, s), 2.22-2.28 (6H, m), 2.40-2.45 (2H, m), 3.34-3.39 (4H, m), 3.77 (3H, s), 3.84-3.90 (3H, m), 5.68 (2H, d, J = 14.3 Hz), 6.63-6.69 (3H, m), | (ESI)+: [M + H]+ = 573.5 |

-continued

| Compound number | | ¹H NMR: δ (ppm) | MS |
|---|---|---|---|
| | | 6.91 (1H, d, J = 8.4 Hz), 7.01 (1H, s), 7.13-7.16 (2H, m), 7.30 (1H, d, J = 8.2 Hz), 8.60 (1H, s) ppm. | |
| 1399 | E77 | δ 1.18-1.38 (2H, m), 1.48-1.76 (2H, m), 1.87 (2H, t, J = 10.6 Hz), 2.15 (3H, s), 2.42-2.48 (2H, m), 2.71-2.88 (4H, m), 2.91-3.01 (2H, m), 3.78 (3H, s), 3.86-3.90 (2H, m), 3.95 (1H, d, J = 14.6 Hz), 5.90 (1H, d, J = 14.6 Hz), 6.68 (2H, brs), 6.79-6.96 (3H, m), 7.02-7.10 (1H, m), 7.13-7.24 (2H, m) ppm. | (ESI)+: [M + H]+ = 488.4 |
| 1400 | E78 | δ 2.15 (3H, s), 3.72 (3H, s), 3.75 (3H, s), 3.96 (1H, d, J = 14.6 Hz), 4.50 (2H, s), 5.80 (1H, d, J = 14.6 Hz), 6.12 (1H, s), 6.45-6.51 (2H, m), 6.64 (1H, s), 6.74-6.92, (3H, m), 7.23 (1H, s) | (APCI)+: [M + H]+ = 441.2, 443.2 |
| 1401 | E79 | δ 0.42-1.38 (3H, m), 2.16 (3H, s), 2.28-2.66 (4H, m), 2.71-3.01 (4H, m), 3.28-3.76 (4H, m), 3.78 (3H, s), 3.96 (1H, d, J = 14.6 Hz), 4.60-4.73 (1H, m), 5.89 (1H, d, J = 14.6 Hz), 6.15 (1H, d, J = 9.1 Hz), 6.71 (2H, s), 6.77-6.98 (3H, m), 7.01-7.21 (3H, m) ppm. | (ESI)+: [M + H]+ = 488.5 |
| 1402 | E80 | δ 0.88 (9H, s), 1.33-1.40 (2H, m), 2.17-2.58 (11H, m), 2.79-2.98 (2H, m), 3.18-3.41 (5H, m), 3.60 (2H, brs), 3.87 (3H, s), 3.88-4.01 (1H, m), 5.92-6.11 (1H, m), 6.78-7.42 (8H, m) ppm. | (ESI)+: [M + H]+ = 557.5 |
| 1403 | E82 | δ 0.89 (9H, s), 1.35-1.41 (2H, m), 1.64 (2H, brs), 1.74-1.84 (2H, m), 2.14 (3H, s), 2.23 (2H, t, J = 7.4 Hz), 2.28-2.38 (6H, m), 2.54 (2H, t, J = 7.4 Hz), 3.34 (2H, t, J = 4.9 Hz), 3.59 (2H, t, J = 4.9 Hz), 6.58-6.78 (4H, m), 6.81-6.92 (1H, m), 7.04-7.09 (3H, m) ppm. | (ESI)+: [M + H]+ = 506.5 |
| 1404 | E83 | δ 0.87 (9H, s), 1.30-1.70 (4H, m), 2.09 (3H, s), 2.20-2.50 (10H, m), 3.41 (2H, brs), 3.58 (4H, brs), 3.74 (3H, s), 3.88-3.98 (1H, m), 5.85-5.95 (1H, m), 6.60-7.22 (9H, m) ppm. | (ESI)+: [M + H]+ = 571.5 |
| 1405 | E84 | δ 1.08-1.47 (2H, m), 1.61-1.86 (4H, m), 2.15 (3H, s), 2.35-2.48 (2H, m), 2.78-2.84 (2H, m), 2.94-3.11 (2H, m), 3.44-3.62 (1H, m), 3.77 (3H, s), 3.72-3.88 (1H, m), 3.95 (1H, d, J = 14.6 Hz), 4.01-4.12 (1H, m), 5.89 (1H, d, J = 14.6 Hz), 6.34 (1H, d, J = 4.7 Hz), 6.66-6.71 (2H, m), 6.76-6.94 (3H, m), 7.01-7.18 (2H, m) ppm. | (ESI)+: [M + H]+ = 474.5 |
| 1406 | E85 | δ 1.36-1.55 (6H, m), 1.71-1.80 (2H, m), 1.82-1.96 (1H, m), 2.02-2.10 (4H, m), 2.68 (3H, s), 2.97-3.10 (2H, m), 3.40-3.55 (4H, m), 3.63 (3H, s), 3.81 (1H, d, J = 14.6 Hz), 5.83 (1H, d, J = 14.6 Hz), 6.42-6.56 (1H, m), 6.61-6.89 (2H, m), 6.95-7.05 (1H, m), 7.17-7.25 (3H, m), 7.33 (1H, s) ppm. | (ESI)+: [M + H]+ = 513.8 |
| 1407 | E86 | δ 0.20-0.27 (2H, m), 0.31-0.42 (2H, m), 0.83-1.10 (2H, m), 1.44-1.83 (4H, m), 2.02-2.10 (1H, m), 2.13 (3H, s), 2.29-2.58 (6H, m), 2.71-2.89 (2H, m), 3.55-3.74 (2H, m), 3.75 (3H, s), 3.95 (1H, d, J = 14.6 Hz), 4.50-4.60 (1H, m), 5.90 (1H, d, J = 14.6 Hz), 6.48-6.75 (3H, m), 6.79-7.22 (5H, m) ppm. | (ESI)+: [M + H]+ = 527.7 |
| 1408 | E87 | δ 0.55-0.64 (2H, m), 0.71-0.81 (2H, m), 1.11-1.24 (2H, m), 1.53-1.62 (2H, m), 1.70-1.91 (1H, m), 2.15 (3H, s), 2.62-2.84 (4H, m), 3.12-3.25 (4H, m), 3.86 (3H, s), 3.90-4.15 (5H, m), 5.67 (1H, d, J = 14.6 Hz), 6.61-6.75 (2H, m), 6.76-6.94 (2H, m), 7.07-7.17 (2H, m), 7.35-7.43 (1H, m), 7.47 (1H, s) ppm. | (ESI)+: [M + H]+ = 527.6 |
| 1409 | E110 | δ 1.91-1.99 (1H, m), 3.32 (2H, s), 3.52-3.85 (8H, m), 3.93 (1H, d, J = 14.6 Hz), 5.81 (1H, d, J = 14.6 Hz), 6.59 (2H, s), 6.80-7.10 (4H, m), 7.10-7.38, (2H, m) ppm | (ESI)+: [M + H]+ = 530.2, 532.2 |
| 1410 | E111 | δ 3.47 (4H, s), 3.67 (6H, s), 3.79 (3H, s), 3.87 (2H, s), 3.95 (1H, d, J = 14.6 Hz), 5.85 (1H, d, J = 14.6 Hz), 6.14 (1H, s), 6.60-6.70 (2H, m), 6.90-7.02 (3H, m), 7.20-7.38 (2H, m) ppm | (ESI)+: [M + H]+ = 458.1 |
| 1411 | E112 | δ 1.28 (1H, s), 2.71 (2H, t, J = 5.3 Hz), 3.64 (2H, t, J = 5.3 Hz), 3.81 (3H, s), 3.95 (2H, s), 4.00 (1H, d, J = 14.7 Hz), 5.74 (1H, d, J = 14.7 Hz), 6.66 (1H, d, J = 8.3 Hz), 6.78 (1H, d, J = 8.3 Hz), 7.02-7.10 (2H, m), 7.22-7.38 (3H, m) ppm | (ESI)+: [M + H]+ = 430.1 |
| 1412 | E116 | (270 MHz, d4-MeOH): δ 0.37-0.48 (2H, m), 0.70-0.81 (2H, m), 1.02-1.18 (1H, m), 1.86-2.11 (4H, m), 2.22 (3H, s), 2.49-2.64 (1H, m), 3.01 (2H, d, J = 7.4 Hz), 3.17-3.30 (2H, m), 3.42 (3H, s), 3.49-3.76 (2H, m), 4.30 (2H, s), 7.06-7.17 (5H, m), 7.23-7.27 (2H, m) ppm. | (APCI)+: [M + H]+ = 454.3/ 456.3 |
| 1413 | E117 | δ 0.91 (9H, s), 1.48-1.58 (2H, m), 1.60-1.79 (4H, m), 2.16 (3H, s), 2.22-2.35 (1H, m), 2.51-2.65 (2H, | (ESI)+: [M + H]+ = 484.4/ |

-continued

| Compound number | $^1$H NMR: δ (ppm) | MS |
|---|---|---|
|  | m), 2.71-2.82 (2H, m), 3.11-3.27 (2H, m), 3.43 (3H, s), 4.25 (2H, d, J = 5.5 Hz), 6.52-6.63 (1H, m), 6.95-7.09 (5H, m), 7.20 (2H, d, J = 8.6 Hz) ppm. | 486.4 |
| 1414 E118 | δ 0.87 (9H, s), 1.34-1.41 (2H, m), 1.62-1.96 (6H, m), 2.04-2.19 (1H, m), 2.17 (3H, s), 2.26-2.33 (2H, m), 2.94-2.99 (1H, m), 3.48 (3H, s), 4.34 (2H, d, J = 5.4 Hz), 6.95 (2H, d, J = 1.0 Hz), 7.14 (2H, d, J = 8.2 Hz), 7.19 (1H, s), 7.49 (2H, d, J = 8.4 Hz) ppm. | (APCI)$^+$: [M + H]$^+$ = 518.4 |
| 1415 E119 | δ 0.64-0.73 (2H, m), 0.90-1.00 (2H, m), 1.25-1.40 (1H, m), 2.12 (3H, s), 2.55 (3H, s), 2.80-2.90 (1H, m), 2.90-2.94 (1H, m), 3.45 (1H, s), 4.30 (2H, d, J = 5.4 Hz), 5.09-5.22 (1H, m), 5.77-5.88 (1H, m), 6.60-6.73 (2H, m), 6.86-6.93 (2H, m), 7.01 (1H, s), 7.14-7.24 (1H, m), 7.76 (1H, dd, J = 1.2, 7.9 Hz) ppm. | (ESI)$^+$: [M + H]$^+$ = 416.3 |
| 1416 E120 | δ 0.87 (9H, s), 1.36-1.45 (2H, m), 1.73-1.82 (2H, m), 1.90-2.07 (2H, m), 2.11 (3H, s), 2.36-2.42 (2H, m), 2.55 (3H, s), 2.80-2.90 (1H, m), 2.90-2.98 (1H, m), 3.10-3.16 (2H, m), 4.28 (2H, d, J = 5.2 Hz), 5.11-5.19 (1H, m), 5.72-5.82 (1H, m), 6.49 (2H, dd, J = 1.5, 6.7 Hz), 6.61-6.72 (2H, m), 6.80-6.97 (2H, m), 7.00 (1H, s), 7.13-7.25 (1H, m), 7.77 (1H, dd, J = 1.5, 7.9 Hz), 8.15 (2H, dd, J = 1.7, 5.2 Hz) ppm. | (APCI)$^+$: [M + H]$^+$ = 543.4 |
| 1417 E121 | δ 0.88 (9H, s), 1.37-1.53 (5H, m), 1.63-1.70 (2H, m), 2.11 (3H, s), 2.45 (3H, s), 2.63-3.46 (8H, m), 2.87-2.94 (2H, m), 4.23 (2H, brd), 5.08 (2H, d, J = 7.9 Hz), 4.96-5.11 (1H, m), 6.60 (2H, t, J = 7.9, 15.1 Hz), 6.81-6.86 (2H, m), 6.95 (2H, d, J = 7.9 Hz), 7.04 (1H, s), 7.12-7.33 (4H, m), 8.22 (1H, dd, J = 1.2, 7.9 Hz) ppm. | (APCI)$^+$: [M + H]$^+$ = 632.4 |
| 1418 E123 | δ 0.64-0.71 (2H, m), 0.89-0.95 (2H, m), 1.33-1.39 (1H, m), 2.10 (3H, s), 2.43 (3H, s), 2.74-2.81 (1H, m), 2.92-3.04 (1H, m), 3.07-3.26 (1H, m), 4.18-4.34 (2H, m), 4.97-5.05 (1H, m), 6.60 (2H, d, J = 7.9 Hz), 6.79-6.84 (2H, m), 7.05 (1H, s), 7.11 (1H, t, J = 7.4, 14.8 Hz), 7.96-8.21 (1H, brs), 10.10-10.60 (1H, brs) ppm. | (APCI)$^+$: [M + H]$^+$ = 415.3 |
| 1419 E125 | δ 1.13 (6H, d, J = 6.9 Hz), 2.15 (3H, s), 2.30-2.40 (1H, m), 2.48 (3H, s), 2.86-3.03 (2H, m), 3.20-3.38 (1H, m), 4.20-4.36 (2H, m), 5.04-5.11 (1H, m), 5.63 (1H, s), 6.53 (1H, d, J = 8.2 Hz), 6.62 (1H, d, J = 7.9 Hz), 6.70-6.90 (2H, m), 7.10 (1H, s), 8.21 (1H, s), 9.39 (1H, s) ppm. | (ESI)+: [M + H]+ = 451.2, 453.2 |

The invention claimed is:

1. A compound according to general formula 1a, or a compound which is a tautomer or a pharmaceutically acceptable salt thereof,

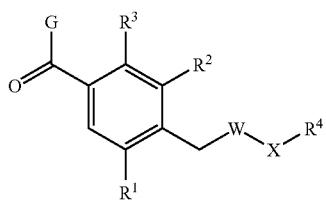

1a wherein G is a group of formula 4a or 5a,

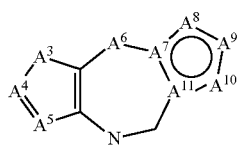

4a

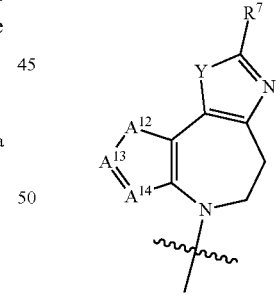

5a wherein:
$A^3$ and $A^{12}$ are independently $-C(R^8)=CH-$;
$A^4$ and $A^{13}$ are independently $C(R^9)$;
$A^5$ and $A^{14}$ are independently $C(R^{10})$;
$A^6$ is NH or N-alkyl;
$A^7$ and $A^{11}$ are C;
$A^8$ is NH or $N(CH_2)_bR^{11}$;
$A^9$ is N;
$A^{10}$ is CH;
wherein the ring constituted by $A^7$, $A^8$, $A^9$, $A^{10}$ and $A^{11}$ is aromatic;

$R^1$, $R^2$ and $R^3$ are independently selected among H, alkyl, O-alkyl, $NO_2$, F, Cl and Br;

$R^4$ is selected among H, alkyl, aryl, heteroaryl, $-(CH_2)_c-R^{12}$ and

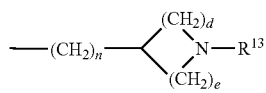

$R^7$ is selected among H, alkyl, aryl, heteroaryl and $-(CH_2)_g-R^{14}$;

$R^8$ is selected among alkoxy, F, Cl, Br, CN, $NH_2$, $NO_2$, NH(alkyl), and $N(alkyl)_2$;

$R^9$ and $R^{10}$ are independently H, alkyl, alkoxy, F, Cl, Br, CN, $NH_2$, $NO_2$, NH(alkyl), or $N(alkyl)_2$;

$R^{11}$ is independently selected among H, alkyl, aryl, heteroaryl, F, OH, O-alkyl, S-alkyl, O-acyl, $NH_2$, NH-alkyl, $N(alkyl)_2$, NH-acyl, N(alkyl)-acyl, $CO_2H$, $CO_2$-alkyl, $CONH_2$, CONH-alkyl, $CON(alkyl)_2$, CN and $CF_3$;

$R^{12}$ is selected among aryl, heteroaryl, F, OH, O-alkyl, S-alkyl, O-acyl, $NH_2$, NH-alkyl, $N(alkyl)_2$, NH-acyl, N(alkyl)-acyl, $CO_2H$, $CO_2$-alkyl, $CONH_2$, CONH-alkyl, $CON(alkyl)_2$, CN and $CF_3$;

$R^{13}$ is selected among H, alkyl, aryl, heteroaryl, $(CH_2)_h-R^{15}$ and $Z-R^{16}$;

$R^{14}$ and $R^{15}$ are independently selected among H, alkyl, alkenyl, aryl, heteroaryl, F, OH, O-alkyl, S-alkyl, O-acyl, $NH_2$, NH-alkyl, $N(alkyl)_2$, NH-acyl, N(alkyl)-acyl, $CO_2H$, $CO_2$-alkyl, CO-alkyl, CO-aryl, $CONH_2$, CONH-alkyl, $CON(alkyl)_2$, alkenyl-$CO_2$-alkyl, alkenyl-aryl, CN and $CF_3$;

$R^{16}$ is selected among H, alkyl, alkenyl, aryl, heteroaryl, O-aryl, $-(CH_2)_i R^{17}$, cyclopropyl-aryl and $O-(CH_2)_i-R^{17}$;

$R^{17}$ is selected among H, alkyl, aryl, heteroaryl, F, OH, O-alkyl, S-alkyl, O-acyl, $NH_2$, NH-alkyl, $N(alkyl)_2$, NH-acyl, N(alkyl)-acyl, $CO_2H$, $CO_2$-alkyl, $CONH_2$, CONH-alkyl, $CON(alkyl)_2$, CN and $CF_3$;

W is selected among O and NH;

X is selected among $(CH_2)_m$, C(=O) and $S(=O)_j$;

Y is selected among O, S, NH and N-alkyl;

Z is selected among $-C(=O)$, $-C(=O)-O$ and $-S(=O)_k$;

b and c are independently selected among 0, 1, 2 and 3;

d and e are independently selected among 1 and 2;

g, h and i are independently selected among 1, 2 and 3;

j and k are independently selected among 1 and 2; and m and n are independently selected among 0, 1 and 2;

wherein heteroaryl is pyridyl, 2-chloropyridyl, 4-methylpyridyl, thienyl, 3-chlorothienyl, 2,3-dimethylthiophenyl, furyl, 2-methylfuryl, pyrrole, N-methylpyrrole, oxazole, imidazole, pyrazole, or triazole; and wherein at least one of $R^1$, $R^2$, or $R^3$ is other than hydrogen.

2. The compound according to claim 1, wherein G is selected among:

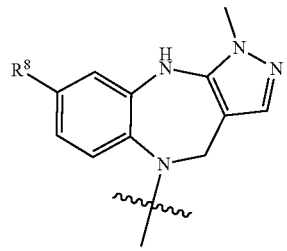

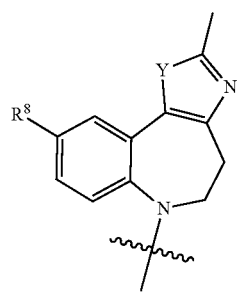

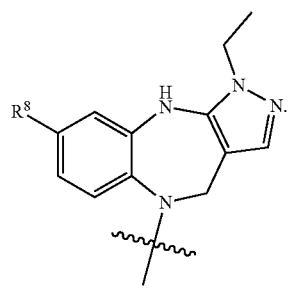

3. The compound according to claim 1, wherein G is:

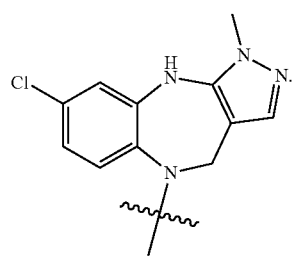

10a

4. The compound according to claim 1, wherein W is NH.

5. The compound according to claim 1, wherein $R^4$ is alkyl.

6. The compound according to claim 1, wherein d is 2 and e is 2.

7. The compound according to claim 1, wherein $R^{13}$ is alkyl.

8. The compound according to claim 1, wherein n is 0.

9. The compound according to claim 1, wherein $R^2$ is H, $R^4$ is a piperidine where d is 2 and e is 2, W is NH, X is C(=O) and n is 0, as shown in formula 18a:

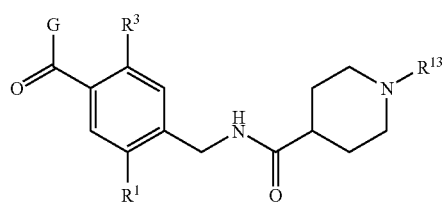

18a wherein R¹ is selected among methyl, chlorine and fluorine, and R³ is H; or R¹ is H, and R³ is selected among methyl, chlorine and fluorine, and R¹³ is alkyl.

10. The compound according to claim 1, wherein X is C(=O), n is 0 and R⁴ is a piperidine where d is 2 and e is 2, as shown in formula 19a:

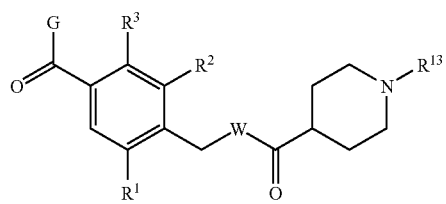

19a wherein G is selected among general formulae 10a, 13a, 16a, and 17a, and R¹³ is alkyl

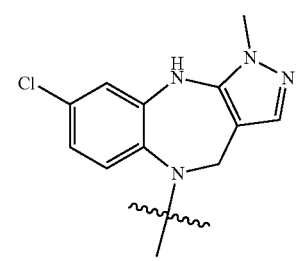

10a

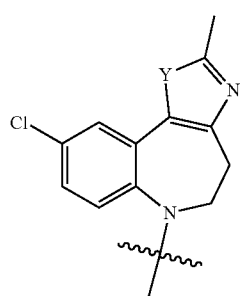

13a

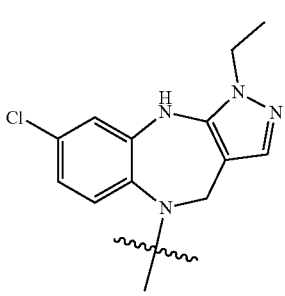

16a

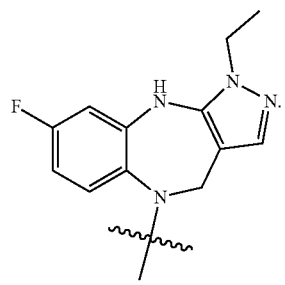

17a

11. The compound according to claim 1, wherein R² is H and W is NH as shown in formula 20a:

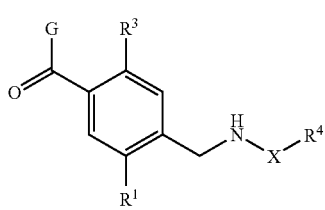

20a wherein either R¹ is selected among methyl, chlorine and fluorine, and R³ is H; or R¹ is H, and R³ is selected among methyl, chlorine and fluorine; and G is selected from general formulae 10a, 13a, 16a, and 17a:

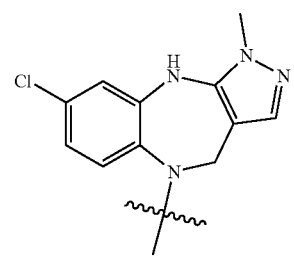

10a

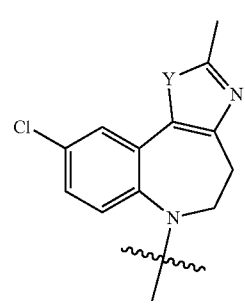

13a

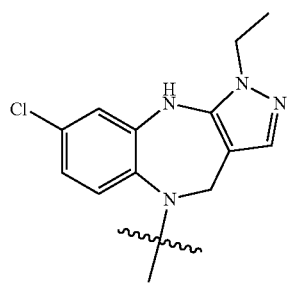
16a

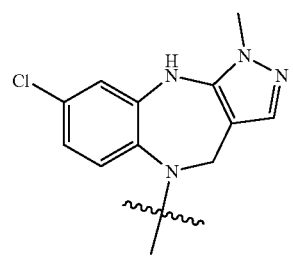
10a

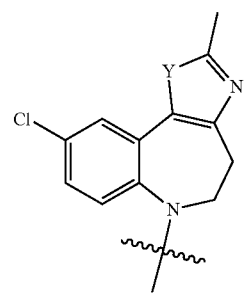
13a

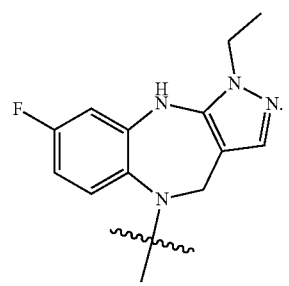
17a

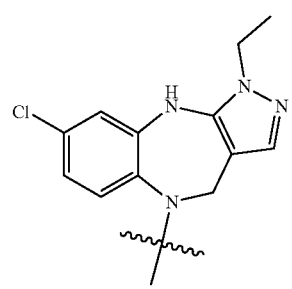
16a

12. The compound according to claim 1, wherein $R^2$ is H, W is NH and X is C(=O) as shown in formula 21a:

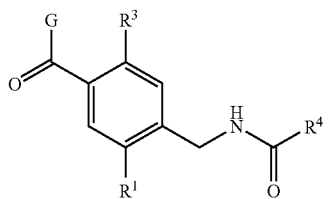
21a

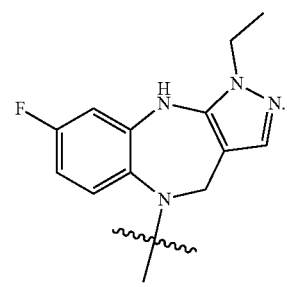
17a wherein $R^1$ is selected among methyl, chlorine and fluorine, and $R^3$ is H; or $R^1$ is H, and $R^3$ is selected among methyl, chlorine and fluorine; and $R^4$ is alkyl.

13. The compound according to claim 1, wherein X is C(=O) as shown in formula 22a:

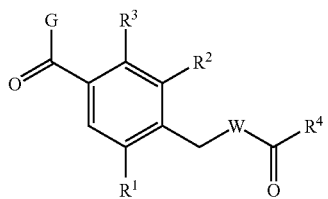
22a wherein G is selected among general formulae 10a, 13a, 16a, and 17a, and $R^4$ is alkyl:

14. The compound according to claim 1, wherein $R^2$ and $R^3$ are both H, W is NH and X is C(=O) as shown in formula 23a:

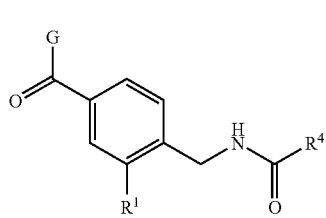
23a wherein G is selected among general formulae 10a, 16a and 17a, $R^1$ is selected among methyl, chlorine and fluorine, and $R^4$ is alkyl

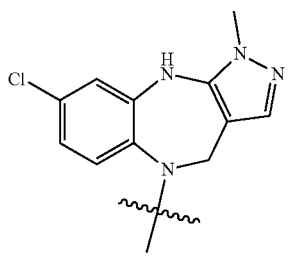

10a

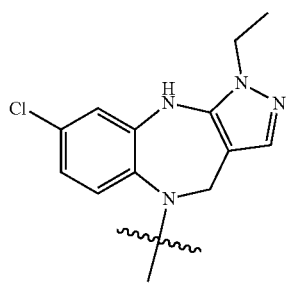

16a

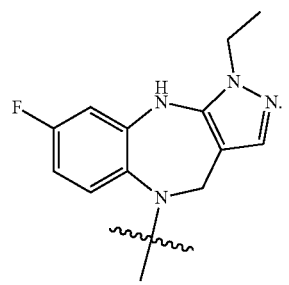

17a

15. The compound according to claim 1, wherein $R^2$ and $R^3$ are both H, $R^4$ is a piperidine where d is 2 and e is 2, W is NH, X is C(=O) and n is 0 as shown in formula 24a:

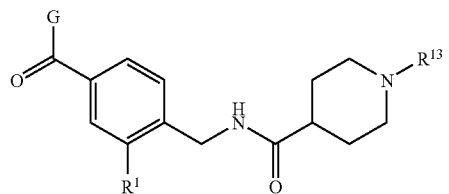

24a wherein G is selected among general formulae 10a, 16a and 17a, $R^1$ is selected among methyl, chlorine and fluorine, and $R^{13}$ is alkyl

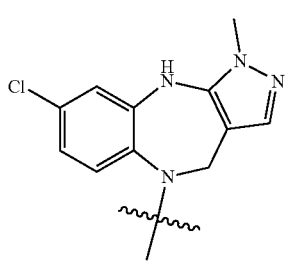

10a

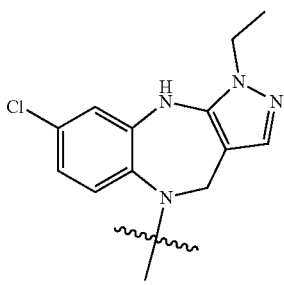

16a

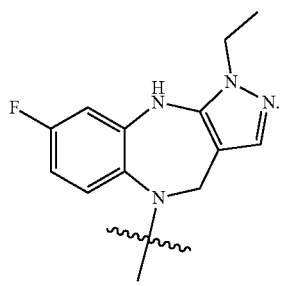

17a

16. The compound according to claim 1, selected among the group consisting of:

1-(3,3-Dimethyl-butyl)-piperidine-4-carboxylic acid 2-chloro-4-(6-chloro-3-methyl-4,10-dihydro-3H-2,3,4,9-tetraaza-benzo-[f]azulene-9-carbonyl)-benzylamide;

1-(3,3-Dimethyl-butyl)-piperidine-4-carboxylic acid 3-chloro-4-(6-chloro-3-methyl-4,10-dihydro-3H-2,3,4,9-tetraaza-benzo-[f]azulene-9-carbonyl)-benzylamide;

1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-2-methyl-benzylamide;

1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-2-fluoro-benzylamide;

1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-3-methyl-benzylamide;

1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-3-fluoro-benzylamide;

1-Cyclopropylmethyl-piperidine-4-carboxylic acid 2-chloro-4-(6-chloro-3-methyl-4,10-dihydro-3H-2,3,4,9-tetraaza-benzo[f]azulene-9-carbonyl)-benzylamide;

1-Cyclopropylmethyl-piperidine-4-carboxylic acid 3-chloro-4-(6-chloro-3-methyl-4,10-dihydro-3H-2,3,4,9-tetraaza-benzo[f]azulene-9-carbonyl)-benzylamide;

1-Cyclopropylmethyl-piperidine-4-carboxylic acid 4-(6-chloro-3-methyl-4,10-dihydro-3H-2,3,4,9-tetraaza-benzo[f]azulene-9-carbonyl)-2-fluoro-benzylamide;

1-Cyclopropylmethyl-piperidine-4-carboxylic acid 4-(6-chloro-3-methyl-4,10-dihydro-3H-2,3,4,9-tetraaza-benzo[f]azulene-9-carbonyl)-2-methyl-benzylamide;

1-Cyclopropylmethyl-piperidine-4-carboxylic acid 4-(6-chloro-3-methyl-4,10-dihydro-3H-2,3,4,9-tetraaza-benzo[f]azulene-9-carbonyl)-3-methyl-benzylamide;

1-Cyclopropylmethyl-piperidine-4-carboxylic acid 4-(6-chloro-3-methyl-4,10-dihydro-3H-2,3,4,9-tetraaza-benzo[f]azulene-9-carbonyl)-3-fluoro-benzylamide;

Cyclobutanecarboxylic acid 2-chloro-4-(6-chloro-3-methyl-4,10-dihydro-3H-2,3,4,9-tetraaza-benzo[f]azulene-9-carbonyl)-benzylamide;

Cyclobutanecarboxylic acid 4-(6-chloro-3-methyl-4,10-dihydro-3H-2,3,4,9-tetraaza-benzo[f]azulene-9-carbonyl)-2-fluoro-benzylamide;
Cyclopentanecarboxylic acid 2-chloro-4-(6-chloro-3-methyl-4,10-dihydro-3H-2,3,4,9-tetraaza-benzo[f]azulene-9-carbonyl)-benzylamide;
Cyclopentanecarboxylic acid 4-(6-chloro-3-methyl-4,10-dihydro-3H-2,3,4,9-tetraaza-benzo[f]azulene-9-carbonyl)-2-fluoro-benzylamide;
Cyclopropanecarboxylic acid 2-chloro-4-(6-chloro-3-methyl-4,10-dihydro-3H-2,3,4,9-tetraaza-benzo[f]azulene-9-carbonyl)-benzylamide;
Cyclopropanecarboxylic acid 3-chloro-4-(6-chloro-3-methyl-4,10-dihydro-3H-2,3,4,9-tetraaza-benzo[f]azulene-9-carbonyl)-benzylamide;
Cyclopropanecarboxylic acid 4-(6-chloro-3-methyl-4,10-dihydro-3H-2,3,4,9-tetraaza-benzo[f]azulene-9-carbonyl)-2-methyl-benzylamide;
Cyclopropanecarboxylic acid 4-(6-chloro-3-methyl-4,10-dihydro-3H-2,3,4,9-tetraaza-benzo[f]azulene-9-carbonyl)-3-fluoro-benzylamide;
Cyclopropanecarboxylic acid 4-(6-chloro-3-methyl-4,10-dihydro-3H-2,3,4,9-tetraazabenzo[f]azulene-9-carbonyl)-2-fluoro-benzylamide;
Cyclopropanecarboxylic acid 4-(6-chloro-3-methyl-4,10-dihydro-3H-2,3,4,9-tetraaza-benzo[f]azulene-9-carbonyl)-3-methyl-benzylamide;
N-[2-Chloro-4-(6-chloro-3-methyl-4,10-dihydro-3H-2,3,4,9-tetraaza-benzo[f]azulene-9-carbonyl)-benzyl]-propionamide;
N-[2-Chloro-4-(6-chloro-3-methyl-4,10-dihydro-3H-2,3,4,9-tetraaza-benzo[f]azulene-9-carbonyl)-benzyl]-2,2-dimethyl-propionamide;
N-[2-Chloro-4-(6-chloro-3-methyl-4,10-dihydro-3H-2,3,4,9-tetraaza-benzo[f]azulene-9-carbonyl)-benzyl]-isobutyramide;
N-[2-Chloro-4-(6-chloro-3-methyl-4,10-dihydro-3H-2,3,4,9-tetraaza-benzo[f]azulene-9-carbonyl)-benzyl]-butyramide;
N-[4-(6-Chloro-3-methyl-4,10-dihydro-3H-2,3,4,9-tetraaza-benzo[f]azulene-9-carbonyl)-2-fluoro-benzyl]-propionamide;
N-[4-(6-Chloro-3-methyl-4,10-dihydro-3H-2,3,4,9-tetraaza-benzo[f]azulene-9-carbonyl)-2-fluoro-benzyl]-2,2-dimethyl-propionamide;
N-[4-(6-Chloro-3-methyl-4,10-dihydro-3H-2,3,4,9-tetraaza-benzo[f]azulene-9-carbonyl)-2-fluoro-benzyl]-isobutyramide;
N-[4-(6-Chloro-3-methyl-4,10-dihydro-3H-2,3,4,9-tetraaza-benzo[f]azulene-9-carbonyl)-2-fluoro-benzyl]-acetamide;
N-[4-(6-Chloro-3-methyl-4,10-dihydro-3H-2,3,4,9-tetraaza-benzo[f]azulene-9-carbonyl)-2-fluoro-benzyl]-butyramide;
N-[4-(6-Chloro-3-methyl-4,10-dihydro-3H-2,3,4,9-tetraaza-benzo[f]azulene-9-carbonyl)-2-fluoro-benzyl]-formamide;
N-[4-(6-Chloro-3-ethyl-4,10-dihydro-3H-2,3,4,9-tetraaza-benzo[f]azulene-9-carbonyl)-2-fluoro-benzyl]-propionamide;
Cyclopropanecarboxylic acid 4-(6-chloro-3-ethyl-4,10-dihydro-3H-2,3,4,9-tetraaza-benzo[f]azulene-9-carbonyl)-2-fluoro-benzylamide;
N-[2-Fluoro-4-(6-fluoro-3-methyl-4,10-dihydro-3H-2,3,4,9-tetraaza-benzo[f]azulene-9-carbonyl)-benzyl]-propionamide;
N-[2-Fluoro-4-(6-fluoro-3-methyl-4,10-dihydro-3H-2,3,4,9-tetraaza-benzo[f]azulene-9-carbonyl)-benzyl]-isobutyramide;
Cyclopropanecarboxylic acid 2-fluoro-4-(6-fluoro-3-methyl-4,10-dihydro-3H-2,3,4,9-tetraaza-benzo[f]azulene-9-carbonyl)-benzylamide; and
N-[4-(9-Chloro-2-methyl-4,5-dihydro-1H-1,3,6-triaza-benzo[e]azulene-6-carbonyl)-2-methyl-benzyl]-isobutyramide.

17. The compound according to claim 1 wherein one of $R^1$, $R^2$ and $R^3$ is selected among methyl, chlorine and fluorine, and the others are hydrogen.

18. The compound according to claim 2, wherein $R^1$, $R^2$, and $R^3$ are each independently selected among H, alkyl, F, Cl, and Br; $R^8$ is selected among F, Cl, and Br; $R^4$ is alkyl; —W— is —NH—; and X— is —C(O)—.

19. The compound according to claim 13, wherein $R^4$ is branched alkyl or cycloalkyl.

20. The compound according to claim 1, wherein said compound is:
1-(3,3-Dimethyl-butyl)-piperidine-4-carboxylic acid 2-chloro-4-(6-chloro-3-methyl-4,10-dihydro-3H-2,3,4,9-tetraaza-benzo-[f]azulene-9-carbonyl)-benzylamide;
1-(3,3-Dimethyl-butyl)-piperidine-4-carboxylic acid 3-chloro-4-(6-chloro-3-methyl-4,10-dihydro-3H-2,3,4,9-tetraaza-benzo-[f]azulene-9-carbonyl)-benzylamide;
1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-2-methyl-benzylamide;
1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-2-fluoro-benzylamide;
1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-3-methyl-benzylamide; or
1-(3,3-Dimethyl-butyl)-piperidine-4-carboxylic acid 4-(6-chloro-3-methyl-4,10-dihydro-3H-2,3,4,9-tetraaza-benzo[f]azulene-9-carbonyl)-3-fluoro-benzylamide.

21. The compound according to claim 1, wherein said compound is:
1-Cyclopropylmethyl-piperidine-4-carboxylic acid 2-chloro-4-(6-chloro-3-methyl-4,10-dihydro-3H-2,3,4,9-tetraaza-benzo[f]azulene-9-carbonyl)-benzylamide;
1-Cyclopropylmethyl-piperidine-4-carboxylic acid 3-chloro-4-(6-chloro-3-methyl-4,10-dihydro-3H-2,3,4,9-tetraaza-benzo[f]azulene-9-carbonyl)-benzylamide;
1-Cyclopropylmethyl-piperidine-4-carboxylic acid 4-(6-chloro-3-methyl-4,10-dihydro-3H-2,3,4,9-tetraaza-benzo[f]azulene-9-carbonyl)-2-fluoro-benzylamide;
1-Cyclopropylmethyl-piperidine-4-carboxylic acid 4-(6-chloro-3-methyl-4,10-dihydro-3H-2,3,4,9-tetraaza-benzo[f]azulene-9-carbonyl)-2-methyl-benzylamide;
1-Cyclopropylmethyl-piperidine-4-carboxylic acid 4-(6-chloro-3-methyl-4,10-dihydro-3H-2,3,4,9-tetraaza-benzo[f]azulene-9-carbonyl)-3-methyl-benzylamide; or
1-Cyclopropylmethyl-piperidine-4-carboxylic acid 4-(6-chloro-3-methyl-4,10-dihydro-3H-2,3,4,9-tetraaza-benzo[f]azulene-9-carbonyl)-3-fluoro-benzylamide.

22. The compound according to claim 1, wherein said compound is:
Cyclobutanecarboxylic acid 2-chloro-4-(6-chloro-3-methyl-4,10-dihydro-3H-2,3,4,9-tetraaza-benzo[f]azulene-9-carbonyl)-benzylamide;

Cyclobutanecarboxylic acid 4-(6-chloro-3-methyl-4,10-dihydro-3H-2,3,4,9-tetraaza-benzo[f]azulene-9-carbonyl)-2-fluoro-benzylamide;
Cyclopentanecarboxylic acid 2-chloro-4-(6-chloro-3-methyl-4,10-dihydro-3H-2,3,4,9-tetraaza-benzo[f]azulene-9-carbonyl)-benzylamide; or
Cyclopentanecarboxylic acid 4-(6-chloro-3-methyl-4,10-dihydro-3H-2,3,4,9-tetraaza-benzo[f]azulene-9-carbonyl)-2-fluoro-benzylamide.

23. The compound according to claim 1, wherein said compound is:
Cyclopropanecarboxylic acid 2-chloro-4-(6-chloro-3-methyl-4,10-dihydro-3H-2,3,4,9-tetraaza-benzo[f]azulene-9-carbonyl)-benzylamide;
Cyclopropanecarboxylic acid 3-chloro-4-(6-chloro-3-methyl-4,10-dihydro-3H-2,3,4,9-tetraaza-benzo[f]azulene-9-carbonyl)-benzylamide;
Cyclopropanecarboxylic acid 4-(6-chloro-3-methyl-4,10-dihydro-3H-2,3,4,9-tetraaza-benzo[f]azulene-9-carbonyl)-2-methyl-benzylamide;
Cyclopropanecarboxylic acid 4-(6-chloro-3-methyl-4,10-dihydro-3H-2,3,4,9-tetraaza-benzo[f]azulene-9-carbonyl)-3-fluoro-benzylamide;
Cyclopropanecarboxylic acid 4-(6-chloro-3-methyl-4,10-dihydro-3H-2,3,4,9-tetraazabenzo[f]azulene-9-carbonyl)-2-fluoro-benzylamide;
Cyclopropanecarboxylic acid 4-(6-chloro-3-methyl-4,10-dihydro-3H-2,3,4,9-tetraaza-benzo[f]azulene-9-carbonyl)-3-methyl-benzylamide;
Cyclopropanecarboxylic acid 4-(6-chloro-3-ethyl-4,10-dihydro-3H-2,3,4,9-tetraaza-benzo[f]azulene-9-carbonyl)-2-fluoro-benzylamide; or
Cyclopropanecarboxylic acid 2-fluoro-4-(6-fluoro-3-methyl-4,10-dihydro-3H-2,3,4,9-tetraaza-benzo[f]azulene-9-carbonyl)-benzylamide.

24. The compound according to claim 1, wherein said compound is:
N-[2-Chloro-4-(6-chloro-3-methyl-4,10-dihydro-3H-2,3,4,9-tetraaza-benzo[f]azulene-9-carbonyl)-benzyl]-propionamide;
N-[-2-Chloro-4-(6-chloro-3-methyl-4,10-dihydro-3H-2,3,4,9-tetraaza-benzo[f]azulene-9-carbonyl)-benzyl]-2,2-dimethyl-propionamide;
N-[2-Chloro-4-(6-chloro-3-methyl-4,10-dihydro-3H-2,3,4,9-tetraaza-benzo[f]azulene-9-carbonyl)-benzyl]-isobutyramide;
N-[2-Chloro-4-(6-chloro-3-methyl-4,10-dihydro-3H-2,3,4,-9-tetraaza-benzo[f]azulene-9-carbonyl)-benzyl]-butyramide;
N-[4-(6-Chloro-3-methyl-4,10-dihydro-3H-2,3,4,9-tetraaza-benzo[f]azulene-9-carbonyl)-2-fluoro-benzyl]-propionamide;
N-[4-(6-Chloro-3-methyl-4,10-dihydro-3H-2,3,4,9-tetraaza-benzo[f]azulene-9-carbonyl)-2-fluoro-benzyl]-2,2-dimethyl-propionamide;
N-[4-(6-Chloro-3-methyl-4,10-dihydro-3H-2,3,4,9-tetraaza-benzo[f]azulene-9-carbonyl)-2-fluoro-benzyl]-isobutyramide;
N-[4-(6-Chloro-3-methyl-4,10-dihydro-3H-2,3,4,9-tetraaza-benzo[f]azulene-9-carbonyl)-2-fluoro-benzyl]-acetamide;
N-[4-(6-Chloro-3-methyl-4,10-dihydro-3H-2,3,4,9-tetraaza-benzo[f]azulene-9-carbonyl)-2-fluoro-benzyl]-butyramide;
N-[4-(6-Chloro-3-methyl-4,10-dihydro-3H-2,3,4,9-tetraaza-benzo[f]azulene-9-carbonyl)-2-fluoro-benzyl]-formamide;
N-[4-(6-Chloro-3-ethyl-4,10-dihydro-3H-2,3,4,9-tetraaza-benzo[f]azulene-9-carbonyl)-2-fluoro-benzyl]-propionamide;
N-[2-Fluoro-4-(6-fluoro-3-methyl-4,10-dihydro-3H-2,3,4,9-tetraaza-benzo[f]azulene-9-carbonyl)-benzyl]-propionamide;
N-[2-Fluoro-4-(6-fluoro-3-methyl-4,10-dihydro-3H-2,3,4,9-tetraaza-benzo[f]azulene-9-carbonyl)-benzyl]-isobutyramide; or
N-[4-(9-Chloro-2-methyl-4,5-dihydro-1H-1,3,6-triaza-benzo[e]azulene-6-carbonyl)-2-methyl-benzyl]-isobutyramide.

25. The compound according to claim 1, which is cyclopropanecarboxylic acid 4-(6-chloro-3-methyl-4,10-dihydro-3H-2,3,4,9-tetraazabenzo[f]azulene-9-carbonyl)-2-fluoro-benzylamide:

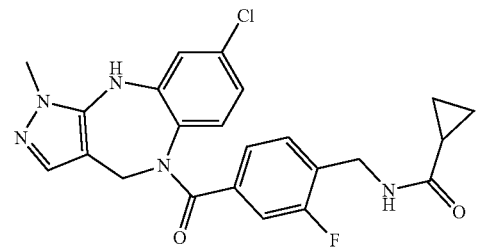

or a tautomer or a pharmaceutically acceptable salt thereof.

26. A pharmaceutical composition comprising a compound according to claim 1, 23, or 25, and a pharmaceutically acceptable excipient.

27. The pharmaceutical composition according to claim 26, formulated in a form suitable for oral administration.

28. A composition of claim 26, comprising an amount of said compound effective for the treatment of dysmenorrhea.

29. A method of treating dysmenorrhoea, comprising the administration to a person in need of such treatment of an effective amount of a compound according to claim 1, 23, or 25.

* * * * *